United States Patent
Edwards et al.

(10) Patent No.: US 10,246,433 B2
(45) Date of Patent: *Apr. 2, 2019

(54) ARYL AND HETEROARYL FUSED LACTAMS

(71) Applicant: Pfizer Inc., New York, NY (US)

(72) Inventors: Martin Paul Edwards, San Diego, CA (US); Robert Arnold Kumpf, Carlsbad, CA (US); Pei-Pei Kung, San Diego, CA (US); Indrawan James McAlpine, San Diego, CA (US); Sacha Ninkovic, La Jolla, CA (US); Eugene Yuanjin Rui, San Diego, CA (US); Scott Channing Sutton, San Diego, CA (US); John Howard Tatlock, San Diego, CA (US); Martin James Wythes, Solana Beach, CA (US); Luke Raymond Zehnder, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/585,880

(22) Filed: May 3, 2017

(65) Prior Publication Data

US 2017/0233368 A1    Aug. 17, 2017

Related U.S. Application Data

(63) Continuation of application No. 14/642,274, filed on Mar. 9, 2015, now abandoned, which is a continuation of application No. 14/132,567, filed on Dec. 18, 2013, now Pat. No. 9,040,515.

(60) Provisional application No. 61/740,596, filed on Dec. 21, 2012.

(51) Int. Cl.
| | |
|---|---|
| *C07D 401/06* | (2006.01) |
| *C07D 401/14* | (2006.01) |
| *C07D 403/14* | (2006.01) |
| *C07D 407/14* | (2006.01) |
| *C07D 405/14* | (2006.01) |
| *C07D 413/06* | (2006.01) |
| *C07D 413/14* | (2006.01) |
| *C07D 471/04* | (2006.01) |
| *C07D 487/04* | (2006.01) |

(52) U.S. Cl.
CPC ......... *C07D 401/06* (2013.01); *C07D 401/14* (2013.01); *C07D 403/14* (2013.01); *C07D 405/14* (2013.01); *C07D 407/14* (2013.01); *C07D 413/06* (2013.01); *C07D 413/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 3,846,412 A | 11/1974 | Nathansohn et al. |
| 8,410,088 B2 | 4/2013 | Kuntz et al. |
| 9,040,515 B2 | 5/2015 | Edwards et al. |
| 9,481,666 B2 | 11/2016 | Kania et al. |
| 2007/0093515 A1 | 4/2007 | Arrington et al. |
| 2008/0182844 A1 | 7/2008 | Bjergarde et al. |
| 2010/0113415 A1 | 5/2010 | Rajapakse et al. |
| 2015/0175572 A1 | 6/2015 | Edwards et al. |
| 2015/0239842 A1 | 8/2015 | Edwards et al. |
| 2015/0307397 A1 | 10/2015 | Bouteiller et al. |
| 2015/0307471 A1 | 10/2015 | Willand et al. |

(Continued)

FOREIGN PATENT DOCUMENTS

| | | |
|---|---|---|
| WO | 2011103016 | 8/2011 |
| WO | 2011140324 | 11/2011 |

(Continued)

OTHER PUBLICATIONS

Bachmann et al., "EZH2 Expression Is Associated With High Proliferation Rate and Aggressive Tumor Subgroups in Cutaneous Melanoma and Cancers of the Endometrium, Prostate, and Breast." J. Clin. Oncol. (2006), 24:268-273.

(Continued)

*Primary Examiner* — Anna Pagonakis
(74) *Attorney, Agent, or Firm* — Feng Shao

(57) ABSTRACT

This invention relates to compounds of general formula (I)

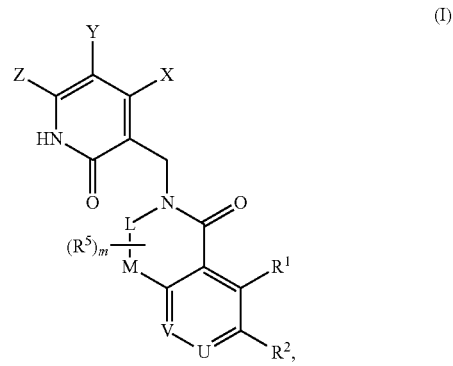

in which $R^1$, $R^2$, U, V, L, M, $R^5$, m, X, Y and Z are as defined herein, and the pharmaceutically acceptable salts thereof, to pharmaceutical compositions comprising such compounds and salts, and to methods of using such compounds, salts and compositions for the treatment of abnormal cell growth, including cancer.

16 Claims, No Drawings

(56) References Cited

U.S. PATENT DOCUMENTS

| | | |
|---|---|---|
| 2015/0361067 A1 | 12/2015 | Collins et al. |
| 2016/0376254 A1 | 12/2016 | Collins et al. |

FOREIGN PATENT DOCUMENTS

| | | |
|---|---|---|
| WO | 2011140325 | 11/2011 |
| WO | 2012005805 | 1/2012 |
| WO | 2012034132 | 3/2012 |
| WO | 2012035078 | 3/2012 |
| WO | 2012068589 | 5/2012 |
| WO | 2012118812 | 9/2012 |
| WO | 2012142504 | 10/2012 |
| WO | 2012142513 | 10/2012 |
| WO | 2013049770 | 4/2013 |
| WO | 2013173441 | 11/2013 |
| WO | 2014049488 | 4/2014 |
| WO | 2014095773 A1 | 6/2014 |
| WO | 2014096145 A1 | 6/2014 |
| WO | 2014096148 A1 | 6/2014 |
| WO | 2014096149 A1 | 6/2014 |
| WO | 2014096150 A1 | 6/2014 |
| WO | 2014096378 A1 | 6/2014 |
| WO | 2014096698 A1 | 6/2014 |
| WO | 2014097041 | 6/2014 |
| WO | 2014100323 A1 | 6/2014 |
| WO | 2014100500 A1 | 6/2014 |
| WO | 2014100505 A1 | 6/2014 |
| WO | 2014100620 A2 | 6/2014 |
| WO | 2014100719 A2 | 6/2014 |
| WO | 2015193765 | 12/2015 |

OTHER PUBLICATIONS

Breuer et al., "Increased expression of the EZH2 polycomb group gene in BMI-1-positive neoplastic cells during bronchial carcinogenesis." Neoplasia (2004), 6:736-43.

Cardoso et al., "The human EZH2 gene: genomic organisation and revised mapping in 7q35 within the critical region for malignant myeloid disorders." Eur. J. Hum. Genet. (2000), 8:174-180.

Crea et al., "Polycomb genes and cancer: Time for clinical application?" Crit. Rev. Oncol. Hematol. (2012), 83:184-193.

Kleer et al., "EZH2 is a marker of aggressive breast cancer and promotes neoplastic transformation of breast epithelial cells." Proc. Natl. Acad. Sci. USA (2003), 100:11606-11.

Lu et al., "Gene alterations identified by expression profiling in tumor-associated endothelial cells from invasive ovarian carcinoma." Cancer Res. (2007), 67:1757-1768.

Majer et al., "A687V EZH2 is a gain-of-function mutation found in lymphoma patients." FEBS Letters (2012), 586:3448-3451.

Matsukawa et al., "Expression of the enhancer of zeste homolog 2 is correlated with poor prognosis in human gastric cancer." Cancer Sci. (2006), 97:484-491.

McCabe et al., Mutation of A677 in histonemethyltransferase EZH2 in human B-cell lymphonoma promotes hypertrimethylation of histone H3 on lysine 27 (H3K27). Proc. Natl. Acad. Sci. USA (2012), 109:2989-2994).

Mimori et al., "Clinical significance of enhancer of zeste homolog 2 expression in colorectal cancer cases." Eur. J. Surg. Oncol. (2005), 31:376-80.

Morin et al., "Somatic mutation of EZH2 (Y641) in Follicular and Diffuse Large B-cell Lymphomas of Germinal Center Origin." Nat. Genetics Feb. 2010; 42(2):181-185.

Ougolkov et al., "Regulation of pancreatic tumor cell proliferation and chemoresistance by the histone methyltransferase enhancer of zeste homologue 2." Clin. Cancer Res. (2008), 14:6790-6796.

Sasaki et al., "The overexpression of polycomb group proteins Bmi1 and EZH2 is associated with the progression and aggressive biological behaviour of hepatocellular carcinoma." Lab. Invest. (2008), 88:873-882.

Sudo et al., "Clinicopathological significance of EZH2 mRNA expression in patients with hepatocellular carcinoma." Br. J. Cancer (2005), 92(9):1754-1758.

Varambally et al., "The polycomb group protein EZH2 is involved in progression of prostate cancer." Nature (2002), 419:624-629.

Wagener et al., "The enhancer of zeste homolog 2 gene contributes to cell proliferation and apoptosis resistance in renal cell carcinoma cells." Int. J. Cancer (2008), 123:1545-1550.

Weikert et al., "Expression levels of the EZH2 polycomb transcriptional repressor correlate with aggressiveness and invasive potential of bladder carcinomas." Int. J. Mol. Med. (2005), 16:349-353.

International Search Report dated Mar. 21, 2014 for International application No. PCT/IB2013/060682, filed Dec. 5, 2013.

Written Opinion of the International Searching Authority for International application No. PCT/IB2013/060682, filed Dec. 5, 2013.

International Search Report dated Jul. 14, 2015 for International application No. PCT/IB2015/054272, filed Jun. 5, 2015.

International Preliminary Report on Patentability dated Dec. 20, 2016 for International application No. PCT/IB2015/054272, filed Jun. 5, 2015.

Written Opinion dated Dec. 23, 2015, for International Application No. PCT/IB2015/054272 filed Jun. 5, 2015 and published as WO2015193765.

Communication, Extended European Search Report dated Apr. 11, 2018 for European Application No. 17206218.4.

Request for Certificate of Correction, for U.S. Pat. No. 9,040,515 (U.S. Appl. No. 14/132,567), filed with the USPTO on Sep. 27, 2018.

U.S. Appl. No. 15/262,230, filed Sep. 12, 2016.

U.S. Appl. No. 15/425,732, filed Feb. 6, 2017.

ARYL AND HETEROARYL FUSED LACTAMS

CROSS-REFERENCE TO RELATED APPLICATIONS

This application is a Continuation Application of U.S. patent application Ser. No. 14/642,274, filed Mar. 9, 2015; which is a Continuation Application of U.S. patent application Ser. No. 14/132,567, filed on Dec. 18, 2013 and issued on May 26, 2015 as U.S. Pat. No. 9,040,515; which claims the benefit of priority to U.S. Provisional Application No. 61/740,596, filed on Dec. 21, 2012, each of which is incorporated by reference herein in its entirety.

FIELD OF THE INVENTION

The present invention relates to compounds of formulae (I)-(IV) and their pharmaceutically acceptable salts, to pharmaceutical compositions comprising such compounds and salts, and to the uses thereof. The compounds, salts and compositions of the present invention are useful for treating or ameliorating abnormal cell proliferative disorders, such as cancer.

BACKGROUND

Epigenetic alterations play an important role in the regulation of cellular processes, including cell proliferation, cell differentiation and cell survival. The epigenetic silencing of tumor suppressor genes and activation of oncogenes may occur through alteration of CpG island methylation patterns, histone modification, and dysregulation of DNA binding protein. Polycomb genes are a set of epigenetic effectors. EZH2 (enhancer of zeste homolog 2) is the catalytic component of the Polycomb Repressor Complex 2 (PRC2), a conserved multi-subunit complex that represses gene transcription by methylating lysine 27 on Histone H3 (H3K27). EZH2 plans a key role in regulating gene expression patterns that regulate cell fate decisions, such as differentiation and self-renewal. EZH2 is overexpressed in certain cancer cells, where it has been linked to cell proliferation, cell invasion, chemoresistance and metastasis.

High EZH2 expression has been correlated with poor prognosis, high grade, and high stage in several cancer types, including breast, colorectal, endometrial, gastric, liver, kidney, lung, melanoma, ovarian, pancreatic, prostate, and bladder cancers. See Crea et al., *Crit. Rev. Oncol. Hematol.* 2012, 83:184-193, and references cited therein; see also Kleer et al., *Proc. Natl. Acad. Sci. USA* 2003, 100:11606-11; Mimori et al., *Eur. J. Surg. Oncol.* 2005, 31:376-80; Bachmann et al., *J. Clin. Oncol.* 2006, 24:268-273; Matsukawa et al., *Cancer Sci.* 2006, 97:484-491; Sasaki et al. *Lab. Invest.* 2008, 88:873-882; Sudo et al., *Br. J. Cancer* 2005, 92(9):1754-1758; Breuer et al., *Neoplasia* 2004, 6:736-43; Lu et al., *Cancer Res.* 2007, 67:1757-1768; Ougolkov et al., *Clin. Cancer Res.* 2008, 14:6790-6796; Varambally et al., *Nature* 2002, 419:624-629; Wagener et al., *Int. J. Cancer* 2008, 123:1545-1550; and Weikert et al., *Int. J. Mol. Med.* 2005, 16:349-353.

Recurring somatic mutations in EZH2 have been identified in diffuse large B-cell lymphoma (DLBCL) and follicular lymphomas (FL). Mutations altering EZH2 tyrosine 641 (e.g., Y641C, Y641F, Y641N, Y641S, and Y641H) were reportedly observed in up to 22% of germinal center B-cell DLBCL and 7% of FL. Morin et al. *Nat. Genetics* 2010 February; 42(2):181-185. Mutations of alanine 677 (A677) and alanine 687 (A687) have also been reported. McCabe et al., *Proc. Natl. Acad. Sci. USA* 2012, 109:2989-2994; Majer et al. *FEBS Letters* 2012, 586:3448-3451. EZH2 activating mutations have been suggested to alter substrate specificity resulting in elevated levels of trimethylated H3K27 (H3K27me3).

Accordingly, compounds that inhibit the activity of wild type and/or mutant forms of EZH2 are of interest for the treatment of cancer.

SUMMARY

The present invention provides, in part, novel compounds and pharmaceutically acceptable salts that can modulate the activity of EZH2, thereby effecting biological functions, including but not limited to inhibiting cell proliferation and cell invasiveness, inhibiting metastasis, inducing apoptosis or inhibiting angiogenesis. Also provided are pharmaceutical compositions and medicaments, comprising the compounds or salts of the invention, alone or in combination with other therapeutic agents or palliative agents. The present invention also provides, in part, methods for preparing the novel compounds, salts and compositions thereof, and methods of using the foregoing.

In one aspect, the invention provides a compound of formula (I):

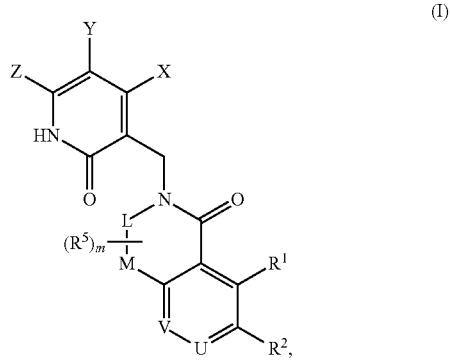

or a pharmaceutically acceptable salt thereof,
wherein:
U is N or $CR^3$;
V is N or $CR^4$;
L is a $C_1$-$C_4$ alkylene linker;
M is a bond or —O—;
$R^1$ is $C_1$-$C_8$ alkyl, $C_1$-$C_8$ alkoxy, halo, —OH, —CN or —$NR^7R^8$, where each said $C_1$-$C_8$ alkyl or $C_1$-$C_8$ alkoxy is optionally substituted by one or more $R^{21}$;
$R^2$ is selected from the group consisting of H, $C_1$-$C_8$ alkyl, $C_1$-$C_8$ alkoxy, —$OR^6$, —$NR^7R^8$, —$C(O)NR^7R^8$, —$SO_2NR^7R^8$, —$NR^7SO_2R_8$, $C_3$-$C_8$ cycloalkyl, 3-12 membered heterocyclyl, $C_6$-$C_{12}$ aryl and 5-12 membered heteroaryl, where each said $C_1$-$C_8$ alkyl or $C_1$-$C_8$ alkoxy is optionally substituted by one or more $R^{22}$, and each said $C_3$-$C_8$ cycloalkyl, 3-12 membered heterocyclyl, $C_6$-$C_{12}$ aryl or 5-12 membered heteroaryl is optionally substituted by one or more $R^{32}$;
$R^3$ is H, $C_1$-$C_8$ alkyl, $C_1$-$C_8$ alkoxy, halo, —OH, —CN or —$NR^7R^8$, where each said $C_1$-$C_8$ alkyl or $C_1$-$C_8$ alkoxy is optionally substituted by one or more $R^{23}$;
$R^4$ is selected from the group consisting of H, halo, $C_1$-$C_8$ alkyl, $C_3$-$C_8$ cycloalkyl, 3-12 membered heterocyclyl, $C_6$-$C_{12}$ aryl, 5-12 membered heteroaryl, —($C_1$-$C_4$ alkyl)$R^z$, —OR$^x$, —CN, —C(O)R$^x$, —CO$_2$R$^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^y$, —NR$^x$SO$_2$R$^y$, —NR$^x$SO$_2$NR$^x$R$^y$, —OC(O)R$^x$ and —OC(O)NR$^x$R$^y$;

each R$^x$ and R$^y$ is independently selected from the group consisting of H, C$_1$-C$_8$ alkyl, C$_3$-C$_8$ cycloalkyl, 3-12 membered heterocyclyl, C$_6$-C$_{12}$ aryl and 5-12 membered heteroaryl; or R$^x$ and R$^y$ may be taken together with the N atom to which they are attached to form a 3-12 membered heterocyclyl or 5-12 membered heteroaryl ring, each optionally containing 1, 2 or 3 additional heteroatoms selected from O, N and S;

each R$^z$ is independently selected from the group consisting of C$_3$-C$_8$ cycloalkyl, 3-12 membered heterocyclyl, C$_6$-C$_{12}$ aryl and 5-12 membered heteroaryl; and wherein each said C$_1$-C$_8$ alkyl in R$^4$, R$^x$ or R$^y$ and each said C$_1$-C$_4$ alkyl in (C$_1$-C$_4$ alkyl)R$^z$ is optionally substituted by one or more R$^{24}$, and each said C$_3$-C$_8$ cycloalkyl, 3-12 membered heterocyclyl, C$_6$-C$_{12}$ aryl, or 5-12 membered heteroaryl in R$^4$, R$^x$, R$^y$, R$^z$, or R$^x$ and R$^y$ taken together is optionally substituted by one or more R$^{34}$;

each R$^5$ is independently selected from the group consisting of halo, —OH, =O, C$_1$-C$_4$ alkyl, C$_1$-C$_4$ alkoxy, —CN, —NR$^9$R$^{10}$ and —C(O)NR$^9$R$^{10}$, where each said C$_1$-C$_4$ alkyl or C$_1$-C$_4$ alkoxy is optionally substituted with 1 to 3 substituents independently selected from the group consisting of halo, —OH, C$_1$-C$_4$ alkoxy, —CN, —NR$^9$R$^{10}$ and —C(O)NR$^9$R$^{10}$;

R$^6$ is —(CR$^{11}$R$^{12}$)$_n$—R$^{13}$;

each R$^7$ and R$^8$ is independently selected from the group consisting of H, C$_1$-C$_8$ alkyl, C$_3$-C$_8$ cycloalkyl, 3-12 membered heterocyclyl, C$_6$-C$_{12}$ aryl, and 5-12 membered heteroaryl; or R$^7$ and R$^8$ may be taken together with the N atom to which they are attached to form a 3-12 membered heterocyclyl or 5-12 membered heteroaryl, each optionally containing 1, 2 or 3 additional heteroatoms selected from O, N and S;

where each said C$_1$-C$_8$ alkyl in R$^7$ or R$^8$ is optionally substituted by one or more R$^{27}$, and each said C$_3$-C$_8$ cycloalkyl, 3-12 membered heterocyclyl, C$_6$-C$_{12}$ aryl, or 5-12 membered heteroaryl in R$^7$, R$^8$, or R$^7$ and R$^8$ taken together is optionally substituted by one or more R$^{37}$;

each R$^9$ and R$^{10}$ is independently H or C$_1$-C$_4$ alkyl; or

R$^9$ and R$^{10}$ may be taken together with the N atom to which they are attached to form a 3-12 membered heterocyclyl or 5-12 membered heteroaryl, each optionally containing 1, 2 or 3 additional heteroatoms selected from O, N and S;

where each said C$_1$-C$_4$ alkyl in R$^9$ or R$^{10}$, and each said 3-12 membered heterocyclyl or 5-12 membered heteroaryl in R$^9$ and R$^{10}$ taken together is optionally substituted by 1 to 3 substituents independently selected from the group consisting of halo, —OH, =O, C$_1$-C$_4$ alkyl, C$_1$-C$_4$ alkoxy, —CN, —NH$_2$, —NH(C$_1$-C$_4$ alkyl) and —N(C$_1$-C$_4$ alkyl)$_2$;

each R$^{11}$ and R$^{12}$ is independently H, halo or C$_1$-C$_4$ alkyl, where each said C$_1$-C$_4$ alkyl is optionally substituted by one or more R$^{22}$;

R$^{13}$ is selected from the group consisting of C$_3$-C$_8$ cycloalkyl, 3-12 membered heterocyclyl, C$_6$-C$_{12}$ aryl, and 5-12 membered heteroaryl, where each said C$_3$-C$_8$ cycloalkyl, 3-12 membered heterocyclyl, C$_6$-C$_{12}$ aryl or 5-12 membered heteroaryl is optionally substituted by one or more R$^{32}$;

m is 0 to 4;

n is 0 to 4;

each R$^{21}$, R$^{22}$, R$^{23}$ and R$^{24}$ is independently selected from the group consisting of halo, C$_1$-C$_8$ alkyl, —CN, =O, —C(O)R$^e$, —CO$_2$R$^e$, —C(O)NR$^e$R$^f$, —OR$^e$, —SR$^e$, —SOR$^e$, —SO$_2$R$^e$, —SO$_2$NR$^e$R$^f$, —NO$_2$, —NR$^e$R$^f$, —NR$^e$C(O)R$^f$, —NR$^e$C(O)NR$^e$R$^f$, —NR$^e$C(O)OR$^f$—NR$^e$SO$_2$R$^f$, —NR$^e$SO$_2$NR$^e$R$^f$, —OC(O)R$^e$, —OC(O)NR$^e$R$^f$, C$_3$-C$_8$ cycloalkyl, 3-12 membered heterocyclyl, C$_6$-C$_{12}$ aryl and 5-12 membered heteroaryl;

each R$^e$ and R$^f$ is independently selected from the group consisting of H, C$_1$-C$_8$ alkyl, C$_3$-C$_8$ cycloalkyl, 3-12 membered heterocyclyl, C$_6$-C$_{12}$ aryl and 5-12 membered heteroaryl; or R$^e$ and R$^f$ may be taken together with the N atom to which they are attached to form a 3-12 membered heterocyclyl or 5-12 membered heteroaryl ring, each optionally containing 1, 2 or 3 additional heteroatoms selected from O, N and S;

wherein each said C$_1$-C$_8$ alkyl, C$_3$-C$_8$ cycloalkyl, 3-12 membered heterocyclyl, C$_6$-C$_{12}$ aryl or 5-12 membered heteroaryl in R$^{21}$, R$^{22}$, R$^{23}$, R$^{24}$, R$^e$, R$^f$, or R$^e$ and R$^f$ taken together is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$;

each R$^{27}$ is independently selected from the group consisting of halo, —OH, C$_1$-C$_4$ alkoxy, —CN, —NR$^9$R$^{10}$, C$_3$-C$_8$ cycloalkyl, 3-12 membered heterocyclyl, C$_6$-C$_{12}$ aryl and 5-12 membered heteroaryl, where each said C$_1$-C$_4$ alkoxy, C$_3$-C$_8$ cycloalkyl, 3-12 membered heterocyclyl, C$_6$-C$_{12}$ aryl or 5-12 membered heteroaryl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$;

each R$^{32}$, R$^{34}$ and R$^{37}$ is independently selected from the group consisting of halo, C$_1$-C$_8$ alkyl, —CN, =O, —C(O)R$^c$, —CO$_2$R$^c$, —C(O)NR$^c$R$^d$, —OR$^c$, —SR$^c$, —SOR$^c$, —SO$_2$R$^c$, —SO$_2$NR$^c$R$^d$, —NO$_2$, —NR$^c$R$^d$, —NR$^c$C(O)R$^d$, —NR$^c$C(O)NR$^c$R$^d$, —NR$^c$C(O)OR$^d$, —NR$^c$SO$_2$R$^d$, —NR$^c$SO$_2$NR$^c$R$^d$, —OC(O)R$^c$, —OC(O)NR$^c$R$^d$, C$_3$-C$_8$ cycloalkyl, 3-12 membered heterocyclyl, C$_6$-C$_{12}$ aryl and 5-12 membered heteroaryl;

each R$^c$ and R$^d$ is independently selected from the group consisting of H, C$_1$-C$_8$ alkyl, C$_3$-C$_8$ cycloalkyl, 3-12 membered heterocyclyl, C$_6$-C$_{12}$ aryl and 5-12 membered heteroaryl; or R$^c$ and R$^d$ may be taken together with the N atom to which they are attached to form a 3-12 membered heterocyclyl or 5-12 membered heteroaryl ring, each optionally containing 1, 2 or 3 additional heteroatoms selected from O, N and S;

wherein each said C$_1$-C$_8$ alkyl, C$_3$-C$_8$ cycloalkyl, 3-12 membered heterocyclyl, C$_6$-C$_{12}$ aryl or 5-12 membered heteroaryl in R$^{32}$, R$^{34}$, R$^{37}$, R$^c$, R$^d$, or R$^c$ and R$^d$ taken together is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$;

X and Z are independently selected from the group consisting of H, C$_1$-C$_8$ alkyl, C$_2$-C$_8$ alkenyl, C$_2$-C$_8$ alkynyl, $C_3$-$C_8$ cycloalkyl, 3-12 membered heterocyclyl, $C_6$-$C_{12}$ aryl, 5-12 membered heteroaryl, halo, CN, —C(O)$R^a$, —CO$_2R^a$, —C(O)N$R^aR^b$, —S$R^a$, —SO$R^a$, —SO$_2R^a$, —SO$_2$N$R^aR^b$, —NO$_2$, —N$R^aR^b$, —N$R^a$C(O)$R^b$, —N$R^a$C(O)N$R^aR^b$, —N$R^a$C(O)O$R^a$, —N$R^a$SO$_2R^b$, —N$R^a$SO$_2$N$R^aR^b$, —O$R^a$, —OC(O)$R^a$ or —OC(O)N$R^aR^b$;

wherein each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl group is optionally substituted by one or more substituents independently selected from the group consisting of halo, —CN, —C(O)$R^a$, —CO$_2R^a$, —C(O)N$R^aR^b$, —S$R^a$, —SO$R^a$, —SO$_2R^a$, —SO$_2$N$R^aR^b$, —NO$_2$, —N$R^aR^b$, —N$R^a$C(O)$R^b$, —N$R^a$C(O)N$R^aR^b$, —N$R^a$C(O)O$R^a$, —N$R^a$SO$_2R^b$, —N$R^a$SO$_2$N$R^aR^b$, —O$R^a$, —OC(O)$R^a$, —OC(O)N$R^aR^b$, $C_3$-$C_8$ cycloalkyl, 3-12 membered heterocyclyl, $C_6$-$C_{12}$ aryl, and 5-12 membered heteroaryl;

each $R^a$ and $R^b$ is independently H, $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl or 5-12 membered heteroaryl, where each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl is optionally substituted by one or more substituents independently selected from the group consisting of halo, $C_1$-$C_4$ alkyl, —O$R^{14}$, —N$R^{14}_2$, —CO$_2R^{14}$, —C(O)N$R^{14}_2$, —SO$_2R^{14}$ and —SO$_2$N$R^{14}_2$, where each $R^{14}$ is independently H or $C_1$-$C_4$ alkyl; or $R^a$ and $R^b$ may be taken together with the N atom to which they are attached to form a 3-12 membered heterocyclyl or 5-12 membered heteroaryl, each optionally containing 1, 2 or 3 additional heteroatoms selected from O, N and S, wherein said heterocyclyl or heteroaryl is optionally substituted by one or more substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$; and Y is H, halo, —OH or $C_1$-$C_4$ alkoxy.

In some aspects, the compound of formula (I) is a compound of formula (I-A), (I-B) or (I-C):

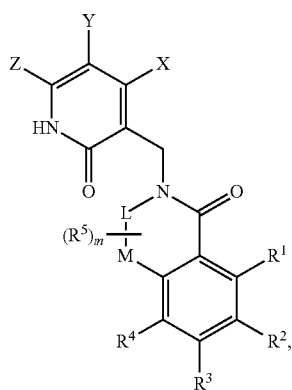
(I-A)

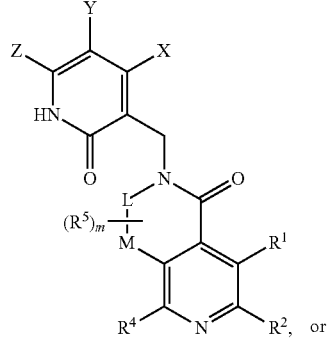
(I-B)

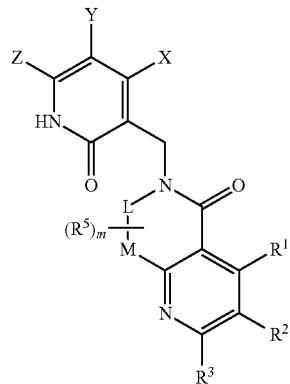
(I-C)

or a pharmaceutically acceptable salt thereof, wherein $R^1$, $R^2$, $R^3$, $R^4$, $R^5$, L, M, m, X, Y and Z are defined as in formula (I).

In another aspect, the invention provides a compound of formula (II):

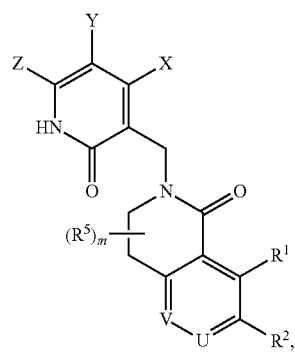
(II)

or a pharmaceutically acceptable salt thereof, wherein $R^1$, $R^2$, U, V, $R^5$, m, X, Y and Z are defined as in formula (I).

In some aspects, the compound of formula (II) is a compound of formula (II-A), (II-B) or (II-C):

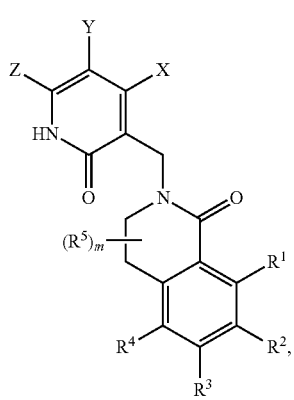

(II-A)

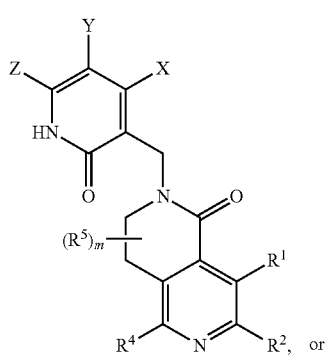

(II-B)

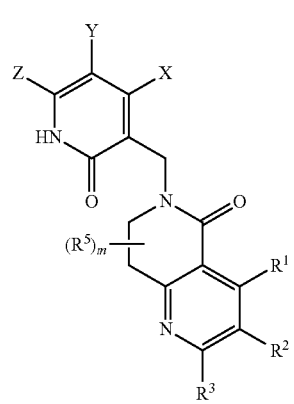

(II-C)

or a pharmaceutically acceptable salt thereof, wherein $R^1$, $R^2$, $R^3$, $R^4$, $R^5$, m, X, Y and Z are defined as in formula (I).

In another aspect, the invention provides a compound of formula (III):

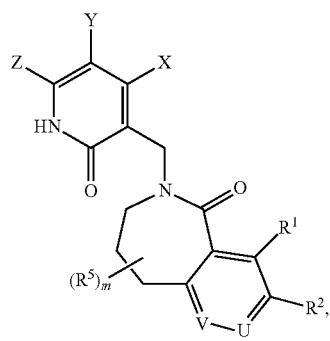

(III)

or a pharmaceutically acceptable salt thereof, wherein $R^1$, $R^2$, U, V, $R^5$, m, X, Y and Z are defined as in formula (I).

In some aspects, the compound of formula (III) is a compound of formula (III-A), (III-B) or (III-C):

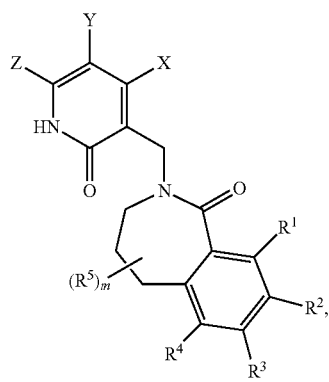

(III-A)

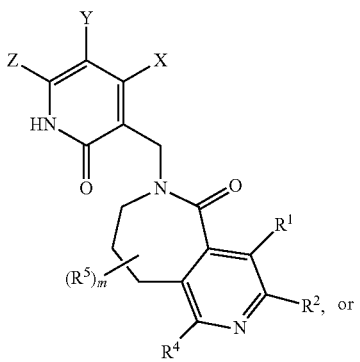

(III-B)

-continued (III-C)

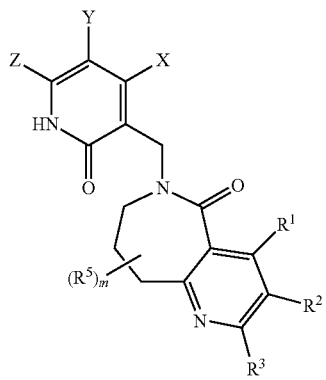

or a pharmaceutically acceptable salt thereof, wherein $R^1$, $R^2$, $R^3$, $R^4$, $R^5$, m, X, Y and Z are defined as in formula (I).

In a further aspect, the invention provides a compound of formula (IV):

(IV)

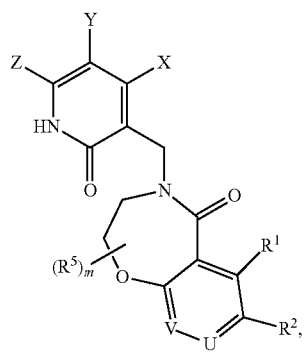

or a pharmaceutically acceptable salt thereof, wherein $R^1$, $R^2$, U, V, $R^5$, m, X, Y and Z are defined as in formula (I).

In some aspects, the compound of formula (IV) is a compound of formula (IV-A), (IV-B) or (IV-C):

(IV-A)

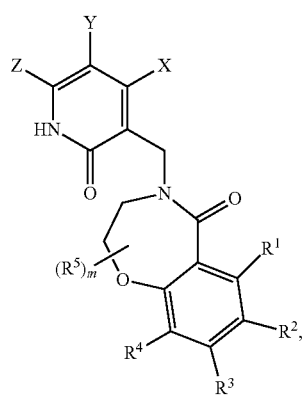

(IV-B)

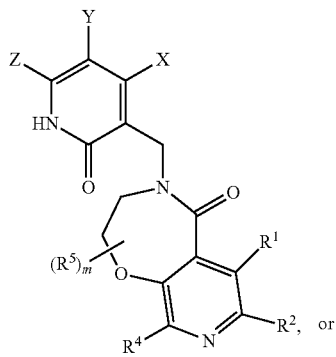

(IV-C)

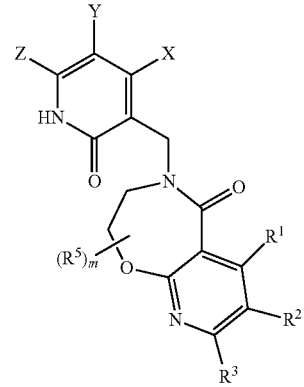

or a pharmaceutically acceptable salt thereof, wherein $R^1$, $R^2$, $R^3$, $R^4$, $R^5$, m, X, Y and Z are defined as in formula (I).

In another aspect, the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

The invention also provides therapeutic methods and uses comprising administering a compound of the invention, or a pharmaceutically acceptable salt thereof.

In one aspect, the invention provides a method for the treatment of abnormal cell growth in a subject comprising administering to the subject a therapeutically effective amount of a compound of the invention, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, in combination with an amount of an anti-tumor agent, which amounts are together effective in treating said abnormal cell growth. In some embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In frequent embodiments of the methods provided herein, the abnormal cell growth is cancer. In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by EZH2 in a subject comprising administering to the subject a compound of the invention, or a pharmaceutically acceptable salt thereof, in an amount that is effective for treating said disorder. The compounds and salts of the present invention inhibit wild-type and certain mutant forms of human histone methyltransferase EZH2.

In another aspect, the invention provides a compound of one of the formulae described herein, or pharmaceutically acceptable salt thereof, for use in the treatment of abnormal cell growth in a subject.

In a further aspect, the invention provides the use of a compound of one of the formulae described herein, or pharmaceutically acceptable salt thereof, for the treatment of abnormal cell growth in a subject.

In yet another aspect, the invention provides the use of a compound of one of the formulae described herein, or a pharmaceutically acceptable salt thereof, for the preparation of a medicament for the treatment of abnormal cell growth.

In frequent embodiments, the abnormal cell growth is cancer and the subject is a human.

In some embodiments, the methods described herein further comprise administering to the subject an amount of an anti-cancer therapeutic agent or a palliative agent, which amounts are together effective in treating said abnormal cell growth. In some such embodiments, one or more anti-cancer therapeutic agent are selected from anti-tumor agents, anti-angiogenesis agents, signal transduction inhibitors and anti-proliferative agents, which amounts are together effective in treating said abnormal cell growth.

In other embodiments, the uses described herein comprise the use of a compound of one of the formulae described herein or pharmaceutically acceptable salt thereof, in combination with one or more substances selected from anti-tumor agents, anti-angiogenesis agents, signal transduction inhibitors and antiproliferative agents.

In some embodiments, the medicaments described herein are adapted for use in combination with one or more substances selected from anti-tumor agents, anti-angiogenesis agents, signal transduction inhibitors and antiproliferative agents.

Each of the embodiments of the compounds of the present invention described below can be combined with one or more other embodiments of the compounds of the present invention described herein not inconsistent with the embodiment(s) with which it is combined. In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein.

DETAILED DESCRIPTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

"Alkyl" refers to a saturated, monovalent aliphatic hydrocarbon radical including straight chain and branched chain groups having the specified number of carbon atoms. Alkyl substituents typically contain 1 to 20 carbon atoms ("$C_1$-$C_{20}$ alkyl"), preferably 1 to 12 carbon atoms ("$C_1$-$C_{12}$ alkyl"), more preferably 1 to 8 carbon atoms ("$C_1$-$C_8$ alkyl"), or 1 to 6 carbon atoms ("$C_1$-$C_6$ alkyl"), or 1 to 4 carbon atoms ("$C_1$-$C_4$ alkyl"). Examples of alkyl groups include methyl, ethyl, n-propyl, isopropyl, n-butyl, iso-butyl, tert-butyl, n-pentyl, isopentyl, neopentyl, n-hexyl, n-heptyl, n-octyl and the like. Alkyl groups may be substituted or unsubstituted. In particular, unless otherwise specified, alkyl groups may be substituted by one or more halo groups, up to the total number of hydrogen atoms present on the alkyl moiety. Thus, $C_1$-$C_4$ alkyl includes halogenated alkyl groups, e.g., trifluoromethyl or difluoroethyl (i.e., $CF_3$ and —$CH_2CHF_2$).

Alkyl groups described herein as optionally substituted by may be substituted by one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, preferably from 1 to 4 optional substituents, or more preferably from 1 to 3 optional substituents.

Optional substituent groups suitable for alkyl include, but are not limited to $C_3$-$C_8$ cycloalkyl, 3-12 membered heterocyclyl, $C_6$-$C_{12}$ aryl and 5-12 membered heteroaryl, halo, =O (oxo), =S (thiono), =N—CN, =N—OR$^x$, =NR$^x$, —CN, —C(O)R$^x$, —CO$_2$R$^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^x$, —NR$^x$SO$_2$R$^y$, —NR$^x$SO$_2$NR$^x$R$^y$, —OR$^x$, —OC(O)R$^x$ and —OC(O)NR$^x$R$^y$; wherein each R$^x$ and R$^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or R$^x$ and R$^y$ may be taken together with the N atom to which they are attached to form a 3-12 membered heterocyclyl or 5-12 membered heteroaryl, each optionally containing 1, 2 or 3 additional heteroatoms selected from O, N and S; each R$^x$ and R$^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, —SR', —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$R', —NR'SO$_2$NR'$_2$, —OR', —OC(O)R' and —OC(O)NR'$_2$, wherein each R' is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or $C_5$-$C_{12}$ heteroaryl; and wherein each said $C_3$-$C_8$ cycloalkyl, 3-12 membered heterocyclyl, $C_6$-$C_{12}$ aryl and 5-12 membered heteroaryl is optionally substituted as further defined herein.

Typical substituent groups on alkyl include halo, —OH, $C_1$-$C_4$ alkoxy, —O—$C_6$-$C_{12}$ aryl, —CN, =O, —COOR$^x$, —OC(O)R$^x$, —C(O)NR$^x$R$^y$, —NR$^x$C(O)R$^y$, —NR$^x$R$^y$, $C_3$-$C_8$ cycloalkyl, $C_6$-$C_{12}$ aryl, 5-12 membered heteroaryl and 3-12 membered heterocyclyl; where each R$^x$ and R$^y$ is independently H or $C_1$-$C_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; wherein each said $C_3$-$C_8$ cycloalkyl, $C_6$-$C_{12}$ aryl, 5-12 membered heteroaryl and 3-12 membered heterocyclyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl), and —N($C_1$-$C_4$ alkyl)$_2$.

In some embodiments, alkyl is optionally substituted by one or more substituents, and preferably by 1 to 3 substituents, which are independently selected from the group consisting of halo, —OH, $C_1$-$C_4$ alkoxy, —O—$C_6$-$C_{12}$ aryl, —CN, =O, —COOR$^x$, —OC(O)R$^x$, —C(O)NR$^x$R$^y$, —NR$^x$C(O)R$^y$, —NR$^x$R$^y$, $C_3$-$C_8$ cycloalkyl, $C_6$-$C_{12}$ aryl, 5-12 membered heteroaryl and 3-12 membered heterocyclyl; where each R$^x$ and R$^y$ is independently H or $C_1$-$C_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; and each said $C_3$-$C_8$ cycloalkyl, $C_6$-$C_{12}$ aryl, 5-12 membered heteroaryl and 3-12 membered heterocyclyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl) and —N($C_1$-$C_4$ alkyl)$_2$.

In other embodiments, alkyl is optionally substituted by one or more substituent, and preferably by 1 to 3 substituents, independently selected from the group consisting of halo, —OH, $C_1$-$C_4$ alkoxy, —CN, —NR$^x$R$^y$, $C_3$-$C_8$ cycloalkyl, 3-12 membered heterocyclyl, $C_6$-$C_{12}$ aryl and 5-12 membered heteroaryl; where each R$^x$ and R$^y$ is independently H or $C_1$-$C_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; and where each said cycloalkyl, heterocyclyl, aryl or heteroaryl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl) and —N($C_1$-$C_4$ alkyl)$_2$.

In some instances, substituted alkyl groups may be specifically named with reference to the substituent group. For example, "haloalkyl" refers to an alkyl group having the specified number of carbon atoms that is substituted by one or more halo substituents, and typically contain 1-6 carbon atoms and 1, 2 or 3 halo atoms (i.e., "$C_1$-$C_6$ haloalkyl"). Thus, a $C_1$-$C_6$ haloalkyl group includes trifluoromethyl (—$CF_3$) and difluoromethyl (—$CF_2H$).

Similarly, "hydroxyalkyl" refers to an alkyl group having the specified number of carbon atoms that is substituted by one or more hydroxy substituents, and typically contain 1-6 carbon atoms and 1, 2 or 3 hydroxy (i.e., "$C_1$-$C_6$ hydroxyalkyl"). Thus, $C_1$-$C_6$ hydroxyalkyl includes hydroxymethyl (—$CH_2OH$) and 2-hydroxyethyl (—$CH_2CH_2OH$).

"Alkoxyalkyl" refers to an alkyl group having the specified number of carbon atoms that is substituted by one or more alkoxy substituents. Alkoxyalkyl groups typically contain 1-6 carbon atoms in the alkyl portion and are substituted by 1, 2 or 3 $C_1$-$C_4$ alkyoxy substituents. Such groups are sometimes described herein as $C_1$-$C_4$ alkyoxy-$C_1$-$C_6$ alkyl.

"Aminoalkyl" refers to alkyl group having the specified number of carbon atoms that is substituted by one or more substituted or unsubstituted amino groups, as such groups are further defined herein. Aminoalkyl groups typically contain 1-6 carbon atoms in the alkyl portion and are substituted by 1, 2 or 3 amino substituents. Thus, a $C_1$-$C_6$ aminoalkyl group includes, for example, aminomethyl (—$CH_2NH_2$), N,N-dimethylamino-ethyl (—$CH_2CH_2N$ ($CH_3$)$_2$), 3-(N-cyclopropylamino)propyl (—$CH_2CH_2CH_2NH$—Pr) and N-pyrrolidinylethyl (—$CH_2CH_2N$-pyrrolidinyl).

"Alkenyl" refers to an alkyl group, as defined herein, consisting of at least two carbon atoms and at least one carbon-carbon double bond. Typically, alkenyl groups have 2 to 20 carbon atoms ("$C_2$-$C_{20}$ alkenyl"), preferably 2 to 12 carbon atoms ("$C_2$-$C_2$ alkenyl"), more preferably 2 to 8 carbon atoms ("$C_2$-$C_8$ alkenyl"), or 2 to 6 carbon atoms ("$C_2$-$C_6$ alkenyl"), or 2 to 4 carbon atoms ("$C_2$-$C_4$ alkenyl"). Representative examples include, but are not limited to, ethenyl, 1-propenyl, 2-propenyl, 1-, 2-, or 3-butenyl, and the like. Alkenyl groups may be unsubstituted or substituted by the same groups that are described herein as suitable for alkyl.

"Alkynyl" refers to an alkyl group, as defined herein, consisting of at least two carbon atoms and at least one carbon-carbon triple bond. Alkynyl groups have 2 to 20 carbon atoms ("$C_2$-$C_{20}$ alkynyl"), preferably 2 to 12 carbon atoms ("$C_2$-$C_2$ alkynyl"), more preferably 2 to 8 carbon atoms ("$C_2$-$C_8$ alkynyl"), or 2 to 6 carbon atoms ("$C_2$-$C_6$ alkynyl"), or 2 to 4 carbon atoms ("$C_2$-$C_4$ alkynyl"). Representative examples include, but are not limited to, ethynyl, 1-propynyl, 2-propynyl, 1-, 2-, or 3-butynyl, and the like. Alkynyl groups may be unsubstituted or substituted by the same groups that are described herein as suitable for alkyl.

"Alkylene" as used herein refers to a divalent hydrocarbyl group having the specified number of carbon atoms which can link two other groups together. Sometimes it refers to —($CH_2$)$_n$— where n is 1-8, and preferably n is 1-4. Where specified, an alkylene can also be substituted by other groups and may include one or more degrees of unsaturation (i.e., an alkenylene or alkynlene moiety) or rings. The open valences of an alkylene need not be at opposite ends of the chain. Thus —CH(Me)- and —C(Me)$_2$- are also included within the scope of the term 'alkylenes', as are cyclic groups such as cyclopropan-1,1-diyl and unsaturated groups such as ethylene (—CH=CH—) or propylene (—$CH_2$—CH=CH—). Where an alkylene group is described as optionally substituted, the substituents include those typically present on alkyl groups as described herein.

"Heteroalkylene" refers to an alkylene group as described above, wherein one or more non-contiguous carbon atoms of the alkylene chain are replaced by —N(R)—, —O— or —S(O)$_q$—, where R is H or $C_1$-$C_4$ alkyl and q is 0-2. For example, the group —O—($CH_2$)$_{1-4}$— is a '$C_2$-$C_5$'-heteroalkylene group, where one of the carbon atoms of the corresponding alkylene is replaced by O.

"Alkoxy" refers to a monovalent —O-alkyl group, wherein the alkyl portion has the specified number of carbon atoms. Alkoxy groups typically contain 1 to 8 carbon atoms ("$C_1$-$C_8$ alkoxy"), or 1 to 6 carbon atoms ("$C_1$-$C_6$ alkoxy"), or 1 to 4 carbon atoms ("$C_1$-$C_4$ alkoxy"). For example, $C_1$-$C_4$ alkoxy includes —$OCH_3$, —$OCH_2CH_3$, —OCH($CH_3$)$_2$, —OC($CH_3$)$_3$, and the like. Such groups may also be referred to herein as methoxy, ethoxy, isopropoxy, tert-butyloxy, etc. Alkoxy groups may be unsubstituted or substituted on the alkyl portion by the same groups that are described herein as suitable for alkyl. In particular, alkoxy groups may be substituted by one or more halo groups, up to the total number of hydrogen atoms present on the alkyl portion. Thus, $C_1$-$C_4$ alkoxy includes halogenated alkoxy groups, e.g., trifluoromethoxy and 2,2-difluoroethoxy (i.e., —$OCF_3$ and —$OCH_2CHF_2$).

Similarly, "thioalkoxy" refers to a monovalent —S-alkyl group, wherein the alkyl portion has the specified number of carbon atoms, and may be optionally substituted on the alkyl portion by the same groups that are described herein as suitable for alkyl. For example, a $C_1$-$C_4$ thioalkoxy includes —$SCH_3$ and —$SCH_2CH_3$.

"Cycloalkyl" refers to a non-aromatic, saturated or partially unsaturated carbocyclic ring system containing the specified number of carbon atoms, which may be a monocyclic, bridged or fused bicyclic or polycyclic ring system that is connected to the base molecule through a carbon atom of the cycloalkyl ring. Typically, the cycloalkyl groups of the invention contain 3 to 12 carbon atoms ("$C_3$-$C_{12}$ cycloalkyl"), preferably 3 to 8 carbon atoms ("$C_3$-$C_8$ cycloalkyl").

Representative examples include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups may be unsubstituted or substituted by the same groups that are described herein as suitable for alkyl.

Illustrative examples of cycloalkyl rings include, but are not limited to, the following:

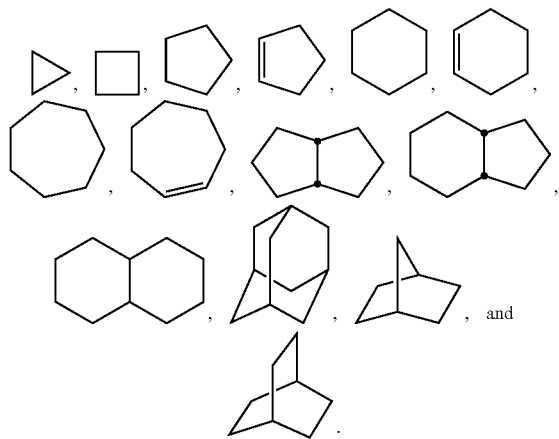

"Cycloalkylalkyl" may be used to describe a cycloalkyl ring, typically a $C_3$-$C_8$ cycloalkyl, which is connected to the base molecule through an alkylene linker, typically a $C_1$-$C_4$ alkylene. Cycloalkylalkyl groups are described by the total number of carbon atoms in the carbocyclic ring and linker, and typically contain from 4-12 carbon atoms ("$C_4$-$C_{12}$ cycloalkylalkyl"). Thus a cyclopropylmethyl group is a $C_4$-cycloalkylalkyl group and a cyclohexylethyl is a $C_8$-cycloalkylalkyl. Cycloalkylalkyl groups may be unsubstituted or substituted on the cycloalkyl and/or alkylene portions by the same groups that are described herein as suitable for alkyl groups.

The terms "heterocyclyl", "heterocyclic" or "heteroalicyclic" may be used interchangeably herein to refer to a non-aromatic, saturated or partially unsaturated ring system containing the specified number of ring atoms, including at least one heteroatom selected from N, O and S as a ring member, wherein the heterocyclic ring is connected to the base molecule via a ring atom, which may be C or N. Heterocyclic rings may be fused to one or more other heterocyclic or carbocyclic rings, which fused rings may be saturated, partially unsaturated or aromatic. Preferably, heterocyclic rings contain 1 to 4 heteroatoms selected from N, O, and S as ring members, and more preferably 1 to 2 ring heteroatoms, provided that such heterocyclic rings do not contain two contiguous oxygen atoms. Heterocyclyl groups may be unsubstituted or substituted by the same groups that are described herein as suitable for alkyl, aryl or heteroaryl. In addition, ring N atoms may be optionally substituted by groups suitable for an amine, e.g., alkyl, acyl, carbamoyl, sulfonyl substituents, etc., and ring S atoms may be optionally substituted by one or two oxo groups (i.e., $S(O)_q$, where q is 0, 1 or 2). Preferred heterocycles include 3-12 membered heterocyclyl groups in accordance with the definition herein.

Illustrative examples of saturated heterocyclic groups include, but are not limited to:

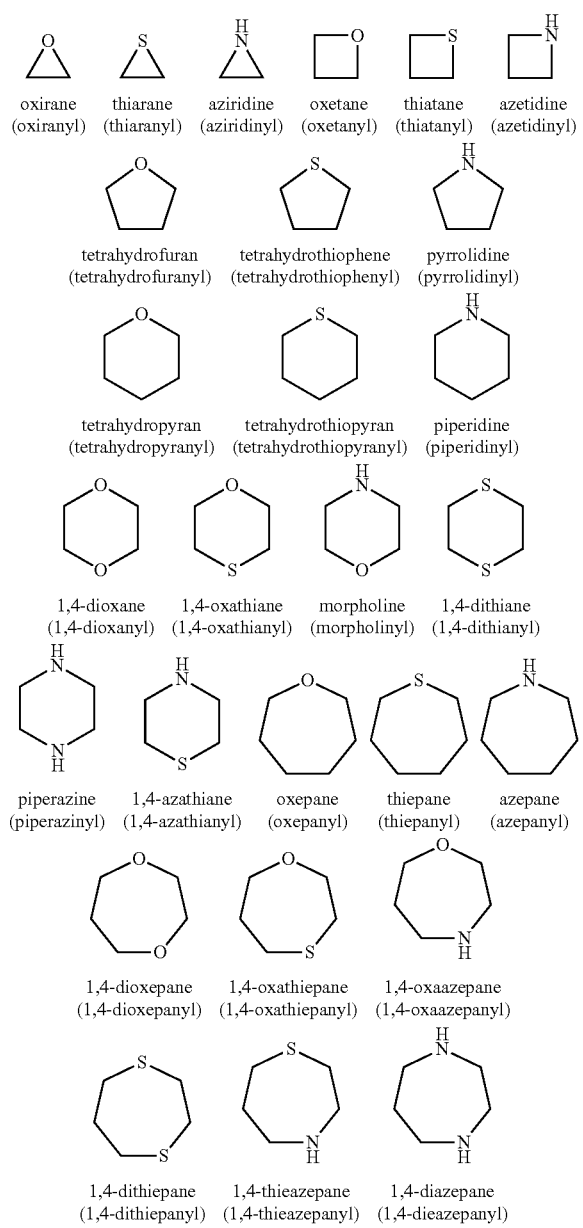

Illustrative examples of partially unsaturated heterocyclic groups include, but are not limited to:

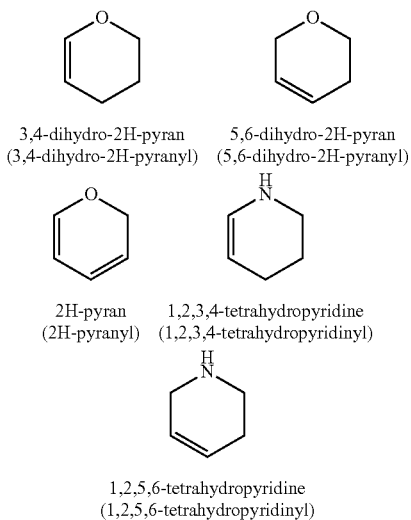

Illustrative examples of bridged and fused heterocyclic groups include, but are not limited to:

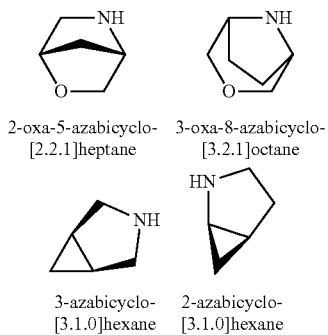

In frequent embodiments, heterocyclic groups contain 3-12 ring members, including both carbon and non-carbon heteroatoms, and preferably 4-6 ring members. In certain preferred embodiments, substituent groups comprising 3-12 membered heterocycles are selected from azetidinyl, pyrrolidinyl, piperidinyl, piperazinyl, morpholinyl and thiomorpholinyl rings, each of which may be optionally substituted per the particular substituent group, to the extent such substitution makes chemical sense.

It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

The term "heterocyclylalkyl" may be used to describe a heterocyclic group of the specified size that is connected to the base molecule through an alkylene linker of the specified length. Typically, such groups contain an optionally substituted 3-12 membered heterocycle attached to the base molecule through a $C_1$-$C_4$ alkylene linker. Where so indicated, such groups may be optionally substituted on the alkylene portion by the same groups that are described herein as suitable for alkyl groups and on the heterocyclic portion by groups described as suitable for heterocyclic rings.

"Aryl" or "aromatic" refer to an optionally substituted monocyclic or fused bicyclic or polycyclic ring system having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl ring, or fused to a saturated or partially unsaturated carbocyclic or heterocyclic ring. The point of attachment to the base molecule on such fused aryl ring systems may be a C atom the aromatic portion or a C or N atom of the non-aromatic portion of the ring system. Examples, without limitation, of aryl groups include phenyl, biphenyl, naphthyl, anthracenyl, phenanthrenyl, indanyl, indenyl, and tetrahydronaphthyl. The aryl group may be unsubstituted or substituted as further described herein.

Similarly, "heteroaryl" or "heteroaromatic" refer to monocyclic or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthryidine and carbazole. In frequent preferred embodiments, 5-6 membered heteroaryl groups are selected from the group consisting of pyrazolyl, imidazolyl, pyrrolyl, triazolyl, pyridinyl and pyrimidinyl rings. The heteroaryl group may be unsubstituted or substituted as further described herein.

Aryl, heteroaryl and heterocyclyl moieties described herein as optionally substituted by may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintain in the case of aryl and heteroaryl rings. Optionally substituted aryl, heteroaryl or heterocyclyl groups typically contain from 1 to 5 optional substituents, sometimes 1 to 4 optional substituents, preferably 1 to 3 optional substituents, or more preferably from 1-2 optional substituents.

Optional substituent groups suitable for aryl, heteroaryl and heterocyclyl rings include, but are not limited to: $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl; and halo, =O, —CN, —C(O)R$^x$, —CO$_2$R$^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^x$, —NR$^x$SO$_2$R$^y$, —NR$^x$SO$_2$NR$^x$R$^y$, —OR$^x$, —OC(O)R$^x$ and —OC(O)NR$^x$R$^y$; where each R$^x$ and R$^y$ is independently H, $C_1$-$C_8$ alkyl, $C_1$-$C_8$ acyl, $C_2$-$C_8$ alkenyl, C$_2$-C$_8$ alkynyl, C$_3$-C$_8$ cycloalkyl, 3-12 membered heterocyclyl, C$_6$-C$_{12}$ aryl, or 5-12 membered heteroaryl, or R$^x$ and R$^y$ may be taken together with the N atom to which they are attached to form a 3-12 membered heterocyclyl or 5-12 membered heteroaryl, each optionally containing 1, 2 or 3 additional heteroatoms selected from O, N and S; each R$^x$ and R$^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, —SR', —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$R', —NR'SO$_2$NR'$_2$, —OR', —OC(O)R' and —OC(O)NR'$_2$, wherein each R' is independently H, C$_1$-C$_8$ alkyl, C$_1$-C$_8$ acyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl, or 5-12 membered heteroaryl; and each said C$_1$-C$_8$ alkyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl and 5-12 membered heteroaryl is optionally substituted as further defined herein.

In typical embodiments, optional substitution on aryl, heteroaryl and heterocyclyl rings includes one or more substituents, and preferably 1 to 3 substituents, independently selected from the group consisting of halo, C$_1$-C$_8$ alkyl, —OH, C$_1$-C$_8$ alkoxy, —CN, =O, —C(O)R$^x$, —CO-OR$^x$, —OC(O)R$^x$, —C(O)NR$^x$R$^y$, —NR$^x$C(O)R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^y$—NR$^x$SO$_2$R$^y$, —NR$^x$SO$_2$NR$^x$R$^y$, —OC(O)R$^x$, —OC(O)NR$^x$R$^y$, C$_3$-C$_8$ cycloalkyl, 3-12 membered heterocyclyl, C$_6$-C$_{12}$ aryl, 5-12 membered heteroaryl, —O—(C$_3$-C$_8$ cycloalkyl), —O-(3-12 membered heterocyclyl), —O—(C$_6$-C$_{12}$ aryl) and —O— (5-12 membered heteroaryl); where each R$^x$ and R$^y$ is independently H or C$_1$-C$_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; and wherein each said C$_1$-C$_8$ alkyl, C$_1$-C$_8$ alkoxy, C$_3$-C$_8$ cycloalkyl, 3-12 membered heterocyclyl, C$_6$-C$_{12}$ aryl, 5-12 membered heteroaryl, —O—(C$_3$-C$_8$ cycloalkyl), —O-(3-12 membered heterocyclyl), —O—(C$_6$-C$_{12}$ aryl) and —O— (5-12 membered heteroaryl) that is described as an optional substituent or is part of R$^x$ or R$^y$ is optionally substituted by 1 to 3 substituents independently selected from the group consisting of halo, —OH, =O, C$_1$-C$_4$ alkyl, C$_1$—C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl), —N(C$_1$-C$_4$ alkyl)$_2$ and N-pyrrolidinyl.

Illustrative examples of monocyclic heteroaryl groups include, but are not limited to:

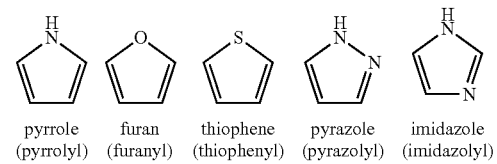

pyrrole (pyrrolyl)  furan (furanyl)  thiophene (thiophenyl)  pyrazole (pyrazolyl)  imidazole (imidazolyl)

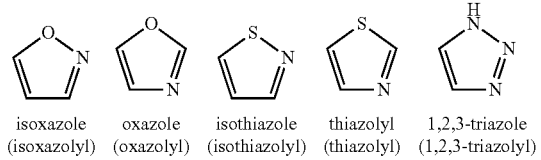

isoxazole (isoxazolyl)  oxazole (oxazolyl)  isothiazole (isothiazolyl)  thiazolyl (thiazolyl)  1,2,3-triazole (1,2,3-triazolyl)

-continued

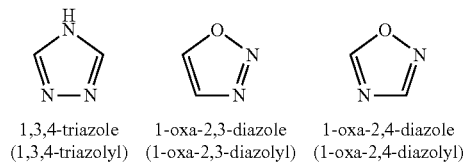

1,3,4-triazole (1,3,4-triazolyl)  1-oxa-2,3-diazole (1-oxa-2,3-diazolyl)  1-oxa-2,4-diazole (1-oxa-2,4-diazolyl)

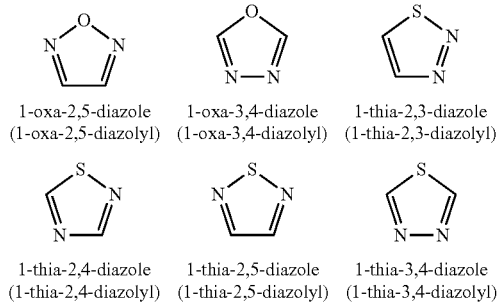

1-oxa-2,5-diazole (1-oxa-2,5-diazolyl)  1-oxa-3,4-diazole (1-oxa-3,4-diazolyl)  1-thia-2,3-diazole (1-thia-2,3-diazolyl)

1-thia-2,4-diazole (1-thia-2,4-diazolyl)  1-thia-2,5-diazole (1-thia-2,5-diazolyl)  1-thia-3,4-diazole (1-thia-3,4-diazolyl)

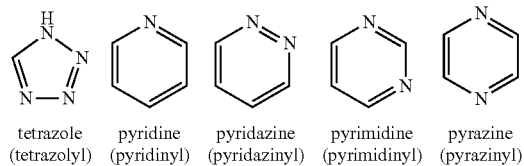

tetrazole (tetrazolyl)  pyridine (pyridinyl)  pyridazine (pyridazinyl)  pyrimidine (pyrimidinyl)  pyrazine (pyrazinyl)

Illustrative examples of fused ring heteroaryl groups include, but are not limited to:

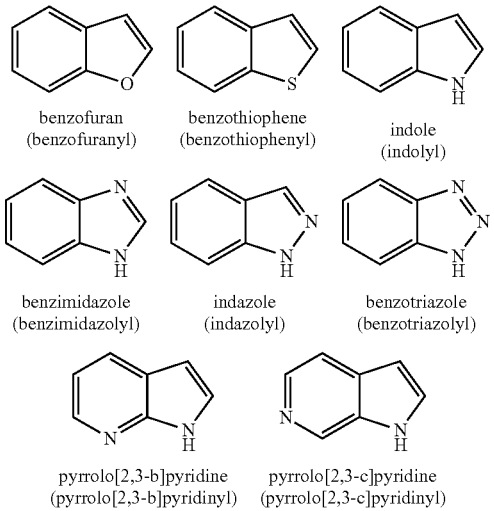

benzofuran (benzofuranyl)  benzothiophene (benzothiophenyl)  indole (indolyl)

benzimidazole (benzimidazolyl)  indazole (indazolyl)  benzotriazole (benzotriazolyl)

pyrrolo[2,3-b]pyridine (pyrrolo[2,3-b]pyridinyl)  pyrrolo[2,3-c]pyridine (pyrrolo[2,3-c]pyridinyl)

pyrrolo[3,2-c]pyridine (pyrrolo[3,2-c]pyridinyl)  pyrrolo[3,2-b]pyridine (pyrrolo[3,2-b]pyridinyl)

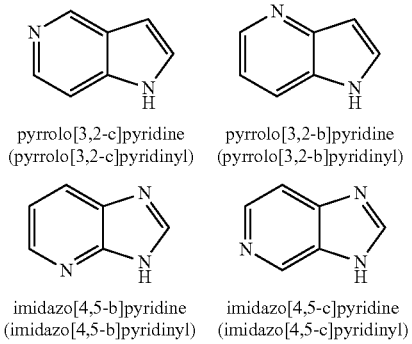

imidazo[4,5-b]pyridine (imidazo[4,5-b]pyridinyl)  imidazo[4,5-c]pyridine (imidazo[4,5-c]pyridinyl)

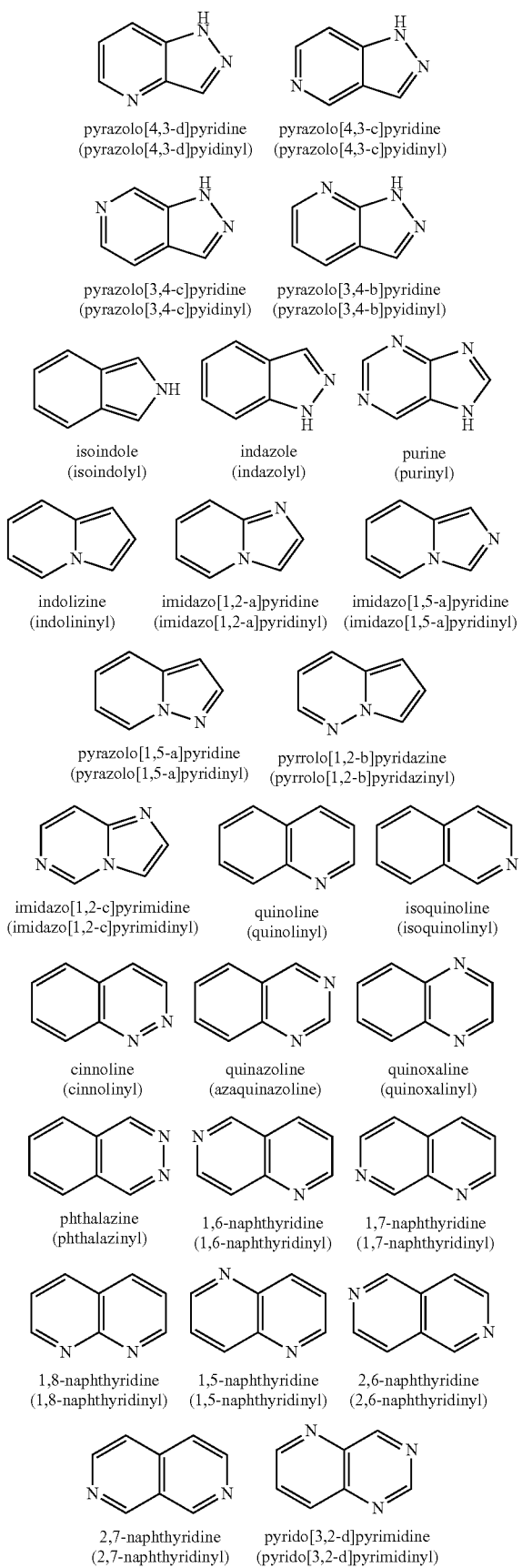

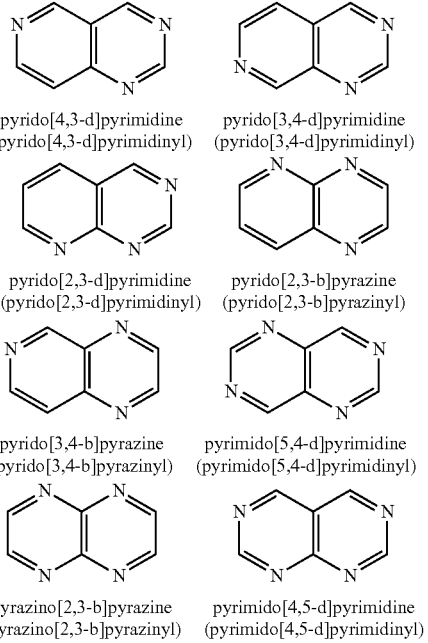

An "arylalkyl" group refers to an aryl group as described herein which is linked to the base molecule through an alkylene or similar linker. Arylalkyl groups are described by the total number of carbon atoms in the ring and linker. Thus a benzyl group is a $C_7$-arylalkyl group and a phenylethyl is a $C_8$-arylalkyl. Typically, arylalkyl groups contain 7-16 carbon atoms ("$C_7$-$C_{16}$ arylalkyl"), wherein the aryl portion contains 6-12 carbon atoms and the alkylene portion contains 1-4 carbon atoms. Such groups may also be represented as —$C_1$-$C_4$ alkylene-$C_6$-$C_{12}$ aryl.

"Heteroarylalkyl" refers to a heteroaryl group as described above that is attached to the base molecule through an alkylene linker, and differs from "arylalkyl" in that at least one ring atom of the aromatic moiety is a heteroatom selected from N, O and S. Heteroarylalkyl groups are sometimes described herein according to the total number of non-hydrogen atoms (i.e., C, N, S and O atoms) in the ring and linker combined, excluding substituent groups. Thus, for example, pyridinylmethyl may be referred to as a "$C_7$"-heteroarylalkyl. Typically, unsubstituted heteroarylalkyl groups contain 6-20 non-hydrogen atoms (including C, N, S and O atoms), wherein the heteroaryl portion typically contains 5-12 atoms and the alkylene portion typically contains 1-4 carbon atoms. Such groups may also be represented as —$C_1$-$C_4$ alkylene-5-12 membered heteroaryl.

Similarly, "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms) in the ring and linker combined. Thus, —O—$CH_2$-phenyl and —O—$CH_2$-pyridinyl groups would be referred to as $C_8$-arylalkoxy and $C_8$-heteroarylalkoxy groups, respectively.

Where an arylalkyl, arylalkoxy, heteroarylalkyl or heteroarylalkoxy group is described as optionally substituted, the substituents may be on either the divalent linker portion or on the aryl or heteroaryl portion of the group. The substituents optionally present on the alkylene or heteroalkylene portion are the same as those described above for alkyl or alkoxy groups generally, while the substituents optionally present on the aryl or heteroaryl portion are the same as those described above for aryl or heteroaryl groups generally.

"Hydroxy" refers to an —OH group.

"Acyloxy" refers to a monovalent group —OC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acyloxy includes an —OC(O)$C_1$-$C_4$ alkyl substituent, e.g., —OC(O)CH$_3$.

"Acylamino" refers to a monovalent group, —NHC(O) alkyl or —NRC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acylamino includes an —NHC(O)$C_1$-$C_4$ alkyl substituent, e.g., —NHC(O)CH$_3$.

"Aryloxy" or "heteroaryloxy" refer to optionally substituted —O-aryl or —O-heteroaryl, in each case where aryl and heteroaryl are as further defined herein.

"Arylamino" or "heteroarylamino" refer to optionally substituted —NH-aryl, —NR-aryl, —NH— heteroaryl or —NR-heteroaryl, in each case where aryl and heteroaryl are as further defined herein and R represents a substituent suitable for an amine, e.g., an alkyl, acyl, carbamoyl or sulfonyl group, or the like.

"Cyano" refers to a —C≡N group.

"Unsubstituted amino" refers to a group —NH$_2$. Where the amino is described as substituted or optionally substituted, the term includes groups of the form —NR$^x$R$^y$, where each or R$^x$ and R$^y$ is independently H, alkyl, alkenyl, alkynyl, cycloalkyl, heterocyclyl, acyl, thioacyl, aryl, heteroaryl, cycloalkylalkyl, arylalkyl or heteroarylalkyl, in each case having the specified number of atoms and optionally substituted as described herein. For example, "alkylamino" refers to a group —NR$^x$R$^y$, wherein one of R$^x$ and R$^y$ is an alkyl moiety and the other is H, and "dialkylamino" refers to —NR$^x$R$^y$ wherein both of R$^x$ and R$^y$ are alkyl moieties, where the alkyl moieties having the specified number of carbon atoms (e.g., —NH—$C_1$-$C_4$ alkyl or —N($C_1$-$C_4$ alkyl)$_2$). Typically, alkyl substituents on amines contain 1 to 8 carbon atoms, preferably 1 to 6 carbon atoms, or more preferably 1 to 4 carbon atoms. The term also includes forms wherein R$^x$ and R$^y$ are taken together with the N atom to which they are attached to form a 3-12 membered heterocyclyl or 5-12 membered heteroaryl ring, each of which may itself be optionally substituted as described herein for heterocyclyl or heteroaryl rings, and which may contain 1 to 3 additional heteroatoms selected from N, O and S as ring members, provided that such rings do not contain two contiguous oxygen atoms.

"Halogen" or "halo" refers to fluoro, chloro, bromo and iodo (F, Cl, Br, I). Preferably, halo refers to fluoro or chloro (F or Cl).

"Heteroform" is sometimes used herein to refer to a derivative of a group such as, e.g., an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optional" or "optionally" means that the subsequently described event or circumstance may but need not occur, and the description includes instances where the event or circumstance occurs and instances in which it does not.

The terms "optionally substituted" and "substituted or unsubstituted" may be used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described, to the extent that such substitution makes chemical sense. Where an optional substituent is attached via a double bond, such as an oxo (=O) substituent, the group occupies two available valences, so the total number of other substituents that may be included is reduced by two. In the case where optional substituents are selected independently from a list of alternatives, the selected groups may be the same or different.

In one aspect, the invention provides a compound of formula (I):

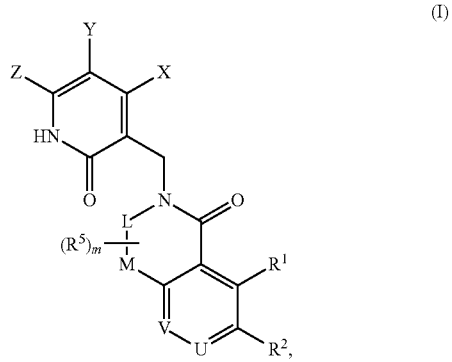

or a pharmaceutically acceptable salt thereof,
wherein:
U is N or CR$^3$;
V is N or CR$^4$;
L is a $C_1$-$C_4$ alkylene linker;
M is a bond or —O—;
R$^1$ is $C_1$-$C_8$ alkyl, $C_1$-$C_8$ alkoxy, halo, —OH, —CN or —NR$^7$R$^8$, where each said $C_1$-$C_8$ alkyl or $C_1$-$C_8$ alkoxy is optionally substituted by one or more R$^{21}$;
R$^2$ is selected from the group consisting of H, $C_1$-$C_8$ alkyl, $C_1$-$C_8$ alkoxy, —OR$^6$, —NR$^7$R$^8$, —C(O)NR$^7$R$^8$, —SO$_2$NR$^7$R$^8$, —NR$^7$SO$_2$R$_8$, $C_3$-$C_8$ cycloalkyl, 3-12 membered heterocyclyl, $C_6$-$C_{12}$ aryl and 5-12 membered heteroaryl, where each said $C_1$-$C_8$ alkyl or $C_1$-$C_8$ alkoxy is optionally substituted by one or more R$^{22}$, and each said $C_3$-$C_8$ cycloalkyl, 3-12 membered heterocyclyl, $C_6$-$C_{12}$ aryl or 5-12 membered heteroaryl is optionally substituted by one or more R$^{32}$;
R$^3$ is H, $C_1$-$C_8$ alkyl, $C_1$-$C_8$ alkoxy, halo, —OH, —CN or —NR$^7$R$^8$, where each said $C_1$-$C_8$ alkyl or $C_1$-$C_8$ alkoxy is optionally substituted by one or more R$^{23}$;
R$^4$ is selected from the group consisting of H, halo, $C_1$-$C_8$ alkyl, $C_3$-$C_8$ cycloalkyl, 3-12 membered heterocyclyl, $C_6$-$C_{12}$ aryl, 5-12 membered heteroaryl, —($C_1$-$C_4$ alkyl)R$^z$, —OR$^x$, —CN, —C(O)R$^x$, —CO$_2$R$^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^y$, —NR$^x$SO$_2$R$^y$, —NR$^x$SO$_2$NR$^x$R$^y$, —OC(O)R$^x$ and —OC(O)NR$^x$R$^y$;

- each R$^x$ and R$^y$ is independently selected from the group consisting of H, C$_1$-C$_8$ alkyl, C$_3$-C$_8$ cycloalkyl, 3-12 membered heterocyclyl, C$_6$-C$_{12}$ aryl and 5-12 membered heteroaryl; or R$^x$ and R$^y$ may be taken together with the N atom to which they are attached to form a 3-12 membered heterocyclyl or 5-12 membered heteroaryl ring, each optionally containing 1, 2 or 3 additional heteroatoms selected from O, N and S;
- each R$^z$ is independently selected from the group consisting of C$_3$-C$_8$ cycloalkyl, 3-12 membered heterocyclyl, C$_6$-C$_{12}$ aryl and 5-12 membered heteroaryl; and
- wherein each said C$_1$-C$_8$ alkyl in R$^4$, R$^x$ or R$^y$ and each said C$_1$-C$_4$ alkyl in (C$_1$-C$_4$ alkyl)R$^z$ is optionally substituted by one or more R$^{24}$, and each said C$_3$-C$_8$ cycloalkyl, 3-12 membered heterocyclyl, C$_6$-C$_{12}$ aryl, or 5-12 membered heteroaryl in R$^4$, R$^x$, R$^y$, R$^z$, or R$^x$ and R$^y$ taken together is optionally substituted by one or more R$^{34}$;
- each R$^5$ is independently selected from the group consisting of halo, —OH, =O, C$_1$-C$_4$ alkyl, C$_1$-C$_4$ alkoxy, —CN, —NR$^9$R$^{10}$ and —C(O)NR$^9$R$^{10}$, where each said C$_1$-C$_4$ alkyl or C$_1$-C$_4$ alkoxy is optionally substituted with 1 to 3 substituents independently selected from the group consisting of halo, —OH, C$_1$-C$_4$ alkoxy, —CN, —NR$^9$R$^{10}$ and —C(O)NR$^9$R$^{10}$;
- R$^6$ is —(CR$^{11}$R$^{12}$)$_n$—R$^{13}$;
- each R$^7$ and R$^8$ is independently selected from the group consisting of H, C$_1$-C$_8$ alkyl, C$_3$-C$_8$ cycloalkyl, 3-12 membered heterocyclyl, C$_6$-C$_{12}$ aryl, and 5-12 membered heteroaryl; or
- R$^7$ and R$^8$ may be taken together with the N atom to which they are attached to form a 3-12 membered heterocyclyl or 5-12 membered heteroaryl, each optionally containing 1, 2 or 3 additional heteroatoms selected from O, N and S;
  - where each said C$_1$-C$_8$ alkyl in R$^7$ or R$^8$ is optionally substituted by one or more R$^{27}$, and each said C$_3$-C$_8$ cycloalkyl, 3-12 membered heterocyclyl, C$_6$-C$_{12}$ aryl, or 5-12 membered heteroaryl in R$^7$, R$^8$, or R$^7$ and R$^8$ taken together is optionally substituted by one or more R$^{37}$;
- each R$^9$ and R$^{10}$ is independently H or C$_1$-C$_4$ alkyl; or R$^9$ and R$^{10}$ may be taken together with the N atom to which they are attached to form a 3-12 membered heterocyclyl or 5-12 membered heteroaryl, each optionally containing 1, 2 or 3 additional heteroatoms selected from O, N and S;
  - where each said C$_1$-C$_4$ alkyl in R$^9$ or R$^{10}$, and each said 3-12 membered heterocyclyl or 5-12 membered heteroaryl in R$^9$ and R$^{10}$ taken together is optionally substituted by 1 to 3 substituents independently selected from the group consisting of halo, —OH, =O, C$_1$-C$_4$ alkyl, C$_1$-C$_4$ alkoxy, —CN, —NH$_2$, —NH(C$_1$-C$_4$ alkyl) and —N(C$_1$-C$_4$ alkyl)$_2$;
- each R$^{11}$ and R$^{12}$ is independently H, halo or C$_1$-C$_4$ alkyl, where each said C$_1$-C$_4$ alkyl is optionally substituted by one or more R$^{22}$;
- R$^{13}$ is selected from the group consisting of C$_3$-C$_8$ cycloalkyl, 3-12 membered heterocyclyl, C$_6$-C$_{12}$ aryl, and 5-12 membered heteroaryl, where each said C$_3$-C$_8$ cycloalkyl, 3-12 membered heterocyclyl, C$_6$-C$_{12}$ aryl or 5-12 membered heteroaryl is optionally substituted by one or more R$^{32}$;
- m is 0 to 4;
- n is 0 to 4;
- each R$^{21}$, R$^{22}$, R$^{23}$ and R$^{24}$ is independently selected from the group consisting of halo, C$_1$-C$_8$ alkyl, —CN, =O, —C(O)R$^e$, —CO$_2$R$^e$, —C(O)NR$^e$R$^f$, —OR$^e$, —SR$^e$, —SOR$^e$, —SO$_2$R$^e$, —SO$_2$NR$^e$R$^f$, —NO$_2$, —NR$^e$R$^f$, —NR$^e$C(O)R$^f$, —NR$^e$C(O)NR$^e$R$^f$, —NR$^e$C(O)OR$^f$, —NR$^e$SO$_2$R$^f$, —NR$^e$SO$_2$NR$^e$R$^f$, —OC(O)R$^e$, —OC(O)NR$^e$R$^f$, C$_3$-C$_8$ cycloalkyl, 3-12 membered heterocyclyl, C$_6$-C$_{12}$ aryl and 5-12 membered heteroaryl;
  - each R$^e$ and R$^f$ is independently selected from the group consisting of H, C$_1$-C$_8$ alkyl, C$_3$-C$_8$ cycloalkyl, 3-12 membered heterocyclyl, C$_6$-C$_{12}$ aryl and 5-12 membered heteroaryl; or
  - R$^e$ and R$^f$ may be taken together with the N atom to which they are attached to form a 3-12 membered heterocyclyl or 5-12 membered heteroaryl ring, each optionally containing 1, 2 or 3 additional heteroatoms selected from O, N and S;
  - wherein each said C$_1$-C$_8$ alkyl, C$_3$-C$_8$ cycloalkyl, 3-12 membered heterocyclyl, C$_6$-C$_{12}$ aryl or 5-12 membered heteroaryl in R$^{21}$, R$^{22}$, R$^{23}$, R$^{24}$, R$^e$, R$^f$, or R$^e$ and R$^f$ taken together is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$;
- each R$^{27}$ is independently selected from the group consisting of halo, —OH, C$_1$-C$_4$ alkoxy, —CN, —NR$^9$R$^{10}$, C$_3$-C$_8$ cycloalkyl, 3-12 membered heterocyclyl, C$_6$-C$_{12}$ aryl and 5-12 membered heteroaryl, where each said C$_1$-C$_4$ alkoxy, C$_3$-C$_8$ cycloalkyl, 3-12 membered heterocyclyl, C$_6$-C$_{12}$ aryl or 5-12 membered heteroaryl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$;
- each R$^{32}$, R$^{34}$ and R$^{37}$ is independently selected from the group consisting of halo, C$_1$-C$_8$ alkyl, —CN, =O, —C(O)R, —CO$_2$R$^c$, —C(O)NR$^c$R$^d$, —OR$^c$, —SR$^c$, —SOR$^c$, —SO$_2$R$^c$, —SO$_2$NR$^c$R$^d$, —NO$_2$, —NR$^c$R$^d$, —NR$^c$C(O)R$^d$, —NR$^c$C(O)NR$^c$R$^d$, —NR$^c$C(O)OR$^d$, —NR$^c$SO$_2$R$^d$, —NR$^c$SO$_2$NR$^c$R$^d$, —OC(O)R, —OC(O)NR$^c$R$^d$, C$_3$-C$_8$ cycloalkyl, 3-12 membered heterocyclyl, C$_6$-C$_{12}$ aryl and 5-12 membered heteroaryl;
  - each R$^c$ and R$^d$ is independently selected from the group consisting of H, C$_1$-C$_8$ alkyl, C$_3$-C$_8$ cycloalkyl, 3-12 membered heterocyclyl, C$_6$-C$_{12}$ aryl and 5-12 membered heteroaryl; or
  - R$^c$ and R$^d$ may be taken together with the N atom to which they are attached to form a 3-12 membered heterocyclyl or 5-12 membered heteroaryl ring, each optionally containing 1, 2 or 3 additional heteroatoms selected from O, N and S;
  - wherein each said C$_1$-C$_8$ alkyl, C$_3$-C$_8$ cycloalkyl, 3-12 membered heterocyclyl, C$_6$-C$_{12}$ aryl or 5-12 membered heteroaryl in R$^{32}$, R$^{34}$, R$^{37}$, R$^c$, R$^d$, or R$^c$ and R$^d$ taken together is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$;
- X and Z are independently selected from the group consisting of H, C$_1$-C$_8$ alkyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl, 5-12 membered heteroaryl, halo, CN, —C(O)R$^a$, —CO$_2$R$^a$, —C(O)NR$^a$R$^b$, —SR$^a$, —SOR$^a$, —SO$_2$R$^a$, —SO$_2$NR$^a$R$^b$, —NO$_2$, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$ or —OC(O)NR$^a$R$^b$;

wherein each said C$_1$-C$_8$ alkyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl, or 5-12 membered heteroaryl group is optionally substituted by one or more substituents independently selected from the group consisting of halo, —CN, —C(O)R$^a$, —CO$_2$R$^a$, —C(O)NR$^a$R$^b$, —SR$^a$, —SOR$^a$, —SO$_2$R$^a$, —SO$_2$NR$^a$R$^b$, —NO$_2$, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, C$_3$-C$_8$ cycloalkyl, 3-12 membered heterocyclyl, C$_6$-C$_{12}$ aryl and 5-12 membered heteroaryl;

each R$^a$ and R$^b$ is independently H, C$_1$-C$_8$ alkyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl or 5-12 membered heteroaryl, where each said C$_1$-C$_8$ alkyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl and 5-12 membered heteroaryl is optionally substituted by one or more substituents independently selected from the group consisting of halo, C$_1$-C$_4$ alkyl, —OR$^{14}$, —NR$^{14}$$_2$, —CO$_2$R$^{14}$, —C(O)NR$^{14}$$_2$, —SO$_2$R$^{14}$ and —SO$_2$NR$^{14}$$_2$, where each R$^{14}$ is independently H or C$_1$-C$_4$ alkyl; or R$^a$ and R$^b$ may be taken together with the N atom to which they are attached to form a 3-12 membered heterocyclyl or 5-12 membered heteroaryl, each optionally containing 1, 2 or 3 additional heteroatoms selected from O, N and S, wherein said heterocyclyl or heteroaryl is optionally substituted by one or more substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$; and Y is H, halo, —OH or C$_1$-C$_4$ alkoxy.

In compounds of formula (I), each of U and V is independently selected from N and a substituted carbon atom (CR$^3$ and CR$^4$, respectively), such that the core ring containing U and V can be variously a phenyl, pyridinyl or pyridazinyl ring. In some embodiments of formula (I), no more than one of U and V is N. In other embodiments of formula (I), both U and V are N. In other embodiments of formula (I), one of U and V is N. In still further embodiments, neither of U or V is N.

In one embodiment of formula (I), U is CR$^3$ and V is CR$^4$, such that the ring containing U and V is a phenyl ring. In some such embodiments, R$^3$ is H or F, preferably H.

In another embodiment of formula (I), U is N and V is CR$^4$, such that the ring containing U and V is a [4,3-c]-fused pyridine ring.

In another embodiment of formula (I), U is CR$^3$ and V is N, such that the ring containing U and V is a [3,2-c]-fused pyridine ring. In some such embodiments, R$^3$ is H or F, preferably H.

In compounds of formula (I), L is a C$_1$-C$_4$ alkylene linker. In preferred embodiments, L is a C$_2$-C$_3$ alkylene linker. In some specific embodiments, L is a methylene, ethylene or propylene linker. In some preferred embodiments, L is an ethylene linker. In other preferred embodiments, L is a propylene linker.

In some embodiments of formula (I), L is a C$_1$-C$_4$ alkylene linker and m is 0, such that the alkylene linker L is unsubstituted. In other embodiments, m is an integer from 1 to 4, such that the alkylene linker L is substituted by 1-4 R$^5$ groups. In one preferred embodiment, L is an ethylene linker and m is 0. In another preferred embodiment, L is a propylene linker and m is 0.

In compounds of formula (I), M is a bond or —O—. In some preferred embodiments, M is a bond. In other preferred embodiments, M is —O—.

In some embodiments of formula (I), L is a C$_1$-C$_4$ alkylene linker and M is a bond. In some embodiments, L is a C$_2$-C$_3$ alkylene linker and M is a bond. In other embodiments, L is a methylene, ethylene, or propylene linker, and M is a bond. In some such embodiments, L is an ethylene linker and M is a bond. In other such embodiments, L is a propylene linker and M is a bond.

In further embodiments, L is a C$_1$-C$_4$ alkylene linker, M is a bond and m is 0, such that the alkylene linker L is unsubstituted. In other embodiments, L is a C$_1$-C$_4$ alkylene linker, M is a bond and m is an integer from 1 to 4, such that the alkylene linker L is substituted by 1 to 4 R$^5$ groups. In some such embodiments, L is a C$_2$-C$_3$ alkylene linker. In other such embodiments, L is a methylene, ethylene, or propylene linker.

In some embodiments of formula (I), L is a C$_1$-C$_4$ alkylene linker and M is —O—. In some embodiments, L is a C$_2$-C$_3$ alkylene linker and M is —O—. In other embodiments, L is a methylene, ethylene, or propylene linker, and M is —O—. In some such embodiments, L is an ethylene linker and M is —O—. In other such embodiments, L is a propylene linker and M is —O—.

In further embodiments, L is a C$_1$-C$_4$ alkylene linker, M is —O— and m is 0, such that the alkylene linker L is unsubstituted. In other embodiments, L is a C$_1$-C$_4$ alkylene linker, M is —O— and m is an integer from 1 to 4, such that the alkylene linker L is substituted by 1 to 4 R$^5$ groups. In some such embodiments, L is a C$_2$-C$_3$ alkylene linker. In other such embodiments, L is a methylene, ethylene, or propylene linker.

In compounds of formula (I), each R$^5$ is independently selected from the group consisting of halo, —OH, =O, C$_1$-C$_4$ alkyl, C$_1$-C$_4$ alkoxy, —CN, —NR$^9$R$^{10}$ and —C(O)NR$^9$R$^{10}$, where each said C$_1$-C$_4$ alkyl or C$_1$-C$_4$ alkoxy is optionally substituted with 1 to 3 substituents independently selected from the group consisting of halo, —OH, C$_1$-C$_4$ alkoxy, —CN, —NR$^9$R$^{10}$ and —C(O)NR$^9$R$^{10}$.

When R$^5$ comprises —NR$^9$R$^{10}$ or —C(O)NR$^9$R$^{10}$, each R$^9$ and R$^{10}$ is independently H or C$_1$-C$_4$ alkyl; or R$^9$ and R$^{10}$ may be taken together with the N atom to which they are attached to form a 3-12 membered heterocyclyl or 5-12 membered heteroaryl, each optionally containing 1, 2 or 3 additional heteroatoms selected from O, N and S. Each said C$_1$-C$_4$ alkyl in R$^9$ or R$^{10}$, and each said 3-12 membered heterocyclyl or 5-12 membered heteroaryl in R$^9$ and R$^{10}$ taken together is optionally substituted by 1 to 3 substituents independently selected from the group consisting of halo, —OH, =O, C$_1$-C$_4$ alkyl, C$_1$-C$_4$ alkoxy, —CN, —NH$_2$, —NH(C$_1$-C$_4$ alkyl) and —N(C$_1$-C$_4$ alkyl)$_2$.

In some embodiments, each R$^5$ is independently selected from the group consisting of halo, —OH, and C$_1$-C$_4$ alkyl. In some such embodiments, each R$^5$ is halo, preferably fluoro. In one embodiment, m is 1 and R$^5$ is F. In another embodiment, m is 2 and each R$^5$ is F. In some such embodiments, m is 2, each R$^5$ is F, and the R$^5$ groups are geminally disubstituted on one carbon atom of L. In other embodiments, m is 1 or 2 and each R$^5$ is independently selected from the group consisting of —OH, =O, C$_1$-C$_4$ alkyl, and C$_1$-C$_4$ alkoxy, where each said C$_1$-C$_4$ alkyl or C$_1$-C$_4$ alkoxy is optionally substituted with 1 to 3 substituents halo, —OH, or $C_1$-$C_4$ alkoxy groups. In some embodiments, m is 1 or 2 and $R^5$ is —OH, methyl or methoxy.

In compounds of formula (I), $R^1$ is $C_1$-$C_8$ alkyl, $C_1$-$C_8$ alkoxy, halo, —OH, —CN or —$NR^7R^8$, where each said $C_1$-$C_8$ alkyl or $C_1$-$C_8$ alkoxy is optionally substituted by one or more $R^{21}$. In some such embodiments, said $C_1$-$C_8$ alkyl or $C_1$-$C_8$ alkoxy is optionally substituted by 1 to 3 $R^{21}$ groups. In some such embodiments, $R^1$ is $C_1$-$C_4$ alkyl or halo, where said $C_1$-$C_4$ alkyl is optionally substituted by 1 to 3 $R^{21}$ groups. In other embodiments, $R^1$ is unsubstituted $C_1$-$C_4$ alkyl or halo.

In some embodiments of formula (I), $R^1$ is halo, preferably chloro (Cl) or fluoro (F). In other embodiments of formula (I), $R^1$ is $C_1$-$C_8$ alkyl, where said $C_1$-$C_8$ alkyl is optionally substituted by 1 to 3 $R^{21}$ groups. In some embodiments, $R^1$ is optionally substituted $C_1$-$C_4$ alkyl. In specific embodiments, $R^1$ is unsubstituted $C_1$-$C_4$ alkyl, preferably methyl or ethyl. In specific embodiments, $R^1$ is methyl, ethyl, chloro or fluoro. In preferred embodiments, $R^1$ is methyl. In other preferred embodiments, $R^1$ is Cl.

In compounds of formula (I), $R^2$ is independently selected from the group consisting of H, $C_1$-$C_8$ alkyl, $C_1$-$C_8$ alkoxy, —$OR^6$, —$NR^7R^8$, —$C(O)NR^7R^8$, —$SO_2NR^7R^8$, —$NR^7SO_2R_8$, $C_3$-$C_8$ cycloalkyl, 3-12 membered heterocyclyl, $C_6$-$C_{12}$ aryl and 5-12 membered heteroaryl, where each said $C_1$-$C_8$ alkyl or $C_1$-$C_8$ alkoxy is optionally substituted by one or more $R^{22}$, and each said $C_3$-$C_8$ cycloalkyl, 3-12 membered heterocyclyl, $C_6$-$C_{12}$ aryl or 5-12 membered heteroaryl is optionally substituted by one or more $R^{32}$. In some embodiments, said $C_1$-$C_8$ alkyl or $C_1$-$C_8$ alkoxy is optionally substituted by 1 to 3 $R^{22}$ groups, and each said $C_3$-$C_8$ cycloalkyl, 3-12 membered heterocyclyl, $C_6$-$C_{12}$ aryl or 5-12 membered heteroaryl is optionally substituted by 1 to 3 $R^{32}$ groups.

In one embodiment, $R^2$ is $C_1$-$C_8$ alkyl, where said $C_1$-$C_8$ alkyl is optionally substituted by one or more $R^{22}$ groups. In some embodiments, $R^2$ is $C_1$-$C_8$ alkyl is optionally substituted by 1 to 3 $R^{22}$ groups. In some such embodiments, $R^2$ is $C_1$-$C_4$ alkyl optionally substituted by 1 to 3 $R^{22}$. In specific embodiments, $R^2$ is $C_1$-$C_4$ alkyl optionally substituted by 1 to 3 $R^{22}$ groups independently selected from halo, —$C(O)NR^eR^f$, —$OR^e$, —$NR^eR^f$, —$NR^eC(O)R^f$ and —$NR^eSO_2R^f$ where $R^e$ and $R^f$ are defined as in formula (I) above. In some such embodiments, $R^e$ and $R^f$ are independently H or $C_1$-$C_4$ alkyl. In other embodiments, $R^e$ and $R^f$ are taken together to form a 4-6 membered heterocyclyl ring selected from a azetidinyl, pyrrolidinyl, piperidinyl, piperazinyl, morpholinyl or thiomorpholinyl, each optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl) and —N($C_1$-$C_4$ alkyl)$_2$.

In some embodiments of formula (I), $R^2$ is $C_1$-$C_8$ alkoxy, where said $C_1$-$C_8$ alkoxy is optionally substituted by one or more $R^{22}$ groups. In some embodiments, $R^2$ is $C_1$-$C_8$ alkoxy optionally substituted by 1 to 5 $R^{22}$ groups. In other embodiments, $R^2$ is $C_1$-$C_8$ alkoxy optionally substituted by 1 to 4 $R^{22}$ groups. In other embodiments, $R^2$ is $C_1$-$C_8$ alkoxy optionally substituted by 1 to 3 $R^{22}$ groups.

In some such embodiments, each $R^{22}$ is independently halo or —OH, preferably fluoro or —OH. In specific embodiments, said $C_1$-$C_8$ alkoxy is methoxy, ethoxy, propoxy, isopropoxy, n-butoxy, sec-butoxy or tert-butoxy, each of which may be independently substituted by 1 to 5 fluoro or OH groups, up to the number of hydrogen atoms. In some embodiments, said $C_1$-$C_8$ alkoxy is methoxy, ethoxy, propoxy, isopropoxy, n-butoxy, sec-butoxy or tert-butoxy. In one embodiment, $R^2$ is isopropoxy. In another embodiment, $R^2$ is ethoxy. In yet another embodiment, $R^2$ is sec-butoxy In further embodiments, $R^2$ is $C_1$-$C_8$ alkoxy independently substituted by 1 to 5 fluoro or —OH groups. Embodiments wherein said $C_1$-$C_8$ alkoxy is substituted by at least one F may also be referred to as $C_1$-$C_8$ fluoroalkoxy groups. Examples of $C_1$-$C_8$ fluoroalkoxy groups include, without limitation, the groups 1,1-difluoromethoxy, trifluoromethoxy, 2,2,2-trifluoroethoxy, 1-(trifluoromethyl)ethoxy, 1,1,1-(trifluoropropan-2-yl)oxy, 3,3,4,4-tetrafluorobutoxy, 3,3,3-trifluoro-2-hydroxypropoxy, 1,1-difluoropropan-2-yl)oxy and 2,2-difluoroethoxy.

In another embodiment, $R^2$ is $C_1$-$C_8$ alkoxy substituted by 1 to 5 $R^{22}$ groups independently selected from halo, —$C(O)NR^eR^f$ and —$OR^e$, where $R^e$ and $R^f$ are independently H or $C_1$-$C_4$ alkyl.

In yet another embodiment, $R^2$ is —$OR^6$, where $R^6$ is —$(CR^{11}R^{12})_n$—$R^{13}$, where n is 0 to 4. In such compounds, each $R^{11}$ and $R^{12}$ is independently H, halo or $C_1$-$C_4$ alkyl, where each said $C_1$-$C_4$ alkyl is optionally substituted by one or more $R^{22}$. Preferably, each $R^{11}$ and $R^{12}$ is independently H, halo or unsubstituted $C_1$-$C_4$ alkyl. In specific embodiments, each $R^{11}$ and $R^{12}$ is independently H or methyl. In the foregoing embodiments, $R^{13}$ is selected from the group consisting of $C_3$-$C_8$ cycloalkyl, 3-12 membered heterocyclyl, $C_6$-$C_{12}$ aryl, and 5-12 membered heteroaryl, where each said $C_3$-$C_8$ cycloalkyl, 3-12 membered heterocyclyl, $C_6$-$C_{12}$ aryl or 5-12 membered heteroaryl is optionally substituted by one or more $R^{32}$. In some such embodiments, n is 0 and $R^{13}$ is $C_3$-$C_8$ cycloalkyl, 3-12 membered heterocyclyl, $C_6$-$C_{12}$ aryl, or 5-12 membered heteroaryl, such that —$OR^6$ comprises a $C_3$-$C_8$ cycloalkyoxy, 3-12 membered heterocycloxy, $C_6$-$C_{12}$ aryloxy or 5-12 membered heteroaryloxy group, respectively, each of which may be optionally substituted by one or more $R^{32}$. In frequent embodiments, n is 1 or 2 and $R^{13}$ is 5-12 membered heteroaryl, optionally substituted by one or more $R^{32}$.

In another embodiment, $R^2$ is selected from the group consisting of —$NR^7R^8$, —$C(O)NR^7R^8$, —$SO_2NR^7R^8$, and —$NR^7SO_2R_8$, where each $R^7$ and $R^8$ is independently selected from the group consisting of H, $C_1$-$C_8$ alkyl, $C_3$-$C_8$ cycloalkyl, 3-12 membered heterocyclyl, $C_6$-$C_{12}$ aryl, and 5-12 membered heteroaryl; or $R^7$ and $R^8$ may be taken together with the N atom to which they are attached to form a 3-12 membered heterocyclyl or 5-12 membered heteroaryl, each optionally containing 1, 2 or 3 additional heteroatoms selected from O, N and S; where each said $C_1$-$C_8$ alkyl in $R^7$ or $R^8$ is optionally substituted by one or more $R^{27}$, and each said $C_3$-$C_8$ cycloalkyl, 3-12 membered heterocyclyl, $C_6$-$C_{12}$ aryl, or 5-12 membered heteroaryl in $R^7$, $R^8$, or $R^7$ and $R^8$ taken together is optionally substituted by one or more $R^{37}$. In some such embodiments, each $R^{37}$ is independently selected from the group consisting of halo, —OH, =O, $C_1$-$C_4$ alkyl, $C_1$-$C_4$ alkoxy, —CN, —$NH_2$, —NH($C_1$-$C_4$ alkyl) and —N($C_1$-$C_4$ alkyl)$_2$. In some such embodiments, when $R^2$ comprises —$NR^7R^8$, —$C(O)NR^7R^8$, or —$SO_2NR^7R^8$, each of $R^7$ and $R^8$ is independently H or $C_1$-$C_4$ alkyl.

In another embodiment of formula (I), $R^2$ is 5-12 membered heteroaryl, where said heteroaryl is optionally substituted by one or more $R^{32}$. In some embodiments, said 5-12 membered heteroaryl is optionally substituted by 1 to 3 $R^{32}$ groups.

In some embodiments, $R^2$ is a 5-6 membered heteroaryl, optionally substituted by 1 to 3 $R^{32}$ groups. In some such embodiments, said 5-6 membered heteroaryl is selected from the group consisting of pyrazolyl, imidazolyl, pyrrolyl, triazolyl, tetrazolyl, thienyl, thiazolyl, isothiazolyl, furanyl, oxazoyl, isoxazolyl, oxadiazolyl, thiadiazolyl, pyridinyl, pyrimidinyl, pyrazinyl and pyridazinyl, each of which may be optionally substituted by 1 to 3 $R^{32}$ groups. In other such embodiments, said 5-6 membered heteroaryl is selected from the group consisting of pyrazolyl, imidazolyl, pyrrolyl, triazolyl, tetrazolyl, thienyl, thiazolyl, isothiazolyl, furanyl, oxazoyl, isoxazolyl, oxadiazolyl, or thiadiazolyl, each of which is optionally substituted by 1 to 3 $R^{32}$ groups. In one preferred embodiment, said 5-6 membered heteroaryl is selected from the group consisting of pyrazolyl, imidazolyl, pyrrolyl, triazolyl, pyridinyl and pyrimidinyl, each optionally substituted by 1 to 3 $R^{32}$ groups. In another preferred embodiment, said 5-6 membered heteroaryl is pyrazolyl or triazolyl, optionally substituted by 1 to 3 $R^{32}$ groups. In another preferred embodiment, said 5-6 membered heteroaryl is pyrazolyl, isoxazoyl or triazolyl, each of which is optionally substituted by 1 to 3 $R^{32}$ groups.

In specific embodiments, $R^2$ may be selected from the following 5-6 membered heteroaryl groups, where the asterisk (*) represents the point of attachment to the base molecule and the optional substituent groups $R^{32}$ may be present on any atom of the heteroaryl ring (N or C) bearing a H atom in its unsubstituted form:

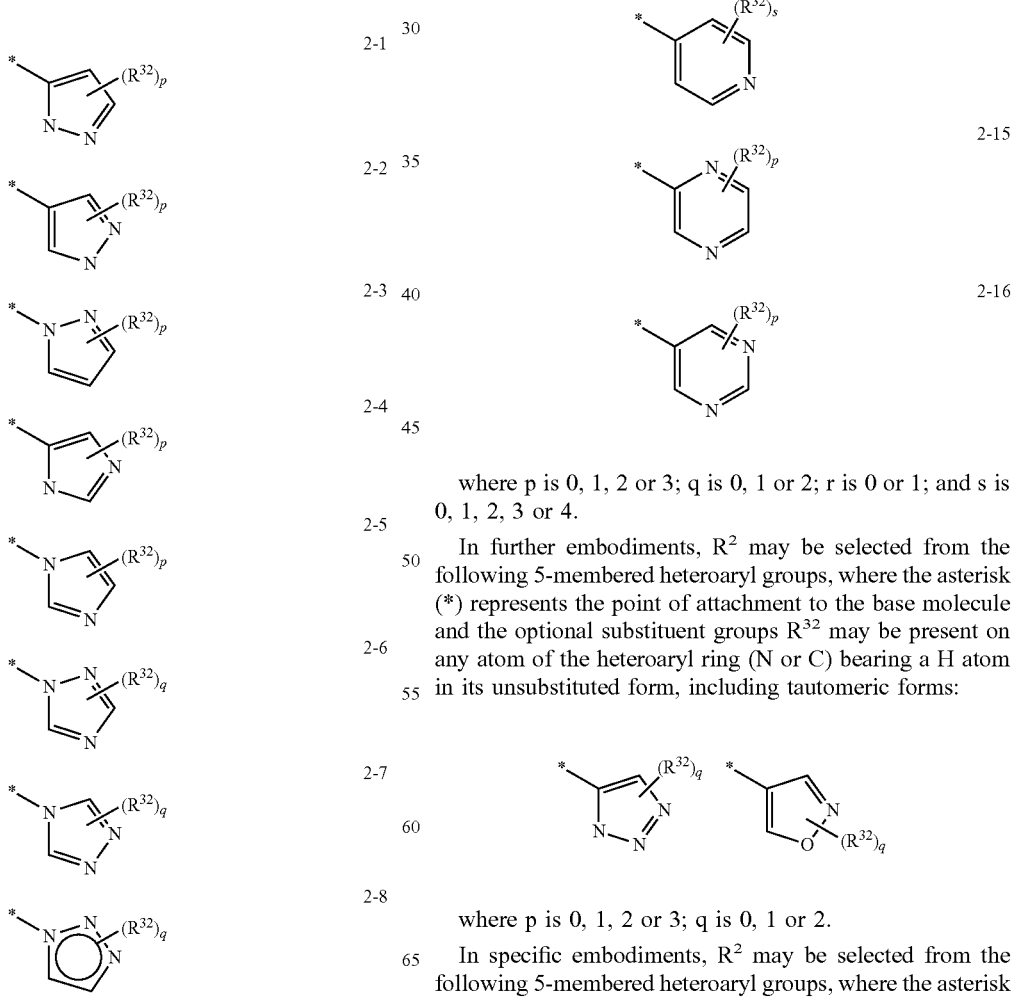

where p is 0, 1, 2 or 3; q is 0, 1 or 2; r is 0 or 1; and s is 0, 1, 2, 3 or 4.

In further embodiments, $R^2$ may be selected from the following 5-membered heteroaryl groups, where the asterisk (*) represents the point of attachment to the base molecule and the optional substituent groups $R^{32}$ may be present on any atom of the heteroaryl ring (N or C) bearing a H atom in its unsubstituted form, including tautomeric forms:

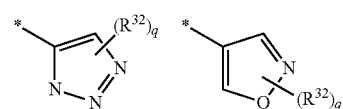

where p is 0, 1, 2 or 3; q is 0, 1 or 2.

In specific embodiments, $R^2$ may be selected from the following 5-membered heteroaryl groups, where the asterisk (*) represents the point of attachment to the base molecule:

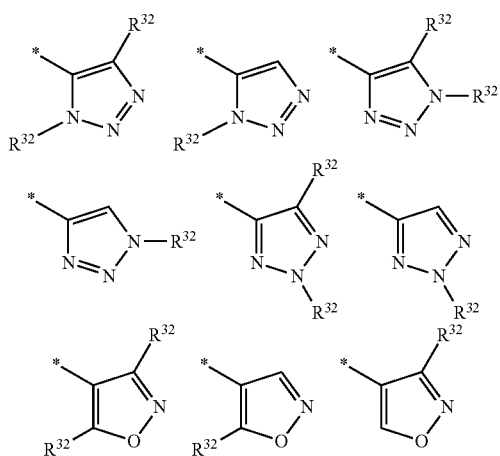

In another embodiment, $R^2$ is 3-12 membered heterocyclyl, where said heterocyclyl is optionally substituted by one or more $R^{32}$. In some embodiments, said heterocyclyl is optionally substituted by 1 to 3 $R^{32}$ groups. In some such embodiments, said 3-12 membered heterocyclyl is selected from the group consisting of azetidinyl, pyrrolidinyl, piperidinyl, morpholinyl, piperazinyl, 2-oxa-5-azabicyclo[2.2.1]heptanyl, 3-oxa-8-azabicyclo[3.2.1]octanyl, dihydropyranyl, tetrahydrofuranyl and tetrahydropyranyl, each optionally substituted by 1 to 3 $R^{32}$ groups.

In yet another embodiment, $R^2$ is $C_6$-$C_{12}$ aryl, where said aryl is optionally substituted by one or more $R^{32}$. In some such embodiments, said aryl is optionally substituted by 1 to 3 $R^{32}$ groups. In specific embodiments, said aryl is selected from the group consisting of phenyl, biphenyl, naphthyl, indanyl, indenyl and tetrahydronaphthyl, each optionally substituted by 1 to 3 $R^{32}$ groups.

In another embodiment, $R^2$ is $C_3$-$C_8$ cycloalkyl, optionally substituted by one or more $R^{32}$. In some such embodiments, said $C_3$-$C_8$ cycloalkyl is optionally substituted by 1 to 3 $R^{32}$ groups. In specific embodiments, said cycloalkyl is selected from the group consisting of cyclopropyl, cyclobutyl, cyclopentyl, cyclohexyl or cycloheptyl, each optionally substituted by 1 to 3 $R^{32}$ groups.

In compounds of formula (I), $R^3$ is H, $C_1$-$C_8$ alkyl, $C_1$-$C_8$ alkoxy, halo, —OH, —CN or —$NR^7R^8$, where each said $C_1$-$C_8$ alkyl or $C_1$-$C_8$ alkoxy is optionally substituted by one or more $R^{23}$. In some embodiments, said $C_1$-$C_8$ alkyl or $C_1$-$C_8$ alkoxy is optionally substituted by 1 to 3 $R^{23}$ groups. In some embodiments, $R^3$ is $C_1$-$C_4$ alkyl or $C_1$-$C_4$ alkoxy, each of which is optionally substituted by 1 to 3 $R^{23}$ groups. In some such embodiments, each $C_1$-$C_4$ alkyl or $C_1$-$C_4$ alkoxy, is optionally substituted by 1 to 3 $R^{23}$ groups selected from halo, —OH or $C_1$-$C_4$ alkoxy. In specific embodiments, $R^3$ is —OMe. In still other $R^3$ is H or halo, preferably H or F. In preferred embodiments, $R^3$ is H. In other embodiments, $R^3$ is F. In still other embodiments, $R^3$ is —CN.

In compounds of formula (I), $R^4$ is selected from the group consisting of H, halo, $C_1$-$C_8$ alkyl, $C_3$-$C_8$ cycloalkyl, 3-12 membered heterocyclyl, $C_6$-$C_{12}$ aryl, 5-12 membered heteroaryl, —($C_1$-$C_4$ alkyl)$R^z$, —$OR^x$, —CN, —$C(O)R^x$, —$CO_2R^x$, —$C(O)NR^xR^y$, —$SR^x$, —$SOR^x$, —$SO_2R^x$, —$SO_2NR^xR^y$, —$NO_2$, —$NR^xR^y$, —$NR^xC(O)R^y$, —$NR^xC(O)NR^xR^y$, —$NR^xC(O)OR^y$, —$NR^xSO_2R^y$, —$NR^xSO_2NR^xR^y$, —$OC(O)R^x$ and —$OC(O)NR^xR^y$, as further defined as in formula (I) above.

Each $R^x$ and $R^y$ is independently selected from the group consisting of H, $C_1$-$C_8$ alkyl, $C_3$-$C_8$ cycloalkyl, 3-12 membered heterocyclyl, $C_6$-$C_{12}$ aryl and 5-12 membered heteroaryl, or $R^x$ and $R^y$ may be taken together with the N atom to which they are attached to form a 3-12 membered heterocyclyl or 5-12 membered heteroaryl ring, each optionally containing 1, 2 or 3 additional heteroatoms selected from O, N and S.

Each $R^z$ is independently selected from the group consisting of $C_3$-$C_8$ cycloalkyl, 3-12 membered heterocyclyl, $C_6$-$C_{12}$ aryl and 5-12 membered heteroaryl.

In each of the foregoing embodiments, each said $C_1$-$C_8$ alkyl in $R^4$, $R^x$ or $R^y$ and each said $C_1$-$C_4$ alkyl in ($C_1$-$C_4$ alkyl)$R^z$ is optionally substituted by one or more $R^{24}$, and each said $C_3$-$C_8$ cycloalkyl, 3-12 membered heterocyclyl, $C_6$-$C_{12}$ aryl, or 5-12 membered heteroaryl in $R^4$, $R^x$, $R^y$, $R^z$, or $R^x$ and $R^y$ taken together is optionally substituted by one or more $R^{34}$.

In one embodiment, $R^4$ is H, halo or —CN. In some such embodiments, $R^4$ is H. In other such embodiments, $R^4$ is halo, preferably Cl or F. In other such embodiments, $R^4$ is halo, preferably Cl or F. In other such embodiments, $R^4$ is Cl or Br. In still other such embodiments, $R^4$ is —CN.

In another embodiment, $R^4$ is —$C(O)NR^xR^y$, where $R^x$ and $R^y$ are defined as in formula (I) above. In some such embodiments, $R^x$ and $R^y$ are independently H or $C_1$-$C_4$ alkyl.

In still another embodiment, $R^4$ is $C_1$-$C_8$ alkyl, optionally substituted by one or more $R^{24}$. In some such embodiments, $R^4$ is $C_1$-$C_8$ alkyl, optionally substituted by 1 to 3 $R^{24}$ groups. In other such embodiments, $R^4$ is $C_1$-$C_4$ alkyl, optionally substituted by 1 to 3 $R^{24}$ groups. In some such embodiments, $R^4$ is $C_1$-$C_4$ alkyl, optionally substituted by 1 to 3 $R^{24}$ groups independently selected from the group consisting of —$OR^e$, —$NR^eR^f$, —$NR^eC(O)R^f$, —$NR^eC(O)OR^f$, $C_3$-$C_8$ cycloalkyl, 3-12 membered heterocyclyl, $C_6$-$C_{12}$ aryl, and 5-12 membered heteroaryl, each of which is further defined and optionally substituted as described in formula (I).

In another embodiment, $R^4$ is —($C_1$-$C_4$ alkyl)-$R^z$, where $R^z$ is independently selected from the group consisting of $C_3$-$C_8$ cycloalkyl, 3-12 membered heterocyclyl, $C_6$-$C_{12}$ aryl and 5-12 membered heteroaryl, wherein each said $C_3$-$C_8$ cycloalkyl, 3-12 membered heterocyclyl, $C_6$-$C_{12}$ aryl, or 5-12 membered heteroaryl in $R^z$ is optionally substituted by one or more $R^{34}$ In one such embodiment, $R^4$ is —($C_1$-$C_4$ alkyl)$R^z$, where $R^z$ is 3-12 membered heterocyclyl, and where said 3-12 membered heterocyclyl in $R^z$ is optionally substituted by one or more $R^{34}$. In some such embodiments, said 3-12 membered heterocyclyl in $R^z$ is optionally substituted by 1 to 3 $R^{34}$ groups.

In another embodiment, $R^4$ is —($C_1$-$C_4$ alkyl)$R^z$, where $R^z$ is 5-12 membered heteroaryl, and where said 5-12 membered heteroaryl in $R^z$ is optionally substituted by one or more $R^{34}$. In some such embodiments, said 5-12 membered heteroaryl in $R^z$ is optionally substituted by 1 to 3 $R^{34}$ groups. In some embodiments, $R^z$ is a 5-6 membered heteroaryl, optionally substituted by 1 to 3 $R^{34}$ groups.

In some embodiments when $R^4$ is —($C_1$-$C_4$ alkyl)-$R^z$, the —($C_1$-$C_4$ alkyl) linker moiety which forms part of —($C_1$-$C_4$ alkyl)-$R^z$ is an unsubstitued $C_1$-$C_4$ alkylene group, selected from a methylene, ethylene, propylene or butylene group attached to $R^z$. In some embodiments, said —($C_1$-$C_4$ alkyl) group is optionally substituted by one or more $R^{24}$ groups. In other embodiments, said —($C_1$-$C_4$ alkyl) group is a methylene, ethylene, propylene or butylene optionally substituted by 1 to 3 $R^{24}$ groups.

In yet another embodiment of formula (I), $R^4$ is selected from the group consisting of $C_3$-$C_8$ cycloalkyl, 3-12 membered heterocyclyl, $C_6$-$C_{12}$ aryl, and 5-12 membered heteroaryl, wherein each said $C_3$-$C_8$ cycloalkyl, 3-12 membered heterocyclyl, $C_6$-$C_{12}$ aryl, or 5-12 membered heteroaryl in $R^4$ is optionally substituted by one or more $R^{34}$ In one such embodiment, $R^4$ is 3-12 membered heterocyclyl, optionally substituted by one or more $R^{34}$. In some such embodiments, said 3-12 membered heterocyclyl is optionally substituted by 1 to 3 $R^{34}$ groups. In some embodiments, said 3-12 membered heterocyclyl is selected from the group consisting of azetidinyl, pyrrolidinyl, piperidinyl, morpholinyl, piperazinyl, and thiomorpholinly, each optionally substituted by 1 to 3 $R^{34}$ groups.

In another embodiment, $R^4$ is a 5-12 membered heteroaryl, optionally substituted by one or more $R^{34}$. In some such embodiments, said 5-12 membered heteroaryl is optionally substituted by 1 to 3 $R^{34}$ groups. In some embodiments, $R^4$ is a 5-6 membered heteroaryl, optionally substituted by 1 to 3 $R^{34}$ groups.

In some embodiments, said 5-6 membered heteroaryl in $R^4$ or $R^z$ is selected from the group consisting of pyrazolyl, imidazolyl, pyrrolyl, triazolyl, tetrazolyl, thienyl, thiazolyl, isothiazolyl, furanyl, oxazoyl, isoxazolyl, oxadiazolyl, thiadiazolyl, pyridinyl, pyrimidinyl, pyrazinyl or pyridazinyl ring, each of which is optionally substituted by 1 to 3 $R^{34}$ groups.

In specific embodiments of each of the formulae herein, $R^4$ may be selected from the following 5-6 membered heteroaryl groups, where the asterisk (*) represents the point of attachment to the base molecule and the optional substituent groups $R^{34}$ may be present on any atom of the heteroaryl ring (N or C) bearing a H atom in its unsubstituted form:

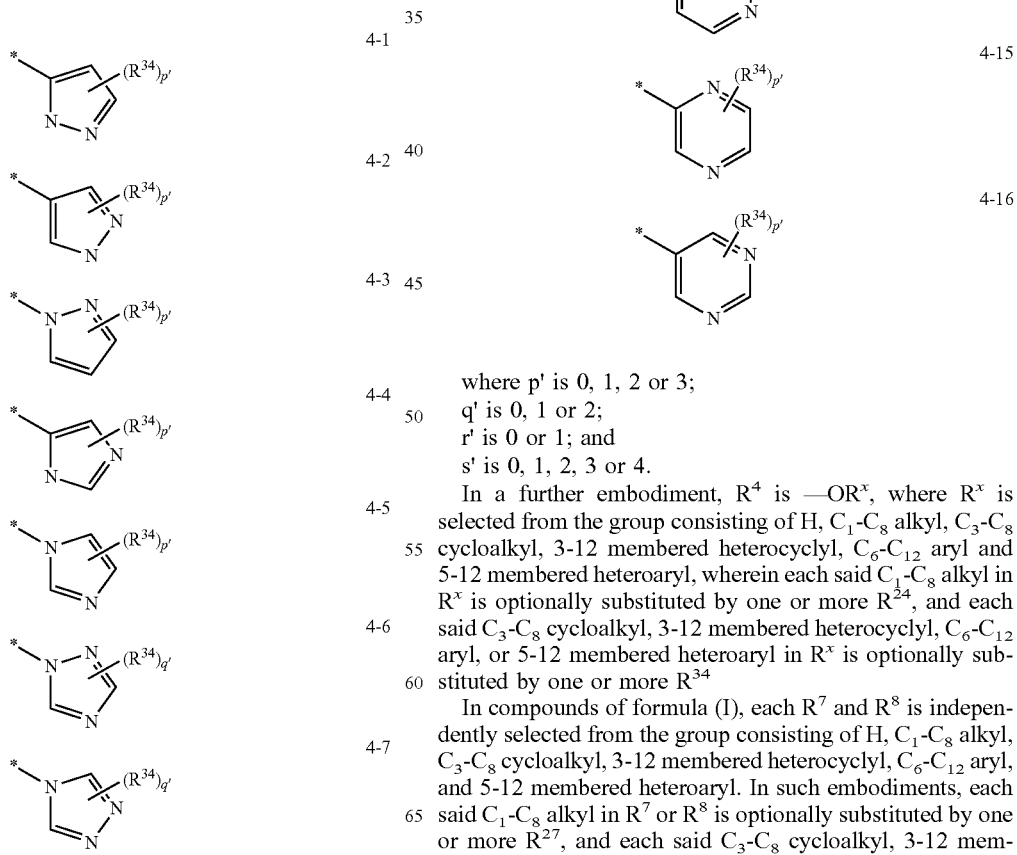

where p' is 0, 1, 2 or 3;
q' is 0, 1 or 2;
r' is 0 or 1; and
s' is 0, 1, 2, 3 or 4.

In a further embodiment, $R^4$ is —$OR^x$, where $R^x$ is selected from the group consisting of H, $C_1$-$C_8$ alkyl, $C_3$-$C_8$ cycloalkyl, 3-12 membered heterocyclyl, $C_6$-$C_{12}$ aryl and 5-12 membered heteroaryl, wherein each said $C_1$-$C_8$ alkyl in $R^x$ is optionally substituted by one or more $R^{24}$, and each said $C_3$-$C_8$ cycloalkyl, 3-12 membered heterocyclyl, $C_6$-$C_{12}$ aryl, or 5-12 membered heteroaryl in $R^x$ is optionally substituted by one or more $R^{34}$ In compounds of formula (I), each $R^7$ and $R^8$ is independently selected from the group consisting of H, $C_1$-$C_8$ alkyl, $C_3$-$C_8$ cycloalkyl, 3-12 membered heterocyclyl, $C_6$-$C_{12}$ aryl, and 5-12 membered heteroaryl. In such embodiments, each said $C_1$-$C_8$ alkyl in $R^7$ or $R^8$ is optionally substituted by one or more $R^{27}$, and each said $C_3$-$C_8$ cycloalkyl, 3-12 membered heterocyclyl, $C_6$-$C_{12}$ aryl, or 5-12 membered heteroaryl in $R^7$ or $R^8$ is optionally substituted by one or more $R^{37}$. In some embodiments of formula (I), each $R^7$ and $R^8$ is independently H or $C_1$-$C_8$ alkyl, where said $C_1$-$C_8$ alkyl is optionally substituted by one or more $R^{27}$. In some such embodiments, said $C_1$-$C_8$ alkyl is optionally substituted by 1 to 3 $R^{27}$ groups.

In other embodiments of formula (I), $R^7$ and $R^8$ are taken together with the N atom to which they are attached to form a 3-12 membered heterocyclyl or 5-12 membered heteroaryl, each optionally containing 1, 2 or 3 additional heteroatoms selected from O, N and S. In such embodiments, each said 3-12 membered heterocyclyl or 5-12 membered heteroaryl in $R^7$ and $R^8$ taken together is optionally substituted by one or more $R^{37}$.

In compounds of formula (I), each $R^{21}$, $R^{22}$, $R^{23}$ and $R^{24}$ is independently selected from the group consisting of halo, $C_1$-$C_8$ alkyl, —CN, =O, —C(O)$R^e$, —CO$_2R^e$, —C(O)NR$^e$R$^f$, —OR$^e$, —SR$^e$, —SOR$^e$, —SO$_2R^e$, —SO$_2$NR$^e$R$^f$, —NO$_2$, —NR$^e$R$^f$, —NR$^e$C(O)R$^f$, —NR$^e$C(O)NR$^e$R$^f$, —NR$^e$C(O)OR$^f$, —NR$^e$SO$_2R^f$, —NR$^e$SO$_2$NR$^e$R$^f$, —OC(O)R$^e$, —OC(O)NR$^e$R$^f$, $C_3$-$C_8$ cycloalkyl, 3-12 membered heterocyclyl, $C_6$-$C_{12}$ aryl and 5-12 membered heteroaryl, as further defined as in formula (I).

In some embodiments of formula (I), each $R^e$ and $R^f$ is independently selected from the group consisting of H, $C_1$-$C_8$ alkyl, $C_3$-$C_8$ cycloalkyl, 3-12 membered heterocyclyl, $C_6$-$C_{12}$ aryl and 5-12 membered heteroaryl.

In other embodiments of formula (I), $R^e$ and $R^f$ are taken together with the N atom to which they are attached to form a 3-12 membered heterocyclyl or 5-12 membered heteroaryl ring, each optionally containing 1, 2 or 3 additional heteroatoms selected from O, N and S.

Each said $C_1$-$C_8$ alkyl, $C_3$-$C_8$ cycloalkyl, 3-12 membered heterocyclyl, $C_6$-$C_{12}$ aryl or 5-12 membered heteroaryl in $R^{21}$, $R^{22}$, $R^{23}$, $R^{24}$, $R^e$, $R^f$, or $R^e$ and $R^f$ taken together is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$.

In specific embodiments, each $R^{21}$, $R^{22}$, $R^{23}$ and $R^{24}$ is independently selected from the group consisting of halo, —OR$^e$, —CN, —NR$^e$R$^f$, —C(O)NR$^e$R$^f$, —NR$^e$C(O)R$^f$, —SO$_2$NR$^e$R$^f$ and —NR$^e$SO$_2R^f$, where $R^e$ and $R^f$ are defined as in formula (I) above. In some such embodiments, each $R^e$ and $R^f$ is independently selected from the group consisting of H and $C_1$-$C_4$ alkyl, where said $C_1$-$C_4$ alkyl is optionally substituted by 1 to 3 substituents independently selected from the group consisting of halo, —OH, $C_1$-$C_4$ alkoxy, —CN, —NH$_2$, —NH($C_1$-$C_4$ alkyl) and —N($C_1$-$C_4$ alkyl)$_2$.

In other such embodiments, when $R^{21}$, $R^{22}$, $R^{23}$ or $R^{24}$ comprises —NR$^e$R$^f$ or —C(O)NR$^e$R$^f$, each $R^e$ and $R^f$ is independently H or $C_1$-$C_4$ alkyl; or $R^e$ and $R^f$ may be taken together with the N atom to which they are attached to form a 3-12 membered heterocyclyl or 5-12 membered heteroaryl, each optionally containing 1, 2 or 3 additional heteroatoms selected from O, N and S, where each said 3-12 membered heterocyclyl or 5-12 membered heteroaryl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$.

In other embodiments of formula (I), each $R^{21}$, $R^{22}$, $R^{23}$ and $R^{24}$ is optionally substituted 3-12 membered heterocyclyl or optionally substituted 5-12 membered heteroaryl. In some embodiments, said 3-12 membered heterocyclyl or said 5-12 membered heteroaryl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$.

In certain embodiments, each $R^{21}$, $R^{22}$, $R^{23}$ and $R^{24}$ is independently selected from the group consisting of Cl, F, —OH, —OCH$_3$, —OC$_2$H$_5$, —OCF$_3$, —CN, C(O)NH$_2$, —C(O)NHCH$_3$, —C(O)N(CH$_3$)$_2$, —NHC(O)CH$_3$, NHSO$_2$CH$_3$ and —N(CH$_3$)SO$_2$CH$_3$, —NH$_2$, —NHCH$_3$, —N(CH$_3$)$_2$, cyclopropyl, optionally substituted 4-6 membered heterocyclyl, optionally substituted phenyl, and optionally substituted 5-6 membered heteroaryl. In some such embodiments, said 4-6 membered heterocyclyl is azetidinyl, pyrrolidinyl, piperidinyl, piperazinyl, morpholinyl or thiomorpholinyl, each of which may be optionally substituted as defined in formula (I). In other such embodiments, said 5-6 membered heteroaryl is optionally substituted pyrazolyl, imidazolyl, pyrrolyl, triazolyl, pyridinyl or pyrimidinyl. In some embodiments, said 4-6 membered heterocyclyl or said 5-6 membered heteroaryl is optionally substituted by 1-3 substituents independently selected from halo, —OH, =O, $C_1$-$C_4$ alkyl, $C_1$-$C_4$ alkoxy, —CN—NH$_2$, —NH($C_1$-$C_4$ alkyl) and —N($C_1$-$C_4$ alkyl)$_2$.

In compounds of formula (I), $R^{27}$ is independently selected from the group consisting of halo, —OH, $C_1$-$C_4$ alkoxy, —CN, —NR$^9$R$^{10}$, $C_3$-$C_8$ cycloalkyl, 3-12 membered heterocyclyl, $C_6$-$C_{12}$ aryl and 5-12 membered heteroaryl, where each said $C_1$-$C_4$ alkoxy, $C_3$-$C_8$ cycloalkyl, 3-12 membered heterocyclyl, $C_6$-$C_{12}$ aryl or 5-12 membered heteroaryl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$. When $R^{27}$ is —NR$^9$R$^{10}$, each $R^9$ and $R^{10}$ is independently H or $C_1$-$C_4$ alkyl; or $R^9$ and $R^{10}$ may be taken together with the N atom to which they are attached to form a 3-12 membered heterocyclyl or 5-12 membered heteroaryl, each optionally containing 1, 2 or 3 additional heteroatoms selected from O, N and S; where each said $C_1$-$C_4$ alkyl in $R^9$ or $R^{10}$ and each said 3-12 membered heterocyclyl or 5-12 membered heteroaryl in $R^9$ and $R^{10}$ taken together is optionally substituted by 1 to 3 substituents independently selected from the group consisting of halo, —OH, =O, $C_1$-$C_4$ alkyl, $C_1$-$C_4$ alkoxy, —CN, —NH$_2$, —NH($C_1$-$C_4$ alkyl) and —N($C_1$-$C_4$ alkyl)$_2$.

In compounds of formula (I), each $R^{32}$, $R^{34}$ and $R^{37}$ is independently selected from the group consisting of halo, $C_1$-$C_8$ alkyl, —CN, =O, —C(O)R, —CO$_2R^c$, —C(O)NR$^c$R$^d$, —OR$^c$, —SR$^c$, —SOR$^c$, —SO$_2$R, —SO$_2$NR$^c$R$^d$, —NO$_2$, —NR$^c$R$^d$, —NRC(O)R$^d$, —NR$^c$C(O)NR$^c$R$^d$, —NR$^c$C(O)OR$^d$, —NR$^c$SO$_2R^d$, —NR$^c$SO$_2$NR$^c$R$^d$, —OC(O)R, —OC(O)NR$^c$R$^d$, $C_3$-$C_8$ cycloalkyl, 3-12 membered heterocyclyl, $C_6$-$C_{12}$ aryl and 5-12 membered heteroaryl; each $R^c$ and $R^d$ is independently selected from the group consisting of H, $C_1$-$C_8$ alkyl, $C_3$-$C_8$ cycloalkyl, 3-12 membered heterocyclyl, $C_6$-$C_{12}$ aryl and 5-12 membered heteroaryl; or $R^c$ and $R^d$ may be taken together with the N atom to which they are attached to form a 3-12 membered heterocyclyl or 5-12 membered heteroaryl ring, each optionally containing 1, 2 or 3 additional heteroatoms selected from O, N and S; wherein each said $C_1$-$C_8$ alkyl, $C_3$-$C_8$ cycloalkyl, 3-12 membered heterocyclyl, $C_6$-$C_{12}$ aryl or 5-12 membered heteroaryl in $R^{32}$, $R^{34}$, $R^{37}$, $R^c$, $R^d$, or $R^c$ and $R^d$ taken together is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl) and —N($C_1$-$C_4$ alkyl)$_2$.

In some such embodiments, each $R^{32}$, $R^{34}$ and $R^{37}$ is independently halo, $C_1$-$C_8$ alkyl, —CN, —C(O)$NR^cR^d$, —$NR^cR^d$, —$NR^cC(O)R^d$, $C_3$-$C_8$ cycloalkyl, 3-12 membered heterocyclyl, $C_6$-$C_{12}$ aryl and 5-12 membered heteroaryl, where said $C_1$-$C_8$ alkyl is optionally substituted by —OH, —$C_1$-$C_4$ alkoxy or halo, each $R^c$ and $R^d$ is independently H or $C_1$-$C_4$ alkyl, and each said $C_3$-$C_8$ cycloalkyl, 3-12 membered heterocyclyl, $C_6$-$C_{12}$ aryl and 5-12 membered heteroaryl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —$NH_2$, —NH($C_1$-$C_4$ alkyl) and —N($C_1$-$C_4$ alkyl)$_2$.

In specific embodiments, each $R^{32}$, $R^{34}$ and $R^{37}$ is independently is independently selected from the group consisting of —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —C(O)$NH_2$, —C(O)$NHCH_3$, —C(O)N($CH_3$)$_2$, —NHC(O)$CH_3$, —$NH_2$, —$NHCH_3$, —N($CH_3$)$_2$, cyclopropyl, 4-6 membered heterocyclyl, phenyl, and 5-6 membered heteroaryl, where said 4-6 membered heterocyclyl, phenyl or 5-6 membered heteroaryl is optionally substituted as defined in formula (I). In specific embodiments, said 4-6 membered heterocyclyl, phenyl or 5-6 membered heteroaryl are optionally substituted by one or more halo, $C_1$-$C_4$ alkyl or $C_1$-$C_4$ alkoxy.

In other specific embodiments, said 4-6 membered heterocyclyl, phenyl or 5-6 membered heteroaryl are optionally substituted by 1-3 substituents independently selected from halo, —OH, $C_1$-$C_4$ alkyl, $C_1$-$C_4$ alkoxy, —CN—$NH_2$, —NH($C_1$-$C_4$ alkyl) and —N($C_1$-$C_4$ alkyl)$_2$.

In some such embodiments, said 4-6 membered heterocyclyl is azetidinyl, pyrrolidinyl, piperidinyl, piperazinyl, morpholinyl or thiomorpholinyl, each of which may be optionally substituted as defined in formula (I). In some such embodiments, said 5-6 membered heteroaryl is optionally substituted pyrazolyl, imidazolyl, pyrrolyl, triazolyl, pyridinyl or pyrimidinyl. In other such embodiments, said 5-6 membered heteroaryl is optionally substituted pyridyl or pyrimidinyl. In still other such embodiments, said 5-6 membered heteroaryl is optionally substituted pyrazolyl or triazolyl.

In compounds of formula (I), X and Z are independently selected from the group consisting of H, $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, 5-12 membered heteroaryl, halo, —CN, —C(O)$R^a$, —$CO_2R^a$, —C(O)$NR^aR^b$, —$SR^a$, —$SOR^a$, —$SO_2R^a$, —$SO_2NR^aR^b$, —$NO_2$, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —OC(O)$R^a$ and —OC(O)$NR^aR^b$; wherein said alkyl, alkenyl, alkynyl, cycloalkyl, heterocyclyl, aryl, and heteroaryl groups may be optionally substituted by 1 to 3 substituents independently selected from the group consisting of halo, —CN, —C(O)$R^a$, —$CO_2R^a$, —C(O)$NR^aR^b$, —$SR^a$, —$SOR^a$, —$SO_2R^a$, —$SO_2NR^aR^b$, —$NO_2$, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —OC(O)$R^a$, —OC(O)$NR^aR^b$, $C_3$-$C_8$ cycloalkyl, 3-12 membered heterocyclyl, $C_6$-$C_{12}$ aryl and 5-12 membered heteroaryl; where $R^a$ and $R^b$ are defined as in formula (I) above.

In some embodiments, X and Z are independently selected from the group consisting of $C_1$-$C_8$ alkyl, $C_3$-$C_8$ cycloalkyl, 3-12 membered heterocyclyl, $C_6$-$C_{12}$ aryl, 5-12 membered heteroaryl, each of which may be optionally substituted as described in formula (I) above. In other embodiments, X and Z are independently selected from the group consisting of —$NR^aR^b$ and —$OR^a$, where $R^a$ and $R^b$ are defined as in formula (I) above. In specific embodiments of formula (I), X and Z are each independently $C_1$-$C_8$ alkyl, preferably $C_1$-$C_4$ alkyl, where said alkyl is optionally substituted by halo, —OH, $C_1$-$C_4$ alkoxy, —CN, —$NH_2$, —NH($C_1$-$C_4$ alkyl) and —N($C_1$-$C_4$ alkyl)$_2$. In preferred embodiments, X and Z are each independently $C_1$-$C_4$ alkyl.

In compounds of formula (I), Y is H, halo, —OH or $C_1$-$C_4$ alkoxy. In specific embodiments, Y is H or F. In some such embodiments, Y is H. In other such embodiments, Y is F. In other embodiments, Y is OH. In still other embodiments, Y is $C_1$-$C_4$ alkoxy.

In preferred embodiments of formula (I), X and Z are each independently selected from $C_1$-$C_8$ alkyl, and Y is H or F. In more preferred embodiments of formula (I), X and Z are each independently selected from $C_1$-$C_4$ alkyl and Y is H.

In some embodiments, the compound of formula (I) is a compound of formula (I-A), (I-B) or (I-C):

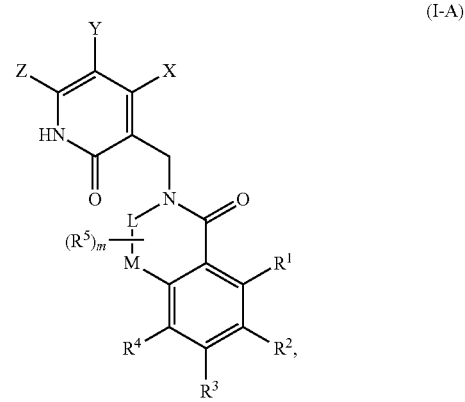

(I-A)

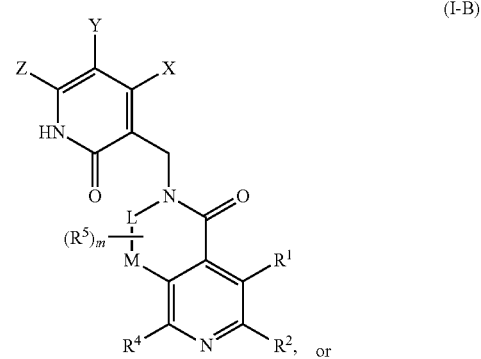

(I-B)

or

-continued $$(I-C)$$

wherein $R^1$, $R^2$, $R^3$, $R^4$, $R^5$, L, M, m, X, Y and Z are defined as in formula (I).

The embodiments described herein with respect to formula (I), and combinations thereof, are also applicable to the corresponding groups in formulae (I-A), (I-B) and (I-C).

In another aspect, the invention provides a compound of formula (II):

$$(II)$$

or a pharmaceutically acceptable salt thereof,
wherein:
U is N or $CR^3$;
V is N or $CR^4$;
$R^1$ is $C_1$-$C_8$ alkyl, $C_1$-$C_8$ alkoxy, halo, —OH, —CN or —$NR^7R^8$, where each said $C_1$-$C_8$ alkyl or $C_1$-$C_8$ alkoxy is optionally substituted by one or more $R^{21}$;
$R^2$ is selected from the group consisting of H, $C_1$-$C_8$ alkyl, $C_1$-$C_8$ alkoxy, —$OR^6$, —$NR^7R^8$, —$C(O)NR^7R^8$, —$SO_2NR^7R^8$, —$NR^7SO_2R_8$, $C_3$-$C_8$ cycloalkyl, 3-12 membered heterocyclyl, $C_6$-$C_{12}$ aryl and 5-12 membered heteroaryl, where each said $C_1$-$C_8$ alkyl or $C_1$-$C_8$ alkoxy is optionally substituted by one or more $R^{22}$, and each said $C_3$-$C_8$ cycloalkyl, 3-12 membered heterocyclyl, $C_6$-$C_{12}$ aryl or 5-12 membered heteroaryl is optionally substituted by one or more $R^{32}$;
$R^3$ is H, $C_1$-$C_8$ alkyl, $C_1$-$C_8$ alkoxy, halo, —OH, —CN or —$NR^7R^8$, where each said $C_1$-$C_8$ alkyl or $C_1$-$C_8$ alkoxy is optionally substituted by one or more $R^{23}$;
$R^4$ is selected from the group consisting of H, halo, $C_1$-$C_8$ alkyl, $C_3$-$C_8$ cycloalkyl, 3-12 membered heterocyclyl, $C_6$-$C_{12}$ aryl, 5-12 membered heteroaryl, —($C_1$-$C_4$ alkyl)$R^z$, —$OR^x$, —CN, —$C(O)R^x$, —$CO_2R^x$, —$C(O)NR^xR^y$, —$SR^x$, —$SOR^x$, —$SO_2R^x$, —$SO_2NR^xR^y$, —$NO_2$, —$NR^xR^y$,
—$NR^xC(O)R^y$, —$NR^xC(O)NR^xR^y$, —$NR^xC(O)OR^y$, —$NR^xSO_2R^y$, —$NR^xSO_2NR^xR^y$, —$OC(O)R^x$ and —$OC(O)NR^xR^y$;
each $R^x$ and $R^y$ is independently selected from the group consisting of H, $C_1$-$C_8$ alkyl, $C_3$-$C_8$ cycloalkyl, 3-12 membered heterocyclyl, $C_6$-$C_{12}$ aryl and 5-12 membered heteroaryl; or $R^x$ and $R^y$ may be taken together with the N atom to which they are attached to form a 3-12 membered heterocyclyl or 5-12 membered heteroaryl ring, each optionally containing 1, 2 or 3 additional heteroatoms selected from O, N and S;
each $R^z$ is independently selected from the group consisting of $C_3$-$C_8$ cycloalkyl, 3-12 membered heterocyclyl, $C_6$-$C_{12}$ aryl and 5-12 membered heteroaryl; and
wherein each said $C_1$-$C_8$ alkyl in $R^4$, $R^x$ or $R^y$ and each said $C_1$-$C_4$ alkyl in ($C_1$-$C_4$ alkyl)$R^z$ is optionally substituted by one or more $R^{24}$, and each said $C_3$-$C_8$ cycloalkyl, 3-12 membered heterocyclyl, $C_6$-$C_{12}$ aryl, or 5-12 membered heteroaryl in $R^4$, $R^x$, $R^y$, $R^z$, or $R^x$ and $R^y$ taken together is optionally substituted by one or more $R^{34}$;
each $R^5$ is independently selected from the group consisting of halo, —OH, =O, $C_1$-$C_4$ alkyl, $C_1$-$C_4$ alkoxy, —CN, —$NR^9R^{10}$ and —$C(O)NR^9R^{10}$, where each said $C_1$-$C_4$ alkyl or $C_1$-$C_4$ alkoxy is optionally substituted with 1 to 3 substituents independently selected from the group consisting of halo, —OH, $C_1$-$C_4$ alkoxy, —CN, —$NR^9R^{10}$ and —$C(O)NR^9R^{10}$;
$R^6$ is —$(CR^{11}R^{12})_n$—$R^{13}$;
each $R^7$ and $R^8$ is independently selected from the group consisting of H, $C_1$-$C_8$ alkyl, $C_3$-$C_8$ cycloalkyl, 3-12 membered heterocyclyl, $C_6$-$C_{12}$ aryl, and 5-12 membered heteroaryl; or
$R^7$ and $R^8$ may be taken together with the N atom to which they are attached to form a 3-12 membered heterocyclyl or 5-12 membered heteroaryl, each optionally containing 1, 2 or 3 additional heteroatoms selected from O, N and S;
where each said $C_1$-$C_8$ alkyl in $R^7$ or $R^8$ is optionally substituted by one or more $R^{27}$, and each said $C_3$-$C_8$ cycloalkyl, 3-12 membered heterocyclyl, $C_6$-$C_{12}$ aryl, or 5-12 membered heteroaryl in $R^7$, $R^8$, or $R^7$ and $R^8$ taken together is optionally substituted by one or more $R^{37}$;
each $R^9$ and $R^{10}$ is independently H or $C_1$-$C_4$ alkyl; or
$R^9$ and $R^{10}$ may be taken together with the N atom to which they are attached to form a 3-12 membered heterocyclyl or 5-12 membered heteroaryl, each optionally containing 1, 2 or 3 additional heteroatoms selected from O, N and S;
where each said $C_1$-$C_4$ alkyl in $R^9$ or $R^{10}$, and each said 3-12 membered heterocyclyl or 5-12 membered heteroaryl in $R^9$ and $R^{10}$ taken together is optionally substituted by 1 to 3 substituents independently selected from the group consisting of halo, —OH, =O, $C_1$-$C_4$ alkyl, $C_1$-$C_4$ alkoxy, —CN, —$NH_2$, —$NH(C_1$-$C_4$ alkyl) and —$N(C_1$-$C_4$ alkyl)$_2$;
each $R^{11}$ and $R^{12}$ is independently H, halo or $C_1$-$C_4$ alkyl, where each said $C_1$-$C_4$ alkyl is optionally substituted by one or more $R^{22}$;
$R^{13}$ is selected from the group consisting of $C_3$-$C_8$ cycloalkyl, 3-12 membered heterocyclyl, $C_6$-$C_{12}$ aryl, and 5-12 membered heteroaryl, where each said $C_3$-$C_8$ cycloalkyl, 3-12 membered heterocyclyl, $C_6$-$C_{12}$ aryl or 5-12 membered heteroaryl is optionally substituted by one or more $R^{32}$;
m is 0 to 4;
n is 0 to 4;

each $R^{21}$, $R^{22}$, $R^{23}$ and $R^{24}$ is independently selected from the group consisting of halo, $C_1$-$C_8$ alkyl, —CN, =O, —C(O)$R^e$, —CO$_2R^e$, —C(O)NR$^e$R$^f$, —OR$^e$, —SR$^e$, —SOR$^e$, —SO$_2$R$^e$, —SO$_2$NR$^e$R$^f$, —NO$_2$, —NR$^e$R$^f$, —NR$^e$C(O)R$^f$, —NR$^e$C(O)NR$^e$R$^f$, —NR$^e$C(O)OR$^f$, —NR$^e$SO$_2$R$^f$, —NR$^e$SO$_2$NR$^e$R$^f$, —OC(O)R$^e$, —OC(O)NR$^e$R$^f$, $C_3$-$C_8$ cycloalkyl, 3-12 membered heterocyclyl, $C_6$-$C_{12}$ aryl and 5-12 membered heteroaryl;

each $R^e$ and $R^f$ is independently selected from the group consisting of H, $C_1$-$C_8$ alkyl, $C_3$-$C_8$ cycloalkyl, 3-12 membered heterocyclyl, $C_6$-$C_{12}$ aryl and 5-12 membered heteroaryl; or $R^e$ and $R^f$ may be taken together with the N atom to which they are attached to form a 3-12 membered heterocyclyl or 5-12 membered heteroaryl ring, each optionally containing 1, 2 or 3 additional heteroatoms selected from O, N and S;

wherein each said $C_1$-$C_8$ alkyl, $C_3$-$C_8$ cycloalkyl, 3-12 membered heterocyclyl, $C_6$-$C_{12}$ aryl or 5-12 membered heteroaryl in $R^{21}$, $R^{22}$, $R^{23}$, $R^{24}$, $R^e$, $R^f$, or $R^e$ and $R^f$ taken together is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$;

each $R^{27}$ is independently selected from the group consisting of halo, —OH, $C_1$-$C_4$ alkoxy, —CN, —NR$^9$R$^{10}$, $C_3$-$C_8$ cycloalkyl, 3-12 membered heterocyclyl, $C_6$-$C_{12}$ aryl and 5-12 membered heteroaryl, where each said $C_1$-$C_4$ alkoxy, $C_3$-$C_8$ cycloalkyl, 3-12 membered heterocyclyl, $C_6$-$C_{12}$ aryl or 5-12 membered heteroaryl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$;

each $R^{32}$, $R^{34}$ and $R^{37}$ is independently selected from the group consisting of halo, $C_1$-$C_8$ alkyl, —CN, =O, —C(O)R$^c$, —CO$_2$R$^c$, —C(O)NR$^c$R$^d$, —OR$^c$, —SR$^c$, —SOR$^c$, —SO$_2$R$^c$, —SO$_2$NR$^c$R$^d$, —NO$_2$, —NR$^c$R$^d$, —NR$^c$C(O)R$^d$, —NR$^c$C(O)NR$^c$R$^d$, —NR$^c$C(O)OR$^d$, —NR$^c$SO$_2$R$^d$, —NR$^c$SO$_2$NR$^c$R$^d$, —OC(O)R, —OC(O)NR$^c$R$^d$, $C_3$-$C_8$ cycloalkyl, 3-12 membered heterocyclyl, $C_6$-$C_{12}$ aryl and 5-12 membered heteroaryl;

each $R^c$ and $R^d$ is independently selected from the group consisting of H, $C_1$-$C_8$ alkyl, $C_3$-$C_8$ cycloalkyl, 3-12 membered heterocyclyl, $C_6$-$C_{12}$ aryl and 5-12 membered heteroaryl; or $R^c$ and $R^d$ may be taken together with the N atom to which they are attached to form a 3-12 membered heterocyclyl or 5-12 membered heteroaryl ring, each optionally containing 1, 2 or 3 additional heteroatoms selected from O, N and S;

wherein each said $C_1$-$C_8$ alkyl, $C_3$-$C_8$ cycloalkyl, 3-12 membered heterocyclyl, $C_6$-$C_{12}$ aryl or 5-12 membered heteroaryl in $R^{32}$, $R^{34}$, $R^{37}$, $R^c$, $R^d$, or $R^c$ and $R^d$ taken together is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$;

X and Z are independently selected from the group consisting of H, $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, 5-12 membered heteroaryl, halo, CN, —C(O)R$^a$, —CO$_2$R$^a$, —C(O)NR$^a$R$^b$, —SR$^a$, —SOR$^a$, —SO$_2$R$^a$, —SO$_2$NR$^a$R$^b$, —NO$_2$, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$ or —OC(O)NR$^a$R$^b$;

wherein each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl group is optionally substituted by one or more substituents independently selected from the group consisting of halo, —CN, —C(O)R$^a$, —CO$_2$R$^a$, —C(O)NR$^a$R$^b$, —SR$^a$, —SOR$^a$, —SO$_2$R$^a$, —SO$_2$NR$^a$R$^b$, —NO$_2$, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, $C_3$-$C_8$ cycloalkyl, 3-12 membered heterocyclyl, $C_6$-$C_{12}$ aryl, and 5-12 membered heteroaryl;

each $R^a$ and $R^b$ is independently H, $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl or 5-12 membered heteroaryl, where each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl is optionally substituted by one or more substituents independently selected from the group consisting of halo, $C_1$-$C_4$ alkyl, —OR$^{14}$, —NR$^{14}$$_2$, —CO$_2$R$^{14}$, —C(O)NR$^{14}$$_2$, —SO$_2$R$^{14}$ and —SO$_2$NR$^{14}$$_2$, where each $R^{14}$ is independently H or $C_1$-$C_4$ alkyl; or $R^a$ and $R^b$ may be taken together with the N atom to which they are attached to form a 3-12 membered heterocyclyl or 5-12 membered heteroaryl, each optionally containing 1, 2 or 3 additional heteroatoms selected from O, N and S, wherein said heterocyclyl or heteroaryl is optionally substituted by one or more substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$; and Y is H, halo, —OH or $C_1$-$C_4$ alkoxy.

The embodiments described herein with formula (I), and combinations thereof, are also applicable to the corresponding groups in formula (II).

In compounds of formula (II), U is N or CR$^3$ and V is N or CR$^4$, and U and V are independently selected.

In frequent embodiments of formula (II), U is CR$^3$ and V is CR$^4$, such that the ring containing U and V is a phenyl ring. Such 3,4-dihydroisoquinolin-1(2H)-one compounds are sometimes represented by formula (II-A). In some such embodiments, R$^3$ is H or halo, preferably H or F, and more preferably H.

In another embodiment of formula (II), U is N and V is CR$^4$, such that the ring containing U and V is a [4,3-c]-fused pyridine ring. Such 3,4-dihydro-2,6-naphthyridin-1(2H)-one compounds are sometimes represented by formula (II-B).

In another embodiment of formula (II), U is CR$^3$ and V is N, such that the ring containing U and V is a [3,2-c]-fused pyridine ring. Such 7,8-dihydro-1,6-naphthyridin-5(6H)-one compounds are sometimes represented by formula (II-C). In some such embodiments, R$^3$ is H or halo, preferably H or F, and more preferably H.

In frequent embodiments of formula (II), m is 0 and R$^5$ is absent. In some embodiments of formula (II), m is 1 or 2, and each R$^5$ is independently selected from the group consisting of halo, —OH, and $C_1$-$C_4$ alkyl. In some embodiments, m is 1 or 2 and R$^5$ is independently selected from the group consisting of F, —OH, and methyl.

In some embodiments of formula (II), $R^1$ is $C_1$-$C_4$ alkyl or halo, optionally substituted by 1 to 3 $R^{21}$ groups. In some such embodiments, $R^1$ is halo, preferably Cl or F. In other such embodiments, $R^1$ is $C_1$-$C_4$ alkyl, where said $C_1$-$C_4$ alkyl is optionally substituted by 1 to 3 $R^{21}$ groups. In specific embodiments, $R^1$ is unsubstituted $C_1$-$C_4$ alkyl, preferably methyl or ethyl. In specific embodiments, $R^1$ is methyl, ethyl, chloro or fluoro. In preferred embodiments, $R^1$ is Cl. In other preferred embodiments, $R^1$ is methyl.

In some embodiments of formula (II), $R^2$ is $C_1$-$C_8$ alkoxy, optionally substituted by 1 to 5 $R^{22}$ groups. In other embodiments, $R^2$ is $C_1$-$C_4$ alkoxy optionally substituted by 1 to 5 $R^{22}$ groups. In other embodiments, $R^2$ is $C_1$-$C_4$ alkoxy optionally substituted by 1 to 3 $R^{22}$ groups. In some such embodiments, each $R^{22}$ is independently selected from halo or —OH, preferably F or —OH. In other such embodiments, each $R^{22}$ is independently selected from halo, —C(O)NR$^e$R$^f$ and —OR$^e$, where R$^e$ and R$^f$ are independently H or $C_1$-$C_4$ alkyl.

In specific embodiments of formula (II), $R^2$ is methoxy, ethoxy, propoxy, isopropoxy, n-butoxy, sec-butoxy or tert-butoxy, each of which may be independently substituted by 1 to 5 fluoro or OH groups, up to the number of hydrogen atoms. In some embodiments, $R^2$ is methoxy, ethoxy, propoxy, isopropoxy, n-butoxy, sec-butoxy or tert-butoxy. In one embodiment, $R^2$ is isopropoxy. In another embodiment, $R^2$ is ethoxy. In yet another embodiment, $R^2$ is sec-butoxy.

In further embodiments of formula (II), $R^2$ is $C_1$-$C_8$ fluoroalkoxy, i.e., a $C_1$-$C_8$ alkoxy group substituted by 1 to 5 F, up to the number of hydrogen atoms. In some such embodiments, $R^2$ is $C_1$-$C_4$ fluoroalkoxy, i.e., a $C_1$-$C_4$ alkoxy group substituted by 1 to 5 F, up to the number of hydrogen atoms. In specific embodiments, $R^2$ is 1,1-difluoromethoxy, trifluoromethoxy, 2,2,2-trifluoroethoxy, 1-(trifluoromethyl)ethoxy, 1,1,1-(trifluoropropan-2-yl)oxy, 3,3,4,4-tetrafluorobutoxy, 3,3,3-trifluoro-2-hydroxypropoxy, 1,1-difluoropropan-2-yl)oxy or 2,2-difluoroethoxy. In a preferred embodiment of formula (II), $R^2$ is $C_1$-$C_4$ alkoxy or $C_1$-$C_4$ fluoroalkoxy.

In another embodiment of formula (II), $R^2$ is 5-12 membered heteroaryl, where said heteroaryl is optionally substituted by 1 to 3 $R^{32}$ groups. In some embodiments, $R^2$ is a 5-6 membered heteroaryl, optionally substituted by 1 to 3 $R^{32}$ groups. In one preferred embodiment, $R^2$ is a 5-6 membered heteroaryl is selected from the group consisting of pyrazolyl, imidazolyl, pyrrolyl, triazolyl, pyridinyl and pyrimidinyl, each optionally substituted by 1 to 3 $R^{32}$ groups. In some such embodiments, $R^2$ is pyrazolyl or triazolyl optionally substituted by 1 to 3 $R^{32}$ groups. In some embodiments of each of the foregoing, each $R^{32}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected.

In other embodiments of formula (II), $R^2$ is $C_1$-$C_8$ alkyl, optionally substituted by 1 to 3 $R^{22}$ groups. In some such embodiments, $R^2$ is $C_1$-$C_4$ alkyl optionally substituted by 1 to 3 $R^{22}$. In specific embodiments, each $R^{22}$ is independently selected from halo, —C(O)NR$^e$R$^f$, —OR$^e$, —NR$^e$R$^f$, —NR$^e$C(O)R$^f$ and —NR$^e$SO$_2$R$^f$ where R$^e$ and R$^f$ are defined as in formula (I) above.

In further embodiments of formula (II), $R^2$ is OR$^6$, where $R^6$ is —(CR$^{11}$R$^{12}$)$_n$—R$^{13}$ and n is 0 to 4. In such compounds, each $R^{11}$ and $R^{12}$ is independently H, halo or $C_1$-$C_4$ alkyl, where each said $C_1$-$C_4$ alkyl is optionally substituted by one or more $R^{22}$. Preferably, each $R^{11}$ and $R^{12}$ is independently H, halo or unsubstituted $C_1$-$C_4$ alkyl. In specific embodiments, each $R^{11}$ and $R^{12}$ is independently H or methyl. In the foregoing embodiments, $R^{13}$ is selected from the group consisting of $C_3$-$C_8$ cycloalkyl, 3-12 membered heterocyclyl, $C_6$-$C_{12}$ aryl, and 5-12 membered heteroaryl, where each said $C_3$-$C_8$ cycloalkyl, 3-12 membered heterocyclyl, $C_6$-$C_{12}$ aryl or 5-12 membered heteroaryl is optionally substituted by one or more $R^{32}$, preferably 1 to 3 $R^{32}$. In some such embodiments, n is 0 and $R^{13}$ is $C_3$-$C_8$ cycloalkyl, 3-12 membered heterocyclyl, $C_6$-$C_{12}$ aryl, or 5-12 membered heteroaryl, such that —OR$^6$ comprises a $C_3$-$C_8$ cycloalkyoxy, 3-12 membered heterocycloxy, $C_6$-$C_{12}$ aryloxy or 5-12 membered heteroaryloxy group, respectively, each of which may be optionally substituted by one or more $R^{32}$, and preferably 1 to 3 $R^{32}$. In other embodiments, n is 1 or 2 and $R^{13}$ is 5-12 membered heteroaryl, optionally substituted by one or more $R^{32}$, preferably 1 to 3 $R^{32}$. In some embodiments when $R^2$ is —OR$^6$, each $R^{32}$ is independently selected from the group consisting of halo and $C_1$-$C_8$ alkyl, where each said $C_1$-$C_8$ alkyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$.

In some embodiments of formula (II), $R^3$ is H, $C_1$-$C_8$ alkyl, $C_1$-$C_8$ alkoxy or halo. In specific embodiments $R^3$ is H or halo, preferably H or F. In preferred embodiments, $R^3$ is H. In other embodiments, $R^3$ is F.

In one embodiment of formula (II), $R^4$ is H, halo or —CN. In some such embodiments, $R^4$ is H. In other such embodiments, $R^4$ is halo, preferably Cl or F. In other such embodiments, $R^4$ is Cl or Br. In still other such embodiments, $R^4$ is —CN.

In another embodiment of formula (II), $R^4$ is $C_1$-$C_8$ alkyl, optionally substituted by 1 to 3 $R^{24}$. In some such embodiments, $R^4$ is $C_1$-$C_4$ alkyl, optionally substituted by 1 to 3 $R^{24}$ groups.

In specific embodiments, each $R^{24}$ is independently selected from the group consisting of halo, —OR$^e$, —NR$^e$R$^f$, —NR$^e$C(O)R$^f$, —NR$^e$C(O)OR$^f$, $C_3$-$C_8$ cycloalkyl, 3-12 membered heterocyclyl, $C_6$-$C_{12}$ aryl, and 5-12 membered heteroaryl, each of which is further defined and optionally substituted as described in formula (I).

In yet another embodiment of formula (II), $R^4$ is selected from the group consisting of $C_3$-$C_8$ cycloalkyl, 3-12 membered heterocyclyl, $C_6$-$C_{12}$ aryl, and 5-12 membered heteroaryl, wherein each said $C_3$-$C_8$ cycloalkyl, 3-12 membered heterocyclyl, $C_6$-$C_{12}$ aryl, or 5-12 membered heteroaryl in $R^4$ is optionally substituted by one or more $R^{34}$.

In a preferred embodiment of formula (II), $R^4$ is a 5-12 membered heteroaryl, optionally substituted by one or more $R^{34}$. In some such embodiments, said 5-12 membered heteroaryl is optionally substituted by 1 to 3 $R^{34}$ groups. In some embodiments, $R^4$ is a 5-6 membered heteroaryl, optionally substituted by 1 to 3 $R^{34}$ groups. In some such embodiments, $R^4$ is selected from the group consisting of pyrazolyl, imidazolyl, pyrrolyl, triazolyl, tetrazolyl, thienyl, thiazolyl, isothiazolyl, furanyl, oxazoyl, isoxazolyl, oxadiazolyl, thiadiazolyl, pyridinyl, pyrimidinyl, pyrazinyl or pyridazinyl ring, each of which is optionally substituted by 1 to 3 $R^{34}$ groups.

In some embodiments, when $R^4$ is $C_3$-$C_8$ cycloalkyl, 3-12 membered heterocyclyl, $C_6$-$C_{12}$ aryl or 5-12 membered heteroaryl, each $R^{34}$ is independently halo, $C_1$-$C_8$ alkyl, —CN, —C(O)NR$^c$R$^d$, —NR$^c$R$^d$, —NR$^c$C(O)R$^d$, $C_3$-$C_8$ cycloalkyl, $C_6$-$C_{12}$ aryl and 5-12 membered heteroaryl, where said $C_1$-$C_8$ alkyl is optionally substituted by —OH, —$C_1$-$C_4$ alkoxy or halo, and each R$^c$ and R$^d$ is independently H or $C_1$-$C_4$ alkyl. In specific embodiments, each $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected.

In a first preferred embodiment of formula (II), U is CR$^3$ and V is CR$^4$ and the compounds have a combination of two or more of the following preferred features:
  $R^1$ is $C_1$-$C_4$ alkyl or halo;
  $R^2$ is $C_1$-$C_8$ alkoxy, optionally substituted by 1 to 5 $R^{22}$ groups;
    each $R^{22}$ is independently halo or —OH;
  $R^3$ is H or F;
  $R^4$ is H, halo or 5-12 membered heteroaryl, where said 5-12 membered heteroaryl is optionally substituted by 1 to 3 $R^{34}$ groups;
    each $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
  m is 0 and $R^5$ is absent; or
  m is 1 or 2, and each $R^5$ is independently selected from the group consisting of halo, —OH, and $C_1$-$C_4$ alkyl;
  X and Z are independently $C_1$-$C_4$ alkyl; and
  Y is H or F.

In a second preferred embodiment of formula (II), U is CR$^3$ and V is CR$^4$ and the compounds have a combination of two or more of the following preferred features:
  $R^1$ is $C_1$-$C_4$ alkyl or halo;
  $R^2$ is a 5-6 membered heteroaryl, optionally substituted by 1 to 3 $R^{32}$ groups;
  $R^3$ is H or F;
  $R^4$ is H, halo or 5-12 membered heteroaryl, where said 5-12 membered heteroaryl is optionally substituted by 1 to 3 $R^{34}$ groups;
    each $R^{32}$ and $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
  m is 0 and $R^5$ is absent; or
  m is 1 or 2, and each $R^5$ is independently selected from the group consisting of halo, —OH, and $C_1$-$C_4$ alkyl;
  X and Z are independently $C_1$-$C_4$ alkyl; and
  Y is H or F.

In a third preferred embodiment of formula (II), U is CR$^3$ and V is CR$^4$ and the compounds have a combination of two or more of the following preferred features:
  $R^1$ is $C_1$-$C_4$ alkyl or halo;
  $R^2$ is a 5-6 membered heteroaryl, optionally substituted by 1 to 3 $R^{32}$ groups;
  $R^3$ is H;
  $R^4$ is H or halo;
    each $R^{32}$ is independently selected from the group consisting of halo, $C_1$-$C_8$ alkyl, —OR$^c$, —SR$^c$, —SO$_2$R' and —NR$^c$R$^d$, and each R$^c$ and R$^d$ is independently H or $C_1$-$C_8$ alkyl; or
    each $R^{32}$ is independently selected from the group consisting of halo and $C_1$-$C_8$ alkyl, where each said $C_1$-$C_8$ alkyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$;
  m is 0 and $R^5$ is absent;
  X and Z are independently $C_1$-$C_4$ alkyl; and
  Y is H.

In a fourth preferred embodiment of formula (II), U is CR$^3$ and V is CR$^4$ and the compounds have a combination of two or more of the following preferred features:
  $R^1$ is $C_1$-$C_4$ alkyl or halo;
  $R^2$ is OR$^6$;
  $R^6$ is —(CR$^{11}$R$^{12}$)$_n$—R$^{13}$;
  n is 0 or 1;
  $R^{13}$ is 3-12 membered heterocyclyl or 5-12 membered heteroaryl, where each said 3-12 membered heterocyclyl or 5-12 membered heteroaryl is optionally substituted by 1 to 3 $R^{32}$; or
  $R^{13}$ is 3-12 membered heterocyclyl, optionally substituted by 1 to 3 $R^{32}$; or
  $R^{13}$ is 5-12 membered heteroaryl, optionally substituted by 1 to 3 $R^{32}$; or
  $R^{13}$ is $C_3$-$C_8$ cycloalkyl, optionally substituted by 1 to 3 $R^{32}$; or
  $R^{13}$ is $C_6$-$C_{12}$ aryl, optionally substituted by 1 to 3 $R^{32}$;
  $R^3$ is H;
  $R^4$ is H or halo;
    each $R^{32}$ is independently selected from the group consisting of halo, $C_1$-$C_8$ alkyl, —OR$^c$, —SR$^c$, —SO$_2$R$^c$ and —NR$^c$R$^d$, and each R$^c$ and R$^d$ is independently H or $C_1$-$C_8$ alkyl; or
    each $R^{32}$ is independently selected from the group consisting of halo and $C_1$-$C_8$ alkyl, where each said $C_1$-$C_8$ alkyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$;
  m is 0 and $R^5$ is absent;
  X and Z are independently $C_1$-$C_4$ alkyl; and
  Y is H.

In a fifth preferred embodiment of formula (II), U is CR$^3$ and V is CR$^4$ and the compounds have a combination of two or more of the following preferred features:
  $R^1$ is $C_1$-$C_4$ alkyl or halo;
  $R^2$ is OR$^6$;
  $R^6$ is —(CR$^{11}$R$^{12}$)$_n$—R$^{13}$;
  n is 0 or 1;
  $R^{13}$ is 3-12 membered heterocyclyl, optionally substituted by 1 to 3 $R^{32}$;
  $R^3$ is H;
  $R^4$ is H or halo;
    each $R^{32}$ is independently selected from the group consisting of halo and $C_1$-$C_8$ alkyl, where each said $C_1$-$C_8$ alkyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$;

m is 0 and $R^5$ is absent;

X and Z are independently $C_1$-$C_4$ alkyl; and

Y is H.

In a sixth preferred embodiment of formula (II), U is $CR^3$ and V is $CR^4$ and the compounds have a combination of two or more of the following preferred features:

$R^1$ is $C_1$-$C_4$ alkyl or halo;

$R^2$ is $C_1$-$C_4$ alkoxy;

$R^3$ is H;

$R^4$ is H or halo or 5-12 membered heteroaryl, where said 5-12 membered heteroaryl is optionally substituted by 1 to 3 $R^{34}$ groups;

each $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent;

X and Z are independently $C_1$-$C_4$ alkyl; and

Y is H.

In another embodiment of formula (II), U is N and V is $CR^4$ and the compounds have a combination of two or more of the following preferred features:

$R^1$ is $C_1$-$C_4$ alkyl or halo;

$R^2$ is $C_1$-$C_8$ alkoxy, optionally substituted by 1 to 5 $R^{22}$ groups;

each $R^{22}$ is independently halo or —OH;

$R^4$ is H, halo or 5-12 membered heteroaryl, where said 5-12 membered heteroaryl is optionally substituted by 1 to 3 $R^{34}$ groups;

each $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In another embodiment of formula (II), U is N and V is $CR^4$ and the compounds have a combination of two or more of the following preferred features:

$R^1$ is $C_1$-$C_4$ alkyl or halo;

$R^2$ is a 5-6 membered heteroaryl, optionally substituted by 1 to 3 $R^{32}$ groups;

$R^4$ is H, halo or 5-12 membered heteroaryl, where said 5-12 membered heteroaryl is optionally substituted by 1 to 3 $R^{34}$ groups;

each $R^{32}$ and $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In another embodiment of formula (II), U is $CR^3$ and V is N and the compounds have a combination of two or more of the following preferred features:

$R^1$ is $C_1$-$C_4$ alkyl or halo;

$R^2$ is $C_1$-$C_8$ alkoxy, optionally substituted by 1 to 5 $R^{22}$ groups;

each $R^{22}$ is independently halo or —OH;

$R^3$ is H or F;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In a further embodiment of formula (II), U is $CR^3$ and V is N and the compounds have a combination of two or more of the following preferred features:

$R^1$ is $C_1$-$C_4$ alkyl or halo;

$R^2$ is a 5-6 membered heteroaryl, optionally substituted by 1 to 3 $R^{32}$ groups;

$R^3$ is H or F;

each $R^{32}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In some particularly preferred embodiments of formula (II), the compounds have a combination of three, four, five, six, seven, eight, nine or ten of the preferred features in each of the sets of preferred embodiments described above.

In some embodiments, the compound of formula (II) is a compound of formula (II-A), (II-B) or (II-C):

(II-A)

-continued

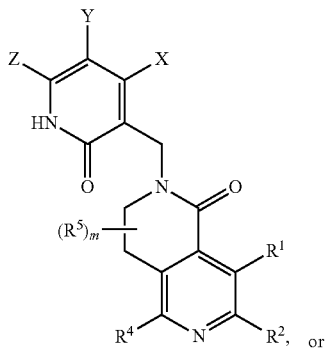
(II-B)

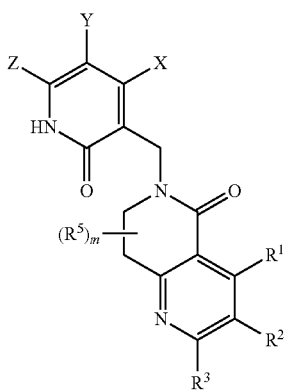
(II-C)

or a pharmaceutically acceptable salt thereof,
wherein $R^1$, $R^2$, $R^3$, $R^4$, $R^5$, m, X, Y and Z are defined as in formula (I).

The embodiments described herein with respect to formula (II), and combinations thereof, are also applicable to the corresponding groups in formulae (II-A), (II-B) and (II-C).

In another aspect, the invention provides a compound of formula (III):

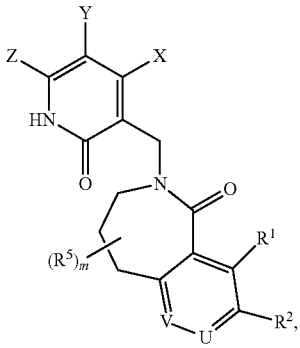
(III)

or a pharmaceutically acceptable salt thereof,
wherein $R^1$, $R^2$, U, V, $R^5$, m, X, Y and Z are defined as in formula (I).

The embodiments described herein with respect to formula (I), and combinations thereof, are also applicable to the corresponding groups in formula (III).

In compounds of formula (III), U is N or $CR^3$ and V is N or $CR^4$, and U and V are independently selected.

In frequent embodiments of formula (III), U is $CR^3$ and V is $CR^4$, such that the ring containing U and V is a phenyl ring. Such 2,3,4,5-tetrahydro-1H-benzo[c]azepin-1-one compounds are sometimes represented by formula (III-A). In some such embodiments, $R^3$ is H or halo, preferably H or F, and more preferably H.

In another embodiment of formula (III), U is N and V is $CR^4$, such that the ring containing U and V is a [4,3-c]-fused pyridine ring. Such 6,7,8,9-tetrahydro-5H-pyrido[4,3-c]azepin-5-one compounds are sometimes represented by formula (III-B).

In another embodiment of formula (III), U is $CR^3$ and V is N, such that the ring containing U and V is a [3,2-c]-fused pyridine ring. Such 6,7,8,9-tetrahydro-5H-pyrido[3,2-c]azepin-5-one compounds are sometimes represented by formula (III-C). In some such embodiments, $R^3$ is H or halo, preferably H or F, and more preferably H.

In frequent embodiments of formula (III), m is 0 and $R^5$ is absent. In some embodiments of formula (III), m is 1 or 2, and each $R^5$ is independently selected from the group consisting of halo, —OH, and $C_1$-$C_4$ alkyl. In some embodiments, m is 1 or 2 and $R^5$ is independently selected from the group consisting of F, —OH, and methyl.

In some embodiments of formula (III), $R^1$ is $C_1$-$C_4$ alkyl or halo, optionally substituted by 1 to 3 $R^{21}$ groups. In some such embodiments, $R^1$ is halo, preferably Cl or F. In other such embodiments, $R^1$ is $C_1$-$C_4$ alkyl, where said $C_1$-$C_4$ alkyl is optionally substituted by 1 to 3 $R^{21}$ groups. In specific embodiments, $R^1$ is unsubstituted $C_1$-$C_4$ alkyl, preferably methyl or ethyl. In specific embodiments, $R^1$ is methyl, ethyl, chloro or fluoro. In preferred embodiments, $R^1$ is Cl. In other preferred embodiments, $R^1$ is methyl.

In some embodiments of formula (III), $R^2$ is $C_1$-$C_8$ alkoxy, optionally substituted by 1 to 5 $R^{22}$ groups. In other embodiments, $R^2$ is $C_1$-$C_4$ alkoxy optionally substituted by 1 to 5 $R^{22}$ groups. In some such embodiments, each $R^{22}$ is independently selected from halo or —OH, preferably F or —OH. In other such embodiments, each $R^{22}$ is independently selected from halo, —C(O)$NR^eR^f$ and —$OR^e$, where $R^e$ and $R^f$ are independently H or $C_1$-$C_4$ alkyl.

In specific embodiments of formula (III), $R^2$ is methoxy, ethoxy, propoxy, isopropoxy, n-butoxy, sec-butoxy or tert-butoxy, each of which may be independently substituted by 1 to 5 fluoro or OH groups, up to the number of hydrogen atoms. In some embodiments, $R^2$ is methoxy, ethoxy, propoxy, isopropoxy, n-butoxy, sec-butoxy or tert-butoxy. In one embodiment, $R^2$ is isopropoxy. In another embodiment, $R^2$ is ethoxy. In yet another embodiment, $R^2$ is sec-butoxy In further embodiments of formula (III), $R^2$ is $C_1$-$C_8$ fluoroalkoxy, i.e., a $C_1$-$C_8$ alkoxy group substituted by 1 to 5 F, up to the number of hydrogen atoms. In some such embodiments, $R^2$ is $C_1$-$C_4$ fluoroalkoxy, i.e., a $C_1$-$C_4$ alkoxy group substituted by 1 to 5 F, up to the number of hydrogen atoms. In specific embodiments, $R^2$ is 1,1-difluoromethoxy, trifluoromethoxy, 2,2,2-trifluoroethoxy, 1-(trifluoromethyl)ethoxy, 1,1,1-(trifluoropropan-2-yl)oxy, 3,3,4,4-tetrafluorobutoxy, 3,3,3-trifluoro-2-hydroxypropoxy, 1,1-difluoropropan-2-yl)oxy or 2,2-difluoroethoxy. In a preferred embodiment of formula (III), $R^2$ is $C_1$-$C_4$ alkoxy or $C_1$-$C_4$ fluoroalkoxy.

In another embodiment of formula (III), $R^2$ is 5-12 membered heteroaryl, where said heteroaryl is optionally substituted by 1 to 3 $R^{32}$ groups. In some embodiments, $R^2$ is a 5-6 membered heteroaryl, optionally substituted by 1 to 3 $R^{32}$ groups. In one preferred embodiment, $R^2$ is a 5-6 membered heteroaryl is selected from the group consisting of pyrazolyl, imidazolyl, pyrrolyl, triazolyl, pyridinyl and pyrimidinyl, each optionally substituted by 1 to 3 $R^{32}$ groups. In some such embodiments, —$R^2$ is pyrazolyl or triazolyl optionally substituted by 1 to 3 $R^{32}$ groups. In some embodiments of each of the foregoing, each $R^{32}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by halo, $C_1$-$C_4$ alkyl or $C_1$-$C_4$ alkoxy.

In other embodiments of formula (III), $R^2$ is $C_1$-$C_8$ alkyl, optionally substituted by 1 to 3 $R^{22}$ groups. In some such embodiments, $R^2$ is $C_1$-$C_4$ alkyl optionally substituted by 1 to 3 $R^{22}$. In specific embodiments, each $R^{22}$ is independently selected from halo, —C(O)NR$^e$R$^f$, —OR$^e$, —NR$^e$R$^f$, —NR$^e$C(O)R$^f$ and —NR$^e$SO$_2$R$^f$ where R$^e$ and R$^f$ are defined as in formula (I) above.

In some embodiments of formula (III), $R^3$ is H, $C_1$-$C_8$ alkyl, $C_1$-$C_8$ alkoxy or halo. In specific embodiments $R^3$ is H or halo, preferably H or F. In preferred embodiments, $R^3$ is H. In other embodiments, $R^3$ is F.

In one embodiment of formula (III), $R^4$ is H, halo or —CN. In some such embodiments, $R^4$ is H. In other such embodiments, $R^4$ is halo, preferably Cl or F. In other such embodiments, $R^4$ is Cl or Br. In still other such embodiments, $R^4$ is —CN.

In another embodiment of formula (III), $R^4$ is $C_1$-$C_8$ alkyl, optionally substituted by 1 to 3 $R^{24}$. In some such embodiments, $R^4$ is $C_1$-$C_4$ alkyl, optionally substituted by 1 to 3 $R^{24}$ groups. In specific embodiments, each $R^{24}$ is independently selected from the group consisting of halo, —OR$^e$, —NR$^e$R$^f$, —NR$^e$C(O)R$^f$, —NR$^e$C(O)OR$^f$, $C_3$-$C_8$ cycloalkyl, 3-12 membered heterocyclyl, $C_6$-$C_{12}$ aryl, and 5-12 membered heteroaryl, each of which is further defined and optionally substituted as described in formula (I).

In yet another embodiment of formula (III), $R^4$ is selected from the group consisting of $C_3$-$C_8$ cycloalkyl, 3-12 membered heterocyclyl, $C_6$-$C_{12}$ aryl, and 5-12 membered heteroaryl, wherein each said $C_3$-$C_8$ cycloalkyl, 3-12 membered heterocyclyl, $C_6$-$C_{12}$ aryl, or 5-12 membered heteroaryl in $R^4$ is optionally substituted by one or more $R^{34}$.

In a preferred embodiment of formula (III), $R^4$ is a 5-12 membered heteroaryl, optionally substituted by one or more $R^{34}$. In some such embodiments, said 5-12 membered heteroaryl is optionally substituted by 1 to 3 $R^{34}$ groups. In some embodiments, $R^4$ is a 5-6 membered heteroaryl, optionally substituted by 1 to 3 $R^{34}$ groups. In some such embodiments, $R^4$ is selected from the group consisting of pyrazolyl, imidazolyl, pyrrolyl, triazolyl, tetrazolyl, thienyl, thiazolyl, isothiazolyl, furanyl, oxazoyl, isoxazolyl, oxadiazolyl, thiadiazolyl, pyridinyl, pyrimidinyl, pyrazinyl or pyridazinyl ring, each of which is optionally substituted by 1 to 3 $R^{34}$ groups.

In some embodiments when $R^4$ is $C_3$-$C_8$ cycloalkyl, 3-12 membered heterocyclyl, $C_6$-$C_{12}$ aryl or 5-12 membered heteroaryl, each $R^{34}$ is independently halo, $C_1$-$C_8$ alkyl, —CN, —C(O)NR$^c$R$^d$, —NR$^c$R$^d$, —NR$^c$C(O)R$^d$, $C_3$-$C_8$ cycloalkyl, $C_6$-$C_{12}$ aryl and 5-12 membered heteroaryl, where said $C_1$-$C_8$ alkyl is optionally substituted by —OH, —$C_1$-$C_4$ alkoxy or halo, and each R$^c$ and R$^d$ is independently H or $C_1$-$C_4$ alkyl. In specific embodiments, each $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by halo, $C_1$-$C_4$ alkyl or $C_1$-$C_4$ alkoxy.

In one preferred embodiment of formulae (III), U is CR$^3$ and V is CR$^4$ and the compounds have a combination of two or more of the following preferred features:

$R^1$ is $C_1$-$C_4$ alkyl or halo;
$R^2$ is $C_1$-$C_8$ alkoxy, optionally substituted by 1 to 5 $R^{22}$ groups;
each $R^{22}$ is independently halo or —OH;
$R^3$ is H or F;
$R^4$ is H, halo or 5-12 membered heteroaryl, where said 5-12 membered heteroaryl is optionally substituted by 1 to 3 $R^{34}$ groups;
each $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
m is 0 and $R^5$ is absent; or
m is 1 or 2, and each $R^5$ is independently selected from the group consisting of halo, —OH, and $C_1$-$C_4$ alkyl;
X and Z are independently $C_1$-$C_4$ alkyl; and
Y is H or F.

In a second preferred embodiment of formula (III), U is CR$^3$ and V is CR$^4$ and the compounds have a combination of two or more of the following preferred features:

$R^1$ is $C_1$-$C_4$ alkyl or halo;
$R^2$ is a 5-6 membered heteroaryl, optionally substituted by 1 to 3 $R^{32}$ groups;
$R^3$ is H or F;
$R^4$ is H, halo or 5-12 membered heteroaryl, where said 5-12 membered heteroaryl is optionally substituted by 1 to 3 $R^{34}$ groups;
each $R^{32}$ and $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
m is 0 and $R^5$ is absent; or
m is 1 or 2, and each $R^5$ is independently selected from the group consisting of halo, —OH, and $C_1$-$C_4$ alkyl;
X and Z are independently $C_1$-$C_4$ alkyl; and
Y is H or F.

In a third preferred embodiment of formula (III), U is N and V is CR$^4$ and the compounds have a combination of two or more of the following preferred features:

$R^1$ is $C_1$-$C_4$ alkyl or halo;
$R^2$ is $C_1$-$C_8$ alkoxy, optionally substituted by 1 to 5 $R^{22}$ groups;
each $R^{22}$ is independently halo or —OH;
$R^4$ is H, halo or 5-12 membered heteroaryl, where said 5-12 membered heteroaryl is optionally substituted by 1 to 3 $R^{34}$ groups;
each $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In a fourth preferred embodiment of formula (III), U is N and V is $CR^4$ and the compounds have a combination of two or more of the following preferred features:

$R^1$ is $C_1$-$C_4$ alkyl or halo;

$R^2$ is a 5-6 membered heteroaryl, optionally substituted by 1 to 3 $R^{32}$ groups;

$R^4$ is H, halo or 5-12 membered heteroaryl, where said 5-12 membered heteroaryl is optionally substituted by 1 to 3 $R^{34}$ groups;

each $R^{32}$ and $R^{34}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In a fifth preferred embodiment of formula (III), U is $CR^3$ and V is N and the compounds have a combination of two or more of the following preferred features:

$R^1$ is $C_1$-$C_4$ alkyl or halo;

$R^2$ is $C_1$-$C_8$ alkoxy, optionally substituted by 1 to 5 $R^{22}$ groups;

each $R^{22}$ is independently halo or —OH;

$R^3$ is H or F;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In a sixth preferred embodiment of formulae (III), U is $CR^3$ and V is N and the compounds have a combination of two or more of the following preferred features:

$R^1$ is $C_1$-$C_4$ alkyl or halo;

$R^2$ is a 5-6 membered heteroaryl, optionally substituted by 1 to 3 $R^{32}$ groups;

$R^3$ is H or F;

each $R^{32}$ is independently —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In particularly preferred embodiments of formula (III), the compounds have a combination of three, four, five, six, seven, eight, nine or ten of the preferred features in each of the sets described above.

In some aspects, the compound of formula (III) is a compound of formula (III-A), (III-B) or (III-C):

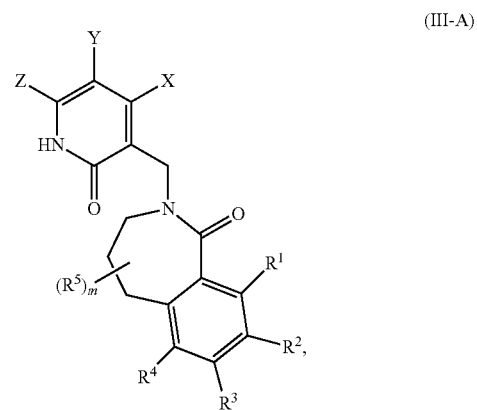

(III-A)

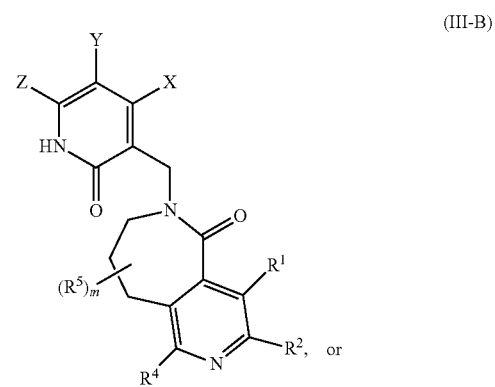

(III-B)

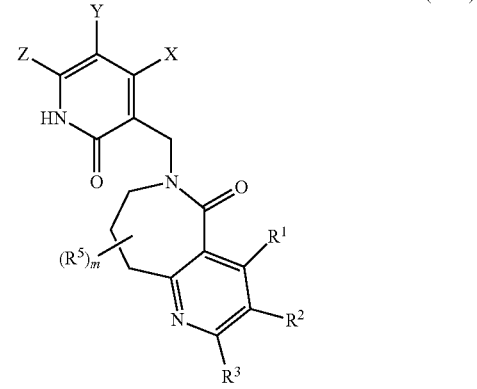

(III-C)

or a pharmaceutically acceptable salt thereof, wherein $R^1$, $R^2$, $R^3$, $R^4$, $R^5$, m, X, Y and Z are defined as in formula (I).

The embodiments described herein with respect to formula (III), and combinations thereof, are also applicable to the corresponding groups in formulae (III-A), (III-B) and (III-C).

In a further aspect, the invention provides a compound of formula (IV):

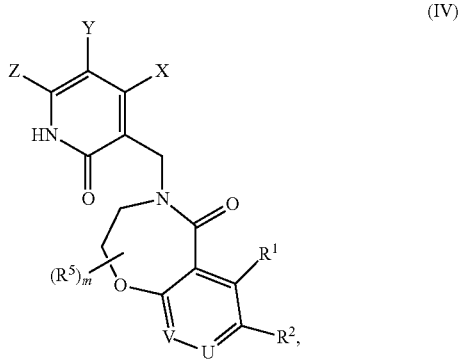
(IV)

or a pharmaceutically acceptable salt thereof,
wherein $R^1$, $R^2$, U, V, $R^5$, m, X, Y and Z are defined as in formula (I).

The embodiments described herein with respect to formula (I), and combinations thereof, are also applicable to the corresponding groups in formula (IV).

In compounds of formula (IV), U is N or $CR^3$ and V is N or $CR^4$, and U and V are independently selected.

In frequent embodiments of formula (IV), U is $CR^3$ and V is $CR^4$, such that the ring containing U and V is a phenyl ring. Such 3,4-dihydrobenzo[f][1,4]oxazepin-5(2H)-one compounds are sometimes represented by formula (IV-A). In some such embodiments, $R^3$ is H or halo, preferably H or F, and more preferably H.

In another embodiment of formula (IV), U is N and V is $CR^4$, such that the ring containing U and V is a [4,3-c]-fused pyridine ring. Such 3,4-dihydropyrido[4,3-f][1,4]oxazepin-5(2H)-one compounds are sometimes represented by formula (IV-B).

In another embodiment of formula (IV), U is $CR^3$ and V is N, such that the ring containing U and V is a [3,2-c]-fused pyridine ring. Such 3,4-dihydropyrido[3,2-f][1,4]oxazepin-5(2H)-one compounds are sometimes represented by formula (IV-C). In some such embodiments, $R^3$ is H or halo, preferably H or F, and more preferably H.

In frequent embodiments of formula (IV), m is 0 and $R^5$ is absent. In some embodiments of formula (IV), m is 1 or 2, and each $R^5$ is independently selected from the group consisting of halo, —OH, and $C_1$-$C_4$ alkyl. In some embodiments, m is 1 or 2 and $R^5$ is independently selected from the group consisting of F, —OH, and methyl.

In some embodiments of formula (IV), $R^1$ is $C_1$-$C_4$ alkyl or halo, optionally substituted by 1 to 3 $R^{21}$ groups. In some such embodiments, $R^1$ is halo, preferably Cl or F. In other such embodiments, $R^1$ is $C_1$-$C_4$ alkyl, where said $C_1$-$C_4$ alkyl is optionally substituted by 1 to 3 $R^{21}$ groups. In specific embodiments, $R^1$ is unsubstituted $C_1$-$C_4$ alkyl, preferably methyl or ethyl. In specific embodiments, $R^1$ is methyl, ethyl, chloro or fluoro. In preferred embodiments, $R^1$ is Cl. In other preferred embodiments, $R^1$ is methyl.

In some embodiments of formula (IV), $R^2$ is $C_1$-$C_8$ alkoxy, optionally substituted by 1 to 5 $R^{22}$ groups. In other embodiments, $R^2$ is $C_1$-$C_4$ alkoxy optionally substituted by 1 to 5 $R^{22}$ groups. In some such embodiments, each $R^{22}$ is independently selected from halo or —OH, preferably F or —OH. In other such embodiments, each $R^{22}$ is independently selected from halo, —C(O)$NR^eR^f$ and —$OR^e$, where $R^e$ and $R^f$ are independently H or $C_1$-$C_4$ alkyl.

In specific embodiments of formula (IV), $R^2$ is methoxy, ethoxy, propoxy, isopropoxy, n-butoxy, sec-butoxy or tert-butoxy, each of which may be independently substituted by 1 to 5 fluoro or OH groups, up to the number of hydrogen atoms. In some embodiments, $R^2$ is methoxy, ethoxy, propoxy, isopropoxy, n-butoxy, sec-butoxy or tert-butoxy. In one embodiment, $R^2$ is isopropoxy. In another embodiment, $R^2$ is ethoxy. In yet another embodiment, $R^2$ is sec-butoxy In further embodiments of formula (IV), $R^2$ is $C_1$-$C_8$ fluoroalkoxy, i.e., a $C_1$-$C_8$ alkoxy group substituted by 1 to 5 F, up to the number of hydrogen atoms. In some such embodiments, $R^2$ is $C_1$-$C_4$ fluoroalkoxy, i.e., a $C_1$-$C_4$ alkoxy group substituted by 1 to 5 F, up to the number of hydrogen atoms. In specific embodiments, $R^2$ is 1,1-difluoromethoxy, trifluoromethoxy, 2,2,2-trifluoroethoxy, 1-(trifluoromethyl) ethoxy, 1,1,1-(trifluoropropan-2-yl)oxy, 3,3,4,4-tetrafluorobutoxy, 3,3,3-trifluoro-2-hydroxypropyl, 1,1-difluoropropan-2-yl)oxy or 2,2-difluoroethoxy. In a preferred embodiment of formula (IV), $R^2$ is $C_1$-$C_4$ alkoxy or $C_1$-$C_4$ fluoroalkoxy.

In another embodiment of formula (IV), $R^2$ is 5-12 membered heteroaryl, where said heteroaryl is optionally substituted by 1 to 3 $R^{32}$ groups. In some embodiments, $R^2$ is a 5-6 membered heteroaryl, optionally substituted by 1 to 3 $R^{32}$ groups. In one preferred embodiment, $R^2$ is a 5-6 membered heteroaryl is selected from the group consisting of pyrazolyl, imidazolyl, pyrrolyl, triazolyl, pyridinyl and pyrimidinyl, each optionally substituted by 1 to 3 $R^{32}$ groups. In some such embodiments, $R^2$ is pyrazolyl optionally substituted by 1 to 3 $R^{32}$ groups. In some embodiments of each of the foregoing, each $R^{32}$ is independently —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —C(O)$NH_2$, —C(O)$NHCH_3$, —C(O)$N(CH_3)_2$, —NHC(O)$CH_3$, —$NH_2$, —$NHCH_3$, —$N(CH_3)_2$, cyclopropyl, 4-6 membered heterocyclyl, phenyl or 5-6 membered heteroaryl, where said 4-6 membered heterocyclyl, phenyl or 5-6 membered heteroaryl are optionally substituted by halo, $C_1$-$C_4$ alkyl or $C_1$-$C_4$ alkoxy.

In other embodiments of formula (IV), $R^2$ is $C_1$-$C_8$ alkyl, optionally substituted by 1 to 3 $R^{22}$ groups. In some such embodiments, $R^2$ is $C_1$-$C_4$ alkyl optionally substituted by 1 to 3 $R^{22}$. In specific embodiments, each $R^{22}$ is independently selected from halo, —C(O)$NR^eR^f$, —$OR^e$, —$NR^eR^f$, —$NR^eC(O)R^f$ and —$NR^eSO_2R^f$ where $R^e$ and $R^f$ are defined as in formula (I) above.

In some embodiments of formula (IV), $R^3$ is H, $C_1$-$C_8$ alkyl, $C_1$-$C_8$ alkoxy or halo. In specific embodiments $R^3$ is H or halo, preferably H or F. In preferred embodiments, $R^3$ is H. In other embodiments, $R^3$ is F.

In one embodiment of formula (IV), $R^4$ is H, halo or —CN. In some such embodiments, $R^4$ is H. In other such embodiments, $R^4$ is halo, preferably Cl or F. In other such embodiments, $R^4$ is Cl or Br. In still other such embodiments, $R^4$ is —CN.

In another embodiment of formula (IV), $R^4$ is $C_1$-$C_8$ alkyl, optionally substituted by 1 to 3 $R^{24}$. In some such embodiments, $R^4$ is $C_1$-$C_4$ alkyl, optionally substituted by 1 to 3 $R^{24}$ groups. In specific embodiments, each $R^{24}$ is independently selected from the group consisting of halo, —$OR^e$, —$NR^eR^f$, —$NR^eC(O)R^f$, —$NR^eC(O)OR^f$, $C_3$-$C_8$ cycloalkyl, 3-12 membered heterocyclyl, $C_6$-$C_{12}$ aryl, and 5-12 membered heteroaryl, each of which is further defined and optionally substituted as described in formula (I).

In yet another embodiment of formula (IV), $R^4$ is selected from the group consisting of $C_3$-$C_8$ cycloalkyl, 3-12 membered heterocyclyl, $C_6$-$C_{12}$ aryl, and 5-12 membered heteroaryl, wherein each said $C_3$-$C_8$ cycloalkyl, 3-12 membered heterocyclyl, $C_6$-$C_{12}$ aryl, or 5-12 membered heteroaryl in $R^4$ is optionally substituted by one or more $R^{34}$.

In a preferred embodiment of formula (IV), $R^4$ is a 5-12 membered heteroaryl, optionally substituted by one or more $R^{34}$. In some such embodiments, said 5-12 membered heteroaryl is optionally substituted by 1 to 3 $R^{34}$ groups. In some embodiments, $R^4$ is a 5-6 membered heteroaryl, optionally substituted by 1 to 3 $R^{34}$ groups. In some such embodiments, $R^4$ is selected from the group consisting of pyrazolyl, imidazolyl, pyrrolyl, triazolyl, tetrazolyl, thienyl, thiazolyl, isothiazolyl, furanyl, oxazoyl, isoxazolyl, oxadiazolyl, thiadiazolyl, pyridinyl, pyrimidinyl, pyrazinyl or pyridazinyl ring, each of which is optionally substituted by 1 to 3 $R^{34}$ groups.

In some embodiments when $R^4$ is $C_3$-$C_8$ cycloalkyl, 3-12 membered heterocyclyl, $C_6$-$C_{12}$ aryl or 5-12 membered heteroaryl, each $R^{34}$ is independently halo, $C_1$-$C_8$ alkyl, —CN, —C(O)$NR^cR^d$, —$NR^cR^d$, —$NR^cC(O)R^d$, $C_3$-$C_8$ cycloalkyl, $C_6$-$C_{12}$ aryl and 5-12 membered heteroaryl, where said $C_1$-$C_8$ alkyl is optionally substituted by —OH, —$C_1$-$C_4$ alkoxy or halo, and each $R^c$ and $R^d$ is independently H or $C_1$-$C_4$ alkyl. In specific embodiments, each $R^{34}$ is independently —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —C(O)$NH_2$, —C(O)$NHCH_3$, —C(O)N($CH_3$)$_2$, —NHC(O)$CH_3$, —$NH_2$, —$NHCH_3$, —N($CH_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by halo, $C_1$-$C_4$ alkyl or $C_1$-$C_4$ alkoxy.

In one preferred embodiment of formula (IV), U is $CR^3$ and V is $CR^4$ and the compounds have a combination of two or more of the following preferred features:
$R^1$ is $C_1$-$C_4$ alkyl or halo;
$R^2$ is $C_1$-$C_8$ alkoxy, optionally substituted by 1 to 5 $R^{22}$ groups;
each $R^{22}$ is independently halo or —OH;
$R^3$ is H or F;
$R^4$ is H, halo or 5-12 membered heteroaryl, where said 5-12 membered heteroaryl is optionally substituted by 1 to 3 $R^{34}$ groups;
each $R^{34}$ is independently —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —C(O)$NH_2$, —C(O)$NHCH_3$, —C(O)N($CH_3$)$_2$, —NHC(O)$CH_3$, —$NH_2$, —$NHCH_3$, —N($CH_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
m is 0 and $R^5$ is absent; or
m is 1 or 2, and each $R^5$ is independently selected from the group consisting of halo, —OH, and $C_1$-$C_4$ alkyl;
X and Z are independently $C_1$-$C_4$ alkyl; and
Y is H or F.

In a second preferred embodiment of formula (IV), U is $CR^3$ and V is $CR^4$ and the compounds have a combination of two or more of the following preferred features:
$R^1$ is $C_1$-$C_4$ alkyl or halo;
$R^2$ is a 5-6 membered heteroaryl, optionally substituted by 1 to 3 $R^{32}$ groups;
$R^3$ is H or F;
$R^4$ is H, halo or 5-12 membered heteroaryl, where said 5-12 membered heteroaryl is optionally substituted by 1 to 3 $R^{34}$ groups;
each $R^{32}$ and $R^{34}$ is independently —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —C(O)$NH_2$, —C(O)$NHCH_3$, —C(O)N($CH_3$)$_2$, —NHC(O)$CH_3$, —$NH_2$, —$NHCH_3$, —N($CH_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
m is 0 and $R^5$ is absent; or
m is 1 or 2, and each $R^5$ is independently selected from the group consisting of halo, —OH, and $C_1$-$C_4$ alkyl;
X and Z are independently $C_1$-$C_4$ alkyl; and
Y is H or F.

In a third preferred embodiment of formula (IV), U is N and V is $CR^4$ and the compounds have a combination of two or more of the following preferred features:
$R^1$ is $C_1$-$C_4$ alkyl or halo;
$R^2$ is $C_1$-$C_8$ alkoxy, optionally substituted by 1 to 5 $R^{22}$ groups;
each $R^{22}$ is independently halo or —OH;
$R^4$ is H, halo or 5-12 membered heteroaryl, where said 5-12 membered heteroaryl is optionally substituted by 1 to 3 $R^{34}$ groups;
each $R^{34}$ is independently —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —C(O)$NH_2$, —C(O)$NHCH_3$, —C(O)N($CH_3$)$_2$, —NHC(O)$CH_3$, —$NH_2$, —$NHCH_3$, —N($CH_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
m is 0 and $R^5$ is absent; or
m is 1 or 2, and each $R^5$ is independently selected from the group consisting of halo, —OH, and $C_1$-$C_4$ alkyl;
X and Z are independently $C_1$-$C_4$ alkyl; and
Y is H or F.

In a fourth preferred embodiment of formula (IV), U is N and V is $CR^4$ and the compounds have a combination of two or more of the following preferred features:
$R^1$ is $C_1$-$C_4$ alkyl or halo;
$R^2$ is a 5-6 membered heteroaryl, optionally substituted by 1 to 3 $R^{32}$ groups;
$R^4$ is H, halo or 5-12 membered heteroaryl, where said 5-12 membered heteroaryl is optionally substituted by 1 to 3 $R^{34}$ groups;
each $R^{32}$ and $R^{34}$ is independently —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —C(O)$NH_2$, —C(O)$NHCH_3$, —C(O)N($CH_3$)$_2$, —NHC(O)$CH_3$, —$NH_2$, —$NHCH_3$, —N($CH_3$)$_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
m is 0 and $R^5$ is absent; or
m is 1 or 2, and each $R^5$ is independently selected from the group consisting of halo, —OH, and $C_1$-$C_4$ alkyl;
X and Z are independently $C_1$-$C_4$ alkyl; and
Y is H or F.

In a fifth preferred embodiment of formula (IV), U is $CR^3$ and V is N and the compounds have a combination of two or more of the following preferred features:
$R^1$ is $C_1$-$C_4$ alkyl or halo;
$R^2$ is $C_1$-$C_8$ alkoxy, optionally substituted by 1 to 5 $R^{22}$ groups;
each $R^{22}$ is independently halo or —OH;
$R^3$ is H or F;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In a sixth preferred embodiment of formulae (IV), U is $CR^3$ and V is N and the compounds have a combination of two or more of the following preferred features:

$R^1$ is $C_1$-$C_4$ alkyl or halo;

$R^2$ is a 5-6 membered heteroaryl, optionally substituted by 1 to 3 $R^{32}$ groups;

$R^3$ is H or F;

each $R^{32}$ is independently —Cl, —F, —OH, —$CH_3$, —$CH_2CH_3$, —$CF_3$, —$CH_2OH$, —$CH_2OCH_3$, —$OCH_3$, —$OC_2H_5$, —$OCF_3$, —CN, —$C(O)NH_2$, —$C(O)NHCH_3$, —$C(O)N(CH_3)_2$, —$NHC(O)CH_3$, —$NH_2$, —$NHCH_3$, —$N(CH_3)_2$, cyclopropyl, 4-6 membered heterocyclyl, phenyl or 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;

m is 0 and $R^5$ is absent; or m is 1 or 2, and each $R^5$ is independently selected from the group consisting of halo, —OH, and $C_1$-$C_4$ alkyl;

X and Z are independently $C_1$-$C_4$ alkyl; and

Y is H or F.

In some particularly preferred embodiments of formula (IV), the compounds have a combination of three, four, five, six, seven, eight, nine or ten of the preferred features in each of the sets described above.

In some aspects, the compound of formula (IV) is a compound of formula (IV-A), (IV-B) or (IV-C):

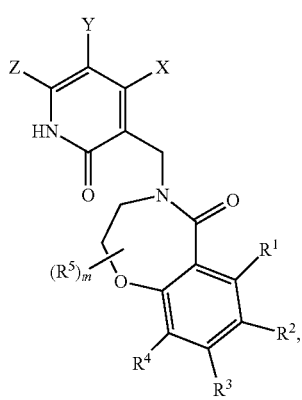

(IV-A)

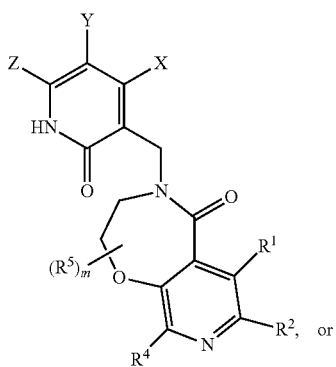

(IV-B)

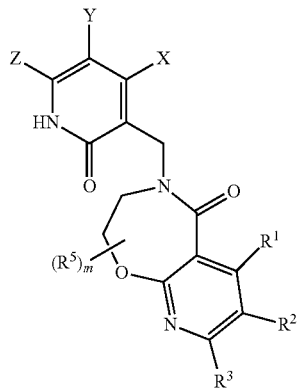

(IV-C)

or a pharmaceutically acceptable salt thereof, wherein $R^1$, $R^2$, $R^3$, $R^4$, $R^5$, m, X, Y and Z are defined as in formula (I).

The embodiments described herein with respect to formula (IV), and combinations thereof, are also applicable to the corresponding groups in formulae (IV-A), (IV-B) and (IV-C).

A "pharmaceutical composition" refers to a mixture of one or more of the compounds described herein, or a pharmaceutically acceptable salt, solvate, hydrate or prodrug thereof as an active ingredient, and at least one pharmaceutically acceptable carrier or excipient. The purpose of a pharmaceutical composition is to facilitate administration of a compound to a subject.

In another aspect the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional an anti-cancer therapeutic agent or a palliative agent. In some such embodiments, the at least one additional medicinal or pharmaceutical agent is an anti-cancer agent as described below. In some such embodiments, the combination provides an additive, greater than additive, or synergistic anti-cancer effect. In some such embodiments, the one or more anti-cancer therapeutic agent is selected from the group consisting of anti-tumor agents, anti-angiogenesis agents, signal transduction inhibitors and antiproliferative agents.

In one aspect, the invention provides a method for the treatment of abnormal cell growth in a subject comprising administering to the subject a therapeutically effective amount of a compound of the invention, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, in combination with an amount of an anti-tumor agent, which amounts are together effective in treating said abnormal cell growth. In some embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In frequent embodiments of the methods provided herein, the abnormal cell growth is cancer. In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by EZH2 in a subject comprising administering to the subject a compound of the invention, or a pharmaceutically acceptable salt thereof, in an amount that is effective for treating said disorder.

In preferred embodiments of the methods provided herein, the subject is a mammal, in particular a human.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Those compounds of the invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt.

This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of prodrugs in accordance with the invention include:

(i) where the compound contains a carboxylic acid functionality (—COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the formulae described herein, i.e., compounds formed in vivo upon administration of the drug.

The compounds of the formulae provided herein may have asymmetric carbon atoms. The carbon-carbon bonds of the compounds of the invention may be depicted herein using a solid line (-), a solid wedge (—), or a dotted wedge (⋯). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

"Enantiomerically pure" as used herein, describes a compound that is present as a single enentiomer and which is described in terms of enantiomeric excess (e.e.). Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, "diastereomerically pure" as used herein, describes a compound that is present as a diastereomer and which is described in terms of diasteriomeric excess (d.e.). Preferably, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of the invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Therapeutic Methods and Uses

The invention further provides therapeutic methods and uses comprising administering the compounds of the invention, or pharmaceutically acceptable salts thereof, alone or in combination with other therapeutic agents or palliative agents.

In one aspect, the invention provides a method for the treatment of abnormal cell growth in a subject comprising administering to the subject a therapeutically effective amount of a compound of the invention, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, in combination with an amount of an anti-tumor agent, which amounts are together effective in treating said abnormal cell growth. In some such embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

Compounds of the invention include compounds of any of the formulae described herein, namely compounds of formulae I, II, III, IV, I-A, I-B, I-C, II-A, II-B, II-C, III-A, III-B, III-C, IV-A, IV-B, or IV-C as provided and defined herein, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, that is effective in treating abnormal cell growth.

In still another aspect, the invention provides a method of inhibiting cancer cell proliferation in a subject, comprising administering to the subject a compound of the invention, or pharmaceutically acceptable salt thereof, in an amount effective to inhibit cell proliferation.

In another aspect, the invention provides a method of inhibiting cancer cell invasiveness in a subject, comprising administering to the subject a compound of the invention, or pharmaceutically acceptable salt thereof, in an amount effective to inhibit cell invasiveness.

In another aspect, the invention provides a method of inducing apoptosis in cancer cells in a subject, comprising administering to the subject a compound of the invention, or pharmaceutically acceptable salt thereof, in an amount effective to induce apoptosis.

In a further aspect, the invention provides a method of inducing apoptosis in a subject, comprising administering to the subject a therapeutically effective amount of a compound of one of the formulae described herein, or pharmaceutically acceptable salt thereof.

In frequent embodiments of the methods provided herein, the abnormal cell growth is cancer, wherein said cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In some embodiments, the compounds of the invention are selective for the mutant form of the EZH2, such that trimethylation of H3K27, which is associated with certain cancers, is inhibited. The methods and uses provided herein can be used to treat cancers including follicular lymphoma and diffuse large B-cell lymphoma (DLBCL).

The compounds of the invention are useful for the treatment of cancers, including, e.g., tumors such as brain, breast, cervical, colorectal, endometrial, esophageal, gastric/stomach, head and neck, hepatocellular, laryngeal, lung, oral, ovarian, prostate, testicular and thyroid carcinomas and sarcomas.

The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "subject" refers to a human or animal subject. In certain preferred embodiments, the subject is a human.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). This includes the abnormal growth of: (1) tumor cells (tumors) that show increased expression of EZH2; (2) benign and malignant cells of other proliferative diseases in which EZH2 is over-expressed; (3) tumors that proliferate by aberrant EZH2 activation; and (4) benign and malignant cells of other proliferative diseases in which aberrant EZH2 activation occurs.

As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. The compounds of the invention inhibit EZH2, and thus are all adapted to therapeutic use as antiproliferative agents (e.g., cancer) or antitumor agent (e.g., effect against solid tumors) in mammals, particularly in humans. In particular, the compounds of the invention are useful in the prevention and treatment of a variety of human hyperproliferative disorders including both malignant and benign abnormal cell growth.

The compounds, compositions and methods provided herein are useful for the treatment of cancers including but not limited to cancers of the:

circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue;

respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma);

bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

reproductive system, for example, gynecological, uterus (endometrial carcinoma), cervix (cervical carcinoma, pretumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs;

hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx;

skin, for example, malignant melanoma, cutaneous melanoma, basal cell carcinoma, squamous cell carcinoma, Karposi's sarcoma, moles dysplastic nevi, lipoma, angioma, dermatofibroma, and keloids;

adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of "cancer" when used herein in connection with the present invention include cancer selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

Still more specifically, examples of "cancer" when used herein in connection with the present invention include cancer selected from lung cancer (NSCLC and SCLC), breast cancer, ovarian cancer, colon cancer, rectal cancer, cancer of the anal region, or a combination of one or more of the foregoing cancers.

In one embodiment of the present invention the non-cancerous conditions include such hyperplastic conditions such as benign hyperplasia of the skin (e.g., psoriasis) and benign hyperplasia of the prostate (e.g., BPH).

In another aspect, the invention provides a method for inhibiting cell proliferation, comprising contacting cells with a compound of the invention or a pharmaceutically acceptable salt thereof in an amount effective to inhibit proliferation of the cells.

In another aspect, the invention provides methods for inducing cell apoptosis, comprising contacting cells with a compound described herein in an amount effective to induce apoptosis of the cells.

"Contacting" refers to bringing a compound or pharmaceutically acceptable salt of the invention and a cell expressing EZH2 together in such a manner that the compound can affect the activity of EZH2, either directly or indirectly. Contacting can be accomplished in vitro (i.e., in an artificial environment such as, e.g., without limitation, in a test tube or culture medium) or in vivo (i.e., within a living organism such as, without limitation, a mouse, rat or rabbit.)

In some embodiments, the cells are in a cell line, such as a cancer cell line. In other embodiments, the cells are in a tissue or tumor, and the tissue or tumor may be in a subject, including a human.

Dosage Forms and Regimens

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinyl-alcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may be used in combination with one or more additional anti-cancer agents which are described below. When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In one embodiment of the present invention the anti-cancer agent used in conjunction with a compound of the invention and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors.

Preferred anti-angiogenesis agents include sunitinib (Sutent™), bevacizumab (Avastin™), axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which can be used in conjunction with a compound of the invention and pharmaceutical compositions described herein include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™).

Other anti-angiogenesis agents include ABT 510 (Abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzumab (Herceptin™), sunitinib (Sutent™), imatinib (Gleevec™), and PD325901 (Pfizer).

Additional examples of signal transduction inhibitors which may be used in conjunction with a compound of the invention and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38).

Other examples of signal transduction inhibitor include PF-2341066 (Pfizer), PF-299804 (Pfizer), canertinib (CI 1033), pertuzumab (Omnitarg™), Lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), lapatinib (Tycerb™), PF-299804 (Pfizer), pelitinib (EKB 569), and pertuzumab (Omnitarg™).

Other examples of signal transduction inhibitors include ARRY 142886 (Array Biopharm), everolimus (Certican™), zotarolimus (Endeavor™), temsirolimus (Torisel™), AP 23573 (ARIAD), and VX 680 (Vertex).

Additionally, other signal transduction inhibitors include XL 647 (Exelixis), sorafenib (Nexavar™), LE-AON (Georgetown University), and GI-4000 (Globelmmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), PD 0332991 (Pfizer), and AG 024322 (Pfizer).

This invention contemplates the use of compounds of the invention together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with compounds of the invention include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

The invention also contemplates the use of the compounds of the invention together with dihydrofolate reductase inhibitors (such as methotrexate and NeuTrexin (trimetersate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with a compound of the invention, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paciltaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy)), bexarotene (Targretin™), Tesmilifene (DPPE—enhances efficacy of cytotoxics)), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof.

Further examples of classical antineoplastic agents used in combination therapy with a compound of the invention, optionally with one or more other agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Another embodiment of the present invention of particular interest relates to a method for the treatment of breast cancer in a human in need of such treatment, comprising administering to said human an amount of a compound of the invention, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

In one embodiment the invention provides a method of treating colorectal cancer in a mammal, such as a human, in need of such treatment, by administering an amount of a compound of the invention, in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615)epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (Cl-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCl 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Another embodiment of the present invention of particular interest relates to a method for the treatment of renal cell carcinoma in a human in need of such treatment, comprising administering to said human an amount of a compound of the invention, in combination with one or more (preferably one to three) anti-cancer agents selected from the group consisting of axitinib (AG 13736), capecitabine (Xeloda), interferon alpha, interleukin-2, bevacizumab (Avastin), gemcitabine (Gemzar), thalidomide, cetuximab (Erbitux), vatalanib (PTK-787), sunitinib (Sutent™), AG-13736, SU-11248, Tarceva, Iressa, Lapatinib and Gleevec, wherein the amounts of the active agent together with the amounts of the combination anticancer agents is effective in treating renal cell carcinoma.

Another embodiment of the present invention of particular interest relates to a method for the treatment of melanoma in a human in need of such treatment, comprising administering to said human an amount of a compound of the invention, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325,901, axitinib (AG 13736), bevacizumab (Avastin), thalidomide, sorafanib, vatalanib (PTK-787), sunitinib (Sutent™), CpG-7909, AG-13736, Iressa, Lapatinib and Gleevec, wherein the amounts of the active agent together with the amounts of the combination anticancer agents is effective in treating melanoma.

Another embodiment of the present invention of particular interest relates to a method for the treatment of lung cancer in a human in need of such treatment, comprising administering to said human an amount of a compound of the invention, in combination with one or more (preferably one to three) anti-cancer agents selected from the group consisting of capecitabine (Xeloda), axitinib (AG 13736), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, sunitinib (Sutent™), and Paraplatin (carboplatin), wherein the amounts of the active agent together with the amounts of the combination anticancer agents is effective in treating lung cancer.

Synthetic Methods

Compounds of the invention are prepared according to the expemplary procedures provided herein and modifications thereof known to those of skill in the art. A variety of routes have been demonstrated for the formation of various fused lactam compounds. One general route to the preparation of compounds of the invention involves ring expansion of a 5-membered ring oxime to provide the 6-membered ring lactam via a Beckman rearrangement (Method A). Similarly, a six membered ring oxime could be subjected to ring expansion to provide a 7-membered ring lactam. Additional functionality on the lactam precursor can be modified by conventional functional group manipulations, such as protection/deprotection, alkylation, acylation, activation or coupling steps. Alternatively, the desired substitution could be installed on the aromatic ring fused to the lactam prior to ring expansion (e.g., Method C). Regardless of the order of steps, the pyridinone moiety can be installed by alkylation of the lactam nitrogen atom under standard conditions. In some embodiments, it may be desirable to modify the substituents on the fused aromatic ring following installation of the pyridinone (e.g., Methods B and D).

An alternative route to preparation of the fused lactam starting materials involves the rearrangement of quinoline or isoquinoline N-oxides to the corresponding unsaturated lactams (e.g., Methods E and I). Reduction, e.g., by hydrogenation, provides the saturated lactam, which can be modified to install the pyridinone moiety and desired functionality on the fused aromatic ring as before. In some cases, it is desirable to install a reactive functional group, such as an aryl halide or triflate on the fused aromatic ring. Such groups can be used as functional group handles in various coupling reactions to install additional substituent groups.

For example, in Method F, Curtius rearrangement of an acyl azide intermediate installs a Boc-protected amino functionality. Such a group could be utilized in coupling reactions, e.g., with activated carbonyl compounds to acylated products. The deprotected aryl amino group can also be converted to a variety of other functional groups via the intermediacy of an aryl diazonium ion. For example, formation of the diazonium ion using $NaNO_2$ in the presence of CuBr results in an aryl bromide intermediate (Method F). Reaction of such diazonium ion with other copper salts, e.g., CuCl or CuCN, would be expected to provide the chloro or cyano substituents, respectively. Diazonium ions can also be converted to iodides or fluorides by reaction with KI or $HBF_4$, or to phenols by reaction with $H_2O$ and a strong acid, such as $H_2SO_4$ at elevated temperature. In other methods, an aryl halide may be installed using known halogenation conditions. In Method L, an aryl bromide is installed by reaction of a phenolic intermediate with NBS. Depending on the other functional groups present, aromatic halogenations could be effected using various electrophilic halogen sources (e.g., $Br_2$, $I_2$, $Cl_2$, NBS, NIS, NCS), or through Friedel-Crafts halogenations, etc.

Aryl halide intermediates can be utilized for cross-coupling using a variety of metal-mediated reactions. As shown in Methods F and P, Suzuki coupling with aryl boronic acids or aryl boronic esters can be used to form aryl-aryl bonds. Similarly, the aryl bromide could be utilized in a variety of other cross-coupling reactions, such as Stille or Sonigashara reactions. In some cases, an aryl halide may be incorporated in the original starting materials (e.g., Method I), and may be utilized in similar reactions.

Other reactive functional groups on the fused aryl ring can be modified through standard functional group transformations. For example, an ester substituent can be hydrolyzed and coupled with amines, as shown in Method G. Alternatively, the ester or acids could be reduced to alcohols, or converted to ketones or aldehydes. Such groups could themselves undergo further modifications. For example, alcohol intermediates could be alkylated to provide alkyoxy or benzyloxy groups. Alcohols could also be converted to leaving groups (e.g., mesylate, tosylate, halide) which can be displaced by nucleophiles such as amines, thiols, alkoxides, phenoxides and the like, or subjected to Mitsunobu or other reactions, greatly expanding the diversity of groups that can be installed. Similarly, ketones or aldehydes can be subjected to nucleophilic addition reactions, reductive alkylations and the like.

Additional routes to the formation of fused lactams are provided in Methods H and J. In each case, a masked alkylamino group of an appropriate length is installed on the carbon atom ortho to a carboxylate ester on an aryl ring. Deprotection of the amine and ester groups allows intramolecular cyclization to occur to provide the fused lactam. Similarly, in Method U, a five-membered ring lactam is formed by N-alkylation of a 2-(bromomethyl)-benzoate ester with a suitable aminomethyl-substituted pyridin-2(1H)-one followed by lactamization. In Method V, the lactam ring is generated by reduction of a 2-cyanomethyl-benzoate ester to provide a 2-aminomethyl-benzoate ester, which likewise undergoes lactamization.

A variety of synthetic routes are provided for the preparation of benzoxazepine compounds, including, e.g., the formation of carbon-oxygen or carbon-nitrogen bonds In Method K, an intramolecular Mitsunobu cyclization is used to form the oxazepine ring by installing a bond between a phenolic oxygen and an activated alcohol the leaving group. In Methods L and M, the lactam amide bond is formed by reaction of a derivatized amine with an activated benzoic acid. In Methods N and Q, the oxazepine ring is formed by base catalyzed cyclization of an N-hydroxyethyl fluorobenzamide intermediate. Method O provides yet another route involving Lewis acid catalyzed lactamization of a secondary amine onto the benzoate. In Method R, the oxazepine ring is formed by base catalyzed lactamization of a 2-aminoethoxy substituted aromatic bearing an ortho carboxylate. Such compounds can be further functionalized, e.g., by Suzuki coupling (Method P), or analogously to the functional group manipulations already described herein.

In some methods, a suitable lactam intermediate may be readily available, and can be modified to install the appropriate substituent groups (e.g., Methods S, T and W). In particular, the nitrogen atom of a lactam can be modified by N-alkylation with a suitably protected pyridin-2(1H)-one, such as 2-benzyloxy-3-chloromethyl-4,6-dimethyl-pyridine, which can be deprotected to provide the substituted pyridin-2(1H)-one.

These and other methods are exemplified in the preparation of the examples provided herein. It will be understood by those of skill in the art that the selection of starting materials and the particular order of the steps, including, e.g., formation of the lactam ring, installation or manipulation of various substituent groups on the fused lactam or its precursors, and installation of the pyridinone moiety, can be varied by selection of a suitable synthetic strategy.

Synthetic examples are provided throughout the Examples and in Tables 1 and 2 below. EZH2 $IC_{50}$ values (µM) for WT EZH2 and Mutant Y641N EZH2 are provided in Table 3 for exemplary compounds of the invention.

The following abbreviations are used throughout the Examples: "Ac" means acetyl, "AcO" or "OAc" means acetoxy, "$Ac_2O$" means acetic anhydride, "ACN" or "MeCN" means acetonitrile, "AIBN" means azobisisobutyronitrile, "BOC", "Boc" or "boc" means N-tert-butoxycarbonyl, "Bn" means benzyl, "BPO" means dibenzoyl peroxide, "Bu" means butyl, "iBu" means isobutyl, "sBu" means sec-butyl, "tBu" means tert-butyl, "tBuOK" or "KOtBu" means potassium tert-butoxide, "CDI" means carbonyldiimidazole, "DCM" (CH$_2$Cl$_2$) means methylene chloride, "DEAD" means diethyl azodicarboxylate, "DIAD" means diisopropyl azodicarboxylate, "DIPEA" or "DIEA" means diisopropyl ethyl amine, "DBU" means 1,8-diazabicyclo[5.4.0]undec-7-ene, "DIBAL-H" means diisobutylaluminum hydride, "DMA" means N,N-dimethylacetamide, "DMAP" means 4-dimethylaminopyridine, "DME" means dimethoxyethane, "DMF" means N—N-dimethyl formamide, "DMS" means dimethylsulfide, "DMSO" means dimethylsulfoxide, "dppf" means (diphenylphosphino)ferrocene, "DPPP" means 1,3-bis(diphenylphosphino)propane, "Et" means ethyl, "EtOAc" means ethyl acetate, "EtOH" means ethanol, "HATU" means 2-(7-Aza-1H-benzotriazole-1-yl)-1,1,3,3-tetramethyluronium hexafluorophosphate, "HOAc" of "AcOH" means acetic acid, "i-Pr" or "$^i$Pr" means isopropyl, "IPA" means isopropyl alcohol, "KHMDS" means potassium hexamethyldisilazide (potassium bis(trimethylsilyl)amide), "LiHMDS" means lithium hexamethyldisilazide (lithium bis(trimethylsilyl)amide), "mCPBA" means meta-chloroperoxy-benzoic acid, "Me" means methyl, "MeOH" means methanol, "Ms" means methanesulfonate (commonly called 'mesylate'), "MTBE" means methyl t-butyl ether, "NBS" means N-bromosuccinimide, "NCS" means N-chlorosuccinimide, "NIS" means N-iodosuccinimide, "NMM" means N-methylmorpholine, "NMP" means 1-methyl 2-pyrrolidinone, "Ph" means phenyl, "RuPhos" means 2-Dicyclohexylphosphino-2',6'-diisopropoxybiphenyl, "Selectfluor" means Chloromethyl-4-fluoro-1,4-diazoniabicyclo[2.2.2]octane bis(tetrafluoroborate), "TEA" means triethyl amine, "TFA" means trifluoroacetic acid, "Tf" means trifluoromethanesulfonate (commonly called 'triflate'), "THF" means tetrahydrofuran, "TMS" means trimethylsilyl, "TMSA" means trimethylsilylazide, "TsCl" means toluenesulfonyl chloride (commonly called 'tosylate'), "SFC" means supercritical fluid chromatography, "TLC" means thin layer chromatography, "Rf" means retention fraction, "~" means approximately, "rt" means room temperature, "h" means hours, "min" means minutes, "eq." means equivalents.

PREPARATION OF SYNTHETIC INTERMEDIATES

Compound F: Methyl 8-chloro-1-oxo-7-(propan-2-yloxy)-1,2,3,4-tetrahydroisoquinoline-5-carboxylate

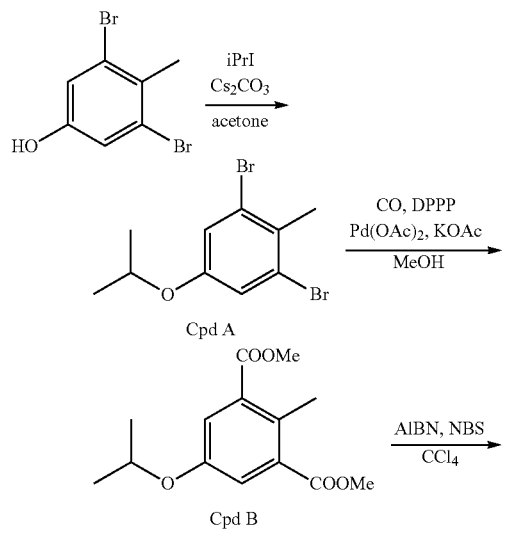

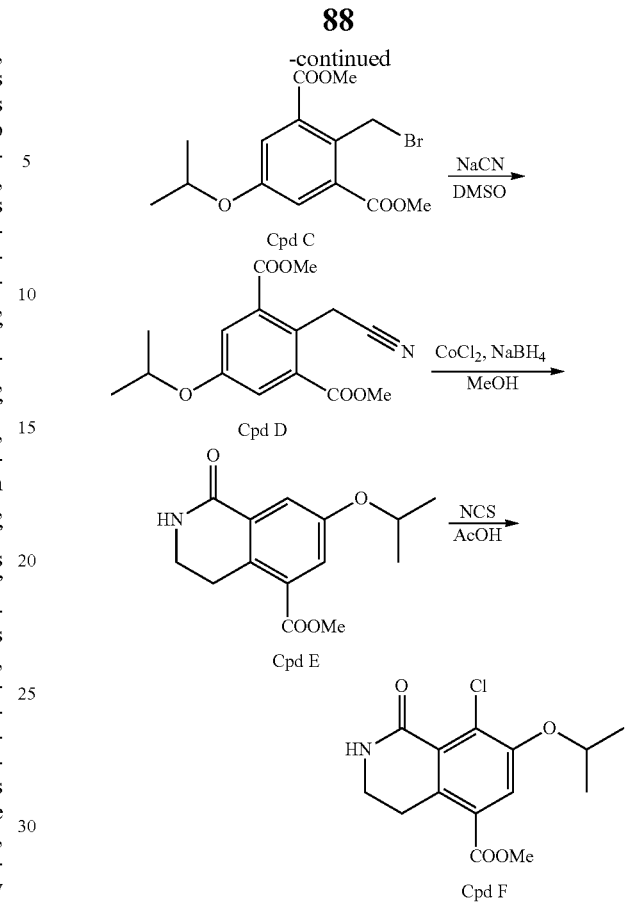

A mixture of 3,5-dibromo-4-methyl-phenol (11.2 g, 42.1 mmol), 2-iodopropane (8.50 mL, 85.0 mmol), potassium carbonate (17.5 g, 126 mmol), and anhydrous DMF (100 mL) was stirred at 80° C. for 3 hours. After cooling to room temperature, the reaction mixture was partitioned between ether (300 mL) and water (300 mL). The organic phase was separated, washed with brine (2×300 mL), dried over sodium sulfate, and concentrated under vacuum to give 1,3-dibromo-5-isopropoxy-2-methyl-benzene (Cpd A, 12.8 g, 99% yield) as an oil.

To a solution of 1,3-dibromo-5-isopropoxy-2-methylbenzene (Cpd A, 12.8 g, 41.6 mmol) in MeOH (250 mL) in a 500 mL Parr bomb were added KOAc (20.0 g, 204 mmol), DPPP (1.25 g, 3.03 mmol), and Pd(OAc)$_2$ (532 mg, 2.38 mmol). The bomb was sealed, purged with nitrogen (3×) and CO (4×), filled with CO (160 psi), and heated at 100° C. The internal pressure rose to 190-200 psi upon heating. After heating at 100° C. overnight the reaction mixture was allowed to cool down to room temperature. The vessel was vented, and purged with nitrogen (2×). Precipitates were filtered through a pad of CELITE® and washed with MeOH. After concentrating under vacuum, the resulting residue was partitioned between ethyl acetate (300 mL) and water (300 mL). The organic phase was separated, washed with brine (1×300 mL), dried over sodium sulfate, and concentrated under vacuum to give 5-isopropoxy-2-methyl-isophthalic acid dimethyl ester (Cpd B, 10.9 g, 99% yield) as an oil.

To a solution of 5-isopropoxy-2-methyl-isophthalic acid dimethyl ester (Cpd B, 14.5 g, 54.5 mmol) in CCl$_4$ (250 mL) was added NBS (11.2 g, 60.0 mmol). After stirring the mixture at 85° C. for 5 minutes, AIBN (2.69 g, 16.4 mmol) was added. The resulting reaction mixture was stirred at 85°

C. for 1 hour. The reaction mixture was chilled in an ice bath and the precipitates were filtered and discarded. The resulting filtrate was concentrated under vacuum and purified by column chromatography (0-40%, EtOAc/heptanes) to give 2-bromomethyl-5-isopropoxy-isophthalic acid dimethyl ester (Cpd C, 17.5 g, 93% yield) as a clear oil which solidified upon standing.

To a solution of 2-bromomethyl-5-isopropoxy-isophthalic acid dimethyl ester (Cpd C, 17.4 g, 50.5 mmol) in DMSO (200 mL) was added NaCN (3.71 g, 75.7 mmol) in $H_2O$ (20 mL). The resulting reaction mixture was stirred at room temperature for 1 hour. The reaction mixture was poured into water (500 mL), and extracted with ethyl acetate (2×300 mL). The combined organic phases were washed with brine (1×300 mL), dried over sodium sulfate, concentrated under vacuum, and purified by column chromatography (0-40%, EtOAc/heptanes) to give Dimethyl 2-(cyanomethyl)-5-(propan-2-yloxy)benzene-1,3-dicarboxylate (Cpd D, 12.8 g, 87% yield) as a clear oil which solidified upon standing.

Dimethyl 2-(cyanomethyl)-5-(propan-2-yloxy)benzene-1,3-dicarboxylate (Cpd D, 1.04 g, 3.57 mmol) and cobalt (11) chloride hexahydrate (2.56 g, 10.7 mmol) were dissolved in MeOH (60 mL) and cooled in an ice bath. $NaBH_4$ (853 mg, 21.4 mmol) was added portionwise and the reaction mixture was stirred at 0° C. for 0.5 hours. To the reaction mixture was added $NH_4Cl$ (sat., aq., 25 mL), $H_2O$ (25 mL), and EtOAc (50 mL). The solution was allowed to sit at room temperature overnight. The residual solids were filtered and the aqueous layer was extracted with EtOAc (3×50 mL). The combined organic layers were washed with brine (1×50 mL), dried over sodium sulfate, concentrated under vacuum, and purified by column chromatography (0-60%, EtOAc/heptanes) to afford methyl 1-oxo-7-(propan-2-yloxy)-1,2,3,4-tetrahydroisoquinoline-5-carboxylate (Cpd E, 644 mg, 69% yield) as a white solid. $^1$H NMR (400 MHz, chloroform-d) δ 1.35 (s, 3H) 1.36 (s, 3H) 3.35 (t, J=6.57 Hz, 2H) 3.52 (td, J=6.57, 3.03 Hz, 2H) 3.91 (s, 3H) 4.61-4.72 (m, 1H) 5.91 (br. s., 1H) 7.62 (d, J=3.03 Hz, 1H) 7.83 (d, J=3.03 Hz, 1H); MS 264.1 [M+H].

To a solution of methyl 1-oxo-7-(propan-2-yloxy)-1,2,3,4-tetrahydroisoquinoline-5-carboxylate (Cpd E, 400 mg, 1.52 mmol) in AcOH (5 mL) was added NCS (416 mg, 3.04 mmol). The reaction mixture was stirred at 100° C. overnight. The reaction mixture was concentrated under vacuum and the residue was diluted with $H_2O$ and $NaHCO_3$ (sat., aq.). The aqueous layer was extracted with EtOAc and the organic layer purified by column chromatography (50% EtOAc/heptanes) to give the title compound (Cpd F, 180 mg, 40%) as a white solid. $^1$H NMR (400 MHz, chloroform-d) δ 1.40 (s, 3H) 1.42 (s, 3H) 3.27-3.36 (m, 2H) 3.37-3.47 (m, 2H) 3.88-3.95 (m, 3H) 4.62 (dt, J=12.07, 6.13 Hz, 1H) 6.06 (br. s., 1H) 7.61 (s, 1H); MS 298.0 [M+H].

Compound K: 2-(benzyloxy)-4-({[tert-butyl(dimethyl)silyl]oxy}methyl)-3-(chloromethyl)-6-methylpyridine

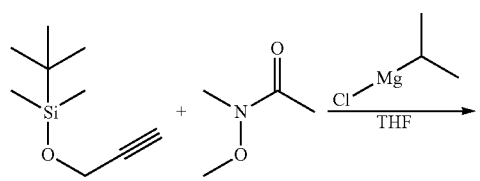
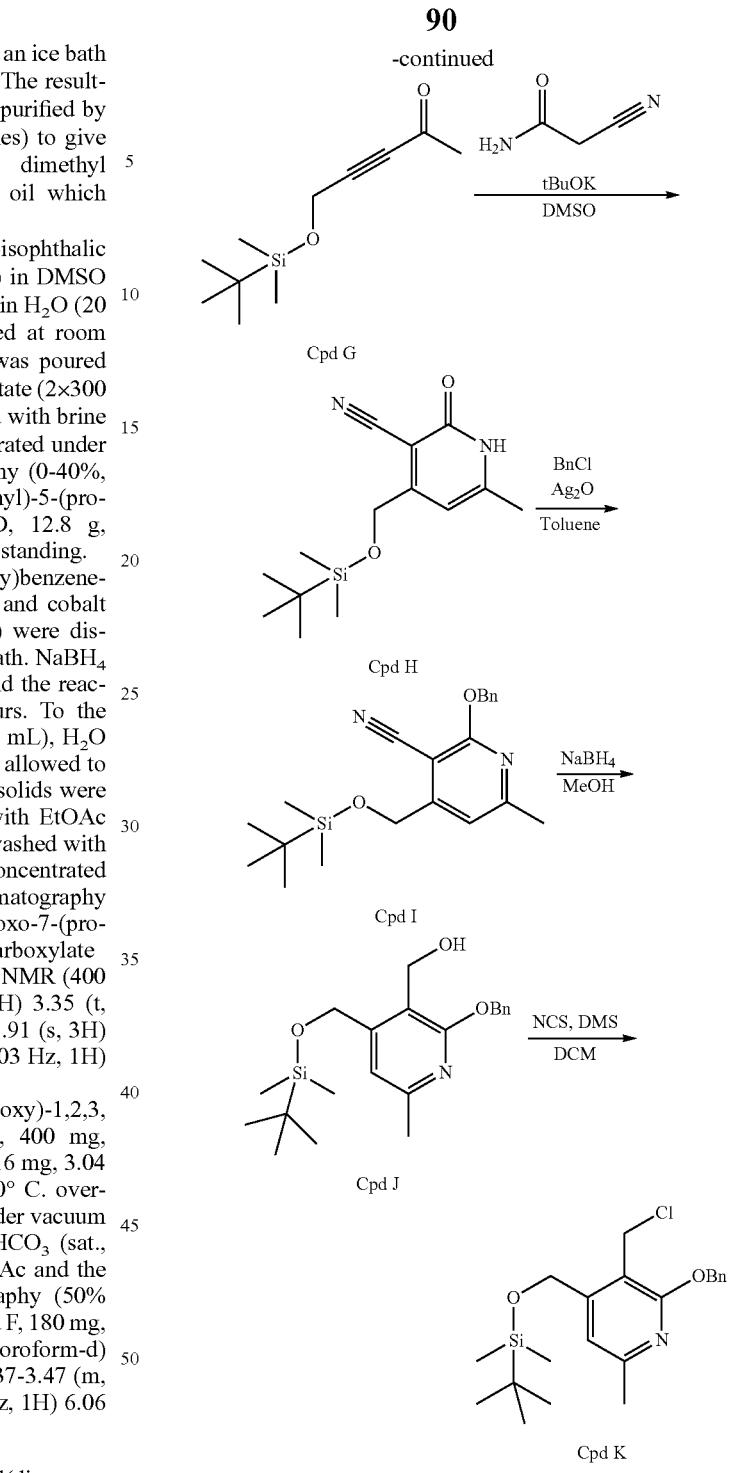

To a −40° C. solution of tert-butyl(dimethyl)(prop-2-yn-1-yloxy)silane (1.70 g, 10 mmol) in THF (6 mL) was added iPrMgCl·LiCl (8.46 mL, 11 mmol) dropwise keeping the internal temperature below −20° C. A solution of the N-methoxy-N-methylacetamide (1.13 g, 11.0 mmol) in THF (4 mL) was cooled to −10° C. and the alkyne solution was added to the Weinreb amide solution via cannula. The reaction mixture was stirred at −10° C. for 10 minutes. The reaction mixture was poured into a mixture of saturated $NH_4Cl$ and ice. The aqueous layer was extracted with EtOAc. The organic layer was washed with brine, dried with Mg$_2$SO$_4$, filtered, then concentrated under vacuum to give 5-{[tert-butyl(dimethyl)silyl]oxy}pent-3-yn-2-one (Cpd G, 1.5 g, 64%) as an oil.

To a 0° C. solution of 2-cyanoacetamide (1.74 g, 20.7 mmol) and tBuOK (2.32 g, 20.7 mmol) in DMSO (48 mL) was added 5-{[tert-butyl(dimethyl)silyl]oxy}pent-3-yn-2-one (Cpd G, 4.4 g, 21.0 mmol) dropwise. The reaction mixture turned bright orange. The reaction mixture was stirred for 2 hours at 0° C., then quenched with NH$_4$Cl (sat., aq.) and diluted with water causing solids to precipitate out. The solids were collected via filtration and dried under vacuum to give 4-({[tert-butyl(dimethyl)silyl]oxy})-6-ml)-6-methyl-2-oxo-1,2-dihydropyridine-3-carbonitrile (Cpd H, 5.0 g, 86%) as a tan solid.

A mixture of 4-({[tert-butyl(dimethyl)silyl]oxy}methyl)-6-methyl-2-oxo-1,2-dihydropyridine-3-carbonitrile (Cpd H, 6.6 g, 24 mmol), Ag$_2$O (6.3 g, 27 mmol), and benzylchloride (4.1 g, 33 mmol) in toluene (79 mL) was heated at 100° C. for 21 hours. The reaction mixture was filtered through CELITE® then concentrated under vacuum. The residue was purified by column chromatography (0-30%, EtOAc/heptane) to give 2-(benzyloxy)-4-({[tert-butyl(dimethyl)-silyl]oxy}methyl)-6-methylpyridine-3-carbonitrile (Cpd I, 6.5 g, 74%) as a tan solid.

To a 0° C. solution of 2-(benzyloxy)-4-({[tert-butyl(dimethyl)silyl]oxy}methyl)-6-methylpyridine-3-carbonitrile (Cpd I, 1.0 g, 2.8 mmol) in MeOH (5 mL) was added NaBH$_4$ (81 mg, 2.1 mmol). The reaction mixture was allowed to stir at room temperature for 24 hours. The reaction mixture was concentrated under vacuum to give [2-(benzyloxy)-4-({[tert-butyl(dimethyl)silyl]oxy}methyl)-6-methylpyridin-3-yl]methanol (Cpd J, 147 mg, 14%) as a solid.

To a 0° C. solution of NCS (70.2 mg, 0.515 mmol) in DCM (2 mL) was added DMS (34.9 mg, 0.562 mmol). The reaction mixture was cooled to −40° C., then a solution of [2-(benzyloxy)-4-({[tert-butyl(dimethyl)silyl]oxy})-6-methylpyridin-3-yl]methanol (Cpd J, 175 mg, 0.468 mmol) in DCM (1 mL) was added drop-wise keeping the internal temperature below −30° C.

Upon complete addition the reaction mixture was warmed to room temperature and stirred for 3 hours. The reaction mixture was washed with brine, dried with MgSO$_4$, filtered, then concentrated under vacuum. The residue was purified by column chromatography (0-30% EtOAc/heptane) to give the title compound (Cpd K, 120 mg, 65%) as an oil. $^1$H NMR (400 MHz, chloroform-d) δ 7.50 (d, J=7.3 Hz, 2H), 7.44-7.29 (m, 3H), 6.94 (s, 1H), 5.46 (s, 2H), 4.83 (s, 2H), 4.70 (s, 2H), 2.47 (s, 3H), 0.97 (s, 9H), 0.14 (s, 6H); MS 392 [M+H].

Compound P: 8-chloro-6-fluoro-7-(propan-2-yloxy)-3,4-dihydroisoquinolin-1(2H)-one

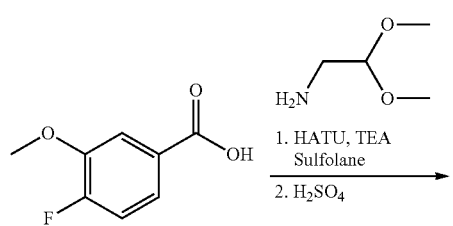

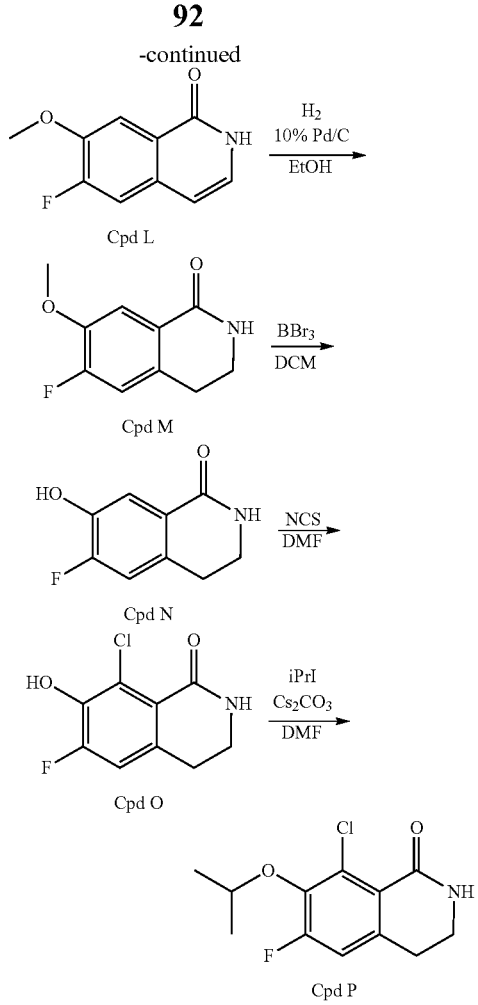

A solution of 4-fluoro-3-methoxybenzoic acid (1.30 g, 7.64 mmol) and TEA (1.25 mL, 8.97 mmol) in sulfolane (6.0 mL) was treated with HATU (3.25 g, 8.55 mmol). After 10 minutes, aminoacetaldehyde dimethylacetal (0.925 mL, 8.58 mmol) was added. The reaction mixture was stirred at room temperature for 30 minutes. The reaction mixture was then treated with conc. H$_2$SO$_4$ (15 mL) and stirred at 60° C. for 2 days. The reaction mixture was poured over ice and brought to pH-4 with 10M NaOH (~55 mL). The precipitate was collected by filtration, washed with water, and dried under vacuum to give 6-fluoro-7-methoxyisoquinolin-1(2H)-one (Cpd L, 1.32 g, 89%) as a white powder.

A suspension of 6-fluoro-7-methoxyisoquinolin-1(2H)-one (Cpd L, 0.531 g, 2.75 mmol) and 10% Pd/C in EtOH (20 mL) was stirred vigorously under a blanket of H$_2$ (balloon) at room temperature for 2 days. The reaction mixture was filtered and the filtrate was concentrated under vacuum to give 6-fluoro-7-methoxy-3,4-dihydroisoquinolin-1(2H)-one (Cpd M, 430 mg, 80%) as a white powder.

To a 0° C. solution of 6-fluoro-7-methoxy-3,4-dihydroisoquinolin-1(2H)-one (Cpd M, 0.428 g, 2.19 mmol) in DCM (15 mL) was added boron tribromide (1.0M in DCM, 6.00 mL, 6.00 mmol). The reaction mixture was stirred for 1 hour, then the reaction mixture was allowed to warm to room temperature. After stirring for 4 hours, water (25 mL) and EtOAc (100 mL) were added and the mixture was stirred vigorously. The layers were separated, and the organic layer was filtered and concentrated under vacuum to give 6-fluoro-7-hydroxy-3,4-dihydroisoquinolin-1(2H)-one (Cpd N, 355 mg, 89%).

To a solution of 6-fluoro-7-hydroxy-3,4-dihydroisoquinolin-1(2H)-one (Cpd N, 0.110 g, 0.607 mmol) in DMF (1 mL) was added n-chlorosuccinamide (0.0780 g, 0.584 mmol). The reaction was stirred at room temperature for 6 hours. The reaction mixture was diluted with water and the solution extracted with DCM (×3). The combined organic layers were concentrated under vacuum to give 8-chloro-6-fluoro-7-hydroxy-3,4-dihydroisoquinolin-1(2H)-one (Cpd O, 131 mg, 100%) as a clear oil.

To a solution of 8-chloro-6-fluoro-7-hydroxy-3,4-dihydroisoquinolin-1(2H)-one (Cpd O, 131 mg, 0.607 mmol) in DMF (3.0 mL) was added cesium carbonate (0.210 g, 0.645 mmol) and iso-propyl iodide (0.0850 mL, 0.850 mmol). The reaction mixture was stirred at room temperature for 20 hours. The reaction mixture was diluted with EtOAc and washed with water (2×) and brine. The organic layer was concentrated under vacuum and the residue was purified by column chromatography (40-100% EtOAc/heptane) to give the title compound (Cpd P, 62 mg, 40%) as a white solid. MS 258 [M+H].

Compound R: 8-chloro-4,4-difluoro-7-methoxy-3,4-dihydroisoquinolin-1(2H)-one

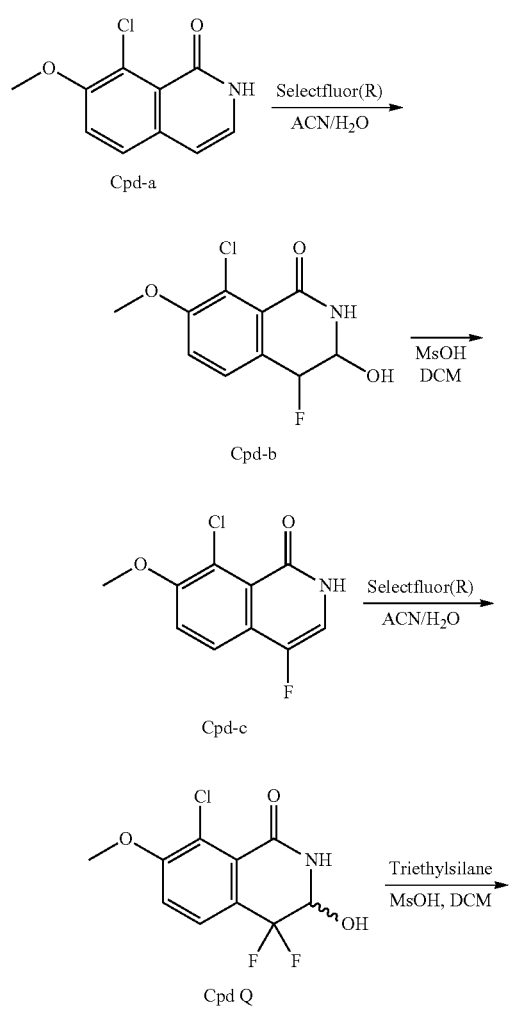

To a solution of Cpd-a (0.451 g, 2.15 mmol) in acetonitrile (25 mL) was added water (0.30 mL) and 1-(chloromethyl)-4-fluoro-1,4-diazoniabicyclo[2.2.2]octane ditetrafluoroborate (0.831 g, 2.35 mmol). The reaction was stirred at room temperature for 72 h. The reaction mixture was poured into ethyl acetate and washed with 1:1 water/brine and then brine. The ethyl acetate layer was concentrated, and the resulting light yellow powder (Cpd-b) was dissolved in dichloromethane (15 mL) and treated with methylsulfonic acid (0.90 mL, 14 mmol). After 3 h at room temperature, the reaction was diluted with dichloromethane and washed with Sat. Aq. NaHCO$_3$. The dichloromethane layer was dried over Na$_2$SO$_4$, filtered, and concentrated to give Cpd-c (0.269 g, 56%) as a pale orange powder. 1H NMR (400 MHz, DMSO-d6) δ 10.89 (br. s., 1H), 7.62 (s, 2H), 7.15 (t, J=5.68 Hz, 1H), 3.88 (s, 3H); MS 228 [M+H]$^+$.

To a solution of 8-chloro-4-fluoro-7-methoxyisoquinolin-1(2H)-one (Cpd-c, 0.267 g, 1.17 mmol) in acetonitrile (15 mL) was added water (1.0 mL) and 1-(chloromethyl)-4-fluoro-1,4-diazoniabicyclo[2.2.2]octane ditetrafluoroborate (0.505 g, 1.43 mmol). The reaction was stirred at room temperature for 2 h and then concentrated under vacuum. The crude residue was dissolved in ethyl acetate and washed with 1:1 Water/brine and then brine. The ethyl acetate layer was concentrated to give 8-chloro-4,4-difluoro-3-hydroxy-7-methoxy-3,4-dihydro-isoquinolin-1(2H)-one (Cpd Q, 309 mg, 99%) as a solid. The solid was dissolved in DCM (12.0 mL) and treated with triethylsilane (1.00 mL, 6.26 mmol) and methylsulfonic acid (0.300 mL, 4.26 mmol). After 8 h at room temperature, the reaction mixture was decanted away from the solids, washed with Sat. Aq. NaHCO$_3$, and concentrated. The resulting residue was purified on silica gel (Biotage SNAP Ultra, 10 g, gradient of 40-90% ethyl acetate in heptane) to give Cpd R (0.038 g, 13%) as a white solid. 1H NMR (400 MHz, DMSO-d6) δ 8.52 (br. s., 1H), 7.67 (d, J=8.59 Hz, 1H), 7.48 (d, J=8.84 Hz, 1H), 3.94 (s, 3H), 3.81 (dt, J=3.54, 12.25 Hz, 2H); MS 248 [M+H]$^+$.

Compound V: 3-(aminomethyl)-4,6-dimethylpyridin-2(1H)-one

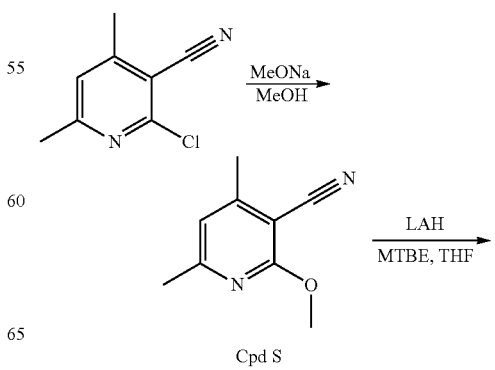

Compound Z: 2-(benzyloxy)-3-(chloromethyl)-4,6-dimethylpyridine

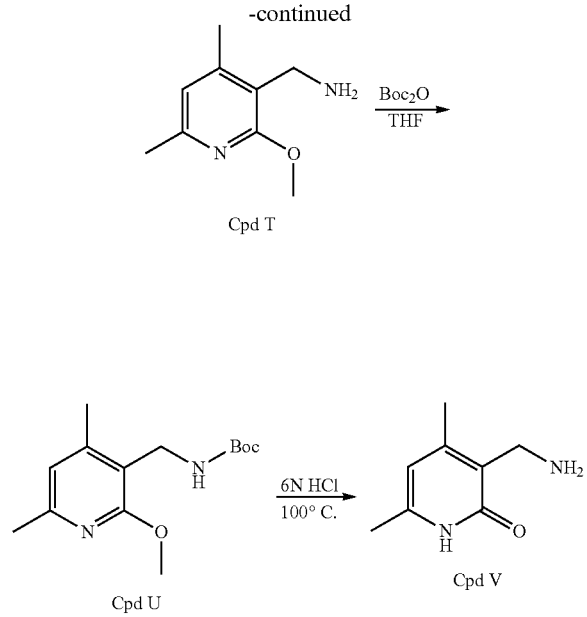

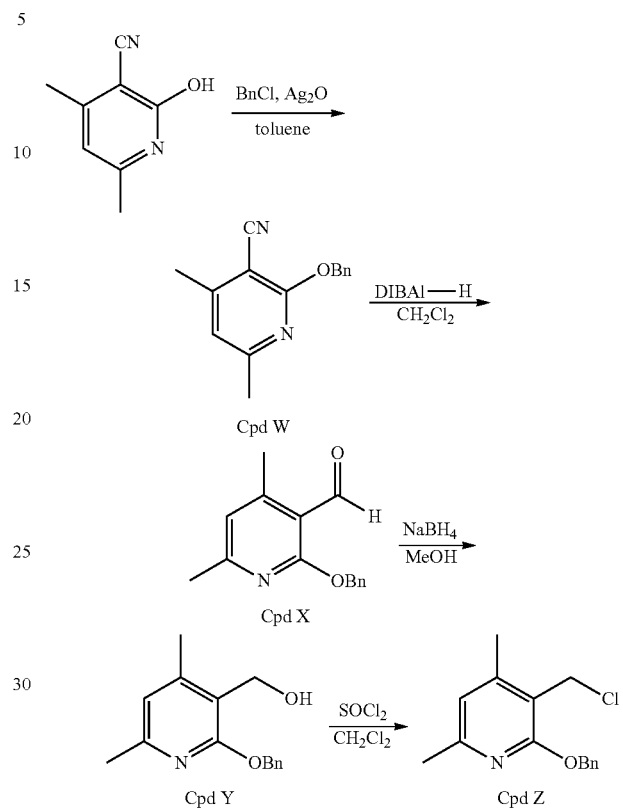

Sodium (23 g, 0.99 mol) was added to dry MeOH (800 mL) portion-wise. After the addition, the mixture was stirred for an hour until the sodium was mostly dissolved. To the reaction mixture was added 2-chloro-4,6-dimethylpyridine-3-carbonitrile (110 g, 0.66 mol). The resulting mixture was heated at 70° C. and stirred for four hours. The suspension was filtered and the filtrate was concentrated under vacuum. The residue was purified by column chromatography (petroleum ether/EtOAc, 10:1) to give 2-methoxy-4,6-dimethyl pyridine-3-carbonitrile (Cpd S, 103 g, 100%) as a white solid.

LiAlH$_4$ (48.0 g, 1.27 mol) was added into MTBE (600 mL) portion-wise at room temperature. To the suspension was added 2-methoxy-4,6-dimethylpyridine-3-carbonitrile (Cpd S, 103 g, 0.636 mol) in MTBE/THF (1:1, 600 mL) portion-wise. The reaction mixture was stirred at room temperature for an hour then quenched with water (75 mL). The precipitate was collected by filtration and the solids washed with THF (3×100 mL). The filtrate was concentrated under vacuum to give the 1-(2-methoxy-4,6-dimethylpyridin-3-yl)methanamine (Cpd T), which was used in the next step directly.

To a solution of 1-(2-methoxy-4,6-dimethylpyridin-3-yl) methanamine (Cpd T) in THF (500 mL) was added Boc$_2$O (138.1 g, 0.636 mol) portion-wise. After the addition, the reaction mixture was stirred at room temperature overnight then concentrated under vacuum. The residue was purified by column chromatography (petroleum ether/EtOAc, 10:1) to give tert-butyl [(2-methoxy-4,6-dimethylpyridin-3-yl)methyl]carbamate (Cpd U, 140 g, 83% via two steps) as a white solid.

A solution of tert-butyl [(2-methoxy-4,6-dimethyl pyridin-3-yl)methyl]carbamate (Cpd U, 140 g, 0.52 mol) in 6N HCl (500 mL) was heated at 100° C. and stirred for six hours. The reaction mixture was concentrated and the residue was re-crystallized with EtOH to afford the title compound (Cpd V, 77 g, 55%) as hydrochloride salts. $^1$H NMR (400 MHz, D$_2$O) δ 6.31 (s, 1H), 4.11 (s, 2H), 2.31-2.30 (s, 6H); MS 175.1 [M+Na].

To a solution of 2-hydroxy-4,6-dimethylpyridine-3-carbonitrile (85.0 g, 0.574 mol) and benzyl chloride (87.0 g, 0.688 mol) in toluene (800 mL) was added Ag$_2$O (146 g, 0.631 mol). The reaction mixture was stirred at 110° C. overnight. The reaction mixture was filtered through CELITE® and the solids washed with CH$_2$Cl$_2$. The filtrate was concentrated under vacuum and purified by column chromatography (petroleum ether/EtOAc) to give 2-(benzyloxy)-4,6-dimethylpyridine-3-carbonitrile (Cpd W, 89 g, 65%) as a white solid.

44.5 g×2 batches: To a stirred solution of 2-(benzyloxy)-4,6-dimethylpyridine-3-carbonitrile (Cpd W, 44.5 g, 187 mmol) in CH$_2$Cl$_2$ (500 mL) was added drop wise DIBAL-H (224 mL, 224 mmol, 1M in toluene) at 0~5° C. The reaction mixture was allowed to warm to room temperature and stirred for an additional 3 hours. The mixture was quenched with 1N HCl (200 mL) and was stirred vigorously for 30 minutes. The reaction mixture was neutralized with 4N NaOH (20 mL) and the biphasic mixture was filtered and washed with CH$_2$Cl$_2$ (500 mL). The aqueous layer was extracted with CH$_2$Cl$_2$ (200 mL), the combined organic layers were dried over Na$_2$SO$_4$, and concentrated under vacuum. The residue was purified by column chromatography (petroleum ether/EtOAc) to give 2-(benzyloxy)-4,6-dimethylpyridine-3-carbaldehyde (Cpd X, 70 g, 78%) as a yellow solid.

35 g×2 batches: To a 00° C. solution of 2-(benzyloxy)-4,6-dimethylpyridine-3-carbaldehyde (Cpd X, 35.0 g, 145 mmol) in CH$_3$OH (1000 mL) was added NaBH$_4$ (6.60 g, 174 mmol) in portions. The reaction mixture was stirred at room temperature for 2 hours. The reaction mixture was concentrated under vacuum and the residue was diluted with NaHCO₃ (sat., aq.). After the bubbling had stopped, the aqueous solution was extracted with EtOAc (2×500 mL). The combined organic layers were dried over Na₂SO₄, concentrated under vacuum, and purified by column chromatography (petroleum ether/EtOAc) to give [2-(benzyloxy)-4,6-dimethylpyridin-3-yl]methanol (Cpd Y, 43 g, 61%) as a colorless oil.

21.5 g×2 batches: To a solution of [2-(benzyloxy)-4,6-dimethylpyridin-3-yl]methanol (Cpd Y, 21.5 g, 88.5 mmol) in anhydrous CH₂Cl₂ (400 mL) was added SOCl₂ (16.0 g, 133 mmol) at −40° C. under N₂. The mixture was stirred at the −40° C. for 30 minutes. The reaction mixture was poured into ice-water (300 mL) and adjusted pH 7-8 with NaHCO₃ (solid). The mixture was separated and the aqueous layer was extracted with CH₂Cl₂ (300 mL). The combined organic layers were washed with brine (300 mL), dried over Na₂SO₄, and concentrated under vacuum. The residue was purified by column chromatography (petroleum ether/EtOAc, 100:1) to give the title compound (Cpd Z, 27.5 g, 60%) as a white solid. ¹H NMR (400 MHz, chloroform-d) δ 7.51-7.49 (d, 2H), 7.41-7.37 (t, 2H), 7.34-7.30 (t, 1H), 6.62 (s, 1H), 5.45 (s, 2H), 4.73 (s, 2H), 2.42 (s, 3H), 2.37 (s, 3H). MS 261.9 [M+H].

Compound EE: 2-(benzyloxy)-3-(chloromethyl)-4-ethyl-6-methylpyridine

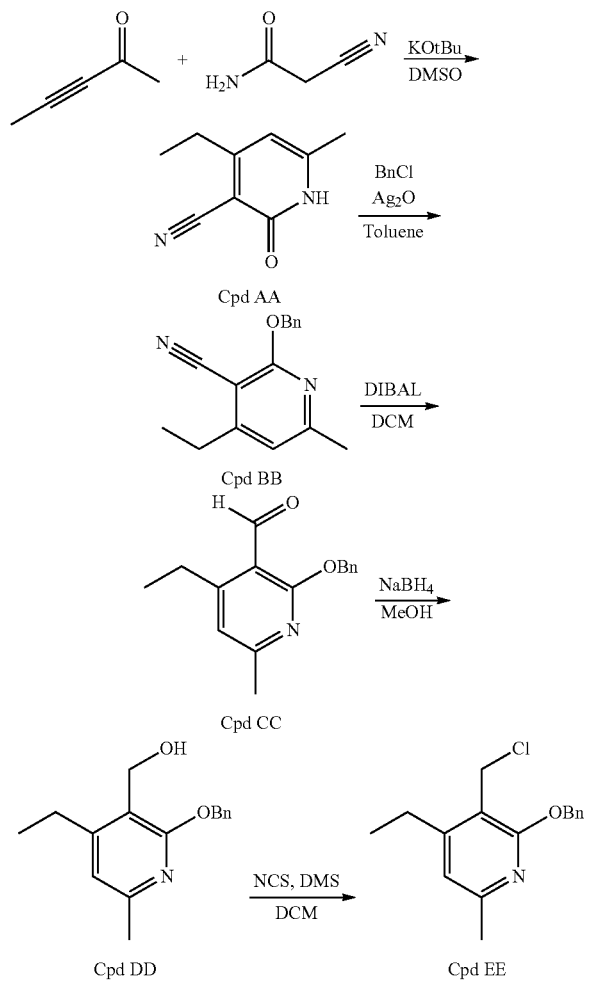

A solution of 2-cyano-acetamide (841 mg, 10.0 mmol) in DMSO (20 mL) and potassium tert-butoxide (1.18 g, 10.5 mmol) was stirred at 23° C. for 30 minutes. The mixture was cooled to 0° C. then pent-3-yn-2-one (1.1 mL, 10 mmol) was added and the reaction mixture was stirred for 2 hours. The reaction mixture was quenched with saturated ammonium chloride (3 mL) then diluted with water (10 mL) causing a solid to precipitate out. The suspension was filtered and the solids dried under vacuum to give 4-ethyl-6-methyl-2-oxo-1,2-dihydropyridine-3-carbonitrile (Cpd AA, 1.2 g, 71%) as a white solid.

A mixture of 4-ethyl-6-methyl-2-oxo-1,2-dihydropyridine-3-carbonitrile (Cpd AA, 1.1 g, 6.8 mmol), (chloromethyl)benzene (1.1 mL, 9.4 mmol, 1.4 equiv) and silver(I) oxide (1.8 g, 7.7 mmol) in anhydrous toluene (22.7 mL) was heated at 110° C. for 17 hours. The reaction mixture was cooled to 23° C. then filtered through CELITE®. The filtrate was concentrated under vacuum. The residue was purified by column chromatography (heptane/EtOAc) to give 2-(benzyloxy)-4-ethyl-6-methylpyridine-3-carbonitrile (Cpd BB, 1.42 g, 83%) as a colorless oil.

To a −5° C. solution of 2-(benzyloxy)-4-ethyl-6-methylpyridine-3-carbonitrile (Cpd BB, 0.687 g, 2.72 mmol) in dichloromethane (9 mL) was added 1M diisobutylaluminum hydride in dichloromethane (3 mL, 3 mmol). After 3 hours the reaction mixture was quenched with 1M aqueous hydrochloric acid (3 mL) then stirred for 15 minutes. A 2M aqueous solution of Rochelle's salt (3 mL) was added then the resulting mixture was filtered through CELITE®. The filtrate was concentrated under vacuum and the residue was extracted with ethyl acetate (40 mL), washed with brine (10 mL), dried over sodium sulfate, filtered, then concentrated under vacuum. The residue was purified by column chromatography (heptane/EtOAc) to give 2-(benzyloxy)-4-ethyl-6-methylpyridine-3-carbaldehyde (Cpd CC, 323 mg, 46%) as a colorless oil.

To a 0° C. solution of 2-(benzyloxy)-4-ethyl-6-methylpyridine-3-carbaldehyde (Cpd CC, 323 mg, 1.28 mmol) in methanol (4.27 mL) was added sodium borohydride (54 mg, 1.41 mmol). After 1 hour, the reaction mixture was concentrated under vacuum then diluted with ethyl acetate (20 mL) and water (10 mL). The organic layer was washed with brine (5 mL), then dried over sodium sulfate, filtered, and concentrated under vacuum. The residue was purified by column chromatography (heptane/EtOAc) to give [2-(benzyloxy)-4-ethyl-6-methyl pyridin-3-yl]methanol (Cpd DD, 280 mg, 85% yield) as a colorless oil.

To a 0° C. solution of N-chloro succinamide (81.5 mg, 0.598 mmol) in dichloromethane (2.47 mL) was added dimethyl sulfide (48 ul, 0.653 mmol). The reaction mixture was then cooled to −20° C. and a solution of [2-(benzyloxy)-4-ethyl-6-methylpyridin-3-yl]methanol (Cpd DD, 140 mg, 0.554 mmol) in dichloromethane (1 mL) was added drop wise. After 2 hours the reaction mixture was poured into brine (5 mL) then extracted with dichloromethane (10 mL). The organic layer was dried over sodium sulfate, filtered, then concentrated under vacuum. The residue was purified by column chromatography (heptane/EtOAc) to give the title compound (Cpd EE, 35 mg, 23% yield) as a colorless oil. ¹H NMR (chloroform-d) δ 7.52 (d, J=7.3 Hz, 2H), 7.29-7.44 (m, 3H), 6.65 (s, 1H), 5.46 (s, 2H), 4.74 (s, 2H), 2.72 (q, J=7.6 Hz, 2H), 2.44 (s, 3H), 1.28 (t, J=7.6 Hz, 3H).

Compound HH: methyl 3-bromo-2-methyl-6-[2-(tetrahydro-2H-pyran-2-yloxy)ethoxy]benzoate

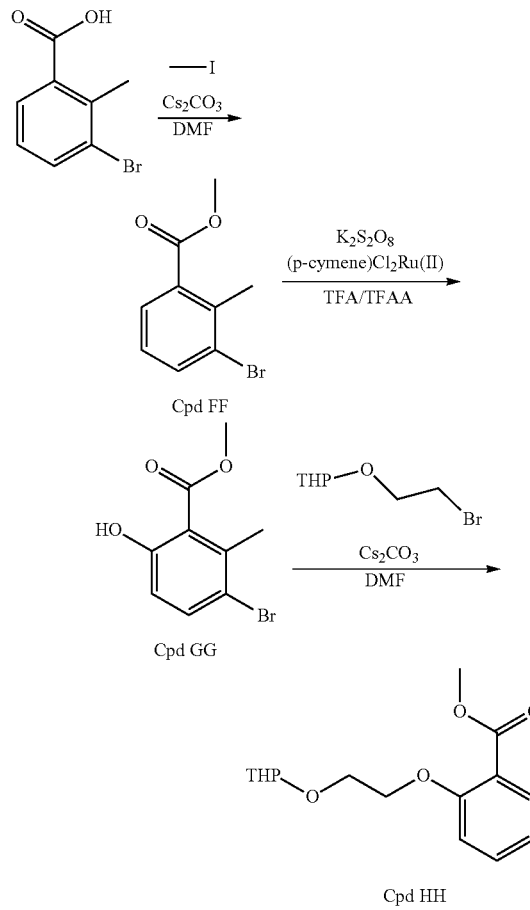

A solution of 3-bromo-2-methylbenzoic acid (2.98 g, 13.9 mmol) in DMF (20 mL) was treated with cesium carbonate (4.56 g, 13.9 mmol) and iodomethane (0.900 mL, 14.4 mmol). The reaction mixture was stirred at room temperature for 3 hours. The solution was poured into ethyl acetate and washed with water (3×) and brine. The ethyl acetate layer was concentrated under vacuum to give methyl 3-bromo-2-methylbenzoate (Cpd FF, 2.70 g, 85% yield) as a clear oil.

A solution of methyl 3-bromo-2-methylbenzoate (Cpd FF, 2.40 g, 10.5 mmol) in trifluoroacetic acid (50 mL) and trifluoroacetic anhydride (20 mL) in a sealed tube was treated with potassium persulfate (3.12 g, 11.5 mmol) and dichloro(p-cymene)ruthenium(II) dimer (0.170 g, 0.278 mmol). The reaction mixture was heated at 85° C. overnight. The volatiles were removed under vacuum and the resulting residue was taken up in dichloromethane and water. The aqueous phase was brought to pH-5 with $K_3PO_4$ (sat. aq.). The layers were separated and the organic layer purified by column chromatography (0-30% ethyl acetate/heptane) to give methyl 3-bromo-6-hydroxy-2-methylbenzoate (Cpd GG, 1.94 g, 75%) as a clear oil.

A solution of methyl 3-bromo-6-hydroxy-2-methylbenzoate (Cpd GG, 1.94 g, 7.90 mmol) in DMF (25 mL) was treated with cesium carbonate (3.45 g, 10.0 mmol) and then 2-(2-bromoethoxy)tetrahydro-2H-pyran (2.06 g, 9.84 mmol). The reaction mixture was heated at 55° C. for 16 hours. The reaction mixture was cooled to room temperature, diluted with ethyl acetate, and washed with water (2×) and brine. The organic layer was concentrated under vacuum to give a brown oil which was purified by column chromatography (0-25%, ethyl acetate/heptane) to give the title compound (Cpd HH, 2.11 g, 67% yield) as a clear oil. $^1$H NMR (400 MHz, chloroform-d) δ 7.50 (d, J=8.80 Hz, 1H), 6.72 (d, J=8.80 Hz, 1H), 4.68 (t, J=3.36 Hz, 1H), 4.13-4.18 (m, 2H), 4.00 (td, J=4.77, 11.37 Hz, 1H), 3.91 (s, 3H), 3.86 (ddd, J=3.06, 8.59, 11.34 Hz, 1H), 3.74-3.80 (m, 1H), 3.49-3.56 (m, 1H), 2.32 (s, 3H), 1.78-1.89 (m, 1H), 1.67-1.77 (m, 1H), 1.58-1.66 (m, 2H), 1.49-1.55 (m, 2H).

Compound LL: tert-butyl ((2-(benzyloxy)-4,6-dimethylpyridin-3-yl)methyl)(2-hydroxyethyl)carbamate

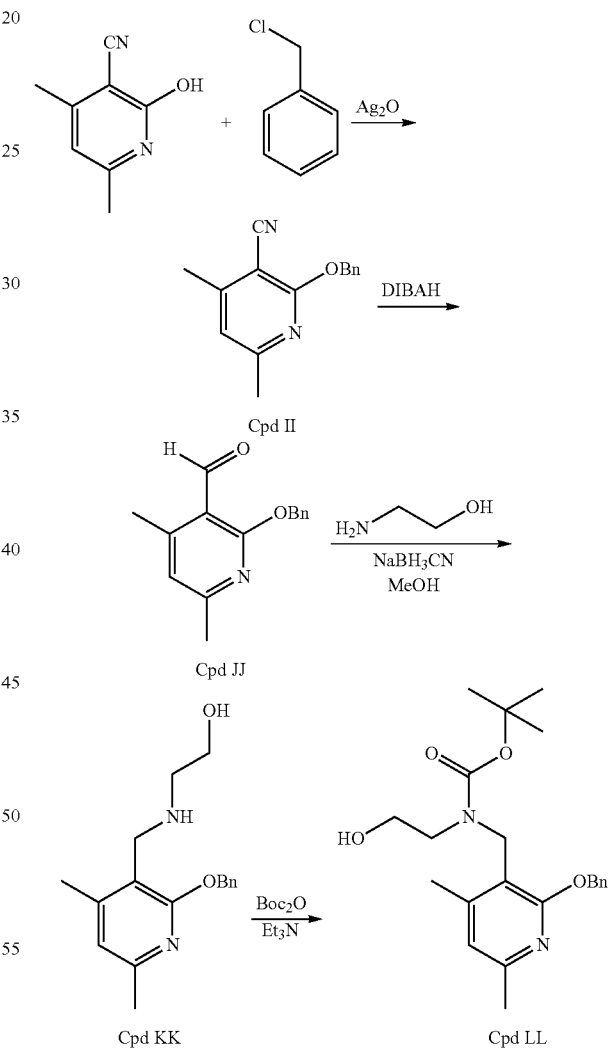

A mixture of 2-hydroxy-4,6-dimethylnicotinonitrile (5.3 g, 36 mmol), benzyl chloride (5.7 mL, 45 mmol), silver(I) oxide (9.2 g, 40 mmol) and toluene (50 mL) were heated at 110° C. in a sealed tube for 20 hours. The mixture was cooled to room temperature and the solids were filtered and rinsed with dichloromethane. The filtrate was concentrated under vacuum and purified by column chromatography (40% EtOAc/Heptane) to give 2-(benzyloxy)-4,6-dimethylnicotinonitrile (Cpd II, 8.1 g, 94% yield) as a white solid.

To a cooled (0° C.) solution of 2-(benzyloxy)-4,6-dimethylnicotinonitrile (Cpd II, 8.1 g, 34 mmol) in dichloromethane (100 mL) was added dropwise diisobutylaluminium hydride solution (1 M in dichloromethane, 41 mL, 41 mmol). The resulting mixture was slowly warmed to room temperature and stirred overnight. The reaction mixture was cooled to 0° C. then carefully quenched by dropwise addition of 1N hydrochloric acid (75 mL). The solution was neutralized with 4N sodium hydroxide then extracted with dichloromethane (2×75 mL). The combined organic extracts were dried over magnesium sulfate and concentrated under vacuum to give 2-(benzyloxy)-4,6-dimethylnicotinaldehyde (Cpd JJ, 6.4 g, 78% yield) as an orange oil.

To a suspension of 2-(benzyloxy)-4,6-dimethylnicotinaldehyde (Cpd JJ, 6.4 g, 27 mmol) in methanol (100 mL) was added 2-aminoethanol (8.34 mL, 133 mmol). The reaction mixture was stirred at room temperature for 1 hour then cooled to 0° C. Sodium cyanoborohydride (4.9 g, 66 mmol) was added in one portion and the reaction was slowly warmed to room temperature and stirred overnight. The methanol was removed under vacuum then the residue was diluted with water (50 mL) and extracted with dichloromethane (2×50 mL). The combined organic extracts were dried over magnesium sulfate, concentrated under vacuum and purified by column chromatography (EtOAc) to give 2-(((2-(benzyloxy)-4,6-dimethylpyridin-3-yl)methyl)amino)-ethanol (Cpd KK, 4.2 g, 55% yield) as a pale yellow solid.

To a suspension of 2-(((2-(benzyloxy)-4,6-dimethylpyridin-3-yl)methyl)amino)ethanol (Cpd KK, 3.0 g, 10 mmol) in dichloromethane (100 mL) was added triethylamine (4.4 mL, 32 mmol) and di-tert-butyl dicarbonate (2.8 g, 13 mmol). The reaction mixture was stirred at room temperature for 18 hours then diluted with water (50 mL) and extracted with dichloromethane (2×75 mL). The combined organic extracts were dried over magnesium sulfate and concentrated to give the title compound (Cpd LL, 4 g, 98% yield) as a clear oil. $^1$H NMR (400 MHz, DMSO-$d_6$) δ 7.45 (2H, d, J=7.07 Hz), 7.32-7.39 (2H, m), 7.25-7.32 (1H, m), 6.71 (1H, s), 5.34 (2H, s), 4.53 (1H, br. s.), 4.47 (2H, s), 3.23-3.30 (2H, m), 2.92-3.06 (2H, m), 2.33 (3H, s), 2.23 (3H, s), 1.36 (9H, br. s.); MS 387 [M+H].

Compound PP: methyl 6-bromo-2-methyl-3-(propan-2-yloxy)benzoate

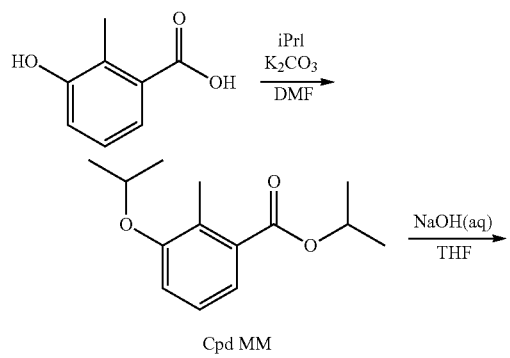

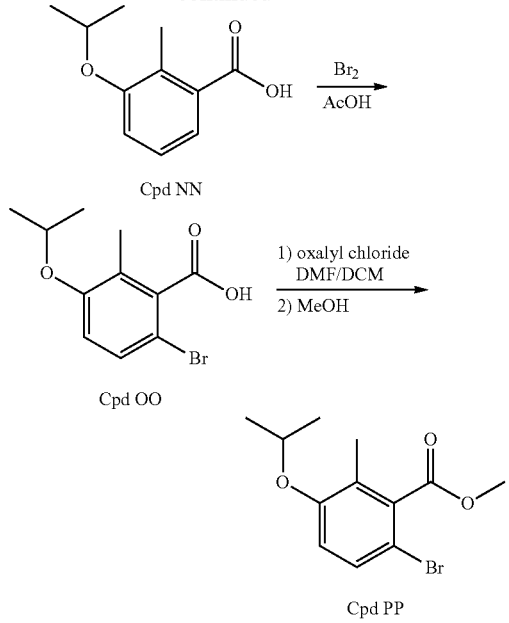

To a solution of 3-hydroxy-2-methylbenzoic acid (6.00 g, 40.0 mmol) in DMF (40 mL) was added $K_2CO_3$ (11.4 g, 82.8 mmol) and 2-iodopropane (8.28 g, 82.8 mmol). The reaction mixture was stirred at room temperature overnight, then heated at 70° C. for 3 hours. The reaction mixture was diluted with EtOAc then filtered through CELITE®. The filtrate was washed with water and brine, dried with $Na_2SO_4$, decanted and concentrated under vacuum. The residue was purified by column chromatography (0-30%, EtOAc/heptane) to give propan-2-yl 2-methyl-3-(propan-2-yloxy)benzoate (Cpd MM, 4.0 g, 40%) as a colorless oil.

To a solution of propan-2-yl 2-methyl-3-(propan-2-yloxy) benzoate (Cpd MM, 3.97 g, 16.8 mmol) in THF (40 mL) was added 2N NaOH (25.2 mL, 50.4 mmol). The reaction mixture turned light yellow and was heated at 65° C. for 3 days. The reaction mixture was cooled to room temperature, then concentrated under vacuum. The residue was acidified with 10% HCl(aq) then extracted with EtOAc. The organic layer was washed with brine, dried with $Na_2SO_4$ then concentrated under vacuum to give 2-methyl-3-(propan-2-yloxy)benzoic acid (Cpd NN, 4.0 g, 100%) as an oil.

To a solution of 2-methyl-3-(propan-2-yloxy)benzoic acid (Cpd NN, 1.08 g, 5.56 mmol) in AcOH (5 mL) was added $Br_2$ (888 mg, 5.56 mmol). The reaction mixture was stirred at room temperature overnight. The reaction mixture was concentrated under vacuum to give an oil. The crude oil was dissolved in MeOH (20 mL) then $H_2SO_4$ was added and the resulting mixture was heated at 65° C. for 2 hours. The reaction mixture was concentrated under vacuum and the residue dissolved in EtOAc. The organic layer was washed with water and brine, dried with $Na_2SO_4$, and concentrated under vacuum to give 6-bromo-2-methyl-3-(propan-2-yloxy)benzoic acid (Cpd OO, 1.3 g, 86%) as an oil which solidified to a tan solid upon standing.

To a 0° C. solution of 6-bromo-2-methyl-3-(propan-2-yloxy)benzoic acid (Cpd OO, 1.30 g, 4.80 mmol) in DCM (5 mL) was added oxalyl chloride (810 mg, 6.19 mmol) followed by DMF (10 mL). The reaction mixture was stirred at 0° C. for 1.5 hours, then concentrated under vacuum. The residue was dissolved in MeOH (15 mL) and stirred at room temperature for 1.5 hours. The reaction mixture was concentrated under vacuum and the residue dissolved in EtOAc. The organic layer was washed with brine, dried with Na$_2$SO$_4$, and concentrated under vacuum. The residue was purified by column chromatography (0-50%, EtOAc/heptane) to give the title compound (Cpd PP, 894 mg, 65%) as an amber oil. $^1$H NMR (400 MHz, chloroform-d) δ 1.33 (d, J=6.11 Hz, 6H) 2.16 (s, 3H) 3.95 (s, 3H) 4.50 (dt, J=12.04, 6.08 Hz, 1H) 6.75 (d, J=8.80 Hz, 1H) 7.31 (d, J=8.80 Hz, 1H); MS 287 [M+H].

Compound QQ: 3-bromo-6-fluoro-2-methylbenzoic acid

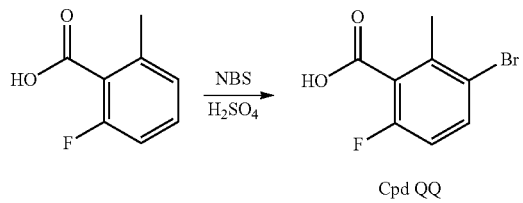

Cpd QQ

To a 0° C. solution of 2-fluoro-6-methyl-benzoic acid (1.48 g, 9.60 mmol) in conc. H$_2$SO$_4$ (40 mL) was added NBS (1.79 g, 10.1 mmol). The mixture was stirred at 0° C. for 3 hours. The reaction mixture was poured into ice water (200 mL), and extracted with ether (2×200 mL). The organic layers were combined, dried over sodium sulfate, and concentrated under vacuum to give the title compound (Compound QQ, 2.15 g, 96% yield) as a solid. $^1$H NMR (400 MHz, chloroform-d) δ 7.64 (dd, J=8.84, 5.31 Hz, 1H), 6.92 (t, J=8.84 Hz, 1H), 2.54 (s, 3H); MS 231.0 [M+H].

EXAMPLES

General Methods and Representative Examples

Method A

Example 1: 8-chloro-7-(difluoromethoxy)-2-[(4,6-dimethyl-2-oxo-1,2-dihydropyridin-3-yl)methyl]-3,4-dihydroisoquinolin-1(2H)-one

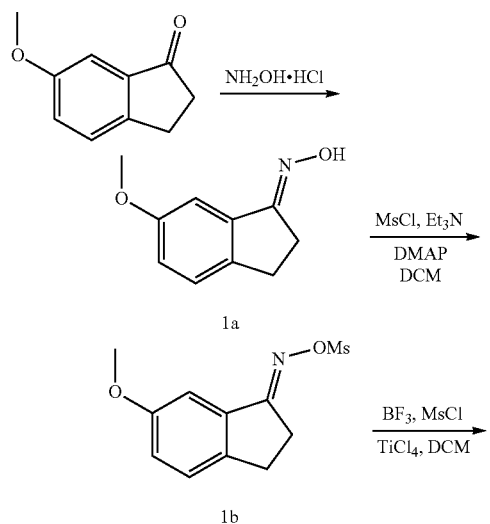

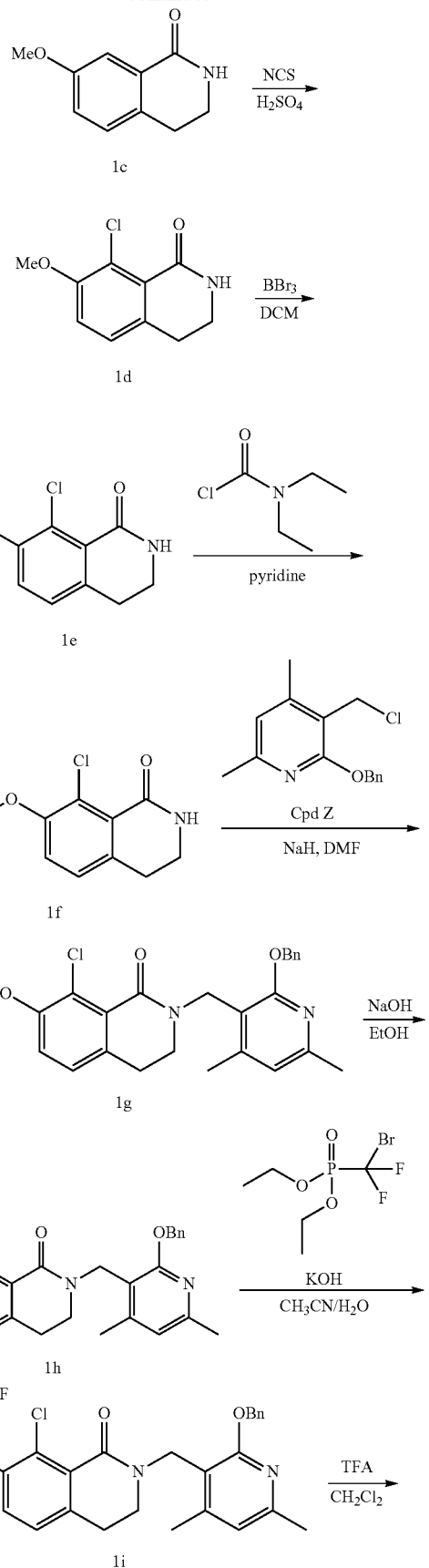

-continued

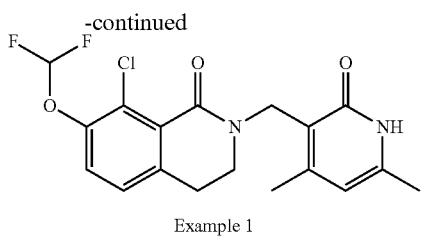

Example 1

To a stirred suspension of 6-methoxy-2,3-dihydro-1H-inden-1-one (15.0 g, 93.0 mmol) and Et$_3$N (28.2 g, 279 mmol) in MeOH (200 mL) was added NH$_2$OH.HCl (12.8 g, 186 mmol) at room temperature. After the addition, the resulting solution was stirred at room temperature for 24 hours. The reaction mixture was concentrated under vacuum. To the residue was added EtOAc (300 mL). The solution was washed with water (2×150 mL), brine (150 mL), dried over Na$_2$SO$_4$, and concentrated under vacuum to give (1E)-N-hydroxy-6-methoxy-2,3-dihydro-1H-inden-1-imine (1a, 17 g, >100%) as a white solid.

To a solution of (1E)-N-hydroxy-6-methoxy-2,3-dihydro-1H-inden-1-imine (1a, 28.0 g, 158 mmol), DMAP (1.93 g, 15.8 mmol) and Et$_3$N (63.8 g, 632 mmol) in dry DCM (200 mL) was added MsCl (27.5 g, 239 mmol) dropwise at 0° C. After the addition, the resulting solution was stirred at room temperature for 14 hours. The reaction mixture was washed with water (150 mL), saturated NH$_4$Cl (130 mL) and brine (130 mL). The organic layer was dried over Na$_2$SO$_4$ and concentrated under vacuum. The residue was purified by column chromatography (petroleum ether/EtOAc, 1:1) to give (1E)-6-methoxy-N-[(methylsulfonyl)oxy]-2,3-dihydro-1H-inden-1-imine (1b, 27 g, 67%) as a yellow solid.

To a stirred suspension of (1E)-6-methoxy-N-[(methylsulfonyl)oxy]-2,3-dihydro-1H-inden-1-imine (1b, 27 g, 106 mmol), BF$_3$/MeOH (14% in MeOH, 16.8 g, 170 mmol) and TiCl$_4$ (32.3 g, 170 mmol) in dry DCM (200 mL) was added MsCl (20.9 g, 183 mmol) dropwise at 0° C. After the addition, the resulting solution was stirred at room temperature for 14 hours. To the reaction mixture was added DCM (200 mL) and the solution was washed with saturated NaHCO$_3$ to pH 7. The organic layer was washed with brine (150 mL), dried over Na$_2$SO$_4$, and concentrated under vacuum. The residue was purified by column chromatography (DCM/MeOH) to give 7-methoxy-3,4-dihydroisoquinolin-1(2H)-one (1c, 22 g, 100%) as a gray solid.

To a mixture of 7-methoxy-3,4-dihydroisoquinolin-1(2H)-one (1c, 13.0 g, 73.9 mmol) in conc. H$_2$SO$_4$ (120 mL) was added portionwise NCS (10.4 g, 77.6 mmol) at 0° C. The reaction mixture was warmed to room temperature and stirred overnight. The reaction mixture was poured onto ice-water (200 mL). The solution was basified with Na$_2$CO$_3$ (s) to pH 8. The reaction mixture was extracted with EtOAc (2×200 mL). The combined organic layers were washed with brine (300 mL), dried over Na$_2$SO$_4$ and concentrated under vacuum. The residue was purified by column chromatography (petroleum ether/EtOAc, 1:1) to give 8-chloro-7-methoxy-3,4-dihydroisoquinolin-1(2H)-one (1d, 7.8 g, 50%) as a yellow solid.

To a 0° C. solution of 8-chloro-7-methoxy-3,4-dihydroisoquinolin-1(2H)-one (1d, 7.8 g, 3.7 mmol) in dry CH$_2$Cl$_2$ (120 mL) was added dropwise BBr$_3$ (11 mL, 111 mmol). After the addition, the mixture was stirred at room temperature overnight. To the reaction mixture was added dropwise H$_2$O (200 mL). The mixture was extracted with EtOAc (8×200 mL), dried over Na$_2$SO$_4$ and concentrated under vacuum. To the residue was added EtOAc (20 mL) and petroleum ether (40 mL). The mixture was filtered and the solids were dried under vacuum to give 8-chloro-7-hydroxy-3,4-dihydroisoquinolin-1(2H)-one (1e, 6.6 g, 91%) as a brown solid.

A mixture of 8-chloro-7-hydroxy-3,4-dihydroisoquinolin-1(2H)-one (1e, 5.6 g, 28 mmol), and diethylcarbamic chloride (4.3 g, 31 mmol) in pyridine (100 mL) was stirred at 100° C. for 5 hours. To the reaction mixture was added H$_2$O (300 mL). The mixture was extracted with EtOAc (2×200 mL). The combined organic layers were washed with 1 N HCl (2×300 mL) and brine (300 mL), dried over Na$_2$SO$_4$ and concentrated under vacuum. The residue was purified by column chromatography (EtOAc) to give 8-chloro-1-oxo-1,2,3,4-tetrahydroisoquinolin-7-yl diethylcarbamate (1f, 7.6 g, 90%) as brown oil.

To a suspension of NaH (2.2 g, 54 mmol, 60% in oil) in dry DMF (20 mL) was added dropwise a solution of 8-chloro-1-oxo-1,2,3,4-tetrahydroisoquinolin-7-yl diethylcarbamate (1f, 8.0 g, 27 mmol) in dry DMF (40 mL) at 0° C. under N$_2$. The mixture was stirred at 0° C. for 15 minutes. 2-(Benzyloxy)-3-(chloromethyl)-4,6-dimethylpyridine (Cpd Z, 8.5 g, 32.4 mmol) was added. The mixture was stirred at room temperature overnight. To the reaction mixture was added dropwise H$_2$O (200 mL) carefully. The mixture was extracted with EtOAc (2×150 mL). The combined organic layers were washed with brine (4×200 mL), dried over Na$_2$SO$_4$, and concentrated under vacuum. The residue was purified by column chromatography (petroleum ether/EtOAc, 3:1) to give 2-{[2-(benzyloxy)-4,6-dimethylpyridin-3-yl]methyl}-8-chloro-1-oxo-1,2,3,4-tetrahydroisoquinolin-7-yl diethylcarbamate (1 g, 14 g, 99%) as yellow oil.

A mixture of 2-{[2-(benzyloxy)-4,6-dimethylpyridin-3-yl]methyl}-8-chloro-1-oxo-1,2,3,4-tetrahydroisoquinolin-7-yl diethylcarbamate (1 g, 14.0 g, 26.8 mmol) and NaOH (10.7 g, 268 mmol) in EtOH (200 mL) was refluxed overnight. The reaction mixture was concentrated under vacuum. To the reaction mixture was added H$_2$O (200 mL) and the solution was acidified with 1 N HCl to pH 3. The reaction mixture was extracted with EtOAc (2×200 mL). The combined organic layers were washed with brine (300 mL), dried over Na$_2$SO$_4$ and concentrated under vacuum. To the residue was added EtOAc (20 mL) and petroleum ether (100 mL). The mixture was filtered and the solids were dried under vacuum to give 2-{[2-(benzyloxy)-4,6-dimethylpyridin-3-yl]methyl}-8-chloro-7-hydroxy-3,4-dihydroisoquinolin-1(2H)-one (1h, 9.8 g, 87%) as an off-white solid.

To a solution of 2-{[2-(benzyloxy)-4,6-dimethylpyridin-3-yl]methyl}-8-chloro-7-hydroxy-3,4-dihydroisoquinolin-1(2H)-one (1h, 0.1 g, 0.237 mmol) and KOH (0.265 g, 4.74 mmol) in CH$_3$CN/H$_2$O (10 mL/1 mL) was added diethyl [bromo(difluoro)methyl]phosphonate (0.126 g, 0.474 mmol) at −78° C. under N$_2$ atmosphere. The resulting mixture was allowed to warm to room temperature and stirred for 30 minutes. The mixture was diluted with EtOAc (20 mL) and H$_2$O (5 mL). The organic layer was separated and the aqueous layer was extracted with EtOAc (2×10 mL). The organic layers were combined, washed with brine (10 mL), dried over Na$_2$SO$_4$, and concentrated under vacuum. The residue was purified by prep. TLC (petroleum ether/EtOAc, 4:1) to obtain 2-{[2-(benzyloxy)-4,6-dimethylpyridin-3-yl]methyl}-8-chloro-7-(difluoromethoxy)-3,4-dihydroisoquinolin-1(2H)-one (1i, 0.08 g, 72%) as a yellow oil.

To a solution of 2-{[2-(benzyloxy)-4,6-dimethylpyridin-3-yl]methyl}-8-chloro-7-(difluoromethoxy)-3,4-dihydroisoquinolin-1(2H)-one (1i, 0.08 g, 0.169 mmol) in CH$_2$Cl$_2$ (10 mL) was added TFA (10 mL) at room temperature. The resulting mixture was stirred at room temperature for 4 hours. The mixture was concentrated under vacuum to give a residue, which was dissolved in CH$_2$Cl$_2$ (20 mL) and then washed with sat. NaHCO$_3$ (5 mL), brine (5 mL), dried over Na$_2$SO$_4$, and concentrated under vacuum. The residue was purified by prep. TLC (EtOAc) to obtain the title compound (Example 1, 43.1 mg, 67%) as a white solid. $^1$H NMR (400 MHz, methanol-d4) δ 7.36-7.34 (m, 1H), 7.24-7.22 (m, 1H), 7.00-6.63 (m, 1H), 6.11 (s, 1H), 4.76 (s, 2H), 3.51-3.48 (m, 2H), 2.90-2.87 (m, 2H), 2.29 (s, 3H), 2.25 (s, 3H); MS 382.9 [M+1].

Method B

Example 53: 2-[(4,6-dimethyl-2-oxo-1,2-dihydropyridin-3-yl)methyl]-7-methoxy-1-oxo-1,2,3,4-tetrahydroisoquinoline-6-carbonitrile

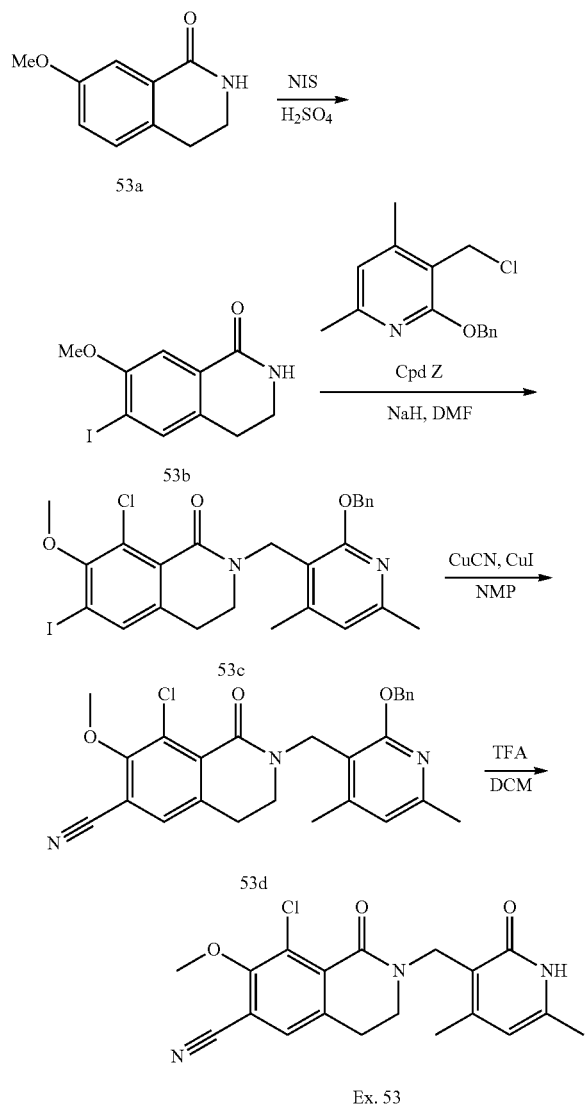

To a mixture of 7-methoxy-3,4-dihydroisoquinolin-1(2H)-one (53a, 1.7 g, 9.6 mmol) in conc. H$_2$SO$_4$ (40 mL) was added portionwise NIS (2.4 g, 11 mmol) at 0° C. The mixture was stirred at room temperature for 14 hours. The mixture was chilled to 0° C. and basified with aq. NaOH to pH 8. The mixture was extracted with EtOAc (5×60 mL). The combined organic layers were washed with brine (3×60 mL), dried over Na$_2$SO$_4$ and concentrated under vacuum. The residue was purified by column chromatography (petroleum ether/EtOAc, 1:1) to give 8-iodo-7-methoxy-3,4-dihydroisoquinolin-1(2H)-one (53b, 2.1 g, 79%) as a yellow solid.

To a solution of 8-iodo-7-methoxy-3,4-dihydroisoquinolin-1(2H)-one (53b, 2.08 mg, 5.22 mmol) in anhydrous DMF (30 mL) was added NaH (420 mg, 10.4 mmol, 60% in oil) at 0° C. under N$_2$ atmosphere for 30 minutes. 2-(benzyloxy)-3-(chloromethyl)-4,6-dimethylpyridine (Cpd Z, 1.89 g, 7.83 mmol) was added to the mixture. The resulting mixture was stirred at room temperature for 14 hours. The mixture was quenched with H$_2$O (60 mL) and extracted with EtOAc (4×80 mL). The combined organic layers were washed with brine (2×50 mL), dried over Na$_2$SO$_4$ and concentrated under vacuum. The residue was purified by prep.HPLC to give 2-{[2-(benzyloxy)-4,6-dimethylpyridin-3-yl]methyl}-8-iodo-7-methoxy-3,4-dihydroisoquinolin-(2H)-one (53c, 2.5 g, 91%) as a yellow solid.

To a solution of 2-{[2-(benzyloxy)-4,6-dimethylpyridin-3-yl]methyl}-8-iodo-7-methoxy-3,4-dihydroisoquinolin-1(2H)-one (53c, 300 mg, 0.568 mmol) in NMP (8 mL, dry) was added CuCN (152 mg, 1.705 mmol) at room temperature. The resulting mixture was stirred at 190° C. for 3 hours. The mixture was cooled to room temperature and H$_2$O (20 mL) was added to the mixture. The mixture was diluted with EtOAc (5×20 mL). The combined organic layers were washed with brine (3×20 mL), dried over Na$_2$SO$_4$, and concentrated under vacuum to give a residue, which was purified by column chromatography (petroleum ether/EtOAc, 3:1) to obtain 2-{[2-(benzyloxy)-4,6-dimethylpyridin-3-yl]methyl}-7-methoxy-1-oxo-1,2,3,4-tetrahydroisoquinoline-8-carbonitrile (53d, ~0.568 mmol, 100%) as a yellow solid.

To a solution of 2-{[2-(benzyloxy)-4,6-dimethylpyridin-3-yl]methyl}-7-methoxy-1-oxo-1,2,3,4-tetrahydroisoquinoline-8-carbonitrile (53d, ~0.568 mmol) in CH$_2$Cl$_2$ (25 mL) was added TFA (12 mL) at room temperature. The resulting mixture was stirred at room temperature for 16 hours. The mixture was concentrated under vacuum. To the residue was added MeOH (100 mL) and stirred for 0.5 hours. The mixture was filtered and the solids were dried under vacuum to give the title compound (Example 53, 15.9 mg, 6.7%) as a yellow solid. $^1$H NMR (400 MHz, DMSO-d6): δ 11.58 (s, 1H), 7.70 (s, 1H), 7.61 (s, 1H), 5.89 (s, 1H), 4.58 (s, 2H), 3.96 (s, 3H), 3.51-3.48 (t, 2H), 2.83-2.80 (t, 2H), 2.16 (s, 3H), 2.12 (s, 3H); MS 338.1 [M+1].

Method C

Example 58: 8-chloro-2-[(4,6-dimethyl-2-oxo-1,2-dihydropyridin-3-yl)methyl]-7-[(1,1,1-trifluoropropan-2-yl)oxy]-3,4-dihydroisoquinolin-1(2H)-one

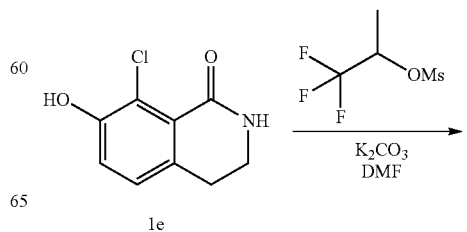

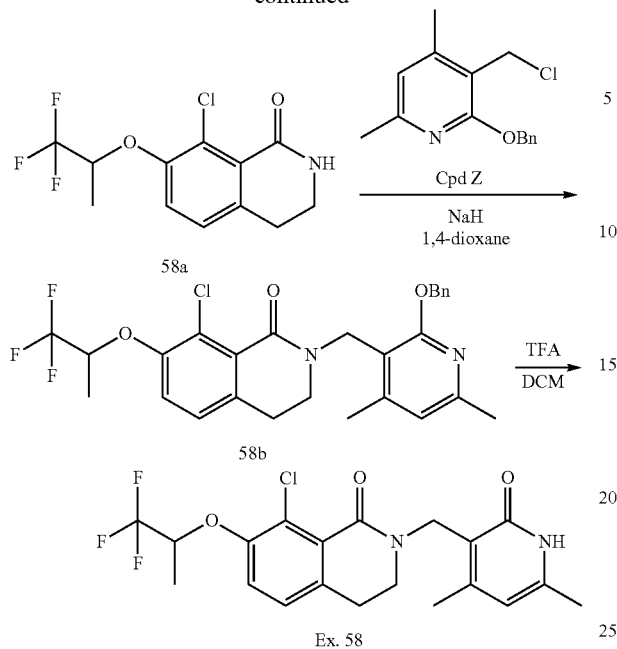

1H), 4.75 (s, 2H), 4.57-4.54 (t, 1H), 3.55 (s, 2H), 2.77 (s, 2H), 2.33-2.25 (d, 6H), 1.55 (s, 3H); MS 428.9 [M+H].

Example 296: 1,4-anhydro-3-deoxy-2-O-{5,8-dichloro-2-[(4,6-dimethyl-2-oxo-1,2-dihydropyridin-3-yl)methyl]-1-oxo-1,2,3,4-tetrahydroisoquinolin-7-yl}-L-threo-pentitol Part 1.

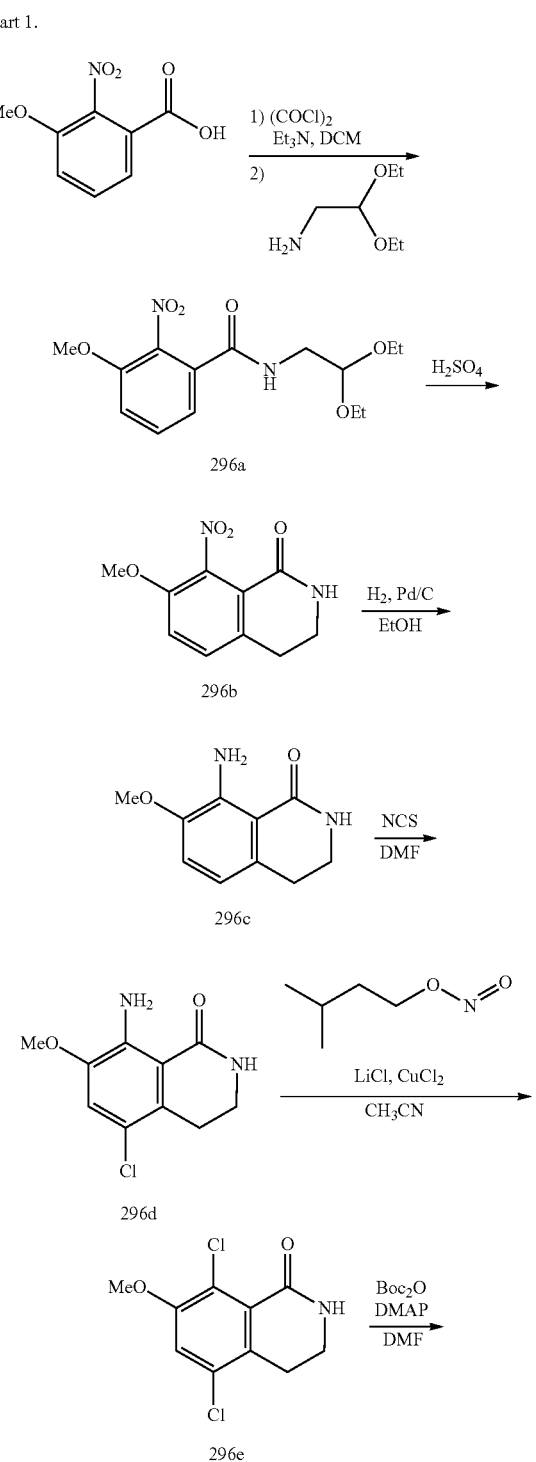

A mixture of 8-chloro-7-hydroxy-3,4-dihydroisoquinolin-1(2H)-one (1e, 120 mg, 0.610 mmol), 1,1,1-trifluoropropan-2-yl methanesulfonate (526 mg, 2.74 mmol), and $K_2CO_3$ (420 mg, 3.05 mmol) in dry DMF (8 mL) was stirred in a sealed-tube at 140° C. for 48 hours. To the reaction mixture was added $H_2O$ (40 mL). The mixture was extracted with EtOAc (2×20 mL). The combined organic layers were washed with brine (4×30 mL), dried over $Na_2SO_4$, and concentrated under vacuum. The residue was purified by preparatory TLC (EtOAc, Rf~0.65) to give 8-chloro-7-[(1,1,1-trifluoropropan-2-yl)oxy]-3,4-dihydroisoquinolin-1(2H)-one (58a, 27 mg, 15%) as a yellow oil.

To a solution of 8-chloro-7-[(1,1,1-trifluoropropan-2-yl)oxy]-3,4-dihydroisoquinolin-1(2H)-one (58a, 50 mg, 0.17 mmol) in dry DMF (6 mL) was added portionwise NaH (60% in oil, 21 mg, 0.51 mmol) at 0° C. under $N_2$ atmosphere. The resulting mixture was stirred at 0° C. for 10 minutes and then 2-(benzyloxy)-3-(chloromethyl)-4,6-dimethylpyridine (Cpd Z, 76 mg, 0.29 mmol) was added. The resulting mixture was stirred at room temperature overnight. To the reaction mixture was added $H_2O$ (20 mL). The mixture was extracted with EtOAc (2×10 mL). The combined organic layers were washed with brine (4×15 mL), dried over $Na_2SO_4$ and concentrated under vacuum. The residue was purified by column chromatography (petroleum ether/EtOAc=6:1) to give 2-{[2-(benzyloxy)-4,6-dimethylpyridin-3-yl]methyl}-8-chloro-7-[(1,1,1-trifluoropropan-2-yl)oxy]-3,4-dihydroisoquinolin-1(2H)-one (58b, 70 mg, 80%) as a colorless oil.

To a solution of 2-{[2-(benzyloxy)-4,6-dimethylpyridin-3-yl]methyl}-8-chloro-7-[(1,1,1-trifluoropropan-2-yl)oxy]-3,4-dihydroisoquinolin-1(2H)-one (58b, 70 mg, 0.14 mmol) in $CH_2Cl_2$ (5 mL) was added TFA (1 mL) at room temperature. The resulting mixture was stirred at room temperature overnight. The mixture was concentrated under vacuum. The residue was purified by column chromatography (EtOAc) to give the title compound (Example 58, 20 mg, 34%) as a white solid. $^1$H NMR (400 MHz, chloroform): δ 11.16 (s, 1H), 7.08-7.05 (d, 1H), 7.00-6.98 (d, 1H), 5.94 (s,

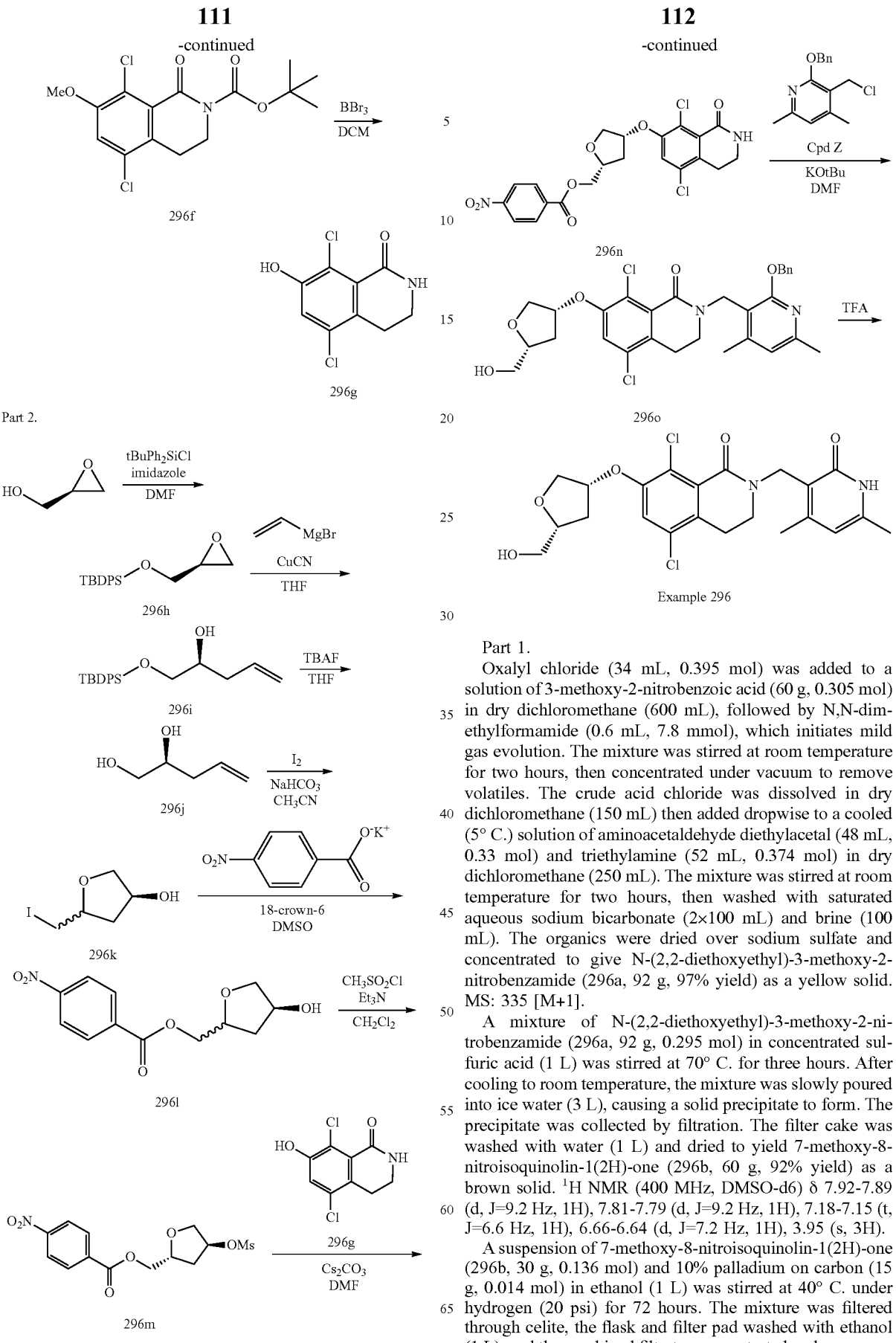

Part 1.

Oxalyl chloride (34 mL, 0.395 mol) was added to a solution of 3-methoxy-2-nitrobenzoic acid (60 g, 0.305 mol) in dry dichloromethane (600 mL), followed by N,N-dimethylformamide (0.6 mL, 7.8 mmol), which initiates mild gas evolution. The mixture was stirred at room temperature for two hours, then concentrated under vacuum to remove volatiles. The crude acid chloride was dissolved in dry dichloromethane (150 mL) then added dropwise to a cooled (5° C.) solution of aminoacetaldehyde diethylacetal (48 mL, 0.33 mol) and triethylamine (52 mL, 0.374 mol) in dry dichloromethane (250 mL). The mixture was stirred at room temperature for two hours, then washed with saturated aqueous sodium bicarbonate (2×100 mL) and brine (100 mL). The organics were dried over sodium sulfate and concentrated to give N-(2,2-diethoxyethyl)-3-methoxy-2-nitrobenzamide (296a, 92 g, 97% yield) as a yellow solid. MS: 335 [M+1].

A mixture of N-(2,2-diethoxyethyl)-3-methoxy-2-nitrobenzamide (296a, 92 g, 0.295 mol) in concentrated sulfuric acid (1 L) was stirred at 70° C. for three hours. After cooling to room temperature, the mixture was slowly poured into ice water (3 L), causing a solid precipitate to form. The precipitate was collected by filtration. The filter cake was washed with water (1 L) and dried to yield 7-methoxy-8-nitroisoquinolin-1(2H)-one (296b, 60 g, 92% yield) as a brown solid. $^1$H NMR (400 MHz, DMSO-d6) δ 7.92-7.89 (d, J=9.2 Hz, 1H), 7.81-7.79 (d, J=9.2 Hz, 1H), 7.18-7.15 (t, J=6.6 Hz, 1H), 6.66-6.64 (d, J=7.2 Hz, 1H), 3.95 (s, 3H).

A suspension of 7-methoxy-8-nitroisoquinolin-1(2H)-one (296b, 30 g, 0.136 mol) and 10% palladium on carbon (15 g, 0.014 mol) in ethanol (1 L) was stirred at 40° C. under hydrogen (20 psi) for 72 hours. The mixture was filtered through celite, the flask and filter pad washed with ethanol (1 L), and the combined filtrates concentrated under vacuum to give 8-amino-7-methoxy-3,4-dihydroisoquinolin-1(2H)-one (296c, 24 g, 92% yield) as a brown oil. MS: 193 [M+1].

N-chlorosuccinimide (20 g, 0.147 mol) was added to a solution of 8-amino-7-methoxy-3,4-dihydroisoquinolin-1(2H)-one (296c, 24 g, 0.125 mol) in N,N-dimethylformamide (250 mL) and stirred at room temperature overnight. The solution was partitioned between water (100 mL) and ethyl acetate (5×100 mL). The combined organic extracts were washed with brine (5×100 mL), dried over sodium sulfate, and concentrated to dryness. The residue was triturated with acetonitrile (200 mL), and the solids collected by filtration. After drying, 8-amino-5-chloro-7-methoxy-3,4-dihydroisoquinolin-1(2H)-one (296d, 12.5 g, 44% yield) was obtained as a blue solid. $^1$H NMR (400 MHz, DMSO-d6): δ 7.84 (s, 1H), 6.93 (s, 1H), 3.80 (s, 3H), 3.29-3.25 (m, 2H), 2.81-2.78 (t, J=6.6 Hz, 2H).

Isopentyl nitrite (20 mL, 0.149 mol) was added dropwise to a heated (55° C.) suspension of copper (II) chloride (40 g, 0.298 mol) and lithium chloride (38 g, 0.905 mol) in acetonitrile (500 mL). The mixture was stirred at that temperature for 5 minutes, then 8-amino-5-chloro-7-methoxy-3,4-dihydroisoquinolin-1(2H)-one (296d, 20 g, 0.089 mol) was added in portions. After the addition was complete, stirring was continued at 55° C. for 45 minutes. The reaction mixture was cooled to room temperature, quenched with saturated aqueous ammonium chloride (300 mL), and extracted with ethyl acetate (4×200 mL). The combined organic layers were washed with aqueous ammonium chloride (200 mL) and brine (100 mL), dried over sodium sulfate, and concentrated under vacuum to give crude 5,8-dichloro-7-methoxy-3,4-dihydroisoquinolin-1(2H)-one (296e, 20 g, 90% purity, 92% yield) as a brown solid. MS: 245 [M+1].

Di-tert-butyl dicarbonate (76 g, 0.352 mol) was added in portions to a cooled (0° C.) solution of crude 5,8-dichloro-7-methoxy-3,4-dihydroisoquinolin-1(2H)-one (296e, 20 g, 0.082 mol) and 4-dimethylaminopyridine (30 g, 0.246 mol) in N,N-dimethylformamide (200 mL). After the addition was complete, the solution was stirred at room temperature overnight, then partitioned between water (200 mL) and ethyl acetate (5×200 mL). The combined organic extracts were dried over sodium sulfate, concentrated, and purified by silica gel chromatography (eluting with petroleum ether/ethyl acetate 100:1 to 10:1) to give tert-butyl 5,8-dichloro-7-methoxy-1-oxo-3,4-dihydroisoquinoline-2(1H)-carboxylate (296f, 11 g, 39% yield) as a light yellow solid. $^1$H NMR (400 MHz, DMSO-d6): δ 7.50 (s, 1H), 4.00 (s, 3H), 3.86-3.83 (t, J=6.8 Hz, 2H), 2.99-2.96 (t, J=5.8 Hz, 2H), 1.54 (s, 9H).

Boron tribromide (10 mL) was added to a cooled (0° C.) solution of tert-butyl 5,8-dichloro-7-methoxy-1-oxo-3,4-dihydroisoquinoline-2(1H)-carboxylate (296f, 14.5 g, 45.4 mmol) in dry dichloromethane (100 mL). The mixture was stirred at room temperature overnight, then water (10 mL) was added, causing a precipitate to form. The precipitate was collected by filtration, washed with water (500 mL), and dried to give 5,8-dichloro-7-hydroxy-3,4-dihydroisoquinolin-1(2H)-one (296 g, 9.2 g, 95% yield) as a light yellow solid. $^1$H NMR (400 MHz, DMSO-d6): δ 10.58 (s, 1H), 8.17 (s, 1H), 7.13 (s, 1H), 3.25-3.23 (m, 2H), 2.83-2.80 (t, J=6.2 Hz, 2H). MS: 232 [M+1].

Part 2.

To an ice-chilled mixture of (2R)-oxiran-2-ylmethanol (2.00 g, 27.0 mmol) and imidazole (3.68 g, 54.0 mmol) in anhydrous dichloromethane (60 mL) was added tert-butyl(chloro)diphenylsilane (8.40 mL, 32.4 mmol) dropwise, causing the formation of a white precipitate. The mixture was stirred at 0° C. for 15 minutes, then the cooling bath removed and stirring continued at room temperature for one hour. Aqueous ammonium chloride solution (2M, 100 mL) was added and the layers separated. The aqueous layer was extracted with dichloromethane (100 mL). The combined organic extracts were dried over sodium sulfate, concentrated, and purified by silica gel chromatography (eluting with a gradient of 0-30% ethyl acetate in heptane), affording tert-butyl[(2S)-oxiran-2-ylmethoxy]diphenylsilane (296h, 8.40 g, 99% yield) as an oil. $^1$H NMR (400 MHz, CDCl$_3$) δ 7.65-7.76 (m, 4H), 7.36-7.49 (m, 6H), 3.88 (dd, J=11.86, 3.30 Hz, 1H), 3.74 (dd, J=11.80, 4.71 Hz, 1H), 3.10-3.20 (m, 1H), 2.76 (dd, J=5.14, 4.16 Hz, 1H), 2.63 (dd, J=5.14, 2.69 Hz, 1H), 1.09 (s, 9H). MS: 330 [M+1].

Copper (I) cyanide (3.60 g, 40.2 mmol) was placed in a three-necked flask under nitrogen and dried by gentle heating with a heat gun under vacuum. It was then allowed to cool to room temperature under nitrogen. This process was repeated three times, and then anhydrous tetrahydrofuran (80 mL) was added. The resulting mixture was cooled to −78° C., and then vinyl magnesium bromide (1 M solution in tetrahydrofuran, 88.5 mL, 88.5 mmol) was added dropwise while maintaining the internal temperature below −68° C. The heterogeneous mixture was warmed to −20° C. and stirred at this temperature for 30 minutes. After cooling the solution back to −78° C., tert-butyl[(2S)-oxiran-2-ylmethoxy]diphenylsilane (296h, 8.38 g, 26.8 mmol) was added dropwise. The mixture was stirred, and allowed to gradually warm to room temperature, overnight. The reaction mixture was quenched with 100 mL ammonium hydroxide/ammonium chloride (1/10 2M NH$_4$Cl), and extracted with ethyl acetate (200 mL). The organic layer was washed with brine (200 mL), dried over sodium sulfate, concentrated to dryness, and purified by silica gel chromatography (eluting with a gradient of 0-20% ethyl acetate in heptane), to give (2S)-1-{[tert-butyl(diphenyl)silyl]oxy}pent-4-en-2-ol (296i, 5.68 g, 62% yield) as a clear oil. $^1$H NMR (400 MHz, CDCl$_3$) δ 7.65-7.71 (m, 4H), 7.36-7.49 (m, 6H), 5.75-5.87 (m, 1H), 5.03-5.14 (m, 2H), 3.76-3.85 (m, 1H), 3.66-3.72 (m, 1H), 3.54-3.61 (m, 1H), 2.45 (d, J=4.03 Hz, 1H), 2.23-2.30 (m, 2H), 1.09 (s, 9H). MS: 358 [M+18].

A solution of (2S)-1-{[tert-butyl(diphenyl)silyl]oxy}pent-4-en-2-ol (296i, 5.60 g, 16.4 mmol) in anhydrous tetrahydrofuran (30 mL) was cooled to 0° C. and treated with tetrabutylammonium fluoride solution (1 M in tetrahydrofuran, 18.3 mL, 18.3 mmol). The mixture was stirred and allowed to warm to room temperature over one hour, then concentrated and purified by silica gel chromatography (eluting with a gradient of 0-100% ethyl acetate in heptane), affording (2S)-pent-4-ene-1,2-diol (296j, 1.25 g, 73% yield) as an oil. $^1$H NMR (400 MHz, CDCl$_3$) δ 5.83 (ddt, J=17.16, 10.10, 7.15, 7.15 Hz, 1H), 5.08-5.21 (m, 2H), 3.73-3.83 (m, 1H), 3.67 (d, J=11.13 Hz, 1H), 3.48 (dd, J=10.94, 7.40 Hz, 1H), 2.51 (br. s., 1H), 2.42 (br. s., 1H), 2.17-2.32 (m, 2H).

A mixture of (2S)-pent-4-ene-1,2-diol (296j, 1.20 g, 11.7 mmol) and sodium bicarbonate (2.96 g, 35.2 mmol) in anhydrous acetonitrile (40 mL) was stirred for ten minutes at room temperature, then cooled to 0° C. in an icebath. Iodine (8.95 g, 35.2 mmol) was added, and stirring continued for two hours, as the mixture was allowed to warm to room temperature. The solution was diluted with diethyl ether (100 mL), washed with 1M aqueous sodium thiosulfate (100 mL) and brine (100 mL), dried over sodium sulfate, concentrated, and purified by silica gel chromatography (eluting with a gradient of 0-100% ethyl acetate in heptane), affording a mixture of (3S,5S)-5-(iodomethyl)

tetrahydrofuran-3-ol and (3S,5R)-5-(iodomethyl)tetrahydrofuran-3-ol (296 k, 2.19 g, 82% yield).

The mixture of (3S,5S)-5-(iodomethyl)tetrahydrofuran-3-ol and (3S,5R)-5-(iodomethyl)tetrahydrofuran-3-ol (296 k, 2.16 g, 9.47 mmol) was dissolved in anhydrous dimethylsulfoxide (40 mL) Potassium 4-nitrobenzoate (2.98 g, 14.2 mmol) and 18-crown-6 (3.76 g, 14.2 mmol) were added and the mixture stirred at 90° C. overnight. After cooling to room temperature, the reaction mixture was partitioned between ethyl acetate (100 mL) and water (100 mL). The organic phase was washed with water (100 mL) and brine (100 mL), dried over sodium sulfate, concentrated to dryness, and purified by silica gel chromatography (eluting with a gradient of 0-100% ethyl acetate in heptane), to give the product as a mixture of diastereomers: ((2 S,4S)-4-hydroxytetrahydrofuran-2-yl)methyl 4-nitrobenzoate and ((2R,4S)-4-hydroxytetrahydrofuran-2-yl)methyl 4-nitrobenzoate (2961, 1.13 g, 45% yield) as a solid. $^1$H NMR (400 MHz, CDCl$_3$) δ 8.21-8.33 (m, 4H), 4.46-4.64 (m, 3H), 4.36 (dd, J=11.68, 6.66 Hz, 1H), 4.05 (dd, J=9.90, 4.03 Hz, 0.76H), 3.93-3.99 (m, 0.24H), 3.80-3.88 (m, 1H), 2.34-2.45 (m, 0.25H), 2.08-2.17 (m, 0.77H), 1.81-1.96 (m, 1H), 1.57 (br. s., 1H).

The mixture of ((2S,4S)-4-hydroxytetrahydrofuran-2-yl) methyl 4-nitrobenzoate and ((2R,4S)-4-hydroxytetrahydrofuran-2-yl)methyl 4-nitrobenzoate (296I, 700 mg, 2.62 mmol) was combined with triethylamine (1.10 mL, 7.89 mmol) in anhydrous dichloromethane (12 mL). Methanesulfonyl chloride (400 µL, 5.17 mmol) was added, causing a slight exotherm. After stirring at room temperature for three hours, the reaction mixture was partitioned between water (50 mL) and dichloromethane (2×50 mL). The combined organic extracts were dried over sodium sulfate, concentrated, and purified by silica gel chromatography (eluting with a gradient of 20-100% ethyl acetate in heptane). The less polar peak was the desired single diastereomer, ((2R,4S)-4-((methylsulfonyl)oxy)tetrahydrofuran-2-yl)methyl 4-nitrobenzoate (296m, 672 mg, 74% yield). $^1$H NMR (400 MHz, CDCl$_3$) δ 8.26-8.33 (m, 2H), 8.17-8.25 (m, 2H), 5.34-5.43 (m, 1H), 4.50-4.60 (m, 2H), 4.34-4.43 (m, 1H), 4.13-4.20 (m, 1H), 4.05-4.12 (m, 1H), 3.07 (s, 3H), 2.47 (dd, J=14.24, 5.81 Hz, 1H), 2.00-2.13 (m, 1H).

A solution of ((2R,4S)-4-((methylsulfonyl)oxy)tetrahydrofuran-2-yl)methyl 4-nitrobenzoate (296m, 300 mg, 0.869 mmol), 5,8-dichloro-7-hydroxy-3,4-dihydroisoquinolin-1 (2H)-one (296 g, 222 mg, 0.956 mmol), and cesium carbonate (566 mg, 1.74 mmol) in N,N-dimethylformamide (8 mL) was heated to 100° C. for three hours. After cooling to room temperature, the reaction mixture was diluted with ethyl acetate (50 mL), washed with water (2×50 mL) and brine (50 mL), dried over sodium sulfate, concentrated to dryness, and purified by silica gel chromatography (eluting with a gradient of 0-100% ethyl acetate in heptane) to give 2,5-anhydro-3-deoxy-4-O— (5,8-dichloro-1-oxo-1,2,3,4-tetrahydroisoquinolin-7-yl)-1-O— (4-nitrobenzoyl)-L-threo-pentitol (296n, 128 mg, 31% yield) as a solid. $^1$H NMR (400 MHz, CDCl$_3$) δ 8.18-8.33 (m, 4H), 7.03 (s, 1H), 6.09 (br. s., 1H), 4.99 (td, J=4.28, 1.96 Hz, 1H), 4.56-4.62 (m, 2H), 4.42-4.52 (m, 1H), 4.27 (d, J=10.64 Hz, 1H), 4.02 (dd, J=10.58, 4.34 Hz, 1H), 3.48 (td, J=6.36, 3.91 Hz, 2H), 2.99-3.09 (m, 2H), 2.56 (ddd, J=14.24, 8.19, 6.42 Hz, 1H), 2.18 (dd, J=14.12, 5.07 Hz, 1H). MS: 481 [M+1]

Potassium tert-butoxide solution in tetrahydrofuran (1.0 M, 645 µL, 0.645 mmol) was added dropwise to a cooled (0° C.) solution of 2,5-anhydro-3-deoxy-4-O— (5,8-dichloro-1-oxo-1,2,3,4-tetrahydroisoquinolin-7-yl)-1-O— (4-nitrobenzoyl)-L-threo-pentitol (296n, 120 mg, 0.249 mmol) in anhydrous N,N-dimethylformamide (4 mL). After stirring for 30 minutes, a solution of 2-(benzyloxy)-3-(chloromethyl)-4,6-dimethylpyridine (compound Z, 71 mg, 0.273 mmol) in anhydrous N,N-dimethylformamide (1 mL) was added and stirring continued at 0° C. for 30 more minutes. The reaction mixture was diluted with ethyl acetate (50 mL), washed with water (2×50 mL) and brine (50 mL), dried over sodium sulfate, concentrated to dryness, and purified by silica gel chromatography (eluting with a gradient of 0-100% ethyl acetate in heptane), affording 1,4-anhydro-2-O-(2-{[2-(benzyloxy)-4,6-di methylpyridin-3-yl]methyl}-5,8-dichloro-1-oxo-1,2,3,4-tetrahydroisoquinolin-7-yl)-3-deoxy-L-threo-pentitol (2960, 36 mg, 26% yield) as a solid. $^1$H NMR (400 MHz, CDCl$_3$) δ 7.45 (d, J=7.21 Hz, 2H), 7.29-7.40 (m, 3H), 6.94 (s, 1H), 6.62 (s, 1H), 5.43 (s, 2H), 4.92 (br. s., 1H), 4.87 (s, 2H), 4.15-4.26 (m, 2H), 3.91 (dd, J=10.39, 3.91 Hz, 1H), 3.75-3.84 (m, 1H), 3.66-3.75 (m, 1H), 3.25 (t, J=6.05 Hz, 2H), 2.69 (t, J=6.05 Hz, 2H), 2.42 (s, 3H), 2.34-2.40 (m, 1H), 2.32 (s, 3H), 2.03-2.16 (m, 2H). MS: 557 [M+1].

A solution of 1,4-anhydro-2-O—(2-{[2-(benzyloxy)-4,6-dimethylpyridin-3-yl]methyl}-5,8-dichloro-1-oxo-1,2,3,4-tetrahydroisoquinolin-7-yl)-3-deoxy-L-threo-pentitol (2960, 36 mg, 0.065 mmol) in trifluoroacetic acid (2 mL) was stirred at room temperature for three hours. The volatiles were removed under vacuum, and the residue partitioned between ethyl acetate (20 mL) and saturated aqueous sodium bicarbonate (20 mL). The aqueous layer was back-extracted with ethyl acetate (2×20 mL). The combined organic extracts were dried over sodium sulfate, concentrated, and purified by silica gel chromatography (eluting with a gradient of 0-10% methanol in ethyl acetate) to yield 1,4-anhydro-3-deoxy-2-O-{5,8-dichloro-2-[(4,6-dimethyl-2-oxo-1,2-dihydropyridin-3-yl)methyl]-1-oxo-1,2,3,4-tetrahydroisoquinolin-7-yl}-L-threo-pentitol (Example 296, 12 mg, 40% yield), as a solid, after lyophilization. $^1$H NMR (400 MHz, methanol-d4) δ 7.14 (s, 1H), 6.00 (s, 1H), 4.93-5.02 (m, 1H), 4.64 (s, 2H), 3.95-4.06 (m, 2H), 3.85 (dd, J=10.39, 4.28 Hz, 1H), 3.56-3.64 (m, 1H), 3.49-3.55 (m, 1H), 3.38 (t, J=6.17 Hz, 2H), 2.80 (t, J=6.24 Hz, 2H), 2.36 (ddd, J=14.09, 7.79, 6.60 Hz, 1H), 2.18 (s, 3H), 2.14 (s, 3H), 1.84 (dd, J=13.94, 5.50 Hz, 1H).

Method D

Example 253: 5,8-dichloro-7-(3,5-dimethyl-1,2-oxazol-4-yl)-2-[(4,6-dimethyl-2-oxo-1,2-dihydropyridin-3-yl)methyl]-3,4-dihydroisoquinolin-1(2H)-one

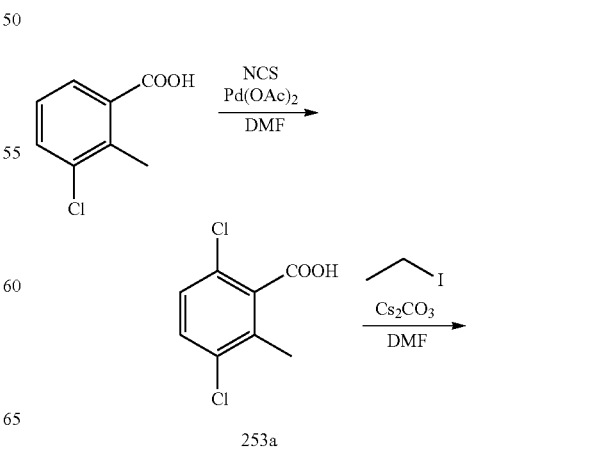

253a

-continued

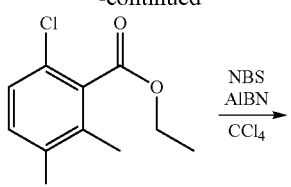
253b

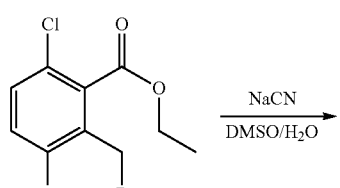
253c

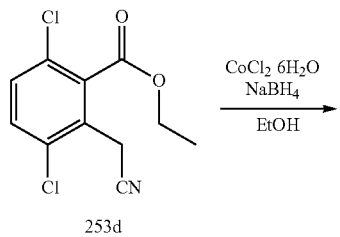
253d

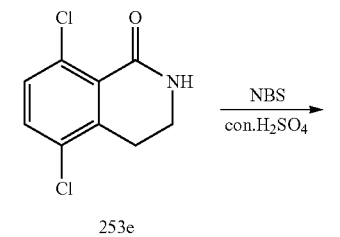
253e

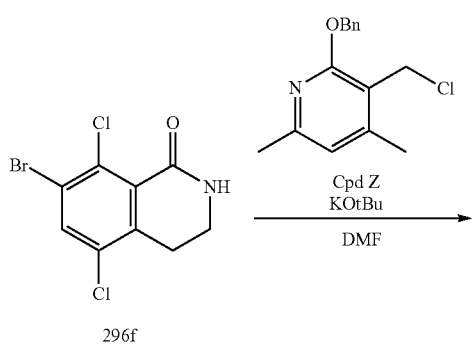
296f

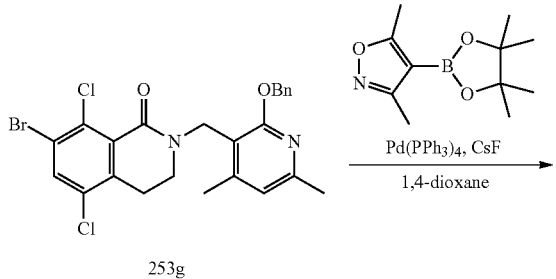
253g

-continued

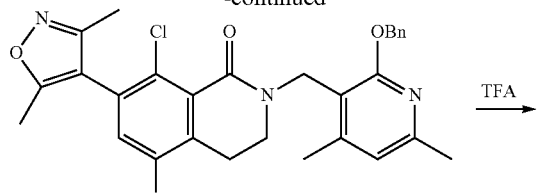
253h

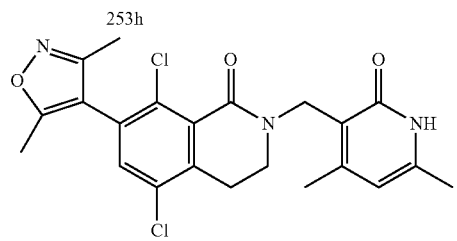
Example 253

A mixture of 3-chloro-2-methylbenzoic acid (100 g, 0.58 mol), N-chlorosuccinimide (90 g, 0.67 mol) and palladium (II) acetate (14.7 g, 65.7 mmol) in N,N-dimethylformamide (1 L) was stirred at 110° C. under a nitrogen atmosphere overnight. After cooling to room temperature, cesium carbonate (378 g, 1.16 mol) and iodoethane (317 g, 2.03 mol) were added and stirring continued at room temperature for 1.5 hours. The reaction mixture was poured into a mixture of water (1 L) and methyl tert-butyl ether (800 mL). Solids were removed by filtration, and the filtrate layers separated. The aqueous layer was extracted with more methyl tert-butyl ether (600 mL). The combined organic extracts were washed with saturated aqueous sodium chloride solution (1.2 L), dried over sodium sulfate, and concentrated in vacuo. The residue was purified by silica gel chromatography (eluting with 50:1 petroleum ether/ethyl acetate), affording ethyl 3,6-dichloro-2-methylbenzoate (253b, 110 g, 80% pure, 80% yield) as a yellow oil.

A solution of 3,6-dichloro-2-methylbenzoate (253b, 120 g, 0.52 mol) and N-bromosuccinimide (147 g, 0.82 mol) in chloroform (1 L) was treated with azobisisobutyronitrile (25.3 g, 0.15 mol) and the mixture refluxed overnight. After cooling to room temperature, the mixture was diluted with dichloromethane (800 mL) and washed with water (1.2 L). The aqueous layer was extracted with dichloromethane (800 mL). The combined organic extracts were washed with saturated aqueous sodium chloride solution (1.5 L), dried over sodium sulfate, and concentrated in vacuo to give ethyl 2-(bromomethyl)-3,6-dichlorobenzoate (253c, 160 g, 100% yield) which was used without further purification.

A solution of sodium cyanide (75.12 g, 1.53 mol) in water (300 mL) was added dropwise to a solution of ethyl 2-(bromomethyl)-3,6-dichlorobenzoate (253c, 320 g, 1.03 mol) in dimethysulfoxide (2.4 L) at room temperature. The mixture was stirred at room temperature for 1.5 hours. The reaction mixture was poured into a mixture of water (4 L) and methyl tert-butyl ether (2 L), and the layers separated. The organic layer was washed with water (2 L) and with saturated aqueous sodium chloride solution (2 L), dried over sodium sulfate, and concentrated in vacuo. The residue was purified by silica gel chromatography (eluting with 30:1 petroleum ether/ethyl acetate), affording ethyl 3,6-dichloro-2-(cyanomethyl)benzoate (253d, 150 g, ~75% pure, 47% yield) as a yellow oil.

Cobalt (II) chloride hexahydrate (166 g, 0.70 mol) was added to a room temperature solution of ethyl 3,6-dichloro-2-(cyanomethyl)benzoate (253d, 90 g, 0.35 mol) in ethanol (1.5 L), and the resulting mixture cooled to 0° C. Sodium borohydride (66.3 g, 1.74 mol) was added in portions. The mixture was stirred at room temperature for 1 hour, and then refluxed overnight. The resulting suspension was filtered and the filtrate concentrated in vacuo. The solids in the filter cake were stirred in ethyl acetate (600 mL), and then filtered again. This procedure was repeated a second time. The combined filtrates were added to the original filtrate residue, and this organic solution washed with water (800 mL) and saturated aqueous sodium chloride solution (800 mL), dried over sodium sulfate, and concentrated in vacuo to give 5,8-dichloro-3,4-dihydroisoquinolin-1(2H)-one (253e, 29.3 g, 39% yield) as an off-white solid.

To a solution of 5,8-dichloro-3,4-dihydroisoquinolin-1(2H)-one (253e, 40 g, 0.186 mol) in concentrated sulfuric acid (200 mL) at 60° C. was added N-bromosuccinimide (49.7 g, 0.279 mol) in portions. Stirring was continued at 60° C. for 2 hours, then more N-bromosuccinimide (5 g. 28 mmol) was added. After stirring at 60° C. for 1 hour more, the mixture was poured onto ice water (500 mL), then extracted with dichloromethane (3×500 mL). The combined organic extracts were washed with saturated aqueous sodium chloride solution (800 mL), dried over sodium sulfate, and concentrated in vacuo. The residue was stirred in ethyl acetate (40 mL) and petroleum ether (20 mL), and the resulting solids collected by filtration and dried under vacuum to give 7-bromo-5,8-dichloro-3,4-dihydroisoquinolin-1(2H)-one (253f, 41 g, 75% yield) as an off-white solid.

Potassium tert-butoxide solution in tetrahydrofuran (1.0 M, 190 mL, 0.19 mol) was added dropwise to a cooled (0° C.) solution of 7-bromo-5,8-dichloro-3,4-dihydroisoquinolin-1(2H)-one (253f, 47 g, 0.16 mol) in anhydrous N,N-dimethylformamide (500 mL) under a nitrogen atmosphere. Stirring was continued at 0° C. for 5 minutes, then 2-(benzyloxy)-3-(chloromethyl)-4,6-dimethylpyridine (compound Z, 40.2 g, 0.15 mol) was added in one portion. After stirring for 10 minutes at 0° C., the mixture was treated with concentrated acetic acid (2 mL) and poured into methyl tert-butyl ether (600 mL). The organic solution was washed with water (800 mL) and saturated aqueous sodium chloride solution (800 mL), dried over sodium sulfate, and concentrated in vacuo. The residue was purified by silica gel chromatography (eluting with 30:1 to 20:1 petroleum ether/ethyl acetate), affording 2-{[2-(benzyloxy)-4,6-dimethylpyridin-3-yl]methyl}-7-bromo-5,8-dichloro-3,4-dihydroisoquinolin-1(2H)-one (253 g, 50 g, 64% yield) as an off-white solid. $^1$H NMR (400 MHz, DMSO-d6): δ 8.08 (s, 1H), 7.45-7.43 (m, 2H), 7.32-7.29 (m, 3H), 6.76 (s, 1H), 5.38 (s, 2H), 4.71 (s, 2H), 3.24 (t, J=6 Hz, 2H), 2.72 (t, J=6 Hz, 2H), 2.36 (s, 3H), 2.31 (s, 3H). MS: 521 [M+1].

A mixture of 2-{[2-(benzyloxy)-4,6-dimethylpyridin-3-yl]methyl}-7-bromo-5,8-dichloro-3,4-dihydroisoquinolin-1(2H)-one (253 g, 500 mg, 0.96 mmol), 3,5-Dimethylisoxazole-4-boronic acid pinacol ester (320 mg, 1.44 mmol), cesium fluoride (437 mg, 2.88 mmol) and tetrakis(triphenylphosphine)palladium(0) (70.0 mg, 0.06 mmol) in dioxane (20 mL) was degassed with nitrogen, then stirred at 100° C. for 18 hours. After cooling, the mixture was partitioned between water (15 mL) and ethyl acetate (3×20 mL). The combined organic layers were washed with saturated aqueous sodium chloride solution (20 mL), dried over sodium sulfate, and concentrated. The residue was purified by silica gel chromatography (eluting with 10:1 petroleum ether/ethyl acetate), affording 2-{[2-(benzyloxy)-4,6-dimethylpyridin-3-yl]methyl}-5,8-dichloro-7-(3,5-dimethyl-1,2-oxazol-4-yl)-3,4-dihydroisoquinolin-1(2H)-one (253h, 400 mg, 78% yield) as a yellow oil.

A solution of 2-{[2-(benzyloxy)-4,6-dimethylpyridin-3-yl]methyl}-5,8-dichloro-7-(3,5-dimethyl-1,2-oxazol-4-yl)-3,4-dihydroisoquinolin-1(2H)-one (253h, 400 mg, 0.75 mmol) in trifluoroacetic acid (10 mL) was stirred at 45° C. for 3 hours, then concentrated under vacuum to remove volatiles. The residue was partitioned between dichloromethane (15 mL) and saturated aqueous sodium bicarbonate solution (4×20 mL). The organic layer was washed with saturated aqueous sodium chloride solution (20 mL), dried over sodium sulfate, concentrated, and purified by silica gel chromatography (eluting with 10:1 dichloromethane/methanol) to give 5,8-dichloro-7-(3,5-dimethyl-1,2-oxazol-4-yl)-2-[(4,6-dimethyl-2-oxo-1,2-dihydropyridin-3-yl)methyl]-3,4-dihydroisoquinolin-1(2H)-one (Example 253, 250 mg, 75% yield) as a white solid. $^1$H NMR (600 MHz, DMSO-17 mm) δ 11.57 (s, 1H), 7.67 (s, 1H), 5.89 (s, 1H), 4.57 (s, 2H), 3.51 (t, J=6.33 Hz, 2H), 2.95 (t, J=6.33 Hz, 2H), 2.24 (s, 3H), 2.18 (s, 3H), 2.12 (s, 3H), 2.06 (s, 3H). MS: 446 [M+1].

Example 229: 5,8-dichloro-7-(1,4-dimethyl-1,2,3-triazol-5-yl)-2-[(4,6-dimethyl-2-oxo-1,2-dihydropyridin-3-yl)methyl]-3,4-dihydroisoquinolin-1(2H)-one

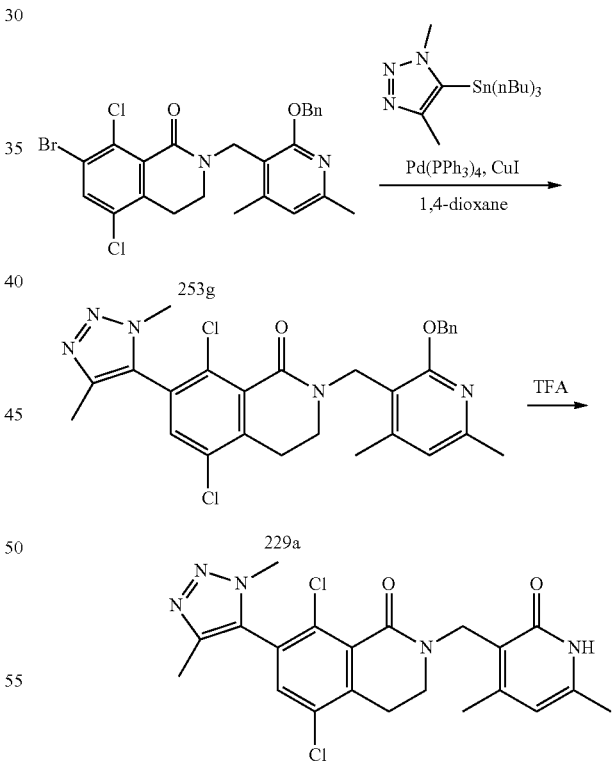

Example 229

To a mixture of 2-{[2-(benzyloxy)-4,6-dimethylpyridin-3-yl]methyl}-7-bromo-5,8-dichloro-3,4-dihydroisoquinolin-1(2H)-one (253 g, 500 mg, 0.96 mmol), and 1,4-dimethyl-5-(tributylstannanyl)-1H-1,2,3-triazole (CAS: 1047637-17-1, 754 mg, 1.95 mmol) in a microwave tube was added 1,4-dioxane (10 mL), copper (I) iodide (28 mg, 0.14 mmol) and tetrakis(triphenylphosphine)palladium(0) (160 mg, 0.14 mmol). The solution was degassed using a stream of argon gas and degassing was continued for 10 minutes. The microwave vial was sealed and the mixture was heated at 125° C. for 2 hours under microwave irradiation. TLC (petroleum ether/ethyl acetate=1:1, Rf: 0.5) showed about 50% of 253 g remained. However, further heating did not prove fruitful. The mixture was diluted with methyl tert-butyl ether (100 mL), washed with water (3×100 mL), dried over sodium sulfate and concentrated to dryness. The residue was purified by flash chromatography eluting with petroleum ether/ethyl acetate=1:1 to yield-{[2-(benzyloxy)-4,6-dimethylpyridin-3-yl]methyl}-5,8-dichloro-7-(1,4-dimethyl-1H-1,2,3-triazol-5-yl)-3,4-dihydroisoquinolin-1(2H)-one (229a, 108 mg, 21% yield) as a white solid. $^1$H NMR (400 MHz, DMSO-d6): δ 7.76 (s, 1H), 7.44 (d, J=1.35 Hz, 2H), 7.28-7.34 (m, 3H), 6.75 (s, 1H), 5.38 (s, 2H), 4.71 (s, 2H), 3.77 (s, 3H), 3.30-3.34 (m, 2H), 2.82 (s, 2H), 2.35 (s, 3H), 2.32 (s, 3H), 2.08 (s, 3H) MS: 446.1 [M+1].

A solution of 229a (1.1 g, 2.1 mmol) was dissolved in trifluoroacetic acid (25 mL) and stirred at 45° C. for 3 hours. TLC (dichloromethane/methanol=10:1, Rf: 0.5) showed the reaction was complete. The mixture was concentrated and diluted with dichloromethane (30 mL), washed with aqueous sodium bicarbonate (4×50 mL) and brine (2×20 mL), dried over sodium sulfate, and concentrated to dryness. The residue was purified by flash chromatography (eluting with 10:1 dichloromethane methanol) to afford 5,8-dichloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-(2H)-one (Example 229, 514 mg, 51% yield) as a white solid. $^1$H NMR (400 MHz, CDCl$_3$): δ 11.73 (s, 1H), 7.31 (s, 1H), 5.95 (s, 1H), 4.77 (s, 2H), 3.85 (s, 3H), 3.77 (t, J=12.8 Hz, 2H), 3.06-3.02 (m, 2H), 2.38 (s, 3H), 2.29 (s, 3H), 2.21 (s, 3H). MS: 446.1 [M+1].

Example 66: 8-chloro-2-[(4,6-dimethyl-2-oxo-1,2-dihydropyridin-3-yl)methyl]-7-(1-methyl-1H-pyrazol-5-yl)-3,4-dihydroisoquinolin-1(2H)-one

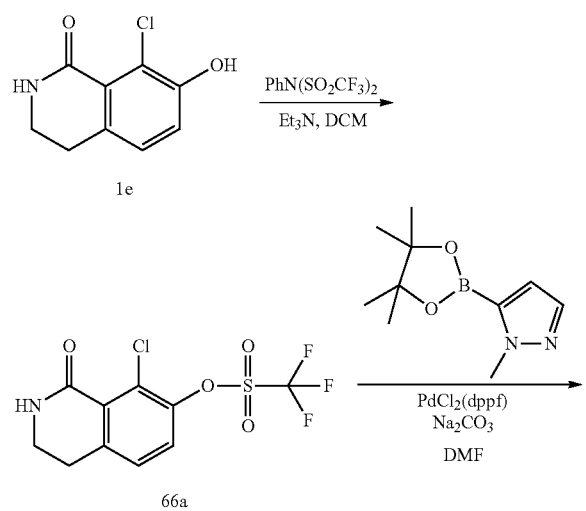

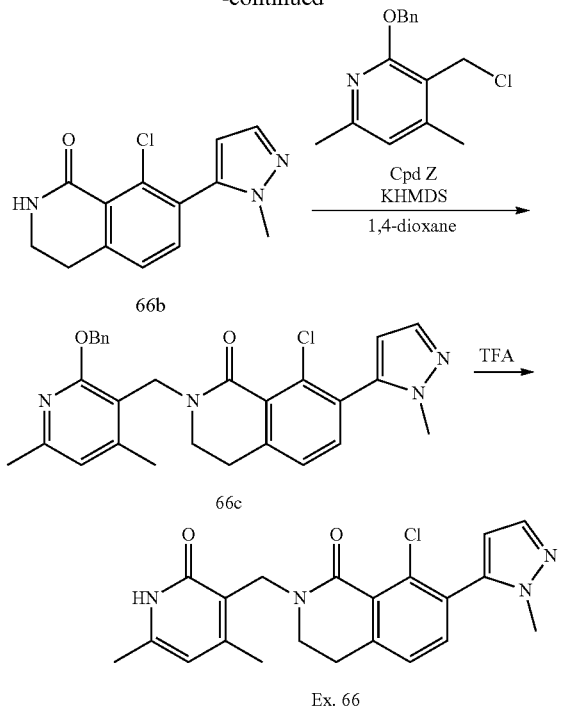

To a solution of 8-chloro-7-hydroxy-3,4-dihydroisoquinolin-1(2H)-one (1e, 535 mg, 2.71 mmol) in DCM (10 mL) was added N-phenyltrifluoromethanesulfonimide (870 mg, 2.44 mmol) and Et$_3$N (630 mg, 6.23 mmol). The reaction mixture was stirred at room temperature overnight. The reaction mixture was concentrated under vacuum and the residue purified by column chromatography to give 8-chloro-1-oxo-1,2,3,4-tetrahydroisoquinolin-7-yl trifluoromethanesulfonate (66a, 795 mg, 89%) as a colorless oil which solidified upon standing.

To a solution of 8-chloro-1-oxo-1,2,3,4-tetrahydroisoquinolin-7-yl trifluoromethanesulfonate (66a, 300 mg, 0.910 mmol) in DMF (5 mL) was added 1-methyl-5-(4,4,5,5-tetramethyl-1,3,2-dioxaborolan-2-yl)-1H-pyrazole (205 mg, 0.956 mmol), PdCl$_2$(dppf)-DCM (74.3 mg, 0.0910 mmol), and Na$_2$CO$_3$ (289 mg, 2.73 mmol). The reaction mixture was degassed with N$_2$ and stirred in a sealed tube at 80° C. for 2 days. The reaction mixture was adjusted to pH 7 and purified by preparative chromatography to give 8-chloro-7-(1-methyl-1H-pyrazol-5-yl)-3,4-dihydroisoquinolin-1(2H)-one (66b, 48 mg, 20%) as an oil.

A solution of 8-chloro-7-(1-methyl-1H-pyrazol-5-yl)-3,4-dihydroisoquinolin-1(2H)-one (66b, 48.0, 0.180 mmol), 2-(benzyloxy)-3-(chloromethyl)-4,6-dimethylpyridine (Cpd Z, 71.7 mg, 0.274 mmol), and KHMDS (182 mg, 0.915 mmol) in 1,4-dioxane (5 mL) was heated at 80° C. overnight. To the reaction mixture was added H$_2$O (10 mL), the solution was extracted with EtOAc (10 mL), the organic layer concentrated under vacuum, and the residue purified by prep chromatography to give 2-{[2-(benzyloxy)-4,6-dimethylpyridin-3-yl]methyl}-8-chloro-7-(1-methyl-1H-pyrazol-5-yl)-3,4-dihydroisoquinolin-1(2H)-one (66c, 60 mg, 67%) as a colorless oil.

A solution of 2-{[2-(benzyloxy)-4,6-dimethylpyridin-3-yl]methyl}-8-chloro-7-(1-methyl-1H-pyrazol-5-yl)-3,4-dihydroisoquinolin-1(2H)-one (66c, 60 mg, 0.12 mmol) in TFA (3 mL) was stirred at room temperature overnight. The reaction mixture was concentrated under vacuum and the residue purified by prep chromatography to give the title compound (Example 66, 8.5 mg, 17%) as a white solid. ¹H NMR (700 MHz, DMSO-d6) δ 11.56 (br. s, 1H) 7.44 (d, J=7.70 Hz, 1H) 7.35 (d, J=7.70 Hz, 1H) 7.50 (d, J=1.76 Hz, 1H) 6.29 (d, J=1.76 Hz, 1H) 5.90 (s, 1H) 4.60 (s, 2H) 3.61 (s, 3H) 3.46-3.50 (m, 2H) 2.91 (t, J=5.83 Hz, 2H) 2.19 (s, 3H) 2.14 (s, 3H); MS 397.0 [M+1].

Method E

Example 76: 2-[(4,6-dimethyl-2-oxo-1,2-dihydro-pyridin-3-yl)methyl]-N,N,8-trimethyl-1-oxo-1,2,3,4-tetrahydroisoquinoline-7-carboxamide

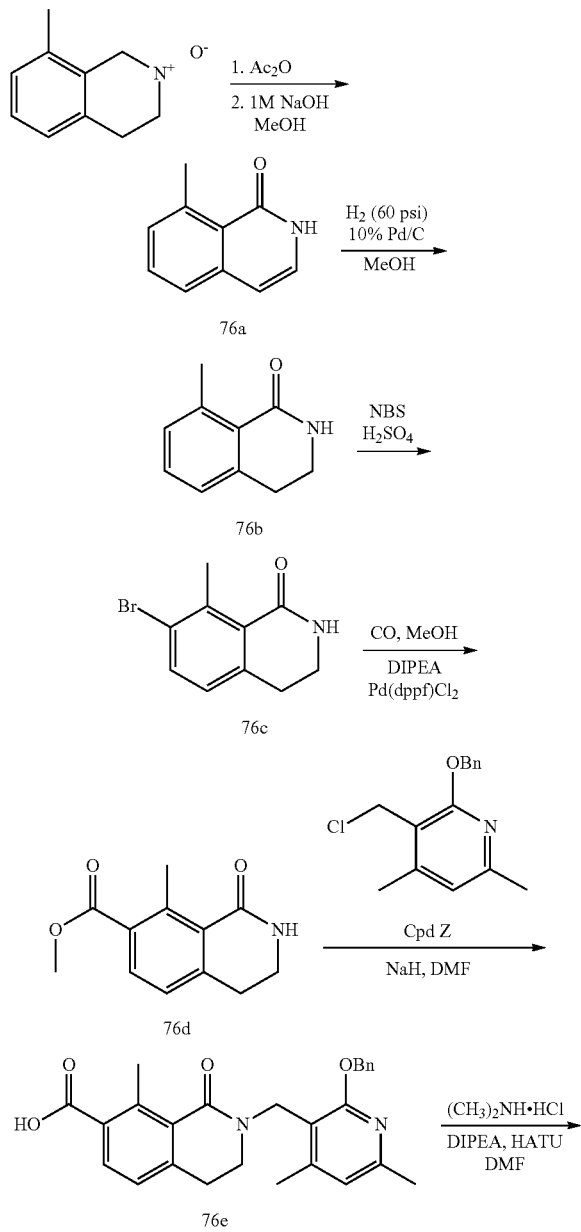

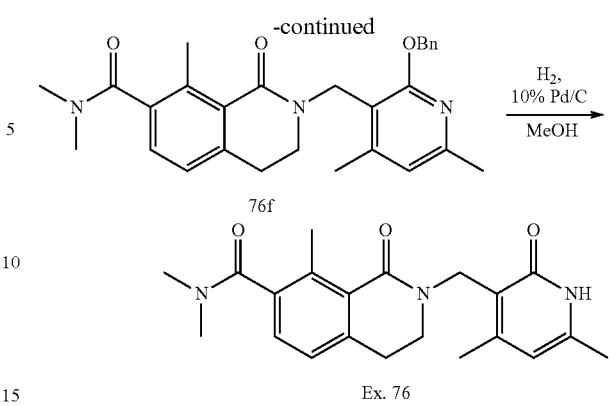

A solution of 8-methylisoquinoline 2-oxide (1.4 g, 8.8 mmol) in Ac₂O (20 mL) was refluxed for 3 hours. The mixture was concentrated under vacuum and the residue was dissolved in MeOH (20 mL). To the reaction mixture was added aq. NaOH (20 mL, 1M). The mixture was refluxed for 1 hour and stirred at room temperature for 10 hours. The mixture was concentrated under vacuum. The residue was diluted with water (20 mL) and extracted with EtOAc (3×20 mL). The combined organic layers were washed with brine (2×10 mL), dried over Na₂SO₄, filtered, and concentrated under vacuum. The residue was purified by column chromatography (petroleum ether/EtOAc, 3:1) to give 8-methylisoquinolin-1(2H)-one (76a, 1 g, 71%) as a yellow solid.

A mixture of 8-methylisoquinolin-1(2H)-one (76a, 1 g, 6.29 mmol) and 10% Pd/C (0.5 g) in MeOH (20 mL) was hydrogenated under H₂ (60 psi) at 80° C. for 48 hours. The reaction mixture was filtered and the solids were washed with MeOH (2×20 mL). The filtrate was concentrated under vacuum to give 8-methyl-3,4-dihydroisoquinolin-1(2H)-one (76b, 1 g, ~100%) as a gray solid.

To cooled conc. H₂SO₄ (10 mL) was added 8-methyl-3,4-dihydroisoquinolin-1(2H)-one (76b, 1 g, 6.21 mmol) and the reaction mixture was stirred for 10 minutes. NBS (1.1 g, 6.21 mmol) was added and the reaction mixture stirred at 60° C. for 2 hours. The mixture was cooled to room temperature and poured into ice-water (30 mL) with stirring. The suspension was extracted with EtOAc (3×20 mL). The combined organic layers were washed with water (20 mL) and brine (20 mL), dried over Na₂SO₄, filtered, and concentrated in vacuum. The residue was purified by column chromatography (petroleum ether/EtOAc=1:1) to give 7-bromo-8-methyl-3,4-dihydroisoquinolin-1(2H)-one (76c, 0.63 g, 42%) as a white solid.

A mixture of 7-bromo-8-methyl-3,4-dihydroisoquinolin-1(2H)-one (76c, 0.6 g, 2.5 mmol), DIPEA (2 mL) and PdCl₂(dppf) (0.12 g) in MeOH (20 mL) was stirred under CO (4 MPa) at 120° C. for 48 hours in a 50 mL autoclave. The mixture was filtered and the solids were washed with MeOH (2×10 mL). The filtrate was concentrated under vacuum. The residue was purified by column chromatography (petroleum ether/EtOAc=1:1) to give methyl 8-methyl-1-oxo-1,2,3,4-tetrahydroisoquinoline-7-carboxylate (76d, 0.41 g, 75%) as a white solid.

To a stirred solution of methyl 8-methyl-1-oxo-1,2,3,4-tetrahydroisoquinoline-7-carboxylate (76d, 100 mg, 0.46 mmol) in DMF (5 mL) was added NaH (0.032 g, 1.32 mmol, 60% in oil) at 0° C. under N₂. After stirring at 0° C. for 30 minutes, 1-(benzyloxy)-2-(chloromethyl)-3,5-dimethylbenzene benzyl 2-(chloromethyl)-3,5-dimethylphenyl ether (Cpd Z, 180 mg, 0.69 mmol) was added and the reaction mixture stirred at room temperature overnight. The reaction mixture was poured into ice-water (20 mL). The reaction mixture was extracted with EtOAc (3×20 mL). The combined organic layers were washed with brine (2×10 mL), dried over $Na_2SO_4$, filtered, and concentrated under vacuum. The residue was purified by column chromatography (petroleum ether/EtOAc=1:1) to obtain 2-{[2-(benzyloxy)-4,6-dimethylpyridin-3-yl]methyl}-8-methyl-1-oxo-1,2,3,4-tetrahydroisoquinoline-7-carboxylic acid (76e, 120 mg, 61%) as a yellow gum.

To a solution of 2-{[2-(benzyloxy)-4,6-dimethylpyridin-3-yl]methyl}-8-methyl-1-oxo-1,2,3,4-tetrahydroisoquinoline-7-carboxylic acid (76e, 120 mg, 0.28 mmol), $(CH_3)_2NH$—HCl (34 mg, 0.42 mmol) and DIPEA (181 mg, 1.4 mmol) in DMF (5 mL) under $N_2$ atmosphere was added HATU (214 mg, 0.56 mmol). The mixture was stirred at room temperature for 3 hours. The reaction mixture was poured into water (10 mL) and extracted with EtOAc (3×10 mL). The combined organic layers were washed with $H_2O$ (10 mL), brine (2×10 mL), dried over $Na_2SO_4$, filtered, and concentrated under vacuum. The residue was purified by column chromatography (petroleum ether/EtOAc=1:1) to give 2-{[2-(benzyloxy)-4,6-dimethylpyridin-3-yl]methyl}-N,N,8-trimethyl-1-oxo-1,2,3,4-tetrahydroisoquinoline-7-carboxamide (76f, 80 mg, 63%) as a colorless gum.

A mixture of 2-{[2-(benzyloxy)-4,6-dimethylpyridin-3-yl]methyl}-N,N,8-trimethyl-1-oxo-1,2,3,4-tetrahydroisoquinoline-7-carboxamide (76f, 80 mg, 0.175 mmol) and 10% Pd/C (10 mg) in MeOH (10 mL) was hydrogenated under $H_2$ balloon at room temperature for 20 hours. The mixture was filtered and the solids were washed with MeOH (2×10 mL). The filtrate was concentrated under vacuum and the residue was purified by column chromatography (EtOAc/MeOH=5:1) to give the title compound (Example 76, 32 mg, 49.7%) as a white solid. $^1H$ NMR (400 MHz, methanol-d4) δ 7.22-7.2 (d, 1H), 7.17-7.15 (d, 1H), 6.11 (s, 1H), 4.77 (s, 2H), 3.45-3.43 (m, 2H), 3.13 (s, 3H), 2.9-2.85 (m, 5H), 2.28 (s, 3H), 2.25 (s, 3H); MS 367.9 [M+H].

Method F

Example 77: 8-chloro-2-[(4,6-dimethyl-2-oxo-1,2-dihydropyridin-3-yl)methyl]-5-[6-(piperazin-1-yl)pyridin-3-yl]-7-(propan-2-yloxy)-3,4-dihydroisoquinolin-1(2H)-one

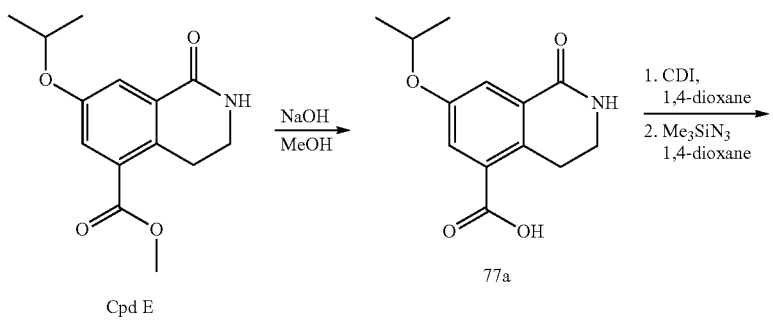

Cpd E

77a

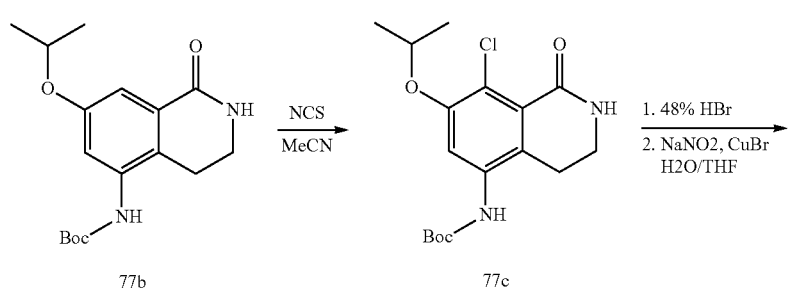

77b

77c

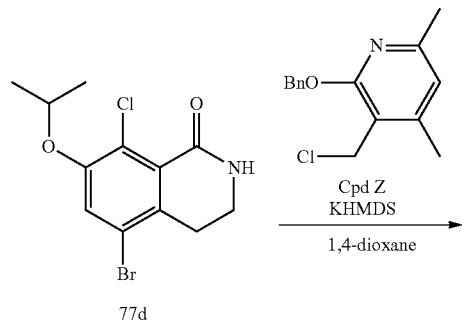

77d

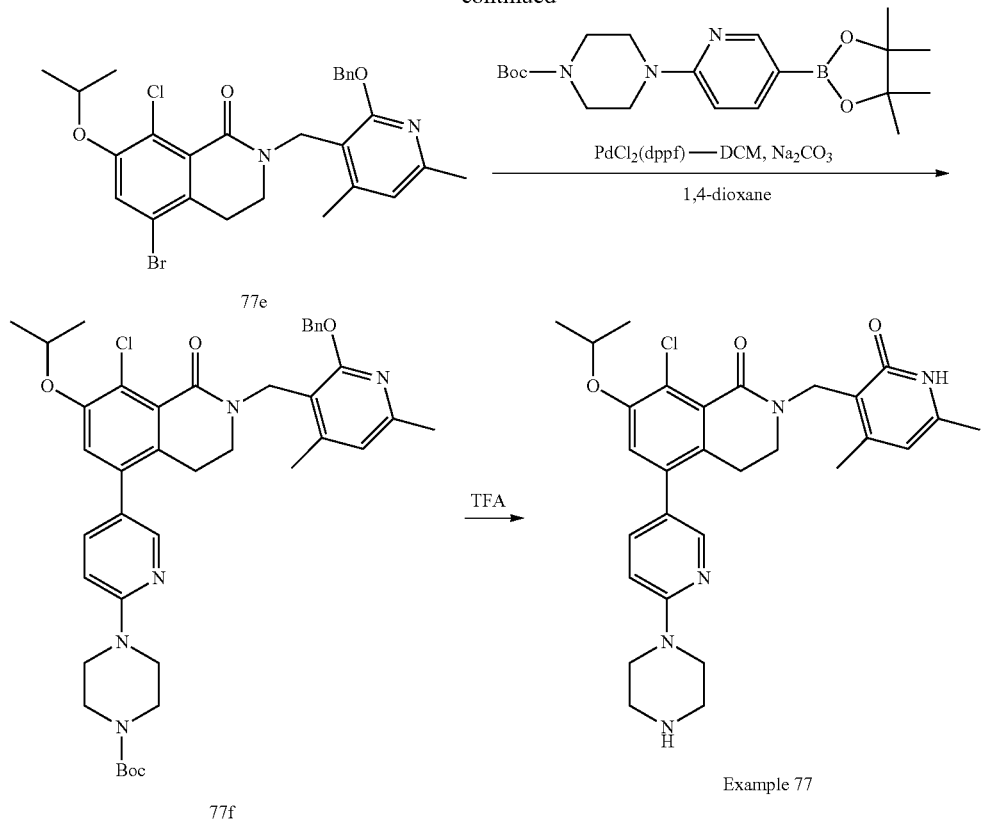

Example 77

To a solution of methyl 1-oxo-7-(propan-2-yloxy)-1,2,3,4-tetrahydroisoquinoline-5-carboxylate (Cpd E, 1.00 g, 3.80 mmol) in MeOH (20 mL) was added NaOH (3.00 mL, 12.0 mmol). The resulting reaction mixture was stirred at 50° C. for 3 hours. Volatiles were removed under vacuum and the resulting residue was dissolved in MeOH (30 mL), and neutralized with 1 M HCl to pH=2-3. Precipitates were formed, collected by filtration, washed with water, and dried in an oven at 60° C. under vacuum to give 1-oxo-7-(propan-2-yloxy)-1,2,3,4-tetrahydroisoquinoline-5-carboxylic acid (77a, 918 mg, 97%) as a white solid.

To a suspension of 1-oxo-7-(propan-2-yloxy)-1,2,3,4-tetrahydroisoquinoline-5-carboxylic acid (77a, 1.76 g, 7.06 mmol) in anhydrous dioxane (100 mL) was added CDI (1.43 g, 8.83 mmol). The resulting mixture was stirred at room temperature for 30 minutes, then stirred at 100° C. for 30 minutes. After cooling down to room temperature, TMSA (1.50 mL, 10.8 mmol) was added. After stirring the reaction mixture for 2 hours, t-butanol (25.0 mL) was added. The resulting mixture was stirred at 100° C. overnight. After cooling to room temperature and concentrating under vacuum, the resulting residue was purified by column chromatography (0-100% EtOAc/heptanes) to give tert-butyl [1-oxo-7-(propan-2-yloxy)-1,2,3,4-tetrahydroisoquinolin-5-yl]carbamate (77b, 958 mg, 42%) as a solid.

A solution of tert-butyl [1-oxo-7-(propan-2-yloxy)-1,2,3,4-tetrahydroisoquinolin-5-yl]carbamate (77b, 875 mg, 2.73 mmol) and NCS (401 mg, 3.00 mmol) in MeCN (80 mL) was stirred at 75° C. for 2 hours. After cooling down to room temperature and concentrating under vacuum, the resulting residue was purified by column chromatography (0-100% EtOAc/heptanes) to give tert-butyl [8-chloro-1-oxo-7-(propan-2-yloxy)-1,2,3,4-tetrahydroisoquinolin-5-yl]carbamate (77c, 893 mg, 92%) as a solid.

To a solution of tert-butyl [8-chloro-1-oxo-7-(propan-2-yloxy)-1,2,3,4-tetrahydroisoquinolin-5-yl]carbamate (77c, 500 mg, 0.282 mmol) in THF (20 mL) was added HBr (10.0 mL, 88.4 mmol, 48% aqueous solution). The resulting mixture was stirred at room temperature for 3 hours. The reaction mixture was cooled to 0° C., CuBr (303 mg, 2.11 mmol) was added, followed by addition of NaNO$_2$ (1.07 mL, 1.55 mmol, 100 mg/mL solution). The resulting reaction mixture was stirred at 0° C. for 1.5 hours. The reaction mixture was neutralized with NaHCO$_3$ and extracted with ethyl acetate (2×50 mL). The combined organic phases were washed with brine (1×100 mL), dried over sodium sulfate, concentrated under vacuum, and purified by column chromatography (0-100% EtOAc/heptanes) to give 5-bromo-8-chloro-7-(propan-2-yloxy)-3,4-dihydroisoquinolin-1(2H)-one (77d, 188 mg, 42% over two steps) as a solid.

To a solution of 5-bromo-8-chloro-7-(propan-2-yloxy)-3,4-dihydroisoquinolin-1(2H)-one (77d, 188 mg, 0.590 mmol) in anhydrous 1,4-dioxane (10 mL) was added KHMDS (2.00 mL, 2.00 mmol). Upon addition, a dark red paste was formed. After stirring at room temperature for 30 minutes, 2-(benzyloxy)-3-(chloromethyl)-4,6-dimethylpyridine (Cpd Z, 170 mg, 0.649 mmol) was added. The resulting reaction mixture was stirred at 100° C. for 5 hours. After cooling to room temperature, the reaction mixture was quenched with water, and extracted with ethyl acetate (2×50 mL). The combined organic phases were dried over sodium sulfate, concentrated under vacuum, and purified by column chromatography (0-40% EtOAc/heptanes) to give 2-{[2-(benzyloxy)-4,6-dimethylpyridin-3-yl]methyl}-5-bromo-8-chloro-7-(propan-2-yloxy)-3,4-dihydroisoquinolin-1(2H)-one (77e, 140 mg, 44%).

A mixture of 2-{[2-(benzyloxy)-4,6-dimethylpyridin-3-yl]methyl}-5-bromo-8-chloro-7-(propan-2-yloxy)-3,4-dihydroisoquinolin-1(2H)-one (77e, 60 mg, 0.110 mmol), tert-butyl 4-[5-(4,4,5,5-tetramethyl-1,3,2-dioxaborolan-2-yl)pyridin-2-yl]piperazine-1-carboxylate (64 mg, 0.164 mmol), Na$_2$CO$_3$ (200 L, 0.400 mmol, 2 M solution), PdCl$_2$(dppf)-DCM (9 mg, 0.011 mmol), and 1,4-dioxane (2 mL) was stirred at 120° C. in microwave for 30 minutes. After cooling to room temperature, the reaction mixture was partitioned between ethyl acetate (20 mL) and water (20 mL). The organic phase was separated, washed with brine (1×20 mL), dried over sodium sulfate, concentrated under vacuum, and purified by column chromatography (0-100% EtOAc/heptanes) to give tert-butyl 4-{5-[2-{[2-(benzyloxy)-4,6-dimethylpyridin-3-yl]methyl}-8-chloro-1-oxo-7-(propan-2-yloxy)-1,2,3,4-tetrahydroisoquinolin-5-yl]pyridin-2-yl}piperazine-1-carboxylate (77f, 46 mg, 58% yield) as a solid.

A mixture of tert-butyl 4-{5-[2-{[2-(benzyloxy)-4,6-dimethylpyridin-3-yl]methyl}-8-chloro-1-oxo-7-(propan-2-yloxy)-1,2,3,4-tetrahydroisoquinolin-5-yl]pyridin-2-yl}piperazine-1-carboxylate (77f, 46 mg, 0.063 mmol) in TFA (2 mL) was stirred at room temperature for 3 hours. After concentrating volatiles under vacuum, the resulting residue was partitioned between ethyl acetate (30 mL) and sodium bicarbonate (30 mL). The organic phase was separated and the aqueous phase was extracted with ethyl acetate (1×30 mL). The combined organic phases were dried over sodium sulfate, concentrated under vacuum, and purified by prep HPLC to give the title compound (Example 77, 5.0 mg, 15% yield) as a solid. $^1$H NMR (400 MHz, methanol-d4) δ 8.09 (d, J=2.27 Hz, 1H), 7.56 (dd, J=8.59, 2.53 Hz, 1H), 7.09 (s, 1H), 6.88 (d, J=8.84 Hz, 1H), 6.10 (s, 1H), 4.77 (s, 2H), 4.60-4.70 (m, 1H), 3.55-3.63 (m, 4H), 3.35 (t, J=6.06 Hz, 2H), 2.92-3.02 (m, 4H), 2.75 (t, J=6.06 Hz, 2H), 2.30 (s, 3H), 2.24 (s, 3H), 1.36 (d, J=5.81 Hz, 6H); MS 536.3 [M+H].

Method G

Example 90: 8-chloro-2-[(4,6-dimethyl-2-oxo-1,2-dihydropyridin-3-yl)methyl]-N, N-dimethyl-1-oxo-7-(propan-2-yloxy)-1,2,3,4-tetrahydroisoquinoline-5-carboxamide

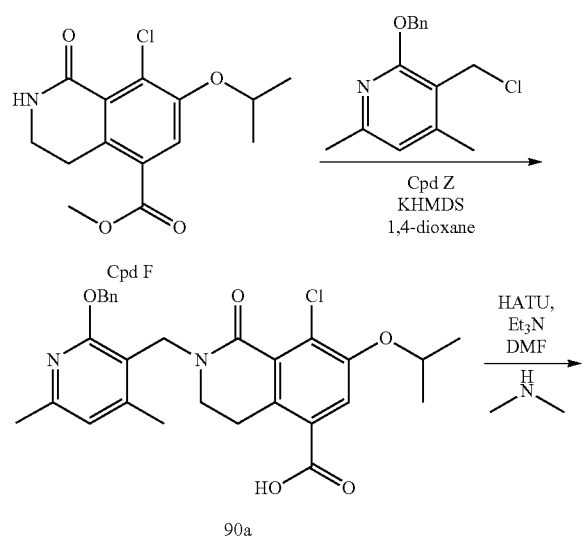

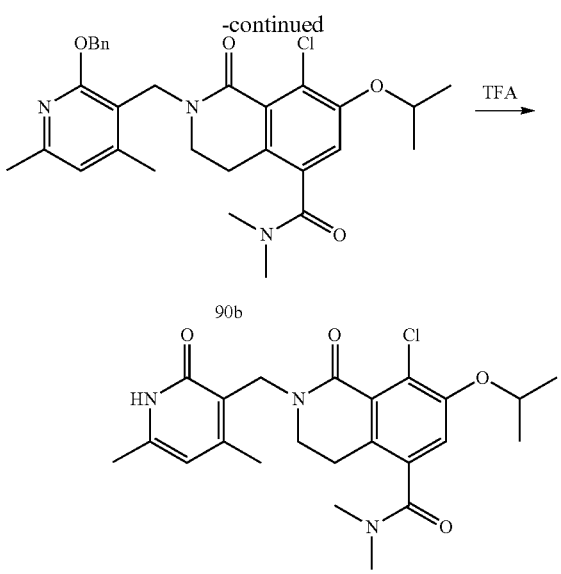

Example 90

To a mixture of methyl 8-chloro-1-oxo-7-(propan-2-yloxy)-1,2,3,4-tetrahydroisoquinoline-5-carboxylate (Cpd F, 92.0 mg, 0.310 mmol) and 2-(benzyloxy)-3-(chloromethyl)-4,6-dimethylpyridine (Cpd Z, 97.1 mg, 0.371 mmol) in 1,4-dioxane (3 mL) was added KHMDS (308 mg, 1.54 mmol). The reaction mixture was heated at 100° C. for 1 hour. The solvent was removed under vacuum and the residue diluted with EtOAc (10 mL) and water (10 mL). The pH of the aqueous layer was adjusted to 3-4 using 1N HCl. The aqueous layer was extracted with EtOAc (25 mL) and the organic layer concentrated under vacuum. The residue was purified by column chromatography (silica gel, heptanes/EtOAc) to give 2-{[2-(benzyloxy)-4,6-dimethylpyridin-3-yl]methyl}-8-chloro-1-oxo-7-(propan-2-yloxy)-1,2,3,4-tetrahydroisoquinoline-5-carboxylic acid (90a, 52 mg, 33% yield) as an oil.

To a solution of 2-{[2-(benzyloxy)-4,6-dimethyl pyridin-3-yl]methyl}-8-chloro-1-oxo-7-(propan-2-yloxy)-1,2,3,4-tetrahydroisoquinoline-5-carboxylic acid (90a, 17 mg, 0.033 mmol) in DMF (1 mL) was added triethylamine (0.023 mL, 0.165 mmol) and HATU (14 mg, 0.035 mmol). The reaction mixture was stirred for 5 minutes, and then dimethylamine-.HCl (4.10 mg, 0.050 mmol) was added. The reaction mixture was stirred at room temperature for 30 minutes. The reaction mixture was diluted with H$_2$O (5 mL) and the solid that precipitated was collected by filtration and dried under vacuum to give 2-{[2-(benzyloxy)-4,6-dimethyl pyridin-3-yl]methyl}-8-chloro-N,N-dimethyl-1-oxo-7-(propan-2-yloxy)-1,2,3,4-tetrahydroisoquinoline-5-carboxamide (90b, 16 mg, 89% yield) as a white solid.

A solution of 2-{[2-(benzyloxy)-4,6-dimethylpyridin-3-yl]methyl}-8-chloro-N,N-dimethyl-1-oxo-7-(propan-2-yloxy)-1,2,3,4-tetrahydroisoquinoline-5-carboxamide (90b, 16 mg, 89% yield) and TFA (1.5 mL) was stirred at room temperature for 24 hours. The volatiles were removed under vacuum and the residue was purified by preparative HPLC to give the title compound (Example 90, 11 mg, 85% yield) as a white solid. $^1$H NMR (700 MHz, DMSO-d6) δ 7.15 (s, 1H) 5.90 (s, 1H) 4.65-4.71 (m, 1H) 4.56 (br. s., 2H) 2.98 (s, 3H) 2.76 (s, 3H) 2.57 (br. s, 2H) 2.17 (s, 3H) 2.13 (s, 3H) 1.28 (s, 3H) 1.28 (s, 3H); MS: 446.1 [M+1].

Modifications of Method G

Example 143. N-({8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}methyl)-2-(pyrrolidin-1-yl)acetamide

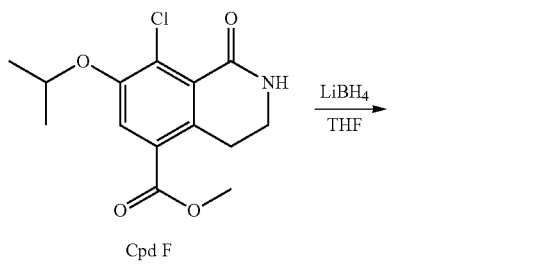

Cpd F

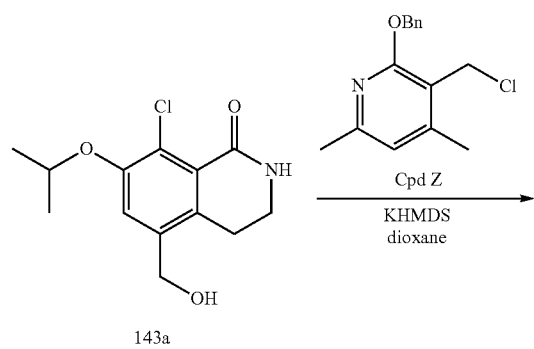

143a

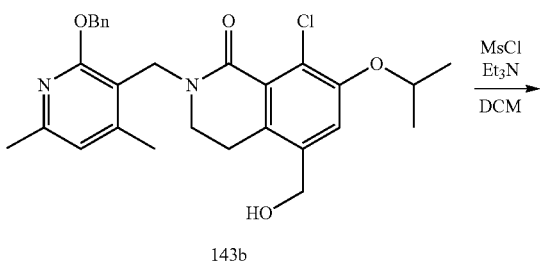

143b

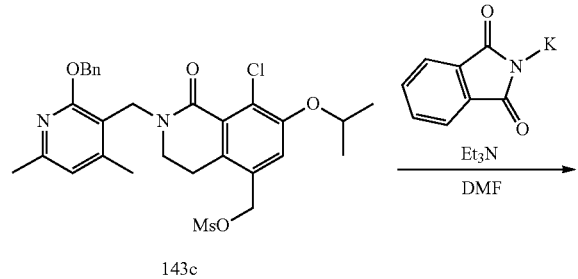

143c

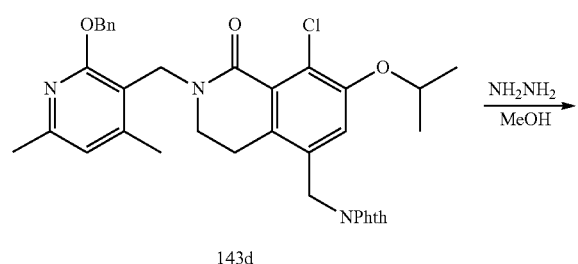

143d

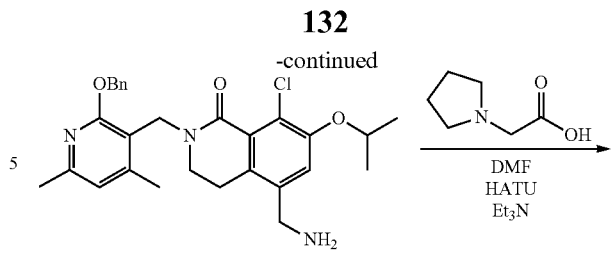

143e

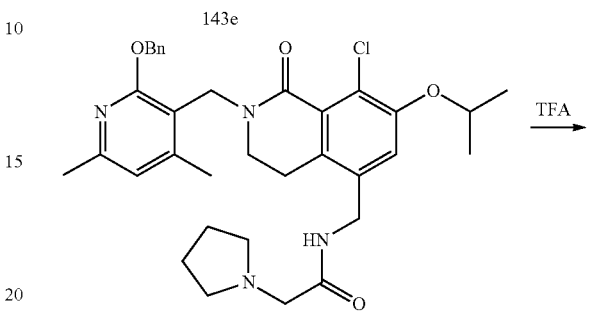

143f

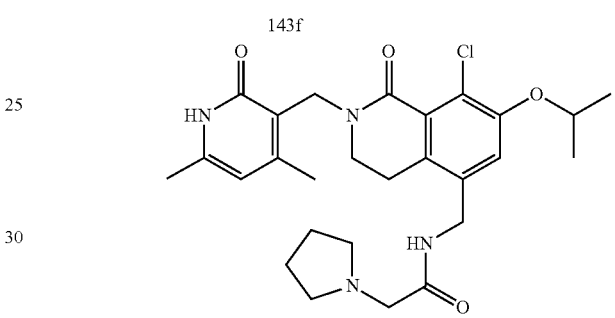

Example 143

Cpd F was reduced using lithium borohydride under standard conditions to provide the primary alcohol intermediate, 143a, which was reacted with Cpd Z under the conditions of Method G to provide the N-alkylated lactam 143b. The free hydroxyl in 143b was converted to mesylate 143c under standard conditions, and then subjected to nucleophilic displacement with potassium phthalimide to provided protected amine 143d. Deprotection of the phthalimide with hydrazine gave the primary amine 143e, which was coupled with 1-pyrrolidineacetic acid using HATU to provide amide 143f. Treatment of 143f with TFA under the conditions of Method G to remove the benzyl ether moiety provided the compound of Example 143: $^1$H NMR (600 MHz, DMSO-17 mm) d ppm 8.34 (br. s., 1H) 8.24 (t, J=5.87 Hz, 1H) 7.12 (s, 1H) 5.91 (s, 1H) 4.56 (s, 2H) 4.50-4.55 (m, 1H) 4.24 (d, J=5.87 Hz, 2H) 3.33-3.36 (m, 2H) 3.09 (s, 2H) 2.71 (t, J=6.05 Hz, 2H) 2.50 (br. s., 4H) 2.15 (s, 3H) 2.13 (s, 2H) 1.69 (br. s., 4H) 1.28 (d, J=6.05 Hz, 6H); MS: 515 [M+1].

Examples 94, 95, 96 and 144 were prepared analogously to Example 143, by amide bond coupling of amine intermediate 143e with the appropriate carboxylic acid, followed by removal of the benzyl ether with TFA as in Method G.

Examples 100, 102, 106 and 254 were prepared from mesylate intermediate 143c by nucleophilic displacement with the appropriate amine under standard conditions, followed by removal of the benzyl ether with TFA as in Method G.

Example 92 was prepared by removal of the benzyl ether in intermediate 143b with TFA, as in Method G.

Examples 97, 98, 99 and 103 were prepared by O-alkylation of intermediate 143b with a suitable alkyly halide, followed by removal of the benzyl ether with TFA as in Method G.

Example 91 and 101 were prepared by oxidation of intermediate 143b to provide the iintermediate carboxaldehyde, addition of an appropriate carbon-centered nucleophile, and removal of the benzyl ether with TFA as in Method G.

Method H

Example 107: 2-[(4,6-dimethyl-2-oxo-1,2-dihydropyridin-3-yl)methyl]-8-methyl-7-(propan-2-yloxy)-3,4-dihydroisoquinolin-1(2H)-one

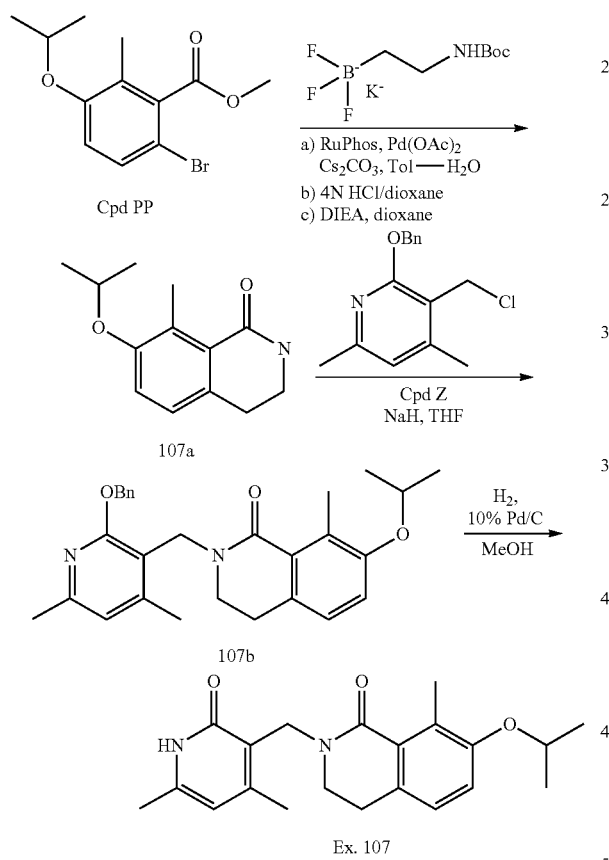

A mixture of methyl 6-bromo-2-methyl-3-(propan-2-yloxy)benzoate (Cpd PP, 154 mg, 0.536 mmol), potassium {2-[(tert-butoxycarbonyl)amino]ethyl}(trifluoro)borate (269 mg, 1.07 mmol, 2 equiv.) and cesium carbonate (613 mg, 1.88 mmol) in a 3:1 mixture of toluene:water (2.22 mL) was degassed with $N_2$. Palladium acetate (7.2 mg, 0.032 mmol) and RuPhos (30.5 mg, 0.064 mmol) were added and the mixture was degassed with $N_2$ then heated at 95° C. for 19 hours. The reaction mixture was cooled to room temperature then acidified with 10% aqueous hydrochloric acid to pH-6. The mixture was extracted with ethyl acetate (20 mL), the organic layer washed with brine (5 mL), dried over sodium sulfate, filtered, concentrated under vacuum, and purified by column chromatography (EtOAc/heptanes, 0-100%). The substrate was dissolved in dichloromethane (2 mL) and 4N hydrochloric acid in anhydrous dioxane (0.3 mL) and was stirred for 16 hours then concentrated to an oil under vacuum. The residue was dissolved in 1,4-dioxane (3 mL) then diisopropylethylamine (25 L) was added. The mixture was heated at 80° C. for 50 hours, concentrated under vacuum, and the residue purified by column chromatography (EtOAc/heptanes, 0-100) to give 8-methyl-7-(propan-2-yloxy)-3,4-dihydroisoquinolin-1(2H)-one (107a, 18.6 mg, 15.8%) as a white solid.

To a 0° C. solution of 8-methyl-7-(propan-2-yloxy)-3,4-dihydroisoquinolin-1(2H)-one (107a, 30 mg, 0.14 mmol) in tetrahydrofuran (0.46 mL) was added 60% sodium hydride (18 mg, 0.45 mmol). After 30 minutes 2-(benzyloxy)-3-(chloromethyl)-4,6-dimethylpyridine (Cpd Z, 43 mg, 0.16 mmol) was added and the resulting mixture was heated at 50° C. for 16 hours. The reaction mixture was quenched with water (1 mL) then extracted with ethyl acetate (20 mL), washed with brine (2 mL), dried over sodium sulfate, filtered, then concentrated under vacuum. The residue was purified by column chromatography (EtOAc/heptanes, 0-100), to give 2-{[2-(benzyloxy)-4,6-dimethylpyridin-3-yl]methyl}-8-methyl-7-(propan-2-yloxy)-3,4-dihydroisoquinolin-1(2H)-one (107b, 46 mg, 76%) as a colorless oil.

A mixture of 2-{[2-(benzyloxy)-4,6-dimethyl pyridin-3-yl]methyl}-8-methyl-7-(propan-2-yloxy)-3,4-dihydroisoquinolin-1(2H)-one (107b, 46 mg, 0.10 mmol) and 10% palladium on carbon (10 mg) in methanol (3 mL) was hydrogenated at 1 atmosphere using a balloon for 26 hours. The reaction mixture was filtered through CELITE® then the filtrate was concentrated under vacuum. The residue was purified by column chromatography (EtOAc/heptanes, 50/50-100/0 then EtOAc/MeOH, 100/0-70/30), to give the title compound (Example 107, 27 mg, 74% yield) as a white solid. $^1$H NMR (400 MHz, DMSO-d6) δ 11.52 (br. s., 1H), 7.05-7.01 (m, 1H), 6.99 (s, 1H), 5.87 (s, 1H), 4.58 (s, 2H), 4.51 (td, J=5.9, 12.1 Hz, 1H), 2.68 (t, J=6.0 Hz, 2H), 2.42 (s, 3H), 2.13 (s, 3H), 2.11 (s, 2H), 1.25 (d, J=5.9 Hz, 6H); MS 355 (M+H).

Method I

Example 108: 2-[(4,6-dimethyl-2-oxo-1,2-dihydropyridin-3-yl)methyl]-8-methyl-5-(1-methyl-1H-pyrazol-4-yl)-7-(propan-2-yloxy)-3,4-dihydroisoquinolin-1(2H)-one

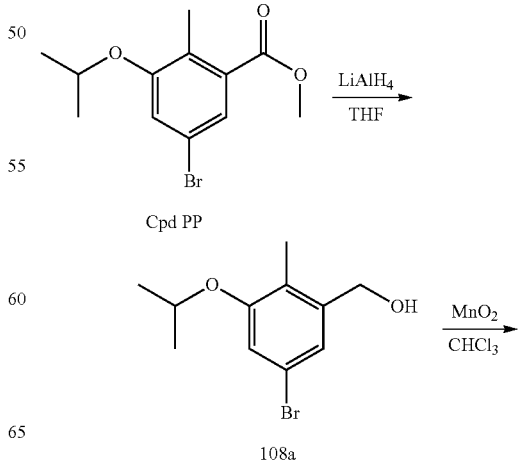

135
-continued
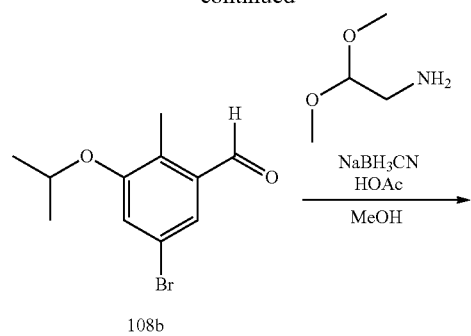
108b
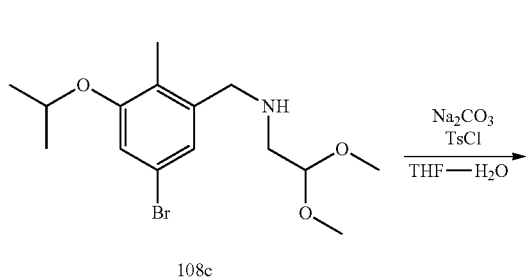
108c
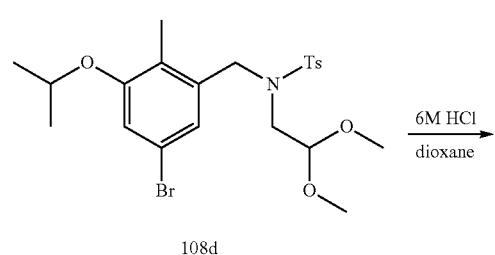
108d
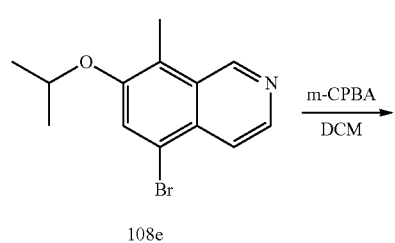
108e
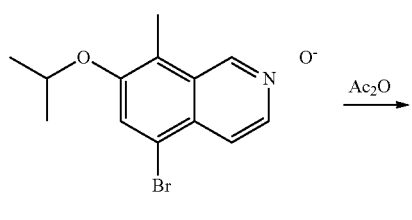
108f
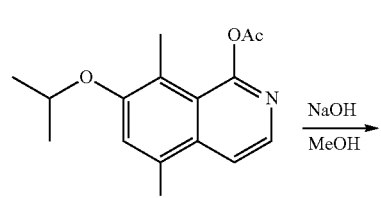
108g
136
-continued
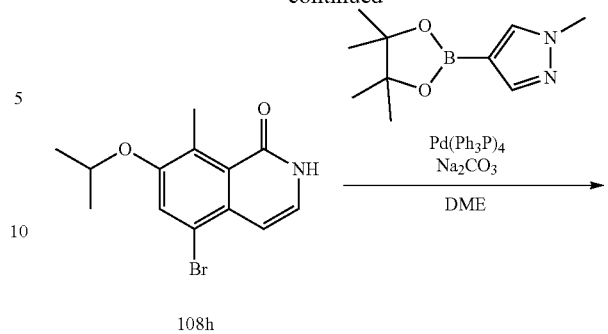
108h
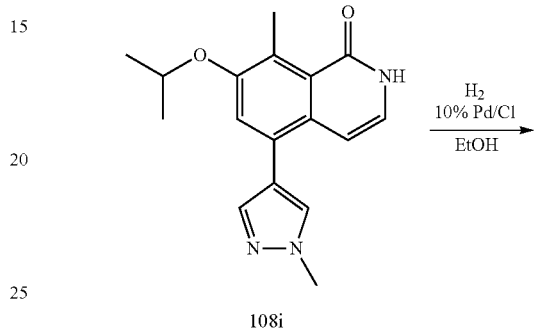
108i
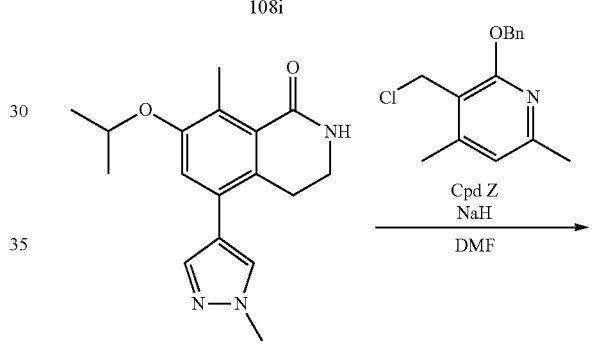
108j
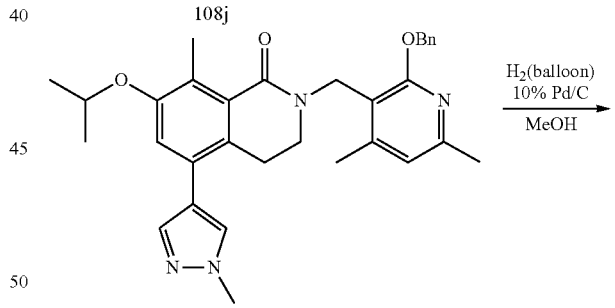
108k
Ex. 108

To a suspension of LiAlH$_4$ (1.90 g, 50.2 mmol) in dry THF (60 mL) was added dropwise methyl 5-bromo-2-methyl-3-(propan-2-yloxy)benzoate (Cpd PP, 17.0 g, 65.6 mmol) in THF (40 mL) at −5° C. After the addition, the resulting mixture was allowed to stir at room temperature for 1 hour. The reaction mixture was quenched with 20% NaOH (10 mL) at −5° C. and then stirred at room temperature for 30 minutes. The resulting mixture was filtered and the solids were washed with EtOAc (3×30 mL). The filtrate was concentrated under vacuum to give [5-bromo-2-methyl-3-(propan-2-yloxy)phenyl]methanol (108a, 8 g, 74%) as a yellow oil.

To a solution of [5-bromo-2-methyl-3-(propan-2-yloxy)phenyl]methanol (108a, 25.0 g, 96.5 mmol) in CHCl$_3$ (300 mL) was added MnO$_2$ (42.0 g, 487 mmol). The mixture was stirred at room temperature for 18 hours. The mixture was filtered and the solids were washed with CH$_2$Cl$_2$ (2×20 mL). The filtrate was concentrated under vacuum to give 5-bromo-2-methyl-3-(propan-2-yloxy)benzaldehyde (108b, 18 g, 73%) as a colorless oil.

To a solution of 5-bromo-2-methyl-3-(propan-2-yloxy)benzaldehyde (108b, 4.5 g, 18 mmol) and 2,2-dimethoxyethanamine (2.2 g, 21 mmol) in MeOH (50 mL) was added NaBH$_3$CN (1.4 g, 22 mmol) and HOAc (1 mL) at 0° C. The reaction mixture was stirred at room temperature overnight. The reaction mixture was quenched with water (50 mL). The reaction mixture was concentrated under vacuum. The residue was extracted with EtOAc (3×30 mL). The combined organic layers were washed with brine (2×30 mL), dried over Na$_2$SO$_4$, filtered, and concentrated under vacuum. The residue was purified by column chromatography (petroleum ether/EtOAc=5:1) to obtain N-[5-bromo-2-methyl-3-(propan-2-yloxy)benzyl]-2,2-dimethoxyethanamine (108c, 3.5 g, 58%) as a colorless oil.

To a mixture of N-[5-bromo-2-methyl-3-(propan-2-yloxy)benzyl]-2,2-dimethoxyethanamine (108c, 3.5 g, 10 mmol) and Na$_2$CO$_3$ (1.6 g, 15 mmol) in THF (40 mL) and H$_2$O (20 mL) was added TsCl (2.0 g, 11 mmol). The reaction mixture was stirred at room temperature for 5 hours, then extracted with EtOAc (4×40 mL). The combined organic layers were washed with H$_2$O (2×30 mL) and brine (2×100 mL), dried over Na$_2$SO$_4$, filtered, and concentrated under vacuum. The residue was purified by column chromatography (petroleum ether/EtOAc=5:1) to give N-[5-bromo-2-methyl-3-(propan-2-yloxy)benzyl]-N-(2,2-dimethoxyethyl)-4-methylbenzenesulfonamide (108d, 4.7 g, 93%) as a colorless oil.

A mixture of N-[5-bromo-2-methyl-3-(propan-2-yloxy)benzyl]-N-(2,2-dimethoxyethyl)-4-methylbenzenesulfonamide (108d, 4.7 g, 9.4 mmol) in 6M HCl (75 mL) and 1,4-dioxane (75 mL) was stirred in a sealed tube at 50° C. for 18 hours. Volatiles were removed under vacuum and the aqueous solution was basified to pH 8-9 with Na$_2$CO$_3$ (s). The mixture was extracted with EtOAc (3×50 mL). The combined organic layers were washed with brine (2×40 mL), dried over Na$_2$SO$_4$, filtered, and concentrated under vacuum to give 5-bromo-8-methyl-7-(propan-2-yloxy)isoquinoline (108e, 1.6 g, 61%) as a brown oil.

To a solution of 5-bromo-8-methyl-7-(propan-2-yloxy)isoquinoline (108e, 1.60 g, 5.71 mmol) in DCM (40 mL) was added m-CPBA (1.47 g, 8.56 mmol) and the reaction mixture was stirred at room temperature for 10 hours. The reaction mixture was washed with NaHSO$_3$ (aq., 2×20 mL), 10% aq. NaOH (2×20 mL) and brine (2×10 mL), dried over Na$_2$SO$_4$, and concentrated under vacuum to give 5-bromo-8-methyl-7-(propan-2-yloxy)isoquinoline 2-oxide (108f, 1.3 g, 77%) as a brown solid.

A solution of 5-bromo-8-methyl-7-(propan-2-yloxy)isoquinoline 2-oxide (108f, 1.3 g, 4.4 mmol) in Ac$_2$O (20 mL) was refluxed for 5 hours. The reaction mixture was concentrated under vacuum and the residue was dissolved into EtOAc (50 mL). The resulting solution was washed with aq. NaHCO$_3$ (20 mL) and brine (20 mL), dried over Na$_2$SO$_4$, filtered, and concentrated under vacuum. The residue was purified by column chromatography (petroleum ether/EtOAc=10:1) to give 5-bromo-8-methyl-7-(propan-2-yloxy)isoquinolin-1-yl acetate (108 g, 0.28 g, 17%).

To a solution of 5-bromo-8-methyl-7-(propan-2-yloxy)isoquinolin-1-yl acetate (108 g, 0.28 g, 0.83 mmol) in MeOH (2 mL) was added 1M NaOH (2 mL). The reaction mixture was refluxed for 1 hour, then concentrated under vacuum. The residue was diluted in water and the pH was adjusted to 4-5 with 1M HCl. The solution was extracted with EtOAc (3×10 mL). The combined organic layers were washed with brine (2×10 mL), dried over Na$_2$SO$_4$, filtered, and concentrated under vacuum to give 5-bromo-8-methyl-7-(propan-2-yloxy)isoquinolin-1(2H)-one (108h, 0.21 g, 86%) as a yellow solid.

A mixture of 5-bromo-8-methyl-7-(propan-2-yloxy)isoquinolin-1(2H)-one (108h, 150 mg, 0.507 mmol), 1-methyl-4-(4,4,5,5-tetramethyl-1,3,2-dioxaborolan-2-yl)-1H-pyrazole (210 mg, 1.01 mmol) and Pd(Ph$_3$P)$_4$ (29 mg, 0.025 mmol) in 1M aq. Na$_2$CO$_3$ (1 mL) and DME (5 mL) was degassed with N$_2$ for 3 minutes. The reaction mixture was stirred at 140° C. in the microwave for 35 minutes. The reaction mixture was dried over Na$_2$SO$_4$, filtered, and concentrated under vacuum. The residue was purified by column chromatography (EtOAc) to give 8-methyl-5-(1-methyl-1H-pyrazol-4-yl)-7-(propan-2-yloxy)isoquinolin-1(2H)-one (108i, 0.14 g, 92.9%) as a white solid.

A mixture of 8-methyl-5-(1-methyl-1H-pyrazol-4-yl)-7-(propan-2-yloxy)isoquinolin-1(2H)-one (108i, 0.14 g, 0.47 mmol) and 10% Pd/C (0.3 g) in EtOH (20 mL) was hydrogenated under H$_2$ (1.6 MPa) at 80° C. for 48 hours in a 50 mL autoclave. The reaction mixture was filtered and the solids were washed with EtOH (2×10 mL). The filtrate was concentrated under vacuum to give 8-methyl-5-(1-methyl-1H-pyrazol-4-yl)-7-(propan-2-yloxy)-3,4-dihydroisoquinolin-1(2H)-one (108j, 0.11 g, 78.7%) as a white solid.

To a stirred solution of 8-methyl-5-(1-methyl-1H-pyrazol-4-yl)-7-(propan-2-yloxy)-3,4-dihydroisoquinolin-1(2H)-one (108j, 60 mg, 0.2 mmol) in DMF (5 mL) was added NaH (9.6 mg, 0.4 mmol, 60% in oil) at 0° C. under N$_2$. After 30 minutes, 1-(benzyloxy)-2-(chloromethyl)-3,5-dimethylbenzene benzyl 2-(chloromethyl)-3,5-dimethylphenyl ether (Cpd Z, 115 mg, 0.44 mmol) was added and stirred at room temperature for 14 hours. The reaction mixture was poured into ice-water (20 mL), then extracted with EtOAc (3×20 mL). The combined organic layers were washed with brine (2×10 mL), dried over Na$_2$SO$_4$, filtered, and concentrated under vacuum. The residue was purified by column chromatography (petroleum ether/EtOAc=1:1) to give 2-{[2-(benzyloxy)-4,6-dimethylpyridin-3-yl]methyl}-8-methyl-5-(1-methyl-1H-pyrazol-4-yl)-7-(propan-2-yloxy)-3,4-dihydroisoquinolin-1(2H)-one (108 k, 40 mg, 38%) as a white solid.

A mixture of 2-{[2-(benzyloxy)-4,6-dimethylpyridin-3-yl]methyl}-8-methyl-5-(1-methyl-1H-pyrazol-4-yl)-7-(propan-2-yloxy)-3,4-dihydroisoquinolin-1(2H)-one (108 k, 40 mg, 0.076 mmol) and 10% Pd/C (20 mg) in MeOH (10 mL) was hydrogenated under an H$_2$ balloon at room temperature for 16 hours. The reaction mixture was filtered and the filtrate was concentrated under vacuum. The residue was purified by prep. TLC (EtOAc) to give the title compound (Example 108, 19 mg, 58%) as a white solid. $^1$H NMR (400 MHz, methanol-d4) δ 7.72 (s, 1H), 7.56 (s, 1H), 7.03 (s, 1H), 6.11 (s, 1H), 4.78 (s, 3H), 4.6-4.57 (m, 1H), 3.92 (s, 3H), 3.92 (s, 3H), 2.82-2.81 (m, 2H), 2.47 (s, 3H), 2.28-2.24 (m, 5H), 1.34-1.32 (d, 6H); MS 435.2 [M+H].

Method J

Example 112: 8-chloro-2-[(4,6-dimethyl-2-oxo-1,2-dihydropyridin-3-yl)methyl]-7-(propan-2-yloxy)-3,4-dihydro-2,6-naphthyridin-1(2H)-one

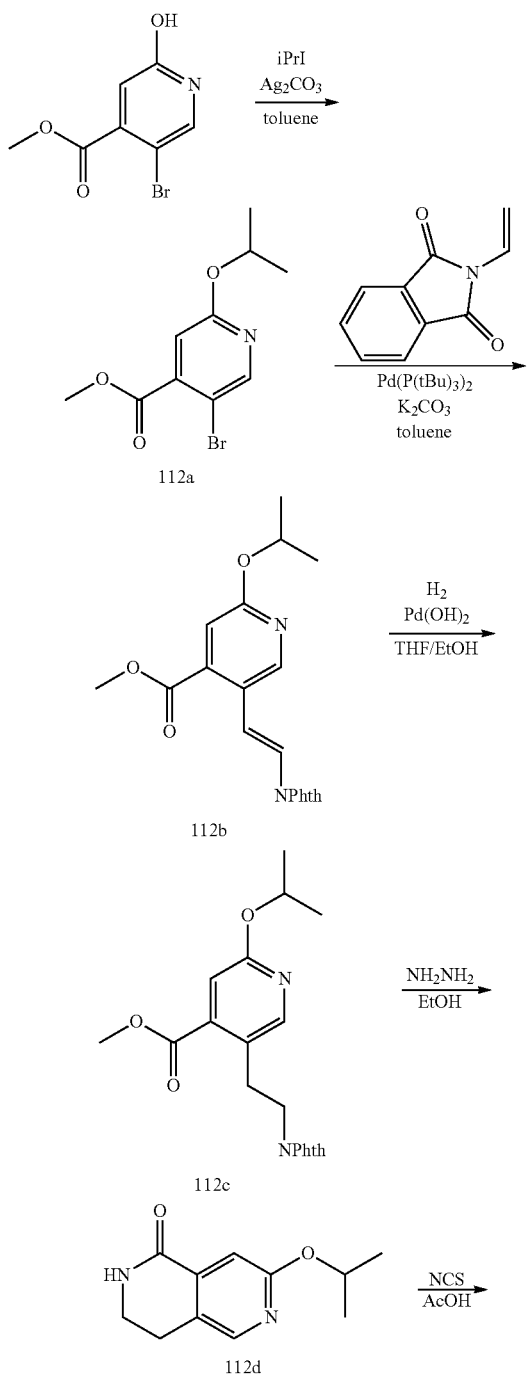

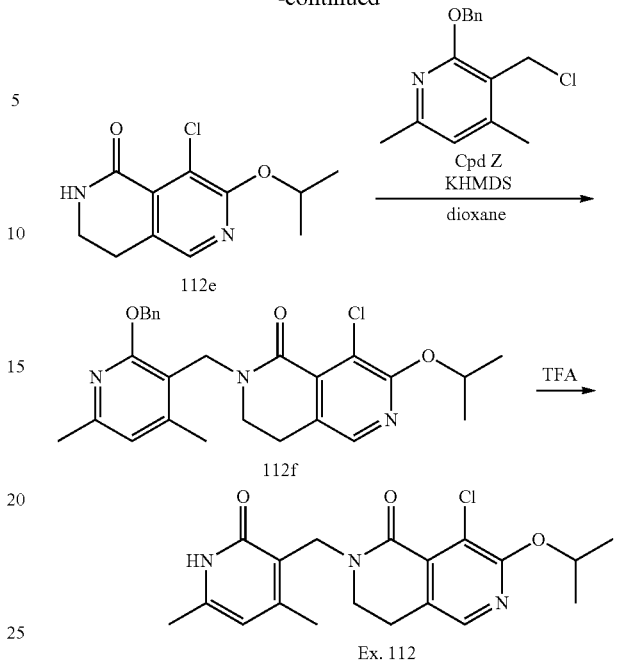

A solution of methyl 5-bromo-2-hydroxypyridine-4-carboxylate (3.00 g, 12.9 mmol), isopropyl iodide (3.30 g, 19.4 mmol) and Ag$_2$CO$_3$ (4.66 g, 16.8 mmol) in toluene (40 mL) was heated at 100° C. for 2 hours. The solid was filtered through CELITE® and the filtrate was concentrated under vacuum and purified by column chromatography (0-20% ethyl acetate/heptanes) to give methyl 5-bromo-2-(propan-2-yloxy)pyridine-4-carboxylate (112a, 3.5 g, 99%) as a colorless oil.

To a solution of methyl 5-bromo-2-(propan-2-yloxy)pyridine-4-carboxylate (112a, 3.40 g, 12.4 mmol) and N-vinylphthalimide (2.58 g, 14.9 mmol) in toluene (124 mL) was added K$_2$CO$_3$ (5.19 g, 37.2 mmol) followed by Pd(P(tBu)$_3$)$_2$(0.400 g, 0.775 mmol). The reaction mixture was degassed and heated in a sealed tube at 110° C. for 18 hours. The reaction mixture was cooled to room temperature and filtered through CELITE®. H$_2$O (100 mL) was added, the organic layer was separated and concentrated under vacuum, and the residue was purified by column chromatography (0-80%, ethyl acetate/heptanes) to give methyl 5-[(E)-2-(1,3-dioxo-1,3-dihydro-2H-isoindol-2-yl)ethenyl]-2-(propan-2-yloxy)pyridine-4-carboxylate (112b, 1.56 g, 34%) as yellow solid.

A solution of methyl 5-[(E)-2-(1,3-dioxo-1,3-dihydro-2H-isoindol-2-yl)ethenyl]-2-(propan-2-yloxy)pyridine-4-carboxylate (112b, 1.56 g, 4.26 mmol) in THF/EtOH (25 mL/5 mL) was hydrogenated on an H-Cube with Wilkinson's catalyst (10 bar, 75° C., 18 hours). The solvent was removed under vacuum and the resulting gum was purified by column chromatography (0-50% ethyl acetate/heptanes) to give methyl 5-[2-(1,3-dioxo-1,3-dihydro-2H-isoindol-2-yl)ethyl]-2-(propan-2-yloxy)pyridine-4-carboxylate (112c, 0.63 g, 40%) as a white solid.

To methyl 5-[2-(1,3-dioxo-1,3-dihydro-2H-isoindol-2-yl)ethyl]-2-(propan-2-yloxy)pyridine-4-carboxylate (112c, 0.630 g, 1.71 mmol) in EtOH (50 mL) was added hydrazine monohydrate (0.850 mL, 17.1 mmol). The reaction mixture was refluxed for 5 hours. The reaction mixture was cooled to room temperature and the white solids collected by filtration and rinsed with EtOH. The mother liquor was concentrated and H₂O (25 mL) was added, then the aqueous layer extracted with EtOAc (3×25 mL) The combined organic layers were concentrated under vacuum and purified by column chromatography (0-80% ethyl acetate/heptanes) to give 7-(propan-2-yloxy)-3,4-dihydro-2,6-naphthyridin-1 (2H)-one (112d, 337 mg, 96%) as a white solid.

A solution of 7-(propan-2-yloxy)-3,4-dihydro-2,6-naphthyridin-1(2H)-one (112d, 75 mg, 0.36 mmol)) and NCS (498 mg, 3.64 mmol) in AcOH (3 mL) was heated at 100° C. for 4.5 hours. The reaction mixture was cooled to room temperature, AcOH was removed under vacuum and the residue was purified by column chromatography (0-80% ethyl acetate/heptanes) to give 8-chloro-7-(propan-2-yloxy)-3,4-dihydro-2,6-naphthyridin-1(2H)-one (112e, 60 mg, 68%) as a white solid.

To a mixture of 8-chloro-7-(propan-2-yloxy)-3,4-dihydro-2,6-naphthyridin-1(2H)-one (112e, 60.0 mg, 0.250 mmol) and 2-(benzyloxy)-3-(chloromethyl)-4,6-dimethylpyridine (Cpd Z, 78 mg, 0.3 mmol) in 1,4-dioxane (3 mL) was added KHMDS in THF (1.0 M, 1.24 mL, 1.24 mmol). The reaction mixture was heated at 100° C. for 1 hour, then cooled to room temperature. The reaction mixture was concentrated, H₂O (10 mL) was added, and the aqueous layer extracted with EtOAc (3×10 mL). The combined organic layers were concentrated under vacuum and the residue purified by preparative HPLC to give 2-{[2-(benzyloxy)-4,6-dimethylpyridin-3-yl]methyl}-8-chloro-7-(propan-2-yloxy)-3,4-dihydro-2,6-naphthyridin-1(2H)-one (112f, 22 mg, 19% yield) as a white solid.

A solution of 2-{[2-(benzyloxy)-4,6-dimethyl pyridin-3-yl]methyl}-8-chloro-7-(propan-2-yloxy)-3,4-dihydro-2,6-naphthyridin-1(2H)-one (112f, 22 mg, 0.05 mmol) in TFA (2 mL) was stirred at room temperature for 24 hours. Volatiles were removed under vacuum and the residue was diluted in MeOH (1 mL). The solution was neutralized by 7N NH₃ in MeOH (1.5 mL) and the product was purified by prep TLC (100% EtOAc) to afford the title compound as a white solid (Example 112, 8 mg, 50%). ¹H NMR (400 MHz, DMSO-d6) δ 1.30 (s, 3H) 1.32 (s, 3H) 2.12 (s, 3H) 2.15 (s, 3H) 2.75 (t, J=6.17 Hz, 2H) 3.43 (t, J=6.17 Hz, 2H) 4.56 (s, 2H) 5.21-5.30 (m, 1H) 5.88 (s, 1H) 8.02 (s, 1H) 11.56 (br. s., 1H); MS 376.2 [M+1].

Method K

Example 114: 4-[(4,6-dimethyl-2-oxo-1,2-dihydropyridin-3-yl)methyl]-7-ethoxy-6-methyl-3,4-dihydro-1,4-benzoxazepin-5(2H)-one

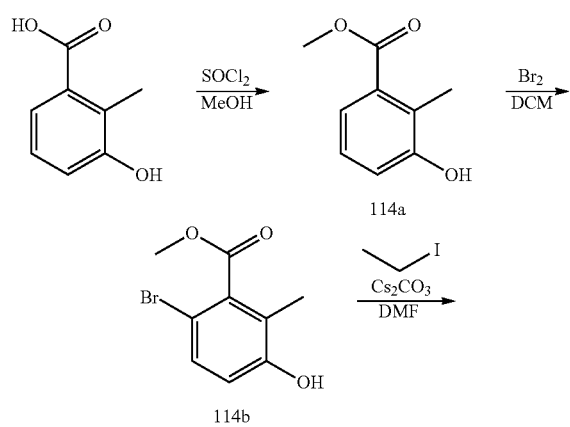

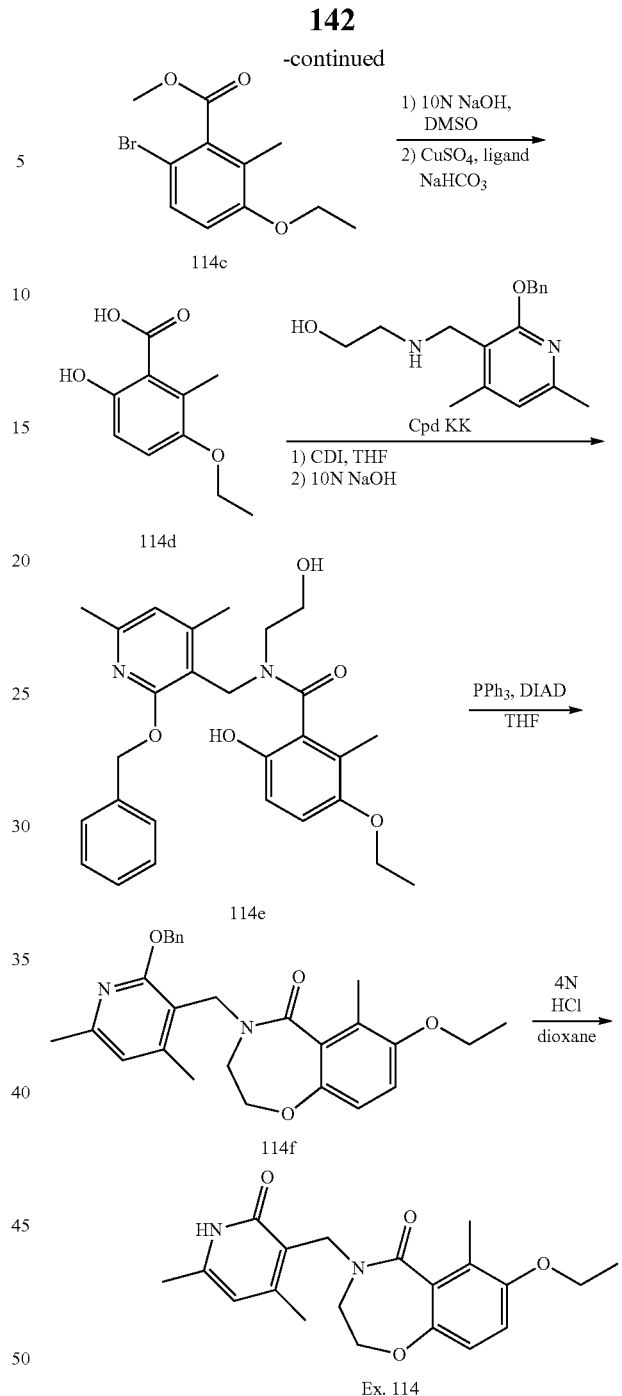

To a solution of 3-hydroxy-2-methylbenzoic acid (3.80 g, 25.0 mmol) in methanol (3.0 mL) at 0° C. was added thionyl chloride (3.00 mL, 41.2 mmol) dropwise. The reaction was allowed to warm to room temperature and was then heated at 50° C. for 2 hours. The solvent was removed under vacuum and the resulting solids were dissolved in ethyl acetate and washed with NaHCO₃ (sat. aq.). The ethyl acetate layer was dried over Na₂SO₄, filtered, and concentrated under vacuum to give methyl 3-hydroxy-2-methylbenzoate (114a, 3.49 g, 84% yield) as a light tan solid.

To a solution of methyl 3-hydroxy-2-methylbenzoate (114a, 3.557 g, 21.40 mmol) in dichloromethane (100 mL) in a dry ice/acetonitrile bath (~-45° C.) was added bromine (1.15 mL, 22.5 mmol) dropwise. The reaction was stirred at −45° C. for 2 hours before Na₂S₂O₃ (sat. aq., 2 mL) was added. The reaction mixture was allowed to warm to room temperature. The reaction mixture was diluted with dichloromethane and washed with water. The dichloromethane layer was concentrated under vacuum, and the resulting crude product was purified by column chromatography (0-40% ethyl acetate/heptane) to give methyl 6-bromo-3-hydroxy-2-methylbenzoate (114b, 4.8 g, 92% yield) as a white solid.

To a solution of methyl 6-bromo-3-hydroxy-2-methylbenzoate (114b, 0.701 g, 2.86 mmol) in DMF (6 mL) was added cesium carbonate (0.997 g, 3.0 mmol) and then iodoethane (0.400 mL, 5.00 mmol). The reaction was stirred at 65° C. for 30 minutes. The reaction mixture was poured into ethyl acetate and washed with water (×2). The ethyl acetate layer was concentrated under vacuum to give methyl 6-bromo-3-ethoxy-2-methylbenzoate (114c, 0.75 g, 96% yield) as a clear oil.

A solution of methyl 6-bromo-3-ethoxy-2-methylbenzoate (114c, 0.298 g, 1.09 mmol) in DMSO (4 mL) was treated with 10M NaOH (1.0 mL, 10 mmol) and heated at 95° C. After 1 hour, the ester was hydrolyzed. The reaction mixture was cooled to room temperature and sodium bicarbonate (0.850 g, 10.1 mmol) and water (3 mL) were added. The suspension was sonicated until homogeneous. A solution of copper(II) sulfate (0.0348 g, 0.218 mmol) and trans-N,N'-dimethylcyclohexane-1,2-diamine (0.071 mL, 0.44 mmol) in water (2.0 mL) was added. The reaction mixture was heated at 95° C. for 1 hour. The reaction mixture was cooled to room temperature, poured into ethyl acetate, and washed with 1N HCl and brine. The organic layer was dried over Na₂SO₄ and concentrated under vacuum to give 3-ethoxy-6-hydroxy-2-methylbenzoic acid (114d, 0.168 g, 79% yield) as a salmon colored solid.

To a solution of 3-ethoxy-6-hydroxy-2-methylbenzoic acid (114d, 0.168 g, 0.856 mmol) in THF (4.0 mL) was added 1,1'-carbonyldiimidazole (0.155 g, 0.91 mmol), and the reaction was stirred at 60° C. for 3 hours. The reaction mixture was allowed to cool to room temperature, and 2-({[2-(benzyloxy)-4,6-dimethylpyridin-3-yl]methyl}amino)ethanol (Cpd KK, 330 mg, 1.10 mmol) was added. Heating was then continued at 60° C. for 16 hour. The reaction mixture was cooled to room temperature, and 10M NaOH (0.3 mL) was added. The reaction mixture was stirred at room temperature for 1 hour and was then poured into ethyl acetate and washed with 1M KH₂PO₄ and water. The organic layer was concentrated and purified by column chromatography (0-80% ethyl acetate/dichloromethane) to give N-{[2-(benzyloxy)-4,6-dimethylpyridin-3-yl]methyl}-3-ethoxy-6-hydroxy-N-(2-hydroxyethyl)-2-methylbenzamide (114e, 0.274 g, 69% yield) as a white solid.

A solution of triphenylphosphine (0.176 g, 0.671 mmol) in THF (5 mL) in an ice bath was treated with diisopropyl azodicarboxylate (0.140 mL, 0.67 mmol) dropwise. After 10 minutes, N-{[2-(benzyloxy)-4,6-dimethylpyridin-3-yl]methyl}-3-ethoxy-6-hydroxy-N-(2-hydroxyethyl)-2-methylbenzamide (114e, 0.155 g, 0.334 mmol) was added in one portion. The reaction mixture was stirred in the ice bath overnight and the reaction mixture gradually warmed to room temperature. The reaction mixture was concentrated under vacuum and purified by column chromatography (0-40% ethyl acetate/heptane) to give 4-{[2-(benzyloxy)-4,6-dimethylpyridin-3-yl]methyl}-7-ethoxy-6-methyl-3,4-dihydro-1,4-benzoxazepin-5(2H)-one (114f, 0.087 g, 58%) as a clear, thick oil.

A solution of 4-{[2-(benzyloxy)-4,6-dimethyl pyridin-3-yl]methyl}-7-ethoxy-6-methyl-3,4-dihydro-1,4-benzoxazepin-5(2H)-one (114f, 0.085 g, 0.19 mmol) in 4N HCl in dioxane (5.0 mL, 20 mmol) was stirred at 45° C. for 16 hours. The reaction was concentrated under vacuum, and the resulting yellow residue was dissolved in hot DMSO (1.5 mL). A small amount of MeOH (1 mL) was added, and a white solid began to precipitate out of solution. The suspension was left overnight. The precipitate was collected by filtration and washed with water to give the title compound (Example 114, 0.061 g, 90% yield) as a bright white powder. ¹H NMR (400 MHz, DMSO-d6) δ 11.59 (s, 1H), 6.96 (d, J=8.80 Hz, 1H), 6.81 (d, J=8.80 Hz, 1H), 5.92 (s, 1H), 4.63 (s, 2H), 4.00 (q, J=6.97 Hz, 2H), 3.91 (t, J=5.32 Hz, 2H), 3.33 (t, J=5.38 Hz, 2H), 2.21 (s, 3H), 2.15 (s, 3H), 2.13 (s, 3H), 1.33 (t, J=6.91 Hz, 3H); MS 357 [M+H]⁺.

Method L

Example 116: 4-[(4,6-dimethyl-2-oxo-1,2-dihydropyridin-3-yl)methyl]-6-methyl-5-oxo-7-(propan-2-yloxy)-2,3,4,5-tetrahydro-1,4-benzoxazepine-9-carbonitrile

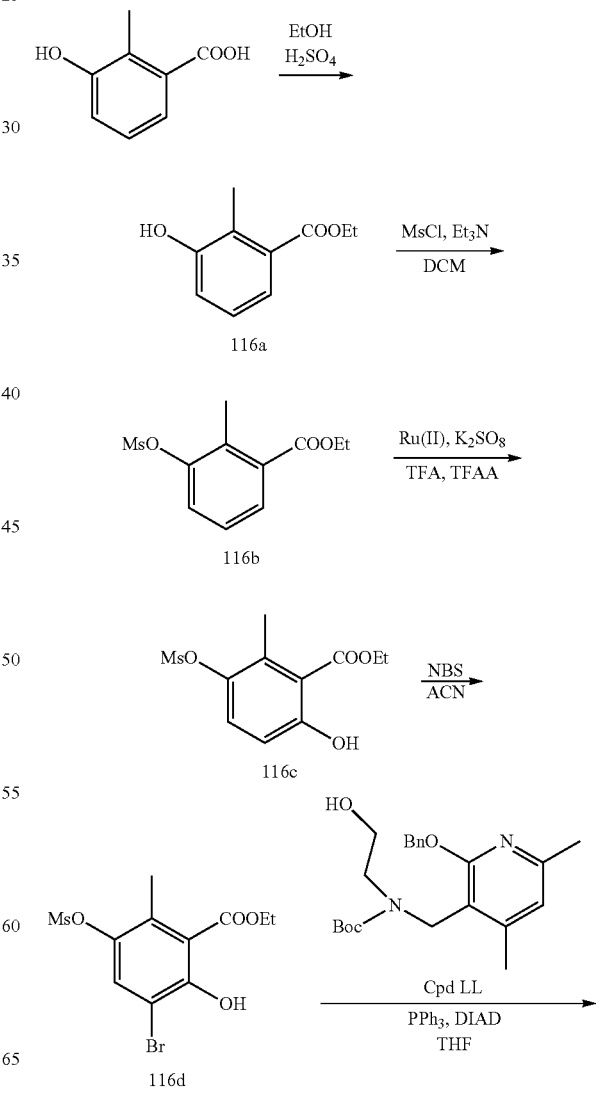

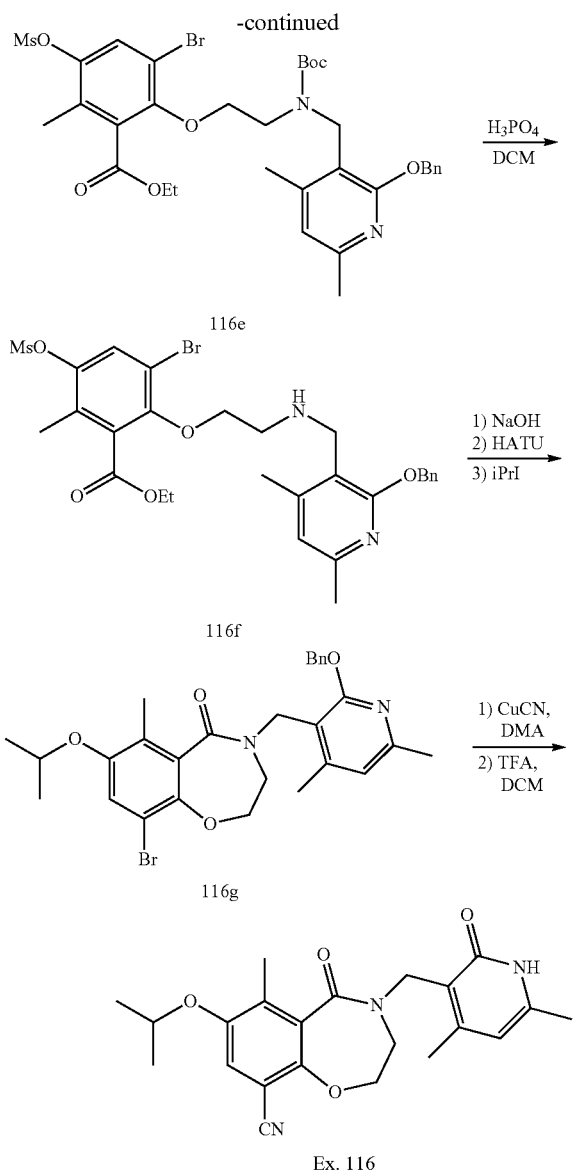

To a solution of ethyl 2-methyl-3-[(methylsulfonyl)oxy]benzoate (116b, 3.0 g, 12 mmol) in trifluoroacetic acid (35 mL) and trifluoroacetic anhydride (15 mL) was added potassium persulfate (3.5 g, 13 mmol) and dichloro(p-cymene)ruthenium(II) dimer (0.36 g, 0.59 mmol). The resulting mixture was stirred at 90° C. in a sealed tube for 22 hours. The reaction mixture was concentrated under vacuum then diluted with water (50 mL) and extracted with dichloromethane (2×75 mL). The combined organic layers were washed with brine (50 mL), dried over magnesium sulfate, concentrated under vacuum, and purified by column chromatography (40% EtOAc/Heptane) to give ethyl 6-hydroxy-2-methyl-3-[(methylsulfonyl)oxy]benzoate (116c, 1.3 g, 41% yield) as a white solid.

To a solution of ethyl 6-hydroxy-2-methyl-3-((methylsulfonyl)oxy)benzoate (116c, 1.3 g, 4.8 mmol) in acetonitrile (63 mL) was added N-bromosuccinimide (1.1 g, 6.2 mmol). The reaction was stirred at room temperature for 20 hours. The reaction mixture was concentrated under vacuum then diluted with water (30 mL) and extracted with dichloromethane (2×50 mL). The combined organic layers were washed with brine (30 mL), dried over magnesium sulfate, concentrated under vacuum, and purified by column chromatography (30% EtOAc/Heptane) to give ethyl 3-bromo-2-hydroxy-6-methyl-5-((methylsulfonyl)oxy)benzoate (116d, 1.3 g, 79% yield) as a yellow solid.

A solution of ethyl 3-bromo-2-hydroxy-6-methyl-5-((methylsulfonyl)oxy)benzoate (116d, 593 mg, 1.5 mmol), triphenylphosphine (0.50 g, 1.9 mmol), and tert-butyl ((2-(benzyloxy)-4,6-dimethylpyridin-3-yl)methyl)(2-hydroxyethyl)carbamate (Cpd LL, 0.54 g, 1.5 mmol) in tetrahydrofuran (12 mL) was cooled to 0° C. then diisopropyl azodicarboxylate (0.40 mL, 1.9 mmol) was added drop wise. The reaction was slowly warmed to room temperature and stirred overnight. The reaction was diluted with water (15 mL) and extracted with ethyl acetate (2×15 mL). The combined organic layers were washed with brine (15 mL), dried over magnesium sulfate, concentrated under vacuum, and purified by column chromatography (20% EtOAc/Heptane) to give ethyl 2-(2-(((2-(benzyloxy)-4,6-dimethylpyridin-3-yl)methyl)(tert-butoxycarbonyl)amino)ethoxy)-3-bromo-6-methyl-5-((methylsulfonyl)oxy)benzoate (116e, 0.58 g, 52% yield) as a white solid.

To a solution of ethyl 2-(2-(((2-(benzyloxy)-4,6-dimethylpyridin-3-yl)methyl)(tert-butoxycarbonyl)amino)ethoxy)-3-bromo-6-methyl-5-((methylsulfonyl)oxy)benzoate (116e, 0.58 g, 0.80 mmol) in dichloromethane (8 mL) was added 85% phosphoric acid (0.20 mL, 2.8 mmol). The mixture was stirred at room temperature for 2 hours then additional 85% phosphoric acid (0.20 mL, 2.8 mmol) was added and stirring was continued for 2 hours. The reaction was carefully quenched with saturated aqueous sodium bicarbonate (10 mL) and extracted with dichloromethane (2×15 mL). The combined organic layers were washed with brine (15 mL), dried over magnesium sulfate, concentrated under vacuum, and purified by column chromatography (20% EtOAc/Heptane) to give ethyl 2-(2-(((2-(benzyloxy)-4,6-dimethylpyridin-3-yl)methyl)amino)ethoxy)-3-bromo-6-methyl-5-((methylsulfonyl)oxy)benzoate (116f, 0.25 g, 50% yield) as a clear sticky solid.

To a solution of ethyl 2-(2-(((2-(benzyloxy)-4,6-dimethylpyridin-3-yl)methyl)amino)-ethoxy)-3-bromo-6-methyl-5-((methylsulfonyl)oxy)benzoate (116f, 0.54 g, 0.86 mmol) in methanol (2 mL) was added sodium hydroxide solution (50% in water, 0.73 g, 9.2 mmol). The reaction mixture was heated at 120° C. in the microwave for 1 hour then diluted with water and acidified with concentrated hydrochloric acid To a solution of 3-hydroxy-2-methylbenzoic acid (2.0 g, 13 mmol) in absolute ethanol (20 mL) was added sulfuric acid (2.0 mL, 37 mmol). The resulting mixture was stirred at 90° C. for 16 hours. The reaction was cooled to room temperature then diluted with water (20 mL). The mixture was extracted with dichloromethane (2×50 mL). The combined organic layers were washed with brine (50 mL), dried over magnesium sulfate and concentrated under vacuum to give ethyl 3-hydroxy-2-methylbenzoate (116a, 2.4 g, 99% yield) as yellow oil.

To a cooled (0° C.) solution of ethyl 3-hydroxy-2-methylbenzoate (116a, 2.4 g, 13 mmol) and N,N-diisopropylethylamine (5.8 mL, 33 mmol) in dichloromethane (50 mL) was added drop wise methanesulfonyl chloride (1.4 mL, 17 mmol). The reaction mixture was stirred at 0° C. for 30 minutes then diluted with water (20 mL) and extracted with dichloromethane (2×25 mL). The combined organic extracts were dried over magnesium sulfate, concentrated under vacuum, and purified by column chromatography (30% EtOAc/Heptane) to give ethyl 2-methyl-3-[(methylsulfonyl)oxy]benzoate (116b, 3.0 g, 88% yield) as a yellow oil.

to pH~4. The resulting precipitate was collected by vacuum filtration then taken up in N,N-dimethylacetamide (5 mL). N,N-diisopropylethyl amine (0.38 mL, 2.2 mmol) and O-(7-azabenzotriazol-1-yl)-N,N,N',N'-tetramethyluronium hexafluorophosphate (HATU, 0.39 g, 1.0 mmol) were added and the reaction was stirred at room temperature overnight. The crude reaction was diluted with water (10 mL) and extracted with dichloromethane (2×15 mL). The combined organic layers were washed with brine (15 mL), dried over magnesium sulfate and concentrated under vacuum. The residue was dissolved in N,N-dimethylacetamide (5 mL) and cesium carbonate (0.51 g, 1.6 mmol) and 2-iodopropane (0.12 mL, 1.2 mmol) were added. The mixture was heated at 75° C. for 1 hour, cooled to room temperature then diluted with water (10 mL) and extracted with ethyl acetate (2×15 mL). The combined organic layers were washed with brine (15 mL), dried over magnesium sulfate, concentrated under vacuum, and purified by column chromatography (30% EtOAc/Heptane) to give 4-((2-(benzyloxy)-4,6-dimethyl-pyridin-3-yl)methyl)-9-bromo-7-isopropoxy-6-methyl-3,4-dihydrobenzo[f][1,4]oxazepin-5(2H)-one (116 g, 242 mg, 48% yield) as a clear sticky solid.

To a solution of 4-((2-(benzyloxy)-4,6-dimethylpyridin-3-yl)methyl)-9-bromo-7-isopropoxy-6-methyl-3,4-dihydrobenzo[f][1,4]oxazepin-5(2H)-one (116 g, 98 mg, 0.18 mmol) in N,N-dimethylacetamide (2 mL) was added cuprous cyanide (50 mg, 0.55 mmol). The reaction mixture was heated at 120° C. in a sealed tube for 20 hours, cooled to room temperature then additional cuprous cyanide (25 mg, 0.26 mmol) was added and the reaction was heated at 150° C. in a sealed tube for 5 hours. The reaction was cooled to room temperature, diluted with water (5 mL) and extracted with methyl tert-butyl ether (2×5 mL). The combined organic layers were washed with brine (5 mL), dried over magnesium sulfate and concentrated under vacuum. The crude residue was taken up in dichloromethane (0.5 mL) and trifluoroacetic acid (0.5 mL, 2 mmol) and stirred at room temperature overnight then concentrated under vacuum. The residue was purified by reverse phase HPLC to provide the title compound (Example 116, 13 mg, 19% yield). $^1$H NMR (700 MHz, DMSO-d6) δ 7.47 (s, 1H), 5.93 (br. s., 1H), 4.58-4.69 (m, 3H), 4.12 (br. s., 2H), 2.19 (d, J=12.91 Hz, 6H), 2.14 (s, 3H), 1.26 (d, J=6.02 Hz, 6H): MS 396 [M+H]. Method M Example 123: 4-[(4,6-dimethyl-2-oxo-1,2-dihydro-pyridin-3-yl)methyl]-9-(propan-2-yloxy)-3,4-di-hydro-1,4-benzoxazepin-5(2H)-one

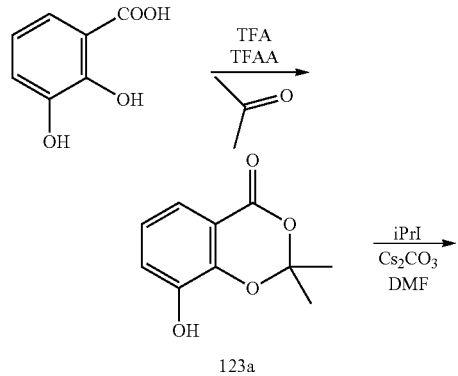

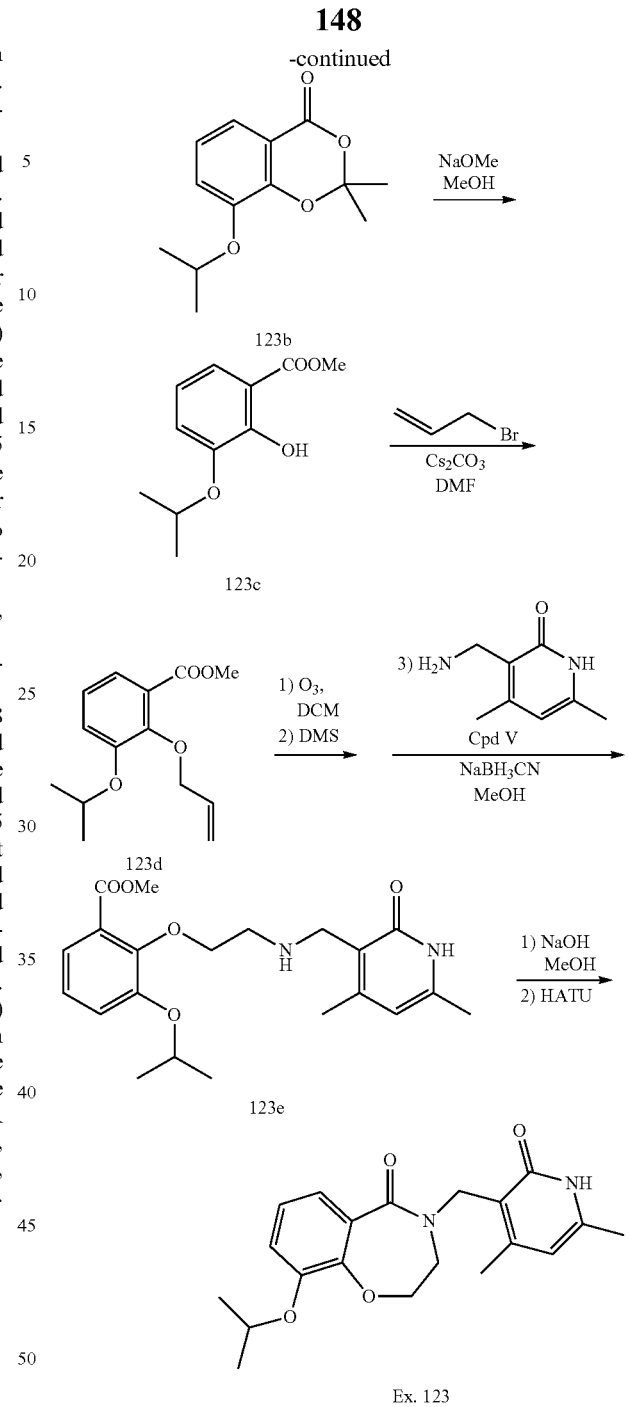

Trifluoroacetic acid anhydride (42.0 mL, 300 mmol) was added dropwise to a cooled (−5° C.) solution of 2,3-dihydroxybenzoic acid (8.30 g, 53.9 mmol) in trifluoroacetic acid (83 mL), with stirring. Acetone (14.0 mL, 190 mmol) was then added dropwise over 27 minutes, and the mixture stirred and allowed to warm gradually to room temperature over 16.5 hours. The volatiles were concentrated under vacuum, the residue was dissolved in ethyl acetate (100 mL), and the solution slowly added to a rapidly stirred saturated aqueous sodium bicarbonate solution (200 mL). After gas evolution ceased, the mixture was extracted with ethyl acetate (3×100 mL). The combined organic extracts were dried over magnesium sulfate, filtered, concentrated, and purified by silica gel chromatography (ethyl acetate/ heptane) to give 8-hydroxy-2,2-dimethyl-4H-1,3-benzodioxin-4-one (123a, 3.55 g, 34% yield) as an off-white solid.

Cesium carbonate (5.46 g, 16.6 mmol) was added to a solution of 8-hydroxy-2,2-dimethyl-4H-1,3-benzodioxin-4-one (123a, 1.50 g, 7.73 mmol) in N,N-dimethylformamide (31 mL) and the mixture stirred at room temperature for five minutes before 2-iodopropane (1.00 mL, 10.0 mmol) was added. The mixture was stirred at room temperature for 80 minutes, then partitioned between deionized water (30 mL) and ethyl acetate (2×75 mL). The combined organic extracts were dried over magnesium sulfate, filtered, concentrated under vacuum, and purified by column chromatography (ethyl acetate/heptane) to give 2,2-dimethyl-8-(propan-2-yloxy)-4H-1,3-benzodioxin-4-one (123b, 1.41 g, 77% yield) as a colorless gel which slowly crystallized to a white solid.

A solution of 2,2-dimethyl-8-(propan-2-yloxy)-4H-1,3-benzodioxin-4-one (123b, 1.40 g, 5.92 mmol) in methanol (12 mL) was treated with sodium methoxide in methanol (0.5 M, 24 mL, 12 mmol) and stirred at room temperature for 3 hours, 40 minutes. The solvents were evaporated and the residue partitioned between ammonium chloride solution (sat., aq., 20 mL) and ethyl acetate (2×30 mL). The combined organic extracts were dried over magnesium sulfate, filtered, and concentrated under vacuum to give methyl 2-hydroxy-3-(propan-2-yloxy)benzoate (123c, 1.24 g, 93% yield) as a colorless liquid.

Cesium carbonate (2.05 g, 6.2 mmol) was added to a solution of methyl 2-hydroxy-3-(propan-2-yloxy)benzoate (123c, 539 mg, 2.40 mmol) in N,N-dimethylformamide (9.6 mL), causing a thick paste to form. Allyl bromide (0.25 mL, 3.0 mmol) was added and the mixture stirred at room temperature for 1.5 hours. Deionized water (15 mL) was added, and the solution extracted with ethyl acetate (2×20 mL). The combined organic extracts were dried over magnesium sulfate, filtered, concentrated under vacuum, and purified by column chromatography (ethyl acetate/heptane) to give methyl 3-(propan-2-yloxy)-2-(prop-2-en-1-yloxy)benzoate (123d, 474.5 mg, 79% yield) as a colorless oil.

Ozone was bubbled through a cooled (−78° C.) solution of methyl 3-(propan-2-yloxy)-2-(prop-2-en-1-yloxy)benzoate (123d, 438.1 mg, 1.75 mmol) in dichloromethane (17.5 mL) until a persistent violet-blue color was obtained (about 5 minutes). Nitrogen was bubbled into the solution for 3 minutes, causing the color to fade, then dimethyl sulfide (1.0 mL, 13.5 mmol) was added and the mixture allowed to warm to room temperature for one hour. The solvents were evaporated and the residue partitioned between sodium carbonate solution (sat., aq., 10 mL) and ethyl acetate (2×20 mL). The combined organic extracts were dried over magnesium sulfate, filtered, and concentrated under vacuum to give the crude residue. This crude aldehyde was dissolved in methanol (10.0 mL) and treated with 3-(aminomethyl)-4,6-dimethylpyridin-2(1H)-one hydrochloride (Cpd V, 334 mg, 1.87 mmol) at room temperature for five minutes, then sodium cyanoborohydride (332 mg, 4.50 mmol) was added and the mixture stirred at room temperature for 14.5 hours. The solvents were evaporated under vacuum and the residue partitioned between deionized water (10 mL) and ethyl acetate (2×20 mL). The combined organic extracts were dried over magnesium sulfate, filtered, concentrated under vacuum, and purified by column chromatography (EtOH+ 5% NH₄OH in ethyl acetate) to give methyl 2-(2-{[(4,6-dimethyl-2-oxo-1,2-dihydropyridin-3-yl)methyl]amino}ethoxy)-3-(propan-2-yloxy)benzoate (123e, 76 mg, 11% yield) as a colorless glass.

A solution of methyl 2-(2-{[(4,6-dimethyl-2-oxo-1,2-dihydropyridin-3-yl)methyl]-amino}ethoxy)-3-(propan-2-yloxy)benzoate (123e, 76.2 mg, 0.196 mmol) in methanol (5.0 mL) was stirred with sodium hydroxide (1.0 M aq., 0.800 mL, 0.800 mmol) for 28 hours at room temperature, then 4.0 M aqueous sodium hydroxide solution (0.5 mL, 2.0 mmol) was added and stirring continued for 25 hours at room temperature. LCMS showed that a portion of the material had spontaneously cyclized, while some uncyclized material remained. The solvents were concentrated under vacuum and the residue acidified to pH-2 with 1N aqueous hydrochloric acid solution. The resulting white precipitate was collected by suction filtration. The mother liquor was extracted with ethyl acetate (2×10 mL), and the combined extracts dried over magnesium sulfate, filtered, concentrated under vacuum, and combined with precipitate. The aqueous layer was lyophilized and the residue suspended in N,N-dimethylformamide (6.0 mL), passed through a 0.2 micron syringe filter to remove inorganic salts, and then treated with triethylamine (0.08 mL) and O-(7-azabenzotriazol-1-yl)-N,N,N',N'-tetramethyluronium hexafluorophosphate (HATU, 87.0 mg, 0.23 mmol) for 20 hours at room temperature. This mixture was partitioned between deionized water (5 mL) and ethyl acetate (3×15 mL); and the combined organics were dried, filtered, and concentrated under vacuum. This batch was combined with the first batch of product and purified by reverse-phase HPLC to give the title compound 4-[(4,6-dimethyl-2-oxo-1,2-dihydropyridin-3-yl)methyl]-9-(propan-2-yloxy)-3,4-dihydro-1,4-benzoxazepin-5(2H)-one (Example 123, 11 mg, 16% yield) as a white solid. ¹H NMR (400 MHz, DMSO-d₆) δ 11.58 (br. s., 1H), 7.05-7.18 (m, 3H), 5.93 (s, 1H), 4.60 (s, 2H), 4.51 (spt, J=6.03 Hz, 1H), 4.01 (t, J=5.38 Hz, 2H), 3.43 (t, J=5.38 Hz, 2H), 2.19 (s, 3H), 2.14 (s, 3H), 1.23 (d, J=6.11 Hz, 6H). MS: 357 [M+H].

Method N

Example 124: 6-chloro-4-[(4,6-dimethyl-2-oxo-1,2-dihydropyridin-3-yl)methyl]-7-(2,2,2-trifluoroethoxy)-3,4-dihydro-1,4-benzoxazepin-5(2H)-one

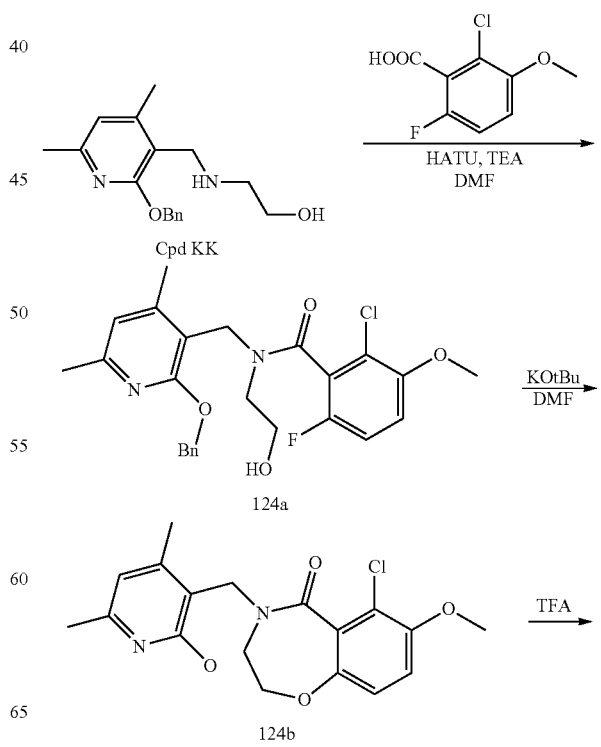

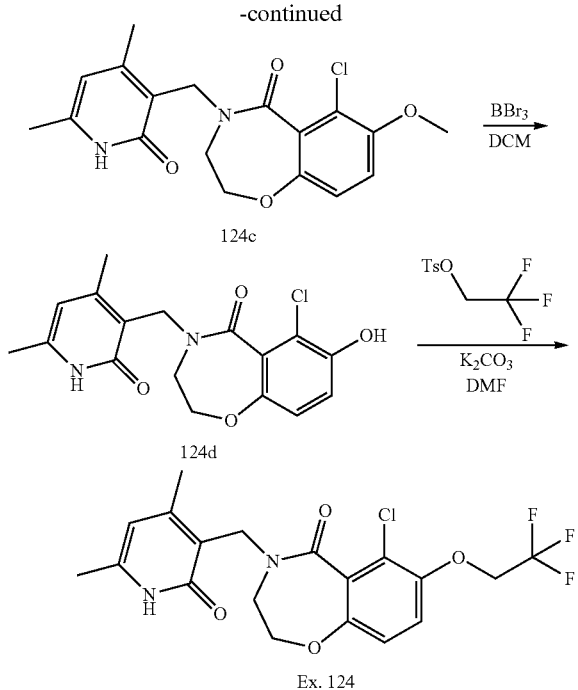

To a solution of 2-chloro-6-fluoro-3-methoxy-benzoic acid (1.00 g, 4.89 mmol) in anhydrous DMF (30 mL) were added HATU (2.30 g, 5.85 mmol) and TEA (1.36 mL, 9.76 mmol). The reaction mixture was stirred for 5 minutes, then 2-[(2-benzyloxy-4,6-dimethyl-pyridin-3-ylmethyl)-amino]-ethanol (Cpd KK, 1.47 g, 5.12 mmol) was added as a solid in one portion. The resulting reaction mixture was stirred at room temperature for 2 hours. The reaction mixture was partitioned between ethyl acetate (200 mL) and water (200 mL). The organic phase was separated, washed with brine (2×200 mL), dried over sodium sulfate, and concentrated under vacuum to give N-{[2-(benzyloxy)-4,6-dimethylpyridin-3-yl]methyl}-2-chloro-6-fluoro-N-(2-hydroxyethyl)-3-methoxybenzamide (124a, 2.31 g, 100%) as a gum.

To a solution of N-(2-benzyloxy-4,6-dimethyl-pyridin-3-ylmethyl)-2-chloro-6-fluoro-N-(2-hydroxy-ethyl)-3-methoxy-benzamide (124a, 2.31 g, 4.88 mmol) in anhydrous DMF (20 mL) was added KOtBu (1 M solution in THF, 12.2 mL, 12.2 mmol). The reaction mixture was stirred at 100° C. for 3 hours. After cooling to room temperature, the reaction mixture was partitioned between ethyl acetate (200 mL) and water (200 mL). The organic phase was separated, washed with brine (2×200 mL), dried over sodium sulfate, and concentrated under vacuum. The residue was purified by column chromatography (silica gel, heptanes/EtOAc) to give 4-{[2-(benzyloxy)-4,6-dimethylpyridin-3-yl]methyl}-6-methyl-9-[2-(methylamino)pyrimidin-5-yl]-7-(propan-2-yloxy)-3,4-dihydro-1,4-benzoxazepin-5(2H)-one (124b, 668 mg, 30% yield) as a solid.

A mixture of 4-{[2-(benzyloxy)-4,6-dimethylpyridin-3-yl]methyl}-6-methyl-9-[2-(methylamino)pyrimidin-5-yl]-7-(propan-2-yloxy)-3,4-dihydro-1,4-benzoxazepin-5(2H)-one (124b, 636 mg, 1.40 mmol) in TFA (10 mL) was stirred at 60° C. for 3 hours. The solvent was removed in vacuum and the resulting residue was partitioned between ether (100 mL) and sodium bicarbonate (100 mL). The organic phase was separated, and washed with brine (100 mL), dried over sodium sulfate, and concentrated under vacuum to give 6-chloro-4-[(4,6-dimethyl-2-oxo-1,2-dihydropyridin-3-yl)methyl]-7-methoxy-3,4-dihydro-1,4-benzoxazepin-5(2H)-one (124c, 503 mg, 99% yield) as a white solid.

To a 0° C. solution of 6-chloro-4-[(4,6-dimethyl-2-oxo-1,2-dihydropyridin-3-yl)methyl]-7-methoxy-3,4-dihydro-1,4-benzoxazepin-5(2H)-one (124c, 500 mg, 1.38 mmol) in anhydrous DCM (10 mL) was added slowly a solution of BBr$_3$ (1 M in DCM, 4.00 mL, 4.00 mmol). The reaction mixture was stirred at 0° C. for 3 hours, then quenched with water, and further diluted with water to 100 mL. The resulting mixture was extracted with DCM (3×100 mL). The combined organic phases were dried over sodium sulfate, and concentrated under vacuum to give 6-chloro-4-[(4,6-dimethyl-2-oxo-1,2-dihydropyridin-3-yl)methyl]-7-hydroxy-3,4-dihydro-1,4-benzoxazepin-5(2H)-one (124d, 456 mg, 95% yield) as a solid.

A mixture of 6-chloro-4-[(4,6-dimethyl-2-oxo-1,2-dihydropyridin-3-yl)methyl]-7-hydroxy-3,4-dihydro-1,4-benzoxazepin-5(2H)-one (124d, 100 mg, 0.287 mmol), toluene-4-sulfonic acid 2,2,2-trifluoro-ethyl ester (73.0 mg, 0.287 mmol), potassium carbonate (79.0 mg, 0.574 mmol), and anhydrous DMF (6 mL) was heated at 150° C. for 45 minutes in the microwave. After cooling to room temperature, the reaction mixture was partitioned between ethyl acetate (50 mL) and water (50 mL). The organic phase was separated, washed with water (50 mL) and brine (50 mL), dried over sodium sulfate, and concentrated under vacuum. The residue was purified by column chromatography (silica gel, MeOH/EtOAc) to give the title compound (Example 124, 18 mg, 16% yield) as a white solid. $^1$H NMR (400 MHz, DMSO-d6) δ 11.62 (br. s., 1H), 7.33 (d, J=8.93 Hz, 1H), 7.05 (d, J=8.93 Hz, 1H), 5.94 (s, 1H), 4.84 (q, J=8.60 Hz, 2H), 4.62 (s, 2H), 4.02 (br. s., 2H), 3.41 (br. s., 2H), 2.21 (s, 3H), 2.14 (s, 3H); MS 431.1 [M+1].

Method O

Example 126: 4-[(4,6-dimethyl-2-oxo-1,2-dihydropyridin-3-yl)methyl]-7-(1,4-dimethyl-1H-pyrazol-5-yl)-6-methyl-3,4-dihydro-1,4-benzoxazepin-5(2H)-one

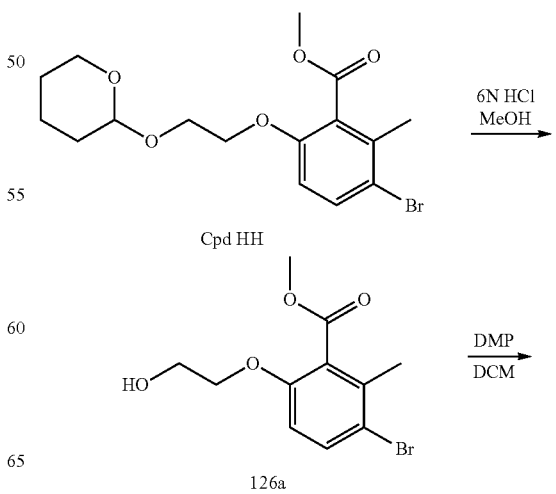

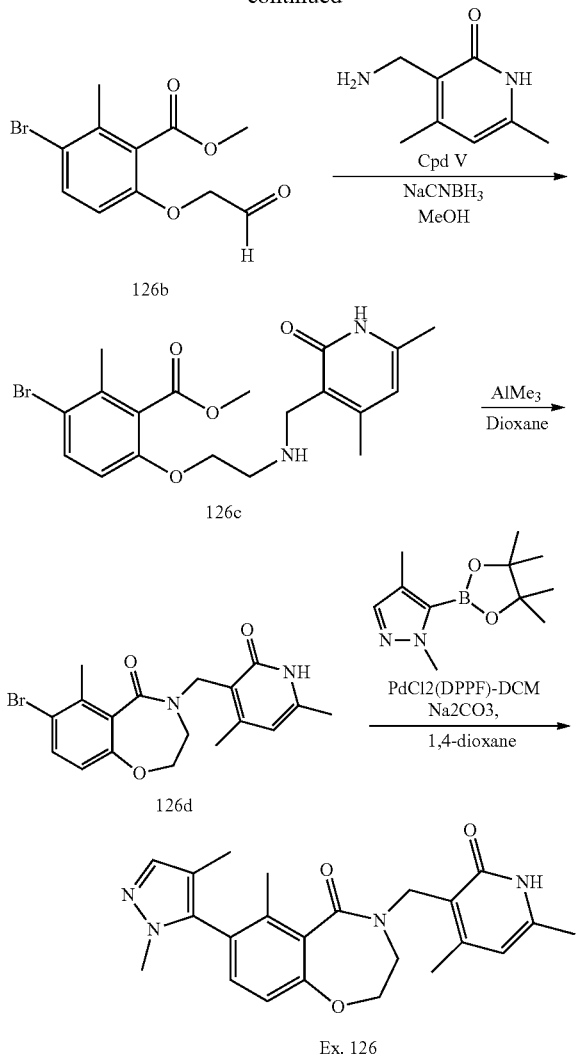

A solution of methyl 3-bromo-2-methyl-6-[2-(tetrahydro-2H-pyran-2-yloxy)ethoxy]-benzoate (Cpd HH, 162 mg, 0.434 mmol) in MeOH (4 mL) was treated with 6N HCl (0.2 mL) and stirred at room temperature for 30 minutes. The solvent was concentrated in vacuum to 1 mL and the solution partitioned between DCM (25 mL) and NaHCO$_3$ (sat., aq., 25 mL). The organic layer was concentrated under vacuum to give methyl 3-bromo-6-(2-hydroxyethoxy)-2-methylbenzoate (126a, 138 mg, 110% yield) as a colorless oil.

To a solution of methyl 3-bromo-6-(2-hydroxyethoxy)-2-methylbenzoate (126a, 126 mg, 0.436 mmol) in DCM (5 mL) was added Dess-Martin periodinane (192 mg, 0.429 mmol). The solution was stirred at room temperature for 2 hours. The solution was purified directly by column chromatography (silica gel, heptanes/EtOAc) to give methyl 3-bromo-2-methyl-6-(2-oxoethoxy)benzoate (126b, 111 mg, 90% yield) as a clear oil.

To a solution of methyl 3-bromo-2-methyl-6-(2-oxoethoxy)benzoate (126b, 109 mg, 0.380 mmol) in MeOH (5 mL) was added Cpd V (122 mg, 0.538 mmol). The suspension was sonicated until the reaction mixture was homogeneous. The solution was stirred at room temperature for 30 minutes before sodium cyanoborohydride (59 mg, 0.800 mmol) was added in one portion. The reaction mixture was stirred for 3 hours, then the solvent was concentrated in vacuum. The residue was dissolved in DCM (25 mL) and the organic layer washed with water (25 mL). The water layer was extracted with DCM and the combined organic layers were concentrated in vacuum to give methyl 3-bromo-6-(2-{[(4,6-dimethyl-2-oxo-1,2-dihydropyridin-3-yl)methyl]amino}ethoxy)-2-methylbenzoate (126c, 161 mg, 83%) as a white foam.

To a solution of methyl 3-bromo-6-(2-{[(4,6-dimethyl-2-oxo-1,2-dihydropyridin-3-yl)methyl]amino}ethoxy)-2-methylbenzoate (126c, 134 mg, 0.317 mmol) in 1,4-dioxane (1 mL) was added trimethylaluminum (2.0M in heptanes, 32.0 mg, 0.440 mmol). The reaction mixture was stirred at room temperature for 30 minutes, heated at 55° C. for 2 hours, and then 75° C. for 4 hours. The reaction mixture was cooled to room temperature, the solvent removed under vacuum, and the residue was stirred vigorously with EtOAc (25 mL) and 10% aq. solution of Rochell's salts. Once the mixture became homogeneous, the layers were separated and the organic layer was purified directly by column chromatography (silica gel, (7N NH$_3$ in MeOH) in EtOAc) to give 7-bromo-4-[(4,6-dimethyl-2-oxo-1,2-dihydropyridin-3-yl)methyl]-6-methyl-3,4-dihydro-1,4-benzoxazepin-5(2H)-one (126d, 36 mg, 27% yield) as a light tan solid.

A suspension of 7-bromo-4-[(4,6-dimethyl-2-oxo-1,2-dihydropyridin-3-yl)methyl]-6-methyl-3,4-dihydro-1,4-benzoxazepin-5(2H)-one (126d, 36 mg), 1,4-dimethyl-5-(4,4,5,5-tetramethyl-1,3,2-dioxaborolan-2-yl)-1H-pyrazole (34 mg, 0.092 mmol), and sodium carbonate (2M aq, 32 mg, 0.30 mmol) in 1,4-dioxane (3 mL) was degassed with N$_2$ for 10 minutes. The reaction mixture was treated with PdCl$_2$(DPPF)-DCM (8.2 mg, 0.010 mmol) and heated at 100° C. in the microwave for 1 hour, then at 120° C. in the microwave for an additional 1 hour. The reaction mixture was poured into DCM (25 mL) and washed with water (3×25 mL). The organic layer was concentrated under vacuum and the residue was purified by preparative HPLC to give the title compound (Example 126, 7 mg, 19% yield) as a white solid. $^1$H NMR (400 MHz, DMSO-d6) δ 7.33 (s, 1H), 7.23 (d, J=8.07 Hz, 1H), 6.99 (d, J=8.19 Hz, 1H), 5.93 (s, 1H), 4.66 (s, 2H), 4.09 (t, J=5.44 Hz, 2H), 3.48 (s, 3H), 3.42-3.46 (m, 2H), 2.23 (s, 3H), 2.14 (s, 3H), 2.03 (s, 3H), 1.79 (s, 3H); MS 407.1 [M+1].

Method P

Example 128: 4-[(4,6-dimethyl-2-oxo-1,2-dihydropyridin-3-yl)methyl]-6-methyl-9-[2-(methylamino)pyrimidin-5-yl]-7-(propan-2-yloxy)-3,4-dihydro-1,4-benzoxazepin-5(2H)-one

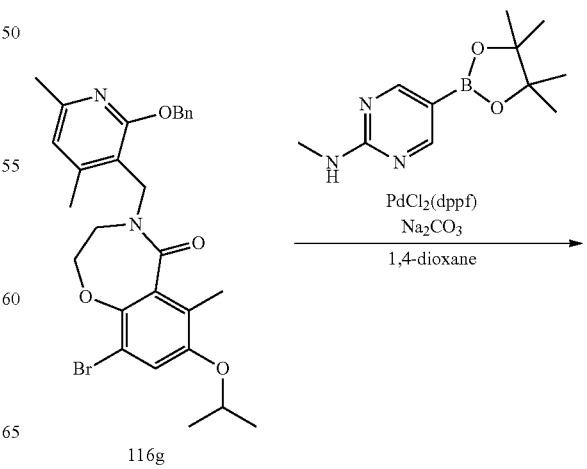

Method Q

Example 130: 4-[(4,6-dimethyl-2-oxo-1,2-dihydro-pyridin-3-yl)methyl]-N,N,6-trimethyl-5-oxo-2,3,4,5-tetrahydro-1,4-benzoxazepine-7-carboxamide

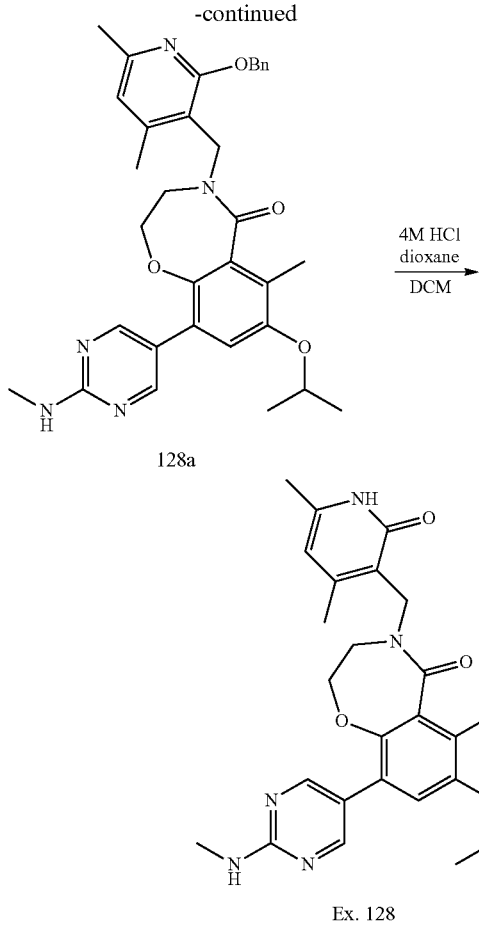

128a

Ex. 128

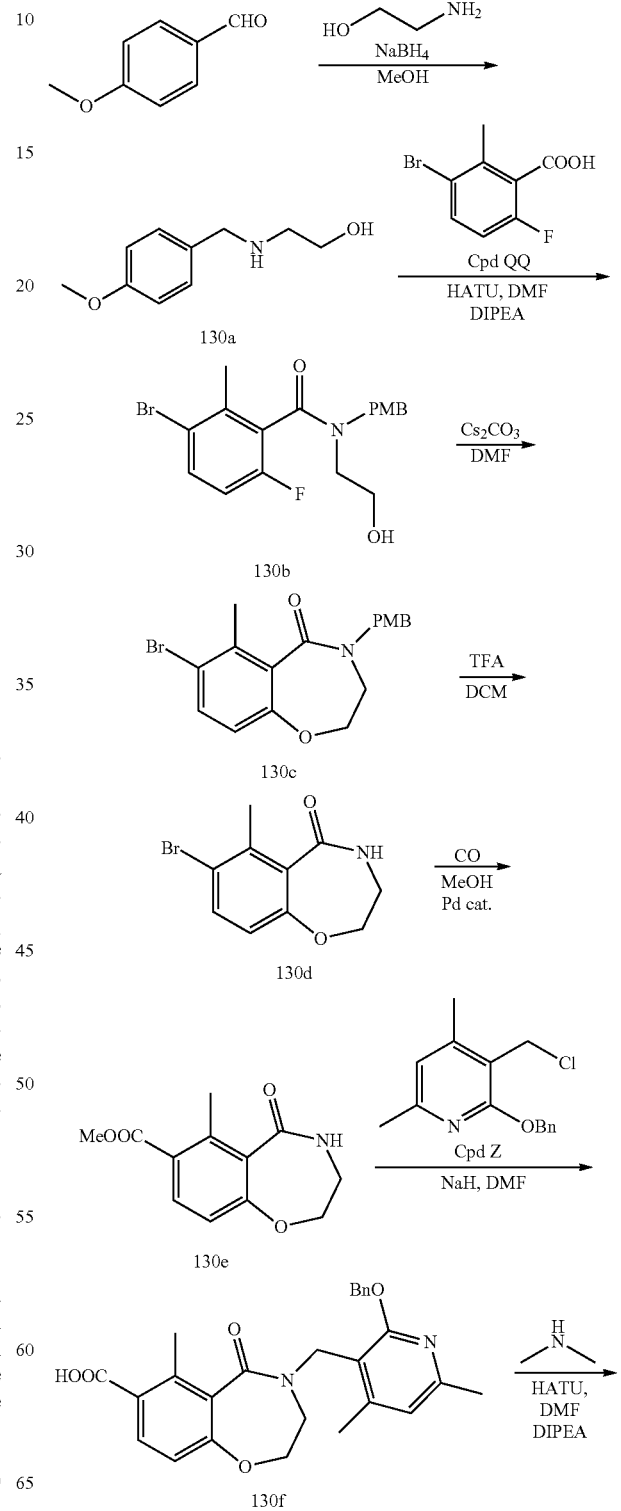

A solution of 4-{[2-(benzyloxy)-4,6-dimethylpyridin-3-yl]methyl}-9-bromo-6-methyl-7-(propan-2-yloxy)-3,4-dihydro-1,4-benzoxazepin-5(2H)-one (116 g, 121 mg, 0.224 mmol), N-methyl-5-(4,4,5,5-tetramethyl-1,3,2-dioxaborolan-2-yl)pyrimidin-2-amine (52.7 mg, 0.224 mmol) and sodium carbonate (2.0 M, 71.2 mg, 0.672 mmol) in 1,4-dioxane (2.0 mL) was degassed (N$_2$) for 5 min, then PdCl$_2$(dppf)-DCM (50.0 mg, 0.0610 mmol) was added. The reaction was heated at 100° C. for 1 hour. The reaction was diluted with water (25 mL) and EtOAc (25 mL). The layers were separated and the organic phase was dried with magnesium sulfate and concentrated under vacuum. The residue was purified by column chromatography (silica gel, heptanes/EtOAc) to give 4-{[2-(benzyloxy)-4,6-dimethylpyridin-3-yl]methyl}-6-methyl-9-[2-(methylamino)pyrimidin-5-yl]-7-(propan-2-yloxy)-3,4-dihydro-1,4-benzoxazepin-5(2H)-one (128a, 94 mg, 74% yield) as a white solid.

To a solution of 4-{[2-(benzyloxy)-4,6-dimethyl pyridin-3-yl]methyl}-6-methyl-9-[2-(methylamino)pyrimidin-5-yl]-7-(propan-2-yloxy)-3,4-dihydro-1,4-benzoxazepin-5(2H)-one (128a, 94 mg, 0.17 mmol) in DCM (1 mL) was added 4M HCl in dioxane (1 mL). The reaction was stirred at room temperature overnight. The solvent was removed in vacuum and the residue was purified by preparative HPLC to give the title compound (Example 128, 40 mg, 50% yield) as a white solid. $^1$H NMR (400 MHz, DMSO-d6) δ 8.43 (s, 2H), 7.19 (q, J=4.63 Hz, 1H), 7.05 (s, 1H), 5.92 (s, 1H), 4.59-4.69 (m, 3H), 3.28 (s, 3H), 3.17 (d, J=5.31 Hz, 2H), 2.83 (d, J=4.80 Hz, 2H), 2.23 (s, 3H), 2.13 (d, J=2.27 Hz, 6H), 1.27 (d, J=6.06 Hz, 6H); MS 478.2 [M+1].

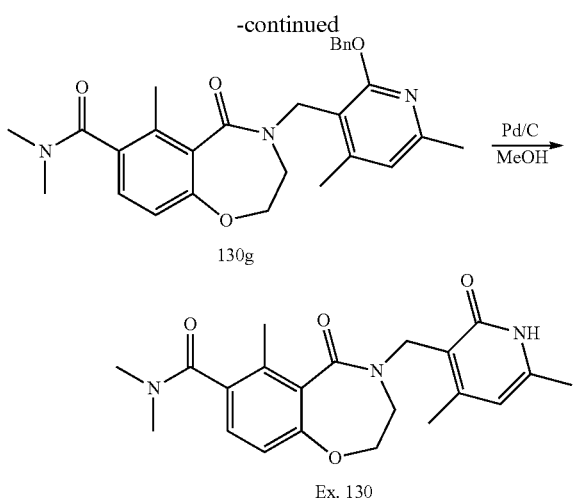

A mixture of 4-methoxybenzaldehyde (10 g, 74 mmol), 2-aminoethanol (4.9 g, 81 mmol) and NaHCO₃ (9.3 g, 110 mmol) in MeOH (100 mL) was refluxed for 3 hours. The reaction mixture was cooled to 15° C. To the mixture was added portionwise NaBH₄ (3.3 g, 88 mmol) at 15° C. The mixture was stirred at room temperature for 2 hours. The reaction mixture was filtered and the filtrate was concentrated under vacuum to give 2-[(4-methoxybenzyl)amino]ethanol (130a, 20 g) as a brown oil.

To a solution of 3-bromo-6-fluoro-2-methylbenzoic acid (Cpd QQ, 4.8 g, 2.4 mmol), 2-[(4-methoxybenzyl)amino]ethanol (130a, 5.5 g, 23 mmol) and DIPEA (8 g, 62 mmol) in dry DMF (80 mL) was added HATU (12 g, 31 mmol). The mixture was stirred at room temperature for 14 hours. To the reaction mixture was added EtOAc (130 mL). The solution was washed with brine (4×60 mL), dried over Na₂SO₄, and concentrated under vacuum. The residue was purified by column chromatography (petroleum ether/EtOAc, 2/1) to give 3-bromo-6-fluoro-N-(2-hydroxyethyl)-N-(4-methoxybenzyl)-2-methylbenzamide (130b, 4 g, 48.8%) as a colorless oil.

A mixture of 3-bromo-6-fluoro-N-(2-hydroxyethyl)-N-(4-methoxybenzyl)-2-methylbenzamide (130b, 5.00 g, 12.6 mmol) and Cs₂CO₃ (8.20 g, 25.3 mmol) in dry DMF (60 mL) was stirred at 65° C. for 14 hours. To the reaction mixture was added brine (100 mL). The mixture was extracted with EtOAc (2×50 mL). The combined organic layers were washed with brine (4×60 mL), dried over Na₂SO₄, and concentrated under vacuum. The residue was purified by column chromatography (petroleum ether/EtOAc, 5/1) to give 7-bromo-4-(4-methoxybenzyl)-6-methyl-3,4-dihydro-1,4-benzoxazepin-5(2H)-one (130c, 2.8 g, 59%) as a colorless oil.

A mixture of 7-bromo-4-(4-methoxybenzyl)-6-methyl-3,4-dihydro-1,4-benzoxazepin-5(2H)-one (130c, 2.8 g, 7.4 mmol) in TFA (30 mL) was refluxed for 14 hours. The reaction mixture was concentrated under vacuum. The residue was purified by column chromatography (petroleum ether/EtOAc, 3/1) to give 7-bromo-6-methyl-3,4-dihydro-1,4-benzoxazepin-5(2H)-one (7-bromo-6-methyl-3,4-dihydro-1,4-benzoxazepin-5(2H)-one (130d, 1.2 g, 63%) as a brown solid.

A mixture of 7-bromo-6-methyl-3,4-dihydro-1,4-benzoxazepin-5(2H)-one (7-bromo-6-methyl-3,4-dihydro-1,4-benzoxazepin-5(2H)-one (130d, 0.80 g, 3.1 mmol), Pd(dppf)Cl₂ (0.11 g, 0.16 mmol) and DIPEA (0.80 g, 6.3 mmol) in MeOH (40 mL) was degassed with CO and the mixture was stirred at 100° C. under 4 MPa for 48 hours. The reaction mixture was concentrated under vacuum. The residue was purified by column chromatography (petroleum ether/EtOAc, 1/1) to give methyl 6-methyl-5-oxo-2,3,4,5-tetrahydro-1,4-benzoxazepine-7-carboxylate (130e, 0.34 g, 46%) as an off-white solid.

To a solution of methyl 6-methyl-5-oxo-2,3,4,5-tetrahydro-1,4-benzoxazepine-7-carboxylate (130e, 0.10 g, 0.45 mmol) in DMF (8 mL) was added NaH (54 mg, 1.36 mmol, 60% in oil) at 0° C. After stirring at 0° C. for 10 minutes, 2-(benzyloxy)-3-(chloromethyl)-4,6-dimethylpyridine (Cpd Z, 0.20 g, 0.77 mmol) was added. The mixture was stirred at room temperature overnight. To the reaction mixture was added H₂O (30 mL). The mixture was extracted with EtOAc (2×20 mL). The aqueous layer was acidified with conc. HCl to pH 3 and extracted with EtOAc (2×20 mL). The combined organic layers were washed with brine (4×30 mL), dried over Na₂SO₄, and concentrated under vacuum to give 4-{[2-(benzyloxy)-4,6-dimethylpyridin-3-yl]methyl}-6-methyl-5-oxo-2,3,4,5-tetrahydro-1,4-benzoxazepine-7-carboxylic acid (130f, 0.17 g, 84.7%) as an off-white solid.

To a solution of 4-{[2-(benzyloxy)-4,6-dimethylpyridin-3-yl]methyl}-6-methyl-5-oxo-2,3,4,5-tetrahydro-1,4-benzoxazepine-7-carboxylic acid (130f, 0.17 g, 0.38 mmol), dimethylamine hydrochloride (47 mg, 0.57 mmol) and DIPEA (0.25 g, 1.90 mmol) in DMF (10 mL) was added HATU (0.29 g, 0.76 mmol). The mixture was stirred at room temperature under N₂ for 5 hours. To the reaction mixture was added H₂O (30 mL). The mixture was extracted with EtOAc (2×20 mL). The combined organic layers were washed with brine (4×30 mL), dried over Na₂SO₄, and concentrated under vacuum. The residue was purified by column chromatography (petroleum ether/EtOAc, 1/1) to give 4-{[2-(benzyloxy)-4,6-dimethyl pyridin-3-yl]methyl}-N,6-dimethyl-5-oxo-2,3,4,5-tetrahydro-1,4-benzoxazepine-7-carboxamide (130 g, 0.17 g, 94.6%) as a white solid.

A mixture of 4-{[2-(benzyloxy)-4,6-dimethylpyridin-3-yl]methyl}-N,6-dimethyl-5-oxo-2,3,4,5-tetrahydro-1,4-benzoxazepine-7-carboxamide (130 g, 0.17 g, 0.36 mmol) and Pd/C (93 mg) in MeOH (15 mL) was stirred at room temperature under an H₂ balloon for 2 hours. The reaction mixture was concentrated under vacuum to give the title compound (Example 130, 130 mg, 94%) as a white solid. ¹H NMR (400 MHz, chloroform-d): δ 11.34 (s, 1H), 7.18-7.16 (d, 1H), 6.88-6.86 (d, 1H), 5.97 (s, 1H), 4.90-4.86 (d, 2H), 4.12 (s, 1H), 3.93 (s, 1H), 3.53 (s, 2H), 3.13 (s, 3H), 2.85 (s, 3H), 2.36-2.35 (d, 6H), 2.27 (s, 3H); MS 256.8 [M+H].

Method R

Example 131: 4-[(4,6-dimethyl-2-oxo-1,2-dihydropyridin-3-yl)methyl]-6-methyl-7-(propan-2-yloxy)-3,4-dihydropyrido[4,3-f][1,4]oxazepin-5(2H)-one

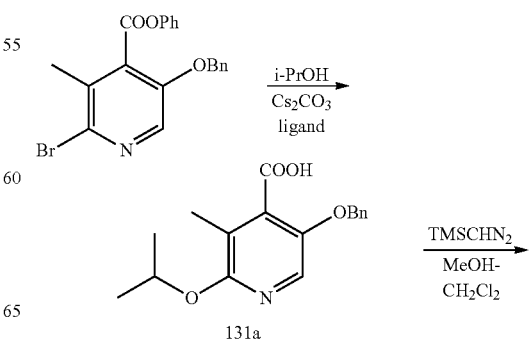

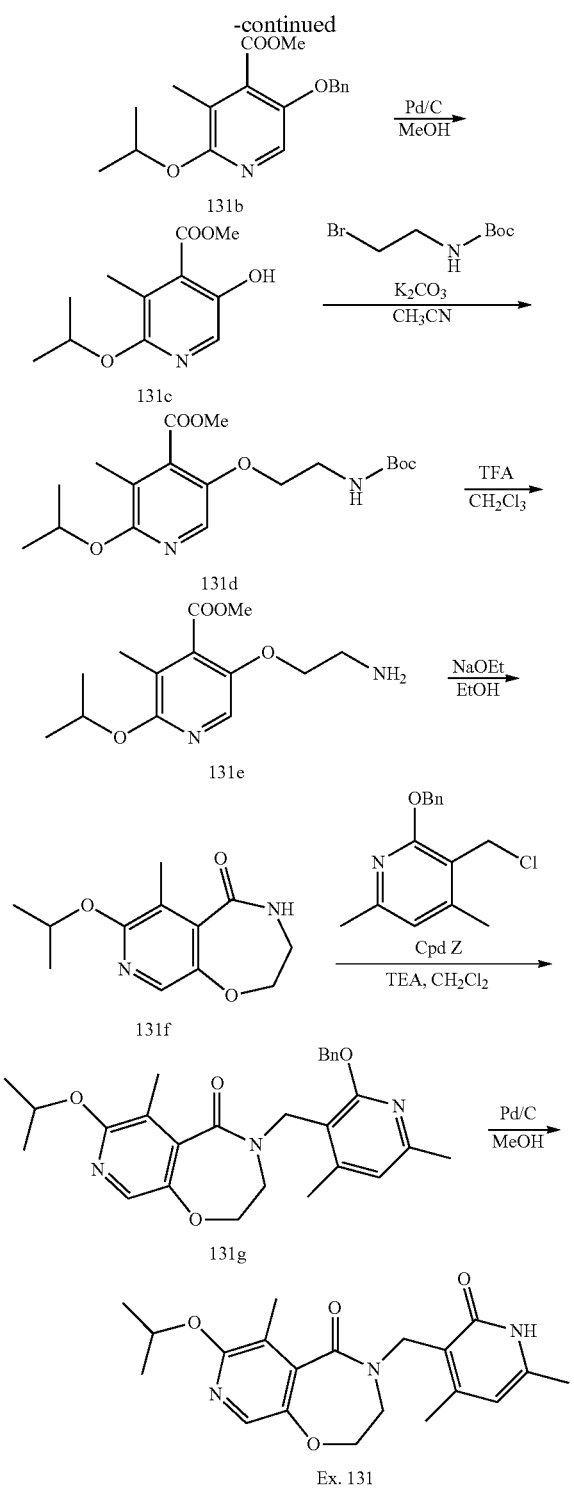

Ex. 131

A suspension of phenyl 5-(benzyloxy)-2-bromo-3-methylpyridine-4-carboxylate (2.4 g, 6.0 mmol) and Cs$_2$CO$_3$ (6.1 g, 19 mmol) in i-PrOH (36 mL) was degassed with N$_2$ for 2 minutes. To the reaction mixture was added Pd$_2$(dba)$_3$ (0.31 g, 0.34 mmol) and t-Bu-BippyPhos (0.34 g, 0.66 mmol, cas: 894086-00-1). The mixture was heated in the microwave at 115° C. for 1 hour. To the reaction mixture was added 4M NaOH (7 mL) and MeOH (7 mL) and the reaction mixture was stirred at 60° C. for 3 hours. The reaction mixture was concentrated under vacuum. To the residue was added EtOAc (60 mL) and H$_2$O (80 mL). The aqueous layer was acidified with conc. HCl to pH 4 and extracted with EtOAc (2×40 mL). The combined organic layers were washed with brine (60 mL), dried over Na$_2$SO$_4$, and concentrated under vacuum to give 5-(benzyloxy)-3-methyl-2-(propan-2-yloxy)pyridine-4-carboxylic acid (131a, 1.1 g, 60%) as a yellow solid.

To a solution of 5-(benzyloxy)-3-methyl-2-(propan-2-yloxy)pyridine-4-carboxylic acid (131a, 1.4 g, 4.7 mmol) in dry CH$_2$Cl$_2$ (50 mL) and dry MeOH (5 mL) was added dropwise TMSCHN$_2$ (2.6 mL, 5.1 mmol, 2M in hexane) at 0° C. under N$_2$. The reaction mixture was stirred at room temperature for 2 hours then concentrated under vacuum. The residue was purified by column chromatography (petroleum ether/EtOAc, 10/1) to give methyl 5-(benzyloxy)-3-methyl-2-(propan-2-yloxy)pyridine-4-carboxylate (131b, 1.1 g, 75%) as a colorless oil.

A mixture of methyl 5-(benzyloxy)-3-methyl-2-(propan-2-yloxy)pyridine-4-carboxylate (131b, 1.1 g, 3.5 mmol) and Pd/C (0.5 g) in MeOH (60 mL) was hydrogenated under an H$_2$ balloon at room temperature for 2 hours. The reaction mixture was filtered through CELITE® and the filtrate was concentrated under vacuum to give methyl 5-hydroxy-3-methyl-2-(propan-2-yloxy)pyridine-4-carboxylate (131c, 0.7 g, 89%) as yellow oil.

A mixture of methyl 5-hydroxy-3-methyl-2-(propan-2-yloxy)pyridine-4-carboxylate (131c, 0.70 g, 3.1 mmol), tert-butyl (2-bromoethyl)carbamate (0.76 g, 3.4 mmol) and K$_2$CO$_3$ (0.86 g, 6.2 mmol) in CH$_3$CN (24 mL) was degassed with N$_2$ and refluxed for 15 hours. To the reaction mixture was added brine (40 mL) and EtOAc (40 mL). The aqueous layer was extracted with EtOAc (20 mL). The combined organic layers were washed with brine (60 mL), dried over Na$_2$SO$_4$ and concentrated under vacuum. The residue was purified by column chromatography (petroleum ether/EtOAc, 10/1) to give methyl 5-{2-[(tert-butoxycarbonyl)amino]ethoxy}-3-methyl-2-(propan-2-yloxy)pyridine-4-carboxylate (131d, 0.74 g, 65%) as yellow oil.

To a solution of methyl 5-{2-[(tert-butoxycarbonyl)amino]ethoxy}-3-methyl-2-(propan-2-yloxy)pyridine-4-carboxylate (131d, 0.74 g, 2.0 mmol) in dry CH$_2$Cl$_2$ (20 mL) was added TFA (5 mL) at 5° C. The mixture was stirred at room temperature for 14 hours. The reaction mixture was concentrated under vacuum to give methyl 5-(2-aminoethoxy)-3-methyl-2-(propan-2-yloxy)pyridine-4-carboxylate (131e, 1.4 g) as brown oil.

A mixture of methyl 5-(2-aminoethoxy)-3-methyl-2-(propan-2-yloxy)pyridine-4-carboxylate (131e, 1.2 g, 2.2 mmol) and NaOEt (3.0 g, 45 mmol) in dry EtOH (60 mL) was refluxed for 14 hours. The reaction mixture was concentrated under vacuum. The residue was dissolved in H$_2$O (30 mL) and extracted with EtOAc (2×20 mL). The combined organic layers were washed with brine (30 mL), dried over Na$_2$SO$_4$, and concentrated under vacuum to give 6-methyl-7-(propan-2-yloxy)-3,4-dihydropyrido[4,3-f][1,4]oxazepin-5(2H)-one (131f, 0.34 g) as a brown solid.

To a solution of 6-methyl-7-(propan-2-yloxy)-3,4-dihydropyrido[4,3-f][1,4]oxazepin-5(2H)-one (131f, 70 mg, 0.30 mmol) in dry DMF (6 mL) was added NaH (36 mg, 0.90 mmol, 60% in oil) at 0° C. The mixture was stirred at 0° C. for 10 minutes. To the mixture was added 2-(benzyloxy)-3-(chloromethyl)-4,6-dimethylpyridine (Cpd Z, 155 mg, 0.6 mmol). The reaction mixture was stirred at room temperature for 14 hours. To the reaction mixture was added EtOAc (20 mL). The solution was washed with brine (5×15 mL), dried over Na$_2$SO$_4$, and concentrated under vacuum. The residue was purified by column chromatography (petroleum ether/EtOAc, 10/1) to give 4-{[2-(benzyloxy)-4,6-dimethylpyridin-3-yl]methyl}-6-methyl-7-(propan-2-yloxy)-3,4-dihydropyrido[4,3-f][1,4]oxazepin-5(2H)-one (131 g, 0.14 g, 100%) as a colorless oil.

A mixture of 4-{[2-(benzyloxy)-4,6-dimethyl pyridin-3-yl]methyl}-6-methyl-7-(propan-2-yloxy)-3,4-dihydropyrido[4,3-f][1,4]oxazepin-5(2H)-one (131 g, 140 mg, 0.30 mmol) and 10% Pd/C (80 mg) in MeOH (15 mL) was stirred under an H$_2$ balloon for 3 hours. The reaction mixture was filtered through a pad of CELITE® and the filtrate was concentrated under vacuum to give the title compound (Example 131, 110 mg, 98%) as a white solid. $^1$H NMR (400 MHz, chloroform-d): δ 11.45 (s, 1H), 7.72 (s, 1H), 5.97 (s, 1H), 5.26-5.21 (m, 1H), 4.87 (s, 2H), 4.00-3.97 (t, 2H), 3.56-3.53 (t, 2H), 2.36 (s, 3H), 2.28-2.26 (d, 6H), 1.35-1.33 (d, 6H); MS 372.2 [M+H].

Method S

Example 132-A: 9-chloro-2-[(4,6-dimethyl-2-oxo-1,2-dihydropyridin-3-yl)methyl]-8-methoxy-2,3,4,5-tetrahydro-1H-2-benzazepin-1-one and Example 132-B: 7-chloro-2-[(4,6-dimethyl-2-oxo-1,2-dihydropyridin-3-yl)methyl]-8-methoxy-2,3,4,5-tetrahydro-1H-2-benzazepin-1-one

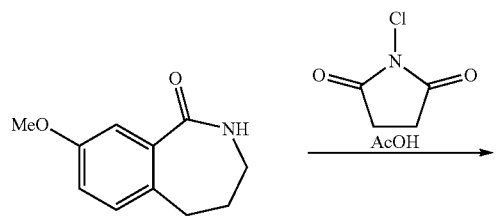

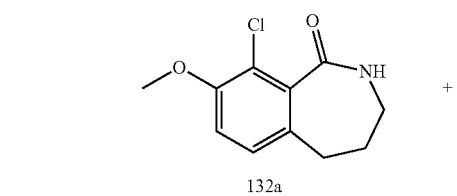

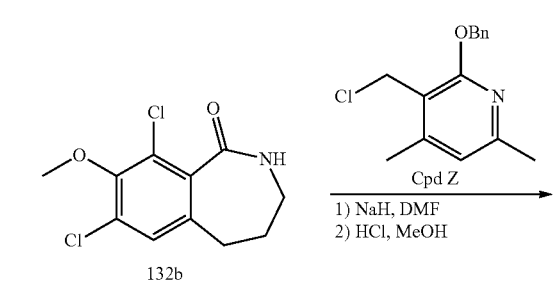

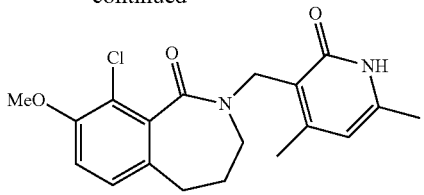

Ex. 132-A

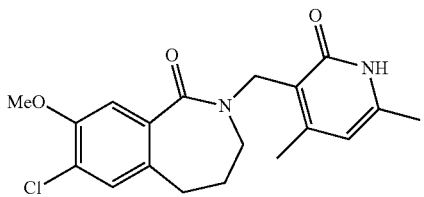

Ex. 132-B

A solution of 8-methoxy-2,3,4,5-tetrahydro-1H-2-benzazepin-1-one (25.0 mg, 0154 mmol) and n-chlorosuccinamide (20.6 mg, 0.154 mmol) in AcOH (3 mL) was stirred at 100° C. for 4.5 hours. The reaction mixture was partitioned between ethyl acetate (20 mL) and water (20 mL). The organic phase was dried over sodium sulfate, and concentrated under vacuum to give a mixture of 9-chloro-8-methoxy-2,3,4,5-tetrahydro-1H-2-benzazepin-1-one (132a) and 7-chloro-8-methoxy-2,3,4,5-tetrahydro-1H-2-benzazepin-1-one (132b) (35 mg, 100%) as a clear oil.

To a mixture of 9-chloro-8-methoxy-2,3,4,5-tetrahydro-1H-2-benzazepin-1-one (132a) and 7-chloro-8-methoxy-2,3,4,5-tetrahydro-1H-2-benzazepin-1-one (132b) (35.0 mg, 0.150 mmol) in DMF (5 mL) was added 2-(benzyloxy)-3-(chloromethyl)-4,6-dimethylpyridine (Cpd Z, 47.1 mg, 0.180 mmol). The reaction mixture was heated at 80° C. for 24 hours. The reaction mixture was poured into a NaOAc—HOAc buffer (5 mL) and extracted with EtOAc (2×10 mL). The combined organic layers were dried over sodium sulfate and concentrated under vacuum. The resulting brown oil was dissolved in MeOH (1 mL) and HCl (3 M in n-butanol, 0.05 mL) was added. The reaction mixture was heated at 70° C. for 24 hours. The solvent was removed in vacuum and the residue was purified by preparative HPLC to give the title compounds (Example 132-A, first eluting product, 20 mg, 36%); $^1$H NMR (400 MHz, methanol-d4) δ 7.09-7.14 (m, 1H), 7.05-7.10 (m, 1H), 6.13 (s, 1H), 4.89 (s, 1H), 4.71-4.79 (m, 1H), 3.88 (s, 3H), 3.38 (dd, J=5.93, 14.86 Hz, 1H), 2.92-3.01 (m, 1H), 2.57-2.73 (m, 2H), 2.35 (s, 3H), 2.25 (s, 3H), 2.06-2.14 (m, 1H), 1.53-1.64 (m, 1H); MS 361.1 [M+1]; and (Example 132-B, second eluting product, 4 mg, 7%); $^1$H NMR (400 MHz, methanol-d4) δ 7.26 (s, 1H), 7.22 (s, 1H), 6.13 (s, 1H), 4.78 (s, 2H), 3.91 (s, 3H), 3.26-3.29 (m, 2H), 2.63 (t, J=7.09 Hz, 2H), 2.34 (s, 3H), 2.26 (s, 3H), 1.78 (t, J=6.66 Hz, 2H); MS 361.1 [M+1]; as a white solids.

Method T

Example 133: 7-chloro-2-[(4,6-dimethyl-2-oxo-1,2-dihydropyridin-3-yl)methyl]-6-(propan-2-yloxy)-2,3-dihydro-1H-isoindol-1-one

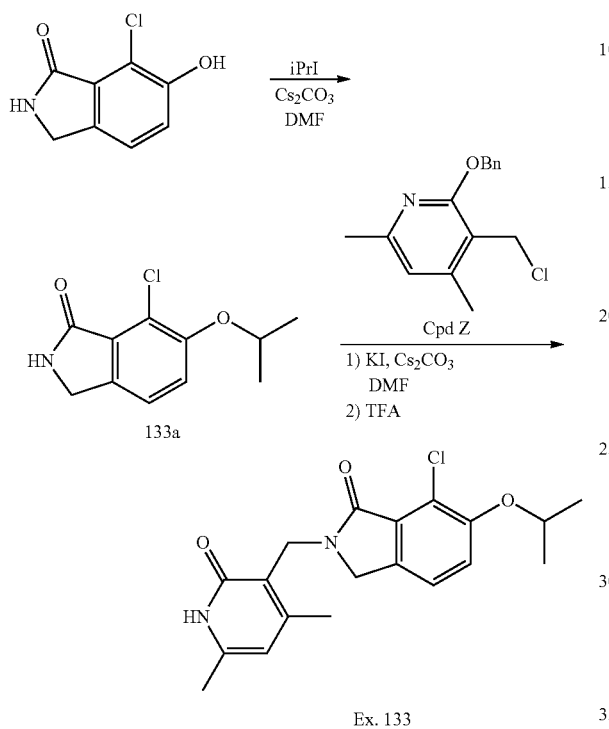

Ex. 133

A mixture of 7-chloro-6-hydroxy-2,3-dihydro-isoindol-1-one (500 mg, 2.72 mmol), 2-iodopropane (556 mg, 3.27 mmol), and cesium carbonate (1.33 mg, 4.08 mmol) in DMF (20 mL) was stirred at 80° C. overnight. The solution was cooled to room temperature and the reaction mixture partitioned between ethyl acetate (50 mL) and water (50 mL). The organic phase was separated, washed with water (50 mL) and brine (50 mL), dried over sodium sulfate and concentrated under vacuum. The residue was purified by column chromatography (silica gel, heptanes/EtOAc) to give 7-chloro-6-isopropoxy-2,3-dihydro-isoindol-1-one (133a, 300 mg, 65% yield) as a solid.

A mixture of 7-chloro-6-isopropoxy-2,3-dihydro-isoindol-1-one (133a, 120 mg, 0.532 mmol), 2-benzyloxy-3-chloromethyl-4,6-dimethyl-pyridine (Cpd Z, 139 mg, 0.532 mmol), cesium carbonate (260 mg, 0.798 mmol), and potassium iodide (132 mg, 0.798 mmol) in DMF (6 mL) was stirred at 100° C. overnight. The solution was cooled to room temperature and the reaction mixture partitioned between ethyl acetate (50 mL) and water (50 mL). The organic phase was separated, washed with water (50 mL) and brine (50 mL), dried over sodium sulfate and concentrated under vacuum. The residue was purified by column chromatography (silica gel, heptanes/EtOAc) and the residue concentrated under vacuum. The residue was treated with TFA at room temperature overnight. Excess TFA was removed under vacuum and the resulting residue was partitioned between ethyl acetate (50 mL) and sodium bicarbonate (50 mL). The organic phase was separated, washed with brine (50 mL), dried over sodium sulfate, and concentrated under vacuum. The residue was purified by column chromatography (silica gel, MeOH/EtOAc, 1/10) to give the title compound (Example 133, 20 mg, 12% yield over two steps) as a solid. $^1$H NMR (400 MHz, chloroform-d) δ 12.09 (br. s., 1H), 7.08-7.13 (m, 1H), 7.02-7.07 (m, 1H), 5.94 (s, 1H), 4.66 (s, 2H), 4.44-4.55 (m, 1H), 4.31 (s, 2H), 2.37 (s, 3H), 2.24 (s, 3H), 1.36 (d, J=6.06 Hz, 6H): MS 361 [M+H].

Method U

Example 134: 2-[(4,6-dimethyl-2-oxo-1,2-dihydropyridin-3-yl)methyl]-6-ethoxy-2,3-dihydro-1H-isoindol-1-one

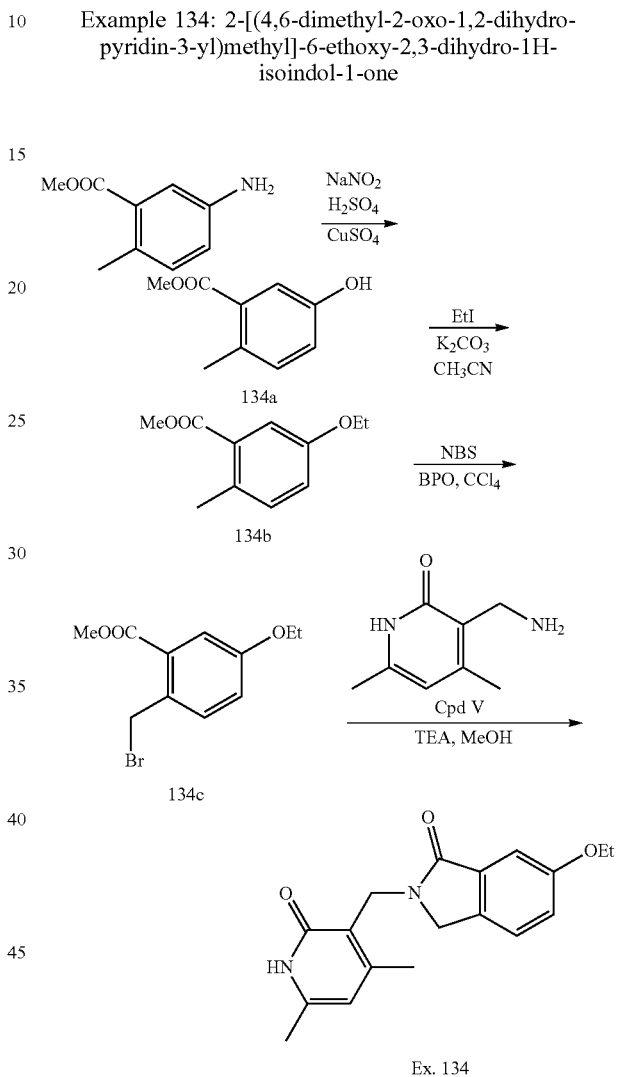

Ex. 134

To a 0° C. solution of methyl 5-amino-2-methylbenzoate (6.25 g, 37.8 mmol) in $H_2SO_4$ (10 mL) and $H_2O$ (160 mL) was added $NaNO_2$ (aq., 3.78 N, 10 mL). The resulting mixture was stirred at 0° C. for 10 minutes. After 10 minutes, the mixture was added to a refluxing solution of $CuSO_4$ (1 N, 100 mL) and refluxed for 1 hour. The mixture was cooled to room temperature and extracted with $CH_2Cl_2$ (2×200 mL). The organic layers were washed with $H_2O$ (50 mL) and brine (50 mL), dried over $Na_2SO_4$ and concentrated under vacuum. The residue was purified by column chromatography (petroleum ether/EtOAc=5:1) to give methyl 5-hydroxy-2-methylbenzoate (134a, 4.2 g, 67%) as a yellow solid.

To a mixture of methyl 5-hydroxy-2-methylbenzoate (134a, 0.600 g, 3.63 mmol) and ethyl iodide (1.13 g, 7.26 mmol) in $CH_3CN$ (10 mL) was added $K_2CO_3$ (1.00 g, 7.26 mmol) at room temperature. The resulting mixture was heated at 100° C. for 12 hours. The reaction mixture was diluted with EtOAc (25 mL) and H₂O (10 mL). The organic layer was separated and washed with NaOH (2 N, 5 mL), H₂O (5 mL) and brine (5 mL), dried over Na₂SO₄ and concentrated under vacuum to give methyl 5-ethoxy-2-methylbenzoate (134b, 0.7 g, 99%) as yellow liquid.

To a solution of methyl 5-ethoxy-2-methylbenzoate (134b, 0.700 g, 3.61 mmol) in CCl₄ (12 mL) was added BPO (18.0 mg, 0.0720 mmol) and NBS (0.706 g, 3.97 mmol) at room temperature. The resulting mixture was heated at 80° C. for 12 hours under N₂ atmosphere. The mixture was diluted with CH₂Cl₂ (10 mL) and brine (3 mL). The organic layer was separated and washed with NaHCO₃ (2 N, 10 mL), H₂O (5 mL) and brine (5 mL), dried over Na₂SO₄ and concentrated under vacuum. The residue was purified by column chromatography (petroleum ether/EtOAc=5:1) to give methyl 2-(bromomethyl)-5-ethoxybenzoate (134c, 0.85 g, 86%) as yellow liquid.

To a solution of methyl 2-(bromomethyl)-5-ethoxybenzoate (134c, 0.636 g, 2.33 mmol) and 3-(aminomethyl)-4,6-dimethylpyridin-2(1H)-one (Cpd V, 0.390 g, 2.56 mmol) in MeOH (20 mL) was added TEA (0.258 g, 2.56 mmol) at room temperature. The resulting mixture was heated at 80° C. for 12 hours. The reaction mixture was concentrated under vacuum to give the crude product, which was purified by column chromatography (CH₂Cl₂/MeOH=20:1) and then re-crystallized from MeOH (15 mL) to give the title compound (Example 134, 32.6 mg, 4.4%) as a white solid. ¹H NMR (400 MHz, methanol-d4) δ 7.39-7.37 (m, 1H), 7.25 (s, 1H), 7.24-7.14 (m, 1H), 6.09 (s, 1H), 4.73 (s, 2H), 4.33 (s, 2H), 4.09-4.07 (q, 2H), 2.30 (s, 3H), 2.24 (s, 3H), 1.43-1.40 (t, 3H); MS 313.0 [M+1].

Method V

Example 217: 8-Chloro-2-(4,6-dimethyl-2-oxo-1,2-dihydro-pyridin-3-ylmethyl)-7-methoxy-4-methyl-3,4-dihydro-2H-isoquinolin-1-one

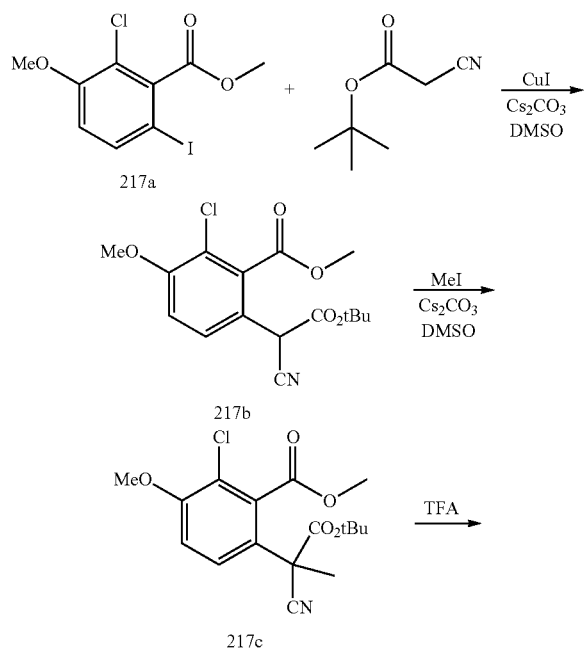

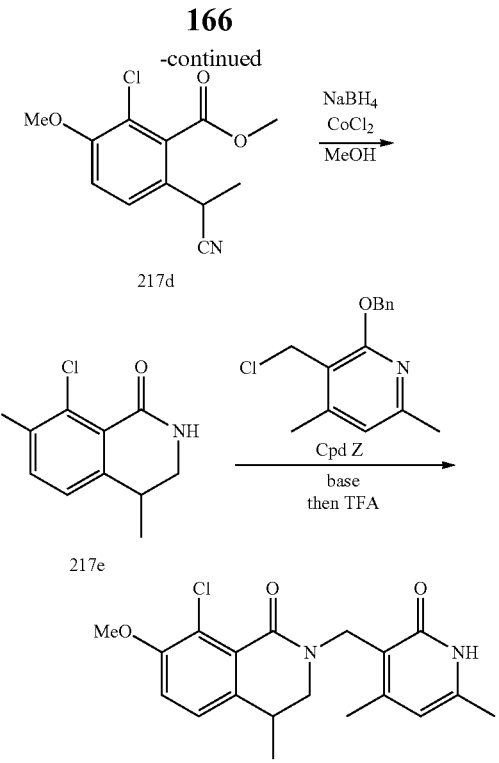

Example 217

A mixture of 2-chloro-6-iodo-3-methoxy-benzoic acid methyl ester (217a, 8.1 g, 24.8 mmol), tert-butyl cyanoacetate (7.0 g, 49.6 mmol), CuI (0.47 g, 2.48 mmol), and Cs₂CO₃ (12.1 g, 37.2 mmol) were mixed in 82.7 mL DMSO. The reaction mixture was degased 3 times and heated in an oil bath at 120° C. overnight to provide 217b. The reaction was cooled to room temperature; methyl iodide (3.59 g, 24.8 mmol) was added, stirred at room temperature overnight. The reaction mixture was added 300 mL H₂O, extracted with EtOAc (300 mL, then 2×150 mL). The combined extracts were washed with brine (2×100 mL), dried over sodium sulfate, and the solvent evaporated under vacuum. The residue was purified by column chromatography with 30% EtOAc/heptane to afford methyl 6-(1-(tert-butoxy)-2-cyano-1-oxopropan-2-yl)-2-chloro-3-methoxybenzoate, 217c, as red oil (2.75 g, 35% yield). ¹H NMR (400 MHz, CDCl₃) δ ppm 7.38 (d, J=8.93 Hz, 1H) 7.00 (d, J=8.93 Hz, 1H) 3.97 (s, 3H) 3.95 (s, 3H) 1.97 (s, 3H) 1.49 (s, 9H).

To a solution of 217c (2.66 g, 7.52 mmol) in 20 mL DCM was added 20 mL TFA. The reaction was stirred at room temperature for 4 hrs. The reaction mixture was added 50 mL H₂O, the layers were separated, the aqueous layer was extracted with EtOAc, the organic layers were combined, concentrated and purified by column chromatography with 20% EtOAc/heptanes to afford Methyl 2-chloro-6-(1-cyanoethyl)-3-methoxybenzoate, 217d, as colorless oil (300 mg, 15.7%). ¹H NMR (400 MHz, CDCl₃) δ ppm 7.46 (d, J=8.68 Hz, 1H) 7.04 (d, J=8.68 Hz, 1H) 3.99 (s, 3H) 3.94 (s, 3H) 3.89 (q, J=7.21 Hz, 1H) 1.61 (d, J=7.21 Hz, 3H).

Ester 217d (0.35 g, 1.4 mmol) and cobalt (11) chloride hexhydrate (0.98 g, 4.1 mmol) were dissolved in 15 mL MeOH, and the purple solution was cooled in ice bath. NaBH4 (0.26 g, 6.9 mmol) was added portionwise, and the reaction was allowed to warm to room temperature and heated at 50° C. for 36 hrs. The solvent was evaporated, the residue was added H₂O 50 mL and EtOAc 50 mL, adjusted the pH to 3-4 by adding concentrated HCl slowly, sonicated to make sure all the inorganic salt dissolved, and the aqueous layer was adjusted to pH 8-9 by 30% KOH and extracted with EtOAc 3×75 mL. The organic layers were combined and concentrated, purified by column chromatography with 30% EtOAc/heptane to afford 8-Chloro-7-methoxy-4-methyl-3,4-dihydroisoquinolin-1(2H)-one, 217e, as white solid (0.18 g, 62% yield). ¹H NMR (400 MHz, CDCl₃) δ ppm 7.18 (br. s., 1H) 7.10 (d, J=8.80 Hz, 1H) 7.01 (d, J=8.44 Hz, 1H) 3.89 (s, 3H) 3.51 (dt, J=12.41, 3.88 Hz, 1H) 3.16 (ddd, J=12.56, 6.14, 4.40 Hz, 1H) 2.93-3.04 (m, 1H) 1.28 (d, J=6.97 Hz, 3H).

To a mixture of 217e (50 mg, 0.22 mmol) and 2-(benzyloxy)-3-(chloromethyl)-4,6-dimethylpyridine (Cpd Z, 61 mg, 0.23 mmol) in 3 mL dioxane was added KHMDS in THF (1.0 M, 0.55 mL). The reaction mixture was heated at 100° C. for 1 hr, and then cooled to room temperature. The reaction mixture was concentrated and 20 mL H₂O was added. The mixture was extracted with EtOAc 3×20 mL, then concentrated and purified by column chromatography with 100% EtOAc to afford 2-((2-(Benzyloxy)-4,6-dimethylpyridin-3-yl)methyl)-8-chloro-7-methoxy-4-methyl-3,4-dihydroisoquinolin-1(2H)-one, 217f, as white solid (94 mg, 94% yield). ¹H NMR (400 MHz, CDCl₃) δ ppm 7.46 (d, J=6.85 Hz, 2H) 7.28-7.39 (m, 3H) 6.93-7.02 (m, 2H) 6.63 (s, 1H) 5.37-5.50 (m, 2H) 4.97 (d, J=14.31 Hz, 1H) 4.88 (d, J=14.31 Hz, 1H) 3.90 (s, 3H) 3.30 (dd, J=12.72, 4.16 Hz, 1H) 3.01 (dd, J=12.72, 6.11 Hz, 1H) 2.76 (td, J=6.54, 4.28 Hz, 1H) 2.43 (s, 3H) 2.28-2.39 (m, 3H) 1.00 (d, J=6.97 Hz, 3H).

To 217f (90 mg, 0.2 mmol) was added 1 mL TFA, and the mixture was stirred at room temperature overnight. Excess TFA was removed by reduced pressure. To the residue was added 1 mL MeOH, and the solution was neutralized by 1.5 mL 7N NH₃ in MeOH. The product was purified by preparative HPLC to afford the compound of Example 217 as white solid (56 mg, 77%). ¹H NMR (700 MHz, DMSO-17 mm) δ ppm 11.54 (br. s., 1H) 7.23 (d, J=8.36 Hz, 1H) 7.20 (d, J=8.36 Hz, 1H) 5.89 (s, 1H) 4.64 (d, J=13.86 Hz, 1H) 4.55 (d, J=13.65 Hz, 1H) 3.85 (s, 3H) 3.45 (dd, J=12.87, 3.85 Hz, 1H) 3.20 (dd, J=12.98, 5.50 Hz, 1H) 2.93 (dd, J=11.00, 5.72 Hz, 1H) 2.17 (s, 3H) 2.13 (s, 3H) 1.06 (d, J=6.82 Hz, 3H); MS: 361 [M+1]

Method W

Example 145: 8-chloro-2-[(4,6-dimethyl-2-oxo-1,2-dihydropyridin-3-yl)methyl]-4,4-difluoro-7-methoxy-3,4-dihydroisoquinolin-1(2H)-one

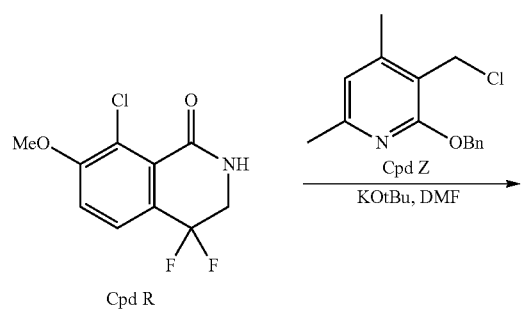

Cpd R

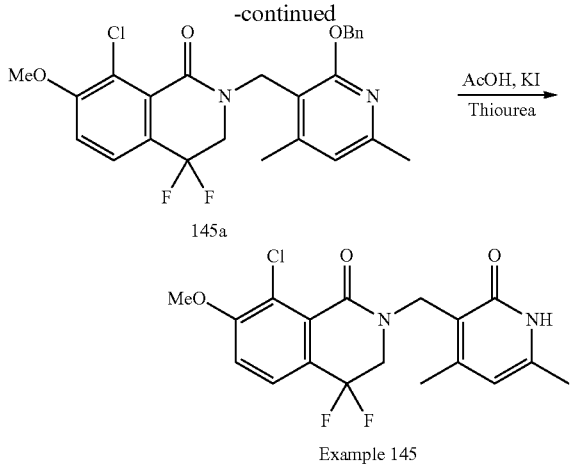

Example 145

To a solution of Cpd R (0.0370 g, 0.149 mmol) in DMF (4.0 mL) in an ice bath was added potassium t-butoxide (1.0M in THF, 0.145 mL, 0.145 mmol). After 5 minutes, Cpd Z (0.0421 g, 0.161 mmol) was added, and the reaction was stirred for 0.5 h in the ice bath. The reaction was acidified with AcOH (1 drop), diluted with ethyl acetate, washed with water (2Xs) and brine, and concentrated under vacuum. The resulting oil was purified on silica gel (Biotage SNAP, 10 g, gradient of 0-50% ethyl acetate in heptane) to give 145a (0.059 g, 84%) as a clear oil which solidified upon standing. 1H NMR (400 MHz, CDCl3-d) δ 7.51 (d, J=8.59 Hz, 1H), 7.42-7.47 (m, 2H), 7.28-7.38 (m, 3H), 7.12 (d, J=8.59 Hz, 1H), 6.65 (s, 1H), 5.44 (s, 2H), 4.94 (s, 2H), 3.97 (s, 3H), 3.59 (t, J=11.62 Hz, 2H), 2.44 (s, 3H), 2.31 (s, 3H); MS 473 [M+H]⁺.

To a solution of 145a (0.057 g, 0.12 mmol) in acetic acid (2.0 mL) was added potassium iodide (0.062 g, 0.37 mmol). The reaction was stirred at 50° C. for 1 h and then thiourea (0.018 g, 0.24 mmol) was added to scavenge the benzyl iodide. After an additional 20 minutes at 50° C., the benzyl iodide was consumed. The reaction mixture was cooled to room temperature, and water (10 mL) was added. The resulting precipitate was collected by filtration, washed with water, and dried under high vacuum to give the title compound of Example 145 (0.042 g, 91%) as a white powder. ¹H NMR (400 MHz, DMSO-d₆) δ 11.63 (br. s., 1H), 7.64 (d, J=8.56 Hz, 1H), 7.46 (d, J=8.68 Hz, 1H), 5.92 (s, 1H), 4.62 (s, 2H), 4.02 (t, J=12.17 Hz, 2H), 3.94 (s, 3H), 2.17 (s, 3H), 2.14 (s, 3H); MS 383 [M+H]⁺.

Method X

Example 293: 5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one

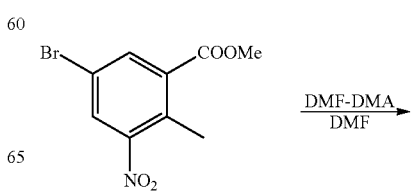

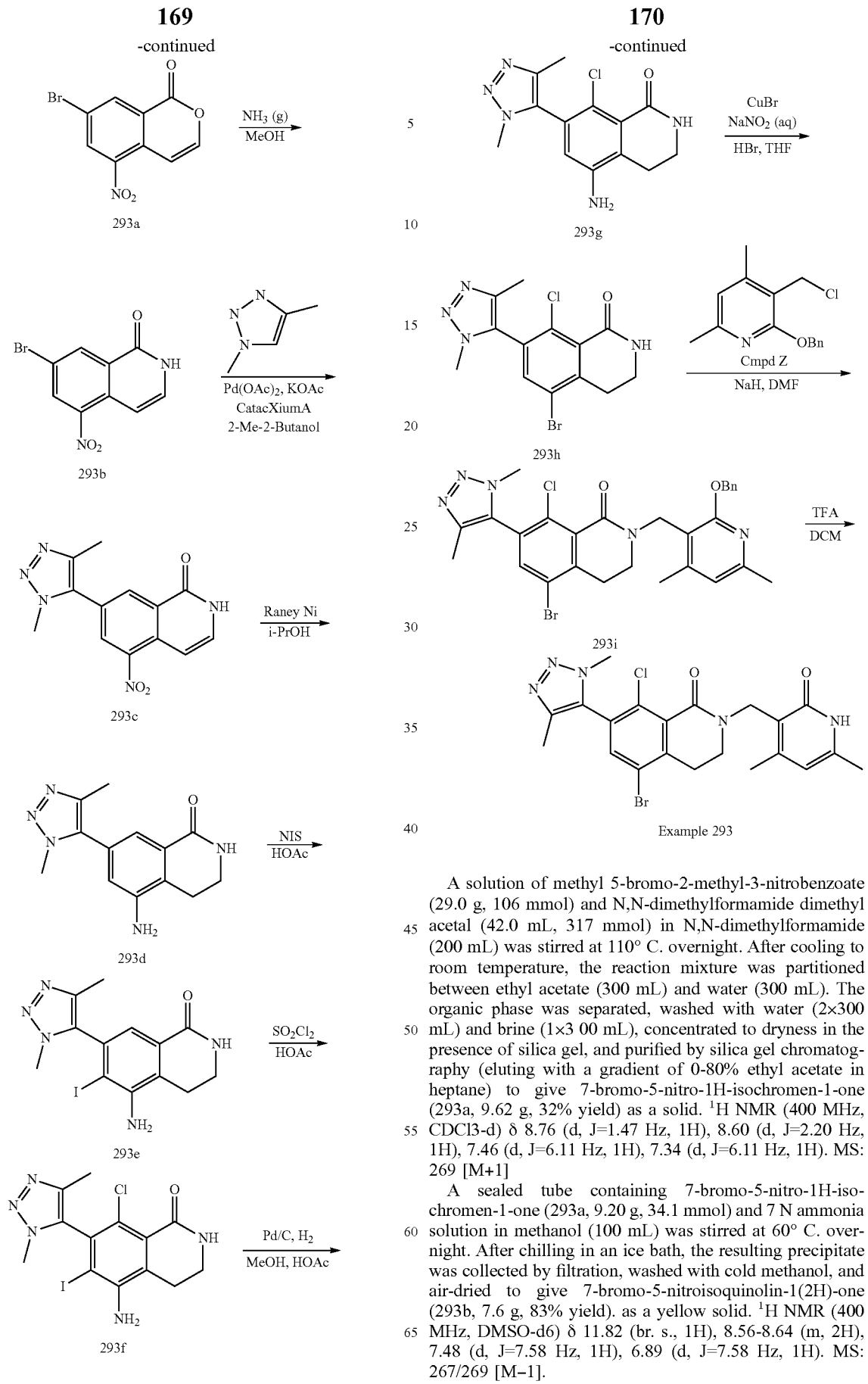

A solution of methyl 5-bromo-2-methyl-3-nitrobenzoate (29.0 g, 106 mmol) and N,N-dimethylformamide dimethyl acetal (42.0 mL, 317 mmol) in N,N-dimethylformamide (200 mL) was stirred at 110° C. overnight. After cooling to room temperature, the reaction mixture was partitioned between ethyl acetate (300 mL) and water (300 mL). The organic phase was separated, washed with water (2×300 mL) and brine (1×300 mL), concentrated to dryness in the presence of silica gel, and purified by silica gel chromatography (eluting with a gradient of 0-80% ethyl acetate in heptane) to give 7-bromo-5-nitro-1H-isochromen-1-one (293a, 9.62 g, 32% yield) as a solid. $^1$H NMR (400 MHz, CDCl3-d) δ 8.76 (d, J=1.47 Hz, 1H), 8.60 (d, J=2.20 Hz, 1H), 7.46 (d, J=6.11 Hz, 1H), 7.34 (d, J=6.11 Hz, 1H). MS: 269 [M+1]

A sealed tube containing 7-bromo-5-nitro-1H-isochromen-1-one (293a, 9.20 g, 34.1 mmol) and 7 N ammonia solution in methanol (100 mL) was stirred at 60° C. overnight. After chilling in an ice bath, the resulting precipitate was collected by filtration, washed with cold methanol, and air-dried to give 7-bromo-5-nitroisoquinolin-1(2H)-one (293b, 7.6 g, 83% yield). as a yellow solid. $^1$H NMR (400 MHz, DMSO-d6) δ 11.82 (br. s., 1H), 8.56-8.64 (m, 2H), 7.48 (d, J=7.58 Hz, 1H), 6.89 (d, J=7.58 Hz, 1H). MS: 267/269 [M−1].

A mixture of 7-bromo-5-nitroisoquinolin-1(2H)-one (293b, 4.00 g, 14.9 mmol), 1,4-dimethyl-1H-1,2,3-triazole (2.17 g, 22.3 mmol), palladium acetate (334 mg, 1.49 mmol), CatacXiumA (butyl di-1-adamantylphosphine) (1.10 g, 2.97 mmol), and potassium acetate (7.30 g, 74.3 mmol) in 2-methyl-2-butanol (100 mL) was degassed with nitrogen, and heated at 120° C. in a sealed tube overnight. After cooling down room temperature, the reaction mixture was partitioned between ethyl acetate (300 mL) and water (300 mL). The organic phase was separated, washed with brine (1×300 mL), dried over sodium sulfate, concentrated to dryness, and purified by silica gel chromatography (eluting with a gradient of 0%-10% methanol in ethyl acetate), affording 7-(1,4-dimethyl-1H-1,2,3-triazol-5-yl)-5-nitroisoquinolin-1(2H)-one (293c, 2.55 g, 60% yield) as a solid. $^1$H NMR (400 MHz, DMSO-d6) δ 11.95 (br. s., 1H), 8.57 (s, 2H), 7.55 (d, J=5.38 Hz, 1H), 6.98 (d, J=7.34 Hz, 1H), 4.00 (s, 3H), 2.29 (s, 3H). MS: 284 [M−1].

A solution of 7-(1,4-dimethyl-1H-1,2,3-triazol-5-yl)-5-nitroisoquinolin-1(2H)-one (293c, 1.0 g, 3.5 mmol) and Raney Nickel (6 g) in isopropanol (60 mL) in a sealed tube was heated at 110-120° C. for three days. Sixteen 1 g batches (16 g 293c total) were prepared by this method, and then combined for purification. The combined solutions were cooled to room temperature and filtered. The filtrate was concentrated under vacuum to ~30 mL, causing a precipitate to form. The precipitate was collected by filtration to give 5-amino-7-(1,4-dimethyl-1H-1,2,3-triazol-5-yl)-3,4-dihydroisoquinolin-1(2H)-one (293d, 4.0 g, 26% yield) as a white solid. The Raney nickel-containing first filter cake was dissolved in methanol/dichloromethane (1:1, 400 mL×4), stirred for 30 minutes, filtered, and the filtrate concentrated under vacuum to give a second batch of 5-amino-7-(1,4-dimethyl-1H-1,2,3-triazol-5-yl)-3,4-dihydroisoquinolin-1(2H)-one (293d, 8.0 g, 54% yield) as a grey solid.

N-iodosuccinimide (5.27 g, 23.43 mmol) was added in portions to a solution of 5-amino-7-(1,4-dimethyl-1H-1,2,3-triazol-5-yl)-3,4-dihydroisoquinolin-1(2H)-one (293d, 5.5 g, 21.3 mmol) in glacial acetic acid (400 mL) and the resulting mixture stirred at room temperature for three days. A second portion of N-iodosuccinimide (2.6 g, 12.7 mmol) was then added and stirring continued at room temperature overnight. The mixture was concentrated under vacuum to remove acetic acid. The residue was dissolved in methanol (200 mL), concentrated to dryness, and purified by silica gel chromatography (eluting with 1:1 to 1:2 petroleum ether/ethyl acetate and then with 100:1 to 50:1 dichloromethane/methanol), to give 5-amino-7-(1,4-dimethyl-1H-1,2,3-triazol-5-yl)-6-iodo-3,4-dihydroisoquinolin-1(2H)-one (293e, 5.0 g, 60% yield) as a yellow solid.

Two batches of 5-amino-7-(1,4-dimethyl-1H-1,2,3-triazol-5-yl)-6-iodo-3,4-dihydroisoquinolin-1(2H)-one (293e, 2.5 g/6.5 mmol each batch, 5.0 g/13 mmol total) in glacial acetic acid (100 mL each batch) were treated with sulfuryl chloride (1 g, 75 mmol each batch), added dropwise at 20-25° C. The mixtures were stirred for 2 hours, then combined and concentrated under vacuum to remove volatiles. The residue was purified by silica gel chromatography (10:1 dichloromethane/methanol) to give 5-amino-8-chloro-7-(1,4-dimethyl-1H-1,2,3-triazol-5-yl)-6-iodo-3,4-dihydroisoquinolin-1(2H)-one (293f, 5.5 g, 90% purity, 90% yield) as a yellow solid.

Two batches were prepared by the following method: a mixture of 5-amino-8-chloro-7-(1,4-dimethyl-1H-1,2,3-triazol-5-yl)-6-iodo-3,4-dihydroisoquinolin-1(2H)-one (293f, 2.9 g, 6.9 mmol each batch) and palladium on carbon (2.9 g) in glacial acetic acid (29 mL) and methanol (290 mL) was stirred under a hydrogen balloon at room temperature overnight. The combined reaction mixtures were filtered through celite, and the filter pad washed with methanol (300 mL). The filtrate was concentrated and the residue purified by silica gel chromatography (eluting with 10:1 dichloromethane/methanol) affording 5-amino-8-chloro-7-(1,4-dimethyl-1H-1,2,3-triazol-5-yl)-3,4-dihydroisoquinolin-1(2H)-one (293 g, 3.6 g, 65% combined yield) as yellow solid. $^1$H NMR (400 MHz, DMSO-d6): δ 8.12 (s, 1H), 6.82 (s, 1H), 3.75 (s, 3H), 3.29-3.28 (m, 2H), 2.70-2.67 (m, 2H), 2.07 (s, 3H). MS: 292 [M+1].

To a solution of 5-amino-8-chloro-7-(1,4-dimethyl-1H-1,2,3-triazol-5-yl)-3,4-dihydroisoquinolin-1(2H)-one (293 g, 300 mg, 1.03 mmol) in tetrahydrofuran (5 mL) chilled in an ice-water bath was added 40% aqueous hydrobromic acid (6.86 g, 33.93 mmol). The mixture was allowed to stir at room temperature for three hours, and then cooled again to 0° C. Copper (I) bromide (295 mg, 2.06 mmol) was added, followed by sodium nitrite (78 mg, 1.13 mmol), and the resulting mixture stirred at 0° C. for two hours. The mixture was neutralized with solid sodium hydroxide and extracted with ethyl acetate (2×100 mL). The combined organic extracts were dried over sodium sulfate, concentrated, and purified by silica gel chromatography to give 5-bromo-8-chloro-7-(1,4-dimethyl-1H-1,2,3-triazol-5-yl)-3,4-dihydroisoquinolin-1(2H)-one (293h, 60 mg, 16.5% yield) as a white solid.

Sodium hydride (60% dispersion in mineral oil, 18 mg, 0.45 mmol) was added to an icebath chilled solution of 5-bromo-8-chloro-7-(1,4-dimethyl-1H-1,2,3-triazol-5-yl)-3,4-dihydroisoquinolin-1(2H)-one (293h, 80 mg, 0.225 mmol) in anhydrous N,N-dimethylformamide (15 mL), and the resulting mixture stirred at 0° C. for 30 minutes. Solid 2-(benzyloxy)-3-(chloromethyl)-4,6-dimethylpyridine (compound Z, 59 mg, 0.225 mmol) was added and stirring continued at 0° C. for one hour. While still cold, the reaction was quenched with water (20 mL). The resulting solution was extracted with ethyl acetate (2×50 mL). The combined organic extracts were washed with brine (5×50 mL), dried over sodium sulfate, concentrated, and purified by silica gel chromatography (eluting with 1:1 petroleum ether/ethyl acetate) to give 2-{[2-(benzyloxy)-4,6-di methylpyridin-3-yl]methyl}-5-bromo-8-chloro-7-(1,4-dimethyl-1H-1,2,3-triazol-5-yl)-3,4-dihydroisoquinolin-1(2H)-one (293i, 76 mg, 58% yield) as a light yellow oil.

A solution of 2-{[2-(benzyloxy)-4,6-dimethylpyridin-3-yl]methyl}-5-bromo-8-chloro-7-(1,4-dimethyl-1H-1,2,3-triazol-5-yl)-3,4-dihydroisoquinolin-1(2H)-one (293i, 76 mg, 0.13 mmol) in dichloromethane (4 mL) was cooled in an ice-water bath. Trifluoroacetic acid (6 mL) was added, and the mixture stirred and allowed to warm to room temperature overnight. After removal of the volatiles under vacuum, the residue was purified by silica gel chromatography (eluting with 10:1 dichloromethane/methanol) to give 5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one (Example 293, 56.9 mg, 90% yield) as a white solid). $^1$H NMR (400 MHZ, Methanol-d4): b 7.79 (s, 1H), 6.10 (s, 1H), 4.75 (s, 2H), 3.84 (s, 3H), 3.59 (t, J=6.2 Hz, 2H), 3.07 (t, J=6.2 Hz, 2H), 2.30 (s, 3H), 2.24 (s, 3H), 2.16 (s, 3H). MS: 492 [M+1].

Additional compounds of the invention were prepared by modifications of the methods exemplified herein. Selected compounds prepared and corresponding characterization data are presented in Table 1 and Table 2 below.

TABLE 1

| Ex. | Structure/Name | ¹H NMR; LC-MS | Method |
|---|---|---|---|
| 2 | 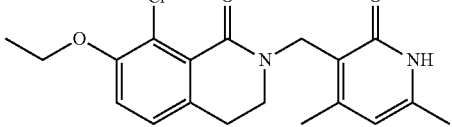<br>8-chloro-2-[(4,6-dimethyl-2-oxo-1,2-dihydropyridin-3-yl)methyl]-7-ethoxy-3,4-dihydroisoquinolin-1(2H)-one | ¹H NMR (400 MHz, chloroform-d) δ 11.03 (s, 1H), 6.98-6.91 (q, 2H), 5.93 (s, 1H), 4.79 (s, 2H), 4.11-4.05 (q, 2H), 3.58-3.55 (t, 2H), 2.77-2.74 (t, 2H), 2.34 (s, 3H), 2.25 (s, 3H), 1.47-1.43 (t, 3H).; MS: 360.9 [M + 1]+ | A |
| 3 | 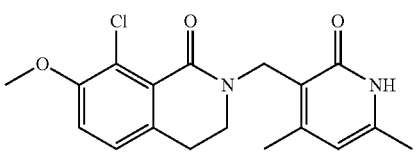<br>8-chloro-2-[(4,6-dimethyl-2-oxo-1,2-dihydropyridin-3-yl)methyl]-7-methoxy-3,4-dihydroisoquinolin-1(2H)-one | ¹H NMR (400 MHz, chloroform-d) δ 7.14 (s, 2H), 6.11 (s, 1H), 4.77 (s, 2H), 3.88 (s, 3H), 3.45 (t, J = 6 Hz, 2H), 3.21 (t, J = 6 Hz, 2H), 2.28 (s, 3H), 2.24 (s, 3H); MS: 347.1 [M + 1]+; 369.1 [M + 23]+; 715.2 [2M + 23]+. | A |
| 4 | 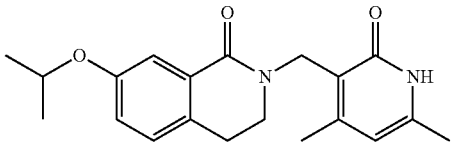<br>2-[(4,6-dimethyl-2-oxo-1,2-dihydropyridin-3-yl)methyl]-7-(propan-2-yloxy)-3,4-dihydroisoquinolin-1(2H)-one | ¹H NMR (400 MHz, methdnol-d4) δ 7.49 (d, J = 2.8 Hz, 1H), 7.15-7.13 (d, J = 8.4 Hz, 1H), 7.02-6.99 (dd, J = 2.8 Hz, 8.4 Hz, 1H), 6.12 (s, 1H), 4..76 (s, 2H), 4.66-4.60 (m, J = 6 Hz, 1H), 3.56-3.52 (t, J = 2.4 Hz, 2H), 2.85-2.82 (t, J = 6.4 Hz, 2H), 2.30 (s, 3H), 2.26 (s, 3H), 1.34-1.32 (d, J = 6 Hz, 6H). MS: 340.9 [M + 1]+ | A |
| 5 | 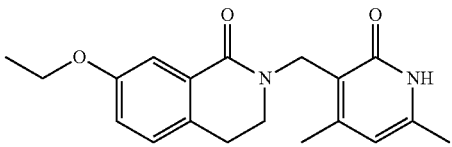<br>2-[(4,6-dimethyl-2-oxo-1,2-dihydropyridin-3-yl)methyl]-7-ethoxy-3,4-dihydroisoquinolin-1(2H)-one | ¹H NMR (400 MHz, methanol-d4) δ 7.49 (s, 1H), 7.16-7.14 (d, J = 8 Hz, 1H), 7.03-7.01 (d, J = 8 Hz, 1H), 6.12 (s, 1H), 4.77 (s, 2H), 4.10-4.05 (q, J = 6.8 Hz, 1H), 3.55-3.52 (t, J = 6 Hz, 2H), 2.86-2.82 (t, J = 6 Hz, 2H), 2.29 (s, 3H), 2.26 (s, 3H), 1.43-1.4 (d, J = 6.8 Hz, 6H). MS: 327.1 [M + 1]+ | A |
| 6 | 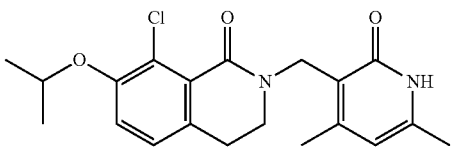<br>8-chloro-2-[(4,6-dimethyl-2-oxo-1,2-dihydropyridin-3-yl)methyl]-7-(propan-2-yloxy)-3,4-dihydroisoquinolin-1(2H)-one | ¹H NMR (400 MHz, DMSO-d6) δ 11.54 (br. s., 1H) 7.15 (d, J = 8.44 Hz, 1H) 7.22 (d, J = 8.31 Hz, 1H) 5.89 (s, 1H) 4.59-4.66 (m, 1H) 4.58 (s, 2H) 3.36-3.43 (m, 2H) 2.75 (t, J = 6.05 Hz, 2H) 2.16 (s, 3 H) 2.13 (s, 3H) 1.29 (s, 3H) 1.28 (s, 3H); MS: 375.1 [M + 1] | A |
| 7 | 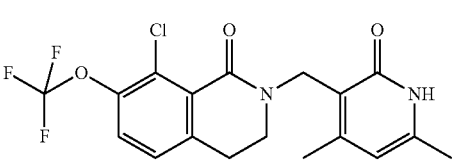<br>8-chloro-2-[(4,6-dimethyl-2-oxo-1,2-dihydropyridin-3-yl)methyl]-7-(trifluoromethoxy)-3,4-dihydroisoquinolin-1(2H)-one | ¹H NMR (400 MHz, chloroform-d) δ 7.33 (d, J = 8.19 Hz, 1H), 7.09 (d, J = 8.31 Hz, 1H), 5.94 (s, 1H), 4.79 (s, 2H), 3.67 (t, J = 6.11 Hz, 2H), 2.87 (t, J = 5.99 Hz, 2H), 2.37 (s, 3H), 2.28 (s, 3H); MS: 401.1 [M + 1] | A |

TABLE 1-continued

| Ex. | Structure/Name | ¹H NMR; LC-MS | Method |
|---|---|---|---|
| 8 | 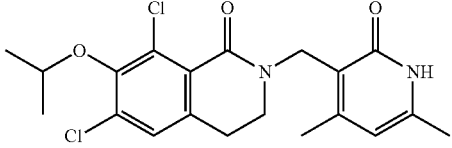<br>6,8-dichloro-2-[(4,6-dimethyl-2-oxo-1,2-dihydropyridin-3-yl)methyl]-7-(propan-2-yloxy)-3,4-dihydroisoquinolin-1(2H)-one | ¹H NMR (600 MHz, DMSO-d6) δ 7.41 (s, 1H), 5.88 (s, 1H), 4.54 (s, 3H), 3.38-3.45 (m, 4H), 2.78 (t, J = 6.14 Hz, 2H), 2.15 (s, 3H), 2.12 (s, 3H), 1.29 (d, J = 6.24 Hz, 6H); MS: 409.1 [M + 1] | A |
| 9 | 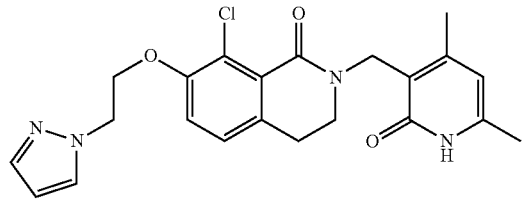<br>8-chloro-2-[(4,6-dimethyl-2-oxo-1,2-dihydropyridin-3-yl)methyl]-7-[2-(1H-pyrazol-1-yl)ethoxy]-3,4-dihydroisoquinolin-1(2H)-one | MS: 427 [M + 1] | A |
| 10 | 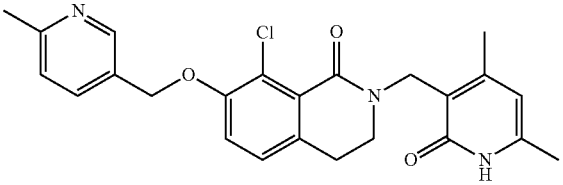<br>8-chloro-2-[(4,6-dimethyl-2-oxo-1,2-dihydropyridin-3-yl)methyl]-7-[(6-methylpyridin-3-yl)methoxy]-3,4-dihydroisoquinolin-1(2H)-one | MS: 438 [M + 1] | A |
| 11 | 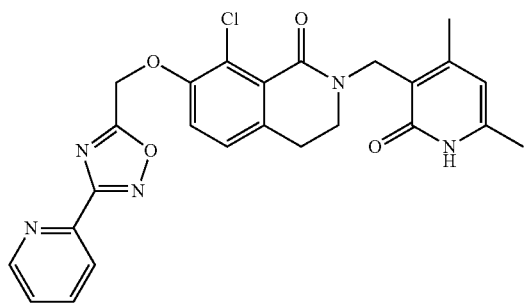<br>8-chloro-2-[(4,6-dimethyl-2-oxo-1,2-dihydropyridin-3-yl)methyl]-7-{[3-(pyridin-2-yl)-1,2,4-oxadiazol-5-yl]methoxy}-3,4-dihydroisoquinolin-1(2H)-one | MS: 492 [M + 1] | A |

TABLE 1-continued

| Ex. | Structure/Name | ¹H NMR; LC-MS | Method |
| --- | --- | --- | --- |
| 12 | 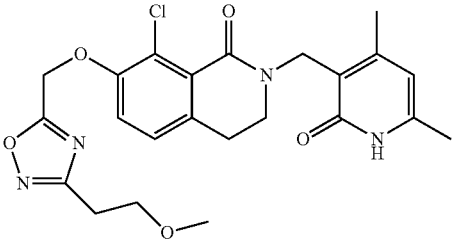<br>8-chloro-2-[(4,6-dimethyl-2-oxo-1,2-dihydropyridin-3-yl)methyl]-7-{[3-(2-methoxyethyl)-1,2,4-oxadiazol-5-yl]methoxy}-3,4-dihydroisoquinolin-1(2H)-one | MS: 473 [M + 1] | A |
| 13 | 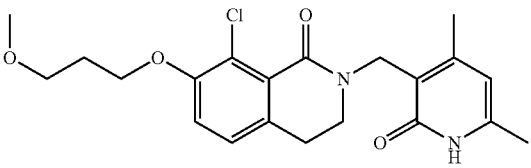<br>8-chloro-2-[(4,6-dimethyl-2-oxo-1,2-dihydropyridin-3-yl)methyl]-7-(3-methoxypropoxy)-3,4-dihydroisoquinolin-1(2H)-one | MS: 405 [M + 1] | A |
| 14 | 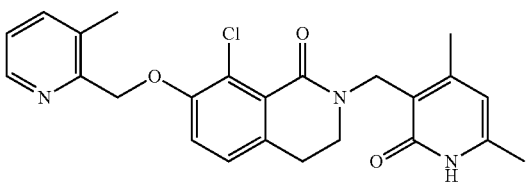<br>8-chloro-2-[(4,6-dimethyl-2-oxo-1,2-dihydropyridin-3-yl)methyl]-7-[(3-methylpyridin-2-yl)methoxy]-3,4-dihydroisoquinolin-1(2H)-one | MS: 438 [M + 1] | A |
| 15 | 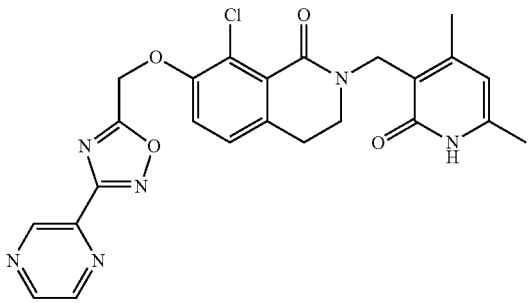<br>8-chloro-2-[(4,6-dimethyl-2-oxo-1,2-dihydropyridin-3-yl)methyl]-7-{[3-(pyrazin-2-yl)-1,2,4-oxadiazol-5-yl]methoxy}-3,4-dihydroisoquinolin-1(2H)-one | MS: 493 [M + 1] | A |

TABLE 1-continued

| Ex. | Structure/Name | ¹H NMR; LC-MS | Method |
|---|---|---|---|
| 16 | 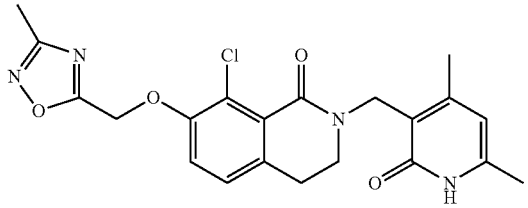<br>8-chloro-2-[(4,6-dimethyl-2-oxo-1,2-dihydropyridin-3-yl)methyl]-7-[(3-methyl-1,2,4-oxadiazol-5-yl)methoxy]-3,4-dihydroisoquinolin-1(2H)-one | MS: 429 [M + 1] | A |
| 17 | 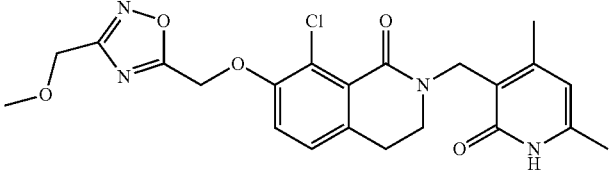<br>8-chloro-2-[(4,6-dimethyl-2-oxo-1,2-dihydropyridin-3-yl)methyl]-7-{[3-(methoxymethyl)-1,2,4-oxadiazol-5-yl]methoxy}-3,4-dihydroisoquinolin-1(2H)-one | MS: 459 [M + 1] | A |
| 18 | 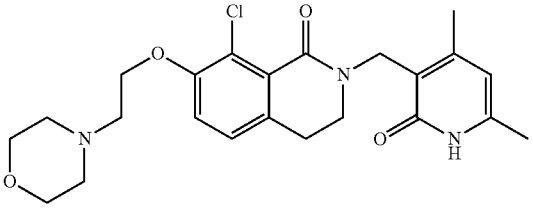<br>8-chloro-2-[(4,6-dimethyl-2-oxo-1,2-dihydropyridin-3-yl)methyl]-7-[2-(morpholin-4-yl)ethoxy]-3,4-dihydroisoquinolin-1(2H)-one | MS: 446 [M + 1] | A |
| 19 | 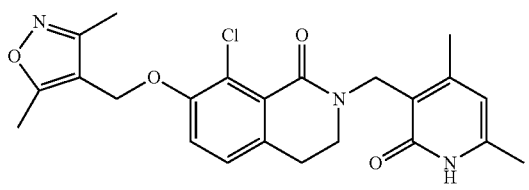<br>8-chloro-7-[(3,5-dimethyl-1,2-oxazol-4-yl)methoxy]-2-[(4,6-dimethyl-2-oxo-1,2-dihydropyridin-3-yl)methyl]-3,4-dihydroisoquinolin-1(2H)-one | MS: 442 [M + 1] | A |

TABLE 1-continued

| Ex. | Structure/Name | ¹H NMR; LC-MS | Method |
|---|---|---|---|
| 20 | 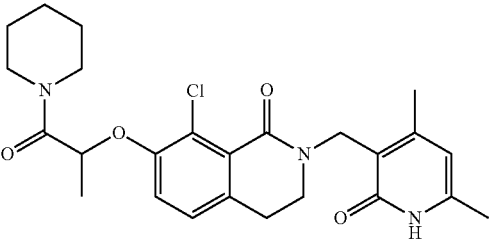<br>8-chloro-2-[(4,6-dimethyl-2-oxo-1,2-dihydropyridin-3-yl)methyl]-7-{[1-oxo-1-(piperidin-1-yl)propan-2-yl]oxy}-3,4-dihydroisoquinolin-1(2H)-one | MS: 472 [M + 1] | A |
| 21 | 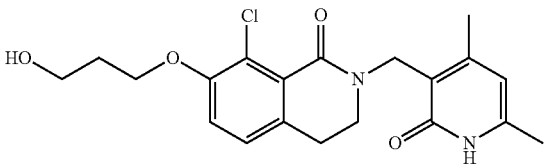<br>8-chloro-2-[(4,6-dimethyl-2-oxo-1,2-dihydropyridin-3-yl)methyl]-7-(3-hydroxypropoxy)-3,4-dihydroisoquinolin-1(2H)-one | MS: 391 [M + 1] | A |
| 22 | 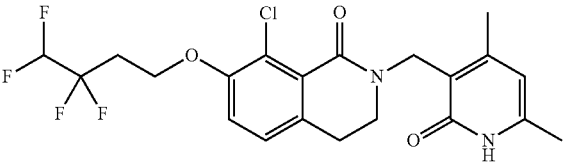<br>8-chloro-2-[(4,6-dimethyl-2-oxo-1,2-dihydropyridin-3-yl)methyl]-7-(3,3,4,4-tetrafluorobutoxy)-3,4-dihydroisoquinolin-1(2H)-one | MS: 461 [M + 1] | A |
| 23 | 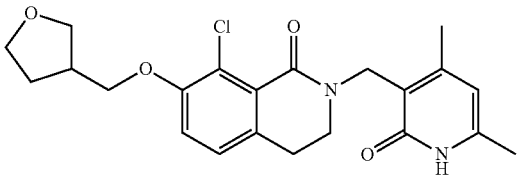<br>8-chloro-2-[(4,6-dimethyl-2-oxo-1,2-dihydropyridin-3-yl)methyl]-7-(tetrahydrofuran-3-ylmethoxy)-3,4-dihydroisoquinolin-1(2H)-one | MS: 417 [M + 1] | A |
| 24 | 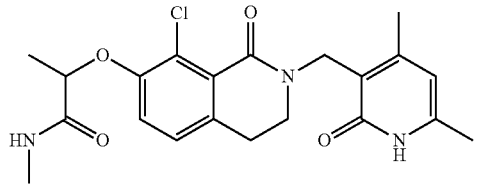<br>2-({8-chloro-2-[(4,6-dimethyl-2-oxo-1,2-dihydropyridin-3-yl)methyl]-1-oxo-1,2,3,4-tetrahydroisoquinolin-7-yl}oxy)-N-methylpropanamide | MS: 418 [M + 1] | A |

TABLE 1-continued

| Ex. | Structure/Name | ¹H NMR; LC-MS | Method |
|---|---|---|---|
| 25 | 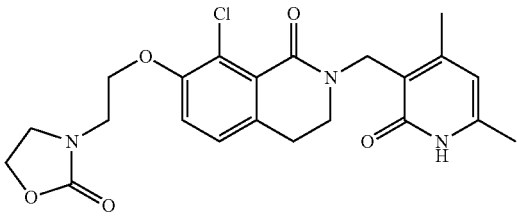

8-chloro-2-[(4,6-dimethyl-2-oxo-1,2-dihydropyridin-3-yl)methyl]-7-[2-(2-oxo-1,3-oxazolidin-3-yl)ethoxy]-3,4-dihydroisoquinolin-1(2H)-one | MS: 446 [M + 1] | A |
| 26 | 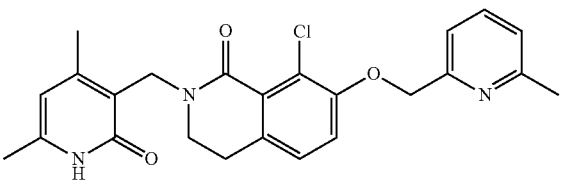

8-chloro-2-[(4,6-dimethyl-2-oxo-1,2-dihydropyridin-3-yl)methyl]-7-[(6-methylpyridin-2-yl)methoxy]-3,4-dihydroisoquinolin-1(2H)-one | MS: 438 [M + 1] | A |
| 27 | 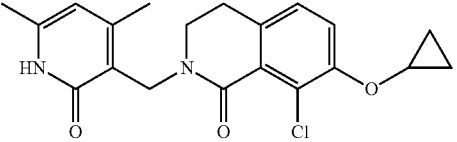

8-chloro-7-(cyclopropyloxy)-2-[(4,6-dimethyl-2-oxo-1,2-dihydropyridin-3-yl)methyl]-3,4-dihydroisoquinolin-1(2H)-one | MS: 373 [M + 1] | A |
| 28 | 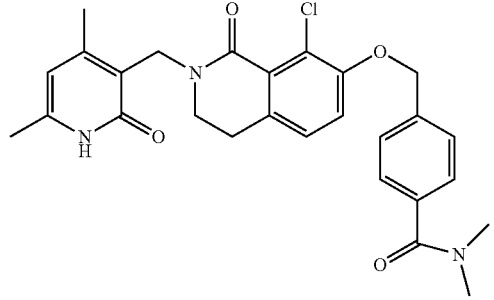

4-[({8-chloro-2-[(4,6-dimethyl-2-oxo-1,2-dihydropyridin-3-yl)methyl]-1-oxo-1,2,3,4-tetrahydroisoquinolin-7-yl}oxy)methyl]-N,N-dimethylbenzamide | MS: 494 [M + 1] | A |

TABLE 1-continued

| Ex. | Structure/Name | ¹H NMR; LC-MS | Method |
|---|---|---|---|
| 29 | 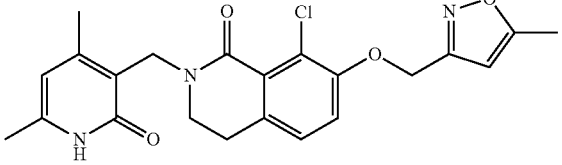<br>8-chloro-2-[(4,6-dimethyl-2-oxo-1,2-dihydropyridin-3-yl)methyl]-7-[(5-methyl-1,2-oxazol-3-yl)methoxy]-3,4-dihydroisoquinolin-1(2H)-one | MS: 428 [M + 1] | A |
| 30 | 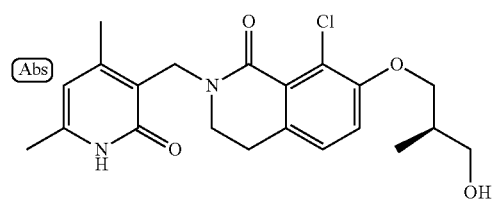<br>8-chloro-2-[(4,6-dimethyl-2-oxo-1,2-dihydropyridin-3-yl)methyl]-7-[(2R)-3-hydroxy-2-methylpropoxy]-3,4-dihydroisoquinolin-1(2H)-one | MS: 405 [M + 1] | A |
| 31 | 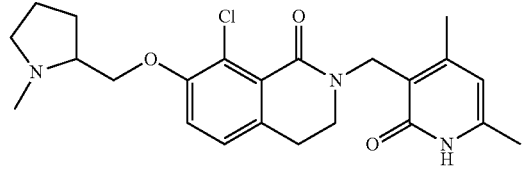<br>8-chloro-2-[(4,6-dimethyl-2-oxo-1,2-dihydropyridin-3-yl)methyl]-7-[(1-methylpyrrolidin-2-yl)methoxy]-3,4-dihydroisoquinolin-1(2H)-one | MS: 430 [M + 1] | A |
| 32 | 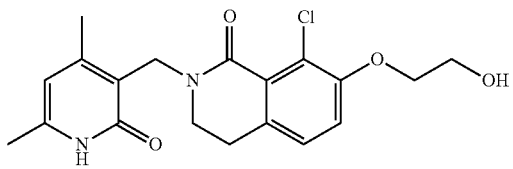<br>8-chloro-2-[(4,6-dimethyl-2-oxo-1,2-dihydropyridin-3-yl)methyl]-7-(2-hydroxyethoxy)-3,4-dihydroisoquinolin-1(2H)-one | MS: 377 [M + 1] | A |
| 33 | 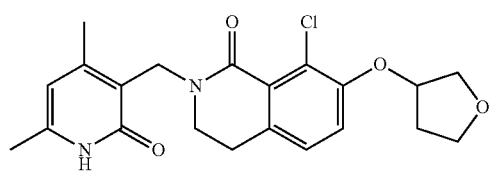<br>8-chloro-2-[(4,6-dimethyl-2-oxo-1,2-dihydropyridin-3-yl)methyl]-7-(tetrahydrofuran-3-yloxy)-3,4-dihydroisoquinolin-1(2H)-one | MS: 403 [M + 1] | A |

TABLE 1-continued

| Ex. | Structure/Name | ¹H NMR; LC-MS | Method |
|---|---|---|---|
| 34 | 2-({8-chloro-2-[(4,6-dimethyl-2-oxo-1,2-dihydropyridin-3-yl)methyl]-1-oxo-1,2,3,4-tetrahydroisoquinolin-7-yl}oxy)propanamide | MS: 404 [M + 1] | A |
| 35 | 8-chloro-7-(1-cyclopropylethoxy)-2-[(4,6-dimethyl-2-oxo-1,2-dihydropyridin-3-yl)methyl]-3,4-dihydroisoquinolin-1(2H)-one | MS: 401 [M + 1] | A |
| 36 | 8-chloro-2-[(4,6-dimethyl-2-oxo-1,2-dihydropyridin-3-yl)methyl]-7-[2-(pyrrolidin-1-yl)ethoxy]-3,4-dihydroisoquinolin-1(2H)-one | MS: 430 [M + 1] | A |
| 37 | 8-chloro-2-[(4,6-dimethyl-2-oxo-1,2-dihydropyridin-3-yl)methyl]-7-(3,3,3-trifluoro-2-hydroxypropoxy)-3,4-dihydroisoquinolin-1(2H)-one | MS: 445 [M + 1] | A |
| 38 | 3-[2-({8-chloro-2-[(4,6-dimethyl-2-oxo-1,2-dihydropyridin-3-yl)methyl]-1-oxo-1,2,3,4-tetrahydroisoquinolin-7-yl}oxy)ethyl]-5,5-dimethyl-1,3-oxazolidine-2,4-dione | MS: 488 [M + 1] | A |

TABLE 1-continued

| Ex. | Structure/Name | ¹H NMR; LC-MS | Method |
|---|---|---|---|
| 39 | 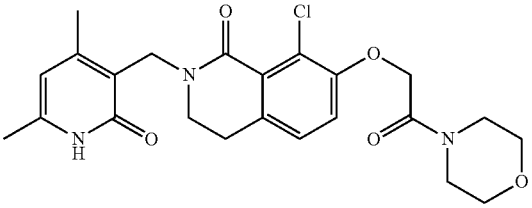<br>8-chloro-2-[(4,6-dimethyl-2-oxo-1,2-dihydropyridin-3-yl)methyl]-7-[2-(morpholin-4-yl)-2-oxoethoxy]-3,4-dihydroisoquinolin-1(2H)-one | MS: 460 [M + 1] | A |
| 40 | 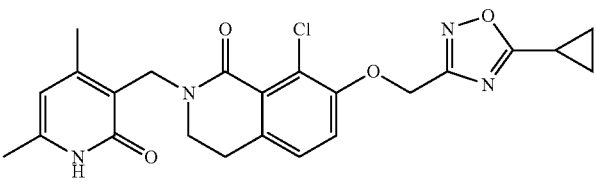<br>8-chloro-7-[(5-cyclopropyl-1,2,4-oxadiazol-3-yl)methoxy]-2-[(4,6-dimethyl-2-oxo-1,2-dihydropyridin-3-yl)methyl]-3,4-dihydroisoquinolin-1(2H)-one | MS: 455 [M + 1] | A |
| 41 | 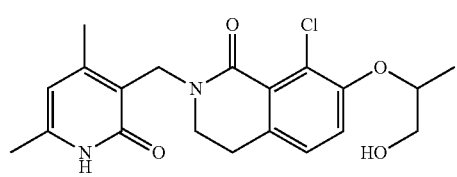<br>8-chloro-2-[(4,6-dimethyl-2-oxo-1,2-dihydropyridin-3-yl)methyl]-7-[(1-hydroxypropan-2-yl)oxy]-3,4-dihydroisoquinolin-1(2H)-one | MS: 391 [M + 1] | A |
| 42 | 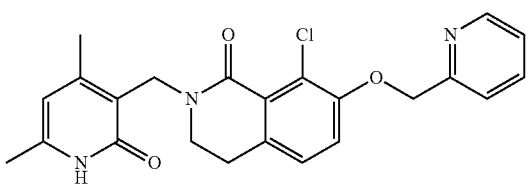<br>8-chloro-2-[(4,6-dimethyl-2-oxo-1,2-dihydropyridin-3-yl)methyl]-7-(pyridin-2-ylmethoxy)-3,4-dihydroisoquinolin-1(2H)-one | MS: 424 [M + 1] | A |
| 43 | 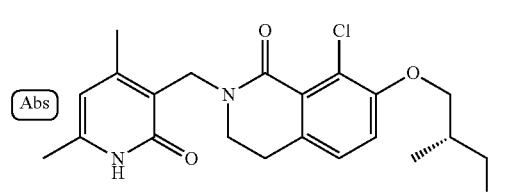<br>8-chloro-2-[(4,6-dimethyl-2-oxo-1,2-dihydropyridin-3-yl)methyl]-7-[(2S)-3-hydroxy-2-methylpropoxy]-3,4-dihydroisoquinolin-1(2H)-one | MS: 405 [M + 1] | A |

TABLE 1-continued

| Ex. | Structure/Name | ¹H NMR; LC-MS | Method |
|---|---|---|---|
| 44 | 8-chloro-2-[(4,6-dimethyl-2-oxo-1,2-dihydropyridin-3-yl)methyl]-7-(2-methoxyethoxy)-3,4-dihydroisoquinolin-1(2H)-one | MS: 391 [M + 1] | A |
| 45 | 7-(butan-2-yloxy)-8-chloro-2-[(4,6-dimethyl-2-oxo-1,2-dihydropyridin-3-yl)methyl]-3,4-dihydroisoquinolin-1(2H)-one | ¹H NMR (400 MHz, methanol-d4) δ 7.08-7.20 (m, 2H), 6.13 (s, 1H), 4.79 (s, 2H), 4.33-4.49 (m, 1H), 3.41-3.52 (m, 2H), 2.82 (t, J = 6.17 Hz, 2H), 2.30 (s, 3H), 2.27 (s, 3H), 1.62-1.86 (m, 2H), 1.31 (d, J = 6.11 Hz, 3H), 1.03 (t, J = 7.46 Hz, 3H); MS: 389.1 [M + 1] | A |
| 46 | 7-(butan-2-yloxy)-8-chloro-2-[(4,6-dimethyl-2-oxo-1,2-dihydropyridin-3-yl)methyl]-3,4-dihydroisoquinolin-1(2H)-one | ¹H NMR (400 MHz, methanol-d4) δ 7.08-7.20 (m, 2H), 6.13 (s, 1H), 4.79 (s, 2H), 4.33-4.49 (m, 1H), 3.41-3.52 (m, 2H), 2.82 (t, J = 6.17 Hz, 2H), 2.30 (s, 3H), 2.27 (s, 3H), 1.62-1.86 (m, 2H), 1.31 (d, J = 6.11 Hz, 3H), 1.03 (t, J = 7.46 Hz, 3H); MS: 389.1 [M + 1] | A |
| 47 | 5-chloro-2-[(4,6-dimethyl-2-oxo-1,2-dihydropyridin-3-yl)methyl]-6,7-dimethoxy-3,4-dihydroisoquinolin-1(2H)-one | ¹H NMR (400 MHz, methanol-d4) δ 7.60 (s, 1H), 6.10 (s, 1H), 4.73 (s, 2H), 3.91 (s, 3H), 3.86 (s, 3H), 3.56 (t, J = 6.82 Hz, 2H), 2.92 (t, J = 6.82 Hz, 2H), 2.28 (s, 3H), 2.25 (s, 3H); MS: 377.0 [M + 1] | A |
| 48 | 7-(butan-2-yloxy)-6-chloro-2-[(4,6-dimethyl-2-oxo-1,2-dihydropyridin-3-yl)methyl]-3,4-dihydroisoquinolin-1(2H)-one | MS: 389.2 [M + 1] | A |

TABLE 1-continued

| Ex. | Structure/Name | ¹H NMR; LC-MS | Method |
|---|---|---|---|
| 49 | 7-(butan-2-yloxy)-8-chloro-2-[(4,6-dimethyl-2-oxo-1,2-dihydropyridin-3-yl)methyl]-3,4-dihydroisoquinolin-1(2H)-one | ¹H NMR (400 MHz, methanol-d4) δ 7.08-7.20 (m, 2H), 6.13 (s, 1H), 4.79 (s, 2H), 4.33-4.49 (m, 1H), 3.41-3.52 (m, 2H), 2.82 (t, J = 6.17 Hz, 2H), 2.30 (s, 3H), 2.27 (s, 3H), 1.62-1.86 (m, 2H), 1.31 (d, J = 6.11 Hz, 3H), 1.03 (t, J = 7.46 Hz, 3H); MS: 389.2 [M + 1] | A |
| 50 | 5,8-dichloro-2-[(4,6-dimethyl-2-oxo-1,2-dihydropyridin-3-yl)methyl]-6,7-dimethoxy-3,4-dihydroisoquinolin-1(2H)-one | ¹H NMR (400 MHz, methanol-d4) δ 6.10 (s, 1H) 4.73 (s, 2H) 3.94 (s, 3H) 3.87 (s, 3H) 3.49 (t, J = 6.24 Hz, 2H) 2.95 (t, J = 6.24 Hz, 2H) 2.28 (s, 3H) 2.24 (s, 3H); MS: 411.1 [M + 1] | A |
| 51 | 8-chloro-2-[(4-ethyl-6-methyl-2-oxo-1,2-dihydropyridin-3-yl)methyl]-7-(propan-2-yloxy)-3,4-dihydroisoquinolin-1(2H)-one | ¹H NMR (400 MHz, chloroform-d) δ 6.97 (s, 2H), 5.98 (s, 1H), 4.84 (s, 2H), 4.50 (spt, J = 6.1 Hz, 1H), 3.56 (t, J = 6.1 Hz, 2H), 2.83-2.68 (m, 4H), 2.29 (s, 3H), 1.37 (d, J = 6.1 Hz, 6H), 1.13 (t, J = 7.6 Hz, 3H); MS: 389.2 [M + 1] | A |
| 52 | 8-chloro-2-({4-[(dimethylamino)methyl]-6-methyl-2-oxo-1,2-dihydropyridin-3-yl}methyl)-7-ethoxy-3,4-dihydroisoquinolin-1(2H)-one | ¹H NMR (600 MHz, DMSO-d6) δ 7.20-7.16 (m, 1H), 7.16-7.13 (m, 1H), 6.13 (s, 1H), 4.62 (s, 2H), 4.08 (q, J = 7.0 Hz, 2H), 3.30 (s, 3H), 2.74 (t, J = 5.9 Hz, 2H), 2.15 (s, 3H), 2.09 (s, 6H), 1.34 (t, J = 6.8 Hz, 3H); MS: 404 [M + 1] | A |
| 54 | 2-[(4,6-dimethyl-2-oxo-1,2-dihydropyridin-3-yl)methyl]-1-oxo-7-(propan-2-yloxy)-1,2-dihydroisoquinoline-6-carbonitrile | ¹H NMR (400 MHz, DMSO-d6) δ 11.62 (br. s., 1H) 8.17 (s, 1H) 7.81 (s, 1H) 7.50 (d, J = 7.58 Hz, 1H) 6.56 (d, J = 7.34 Hz, 1H) 5.91 (s, 1H) 4.95 (s, 2H) 4.84-4.94 (m, 1H) 2.26 (s, 3H) 2.12 (s, 3H) 1.57 (s, 6H) 1.36 (d, J = 6.11 Hz, 6H); MS: 364.2 [M + 1] | B |

TABLE 1-continued

| Ex. | Structure/Name | $^1$H NMR; LC-MS | Method |
|---|---|---|---|
| 55 | 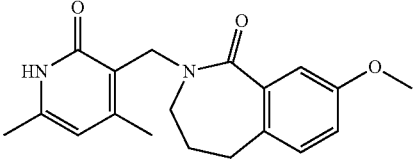<br>2-[(4,6-dimethyl-2-oxo-1,2-dihydropyridin-3-yl)methyl]-8-methoxy-2,3,4,5-tetrahydro-1H-2-benzazepin-1-one | $^1$H NMR (400 MHz, DMSO-d6) δ 11.55 (br s., 1H), 7.10 (d, J = 8.31 Hz, 1H), 7.04 (d, J = 2.81 Hz, 1H), 6.92-6.97 (m, 1H), 5.91 (s, 1H), 4.58 (s, 2H), 3.76 (s, 3H), 3.29 (br. s., 1H), 3.13-3.19 (m, 2H), 2.53-2.56 (m, 1H), 2.19 (s, 3H), 2.14 (s, 3H), 1.56-1.65 (m, 2H); MS: 327.2 [M + 1] | B |
| 56 | 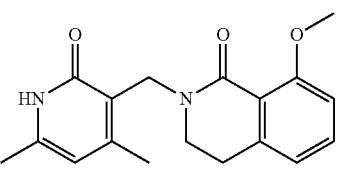<br>2-[(4,6-dimethyl-2-oxo-1,2-dihydropyridin-3-yl)methyl]-8-methoxy-3,4-dihydroisoquinolin-1(2H)-one | $^1$H NMR (400 MHz, DMSO-d6) δ 11.51 (br. s., 1H), 7.34 (t, J = 7.96 Hz, 1H), 6.95 (d, J = 8.34 Hz, 1H), 6.78 (d, J = 7.58 Hz, 1H), 5.87 (s, 1H), 4.52 (s, 2H), 3.76 (s, 3H), 3.33-3.39 (m, 2H), 2.73 (t, J = 6.06 Hz, 2H), 2.15 (s, 3H), 2.11 (s, 3H); MS: 313.1 [M + 1] | |
| 57 | 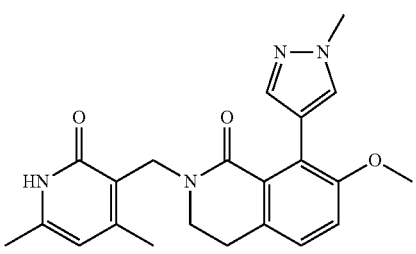<br>2-[(4,6-dimethyl-2-oxo-1,2-dihydropyridin-3-yl)methyl]-7-methoxy-8-(1-methyl-1H-pyrazol-4-yl)-3,4-dihydroisoquinolin-1(2H)-one | $^1$H NMR (400 MHz, DMSO-d6) δ 11.51 (br. s., 1H) 7.59 (s, 1H) 7.44 (d, J = 1.71 Hz, 1H) 7.16 (s, 1H) 6.27 (d, J = 1.59 Hz, 1H) 5.88 (s, 1H) 4.60 (s, 2H) 3.83 (s, 3H) 3.62 (s, 3H) 3.49 (t, J = 6.54 Hz, 2 H) 2.82 (t, J = 6.54 Hz, 2H) 2.17 (s, 3H) 2.13 (s, 3H); MS: 393.3 [M + 1] | B |
| 59 | 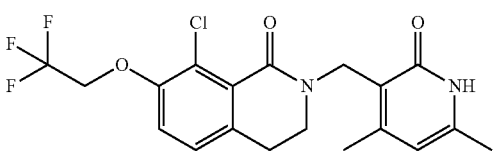<br>8-chloro-2-[(4,6-dimethyl-2-oxo-1,2-dihydropyridin-3-yl)methyl]-7-(2,2,2-trifluoroethoxy)-3,4-dihydroisoquinolin-1(2H)-one | $^1$H NMR (400 MHz, methanol-d4) δ 7.25-7.19 (m, 2H), 6.11 (s, 1H), 4.76 (s, 2H), 4.63-4.58 (m, 2H), 3.48-3.45 (m, 2H), 2.86-2.83 (m, 2H), 2.28 (s, 3H), 2.24 (s, 3H); MS: 415.0 [M + 1]$^+$ | C |
| 60 | 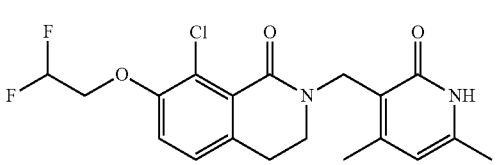<br>8-chooro-7-(2,2-difluoroethoxy)-2-[(4,6-dimethyl-2-oxo-1,2-dihydropyridin-3-yl)methyl]-3,4-dihydroisoquinolin-1(2H)-one | $^1$H NMR (400 MHz, chloroform-d) δ 10.89 (br, 1H), 7.03-6.97 (m, 2H), 6.29-5.99 (m, 1H), 5.92 (s, 1H), 4.79 (s, 2H), 4.25-4.18 (m, 2H), 3.61-3.58 (t, J = 6 Hz, 2H), 2.81-2.78 (t, J = 6 Hz, 2H), 2.42 (s, 3H), 2.26 (s, 3H); MS: 397.0 [M + 1]+ | C |

TABLE 1-continued

| Ex. | Structure/Name | ¹H NMR; LC-MS | Method |
|---|---|---|---|
| 61 | 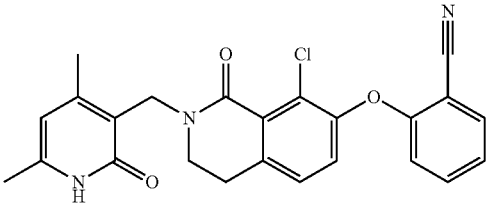<br>2-({8-chloro-2-[(4,6-dimethyl-2-oxo-1,2-dihydropyridin-3-yl)methyl]-1-oxo-1,2,3,4-tetrahydroisoquinolin-7-yl}oxy)benzonitrile | ¹H NMR (400 MHz, DMSO): δ 11.58 (s, 1H), 7.93-7.9 (d, J = 9.2 Hz, 1H), 7.62 (t, 1H) 7.45-7.43 (d, J = 8.0 Hz, 1H), 7.37-7.35 (d, J = 8.4 Hz, 1H), 7.29-7.25 (t, 1H), 6.73-6.71 (d, J = 8.4 Hz, 1H), 5.91 (s, 1H), 4.58 (s, 2H), 3.49-3.46 (m, 2H), 2.86-2.89 (s, 3H), 2.18 (s, 3H), 2.13 (s, 3H); MS: 433.9 [M + 1]+ | C |
| 62 | 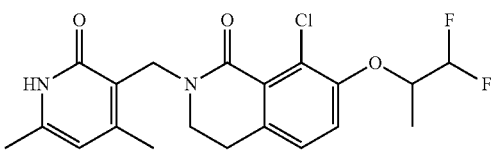<br>8-chloro-7-[(1,1-difluoropropan-2-yl)oxy]-2-[(4,6-dimethyl-2-oxo-1,2-dihydropyridin-3-yl)methyl]-3,4-dihydroisoquinolin-1(2H)-one | ¹H NMR (400 MHz, methanol-d4): δ 7.273-7.252 (d, J = 8.4 Hz, 1H), 7.177-7.156 (d, J = 8.4 Hz, 1H), 6.14-5.86 (m, 2H), 4.78 (s, 2H), 4.65-4.59 (m, 1H), 3.49-3.46 (t, 2H), 2.86-2.83 (t, 2H), 2.30 (s, 3H), 2.26 (s, 3H), 1.415-1.399 (d, J = 6.4 Hz, 3H); MS: 411.1 [M + 1] | C |
| 63 | 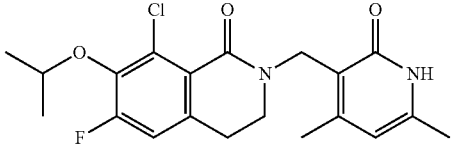<br>8-chloro-2-[(4,6-dimethyl-2-oxo-1,2-dihydropyridin-3-yl)methyl]-6-fluoro-7-(propan-2-yloxy)-3,4-dihdyroisoquinolin-1(2H)-one | ¹H NMR (400 MHz, DMSO-d6) δ 11.54 (br. s., 1H), 7.23 (d, J = 10.51 Hz, 1H), 5.89 (s, 1H), 4.56 (s, 2H), 4.39 (td, J = 5.99, 12.23 Hz, 1H), 3.41 (t, J = 6.17 Hz, 2H), 2.79 (t, J = 6.17 Hz, 2H), 2.17 (s, 3H), 2.13 (s, 3H), 1.29 (d, J = 5.99 Hz, 6H); MS: 393.2 [M + 1] | C |
| 64 | 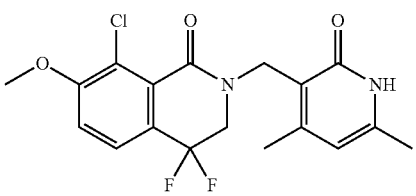<br>8-chloro-2-[(4,6-dimethyl-2-oxo-1,2-dihydropyridin-3-yl)methyl]-4,4-difluoro-7-methoxy-3,4-dihydroisoquinolin-1(2H)-one | ¹H NMR (400 MHz, DMSO-d6) δ 11.62 (br. s., 1H), 7.63 (d, J = 8.56 Hz, 1H), 7.46 (d, J = 8.68 Hz, 1H), 5.91 (s, 1H), 4.61 (s, 2H), 4.02 (t, J = 12.17 Hz, 2H), 3.94 (s, 3H), 2.17 (s, 3H), 2.13 (s, 3H); MS: 383.1 [M + 1] | C |
| 65 | 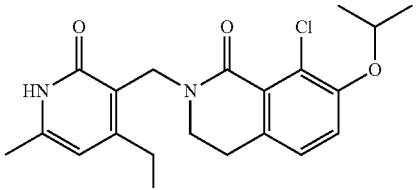<br>8-chloro-2-{[4-(hydroxymethyl)-6-methyl-2-oxo-1,2-dihydropyridin-3-yl]methyl}-7-(propan-2-yloxy)-3,4-dihydroisoquinolin-1(2H)-one | ¹H NMR (400 MHz, chloroform-d) δ 6.96 (s, 2H), 6.20 (s, 1H), 4.70 (br. s., 2H), 4.68 (br. s., 2H), 4.47 (td, J = 5.9, 12.1 Hz, 1H), 3.88 (br. s., 2H), 2.83 (t, J = 5.5 Hz, 2H), 2.30 (s, 3H), 1.34 (d, J = 5.9 Hz, 6H); MS: 391 [M + 1] | C |

TABLE 1-continued

| Ex. | Structure/Name | ¹H NMR; LC-MS | Method |
|---|---|---|---|
| 67 | 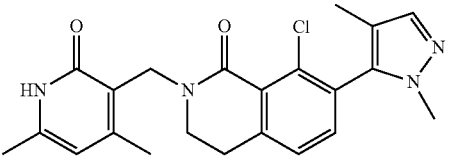<br>8-chloro-2-[(4,6-dimethyl-2-oxo-1,2-dihydropyridin-3-yl)methyl]-7-(1,4-dimethyl-1H-pyrazol-5-yl)-3,4-dihydroisoquinolin-1(2H)-one | ¹H NMR (400 MHz, chloroform-d) δ 7.23 (d, J = 7.58 Hz, 1H) 7.16 (d, J = 7.58 Hz, 1H) 7.40 (br. s., 1H) 6.01 (s, 1H) 4.77 (s, 2H) 3.73 (br. s., 2H) 3.64 (s, 3H) 2.94 (d, J = 4.04 Hz, 2H) 2.42 (s, 3H) 2.29 (s, 3H) 1.89 (s, 3H); MS: 411.0 [M + 1] | D |
| 68 | 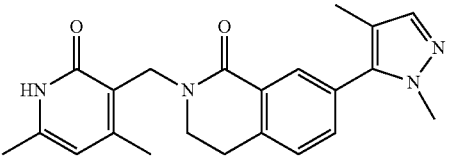<br>2-[(4,6-dimethyl-2-oxo-1,2-dihydropyridin-3-yl)methyl]-7-(1,4-dimethyl-1H-pyrazol-5-yl)-3,4-dihydroisoquinolin-1(2H)-one | ¹H NMR (400 MHz, DMSO-d6) δ 11.56 (br. s., 1H) 7.84 (d, J = 1.71 Hz, 1H) 7.51 (dd, J = 7.76, 1.90 Hz, 1H) 7.41 (d, J = 7.82 Hz, 1H) 7.35 (s, 1H) 5.90 (s, 1H) 4.60 (s, 2H) 3.70 (s, 3H) 3.54 (t, J = 6.54 Hz, 2H) 2.93 (t, J = 6.54 Hz, 2H) 2.18 (s, 3H) 2.14 (s, 3H) 1.96 (s, 3H); MS: 377.2 [M + 1] | D |
| 69 | 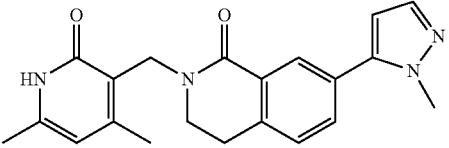<br>2-[(4,6-dimethyl-2-oxo-1,2-dihydropyridin-3-yl)methyl]-7-(1,4-dimethyl-1H-pyrazol-5-yl)-3,4-dihydroisoquinolin-1(2H)-one | ¹H NMR (400 MHz, DMSO-d6) δ 11.55 (br. s., 1H) 7.97 (d, J = 1.83 Hz, 1H) 7.63 (dd, J = 7.76, 2.02 Hz, 1H) 7.49 (d, J = 1.83 Hz, 1H) 7.40 (d, J = 7.95 Hz, 1H) 6.43 (d, J = 1.83 Hz, 1H) 5.90 (s, 1H) 4.60 (s, 2H) 3.86 (s, 3H) 3.53 (t, J = 6.54 Hz, 2H) 2.92 (t, J = 6.54 Hz, 2H) 2.18 (s, 3H) 2.14 (s, 3H); MS: 363.1 [M + 1] | D |
| 70 | 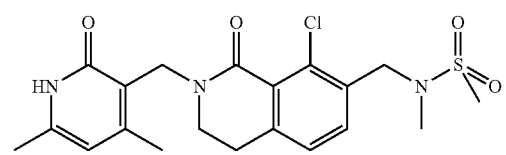<br>N-({8-chloro-2-[(4,6-dimethyl-2-oxo-1,2-dihydropyridin-3-yl)methyl]-1-oxo-1,2,3,4-tetrahydroisoquinolin-7-yl}methyl)-N-methylmethanesulfonamide | ¹H NMR (400 MHz, DMSO-d6) δ 11.54 (br. s., 1H), 7.48 (d, J = 7.83 Hz, 1H), 7.28 (d, J = 7.83 Hz, 1H), 5.88 (s, 1H), 4.58 (s, 2H), 4.39 (s, 2H), 3.40 (t, J = 6.06 Hz, 2H), 3.02 (s, 3H), 2.82 (t, J = 6.06 Hz, 2H), 2.73 (s, 3H), 2.15 (s, 3H), 2.12 (s, 3H); MS: 438.0 [M + 1] | D |
| 71 | 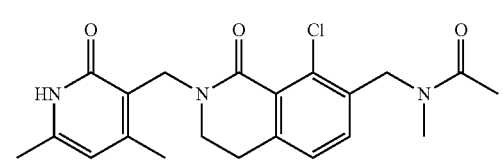<br>N-({8-chloro-2-[(4,6-dimethyl-2-oxo-1,2-dihydropyridin-3-yl)methyl]-1-oxo-1,2,3,4-tetrahydroisoquinolin-7-yl}methyl)-N-methylacetamide | ¹H NMR (400 MHz, 80° C., DMSO-d6) δ 7.09 (br. s., 2H), 5.76 (s, 1H), 4.52 (s, 4H), 3.35 (t, J = 6.17 Hz, 2H), 2.74 (t, J = 5.75 Hz, 2H), 2.10 (s, 3H), 2.05 (s, 3H), 1.78 (s, 4H); MS: 402.1 [M + 1] | D |

TABLE 1-continued

| Ex. | Structure/Name | ¹H NMR; LC-MS | Method |
|---|---|---|---|
| 72 | 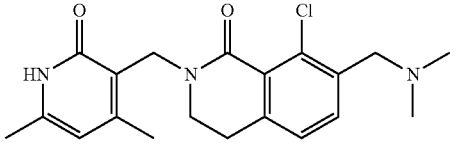<br>8-chloro-7-[(dimethylamino)methyl]-2-[(4,6-dimethyl-2-oxo-1,2-dihydropyridin-3-yl)methyl]-3,4-dihydroisoquinolin-1(2H)-one | ¹H NMR (400 MHz, methanol-d4) δ 7.54 (d, J = 7.58 Hz, 1H), 7.22 (d, J = 7.83 Hz, 1H), 6.11 (s, 1H), 4.77 (s, 2H), 3.83 (s, 2H), 3.48 (t, J = 6.19 Hz, 2H), 2.89 (t, J = 6.06 Hz, 2H), 2.41 (s, 6H), 2.29 (s, 3H), 2.25 (s, 3H); MS: 374.1 [M + 1] | D |
| 73 | 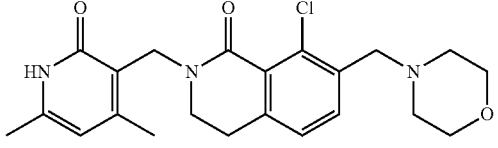<br>8-chloro-2-[(4,6-dimethyl-2-oxo-1,2-dihydropyridin-3-yl)methyl]-7-(morpholin-4-ylmethyl)-3,4-dihydroisoquinolin-1(2H)-one | ¹H NMR (700 MHz, DMSO-d6) δ 7.51 (d, J = 7.74 Hz, 1H), 7.19 (d, J = 7.74 Hz, 1H), 5.88 (s, 1H), 4.57 (s, 2H), 3.53-3.63 (m, 4H), 2.79 (t, J = 6.02 Hz, 2H), 2.41 (br. s., 4H), 2.15 (s, 3H), 2.12 (s, 3H); MS: 416.1 [M + 1] | D |
| 74 | 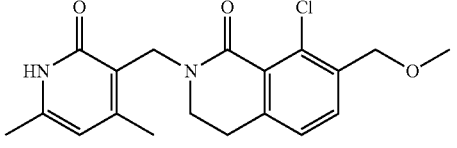<br>8-chloro-2-[(4,6-dimethyl-2-oxo-1,2-dihydropyridin-3-yl)methyl]-7-(methoxymethyl)-3,4-dihydroisoquinolin-1(2H)-one | ¹H NMR (400 MHz, DMSO-d6) δ 11.46 (br. s., 1H), 7.40 (d, J = 7.58 Hz, 1H), 7.15 (d, J = 7.83 Hz, 1H), 5.80 (s, 1H), 4.50 (s, 2H), 4.42 (s, 2H), 3.30-3.33 (m, 2H), 3.28 (s, 3H), 2.73 (t, J = 6.06 Hz, 2H), 2.07 (s, 3H), 2.04 (s, 3H); MS: 361.1 [M + 1] | D |
| 75 | 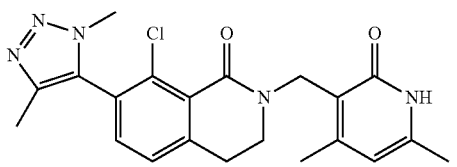<br>8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one | ¹H NMR (400 MHz, DMSO-d6): δ 7.50-7.48 (d, J = 7.6 Hz, 1H), 74.1-7.39 (d, J = 7.6 Hz, 1H), 5.90 (s, 1H), 4.58 (s, 2H), 3.76 (s, 3H), 3.51-3.48 (t, J = 5.6 Hz, 2H), 2.94-2.91 (t, J = 6 Hz, 2H), 2.19 (s, 3H), 2.13 (s, 3H), 2.08 (s, 3H); MS: 412.1 [M + 1] | D |

TABLE 1-continued

| Ex. | Structure/Name | ¹H NMR; LC-MS | Method |
|---|---|---|---|
| 78 | 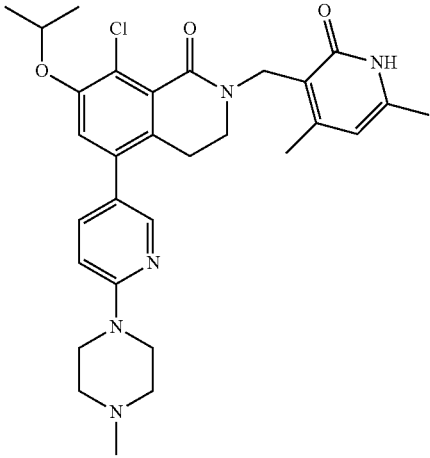<br>8-chloro-2-[(4,6-dimethyl-2-oxo-1,2-dihydropyridin-3-yl)methyl]-5-[6-(4-methylpiperazin-1-yl)pyridin-3-yl]-7-(propan-2-yloxy)-3,4-dihydroisoquinolin-1(2H)-one | ¹H NMR (400 MHz, DMSO-d6) δ 11.52 (br. s., 1H), 8.14 (d, J = 2.02 Hz, 1H), 7.58 (dd, J = 8.84, 2.27 Hz, 1H), 7.13 (s, 1H), 6.87 (d, J = 8.84 Hz, 1H), 5.88 (s, 1H), 4.65-4.77 (m, 1H), 4.57 (s, 2H), 3.49-3.55 (m, 4H), 3.25-3.27 (m, 2H), 2.63-2.71 (m, 2H), 2.35-2.43 (m, 4H), 2.22 (s, 3H), 2.17 (s, 3H), 2.11 (s, 3H), 1.29 (d, J = 5.81 Hz, 6H); MS: 550.2 [M + 1] | F |
| 79 | 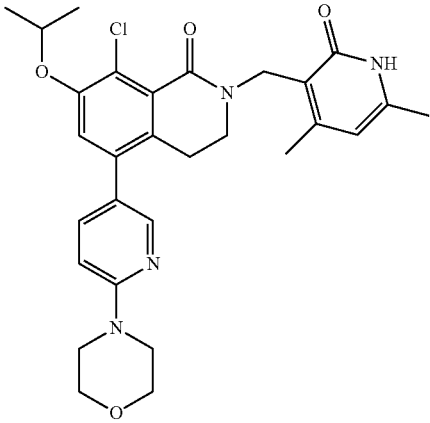<br>8-chloro-2-[(4,6-dimethyl-2-oxo-1,2-dihydropyridin-3-yl)methyl]-5-[6-(morpholin-4-yl)pyridin-3-yl]-7-(propan-2-yloxy)-3,4-dihydroisoquinolin-1(2H)-one | ¹H NMR (400 MHz, DMSO-d6) δ 11.19 (br. s., 1H), 8.12 (d, J = 2.20 Hz, 1H), 7.56 (dd, J = 8.74, 2.51 Hz, 1H), 7.08 (s, 1H), 6.83 (d, J = 8.80 Hz, 1H), 5.83 (s, 1H), 4.60-4.72 (m, 1H), 4.58 (s, 2H), 3.67-3.75 (m, 4H), 3.46-3.54 (m, 4H), 3.30 (t, J = 5.99 Hz, 2H), 2.66 (t, J = 5.93 Hz, 2H), 2.18 (s, 3H), 2.12 (s, 3H), 1.30 (d, J = 5.99 Hz, 6H); MS: 537.2 [M + 1] | F |
| 80 | 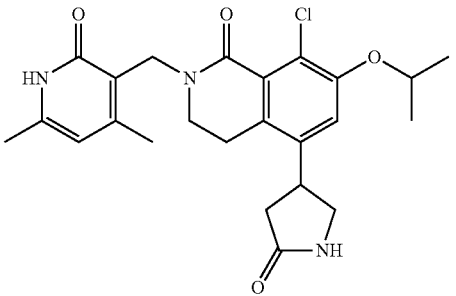<br>8-chloro-2-[(4,6-dimethyl-2-oxo-1,2-dihydropyridin-3-yl)methyl]-5-(5-oxopyrrolidin-3-yl)-7-(propan-2-yloxy)-3,4-dihydroisoquinolin-1(2H)-one | ¹H NMR (700 MHz, DMSO-d6) δ 11.54 (br. s., 1H) 7.70 (s, 1H) 7.21 (br. s., 1H) 5.88 (s, 1H) 4.63-4.70 (m, 1H) 4.55 (s, 2H) 3.74 (t, J = 7.92 Hz, 1H) 3.54 (t, J = 8.69 Hz, 1H) 3.18 (dd, J = 9.46, 7.48 Hz, 1H) 2.74 (q, J = 6.31 Hz, 2H) 2.46 (dd, J = 16.40, 8.69 Hz, 1H) 2.33 (dd, J = 16.29, 8.58 Hz, 1H) 2.15 (s, 3H) 2.12 (s, 3H) 1.26 (d, J = 5.94 Hz, 6H); MS: 458.1 [M + 1] | F |

| Ex. | Structure/Name | ¹H NMR; LC-MS | Method |
|---|---|---|---|
| 81 | 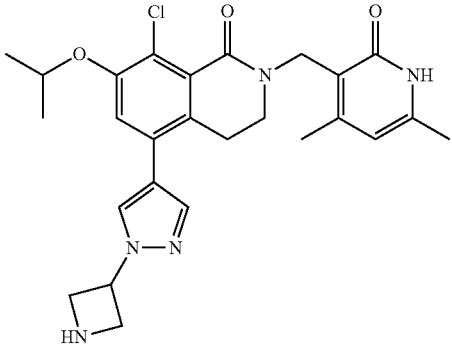<br>5-[1-(azetidin-3-yl)-1H-pyrazol-4-yl]-8-chloro-2-[(4,6-dimethyl-2-oxo-1,2-dihydropyridin-3-yl)methyl]-7-(propan-2-yloxy)-3,4-dihydroisoquinolin-1(2H)-one | ¹H NMR (400 MHz, methanol-d4) δ 7.93 (s, 1H), 7.88 (s, 1H), 7.23 (s, 1H), 6.36 (m, 2H), 5.49 (s, 1H), 4.82 (s, 2H), 4.70-4.67 (m, 1H), 4.60-4.58 (d, J = 8 Hz, 4H), 3.49 (s, 2H), 2.94 (s, 2H), 2.43-2.41 (d, J = 8 Hz, 3H), 2.35-2.33 (d, J = 8 Hz, 3H), 1.38-1.37 (d, J = 4 Hz, 6H); MS: 496.0 [M + 1] | F |
| 82 | 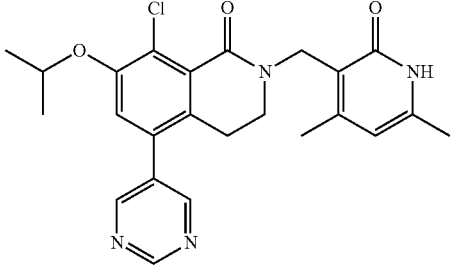<br>8-chloro-2-[(4,6-dimethyl-2-oxo-1,2-dihydropyridin-3-yl)methyl]-7-(propan-2-yloxy)-5-(pyrimidin-5-yl)-3,4-dihydroisoquinolin-1(2H)-one | ¹H NMR (400 MHz, DMSO-d6) δ 11.57 (s, 1H), 9.23 (s, 1H), 8.92 (s, 2H), 7.36 (s, 1H), 5.90 (s, 1H), 4.80-4.77 (t, J = 5.2 Hz, 1H), 4.59 (s, 2H), 3.42 (s, 2H), 3.31-3.29 (d, J= 6.4 Hz, 2H), 2.18 (s, 3H), 2.12 (s, 3H), 1.32-1.30 (d, J = 6.0 Hz, 6H); MS: 452.9 [M + 1] | F |
| 83 | 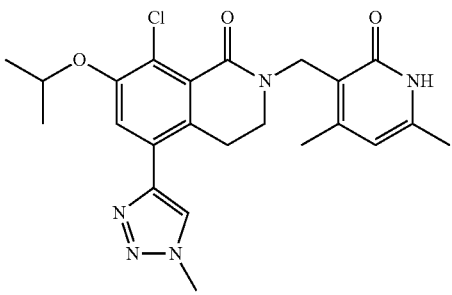<br>8-chloro-2-[(4,6-dimethyl-2-oxo-1,2-dihydropyridin-3-yl)methyl]-5-(1-methyl-1H-1,2,3-triazol-4-yl)-7-(propan-2-yloxy)-3,4-dihydroisoquinolin-1(2H)-one | ¹H NMR (400 MHz, DMSO-d6): δ 12.00 (s, 1H), 8.41 (s, 1H), 7.55 (s, 1H), 5.90 (s, 1H), 4.70-4.60 (m, 1H), 4.58 (s, 2H), 4.09 (s, 3H), 3.35-3.30 (m, 2H), 2.87-2.85 (m, 2H), 2.17 (s, 3H), 2.12 (s, 3H), 1.32-1.31 (d, J = 5.6 Hz, 6H); MS: 456.0 [M + 1] | F |

TABLE 1-continued

| Ex. | Structure/Name | ¹H NMR; LC-MS | Method |
|---|---|---|---|
| 84 | 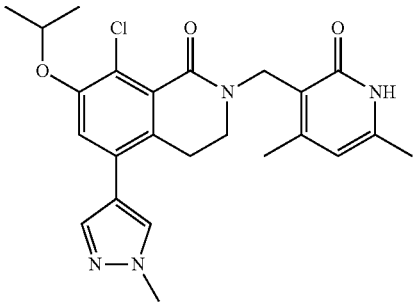<br>8-chloro-2-[(4,6-dimethyl-2-oxo-1,2-dihydropyridin-3-yl)methyl]-5-(1-methyl-1H-pyrazol-4-yl)-7-(propan-2-yloxy)-3,4-dihydroisoquinolin-1(2H)-one | ¹H NMR (400 MHz, chloroform-d): δ 12.16 (s, 1H), 7.49 (s, 1H), 7.39 (s, 1H), 6.99 (s, 1H), 5.93 (s, 1H), 4.79 (s, 2H), 4.54-4.51 (t, 1H, J = 6), 3.94 (s, 3H), 3.51-3.48 (t, 2H, J = 5.6), 2.81-2.79 (t, 2H, J = 5.6), 2.35 (s, 3H), 2.26 (s, 3H), 1.38-1.36 (d, 6H, J = 6); MS: 455.1 [M + 1] | F |
| 85 | 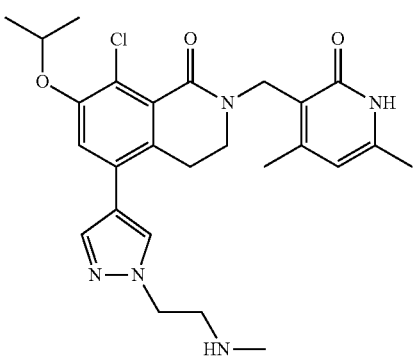<br>8-chloro-2-[(4,6-dimethyl-2-oxo-1,2-dihydropyridin-3-yl)methyl]-5-{1-[2-(methylamino)ethyl]-1H-pyrazol-4-yl}-7-(propan-2-yloxy)-3,4-dihydroisoquinolin-1(2H)-one | ¹H NMR (400 MHz, methanol-d4) δ 7.94 (s, 1H), 7.76 (s, 1H), 7.21 (s, 1H), 6.15 (s, 1H), 4.89 (s, 2H), 4.79 (s, 1H), 4.56 (s, 2H), 3.54 (s, 2H), 3.41 (s, 2H), 2.90 (s, 2H), 2.78 (s, 3H), 2.33 (s, 3H), 2.27 (s, 3H), 1.38-1.37 (d, 6H, J = 6); MS: 498.0 [M + 1] | F |
| 86 | 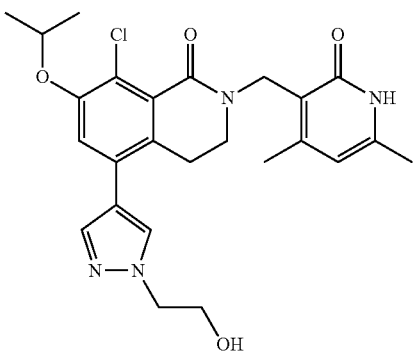<br>8-chloro-2-[(4,6-dimethyl-2-oxo-1,2-dihydropyridin-3-yl)methyl]-5-[1-(2-hydroxyethyl)-1H-pyrazol-4-yl]-7-(propan-2-yloxy)-3,4-dihydroisoquinolin-1(2H)-one | ¹H NMR (400 MHz, DMSO-d6) δ 11.58 (s, 1H), 8.00 (s, 1H), 7.72 (s, 1H), 7.24 (s, 1H), 5.90 (s, 1H), 4.94-4.91 (t, 1H, J = 5.2), 4.73 (s, 1H), 4.59 (s, 2H), 4.18-4.15 (t, 2H, J = 6), 3.78-3.74 (q, 2H), 3.35-3.31 (t, 2H), 2.81 (s, 9H), 2.18 (s, 3H), 2.13 (s, 3H), 1.30-1.29 (d, J = 6.0 Hz, 6H); MS: 485.1 [M + 1] | F |

TABLE 1-continued

| Ex. | Structure/Name | ¹H NMR; LC-MS | Method |
|---|---|---|---|
| 87 | 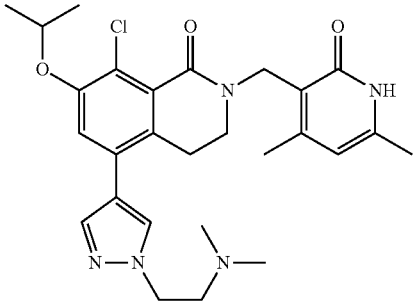<br>8-chloro-5-{1-[2-(dimethylamino)ethyl]-1H-pyrazol-4-yl}-2-[(4,6-dimethyl-2-oxo-1,2-dihydropyridin-3-yl)methyl]-7-(propan-2-yloxy)-3,4-dihydrosoquinolin-1(2H)-one | ¹H NMR (400 MHz, DMSO-d6) δ 8.27 (s, 1H), 8.03 (s, 1H), 7.71 (s, 1H), 7.24 (s, 1H), 5.90 (s, 1H), 4.73 (s, 1H), 4.59 (s, 2H), 4.23-4.20 (t, 3H, J = 6), 3.31 (s, 3H), 2.80 (s, 2H), 2.71-2.68 (t, 2H, J = 6.4), 2.18 (s, 9H), 2.13 (s, 3H), 1.30 (s, 6H); MS: 512 [M + 1] | F |
| 88 | 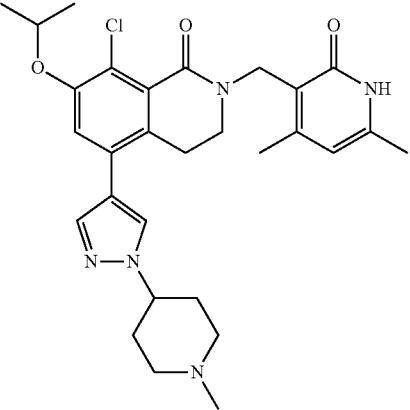<br>8-chloro-2-[(4,6-dimethyl-2-oxo-1,2-dihydropyridin-3-yl)methyl]-5-[1-(1-methylpiperidin-4-yl)-1H-pyrazol-4-yl]-7-(propan-2-yloxy)-3,4-dihydroisoquinolin-1(2H)-one | ¹H NMR (400 MHz, methanol-d4) δ 7.90 (s, 1H), 7.66 (s, 1H), 7.19 (s, 1H), 6.12 (s, 1H), 4.70-4.60 (m, 2H), 4.35-4.35 (m, 1H), 3.39-3.36 (t, J = 5.6 Hz, 2H), 3.18-3.15 (d, J = 10.8 Hz, 2H), 2.89-2.86 (t, J = 5.6 Hz, 2H), 2.49 (br. s., 5H), 2.30 (s, 3H), 2.24 (s, 3H), 2.25-2.10 (m, 4H), 1.36-1.35 (d, J = 6.4 Hz, 6H); MS: 538.0 [M + 1] | F |
| 89 | 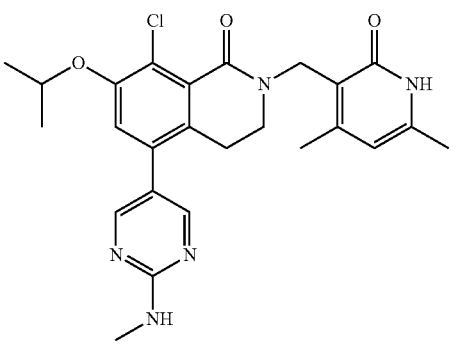<br>8-chloro-2-[(4,6-dimethyl-2-oxo-1,2-dihydropyridin-3-yl)methyl]-5-[2-(methylamino)pyrimidin-5-yl]-7-(propan-2-yloxy)-3,4-dihydroisoquinolin-1(2H)-one | ¹H NMR (400 MHz, chloroform-d) δ 11.56 (s, 1H), 8.35 (s, 2H), 7.32-7.33 (d, 1H), 7.20 (s, 1H), 5.89 (s, 1H), 4.73-4.76 (m, 1H), 4.57 (s, 2H), 3.27-3.28 (m, 2H), 2.83-2.84 (d, 3H), 2.68-2.70 (m, 2H), 2.12-2.17 (d, 6H), 1.29-1.30 (d, 6H); MS: 482.0 [M + 1] | F |

| Ex. | Structure/Name | ¹H NMR; LC-MS | Method |
|---|---|---|---|
| 91 | 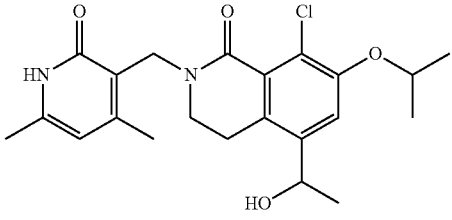<br>8-chloro-2-[(4,6-dimethyl-2-oxo-1,2-dihydropyridin-3-yl)methyl]-5-(1-hydroxyethyl)-7-(propan-2-yloxy)-3,4-dihydroisoquinolin-1(2H)-one | ¹H NMR (700 MHz, DMSO-d6) δ 7.32 (s, 1H) 5.90 (s, 1H) 5.31 (br. s., 1H) 4.87 (q, J = 6.38 Hz, 1 H) 4.53-4.62 (m, 3H) 3.33-3.37 (m, 1H) 3.30 (ddd, J = 12.87, 9.24, 4.07 Hz, 1H) 2.77 (ddd, J = 15.85, 6.71, 4.07 Hz, 1H) 2.63-2.69 (m, 1H) 2.16 (s, 3H) 2.13 (s, 3H) 1.30 (d, J = 5.94 Hz, 3H) 1.29 (d, J = 6.16 Hz, 3H) 1.25 (d, J = 6.38 Hz, 3H); MS: 419.1 [M + 1] | G |
| 92 | 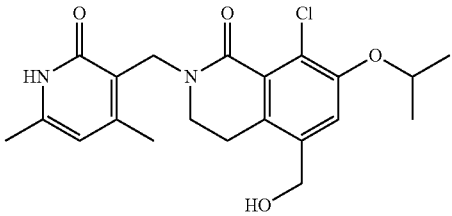 [SMILES: Cc1cc(C)c(CN2CCc3c(CO)cc(OC(C)C)c(Cl)c3C2=O)c(=O)[nH]1]<br>8-chloro-2-[(4,6-dimethyl-2-oxo-1,2-dihydropyridin-3-yl)methyl]-5-(hydroxymethyl)-7-(propan-2-yloxy)-3,4-dihydroisoquinolin-1(2H)-one | ¹H NMR (700 MHz, DMSO-d6) δ 7.25 (s, 1H) 5.88 (s, 1H) 4.56-4.60 (m, 1H) 4.55 (s, 2H) 4.45 (s, 2H) 3.33-3.35 (m, 2H) 2.65 (t, J = 6.27 Hz, 2H) 2.14 (s, 3H) 2.12 (s, 3H) 1.29 (s, 3H) 1.28 (s, 3H); MS: 405.1 [M + 1] | G |
| 93 | 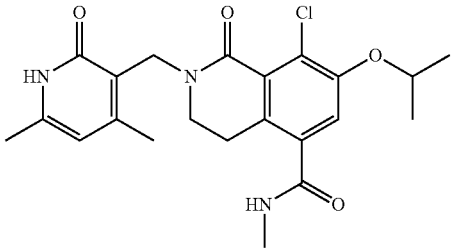<br>8-chloro-2-[(4,6-dimethyl-2-oxo-1,2-dihydropyridin-3-yl)methyl]-N-methyl-1-oxo-7-(propan-2-yloxy)-1,2,3,4-tetrahydroisoquinoline-5-carboxamide | ¹H NMR (700 MHz, DMSO-d6) δ 11.54 (br. s., 1H) 8.23-8.34 (m, 1H) 7.15-7.27 (m, 1H) 5.90 (d, J = 3.52 Hz, 1H) 4.62-4.75 (m, 1 H) 4.49-4.62 (m, 2H) 3.35 (br. s., 2H) 2.76-2.80 (m, 2H) 2.74 (t, J = 4.95 Hz, 3H) 2.15-2.19 (m, 3H) 2.14 (d, J = 2.64 Hz, 3H) 1.30 (dt, J = 5.50, 2.97 Hz, 6H); MS: 432.1 [M + 1] | G |
| 94 | 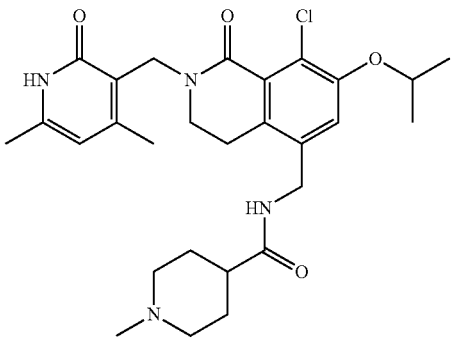<br>N-({8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}methyl)-1-methylpiperidine-4-carboxamide | ¹H NMR (600 MHz, DMSO-d6) δ 8.35 (br. s., 2H) 8.27 (t, J = 5.14 Hz, 1H) 7.07 (s, 1H) 5.91 (s, 1 H) 4.50-4.60 (m, 3H) 4.20 (d, J = 5.50 Hz, 2H) 3.32-3.37 (m, 2 H) 2.89 (d, J = 9.54 Hz, 2H) 2.67 (t, J = 5.96 Hz, 2H) 2.22-2.28 (m, 3H) 2.11-2.21 (m, 7 H) 2.02-2.11 (m, 2H) 1.58-1.71 (m, 4H) 1.28 (d, J = 6.05 Hz, 6H); MS: 529.2 [M + 1] | G |

TABLE 1-continued

| Ex. | Structure/Name | $^1$H NMR; LC-MS | Method |
|---|---|---|---|
| 95 | 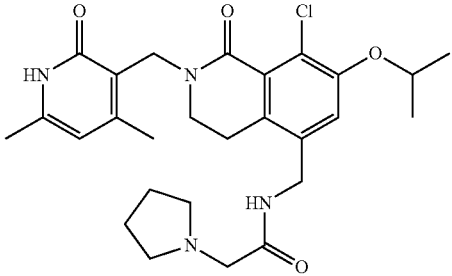<br>N-({8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}methyl)-2-(pyrrolidin-1-yl)acetamide | $^1$H NMR (600 MHz, DMSO-d6) δ 8.34 (br. s., 1H) 8.24 (t, J = 5.87 Hz, 1H) 7.12 (s, 1H) 5.91 (s, 1 H) 4.56 (s, 2H) 4.50-4.55 (m, 1 H) 4.24 (d, J = 5.87 Hz, 2H) 3.33-3.36 (m, 2H) 3.09 (s, 2H) 2.71 (t, J = 6.05 Hz, 2H) 2.50 (br. s., 4H) 2.15 (s, 3H) 2.13 (s, 2H) 1.69 (br. s., 4H) 1.28 (d, J = 6.05 Hz, 6 H); MS: 515.2 [M + 1] | G |
| 96 | 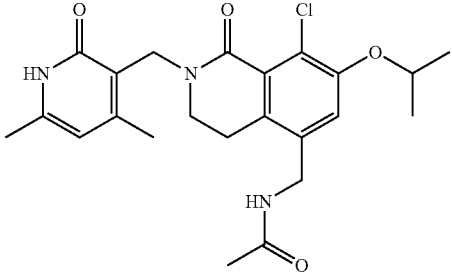<br>N-({8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}methyl)acetamide | $^1$H NMR (600 MHz, DMSO-d6) δ 8.42 (br. s., 1H) 8.24 (d, J = 4.95 Hz, 1H) 7.13 (s, 1H) 5.91 (s, 1 H) 4.51-4.61 (m, 3H) 4.20 (d, J= 5.69 Hz, 2H) 3.32-3.38 (m ,2 H) 2.69 (t, J = 5.96 Hz, 2H) 2.16 (s, 3H) 2.13 (s, 3H) 1.85 (s, 3H) 1.29 (d, J = 6.05 Hz, 6H); MS: 446.1 [M + 1] | G |
| 97 | 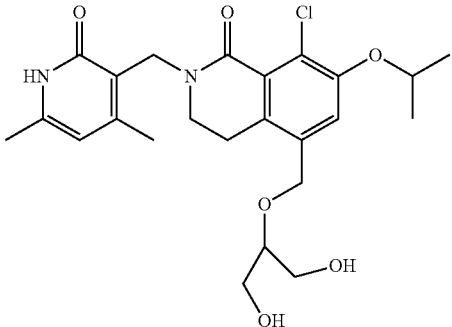<br>8-chloro-5-{[(1,3-dihydroxypropan-2-yl)oxy]methyl}-2-[(4,6-dimethyl-2-oxo-1,2-dihydropyridin-3-yl)methyl]-7-(propan-2-yloxy)-3,4-dihydroisoquinolin-1(2H)-one | $^1$H NMR (400 MHz, chloroform-d) δ 10.58 (br. s., 1H) 7.03 (s, 1H) 5.92 (s, 1H) 4.75 (s, 2H) 4.59 (s, 2H) 4.52 (dt, J = 12.13, 6.06 Hz, 1 H) 3.76 (dd, J = 11.62, 4.29 Hz, 2 H) 3.69 (dd, J = 11.62, 4.80 Hz, 2 H) 3.57 (t, J = 5.94 Hz, 2H) 3.48-3.54 (m, 1H) 2.80 (t, J = 6.06 Hz, 2H) 2.36 (s, 3H) 2.24 (s, 3H) 1.36 (d, J = 6.06 Hz, 6H); MS: 479.1 [M + 1] | G |

TABLE 1-continued

| Ex. | Structure/Name | ¹H NMR; LC-MS | Method |
|---|---|---|---|
| 98 | 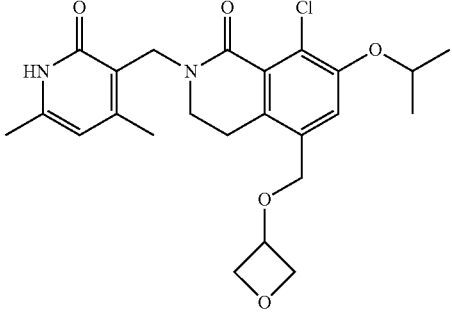<br>8-chloro-2-[(4,6-dimethyl-2-oxo-1,2-dihydropyridin-3-yl)methyl]-5-[(oxetan-3-yloxy)methyl]-7-(propan-2-yloxy)-3,4-dihydroisoquinolin-1(2H)-one | ¹H NMR (400 MHz, chloroform-d) δ 9.86 (br. s., 1H) 7.02 (s, 1H) 5.91 (s, 1H) 4.79 (s, 2H) 4.69-4.76 (m, 2H) 4.56-4.65 (m, 3H) 4.48-4.56 (m, 1H) 4.36 (s, 2H), 3.61 (t, J = 6.17 Hz, 2H) 2.78 (t, J = 6.17 Hz, 2H) 2.36 (s, 3H) 2.25 (s, 3H) 1.38 (d, J = 6.11 Hz, 6H); MS: 461.1 [M + 1] | G |
| 99 | 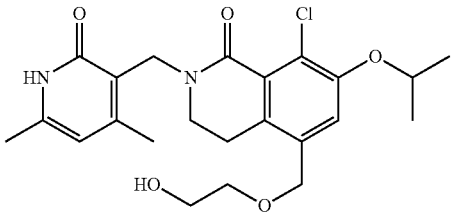<br>8-chloro-2-[(4,6-dimethyl-2-oxo-1,2-dihydropyridin-3-yl)methyl]-5-[(2-hydroxyethoxy)methyl]-7-(propan-2-yloxy)-3,4-dihydroisoquinolin-1(2H)-one | ¹H NMR (600 MHz, DMSO-d6) δ 7.27 (s, 1H) 5.89 (s, 1H) 4.61 (dt, J = 11.88, 6.08 Hz, 1H) 4.55 (s, 2H) 4.46 (s, 2H) 3.31-3.36 (m, 2H) 2.69 (t, J = 6.05 Hz, 2H) 2.14 (s, 3H) 2.12 (s, 3H) 1.27 (d, J = 5.87 Hz, 6H); MS: 449.1 [M + 1] | G |
| 100 | 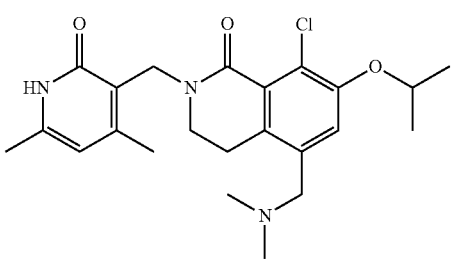<br>8-chloro-5-[(dimethylamino)methyl]-2-[(4,6-dimethyl-2-oxo-1,2-dihydropyridin-3-yl)methyl]-7-(propan-2-yloxy)-3,4-dihydroisoquinolin-1(2H)-one | ¹H NMR (600 MHz, DMSO-d6) δ 7.15 (s, 1H) 5.91 (s, 1H) 4.58-4.63 (m, 1H) 4.55 (s, 2H) 3.34 (m, 2H) 3.33 (s, 2H) 2.76 (d, J = 7.52 Hz, 2H) 2.16 (s, 3H) 2.13 (s, 3H) 2.11 (s, 6H) 1.27 (d, J = 6.05 Hz, 6H); MS: 432.1 [M + 1] | G |
| 101 | 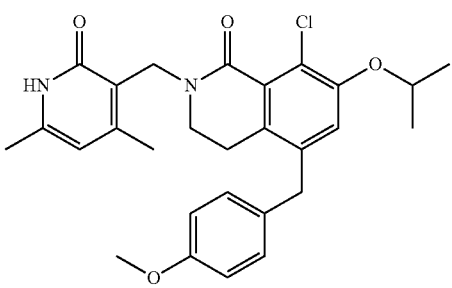<br>8-chloro-2-[(4,6-dimethyl-2-oxo-1,2-dihydropyridin-3-yl)methyl]-5-(4-methoxybenzyl)-7-(propan-2-yloxy)-3,4-dihydroisoquinolin-1(2H)-one | ¹H NMR (600 MHz, DMSO-d6) δ 11.58 (s, 1H) 7.17 (s, 1H) 7.02 (m, J = 8.44 Hz, 2H) 6.82 (m, J = 8.62 Hz, 2H) 5.88 (s, 1H) 4.55-4.62 (m, 1H) 4.50 (s, 2H) 3.89 (s, 2H) 3.68 (s, 3H) 3.28 (t, J = 5.78 Hz, 2H) 2.54-2.59 (m, 2H) 2.12 (s, 3H) 2.10 (s, 3H) 1.25 (d, J = 6.05 Hz, 6H); MS: 495.0 [M + 1] | G |

TABLE 1-continued

| Ex. | Structure/Name | ¹H NMR; LC-MS | Method |
|---|---|---|---|
| 102 | 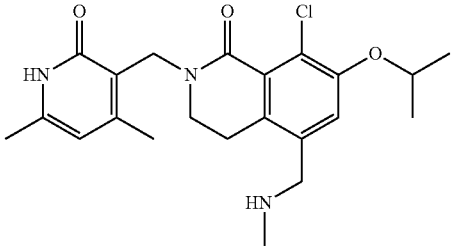<br>8-chloro-2-[(4,6-dimethyl-2-oxo-1,2-dihydropyridin-3-yl)methyl]-5-[(methylamino)methyl]-7-(propan-2-yloxy)-3,4-dihydroisoquinolin-1(2H)-one | ¹H NMR (600 MHz, DMSO-d6) δ 7.22 (s, 1H) 5.90 (s, 1H) 4.57-4.63 (m, 1H) 4.54 (s, 2H) 3.30-3.34 (m, 2H) 2.65-2.73 (m, 2H) 2.25 (s, 3H) 2.13 (s, 3H) 2.11 (s, 3H) 1.27 (d, J = 6.05 Hz, 6H); MS: 418.1 [M + 1] | G |
| 103 | 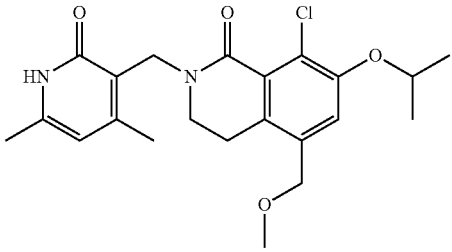<br>8-chloro-2-[(4,6-dimethyl-2-oxo-1,2-dihydropyridin-3-yl)methyl]-5-(methoxymethyl)-7-(propan-2-yloxy)-3,4-dihydroisoquinolin-1(2H)-one | ¹H NMR (700 MHz, DMSO-d6) δ 11.54 (br. s., 1H) 7.24 (s, 1H) 5.89 (s, 1H) 4.62 (quin, J = 6.05 Hz, 1H) 4.57 (s, 2H) 4.40 (s, 2H) 3.37-3.39 (m, 2H) 3.29 (s, 3H) 2.69 (t, J = 6.16 Hz, 2H) 2.17 (s, 3H) 2.13 (s, 3H) 1.29 (d, J = 5.94 Hz, 6H); MS: 419.1 [M + 1] | G |
| 104 | 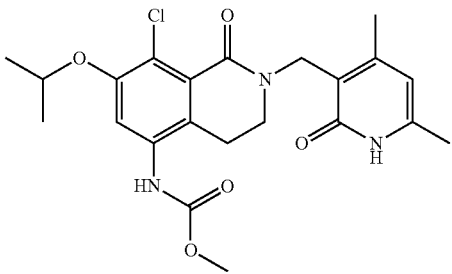<br>Methyl {8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}carbamate | ¹H NMR (400 MHz, DMSO-d6) δ 7.24 (s, 1H), 5.92 (s, 1H), 4.49-4.52 (m, 3H), 3.62 (s, 3H), 3.26-3.29 (t, J = 5.8 Hz, 2H), 2.53-2.56 (t, J = 6 Hz, 2H), 2.11-2.13 (d, J = 12 Hz, 6H), 1.25-1.26 (d, J = 6 Hz, 6H); MS: 448.2 [M + 1] | F |
| 105 | 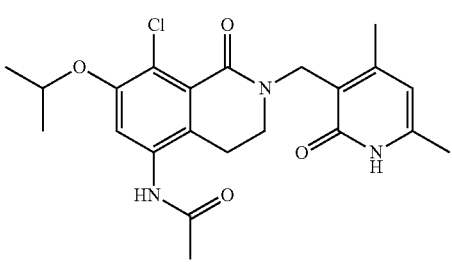<br>N-{8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}acetamide | ¹H NMR (400 MHz, DMSO-d6) δ 9.61 (br. s., 1H), 7.29 (s, 1H), 5.88 (s, 1H), 4.50-4.54 (m, 3H), 3.30-3.33 (t, J = 6 Hz, 2H), 2.53-2.56 (t, J = 6 Hz, 2H), 2.11-2.14 (d, J = 12.4 Hz, 6H), 2.02 (s, 3H), 1.26-1.28 (d, J = 6 Hz, 6H); MS: 432.2 [M + 1] | F |

TABLE 1-continued

| Ex. | Structure/Name | ¹H NMR; LC-MS | Method |
|---|---|---|---|
| 106 | N-{8-chloro-2-[(4,6-dimethyl-2-oxo-1,2-dihydropyridin-3-yl)methyl]-7-(propan-2-yloxy)-5-(pyrrolidin-1-ylmethyl)-3,4-dihydroisoquinolin-1(2H)-one | ¹H NMR (700 MHz, DMSO-d6) δ 11.56 (br. s., 1H) 9.67 (br. s., 1H) 7.46 (s, 1H) 5.90 (s, 1H) 4.66 (dt, J = 12.10, 6.05 Hz, 1H) 4.57 (s, 2H) 4.33-4.45 (m, 2H) 3.42-3.46 (m, 4H) 3.11 (br. s., 2H) 2.86 (t, J = 6.05 Hz, 2H) 2.19 (s, 3H) 2.14 (s, 3H) 2.05 (br. s., 2H) 1.87 (d, J = 5.94 Hz, 2H) 1.33 (d, J = 5.94 Hz, 6H); MS: 458.1 [M + 1] | G |
| 109 | 8-chloro-2-[(4,6-dimethyl-2-oxo-1,2-dihydropyridin-3-yl)methyl]-3,4-dihydroisoquinolin-1(2H)-one | ¹H NMR (400 MHz, chloroform-d) δ 11.40 (s, 1H), 7.35-7.32 (d, J = 8 Hz, 1H), 7.26-7.22 (t, 1H), 7.04-7.03 (d, J = 7.2 Hz, 1H), 5.93 (s, 1H), 4.77 (s, 2H), 3.62-3.59 (t, 2H), 2.85-2.82 (t, 2H), 2.35 (s, 3H), 2.26 (s, 3H); MS: 316.9 [M + 1]⁺ | I |
| 110 | 2-[(4,6-dimethyl-2-oxo-1,2-dihydropyridin-3-yl)methyl]-8-methyl-3,4-dihydroisoquinolin-1(2H)-one | ¹H NMR (400 MHz, methanol-d4) δ 7.28-7.26 (t, J = 7.6 Hz, 1H), 7.14-7.12 (d, J = 7.6 Hz, 1H), 7.05-7.03 (d, J = 7.2 Hz, 1H), 6.11 (s, 1H), 4.77 (s, 2H), 3.42-3.39 (t, J = 6.4 Hz, 2H), 2.85-2.82 (t, J = 6.4 Hz, 2H), 2.63 (s, 3H), 2.26 (s, 3H), 2.25 (s, 3H); MS: 296.9 [M + 1]+, 318.9 [M + 23]+ | I |
| 111 | 2-[(4,6-dimethyl-2-oxo-1,2-dihydropyridin-3-yl)methyl]-5-(propan-2-yloxy)-3,4-dihydroisoquinolin-1(2H)-one | ¹H NMR (400 MHz, chloroform-d): δ 12.21 (brs, 1H), 7.70-7.68 (d, J = 7.2 Hz, 1H), 7.24-7.22 (t, J = 7.6 Hz, 1H), 6.97-6.95 (d, J = 8 Hz, H), 5.92 (s, 1H), 4.78 (s, 2H), 4.51-4.48 (t, J = 5.6 Hz, 1H), 3.60-3.59 (t, J = 3 Hz, 2H), 2.85-2.84 (t, J = 3 Hz, 2H), 2.30 (s, 3H), 2.25 (s, 3H), 1.38-1.30 (d, J = 26 Hz, 6H); MS: 340.9 [M + 1]+ | I |
| 113 | 2-[(4,6-dimethyl-2-oxo-1,2-dihydropyridin-3-yl)methyl]-7-(propan-2-yloxy)-3,4-dihydro-2,6-naphthyridin-1(2H)-one | ¹H NMR (400 MHz, DMSO-d6) δ 11.56 (br. s., 1H) 8.11 (s, 1H) 7.03 (s, 1H) 5.89 (s, 1H) 5.22 (quin, J = 6.17 Hz, 1H) 4.57 (s, 2H) 3.47 (t, J = 6.48 Hz, 2H) 2.78 (t, J = 6.48 Hz, 2H) 2.14 (s, 3H) 2.13 (s, 3H) 1.29 (s, 3H) 1.28 (s, 3H); MS: 342.2 [M + 1] | J |

TABLE 1-continued

| Ex. | Structure/Name | ¹H NMR; LC-MS | Method |
|---|---|---|---|
| 115 | 4-[(4,6-dimethyl-2-oxo-1,2-dihydropyridin-3-yl)methyl]-7-methoxy-6-methyl-3,4-dihydro-1,4-benzoxazepin-5(2H)-one | ¹H NMR (400 MHz, DMSO-d6) δ 11.58 (s, 1H), 6.98 (d, J = 8.84 Hz, 1H), 6.83 (d, J = 8.84 Hz, 1H), 5.92 (s, 1H), 4.63 (s, 2H), 3.92 (t, J = 5.43 Hz, 2H), 3.77 (s, 3H), 3.33 (t, J = 5.56 Hz, 2H), 2.21 (s, 3H), 2.14 (s, 3H), 2.13 (s, 3H); MS: 343.1 [M + 1] | K |
| 117 | 4-[(4,6-dimethyl-2-oxo-1,2-dihydropyridin-3-yl)methyl]-6-fluoro-7-(propan-2-yloxy)-3,4-dihydro-1,4-benzoxazepin-5(2H)-one | ¹H NMR (400 MHz, chloroform-d) δ 12.62 (br. s., 1H), 6.99 (t, J = 8.84 Hz, 1H), 6.71 (d, J = 8.84 Hz, 1H), 6.01 (s, 1H), 4.86 (s, 2H), 4.44 (spt, J = 6.02 Hz, 1H), 4.05 (t, J = 5.43 Hz, 2H), 3.62 (t, J = 5.31 Hz, 2H), 2.38 (s, 3H), 2.29 (s, 3H), 1.33 (d, J = 6.06 Hz, 6H); MS: 375.2 [M + 1] | L |
| 118 | 4-[(4,6-dimethyl-2-oxo-1,2-dihydropyridin-3-yl)methyl]-6-fluoro-7-methoxy-3,4-dihydro-1,4-benzoxazepin-5(2H)-one | ¹H NMR (400 MHz, chloroform-d) δ 12.36 (br. s., 1H), 6.97 (t, J = 8.84 Hz, 1H), 6.75 (dd, J = 8.84, 1.77 Hz, 1H), 5.99 (s, 1H), 4.86 (s, 2H), 4.04 (t, J = 5.56 Hz, 2H), 3.88 (s, 3H), 3.62 (t, J = 5.56 Hz, 2H), 2.38 (s, 3H), 2.28 (s, 3H); MS: 347.2 [M + 1] | L |
| 119 | 6-chloro-4-[(4,6-dimethyl-2-oxo-1,2-dihydropyridin-3-yl)methyl]-7-(propan-2-yloxy)-3,4-dihydro-1,4-benzoxazepin-5(2H)-one | ¹H NMR (700 MHz, DMSO-d6) δ 7.21 (d, J = 8.60 Hz, 1H), 6.97 (d, J = 9.03 Hz, 1H), 5.93 (s, 1H), 4.61 (s, 2H), 4.58 (td, J = 6.08, 12.37 Hz, 1H), 3.98 (br. s., 2H), 2.21 (s, 3H), 2.14 (s, 3H), 1.27 (d, J = 6.02 Hz, 6H); MS: 391.1 [M + 1] | L |
| 120 | 6-chloro-4-[(4,6-dimethyl-2-oxo-1,2-dihydropyridin-3-yl)methyl]-7-methoxy-3,4-dihydro-1,4-benzoxazepin-5(2H)-one | ¹H NMR (700 MHz, DMSO-d6) δ 7.19 (d, J = 8.60 Hz, 1H), 7.01 (d, J = 9.03 Hz, 1H), 5.93 (br. s., 1H), 4.62 (br. s., 2H), 3.99 (br. s., 2H), 3.83 (s, 3H), 2.21 (s, 3H), 2.14 (br. s., 3H); MS: 363.0 [M + 1] | L |

TABLE 1-continued

| Ex. | Structure/Name | ¹H NMR; LC-MS | Method |
|---|---|---|---|
| 121 | 9-bromo-4-[(4,6-dimethyl-2-oxo-1,2-dihydropyridin-3-yl)methyl]-6-methyl-7-(propan-2-yloxy)-3,4-dihydro-1,4-benzoxazepin-5(2H)-one | ¹H NMR (700 MHz, DMSO-d6) δ 7.28 (1 H, s), 5.93 (1 H, s), 4.63 (2 H, s), 4.57 (1 H, spt, J = 6.02 Hz), 3.96 (2 H, br. s.), 2.20 (3 H, s), 2.14 (3 H, s), 2.09 (3 H, s), 1.25 (6 H, d, J = 5.94 Hz); MS: 449.1 [M + 1] | L |
| 122 | 4-[(4,6-dimethyl-2-oxo-1,2-dihydropyridin-3-yl)methyl]-6-methyl-7-(propan-2-yloxy)-3,4-dihydro-1,4-benzoxazepin-5(2H)-one | ¹H NMR (400 MHz, DMSO-d6) δ 11.59 (br. s., 1H) 7.00 (d, J = 8.80 Hz, 1H) 6.81 (d, J = 8.80 Hz, 1H) 5.93 (s, 1H) 4.63 (s, 2H) 4.50 (dt, J = 12.04, 6.08 Hz, 1H) 3.92 (t, J = 5.26 Hz, 2H) 2.21 (s, 3H) 2.14 (d, J = 1.96 Hz, 6H) 1.21-1.30 (m, 6H); MS: 371.1 [M + 1] | L |
| 125 | 6-chloro-7-(2,2-difluoroethoxy)-4-[(4,6-dimethyl-2-oxo-1,2-dihydropyridin-3-yl)methyl]-3,4-dihydro-1,4-benzoxazepin-5(2H)-one | ¹H NMR (400 MHz, DMSO-d6) δ 11.61 (br. s., 1H), 7.30 (d, J = 8.93 Hz, 1H), 7.03 (d, J = 8.93 Hz, 1 H), 6.20-6.59 (m, 1H), 5.94 (s, 1 H), 4.63 (s, 2H), 4.39 (td, J = 14.46, 3.24 Hz, 2H), 4.01 (br. s., 2H), 3.41 (br. s., 2H), 2.22 (s, 3H), 2.15 (s, 3H); MS: 413.1 [M + 1] | N |
| 127 | 4-[(4,6-dimethyl-2-oxo-1,2-dihydropyridin-3-yl)methyl]-6-methyl-7-(1-methyl-1H-pyrazol-5-yl)-3,4-dihydro-12,4-benzoxazepin-5(2H)-one | ¹H NMR (400 MHz, DMSO-d6) δ 11.60 (br. s., 1H), 7.49 (d, J = 1.77 Hz, 1H), 7.29 (d, J = 8.34 Hz, 1H), 6.98 (d, J = 8.34 Hz, 1H), 6.24 (d, J = 1.77 Hz, 1H), 5.93 (s, 1H), 4.66 (s, 2H), 4.08 (t, J = 5.31 Hz, 2H), 3.56 (s, 3H), 3.44 (t, J = 5.43 Hz, 2H), 2.23 (s, 3H), 2.14 (s, 3H), 2.09 (s, 3H); MS: 393.1 [M + 1] | O |

TABLE 1-continued

| Ex. | Structure/Name | ¹H NMR; LC-MS | Method |
|---|---|---|---|
| 129 | 4-[(4,6-dimethyl-2-oxo-1,2-dihydropyridin-3-yl)methyl]-6-methyl-9-(1-methyl-1H-pyrazol-4-yl)-7-(propan-2-yloxy)-3,4-dihydro-1,4-benzoxazepin-5(2H)-one | ¹H NMR (400 MHz, DMSO-d6) δ 8.14 (s, 1H), 7.91 (s, 1H), 7.24 (s, 1H), 5.94 (s, 1H), 4.58-4.71 (m, 3H), 3.91 (br. s., 2H), 3.85 (s, 3H), 3.34 (br. s., 2H), 2.23 (s, 3H), 2.14 (s, 3H), 2.11 (s, 3H), 1.27 (d, J = 6.06 Hz, 6H); MS: 451.2 [M + 1] | P |
| 135 | 2-[(4,6-dimethyl-2-oxo-1,2-dihydropyridin-3-yl)methyl]-6-(propan-2-yloxy)-2,3-dihydro-1H-isoindol-1-one | ¹H NMR (400 MHz, methanol-d4): δ 7.39-7.37 (d, J = 8.4 Hz, 1H), 7.26-7.25 (d, J = 2.4 Hz, 1H), 7.12-7.09 (m, 1H), 6.11 (s, 1H), 4.74 (s, 2H), 4.68-4.62 (m, 1H), 2.32 (s, 3H), 2.25 (s, 3H), 1.34-1.31 (m, 6H); MS: 327.0 [M + 1]+ | U |

TABLE 2

| Ex. | Structure/Name | 1H NMR/LCMS (M + H) | Method |
|---|---|---|---|
| 136 | 8-chloro-2-[(4,6-dimethyl-2-oxo-1,2-dihydropyridin-3-yl)methyl]-5-(hydroxymethyl)-7-(propan-2-yloxy)-3,4-dihydroisoquinolin-1(2H)-one | ¹H NMR (700 MHz, DMSO-17 mm) d ppm 7.25 (s, 1H) 5.88 (s, 1H) 4.56-4.60 (m, 1H) 4.55 (s, 2H) 4.45 (s, 2H) 3.33-3.35 (m, 2H) 2.65 (t, J = 6.27 Hz, 2H) 2.14 (s, 3H) 2.12 (s, 3H) 1.29 (s, 3H) 1.28 (s, 3H); MS: 405 [M + 1] | G |
| 137 | 8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one | ¹H NMR (400 MHz, DMSO-d6): δ 7.50-7.48 (m, 1H), 7.41-7.39 (m, 1H), 5.90 (s,1H), 4.58 (s, 2H), 3.76 (s, 3H), 3.51-3.48 (m, 2H), 2.94-2.91 (m, 2H), 2.19 (s, 3H), 2.13 (s, 3H), 2.08 (s, 3H); MS: 412 [M + 1] | D |

TABLE 2-continued

| Ex. | Structure/Name | 1H NMR/LCMS (M + H) | Method |
|---|---|---|---|
| 138 | 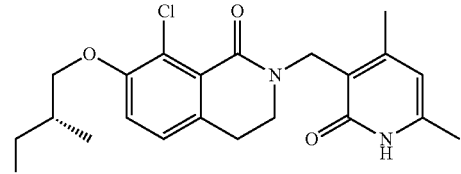<br>Chiral<br>8-chloro-2-[(4,6-dimethyl-2-oxo-1,2-dihydropyridin-3-yl)methyl]-7-{[(2S)-3-hydroxy-2-methylpropyl]oxy}-3,4-dihydroisoquinolin-1(2H)-one | $^1$H NMR (400 MHz, DMSO-d6) δ 11.55 (s, 1H), 7.24 (s, 2H), 5.88 (s, 1H), 4.60-4.57 (d, J = 12, 3H), 4.06-3.89 (m, 3H), 3.45-3.40 (m, 3H), 2.74 (s, 2H), 2.14-2.01 (m, 7H), 0.98-0.97 (d, J = 4, 3H); MS: 427 [M + Na] | A |
| 139 | 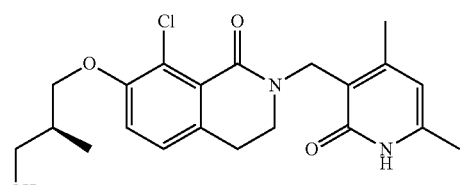<br>Chiral<br>8-chloro-2-[(4,6-dimethyl-2-oxo-1,2-dihydropyridin-3-yl)methyl]-7-{[(2R)-3-hydroxy-2-methylpropyl]oxy}-3,4-dihydroisoquinolin-1(2H)-one | $^1$H NMR (400 MHz, DMSO-d6): δ 11.56 (s, 1H), 7.19-7.14 (t, 2H), 5.88 (s, 1H), 4.61-4.57 (m, 3H), 3.99-3.88 (m, 3H), 3.45-3.40 (m, 3H), 2.75-2.72 (t, 2H), 2.14-1.98 (m, 7H), 0.98-0.97 (m, J = 4 Hz, 7H); MS: 405 [M + 1] | A |
| 140 | 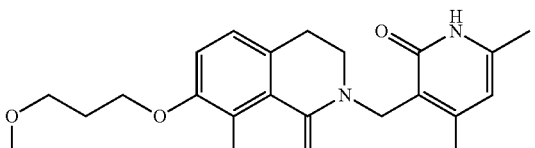<br>8-chloro-2-[(4,6-dimethyl-2-oxo-1,2-dihydropyridin-3-yl)methyl]-7-(3-methoxypropoxy)-3,4-dihydroisoquinolin-1(2H)-one | $^1$H NMR (400 MHz, DMSO-d6) d 11.54 (br. s., 1H), 7.10-7.28 (m, 2H), 5.88 (s, 1H), 4.57 (s, 2H), 4.07 (t, J = 6.24 Hz, 2H), 3.50 (t, J = 6.24 Hz, 2H), 3.36 (t, J = 5.75 Hz, 2H), 3.24 (s, 3H), 2.74 (t, J = 5.62 Hz, 2H), 2.13 (d, J = 11.25 Hz, 6H), 1.96 (quin, J = 6.11 Hz, 2H); MS: 405 [M + 1] | C |
| 141 | 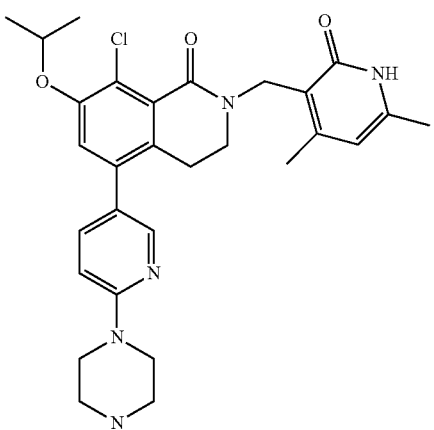<br>8-chloro-2-[(4,6-dimethyl-2-oxo-1,2-dihydropyridin-3-yl)methyl]-5-[6-(piperazin-1-yl)pyridin-3-yl]-7-(propan-2-yloxy)-3,4-dihydroisoquinolin-1(2H)-one | $^1$H NMR (400 MHz, methanol-d4) d ppm 8.09 (d, J = 2.27 Hz, 1 H), 7.56 (dd, J = 8.59, 2.53 Hz, 1 H), 7.09 (s, 1H), 6.88 (d, J = 8.84 Hz, 1H), 6.10 (s, 1H), 4.77 (s, 2H), 4.60-4.70 (m, 1H), 3.55-3.63 (m, 4H), 3.35 (t, J = 6.06 Hz, 2H), 2.92-3.02 (m, 4H), 2.75 (t, J = 6.06 Hz, 2H), 2.30 (s, 3H), 2.24 (s, 3H), 1.36 (d, J = 5.81 Hz, 6H); MS: 536 [M + 1] | F |
| 142 | 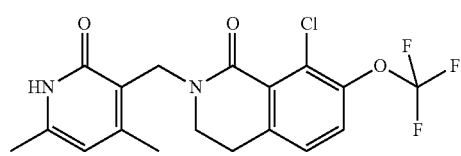 [SMILES: Cc1cc(C)c(CN2CCc3ccc(OC(F)(F)F)c(Cl)c3C2=O)c(=O)[nH]1]<br>8-chloro-2-[(4,6-dimethyl-2-oxo-1,2-dihydropyridin-3-yl)methyl]-7-(trifluoromethoxy)-3,4-dihydroisoquinolin-1(2H)-one | $^1$H NMR (400 MHz, CDCl$_3$) d 7.33 (d, J = 8.19 Hz, 1H), 7.09 (d, J = 8.31 Hz, 1H), 5.94 (s, 1H), 4.79 (s, 2H), 3.67 (t, J = 6.11 Hz, 2H), 2.87 (t, J = 5.99 Hz, 2H), 2.37 (s, 3H), 2.28 (s, 3H); MS: 401 [M + 1] | A |

TABLE 2-continued

| Ex. | Structure/Name | 1H NMR/LCMS (M + H) | Method |
|---|---|---|---|
| 144 | N-({8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}methyl)-1-methylpiperidine-4-carboxamide | $^1$H NMR (600 MHz, DMSO-17 mm) d ppm 8.35 (br. s., 2H) 8.27 (t, J = 5.14 Hz, 1H) 7.07 (S, 1 H) 5.91 (s, 1H) 4.50-4.60 (m, 3 H) 4.20 (d, J = 5.50 Hz, 2H) 3.32-3.37 (m, 2H) 2.89 (d, J = 9.54 Hz, 2H) 2.67 (t, J = 5.96 Hz, 2H) 2.22-2.28 (m, 3H) 2.11-2.21 (m, 7 H) 2.02-2.11 (m, 2H) 1.58-1.71 (m, 4H) 1.28 (d, J = 6.05 Hz, 6H); MS: 529 [M + 1] | G |
| 146 | 5,8-dichloro-2-[(4,6-dimethyl-2-oxo-1,2-dihydropyridin-3-yl)methyl]-6,7-dimethoxy-3,4-dihydroisoquinolin-1(2H)-one | $^1$H NMR (400 MHz, methanol-d4) δ 6.10 (s, 1H), 4.73 (s, 2H), 3.94 (s, 3H), 3.87 (s, 3H), 3.48 (t, J = 6.24 Hz, 2H), 2.95 (t, J = 6.24 Hz, 2H), 2.28 (s, 3H), 2.24 (s, 3H); MS: 411 [M + 1] | C |
| 147 | 8-chloro-7-[(1,1-difluoropropan-2-yl)oxy]-2-[(4,6-dimethyl-2-oxo-1,2-dihydropyridin-3-yl)methyl]-3,4-dihydroisoquinolin-1(2H)-one | $^1$H NMR (400 MHz, Methanol-d4): δ 7.26 (d, J = 8.4 Hz, 1H), 7.17 (d, J = 8.4 Hz, 1H), 6.14-5.86 (m, 2H), 4.78 (s, 2H), 4.65-4.59 (m, 1H), 3.48 (t, J = 6 Hz, 2H), 2.84 (t, J = 6 Hz, 2H), 2.30 (s, 3H), 2.26 (s, 3H), 1.41 (d, J = 6.4 Hz, 3H); MS: 411 [M + 1] | C |
| 148 | 7-(butan-2-yloxy)-8-chloro-2-[(4,6-dimethyl-2-oxo-1,2-dihydropyridin-3-yl)methyl]-3,4-dihydroisoquinolin-1(2H)-one | $^1$H NMR (400 MHz, methanol-d4) δ 7.07-7.15 (m, 2H), 6.10 (s, 1H), 4.76 (s, 2H), 4.39 (sxt, J = 5.97 Hz, 1H), 3.44 (t, J = 6.11 Hz, 2H), 2.79 (t, J = 6.11 Hz, 2H), 2.27 (s, 3H), 2.24 (s, 3H), 1.60-1.82 (m, 2H), 1.28 (d, J = 6.11 Hz, 3H), 1.00 (1, J = 7.46 Hz, 3H); MS: 389 [M + 1] | C |
| 149 | 7-(butan-2-yloxy)-6-chloro-2-[(4,6-dimethyl-2-oxo-1,2-dihydropyridin-3-yl)methyl]-3,4-dihydroisoquinolin-1(2H)-one | MS: 389 [M + 1] | C |

TABLE 2-continued

| Ex. | Structure/Name | 1H NMR/LCMS (M + H) | Method |
|---|---|---|---|
| 150 | 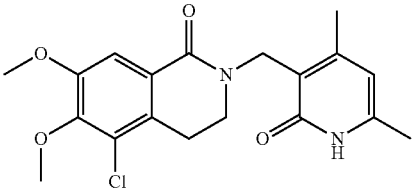<br>5-chloro-2-[(4,6-dimethyl-2-oxo-1,2-dihydropyridin-3-yl)methyl]-6,7-dimethoxy-3,4-dihydroisoquinolin-1(2H)-one | ¹H NMR (400 MHz, methanol-d4) δ 7.52 (s, 1H), 6.03 (s, 1H), 4.65 (s, 2H), 3.84 (s, 3H), 3.79 (s, 3H), 3.49 (t, J = 6.82 Hz, 2H), 2.85 (t, J = 6.69 Hz, 2H), 2.21 (s, 3H), 2.17 (s, 3H); MS: 377 [M + 1] | C |
| 151 | 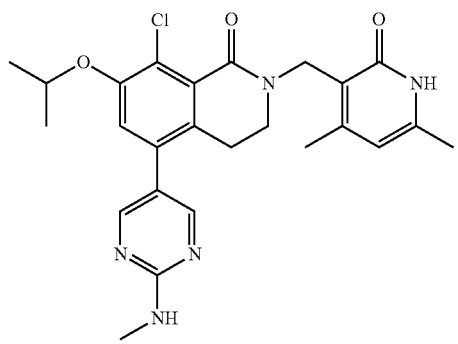 [SMILES: CNc1ncc(-c2cc(OC(C)C)c(Cl)c3c2CCN(Cc2c(C)cc(C)[nH]c2=O)C3=O)cn1]<br>8-chloro-2-[(4,6-dimethyl-2-oxo-1,2-dihydropyridin-3-yl)methyl]-5-[2-(methylamino)pyrimidin-5-yl]-7-(propan-2-yloxy)-3,4-dihydroisoquinolin-1(2H)-one | ¹H NMR (400 MHz, DMSO): δ 11.56 (s, 1H), 8.35 (s, 2H), 7.32-7.33 (d, 1H), 7.20 (s, 1H), 5.89 (s, 1H), 4.73-4.76 (m, 1H), 4.57 (s, 2H), 3.27-3.28 (m, 2H), 2.83-2.84 (d, 3H), 2.68-2.70 (m, 2H), 2.12-2.17 (d, 6H), 1.29-1.30 (d, 6H); MS: 482 [M + 1] | F |
| 152 | 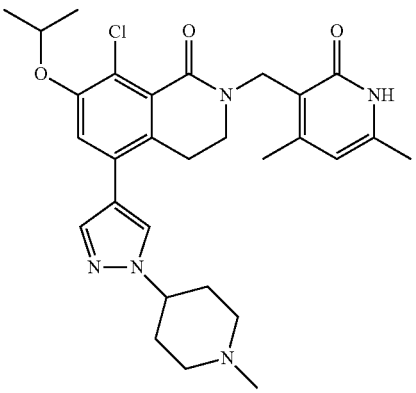 [SMILES: Cc1cc(C)c(CN2CCc3c(-c4cnn(C5CCN(C)CC5)c4)cc(OC(C)C)c(Cl)c3C2=O)c(=O)[nH]1]<br>8-chloro-2-[(4,6-dimethyl-2-oxo-1,2-dihydropyridin-3-yl)methyl]-5-[1-(1-methylpiperidin-4-yl)-1H-pyrazol-4-yl]-7-(propan-2-yloxy)-3,4-dihydroisoquinolin-1(2H)-one | ¹H NMR (400 MHz, Methanol): δ 7.90 (s, 1H), 7.66 (s, 1H), 7.19 (s, 1H), 6.12 (s, 1H), 4.70-4.60 (m, 2H), 4.35-4.35 (m, 1H), 3.39-3.36 (m, 2H), 3.18-3.15 (m, 2H), 2.89-2.86 (m, 2H), 2.49 (m, 5H), 2.30 (s, 3H), 2.24 (s, 3H), 2.25-2.10 (m, 4H), 1.36-1.35 (m, 6H); MS: 538 [M + 1] | F |
| 153 | 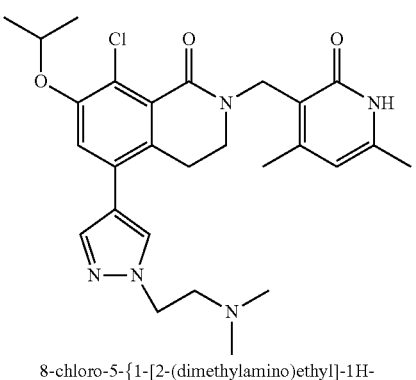<br>8-chloro-5-{1-[2-(dimethylamino)ethyl]-1H-pyrazol-4-yl}-2-[(4,6-dimethyl-2-oxo-1,2-dihydropyridin-3-yl)methyl]-7-(propan-2-yloxy)-3,4-dihydroisoquinolin-1(2H)-one | ¹H NMR (400 MHz, DMSO-d6): δ 8.27 (s, 1H), 8.03 (s, 1H), 7.71 (s, 1H), 7.24 (s, 1H), 5.90 (s, 1H), 4.73 (s, 1H), 4.59 (s, 2H), 4.21 (t, J = 6.0 Hz, 2H), 3.31 (m, 2H), 2.80 (s, 2H), 2.69 (t, J = 6.4 Hz, 2H), 2.18 (s, 9H), 2.13 (s, 3H), 1.30 (d, J = 6.0 Hz, 6H); MS: 512 [M + 1] | F |

TABLE 2-continued

| Ex. | Structure/Name | 1H NMR/LCMS (M + H) | Method |
|---|---|---|---|
| 154 | 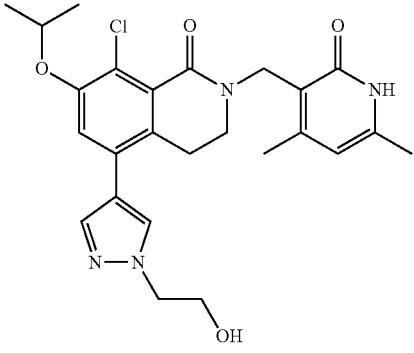 [SMILES: Cc1cc(C)c(CN2CCc3c(-c4cnn(CCO)c4)cc(OC(C)C)c(Cl)c3C2=O)c(=O)[nH]1]<br>8-chloro-2-[(4,6-dimethyl-2-oxo-1,2-dihydropyridin-3-yl)methyl]-5-[1-(2-hydroxyethyl)-1H-pyrazol-4-yl]-7-(propan-2-yloxy)-3,4-dihydroisoquinolin-1(2H)-one | $^1$H NMR (400 MHz, DMSO-d6): δ 11.58 (brs, 1H), 8.00 (s, 1H), 7.72 (s, 1H), 7.24 (s, 1H), 5.90 (s, 1H), 4.93 (t, J = 5.2 Hz, 1H), 4.73 (m, 1H), 4.59 (s, 2H), 4.16 (t, J = 6.0 Hz, 2H), 3.78-3.74 (m, 2H), 3.35-3.31 (m, 2H), 2.81 (m, 2H), 2.18 (s, 3H), 2.13 (s, 3H), 1.30 (d, J = 6.0 Hz, 6H); MS: 485 [M + 1] | F |
| 155 | 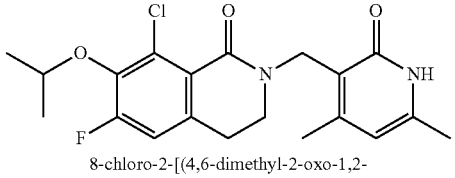<br>8-chloro-2-[(4,6-dimethyl-2-oxo-1,2-dihydropyridin-3-yl)methyl]-6-fluoro-7-(propan-2-yloxy)-3,4-dihydroisoquinolin-1(2H)-one | $^1$H NMR (400 MHz, DMSO-d6) d 11.54 (br. s., 1H), 7.23 (d, J = 10.51 Hz, 1H), 5.89 (s, 1H), 4.56 (s, 2H), 4.39 (td, J = 5.99, 12.23 Hz, 1H), 3.41 (t, J = 6.17 Hz, 2H), 2.79 (t, J = 6.17 Hz, 2H), 2.17 (s, 3H), 2.13 (s, 3H), 1.29 (d, J = 5.99 Hz, 6H); MS: 393 [M + 1] | C |
| 156 | 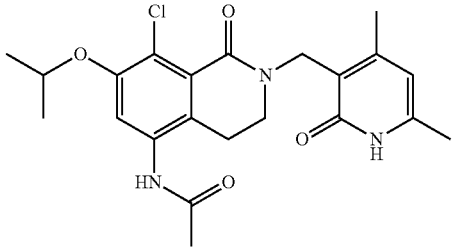 [SMILES: CC(=O)Nc1cc(OC(C)C)c(Cl)c2c1CCN(Cc1c(C)cc(C)[nH]c1=O)C2=O]<br>N-{8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}acetamide | $^1$H NMR (400 MHz, DMSO): δ 9.62 (s, 1H), 7.30 (s, 1H), 5.88 (s, 1H), 4.54-4.51 (m, 3H), δ 3.35-3.44 (m, 2H), 2.55-2.53 (m, 2H), 2.16-2.12 (d, 6H), 2.03 (s, 3H), 1.29-1.27 (s, 6H); MS: 432 [M + 1] | Y |
| 157 | 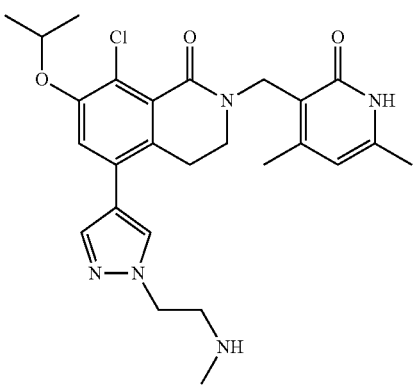 [SMILES: CNCCn1cc(-c2cc(OC(C)C)c(Cl)c3c2CCN(Cc2c(C)cc(C)[nH]c2=O)C3=O)cn1]<br>8-chloro-2-[(4,6-dimethyl-2-oxo-1,2-dihydropyridin-3-yl)methyl]-5-{1-(2-(methylamino)ethyl]-1H-pyrazol-4-yl}-7-(propan-2-yloxy)-3,4-dihydroisoquinolin-1(2H)-one | $^1$H NMR (400 MHz, Methanol-d4): δ 7.94 (s, 1H), 7.76 (s, 1H), 7.21 (s, 1H), 6.15 (s, 1H), 4.79 (s, 2H), 4.70-4.60 (m, 1H), 4.56 (s, 2H), 3.54 (s, 2H), 3.41 (s, 2H), 2.90 (s, 2H), 2.78 (s, 3H), 2.33 (s, 3H), 2.27 (s, 3H), 1.37 (d, J = 6 Hz, 6H); MS: 498 [M + 1] | F |

| Ex. | Structure/Name | 1H NMR/LCMS (M + H) | Method |
|---|---|---|---|
| 158 | 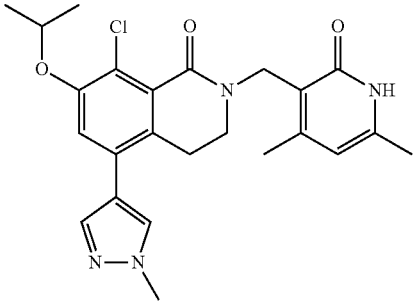 [SMILES: Cc1cc(C)c(CN2CCc3c(-c4cnn(C)c4)cc(OC(C)C)c(Cl)c3C2=O)c(=O)[nH]1]<br>8-chloro-2-[(4,6-dimethyl-2-oxo-1,2-dihydropyridin-3-yl)methyl]-5-(1-methyl-1H-pyrazol-4-yl)-7-(propan-2-yloxy)-3,4-dihydroisoquinolin-1(2H)-one | $^1$H NMR (400 MHz, CDCl3): δ 12.16 (s, 1H), 7.49 (s, 1H), 7.39 (s, 1H), 6.99 (s, 1H), 5.93 (s, 1H), 4.79 (s, 2H), 4.54-4.51 (m, 1H), 3.94 (s, 3H), 3.49 (t, J = 5.6 Hz, 2H), 2.80 (t, J = 5.6 Hz, 2H), 2.35 (s, 3H), 2.26 (s, 3H), 1.37 (d, J = 6 Hz, 6H); MS: 455 [M + 1] | F |
| 159 | 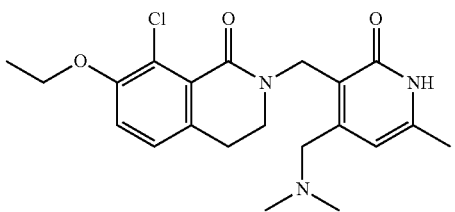 [SMILES: CCOc1ccc2c(c1Cl)C(=O)N(Cc1c(CN(C)C)cc(C)[nH]c1=O)CC2]<br>8-chloro-2-({4-[(dimethylamino)methyl]-6-methyl-2-oxo-1,2-dihydropyridin-3-yl}methyl)-7-ethoxy-3,4-dihydroisoquinolin-1(2H)-one | $^1$H NMR (600 MHz, DMSO-17 mm) d 7.20-7.16 (m, 1H), 7.16-7.13 (m, 1H), 6.13 (s, 1H), 4.62 (s, 2H), 4.08 (q, J = 7.0 Hz, 2H), 3.30 (s, 3H), 2.74 (t, J = 5.9 Hz, 2H), 2.15 (s, 3H), 2.09 (s, 6H), 1.34 (t, J = 6.8 Hz, 3H); MS: 404 [M + 1] | C |
| 160 | 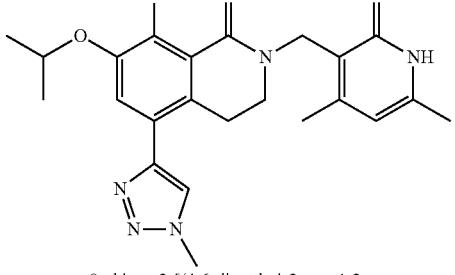<br>8-chloro-2-[(4,6-dimethyl-2-oxo-1,2-dihydropyridin-3-yl)methyl]-5-(1-methyl-1H-1,2,3-triazol-4-yl)-7-(propan-2-yloxy)-3,4-dihydroisoquinolin-1(2H)-one | $^1$H NMR (400 MHz, DMSO-d6): δ 12.00 (s, 1H), 8.41 (s, 1H), 7.55 (s, 1H), 5.90 (s, 1H), 4.70-4.60 (m, 1H), 4.58 (s, 2H), 4.09 (s, 3H), 3.35-3.30 (m, 2H), 2.87-2.85 (m, 2H), 2.17 (s, 3H), 2.12 (s, 3H), 1.32-1.31 (m, 6H); MS: 456 [M + 1] | F |
| 161 | 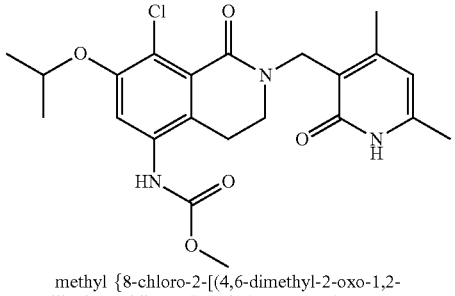<br>methyl {8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}carbamate | $^1$H NMR (400 MHz, DMSO): δ 11.56 (s, 1H), 9.39 (s, 1H), 7.28 (s, 1H), 5.88 (s, 1H), δ 4.50 (t, J = 9.0 Hz, 3H), 3.65 (s, 3H), 3.32-3.30 (m, 2H), 2.57 (t, J = 5.8 Hz, 2H), 2.15 (s, 3H), 2.12 (s, 3H), 1.28 (d, J = 6.0 Hz, 6H); MS: 448 [M + 1] | Y |
| 162 | 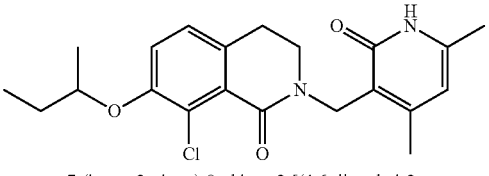<br>7-(butan-2-yloxy)-8-chloro-2-[(4,6-dimethyl-2- | $^1$H NMR (400 MHz. DMSO-d6) δ 11.53 (br. s., 1H), 7.20 (d, J = 8.56 Hz, 1H), 7.13 (d, J = 8.19 Hz, 1H), 5.88 (s, 1H), 4.56 (s, 2H), 4.42 (sxt, J = 5.97 Hz, 1H), 3.35-3.40 (m, 2H), 2.73 (t, J = 6.05 Hz, 2H), 2.15 (s, 3H), 2.12 (s, 3H), 1.55-1.73 (m, 2H), 1.23 (d, J = 5.99 Hz, 3H), 0.93 (t, J = | C |

TABLE 2-continued

| Ex. | Structure/Name | 1H NMR/LCMS (M + H) | Method |
|---|---|---|---|
| | oxo-1,2-dihydropyridin-3-yl)methyl]-3,4-dihydroisoquinolin-1(2H)-one | 7.40 Hz, 3H); MS: 389 [M + 1] | |
| 163 | 7-(butan-2-yloxy)-8-chloro-2-[(4,6-dimethyl-2-oxo-1,2-dihydropyridin-3-yl)methyl]-3,4-dihydroisoquinolin-1(2H)-one | $^1$H NMR (400 MHz, DMSO-d6) δ 11.54 (br. s., 1H), 7.21 (d, J = 8.31 Hz, 1H), 7.14 (d, J = 8.56 Hz, 1H), 5.89 (s, 1H), 4.58 (s, 2H), 4.43 (sxt, J = 5.92 Hz, 1H), 3.36-3.42 (m, 2H), 2.74 (t, J = 5.99 Hz, 2H), 2.16 (s, 3H), 2.13 (s, 3H), 1.65 (tq, J = 6.72, 13.37 Hz, 2H), 1.24 (d, J = 6.11 Hz, 3H), 0.94 (t, J = 7.46 Hz, 3H); MS: 389 [M + 1] | C |
| 164 | 8-chloro-2-[(4,6-dimethyl-2-oxo-1,2-dihydropyridin-3-yl)methyl]-7-(propan-2-yloxy)-5-(pyrimidin-5-yl)-3,4-dihydroisoquinolin-1(2H)-one | $^1$H NMR (400 MHz, DMSO-d6): δ 11.57 (brs, 1H), 9.23 (s, 1H), 8.92 (s, 2H), 7.36 (s, 1H), 5.90 (s, 1H), 4.78 (t, J = 5.2 Hz, 1H), 4.59 (s, 2H), 3.42 (s, 2H), 3.30 (m, 2H), 2.18 (s, 3H), 2.12 (s, 3H), 1.31 (d, J = 6.0 Hz, 6H); MS: 452 [M + 1] | F |
| 165 | 5-[1-(azetidin-3-yl)-1H-pyrazol-4-yl]-8-chloro-2-[(4,6-dimethyl-2-oxo-1,2-dihydropyridin-3-yl)methyl]-7-(propan-2-yloxy)-3,4-dihydroisoquinolin-1(2H)-one | $^1$H NMR (400 MHz, Methanol-d4): δ ppm 7.93 (s, 1H), 7.88 (s, 1H), 7.23 (s, 1H), 6.35-6.46 (m, 2H), 5.44-5.54 (m, 1H), 4.82 (s, 2H), 4.70-4.67 (m, 1H), 4.59 (d, J = 8 Hz, 4H), 3.49 (s, 2H), 2.94 (s, 2H), 2.42 (d, J = 8 Hz, 3H), 2.34 (d, J = 8 Hz, 3H), 1.38 (d, J = 4 Hz, 6H); MS: 496 [M + 1] | F |
| 166 | 8-chloro-2-[(4-ethyl-6-methyl-2-oxo-1,2-dihydropyridin-3-yl)methyl]-7-(propan-2-yloxy)-3,4-dihydro-2,6-naphthyridin-1(2H)-one | $^1$H NMR (400 MHz, DMSO-d6) d 11.56 (br. s., 1H), 8.02 (s, 1H), 5.93 (s, 1H), 5.25 (quin, J = 6.14 Hz, 1H), 4.61 (s, 2H), 3.42 (t, J = 6.05 Hz, 2H), 2.76 (t, J = 5.87 Hz, 2H), 2.14 (s, 3H), 1.31 (d, J = 6.11 Hz, 6H), 1.00 (t, J = 7.58 Hz, 3H); MS: 390 [M + 1] | J |

TABLE 2-continued

| Ex. | Structure/Name | 1H NMR/LCMS (M + H) | Method |
|---|---|---|---|
| 167 | 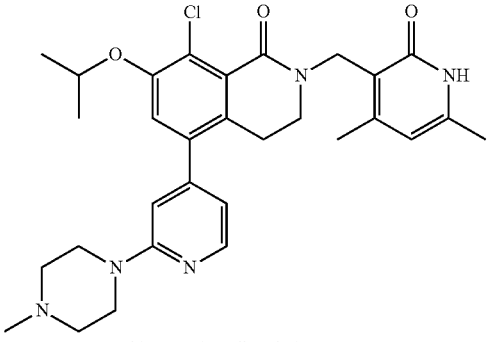<br>8-chloro-2-[(4,6-dimethyl-2-oxo-1,2-dihydropyridin-3-yl)methyl]-5-[2-(4-methylpiperazin-1-yl)pyridin-4-yl]-7-(propan-2-yloxy)-3,4-dihydroisoquinolin-1(2H)-one | ¹H NMR (400 MHz, Methanol-d4): δ 8.21 (d, J = 5.2 Hz, 1H), 7.13 (s, 1H), 6.85 (s, 1H), 6.74 (d, J = 4.8 Hz, 1H), 6.13 (s, 1H), 4.90 (m, 1H), 4.78 (s, 2H), 4.70-4.67 (m, 2H), 3.77 & 3.05 (m, 8H), 2.75 (t, J = 6.4 Hz, 2H), 2.71 (s, 3H), 2.33 (s, 3H), 2.25 (s, 3H), 1.37 (d, J = 6.0 Hz, 6H); MS: 550 [M + 1]. | F |
| 168 | 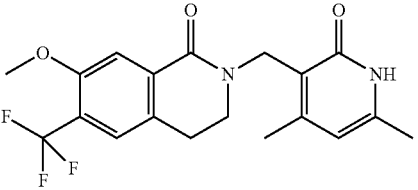<br>2-[(4,6-dimethyl-2-oxo-1,2-dihydropyridin-3-yl)methyl]-7-methoxy-6-(trifluoromethyl)-3,4-dihydroisoquinolin-1(2H)-one | ¹H NMR (400 MHz, CDCl₃) d 7.74 (s, 1H), 7.37 (s, 1H), 5.95 (s, 1H), 4.76 (s, 2H), 3.95 (s, 3H), 3.73 (t, J = 6.66 Hz, 2H), 2.87 (t, J = 6.66 Hz, 2H), 2.36 (s, 3H), 2.28 (s, 3H); MS: 381 [M + 1] | B |
| 169 | 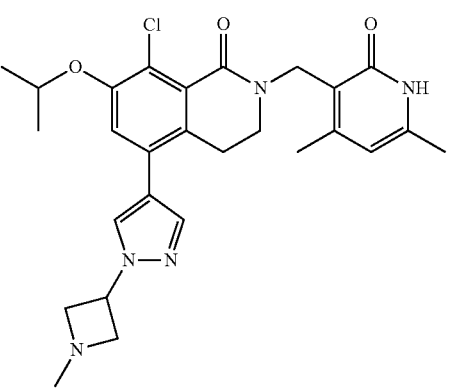 [SMILES: Cc1cc(C)c(CN2CCc3c(-c4cnn(C5CN(C)C5)c4)cc(OC(C)C)c(Cl)c3C2=O)c(=O)[nH]1]<br>8-chloro-2-[(4,6-dimethyl-2-oxo-1,2-dihydropyridin-3-yl)methyl]-5-[1-(1-methylazetidin-3-yl)-1H-pyrazol-4-yl]-7-(propan-2-yloxy)-3,4-dihydroisoquinolin-1(2H)-one | ¹H NMR (400 MHz, Methanol-d4): δ ppm 7.97 (s, 1H), 7.78 (s, 1H), 7.21 (s, 1H), 6.14 (s, 1H), 5.15 (s, 1H), 4.79 (s, 2H), 4.05-4.13 (m, 2H), 3.85-3.94 (m, 2H), 3.40 (s, 3H), 2.90 (t, J = 6 Hz, 2H), 2.66 (s, 3H), 2.32 (s, 3H), 2.26 (s, 3H), 1.38 (d, J = 4 Hz, 6H); MS: 510 [M + 1] | F |
| 170 | 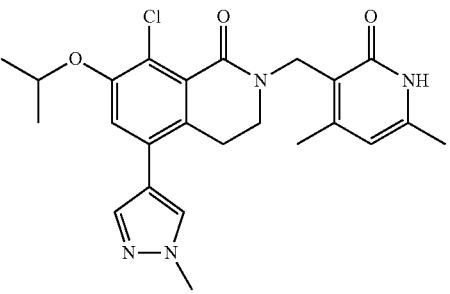 [SMILES: Cc1cc(C)c(CN2CCc3c(-c4cnn(C)c4)cc(OC(C)C)c(Cl)c3C2=O)c(=O)[nH]1]<br>8-chloro-2-[(4,6-dimethyl-2-oxo-1,2-dihydropyridin-3-yl)methyl]-5-(1-methyl-1H-pyrazol-3-yl)-7-(propan-2-yloxy)-3,4-dihydroisoquinolin-1(2H)-one | ¹H NMR (400 MHz, DMSO-d6): δ 11.56 (s, 1H), 7.50 (s, 1H), 7.23 (s, 1H), 6.34 (s, 1H), 5.89 (s, 1H), 4.74-4.71 (m, 1H), 4.57 (s, 2H), 3.65 (s, 3H), 3.33-3.30 (m, 2H), 2.17 (s, 3H), 2.11 (s, 3H), 1.29 (d, J = 6 Hz, 6H); MS: 455 [M + 1] | F |

TABLE 2-continued

| Ex. | Structure/Name | 1H NMR/LCMS (M + H) | Method |
|---|---|---|---|
| 171 | Chiral<br><br>8-chloro-2-[(4,6-dimethyl-2-oxo-1,2-dihydropyridin-3-yl)methyl]-7-[(3S)-tetrahydrofuran-3-yloxy]-3,4-dihydroisoquinolin-1(2H)-one | $^1$H NMR (400 MHz, DMSO-d6) d 7.21 (d, J = 8.19 Hz, 1H), 7.17 (d, J = 8.44 Hz, 1H), 5.89 (s, 1H), 5.06-5.12 (m, 1H), 4.57 (s, 2H), 3.74-3.93 (m, 4H), 3.38 (t, J = 5.87 Hz, 2H), 2.75 (t, J = 6.17 Hz, 2H), 2.17-2.26 (m, 1H), 2.15 (s, 3H), 2.13 (s, 3H), 1.93-2.01 (m, 1H); MS: 403 [M + 1] | C |
| 172 | 3-{8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}-1,1-dimethylurea | $^1$H NMR (400 MHz, DMSO): δ 11.56 (s, 1H), 8.09 (s, 1H), 7.14 (s, 1H), 5.75 (s, 1H), δ 4.53-4.49 (m, 3H), 3.31-3.29 (m, 2H), 2.90 (s, 6H), 2.47 (s, 2H), 2.16-2.12 (d, 6H), 1.30-1.28 (d, 6H); MS: 461 [M + 1] | Y |
| 173 | Chiral<br><br>8-chloro-2-[(4,6-dimethyl-2-oxo-1,2-dihydropyridin-3-yl)methyl]-7-[(3R)-tetrahydrofuran-3-yloxy]-3,4-dihydroisoquinolin-1(2H)-one | $^1$H NMR (400 MHz, DMSO-d6) d 11.30 (br. s., 1H), 7.20 (d, J = 8.31 Hz, 1H), 7.16 (d, J = 8.31 Hz, 1H), 5.87 (s, 1H), 5.05-5.10 (m, 1H), 4.57 (s, 2H), 3.73-3.92 (m, 4H), 3.37 (t, J = 6.11 Hz, 2H), 2.74 (t, J = 6.11 Hz, 2H), 2.16-2.25 (m, 1H), 2.14 (s, 3H), 2.11 (s, 3H), 1.92-2.01 (m, 1H); MS: 403 [M + 1] | C |
| 174 | 8-chloro-2-[(4,6-dimethyl-2-oxo-1,2-dihydropyridin-3-yl)methyl]-5-(2-oxoimidazolidin-1-yl)-7-(propan-2-yloxy)-3,4-dihydroisoquinolin-1(2H)-one | $^1$H NMR (400 MHz, DMSO): δ 11.56 (s, 1H), 7.18 (s, 1H), 6.84 (s, 1H), 5.88 (s, 1H), 4.64-4.54 (m, 2H), 4.54 (s, 2H), 3.79-3.75 (m, 2H), 3.41-3.31 (m, 2H), 2.58-2.57 (m, 2H), 2.16 (s, 3H), 2.12 (s, 3H), 1.28 (d, J = 6.0 Hz, 6H); MS: 459 [M + 1] | X |
| 175 | 2,5-anhydro-3-O-{8-chloro-2-[(4,6-dimethyl-2-oxo-1,2-dihydropyridin-3-yl)methyl]-1-oxo-1,2,3,4-tetrahydroisoquinolin-7-yl}-1,4-dideoxy-D-erythro-pentitol | $^1$H NMR (400 MHz, DMSO-d6) d 11.35 (br. s., 1H), 7.19-7.23 (m, 1H), 7.14-7.18 (m, 1H), 5.87 (s, 1H), 4.61-4.67 (m, 1H), 4.57 (s, 2H), 4.03 (dq, J = 2.38, 6.46 Hz, 1H), 3.92 (dt, J = 3.00, 8.34 Hz, 1H), 3.76-3.86 (m, 1H), 3.37 (t, J = 6.05 Hz, 2H), 2.75 (t, J = 6.05 Hz, 2H), 2.19-2.32 (m, 1H), 2.14 (s, 3H), 2.11 (s, 3H), 1.86-1.95 (m, 1H), 1.18 (d, J = 6.60 Hz, 3H); MS: 417 [M + 1] | C |

| Ex. | Structure/Name | 1H NMR/LCMS (M + H) | Method |
|---|---|---|---|
| 176 | 8-chloro-2-[(4,6-dimethyl-2-oxo-1,2-dihydropyridin-3-yl)methyl]-5-(methylsulfonyl)-7-(propan-2-yloxy)-3,4-dihydroisoquinolin-1(2H)-one | $^1$H NMR (400 MHz, (CD3)2CO): δ 7.69 (s, 1H), 5.93 (s, 1H), 4.79-4.76 (m, 1H), 4.68 (s, 2H), 3.65-3.62 (m, 2H), 3.32-3.29 (m, 2H), 3.22 (s, 3H), 2.30 (s, 3H), 2.26 (s, 3H), 1.40-1.39 (d, J = 6.0, 6H); MS: 453 [M + 1] | X |
| 177 | N-{8-chloro-2-[(4,6-dimethyl-2-oxo-1,2-dihydropyridin-3-yl)methyl]-1-oxo-7-(propan-2-yloxy)-1,2,3,4-tetrahydroisoquinolin-5-yl}methanesulfonamide | $^1$H NMR (400 MHz, DMSO): δ 11.58 (s, 1H), 7.13 (s, 1H), 5.88 (s, 1H), δ 4.61-4.55 (m, 3H), 3.31-3.25 (m, 2H), 2.97 (s, 3H), 2.76-2.73 (s, 2H), 2.15 (s, 3H), 2.12 (s, 3H), 1.29 (d, J = 6.4 Hz, 6H); Ms: 490 [M + Na] | X |
| 178 | 8-chloro-7-(1,4-dimethyl-1H-1,2,3-triazol-5-yl)-2-[(4-ethyl-6-methyl-2-oxo-1,2-dihydropyridin-3-yl)methyl]-3,4-dihydroisoquinolin-1(2H)-one | $^1$H NMR (400 MHz, Methanol-d4): δ 7.47-7.40 (m, 2H), 6.19 (s, 1H), 4.84 (s, 3H), 3.86 (s, 3H), 3.68 (t, J = 6 0 Hz, 2H), 3.01 (t, J = 6.8 Hz, 2H), 2.71 (d, J = 7.6 Hz, 2H), 2.29 (s, 3H), 2.18 (s, 3H), 1.16 (t, J = 7.6 Hz, 3H); MS: 426 [M + 1] | D |
| 179 | 8-chloro-2-[(4,6-dimethyl-2-oxo-1,2-dihydropyridin-3-yl)methyl]-7-(1,5-dimethyl-1H-1,2,3-triazol-4-yl)-3,4-dihydroisoquinolin-1(2H)-one | $^1$H NMR (400 MHz, DMSO-d6) d 11.55 (br. s., 1H), 7.41 (d, J = 7.70 Hz, 1H), 7.31 (d, J = 7.70 Hz, 1H), 5.89 (s, 1H), 4.59 (s, 2H), 3.99 (s, 3H), 3.46 (t, J = 6.11 Hz, 2H), 2.88 (t, J = 6.05 Hz, 2H), 2.20 (s, 3H), 2.17 (s, 3H), 2.13 (s, 3H); MS: 412 [M + 1] | D |
| 180 | 8-chloro-7-(cyclopentyloxy)-2-[(4,6-dimethyl-2-oxo-1,2-dihydropyridin-3-yl)methyl]-3,4-dihydroisoquinolin-1(2H)-one | $^1$H NMR (400 MHz, methanol-d4) δ 7.06-7.20 (m, 2H), 6.12 (s, 1H), 4.78 (s, 2H), 3.46 (t, J = 6.17 Hz, 2H), 2.82 (t, J = 6.11 Hz, 2H), 2.30 (s, 3H), 2.26 (s, 3H), 1.79-2.04 (m, 6H), 1.68 (br. s., 2H); MS: 401 [M + 1] | C |

TABLE 2-continued

| Ex. | Structure/Name | 1H NMR/LCMS (M + H) | Method |
|---|---|---|---|
| 181 | 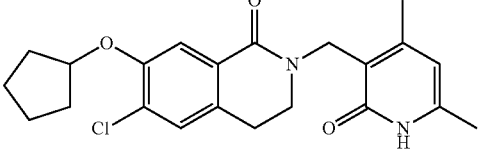<br>6-chloro-7-(cyclopentyloxy)-2-[(4,6-dimethyl-2-oxo-1,2-dihydropyridin-3-yl)methyl]-3,4-dihydroisoquinolin-1(2H)-one | $^1$H NMR (400 MHz, DMSO-d6) δ 11.53 (br. s., 1H), 7.53 (s, 1H), 7.34 (s, 1H), 5.87 (s, 1H), 4.92 (t, J = 5.62 Hz, 1H), 4.54 (s, 2H), 3.47 (t, J = 6.60 Hz, 3H), 2.76 (t, J = 6.48 Hz, 2H), 2.16 (s, 3H), 2.12 (s, 3H), 1.85-1.98 (m, 2H), 1.68-1.78 (m, 4H), 1.57-1.68 (m, 2H); MS: 401 [M + 1] | C |
| 182 | 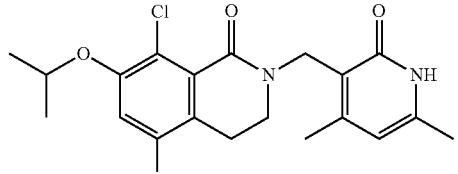<br>5,8-dichloro-2-[(4,6-dimethyl-2-oxo-1,2-dihydropyridin-3-yl)methyl]-7-(propan-2-yloxy)-3,4-dihydroisoquinolin-1(2H)-one | $^1$H NMR (400 MHz, DMSO-d6) d 11.54 (br. s., 1H), 7.41 (s, 1H), 5.88 (s, 1H), 4.71 (td, J = 6.01, 12.07 Hz, 1H), 4.55 (s, 2H), 3.41 (t, J = 6.17 Hz, 2H), 2.80 (t, J = 6.11 Hz, 2H), 2.15 (s, 3H), 2.12 (s, 3H), 1.28 (d, J = 5.99 Hz, 6H); MS: 409 [M + 1] | C |
| 183 | 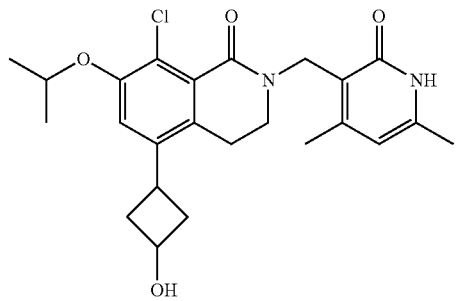 [SMILES: Cc1cc(C)c(CN2CCc3c(C4CC(O)C4)cc(OC(C)C)c(Cl)c3C2=O)c(=O)[nH]1]<br>8-chloro-2-[(4,6-dimethyl-2-oxo-1,2-dihydropyridin-3-yl)methyl]-5-(3-hydroxycyclobutyl)-7-(propan-2-yloxy)-3,4-dihydroisoquinolin-1(2H)-one | $^1$H NMR (400 MHz, Methanol-d4): 7.14 (s, 1H), 6.13 (s, 1H), 4.77 (s, 2H), 4.65 (t, J = 6.4, 1H), 4.36 (t, J = 5.6, 1H), 3.71 (d, J = 6.8, 1H), 3.42 (t, J = 5.6, 2H), 2.68 (t, J = 5.6, 2H), 2.40 (t, J = 7.2, 4H), 2.30 (s, 3H), 2.26 (s, 3H), 1.36 (d, J = 6, 6H); MS: 445 [M + 1] | F |
| 184 | 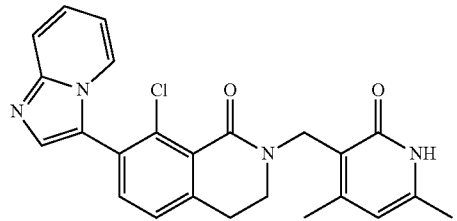 [SMILES: Cc1cc(C)c(CN2CCc3ccc(-c4cnc5ccccn45)c(Cl)c3C2=O)c(=O)[nH]1]<br>8-chloro-2-[(4,6-dimethyl-2-oxo-1,2-dihydropyridin-3-yl)methyl]-7-(imidazo[1,2-a]pyridin-3-yl)-3,4-dihydroisoquinolin-1(2H)-one | $^1$H NMR (400 MHz, D2O): δ 7.99 (d, J = 6.8 Hz, 1H), 7.85-7.81 (m, 3H), 7.45 (d, J = 7.6 Hz, 1H), 7.29-7.25 (m, 2H), 6.17 (s, 1H), 4.54 (s, 2H), 3.27 (t, J = 6.2 Hz, 2H), 2.80 (t, J = 6.0 Hz, 2H), 2.11 (s, 3H), 2.07 (s, 3H); MS: 433 [M + 1] | unique |
| 185 | 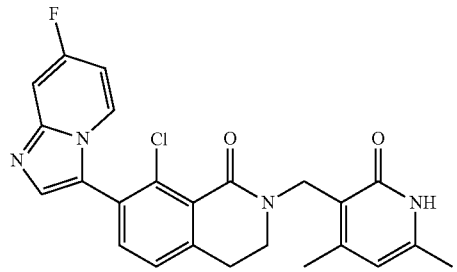 [SMILES: Cc1cc(C)c(CN2CCc3ccc(-c4cnc5cc(F)ccn45)c(Cl)c3C2=O)c(=O)[nH]1]<br>8-chloro-2-[(4,6-dimethyl-2-oxo-1,2-dihydropyridin-3-yl)methyl]-7-(7-fluoroimidazo[1,2-a]pyridin-3-yl)-3,4-dihydroisoquinolin-1(2H)-one | $^1$H NMR (400 MHz, D2O): δ 8.19 (t, J = 3.8 Hz, 1H), 7.94 (s, 1H), 7.71-7.69 (m, 1H), 7.56 (d, J = 7.6 Hz, 1H), 7.38 (d, J = 8 Hz, 1H), 7.32 (t, J = 3.8 Hz, 1H), 6.24 (s, 1H), 4.68 (s, 2H), 3.39 (t, J = 6 Hz, 2H), 2.93 (t, J = 5.8 Hz, 2H), 2.22 (s, 3H), 2.19 (s, 3H); MS: 451 [M + 1] | unique |

TABLE 2-continued

| Ex. | Structure/Name | 1H NMR/LCMS (M + H) | Method |
|---|---|---|---|
| 186 | 8-chloro-2-[(4,6-dimethyl-2-oxo-1,2-dihydropyridin-3-yl)methyl]-7-(imidazo[1,2-a]pyrazin-3-yl)-3,4-dihydroisoquinolin-1(2H)-one | $^1$H NMR (400 MHz, D2O): δ 9.40 (s, 1H), 8.27 (d, J = 5.2 Hz, 1H), 8.26 (s, 1H), 8.21 (d, J = 4.8 Hz, 1H), 7.50 (d, J = 8 Hz, 1H), 7.32 (d, J = 8 Hz, 1H), 6.22 (s, 1H), 4.60 (s, 2H), 3.32 (t, J = 6 Hz, 2H), 2.85 (t, J = 6.2 Hz, 2H), 2.16 (s, 3H), 2.14 (s, 3H); MS: 434 [M + 1] | unique |
| 187 | 8-chloro-7-(1,4-dimethyl-1H-1,2,3-triazol-5-yl)-2-[(6-methyl-2-oxo-4-propyl-1,2-dihydropyridin-3-yl)methyl]-3,4-dihydroisoquinolin-1(2H)-one | $^1$H NMR: (400 MHz, Methanol-d4): δ 7.44 (q, J = 8.5 Hz, 2H), 6.17 (s, 1H), 4.84 (s, 2H), 3.86 (s, 3H), 3.58 (t, J = 6.4 Hz, 2H), 3.02 (t, J = 6.2 Hz, 2H), 2.66 (t, J = 7.2 Hz, 2H), 2.28 (s, 3H), 2.18 (s, 3H), 1.59 (q, J = 7.3 Hz, 2H), 0.99 (t, J = 7.2 Hz, 3H); MS: 440 [M + 1] | D |
| 188 | 8-chloro-7-(1,4-dimethyl-1H-1,2,3-triazol-5-yl)-2-{[4-(methoxymethyl)-6-methyl-2-oxo-1,2-dihydropyridin-3-yl]methyl}-3,4-dihydroisoquinolin-1(2H)-one | $^1$H NMR (400 MHz, Methanol-d4): δ 7.47-7.40 (m, 2H), 6.40 (s, 1H), 4.76 (s, 2H), 4.57 (s, 2H), 3.86 (s, 3H), 3.64 (t, J = 7.2 Hz, 2H), 3.41 (s, 3H), 3.03 (t, J = 6 Hz, 2H), 2.31 (s, 3H), 2.18 (s, 3H); MS: 442 [M + 1] | D |
| 189 | 5-[1-(azetidin-3-yl)-1H-1,2,3-triazol-4-yl]-8-chloro-2-[(4,6-dimethyl-2-oxo-1,2-dihydropyridin-3-yl)methyl]-7-(propan-2-yloxy)-3,4-dihydroisoquinolin-1(2H)-one | $^1$H NMR (400 MHz, Methanol): δ 8.36 (s, 1H), 7.55 (s, 1H), 6.14 (s, 1H), 5.75-5.70 (m, 1H), 4.80 (s, 2H), 4.75-4.65 (m, 1H), 4.55-4.45 (m, 4H), 3.47-3.40 (m, 2H), 2.95-2.90 (m, 2H), 2.33 (s, 3H), 2.26 (s, 3H), 1.41-1.39 (m, 6H); MS: 497 [M + 1] | F |

| Ex. | Structure/Name | 1H NMR/LCMS (M + H) | Method |
| --- | --- | --- | --- |
| 190 | 8-chloro-2-[(4,6-dimethyl-2-oxo-1,2-dihydropyridin-3-yl)methyl]-7-(propan-2-yloxy)-5-[1-(tetrahydrofuran-3-yl)-1H-1,2,3-triazol-4-yl]-3,4-dihydroisoquinolin-1(2H)-one | $^1$H NMR (400 MHz, Methanol-d4): δ 8.24 (s, 1H), 7.50 (s, 1H), 6.14 (s, 1H), 5.42-5.40 (m, 1H), 4.81 (s, 2H), 4.75-4.70 (m, 1H), 4.25-4.10 (m, 3H), 4.00-3.90 (m, 1H), 3.45-3.40 (m, 2H), 2.95-2.90 (m, 2H), 2.65-2.60 (m, 1H), 2.50-2.45 (m, 1H), 2.33 (s, 3H), 2.26 (s, 3H), 1.40 (d, J = 6 Hz, 6H); MS: 512 [M + 1] | F |
| 191 | 8-chloro-2-[(4,6-dimethyl-2-oxo-1,2-dihydropyridin-3-yl)methyl]-7-(propan-2-yloxy)-5-(1H-1,2,3-triazol-1-yl)-3,4-dihydroisoquinolin-1(2H)-one | $^1$H NMR (400 MHz, CDCl3): δ 11.32 (s, 1H), 7.825 (s, 2H), 7.34 (s, 1H), 5.92 (s, 1H), 4.79 (s, 2H), 4.61 (m, 1H), 3.51 (m, 2H), 2.82-2.80 (m, 2H), 2.35 (s, 3H), 2.24 (s, 3H), 1.41-1.39 (d, J = 6.4 Hz, 6H); MS: 442 [M + 1] | F |
| 192 | 5-chloro-3-[(4,6-dimethyl-2-oxo-1,2-dihydropyridin-3-yl)methyl]-6-methoxy-2,3-dihydro-4H-1,3-benzoxazin-4-one | $^1$H NMR (400 MHz, DMSO-d6) δ 11.57 (br. s., 1H), 7.30 (d, J = 9.05 Hz, 1H), 7.01 (d, J = 9.05 Hz, 1H), 5.89 (s, 1H), 5.27 (s, 2H), 4.45 (s, 2H), 3.82 (s, 3H), 2.25 (s, 3H), 2.12 (s, 3H); MS: 349 [M + 1] | C |
| 193 | 8-chloro-2-[(4,6-dimethyl-2-oxo-1,2-dihydropyridin-3-yl)methyl]-5-[1-(oxetan-3-yl)-1H-1,2-triazol-4-yl]-7-(propan-2-yloxy)-3,4-dihydroisoquinolin-1(2H)-one | $^1$H NMR (400 MHz, Methanol-d4): δ 8.45 (s, 1H), 7.54 (s, 1H), 6.14 (s, 1H), 5.92-5.89 (m, 1H), 5.18 (t, J = 7.2 Hz, 2H), 5.12 (t, J = 6.4 Hz, 2H), 4.81 (s, 2H), 4.75-4.70 (m, 1H), 3.44 (t, J = 6 Hz, 2H), 2.96 (t, J = 6.4 Hz, 2H), 2.33 (s, 3H), 2.26 (s, 3H), 1.40 (d, J = 6 Hz, 6H); MS: 498 [M + 1] | F |

TABLE 2-continued

| Ex. | Structure/Name | 1H NMR/LCMS (M + H) | Method |
|---|---|---|---|
| 194 | 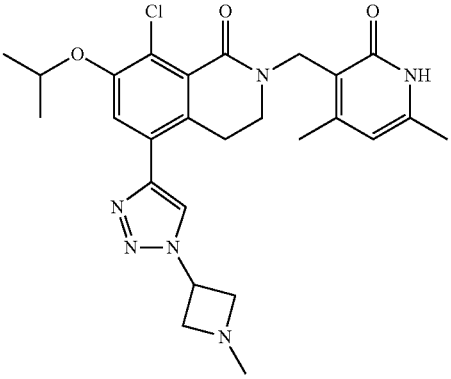 [SMILES: Cc1cc(C)c(CN2CCc3c(-c4cn(C5CN(C)C5)nn4)cc(OC(C)C)c(Cl)c3C2=O)c(=O)[nH]1]<br>8-chloro-2-[(4,6-dimethyl-2-oxo-1,2-dihydropyridin-3-yl)methyl]-5-[1-(1-methylazetidin-3-yl)-1H-1,2,3-triazol-4-yl]-7-(propan-2-yloxy)-3,4-dihydroisoquinolin-1(2H)-one | $^1$H NMR (400 MHz, Methanol): δ 8.36 (s, 1H), 7.50 (s, 1H), 6.14 (s, 1H), 5.40-5.35 (m, 1H), 4.80 (s, 2H), 4.75-4.65 (m, 1H), 4.05-3.95 (m, 2H), 3.85-3.75 (m, 2H), 3.45-3.40 (m, 2H), 2.95-2.85 (m, 2H), 2.54 (s, 3H), 2.31 (s, 3H), 2.24 (s, 3H), 1.39 (s, 3H), 1.37 (s, 3H); MS: 511 [M + 1] | F |
| 195 | 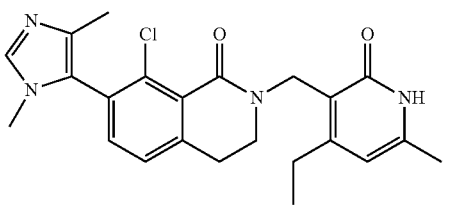 [SMILES: CCc1cc(C)[nH]c(=O)c1CN1CCc2ccc(-c3c(C)ncn3C)c(Cl)c2C1=O]<br>8-chloro-7-(1,4-dimethyl-1H-imidazol-5-yl)-2-[(4-ethyl-6-methyl-2-oxo-1,2-dihydropyridin-3-yl)methyl]-3,4-dihydroisoquinolin-1(2H)-one | $^1$H NMR (400 MHz, Methanol): δ 8.01 (br. s, 1H), 7.44-7.37 (m, 2H), 6.17 (s, 1H), 4.80 (s, 2H), 3.55-3.54 (m, 2H), 3.50 (s, 3H), 3.05-2.95 (m, 2H), 2.75-2.65 (m, 2H), 2.27 (s, 3H), 2.02 (s, 3H), 1.15-1.10 (m, 3H); MS: 425 [M + 1] | D |
| 196 | 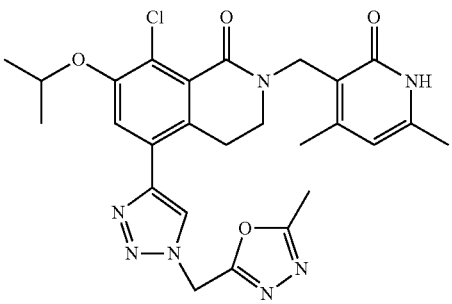 [SMILES: Cc1cc(C)c(CN2CCc3c(-c4cn(Cc5nnc(C)o5)nn4)cc(OC(C)C)c(Cl)c3C2=O)c(=O)[nH]1]<br>8-chloro-2-[(4,6-dimethyl-2-oxo-1,2-dihydropyridin-3-yl)methyl]-5-{1-[(5-methyl-1,3,4-oxadiazol-2-yl)methyl]-1H-1,2,3-triazol-4-yl}-7-(propan-2-yloxy)-3,4-dihydroisoquinolin-1(2H)-one | $^1$H NMR (400 MHz, Methanol-d4): δ 8.40 (s, 1H), 7.53 (s, 1H), 6.14 (s, 1H), 6.02 (s, 2H), 4.75 (s, 2H), 4.74-4.69 (m, 1H), 3.44 (t, J = 6.0 Hz, 2H), 2.95 (t, J = 6.8 Hz, 2H), 2.56 (s, 3H), 2.33 (s, 3H), 2.26 (s, 3H), 1.40 (d, J = 6.4 Hz, 6H); MS: 538 [M + 1] | F |
| 197 | 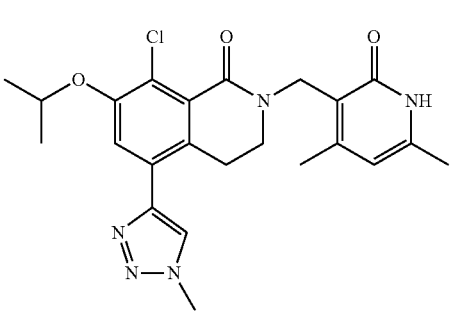 [SMILES: Cc1cc(C)c(CN2CCc3c(-c4cn(C)nn4)cc(OC(C)C)c(Cl)c3C2=O)c(=O)[nH]1]<br>8-chloro-2-[(4,6-dimethyl-2-oxo-1,2-dihydropyridin-3-yl)methyl]-5-(2-methyl-2H-tetrazol-5-yl)-7-(propan-2-yloxy)-3,4-dihydroisoquinolin-1(2H)-one | $^1$H NMR (400 MHz, Methanol): δ 7.76 (s, 1H), 6.12 (s, 1H), 4.84 (s, 2H), 4.81-4.77 (m, 1H), 4.43 (s, 3H), 3.45 (t, J = 6.2 Hz, 2H), 3.16 (t, J = 6 Hz, 2H), 2.31 (s, 3H), 2.25 (s, 3H), 1.39 (d, J = 6 Hz, 6H); MS: 457 [M + 1] | F |

TABLE 2-continued

| Ex. | Structure/Name | 1H NMR/LCMS (M + H) | Method |
|---|---|---|---|
| 198 | 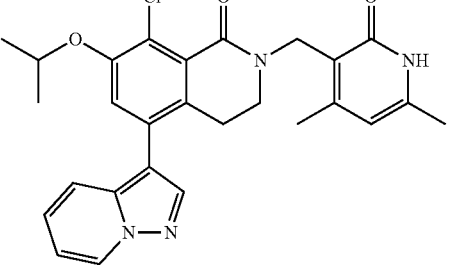<br>8-chloro-2-[(4,6-dimethyl-2-oxo-1,2-dihydropyridin-3-yl)methyl]-7-(propan-2-yloxy)-5-(pyrazolo[1,5-a]pyridin-3-yl)-3,4-dihydroisoquinolin-1(2H)-one | $^1$H NMR (400 MHz, DMSO-d6): δ 11.57-11.52 (br s, 1H), 8.75 (d, J = 6.8 Hz, 1H), 8.19-8.15 (s, 1H), 7.58 (d, J = 8.8 Hz, 1H), 7.31 (t, J = 6.8 Hz, 1H), 7.26-7.21 (s, 1H), 6.97 (t, J = 7.0 Hz, 1H), 5.92-5.88 (m, 1H), 4.75-4.67 (m, 1H), 4.61-4.56 (s, 2H), 3.28-3.23 (m, 2H), 2.72-2.67 (m, 2H), 2.19 (d, J = 20 Hz, 6H), 1.31 (d, J = 6.2 Hz, 6H); MS: 491 [M + 1] | F |
| 199 | 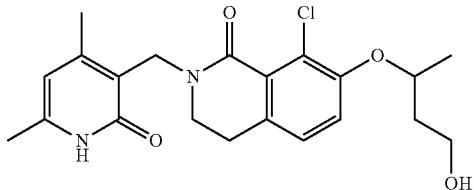 [SMILES: Cc1cc(C)c(CN2CCc3ccc(OC(C)CCO)c(Cl)c3C2=O)c(=O)[nH]1]<br>8-chloro-2-[(4,6-dimethyl-2-oxo-1,2-dihydropyridin-3-yl)methyl]-7-[(4-hydroxybutan-2-yl)oxy]-3,4-dihydroisoquinolin-1(2H)-one | $^1$H NMR (400 MHz, CDCl3): δ 11.88 (s, 1H), 7.01-6.96 (m, 2H), 5.93 (s, 1H), 4.84-4.76 (m, 2H), 4.65-4.61 (m, 1H), 3.93-3.83 (m, 2H), 3.57 (t, J = 6 Hz, 2H), 2.76 (t, J = 6 Hz, 2H), 2.33 (s, 3H), 2.28 (s, 3H), 2.05-2.03 (m, 1H), 2.03-1.97 (m, 2H), 1.34 (d, J = 6 Hz, 3H); MS: 406 [M + 1] | A |
| 200 | 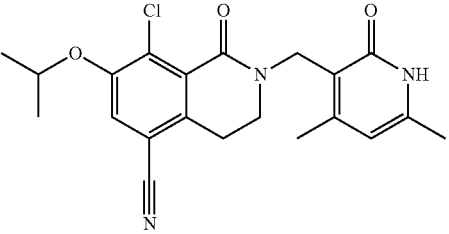 [SMILES: Cc1cc(C)c(CN2CCc3c(C#N)cc(OC(C)C)c(Cl)c3C2=O)c(=O)[nH]1]<br>8-chloro-2-[(4,6-dimethyl-2-oxo-1,2-dihydropyridin-3-yl)methyl]-1-oxo-7-(propan-2-yloxy)-1,2,3,4-tetrahydroisoquinoline-5-carbonitrile | $^1$H NMR (400 MHz, Methanol): δ 7.56 (s, 1H), 6.13 (s, 1H), 4.77 (s, 2H), 4.74-4.71 (m, 1H), 3.58 (t, J = 6Hz, 2H), 3.05 (t, J = 6.2 Hz, 2H), 2.31 (s, 3H), 2.27 (s, 3H), 1.38 (d, J = 6 Hz, 6H); MS: 400 [M + 1] | F |
| 201 | 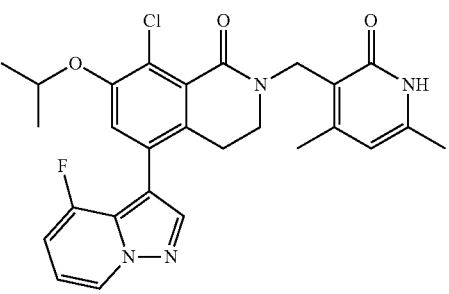 [SMILES: Cc1cc(C)c(CN2CCc3c(-c4cnn5cccc(F)c45)cc(OC(C)C)c(Cl)c3C2=O)c(=O)[nH]1]<br>8-chloro-2-[(4,6-dimethyl-2-oxo-1,2-dihydropyridin-3-yl)methyl]-5-(4-fluoropyrazolo[1,5-a]pyridin-3-yl)-7-(propan-2-yloxy)-3,4-dihydroisoquinolin-1(2H)-one | $^1$H NMR (400 MHz, DMSO-d6): δ 11.56 (s, 1H), 8.66 (d, J = 6.8 Hz, 1H), 8.18 (s, 1H), 7.29 (s, 1H), 7.18 (d, J = 18.8 Hz, 1H), 6.95-9.91 (m, 1H), 5.89 (s, 1H), 4.62-8.68 (m, 1H), 4.57 (s, 2H), 3.29-3.16 (m, 2H), 2.67-2.59 (m, 2H), 2.11 (d, J = 26 Hz, 6H), 1.29 (d, J = 6 Hz, 6H); MS: 509 [M + 1] | F |
| 202 | 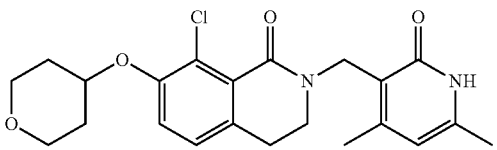 [SMILES: Cc1cc(C)c(CN2CCc3ccc(OC4CCOCC4)c(Cl)c3C2=O)c(=O)[nH]1]<br>8-chloro-2-[(4,6-dimethyl-2-oxo-1,2-dihydropyridin-3-yl)methyl]-7-(tetrahydro-2H-pyran-4-yloxy)-3,4-dihydroisoquinolin-1(2H)-one | $^1$H NMR (400 MHz, DMSO-d6): δ 11.57 (brs, 1H), 7.29 (d, J = 8.8 Hz, 1H), 7.15 (d, J = 8.4 Hz, 1H), 5.89 (s, 1H), 4.63-4.62 (m, 1H), 4.57 (s, 2H), 3.85 (t, J = 7.2 Hz, 2H), 3.50-3.45 (m, 3H), 3.45-3.37 (m, 1H), 2.74 (t, J = 6.2 Hz, 2H), 2.14 (d, J = 11.2 Hz, 6H), 1.95-1.92 (m, 2H), 1.63-1.61 (m, 2H); MS: 417 [M + 1] | A |

TABLE 2-continued

| Ex. | Structure/Name | 1H NMR/LCMS (M + H) | Method |
|---|---|---|---|
| 203 | 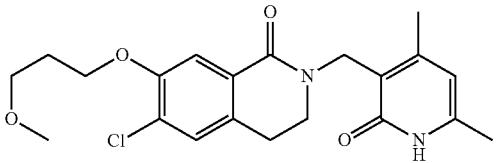 [SMILES: COCCCOc1cc2c(cc1Cl)CCN(Cc1c(C)cc(C)[nH]c1=O)C2=O]<br>6-chloro-2-[(4,6-dimethyl-2-oxo-1,2-dihydropyridin-3-yl)methyl]-7-(3-methoxypropoxy)-3,4-dihydroisoquinolin-1(2H)-one | ¹H NMR (400 MHz, DMSO-d6) δ 11.53 (br. s., 1H), 7.53 (s, 1H), 7.36 (s, 1H), 5.87 (s, 1H), 4.55 (s, 2H), 4.13 (t, J = 6.36 Hz, 2H), 3.39-3.58 (m, 4H), 3.25 (s, 3H), 2.77 (t, J = 6.48 Hz, 2H), 2.15 (s, 3H), 2.12 (s, 3H), 1.94-2.02 (m, 2H); MS: 405 [M + 1] | C |
| 204 | 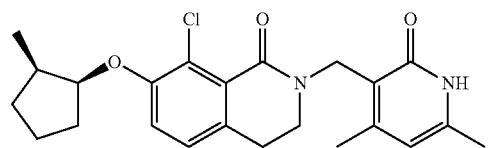 [SMILES: Cc1cc(C)c(CN2CCc3ccc(O[C@H]4CCC[C@H]4C)c(Cl)c3C2=O)c(=O)[nH]1]<br>2,5-anhydro-3-O-{8-chloro-2-[(4,6-dimethyl-2-oxo-1,2-dihydropyridin-3-yl)methyl]-1-oxo-1,2,3,4-tetrahydroisoquinolin-7-yl}-1,4-dideoxy-L-threo-pentitol | ¹H NMR (700 MHz, DMSO-17 mm) d 11.53 (br. s., 1H), 7.20 (d, J = 8.58 Hz, 1H), 7.15 (d, J = 8.14 Hz, 1H), 5.88 (s, 1H), 4.81-4.85 (m, 1H), 4.57 (s, 2H), 3.93-3.97 (m, 1H), 3.89-3.93 (m, 1H), 3.64 (dt, J = 5.94, 8.47 Hz, 1H), 3.36 (t, J = 6.38 Hz, 2H), 2.74 (t, J = 6.16 Hz, 2H), 2.31-2.37 (m, 1H), 2.14 (s, 3H), 2.12 (s, 3H), 1.88 (dddd, J = 1.76, 5.94, 7.76, 13.59 Hz, 1H), 1.27 (d, J = 6.38 Hz, 3H); MS: 417 [M + 1] | A |
| 205 | 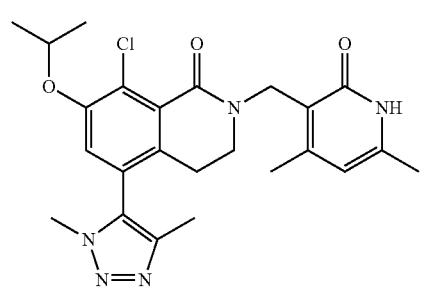 [SMILES: Cc1cc(C)c(CN2CCc3c(-c4c(C)nnn4C)cc(OC(C)C)c(Cl)c3C2=O)c(=O)[nH]1]<br>8-chloro-2-[(4,6-dimethyl-2-oxo-1,2-dihydropyridin-3-yl)methyl]-5-(1,4-dimethyl-1H-1,2,3-triazol-5-yl)-7-(propan-2-yloxy)-3,4-dihydroisoquinolin-1(2H)-one | ¹H NMR (400 MHz, Methanol-d4): δ 7.20 (s, 1H), 6.13 (s, 1H), 4.78 (s, 2H), 4.70-4.60 (m, 1H), 3.85 (s, 3H), 3.45-3.41 (m, 2H), 2.50-2.47 (m, 2H), 2.32 (s, 3H), 2.25 (s, 3H), 2.17 (s, 3H), 1.39-1.36 (m, 6H); MS: 470 [M + 1] | F |
| 206 | 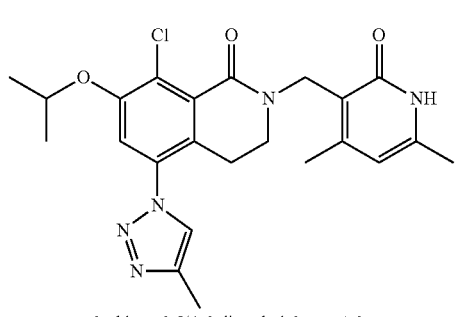<br>8-chloro-2-[(4,6-dimethyl-2-oxo-1,2-dihydropyridin-3-yl)methyl]-5-(4-methyl-1H-1,2,3-triazol-1-yl)-7-(propan-2-yloxy)-3,4-dihydroisoquinolin-1(2H)-one | ¹H NMR (400 MHz, MeOD): δ 7.75 (s, 1H), 7.46 (s, 1H), 6.13 (s, 1H), 4.79 (s, 2H), 4.72-4.69 (m, 1H), 3.43-3.40 (m, 2H), 2.87-2.84 (m, 2H), 2.40 (s, 3H), 2.33 (s, 3H), 2.26 (s, 3H), 1.41-1.39 (d, J = 6.0 Hz, 6H); MS: 456 [M + 1] | F |
| 207 | 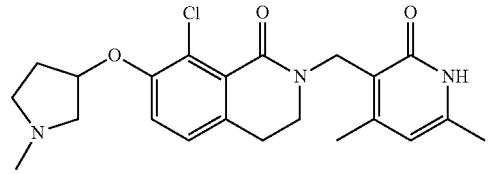 [SMILES: Cc1cc(C)c(CN2CCc3ccc(OC4CCN(C)C4)c(Cl)c3C2=O)c(=O)[nH]1]<br>8-chloro-2-[(4,6-dimethyl-2-oxo-1,2-dihydropyridin-3-yl)methyl]-7-[(1-methylpyrrolidin-3-yl)oxy]-3,4-dihydroisoquinolin-1(2H)-one | ¹H NMR (400 MHz, Methanol-d4): δ 7.21 (s, 2H), 6.13 (s, 1H), 5.18 (s, 1H), 4.78 (s, 2H), 3.58-3.47 (m, 5H), 2.92 (s, 3H), 2.85 (t, J = 6 Hz, 2H), 2.51-2.47 (m, 1H), 2.31-2.66 (m, 7H); MS: 416 [M + 1] | A |

TABLE 2-continued

| Ex. | Structure/Name | 1H NMR/LCMS (M + H) | Method |
|---|---|---|---|
| 208 | 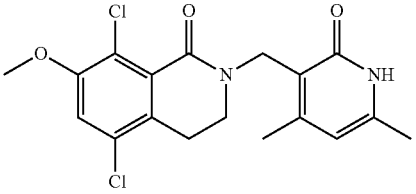<br>5,8-dichloro-2-[(4,6-dimethyl-2-oxo-1,2-dihydropyridin-3-yl)methyl]-7-methoxy-3,4-dihydroisoquinolin-1(2H)-one | $^{1}$H NMR (400 MHz, DMSO-d6) δ 11.54 (br. s., 1H), 7.38 (s, 1H), 5.88 (s, 1H), 4.56 (s, 2H), 3.88 (s, 3H), 3.41 (t, J = 6.11 Hz, 2H), 2.81 (t, J = 6.11 Hz, 2H), 2.15 (s, 3H), 2.12 (s, 3H); MS: 381 [M + 1] | C |
| 209 | 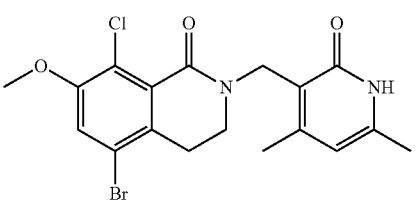<br>5-bromo-8-chloro-2-[(4,6-dimethyl-2-oxo-1,2-dihydropyridin-3-yl)methyl]-7-methoxy-3,4-dihydroisoquinolin-1(2H)-one | $^{1}$H NMR (400 MHz, DMSO-d6) δ 11.54 (br. s., 1H), 7.49 (s, 1H), 5.88 (s, 1H), 4.55 (s, 2H), 3.88 (s, 3H), 3.41 (t, J = 6.11 Hz, 2H), 2.81 (t, J = 6.11 Hz, 2H), 2.15 (s, 3H), 2.12 (s, 3H); MS: 425 [M + 1] | C |
| 210 | 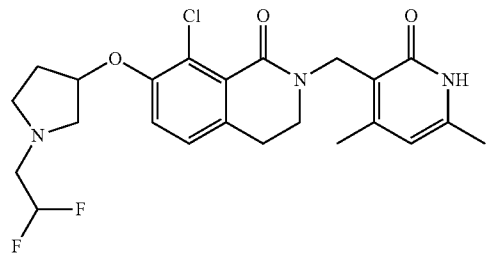 [SMILES: Cc1cc(C)c(CN2CCc3ccc(OC4CCN(CC(F)F)C4)c(Cl)c3C2=O)c(=O)[nH]1]<br>8-chloro-7-{[1-(2,2-difluoroethyl)pyrrolidin-3-yl]oxy}-2-2[(4,6-dimethyl-2-oxo-1,2-dihydropyridin-3-yl)methyl]-3,4-dihydroisoquinolin-1(2H)-one | $^{1}$H NMR (400 MHz, Methanol-d4): δ 7.13 (q, J = 8 Hz, 2H), 6.13-5.84 (m, 2H), 4.78 (s, 2H), 3.47 (t, J = 6 Hz, 2H), 3.17-3.14 (m, 1H), 2.99-2.92 (m, 4H), 2.84-2.78 (m, 3H), 2.33-2.26 (m, 7H), 2.05-2.01 (m, 1H); MS: 466 [M + 1] | A |
| 211 | 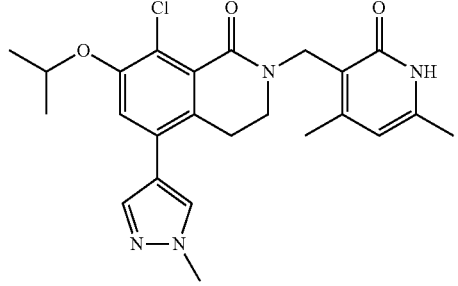 [SMILES: Cc1cc(C)c(CN2CCc3c(-c4cnn(C)c4)cc(OC(C)C)c(Cl)c3C2=O)c(=O)[nH]1]<br>8-chloro-2-[(4,6-dimethyl-2-oxo-1,2-dihydropyridin-3-yl)methyl]-5-(2-methyl-2H-1,2,3-triazol-4-yl)-7-(propan-2-yloxy)-3,4-dihydroisoquinolin-1(2H)-one | $^{1}$H NMR (400 MHz, MeOD): δ 7.88 (s, 1H), 7.43 (s, 1H), 6.14 (s, 1H), 4.79 (s, 2H), 4.72-4.69 (m, 1H), 4.24 (s, 3H), 3.44-3.41 (m, 2H), 2.99-2.96 (m, 2H), 2.32 (s, 3H), 2.26 (s, 3H), 1.38 (d, J = 6 Hz, 6H); MS: 456 [M + 1] | F |
| 212 | 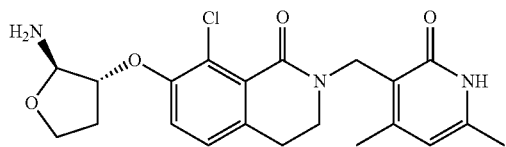 [SMILES: Cc1cc(C)c(CN2CCc3ccc(O[C@@H]4CCO[C@H]4N)c(Cl)c3C2=O)c(=O)[nH]1]<br>7-{[(3S,4R)-4-aminotetrahydrofuran-3-yl]oxy}-8-chloro-2-[(4,6-dimethyl-2-oxo-1,2-dihydropyridin-3-yl)methyl]-3,4-dihydroisoquinolin-1(2H)-one | $^{1}$H NMR (400 MHz, DMSO-d6) d 11.55 (br. s., 1H), 7.30 (d, J = 8.44 Hz, 1H), 7.19 (d, J = 8.31 Hz, 1H), 5.88 (s, 1H), 4.79 (d, J = 3.67 Hz, 1H), 4.57 (s, 2H), 4.16 (dd, J = 4.34, 10.33 Hz, 1H), 4.00 (dd, J = 4.28, 8.56 Hz, 1H), 3.79 (d, J = 10.03 Hz, 1H), 3.59-3.67 (m, 2H), 3.38 (t, J = 5.93 Hz, 2H), 2.76 (t, J = 5.75 Hz, 2H), 2.14 (s, 3H), 2.12 (s, 3H); MS: 418 [M + 1] | A |

TABLE 2-continued

| Ex. | Structure/Name | 1H NMR/LCMS (M + H) | Method |
|---|---|---|---|
| 213 | 8-chloro-2-[(4,6-dimethyl-2-oxo-1,2-dihydropyridin-3-yl)methyl]-1-oxo-7-[(3R)-tetrahydrofuran-3-yloxy]-1,2,3,4-tetrahydroisoquinoline-5-carbonitrile | ¹H NMR (400 MHz, CDCl3): δ 12.20 (br s, 1H), 7.11 (s, 1H), 6.09 (s, 1H), 4.94-4.93 (m, 1H), 4.73 (s, 2H), 4.04-3.94 (m, 4H), 3.68-3.67 (m, 2H), 3.02-3.00 (m, 2H), 2.40 (s, 3H), 2.32 (s, 3H), 2.28-2.17 (m, 2H); MS: 428 [M + 1] | F |
| 214 | 8-chloro-2-[(4,6-dimethyl-2-oxo-1,2-dihydropyridin-3-yl)methyl]-5-(1,5-dimethyl-1H-1,2,3-triazol-4-yl)-7-(propan-2-yloxy)-3,4-dihydroisoquinolin-1(2H)-one | ¹H NMR (400 MHz, Methanol-d4): δ 7.14 (s, 1H), 6.11 (s, 1H), 4.78 (s, 2H), 4.70-4.60 (m, 1H), 4.02 (s, 3H), 3.38-3.35 (m,2H), 2.70-2.66 (m, 2H), 2.30 (s, 3H), 2.28 (s, 3H), 2.35 (s, 3H), 1.37-1.35 (m, 6H); MS: 470 [M + 1] | F |
| 215 | 8-chloro-2-[(4,6-dimethyl-2-oxo-1,2-dihydropyridin-3-yl)methyl]-5-methyl-7-[(3R)-tetrahydrofuran-3-yloxy]-3,4-dihydroisoquinolin-1(2H)-one | ¹H NMR (400 MHz, CDCl3): δ 12.20 (br s, 1H), 6.79 (s, 1H), 6.02 (s, 1H), 4.93-4.91 (m, 1H), 478 (s, 2H), 4.04-3.92 (m, 4H), 3.56-3.55 (m, 2H), 2.69-2.67 (m, 2H), 2.37 (s, 3H), 2.31 (s, 3H), 2.22 (s, 3H), 2.19-2.16 (m, 2H); MS: 417 [M + 1] | F |
| 216 | 8-chloro-5-{1-[2-(dimethylamino)ethyl]-1H-pyrazol-4-yl}-2-[(4,6-dimethyl-2-oxo-1,2-dihydropyridin-3-yl)methyl]-7-[(3R)-tetrahydrofuran-3-yloxy]-3,4-dihydroisoquinolin-1(2H)-one | ¹H NMR (400 MHz, MeOD): δ 7.91 (s, 1H), 7.71 (s, 1H), 7.20 (s, 1H), 6.13 (s, 1H), 5.14 (m, 1H), 4.79 (s, 2H), 4.38-4.35 (m, 2H), 4.02-3.91 (m, 4H), 3.41-3.39 (m, 2H), 2.97-2.90 (m, 4H), 2.41 (s, 6H), 2.32 (s, 3H), 2.26 (s, 3H); MS: 562 [M + Na] | F |

TABLE 2-continued

| Ex. | Structure/Name | 1H NMR/LCMS (M + H) | Method |
|---|---|---|---|
| 218 | 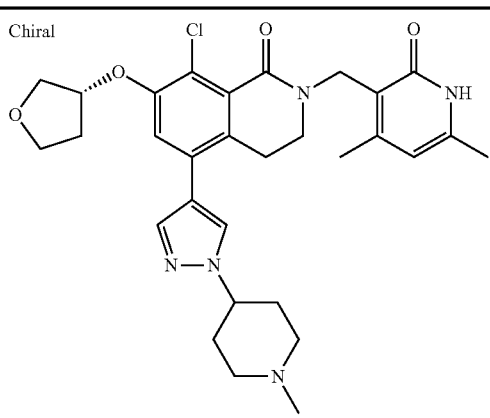<br>8-chloro-2-[(4,6-dimethyl-2-oxo-1,2-dihydropyridin-3-yl)methyl]-5-[1-(1-methylpiperidin-4-yl)-1H-pyrazol-4-yl]-7-[(3R)-tetrahydrofuran-3-yloxy]-3,4-dihydroisoquinolin-1(2H)-one | $^1$H NMR (400 MHz, Methanol-d4): δ 7.93 (s, 1H), 7.69 (s, 1H), 7.20 (s, 1H), 6.14 (s, 1H), 5.18 (s, 1H), 4.79 (s, 2H), 4.61 (s, 4H), 4.33 (s, 1H), 3.96-3.92 (m, 4H), 3.39-3.37 (m, 2H), 3.29-3.21 (m, 2H), 2.91-2.89 (m, 2H), 2.51 (s, 3H), 2.32 (s, 3H), 2.26 (s, 3H), 2.22-2.17 (m, 4H); MS: 566 [M + 1] | F |
| 219 | 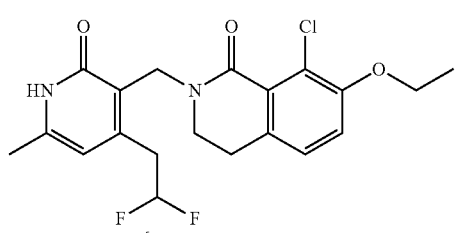<br>8-chloro-2-{[4-(2,2-difluoroethyl)-6-methyl-2-oxo-1,2-dihydropyridin-3-yl]methyl}-7-ethoxy-3,4-dihydroisoquinolin-1(2H)-one | $^1$H NMR (400 MHz, DMSO-d6) d 11.74 (br. s., 1H), 7.18 (d, J = 8.31 Hz, 1H), 7.15 (d, J = 8.31 Hz, 1H), 6.08-6.41 (m, 1H), 5.99 (s, 1H), 4.54 (s, 2H), 4.08 (q, J = 7.09 Hz, 2H), 3.50 (t, J = 6.11 Hz, 2H), 3.32 (dt, J = 4.40, 18.10 Hz, 2H), 2.75 (t, J = 5.99 Hz, 2H), 2.15 (s, 3H), 1.34 (t, J = 6.97 Hz, 3H); MS: 411 [M + 1] | C |
| 220 | 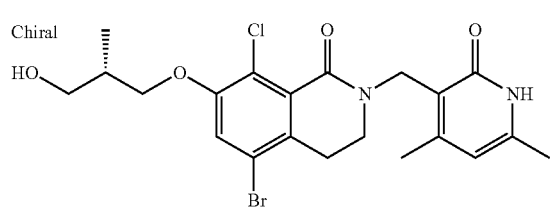 [SMILES: Cc1cc(C)c(CN2CCc3c(Br)cc(OC[C@@H](C)CO)c(Cl)c3C2=O)c(=O)[nH]1]<br>5-bromo-8-chloro-2-[(4,6-dimethyl-2-oxo-1,2-dihydropyridin-3-yl)methyl]-7-{[(2S)-3-hydroxy-2-methylpropyl]oxy}-3,4-dihydroisoquinolin-1(2H)-one | $^1$H NMR (600 MHz, DMSO-17 mm) δ 7.47 (s, 1H), 5.88 (s, 1H), 4.55 (s, 2H), 4.02 (dd, J = 5.69, 9.35 Hz, 2H), 3.93 (dd, J = 6.24, 9.17 Hz, 1H), 3.41-3.49 (m, 5H), 2.79 (t, J = 6.05 Hz, 2H), 2.14 (s, 3H), 2.12 (s, 3H), 1.96-2.04 (m, 1H), 0.97 (d, J = 6.97 Hz, 3H); MS: 485 [M + 1] | C |
| 221 | 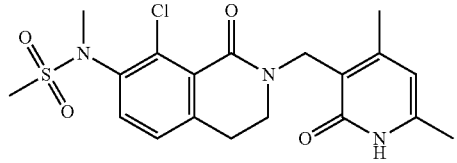<br>N-{8-chloro-2-[(4,6-dimethyl-2-oxo-1,2-dihydropyridin-3-yl)methyl]-1-oxo-1,2,3,4-tetrahydroisoquinolin-7-yl}-N-methylmethanesulfonamide | $^1$H NMR (600 MHz, DMSO-17 mm): δ 7.72 (d, J = 7.89 Hz, 1H), 7.62 (s, 1H), 7.39 (d, J = 8.07 Hz, 1H), 7.17 (s, 1H), 4.71-4.82 (m, 1H), 4.63-4.70 (m, 1H), 3.69 (s, 4H), 3.21 (s, 3H), 2.78-3.04 (m, 2H), 2.33-2.45 (m, 6H); MS: 424 [M + 1] | D |
| 222 | 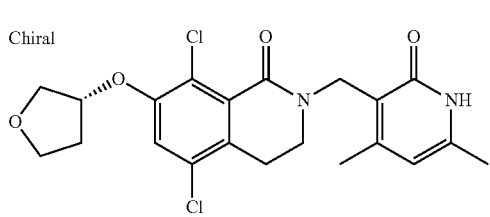 [SMILES: Cc1cc(C)c(CN2CCc3c(Cl)cc(O[C@@H]4CCOC4)c(Cl)c3C2=O)c(=O)[nH]1]<br>5,8-dichloro-2-[(4,6-dimethyl-2-oxo-1,2-dihydropyridin-3-yl)methyl]-7-[(3R)-tetrahydrofuran-3-yloxy]-3,4-dihydroisoquinolin- | $^1$H NMR (400 MHz, DMSO): δ 11.56 (s, 1H), 7.42 (s, 1H), 5.89 (s, 1H), 5.18 (s, 1H), 4.56 (s, 2H), 3.79-3.90 (m, 4H), 3.41-3.43 (m, 2H), 2.80-2.83 (m, 2H), 2.19-2.27 (m, 1H), 2.15 (s, 3H), 2.13 (s, 3H), 1.91-1.99 (m, 1H); MS: 437 [M + 1] | C |

| Ex. | Structure/Name | 1H NMR/LCMS (M + H) | Method |
|---|---|---|---|
| | 1(2H)-one | | |
| 223 | 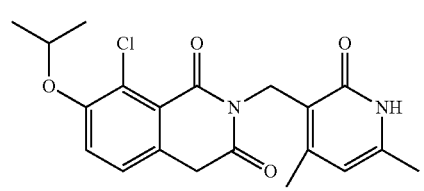 [SMILES: Cc1cc(C)c(CN2C(=O)Cc3ccc(OC(C)C)c(Cl)c3C2=O)c(=O)[nH]1]<br>5-chloro-3-[(4,6-dimethyl-2-oxo-1,2-dihydropyridin-3-yl)methyl]-6-(propan-2-yloxy)-2H-1,3-benzoxazine-2,4(3H)-dione | $^1$H NMR (400 MHz, DMSO-d6): δ 11.26 (s, 1H), 7.64 (d, J = 9.2 Hz, 1H), 7.37 (d, J = 9.2 Hz, 1H), 5.86 (s, 1H), 4.87 (s, 2H), 4.73-4.67 (m, 1H), 2.23 (s, 3H), 2.09 (s, 3H), 1.29 (d, J = 6 Hz, 6H); MS: 391 [M + 1] | unique |
| 224 | 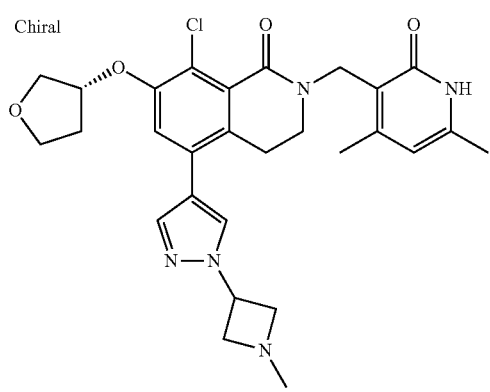<br>8-chloro-2-[(4,6-dimethyl-2-oxo-1,2-dihydropyridin-3-yl)methyl]-4-methyl-7-(propan-2-yloxy)-3,4-dihydroisoquinolin-1(2H)-one | $^1$H NMR (700 MHz, DMSO-17mm) d ppm 11.54 (br. s., 1H) 7.24 (d, J = 8.36 Hz, 1H) 7.17 (d, J = 8.58 Hz, 1H) 5.89 (s, 1H) 4.59-4.66 (m, 2H) 4.52-4.57 (m, 1 H) 3.44 (dd, J = 12.76, 3.96 Hz, 1 H) 3.19 (dd, J = 12.98, 5.50 Hz, 1 H) 2.91 (dd, J = 10.89, 5.39 Hz, 1 H) 2.17 (s, 3H) 2.13 (s, 3H) 1.29 (dd, J = 5.94, 3.08 Hz, 6H) 1.05 (d, J = 6.82 Hz, 3H); MS: 389 [M + 1] | V |
| 225 | Chiral<br>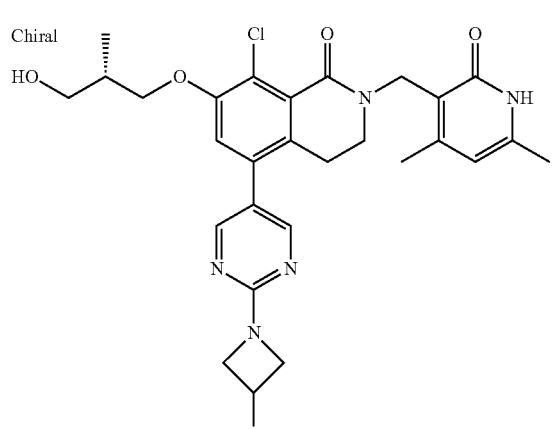<br>8-chloro-2-[(4,6-dimethyl-2-oxo-1,2-dihydropyridin-3-yl)methyl]-5-[1-(1-methylazetidin-3-yl)-1H-pyrazol-4-yl]-7-[(3R)-tetrahydrofuran-3-yloxy]-3,4-dihydroisoquinolin-1(2H)-one | $^1$H NMR (400 MHz, MeOD): δ 8.39 (m, 1H), 7.94 (s, 1H), 7.88 (s, 1H), 7.18 (s, 1H), 6.14 (s, 1H), 5.39 (t, J = 6.4, 1H), 5.15 (brs, 1H), 4.78 (s, 2H), 4.66-4.61 (m, 2H), 4.49-4.45 (m, 2H), 4.05-4.00 (m, 3H), 3.93-3.90 (m. 1H), 3.41 (t, J = 5.6, 2H), 3.05 (s, 3H), 2.90 (t, J = 5.6, 2H), 2.32 (s, 3H), 2.26-2.24 (m, 4H), 2.18-2.14 (m, 1H); MS: 538 [M + 1] | F |
| 226 | Chiral<br><br>8-chloro-2-[(4,6-dimethyl-2-oxo-1,2-dihydropyridin-3-yl)methyl]-5-[2-(3-fluoroazetidin-1-yl)pyrimidin-5-yl]-7-{[(2S)-3-hydroxy-2-methylpropyl]oxy}-3,4-dihydroisoquinolin-1(2H)-one | $^1$H NMR (400 MHz, DMSO-d6) d 11.53 (br. s., 1H), 8.46 (s, 2H), 7.18 (s, 1H), 5.88 (s, 1H), 5.53 (sptd, J = 3.18, 57.46 Hz, 1H), 4.54-4.60 (m, 3H), 4.34-4.47 (m, 2H), 4.12-4.19 (m, 1H), 4.03-4.12 (m, 3H), 3.96 (dd, J = 6.24, 9.41 Hz, 1H),3.44 (dtd, J = 4.89, 10.55, 15.83 Hz, 2H), 3.26 (d, J = 6.11 Hz, 2H), 2.64-2.71 (m. 2H), 2.17 (s, 3H), 2.11 (s, 3H), 0.98 (d, J = 6.85 Hz, 3H); MS: 556 [M + 1] | F |

TABLE 2-continued

| Ex. | Structure/Name | 1H NMR/LCMS (M + H) | Method |
|---|---|---|---|
| 227 | 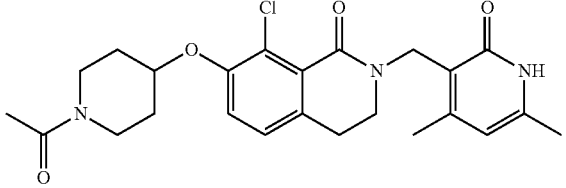 [SMILES: CC(=O)N1CCC(Oc2ccc3c(c2Cl)C(=O)N(Cc2c(C)cc(C)[nH]c2=O)CC3)CC1]<br>7-[(1-acetylpiperidin-4-yl)oxy]-8-chloro-2-[(4,6-dimethyl-2-oxo-1,2-dihydropyridin-3-yl)methyl]-3,4-dihydroisoquinolin-1(2H)-one | ¹H NMR (400 MHz, DMSO-d6) d 11.54 (br. s., 1H), 7.30 (d, J = 8.56 Hz, 1H), 7.16 (d, J = 8.56 Hz, 1H), 5.88 (s, 1H), 4.68 (tt, J = 3.30, 6.85 Hz, 1H), 4.57 (s, 2H), 3.58-371 (m, 2H), 3.34-3.46 (m, 4H), 2.75 (t, J = 5.99 Hz, 2H), 2.15 (s, 3H), 2.12 (s, 3H), 2.01 (s, 3H), 1.86-1.96 (m, 1H), 1.77-1.86 (m, 1H), 1.63-1.73 (m, 1H), 1.51-1.63 (m, 1H); MS: 458 [M + 1] | C |
| 228 | 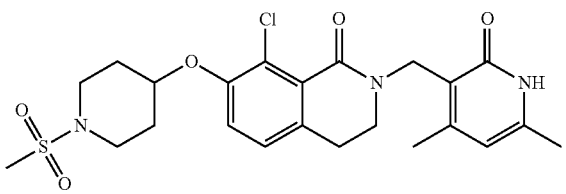<br>8-chloro-2-[(4,6-dimethyl-2-oxo-1,2-dihydropyridin-3-yl)methyl]-7-{[1-(methylsulfonyl)piperidin-4-yl]oxy}-3,4-dihydroisoquinolin-1(2H)-one | ¹H NMR (400 MHz, DMSO-d6) δ 11.52 (br. s., 1H), 7.29 (d, J = 8.31 Hz, 1H), 7.16 (d, J = 8.31 Hz, 1H), 5.88 (s, 1H), 4.63 (tt, J = 3.24, 6.17 Hz, 1H), 4.56 (s, 2H), 3.38 (t, J = 6.11 Hz, 2H), 3.25-3.29 (m, J = 3.18 Hz, 2H), 3.14-3.21 (m, 2H), 2.89 (s, 3H), 2.75 (t, J = 5.99 Hz, 2H), 2.15 (s, 3H), 2.12 (s, 3H), 1.91-2.00 (m, J = 4.16, 8.68, 8.68 Hz, 2H), 1.80 (dtd, J = 3.18, 6.48, 13.20 Hz, 2H); MS: 494 [M + 1] | C |
| 230 | 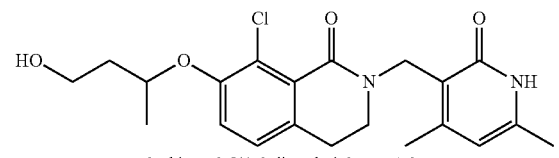<br>8-chloro-2-[(4,6-dimethyl-2-oxo-1,2-dihydropyridin-3-yl)methyl]-7-[(4-hydroxybutan-2-yl)oxy]-3,4-dihydroisoquinolin-1(2H)-one | ¹H NMR (400 MHz, CDCl3-d) 11.0 (br. s. 1H), 7.00 (d, J = 2.81 Hz, 2H), 5.92 (s, 1H), 4.81 (d, J = 1.71 Hz, 2H), 4.62 (br. s., 1H), 3.92 (br. s., 1H), 3.86 (br. s., 1H), 3.59 (t, J = 6.17 Hz, 2H), 2.78 (t, J = 6.05 Hz, 2H), 2.35 (s, 3H), 2.26 (s, 3H), 2.12-2.05 (m, 1H), 1.99-2.05; MS: 405 [M + 1] | C |
| 231 | 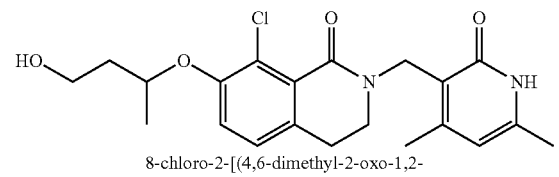<br>8-chloro-2-[(4,6-dimethyl-2-oxo-1,2-dihydropyridin-3-yl)methyl]-7-[(4-hydroxybutan-2-yl)oxyl-3,4-dihydroisoquinolin-1(2H)-one | ¹H NMR (400 MHz, CDCl3-d) 11.0 (br. s, 1H), 7.00 (d, J = 2.81 Hz, 2H), 5.92 (s, 1H), 4.81 (d, J = 1.71 Hz, 2H), 4.62 (br. s., 1H), 3.92 (br. s., 1H), 3.86 (br. s., 1H), 3.59 (t, J = 6.17 Hz, 2H), 2.78 (t, J = 6.05 Hz, 2H), 2.35 (s, 3H), 2.26 (s, 3H), 2.12-2.05 (m, 1H), 1.99-2.05; MS: 405 [M + 1] | C |
| 232 | 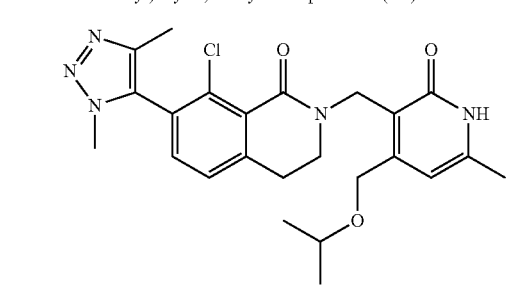<br>8-chloro-7-(1,4-dimethyl-1H-1,2,3-triazol-5-yl)-2-({6-methyl-2-oxo-4-[(propan-2-yloxy)methyl]-1,2-dihydropyridin-3-yl}methyl)-3,4-dihydroisoquinolin-1(2H)-one | ¹H NMR (400 MHz, Methanol-d4): δ 7.47-7.42 (m, 2H), 6.42 (s, 1H), 4.79 (s, 2H), 4.59 (s, 2H), 3.86 (s, 3H), 3.72-3.70 (m, 1H), 3.62 (t, J = 6 Hz, 2H), 3.03 (t, J = 6.2 Hz, 2H), 2.32 (s, 3H), 2.18 (s, 3H), 1.18 (d, J = 6 Hz, 6H); MS: 470 [M + 1] | D |
| 233 | 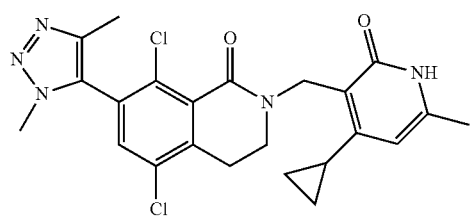 [SMILES: Cc1cc(C2CC2)c(CN2CCc3c(Cl)cc(-c4c(C)nnn4C)c(Cl)c3C2=O)c(=O)[nH]1]<br>5,8-dichloro-2-[(4-cyclopropyl-6-methyl-2-oxo-1,2-dihydropyridin-3-yl)methyl]-7-(1,4-dimethyl- | ¹H NMR (400 MHz, DMSO-d6) d 11.54 (s, 1H), 7.79 (s, 1H), 5.52 (s, 1H), 4.79 (s, 2H), 3.78 (s, 3H), 3.46 (t, J = 6.36 Hz, 2H), 2.98 (t, J = 6.24 Hz, 2H), 2.12-2.20 (m, 1H), 2.11 (s, 3H), 2.09 (s, 3H), 0.86-0.92 (m, 2H), 0.70-0.75 (m, 2H); MS: 472, 474 [M + 1] | D |

TABLE 2-continued

| Ex. | Structure/Name | 1H NMR/LCMS (M + H) | Method |
|---|---|---|---|
| | 1H-1,2,3-triazol-5-yl)-3,4-dihydroisoquinolin-1(2H)-one | | |
| 234 | Chiral 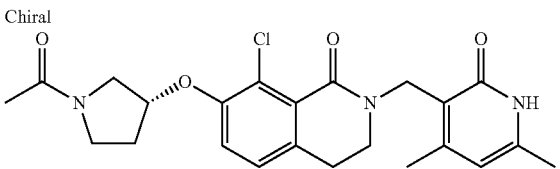 [SMILES: CC(=O)N1CC[C@@H](Oc2ccc3c(c2Cl)C(=O)N(Cc2c(C)cc(C)[nH]c2=O)CC3)C1]<br>7-{[(3R)-1-acetylpyrrolidin-3-yl]oxy}-8-chloro-2-[(4,6-dimethyl-2-oxo-1,2-dihydropyridin-3-yl)methyl]-3,4-dihydroisoquinolin-1(2H)-one | ¹H NMR (400 MHz, DMSO-d6) δ 11.53 (br. s., 1H), 7.24-7.32 (m, 1H), 7.18 (dd, J = 2.45, 8.31 Hz, 1H), 5.88 (s, 1H), 5.04-5.16 (m, 1H), 4.56 (s, 2H), 3.43-3.84 (m, 4H), 3.38 (t, J = 5.50 Hz, 3H), 2.75 (t, J = 4.52 Hz, 2H), 2.14 (s, 3H), 2.12 (s, 3H), 2.01-2.07 (m, 1H), 1.95 (d, J = 17.12 Hz, 3H); MS: 444 [M + 1] | C |
| 235 | Chiral 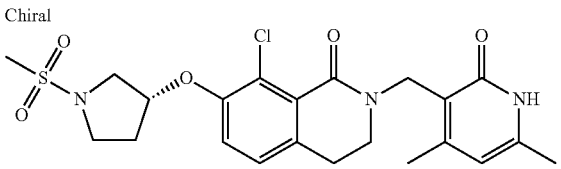<br>8-chloro-2-[(4,6-dimethyl-2-oxo-1,2-dihydropyridin-3-yl)methyl]-7-{[(3R)-1-(methylsulfonyl)pyrrolidin-3-yl]oxy}-3,4-dihydroisoquinolin-1(2H)-one | ¹H NMR (400 MHz, DMSO-d6) δ 11.53 (br. s., 1H), 7.27 (d, J = 8.56 Hz, 1H), 7.18 (d, J = 8.31 Hz, 1H), 5.88 (s, 1H), 5.10 (br. s., 1H), 4.56 (s, 2H), 3.61 (dd, J = 4.16, 11.98 Hz, 1H), 3.35-3.46 (m, 5H), 2.92 (s, 3H), 2.76 (t, J = 5.99 Hz, 2H), 2.15 (s, 3H), 2.12 (s, 3H), 2.05-2.26 (m, 2H); MS: 480 [M + 1] | C |
| 236 | 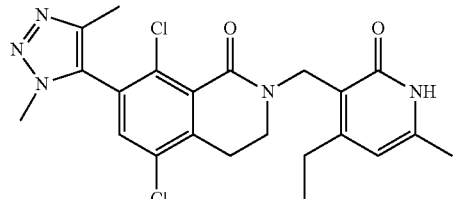<br>5,8-dichloro-7-(1,4-dimethyl-1H-1,2,3-triazol-5-yl)-2-[(4-ethyl-6-methyl-2-oxo-1,2-dihydropyridin-3-yl)methyl]-3,4-dihydroisoquinolin-1(2H)-one | ¹H NMR (400 MHz, DMSO-d6) d 11.56 (br. s., 1H), 7.78 (s, 1H), 5.95 (s, 1H), 4.62 (s, 2H), 3.79 (s, 3H), 3.54 (t, J = 6.60 Hz, 2H), 2.99 (t, J = 6.11 Hz, 2H), 2.57 (q, J = 7.34 Hz, 2H), 2.16 (s, 3H), 2.10 (s, 3H), 1.05 (t, J = 7.58 Hz, 3H); MS: 460, 462 [M + 1] | D |
| 237 | Chiral 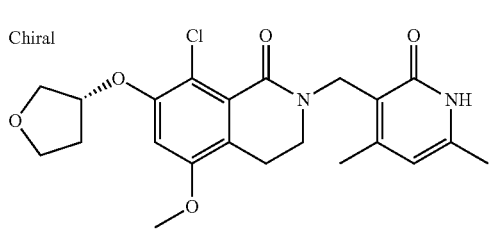 [SMILES: COc1cc(O[C@@H]2CCOC2)c(Cl)c2c1CCN(Cc1c(C)cc(C)[nH]c1=O)C2=O]<br>8-chloro-2-[(4,6-dimethyl-2-oxo-1,2-dihydropyridin-3-yl)methyl]-5-methoxy-7-[(3R)-tetrahydrofuran-3-yloxy]-3,4-dihydroisoquinolin-1(2H)-one | ¹H NMR (400 MHz, MeOD): δ 6.83 (s, 1H), 6.11 (s, 1H), 5.15-5.14 (m, 1H), 4.76 (s, 2H), 4.03-3.91 (m, 4H), 3.87 (s, 3H), 3.43-3.40-3.39 (m, 2H), 2.77-2.74 (m, 2H), 2.28 (s, 3H), 2.25 (s, 3H), 2.23-2.17 (m, 2H); MS: 433 [M + 1] | C |
| 238 | Chiral 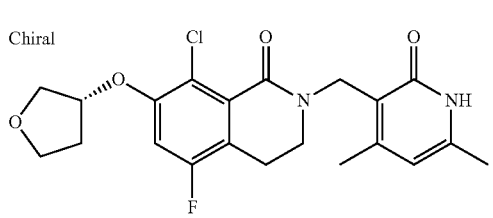 [SMILES: Cc1cc(C)c(CN2CCc3c(F)cc(O[C@@H]4CCOC4)c(Cl)c3C2=O)c(=O)[nH]1]<br>8-chloro-2-[(4,6-dimethyl-2-oxo-1,2-dihydropyridin-3-yl)methyl]-5-fluoro-7-[(3R)-tetrahydrofuran-3-yloxy]-3,4-dihydroisoquinolin-1(2H)-one | ¹H NMR (400 MHz, CDCl3): δ 12.70-12.50 (br s, 1H), 6.71 (d, J = 9.6 Hz, 1H), 6.15 (s, 1H), 4.89-4.88 (m, 1H), 4.73 (s, 2H), 4.02-3.94 (m, 4H), 3.65-3.50 (m, 2H), 2.80-2.77 (m, 2H), 2.19 (s, 3H), 2.17 (s, 3H), 2.16-2.15 (m, 2H); MS: 421 [M + 1] | C |

| Ex. | Structure/Name | 1H NMR/LCMS (M + H) | Method |
|---|---|---|---|
| 239 | 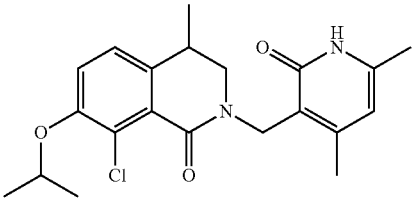 [SMILES: Cc1cc(C)c(CN2CC(C)c3ccc(OC(C)C)c(Cl)c3C2=O)c(=O)[nH]1]<br>8-chloro-2-[(4,6-dimethyl-2-oxo-1,2-dihydropyridin-3-yl)methyl]-4-methyl-7-(propan-2-yloxy)-3,4-dihydroisoquinolin-1(2H)-one | $^1$H NMR (600 MHz, DMSO-d6, flow NMR with large water peak at 3.38 ppm obscuring one of the expected peaks) d 11.54 (br. s., 1 H), 7.23 (d, J = 8.44 Hz, 1H), 7.16 (d, J = 8.44 Hz, 1H), 5.88 (s, 1H), 4.61 (t, J = 2.75 Hz, 1H), 4.57-4.64 (m, 1H), 4.49-4.56 (m, 1 H), 3.18 (d, J = 12.65 Hz, 1H), 2.87-2.92 (m, 1H), 2.15 (s, 3H), 2.12 (s, 3H), 1.27 (dd, J = 5.96, 2.48 Hz, 6H), 1.04 (d, J = 6.79 Hz, 3H); MS: 389 [M + 1] | V |
| 240 | 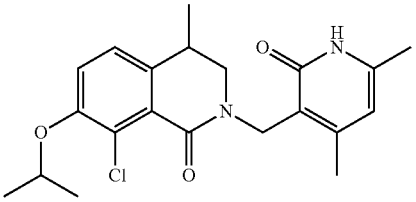 [SMILES: Cc1cc(C)c(CN2CC(C)c3ccc(OC(C)C)c(Cl)c3C2=O)c(=O)[nH]1]<br>8-chloro-2-[(4,6-dimethyl-2-oxo-1,2-dihydropyridin-3-yl)methyl]-4-methyl-7-(propan-2-yloxy)-3,4-dihydroisoquinolin-1(2H)-one | $^1$H NMR (600 MHz, DMSO-d6, flow NMR with large water peak at 3.38 ppm obscuring one of the expected peaks) d 11.54 (br. s., 1 H),7.23(d, J = 8.44 Hz, 1H), 7.16 (d, J = 8.44 Hz, 1H), 5.88 (s, 1H), 4.61 (t, J = 2.75 Hz, 1H), 4.57-4.64 (m, 1H), 4.49-4.56 (m, 1 H), 3.18 (d, J = 12.65 Hz, 1H), 2.87-2.92 (m, 1H), 2.15 (s, 3H), 2.12 (s, 3H), 1.27 (dd, J = 5.96, 2.48 Hz, 6H), 1.04 (d, J = 6.79 Hz, 3H); MS: 389 [M + 1] | V |
| 241 | 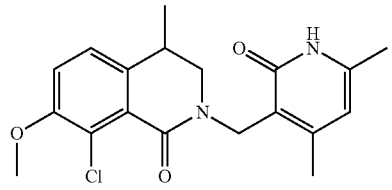 [SMILES: COc1ccc2c(c1Cl)C(=O)N(Cc1c(C)cc(C)[nH]c1=O)CC2C]<br>8-chloro-2-[(4,6-dimethyl-2-oxo-1,2-dihydropyrtdin-3-yl)methyl]-7-methoxy-4-methyl-3,4-dihydroisoquinolin-1(2H)-one | $^1$H NMR (600 MHz, DMSO-d6, flow NMR with large water peak at 3.38 ppm obscuring some of the expected peaks) 11.55 (br. s., 1H). 7.20 (q, J = 8.62 Hz, 2H), 5.88 (s, 1H), 4.62 (d, J = 13.76 Hz, 2H), 4.53 (d, J = 13.75 Hz, 2H), 3.83 (s, 3H), 2.87-2.96 (m, 1H), 2.12 (s, 3H), 2.15 (s, 3H); MS: 361 [M + 1] | V |
| 242 | 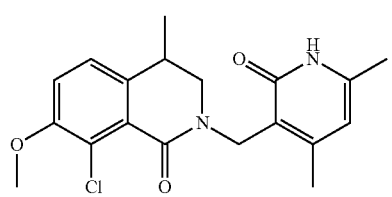 [SMILES: COc1ccc2c(c1Cl)C(=O)N(Cc1c(C)cc(C)[nH]c1=O)CC2C]<br>8-chloro-2-[(4,6-dimethyl-2-oxo-1,2-dihydropyridin-3-yl)methyl]-7-methoxy-4-methyl-3,4-dihydroisoquinolin-1(2H)-one | $^1$H NMR (600 MHz, DMSO-d6, flow NMR with large water peak at 3.38 ppm obscuring some of the expected peaks) 11.55 (br. s., 1H), 7.20 (q, J = 8.62 Hz, 2H), 5.88 (s, 1H), 4.62 (d, J = 13.76 Hz, 2H). 4.53 (d, J = 13.75 Hz, 2H), 3.83 (s, 3H), 2.87-2.96 (m, 1H), 2.12 (s, 3H), 2.15 (s, 3H); MS: 361 [M + 1] | V |
| 243 | 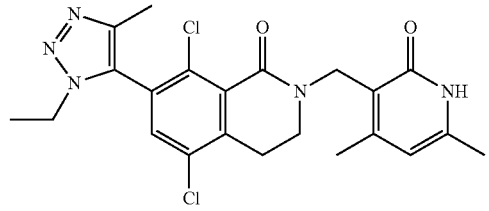 [SMILES: CCn1nnc(C)c1-c1cc(Cl)c2c(c1Cl)C(=O)N(Cc1c(C)cc(C)[nH]c1=O)CC2]<br>5,8-dichloro-2-((4,6-dimethyl-2-oxo-1,2-dihydropyridin-3-yl)methyl]-7-(1-ethyl-4-triethyl-1H-1,2,3-triazol-5-yl)-3,4-dihydroisoquinolin-1(2H)-one | $^1$H NMR (400 MHz, DMSO-d6) d 11.54 (s, 1H), 7.78 (s, 1H), 5.89 (s, 1H), 4.57 (s, 2H), 4.00-4.17 (m, 2H), 3.55 (t, J = 6.30 Hz, 2H), 2.99 (t, J = 6.17 Hz, 2H), 2.19 (s, 3H), 2.13 (s, 3H), 2.08 (s, 3H), 1.26 (t, J = 7.27 Hz, 3H); MS: 460, 462 [M + 1] | D |

TABLE 2-continued

| Ex. | Structure/Name | 1H NMR/LCMS (M + H) | Method |
|---|---|---|---|
| 244 | 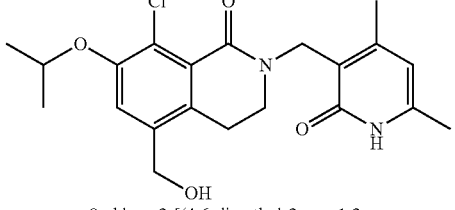<br>8-chloro-2-[(4,6-dimethyl-2-oxo-1,2-dihydropyridin-3-yl)methyl]-4-(hydroxymethyl)-7-(propan-2-yloxy)-3,4-dihydroisoquinolin-1(2H)-one | ¹H NMR (400 MHz, DMSO-d6): δ 11.60 (br. s., 1H), 7.21-7.32 (m, 1H), 7.10-7.21 (m, 1H), 5.91 (s, 1H), 4.90 (br. s., 1H), 4.62 (td, J = 5.99, 11.98 Hz, 1H), 4.41-4.58 (m, 2H), 3.63 (d, J = 10.76 Hz, 1H), 3.40-3.48 (m, 1H), 2.81 (br. s., 1H), 2.20 (s, 3H), 2.13 (s, 3H), 1.16-1.35 (m, 6H); MS: 405 [M + 1] | V |
| 245 | 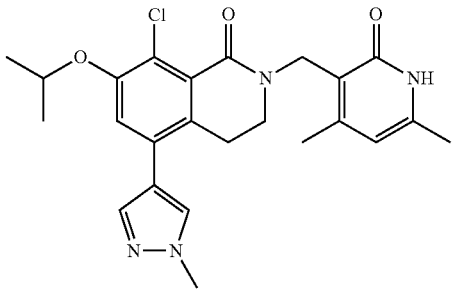 [SMILES: Cc1cc(C)c(CN2CCc3c(-c4cnn(C)c4)cc(OC(C)C)c(Cl)c3C2=O)c(=O)[nH]1]<br>8-chloro-2-[(4,6-dimethyl-2-oxo-1,2-dihydropyridin-3-yl)methyl]-5-(1-methyl-1H-imidazol-4-yl)-7-(propan-2-yloxy)-3,4-dihydroisoquinolin-1(2H)-one | ¹H NMR (400 MHz, Methanol-d4): δ 7.70 (s, 1H), 7.43 (s, 1H), 7.27 (s, 1H), 6.12 (s, 1H), 4.79 (s, 2H), 4.63 (m, 1H), 3.78 (s, 3H), 3.38-3.37 (t, J = 6.4 Hz, 2H), 2.97-2.906 (t, J = 6.4 Hz, 2H), 2.30 (s, 3H), 2.24 (s, 3H), 1.37-1.36 (d, J = 6 Hz, 6H); MS: 455 [M + 1] | F |
| 246 | 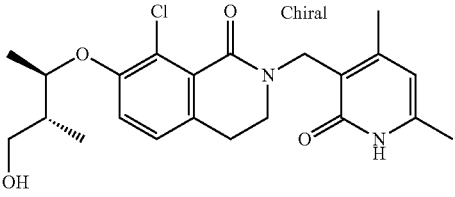 [SMILES: Cc1cc(C)c(CN2CCc3ccc(O[C@H](C)[C@H](C)CO)c(Cl)c3C2=O)c(=O)[nH]1]<br>8-chloro-2-[(4,6-dimethyl-2-oxo-1,2-dihydropyridin-3-yl)methyl]-7-{[(2S,3S)-4-hydroxy-3-methylbutan-2-yl]oxy}-3,4-dihydroisoquinolin-1(2H)-one | ¹H NMR (400 MHz, Methanol-d4): δ 7.16-7.12 (m, 2H), 6.11 (s, 1H), 4.77 (s, 2H), 3.70-3.65 (m, 1H), 3.55-3.52 (m, 1H), 3.46-3.42 (m, 2H), 2.81-2.80 (m, 2H), 2.29 (s, 3H), 2.28 (s, 3H), 2.15 (s, 1H), 1.94-1.91 (m, 2H), 1.29 (m, 3H), 1.10-1.08 (m, 3H); MS: 419 [M + 1] | A |
| 247 | 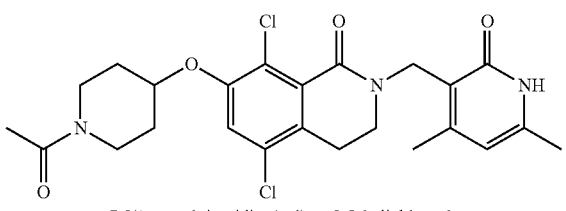<br>7-[(1-acetylpiperidin-4-yl)oxy]-5,8-dichloro-2-[(4,6-dimethyl-2-oxo-1,2-dihydropyridin-3-yl)methyl]-3,4-dihydroisoquinolin-1(2H)-one | ¹H NMR (400 MHz, DMSO-d6): δ 7.55 (s, 1H), 5.89 (s, 1H), 4.82-4.81 (d, J = 3.2 Hz, 1H), 4.56 (s, 2H), 3.65-3.63 (t, J = 4.4 Hz, 2H), 3.43-3.39 (m, 4H), 2.83-2.80 (t, J = 6 Hz, 2H), 2.51 (s, 6H), 2.15 (s, 3H), 2.12 (m, 1H), 2.02 (m, 1H), 1.92 (m, 1H), 1.82 (m, 1H); MS: 492 [M + 1] | C |
| 248 | 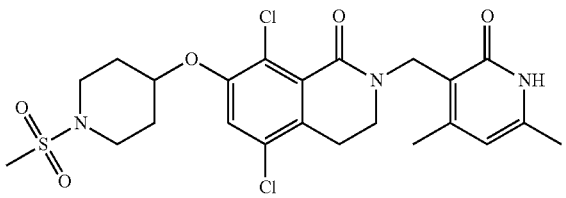<br>5,8-dichloro-2-[(4,6-dimethyl-2-oxo-1,2-dihydropyridin-3-yl)methyl]-7-{[1-(methylsulfonyl)piperidin-4-yl]oxy}-3,4-dihydroisoquinolin-1(2H)-one | ¹H NMR (400 MHz, DMSO-d6): δ 7.55 (s, 1H), 5.89 (s, 1H), 4.77-4.76 (t, J = 2.8 Hz, 1H), 4.56 (s, 2H), 3.43-3.42 (m, 2H), 3.40-3.35 (m, 2H), 3.28 (m, 2H), 2.91 (s, 3H), 2.83-2.82 (t, 2H), 2.15-2.12 (d, J = 12.4 Hz, 6H), 1.95-1.94 (m, 2H), 1.81-1.79 (m, 2H); MS: 528 [M + 1] | C |

TABLE 2-continued

| Ex. | Structure/Name | 1H NMR/LCMS (M + H) | Method |
|---|---|---|---|
| 249 | 8-chloro-2-[(4,6-dimethyl-2-oxo-1,2-dihydropyridin-3-yl)methyl]-7-[(3R)-tetrahydrofuran-3-yloxy]-6-(trifluoromethyl)-3,4-dihydroisoquinolin-1(2H)-one | $^1$H NMR (400 MHz, DMSO-d6): δ 7.62 (s, 1H), 5.90 (s, 1H), 5.76 (s, 2H), 5.14 (d, J = 2.57 Hz, 1H), 4.58 (s, 2H), 3.80-3.95 (m, 3H), 3.67-3.79 (m, 1H), 3.45 (t, J = 6.24 Hz, 3H), 2.88 (t, J = 6.11 Hz, 2H), 2.17 (s, 3H), 2.13 (s, 3H); MS: 471 [M + 1] | C |
| 250 | 8-chloro-2-[(4,6-dimethyl-2-oxo-1,2-dihydropyridin-3-yl)methyl]-7-(pyridazin-4-yloxy)-3,4-dihydroisoquinolin-1(2H)-one | $^1$H NMR (600 MHz, DMSO-17 mm) d 11.56 (br. s., 1H), 9.15 (d, J = 2.75 Hz, 1H), 9.03 (d, J = 6.05 Hz, 1H), 7.52 (d, J = 8.44 Hz, 1H), 7.39 (d, J = 8.25 Hz, 1H), 6.96 (dd, J = 2.93, 5.87 Hz, 1H), 5.89 (s, 1H), 4.57 (s, 2H), 3.46-3.48 (m, 2H), 2.89 (t, J = 6.05 Hz, 2H), 2.17 (s, 3H), 2.12 (s, 3H); MS: 411 [M + 1] | C |
| 251 | 8-chloro-2-[(4,6-dimethyl-2-oxo-1,2-dihydropyridin-3-yl)methyl]-4-(methoxymethyl)-7-(propan-2-yloxy)-3,4-dihydroisoquinolin-1(2H)-one | $^1$H NMR (400 MHz, DMSO-d6): δ 11.52 (br. s., 1H), 7.22-7.31 (m, 1H), 7.12-7.22 (m, 1H), 5.88 (s, 1H), 4.70 (d, J = 13.69 Hz, 1H), 4.62 (td, J = 5.96, 12.04 Hz, 1H), 4.42 (d, J = 13.69 Hz, 1H), 3.37-3.55 (m, 2H), 3.24 (dd, J = 5.44, 9.23 Hz, 1H), 3.11-3.19 (m, 1H), 3.10 (s, 3H), 2.90-3.00 (m, 1H), 2.15 (s, 3H), 2.12 (s, 3H), 1.28 (dd, J = 4.65, 5.75 Hz, 6H); MS: 419 [M + 1] | V |
| 252 | 7-[(1-acetylazetidin-3-yl)oxy]-8-chloro-2-[(4,6-dimethyl-2-oxo-1,2-dihydropyridin-3-yl)methyl]-3,4-dihydroisoquinolin-1(2H)-one | $^1$H NMR (400 MHz, DMSO-d6) δ 11.52 (br. s., 1H), 7.17 (d, J = 8.44 Hz, 1H), 6.96 (d, J = 8.31 Hz, 1H), 5.88 (s, 1H), 5.06 (tt, J = 3.84, 6.50 Hz, 1H), 4.57 (s, 2H), 4.52-4.56 (m, 1H), 4.29 (dd, J = 6.30, 10.33 Hz, 1H), 4.12 (dd, J = 3.12, 9.48 Hz, 1H), 3.78 (dd, J = 3.85, 10.58 Hz, 1H), 3.38 (t, J = 6.17 Hz, 2H), 2.76 (t, J = 6.05 Hz, 2H), 2.15 (s, 3H), 2.12 (s, 3H), 1.79 (s, 3H); MS: 430 [M + 1] | C |
| 254 | 5-(aminomethyl)-8-chloro-2-[(4,6-dimethyl-2-oxo-1,2-dihydropyridin-3-yl)methyl]-7-(propan-2-yloxy)-3,4-dihydroisoquinolin-1(2H)-one | $^1$H NMR (400 MHz, Methanol): δ 7.27 (s, 1H), 6.11 (s, 1H), 4.76 (s, 2H), 4.64-4.67 (m, 1H), 4.09 (s, 2H), 3.48-3.50 (t, J = 5.6 Hz, 2H), 2.84-2.87 (t, J = 6.0 Hz, 2H), 2.29 (s, 3H), 2.24 (s, 3H), 1.36-1.38 (d, J = 6.0 Hz, 6H); MS: 404 [M + 1] | G |

TABLE 2-continued

| Ex. | Structure/Name | 1H NMR/LCMS (M + H) | Method |
|---|---|---|---|
| 255 | 8-chloro-6-(difluoromethyl)-2-[(4,6-dimethyl-2-oxo-1,2-dihydropyridin-3-yl)methyl]-7-[(3R)-tetrahydrofuran-3-yloxy]-3,4-dihydroisoquinolin-1(2H)-one | ¹H NMR (600 MHz, DMSO-17 mm): δ 7.48 (s, 1H), 6.67-7.23 (m, 1H), 5.89 (s, 1H), 5.07 (d, J = 3.67 Hz, 1H), 4.57 (s, 2H), 3.96 (q, J = 7.83 Hz, 1H), 3.84 (d, J = 10.64 Hz, 1H), 3.71-3.81 (m, 1H), 3.65 (dd, J = 3.85, 10.64 Hz, 1H), 3.42 (t, J = 6.24 Hz, 3H), 2.86 (t, J = 6.14 Hz, 2H), 2.14 (br. s, 3H), 2.06-2.14 (m, 4H); MS: 453 [M + 1] | C |
| 256 | 7,9-dichloro-2-[(4,6-dimethyl-2-oxo-1,2-dihydropyridin-3-yl)methyl]-8-[(3R)-tetrahydrofuran-3-yloxy]-2,3,4,5-tetrahydro-1H-2-benzazepin-1-one | ¹H NMR (400 MHz, DMSO-d6) δ 11.55 (br. s., 1H), 7.40 (s, 1H), 5.91 (s, 1H), 5.00 (d, J = 2.45 Hz, 1H), 4.60 (d, J = 4.40 Hz, 2H), 3.89-4.07 (m, 2H), 3.70-3.89 (m, 2H), 3.35 (d, J = 5.87 Hz, 1H), 2.80-2.97 (m, 1H), 2.72 (dd, J = 6.36, 13.69 Hz, 1H), 2.21 (s, 3H), 2.13 (s, 4H), 1.99-2.09 (m, 1H), 1.81-1.94 (m, 1H), 1.44-1.62 (m, 1H); MS: 452 [M + 1] | S |
| 257 | 7-chloro-2-[(4,6-dimethyl-2-oxo-1,2-dihydropyridin-3-yl)methyl]-8-[(3R)-tetrahydrofuran-3-yloxy]-2,3,4,5-tetrahydro-1H-2-benzazepin-1-one | ¹H NMR (400 MHz, DMSO-d6) δ 7.11 (s, 2H), 5.91 (s, 1H), 4.93-5.19 (m, 1H), 4.61 (d, J = 3.18 Hz, 2H), 3.84-4.00 (m, 2H), 3.72-3.84 (m, 2H), 2.83 (d, J = 3.67 Hz, 1H), 2.61-2.72 (m, 1H), 2.39-2.47 (m, 2H), 2.20-2.25 (m, 3H), 2.10-2.15 (m, 3H), 1.94-2.03 (m, 2H), 1.83-1.93 (m, 1H), 1.44-1.56 (m, 1H), 1.24 (s, 2H); MS: 417 [M + 1] | S |
| 258 | 8-chloro-2-[(4,6-dimethyl-2-oxo-1,2-dihydropyridin-3-yl)methyl]-7-{[(2S,3R)-4-hydroxy-3-methylbutan-2-yl]oxy}-3,4-dihydroisoquinolin-1(2H)-one | ¹H NMR (400 MHz, Methanol-d4): δ 7.18-7.11 (m, 2H), 6.11 (s, 1H), 4.77 (s, 2H), 3.65-3.60 (m, 2H), 3.44-3.43 (m, 2H), 2.82-2.79 (m, 2H), 2.28 (s, 3H), 2.25 (s, 3H), 2.07-2.03 (m, 1H), 1.27-1.26 (m, 3H), 1.03-1.02 (m, 3H); MS: 419 [M + 1] | A |
| 259 | 8-chloro-5-(difluoromethyl)-2-[(4,6-dimethyl-2-oxo-1,2-dihydropyridin-3-yl)methyl]-7-[(3R)-tetrahydrofuran-3-yloxy]-3,4-dihydroisoquinolin-1(2H)-one | ¹H NMR (400 MHz, Methanol-d4): δ 7.35 (s, 1H), 6.76-7.11 (m, 1H), 6.12 (s, 1H), 5.16 (br. s., 1H), 4.77 (s, 2H), 3.96-4.08 (m, 3H), 3.92 (dt, J = 3.97, 8.28 Hz, 1H), 3.50 (t, J = 5.93 Hz, 2H), 2.94 (t, J = 6.05 Hz, 2H), 2.27-2.35 (m, 4H), 2.23-2.28 (m, 4H), 2.05-2.21 (m, 1H); MS: 453 [M + 1] | C |

TABLE 2-continued

| Ex. | Structure/Name | 1H NMR/LCMS (M + H) | Method |
|---|---|---|---|
| 260 | Chiral<br><br>2-[(4,6-dimethyl-2-oxo-1,2-dihydropyridin-3-yl)methyl]-7-[(3R)-tetrahydrofuran-3-yloxy]-5,8-bis(trifluoromethyl)-3,4-dihydroisoquinolin-1(2H)-one | $^1$H NMR (400 MHz. DMSO-d6): δ 11.60 (br. s., 1H), 7.60 (s, 1H), 5.90 (s, 1H), 5.43 (br. s., 1H), 4.58 (s, 2H), 3.86-4.02 (m, 1H), 3.70-3.86 (m, 3H), 3.50 (t, J = 5.62 Hz, 2H), 2.89 (br. s., 2H), 2.18-2.30 (m, 1H), 2.14 (s, 3H), 2.13 (s, 3H), 1.93-2.04 (m, 1H); MS: 505 [M + 1] | F |
| 261 | 5,8-dichloro-2-[(4,6-dimethyl-2-oxo-1,2-dihydropyridin-3-yl)methyl]-7-{[1-(methoxyacetyl)piperidin-4-yl]oxy}-3,4-dihydroisoquinolin-1(2H)-one | $^1$H NMR (600 MHz, DMSO-17 mm) d ppm: 7.53 (s, 1H), 5.90 (s, 1H), 4.80 (m, 1H), 4.56 (s, 2 H), 4.10 (s, 2H), 3.52-3.72 (m, 1 H), 3.41-3.52 (m, 2H), 2.82 (t, J = 6.15 Hz, 2H), 2.16 (s, 3H), 2.13 (s, 3H), 1.81-1.96 (m, 2H), 1.55-1.72 (m, 2H); MS: 522 [M + 1] | C |
| 262 | 5,8-dichloro-2-[(4,6-dimethyl-2-oxo-1,2-dihydropyridin-3-yl)methyl]-7-{[1-(hydroxyacetyl)piperidin-4-yl]oxy}-3,4-dihydroisoquinolin-1(2H)-one | $^1$H NMR (600 MHz, DMSO-17 mm) d ppm 7.55 (s, 1H), 5.90 (s, 1H), 4.77-4.87 (m, 1H), 4.57 (s, 2H), 4.12 (s, 2H), 3.65-3.74 (m, 1H), 3.50-3.58 (m, 1H), 2.82 (t, J = 6.15 Hz, 2H), 2.16 (s, 3H), 2.13 (s, 3H), 1.82-1.98 (m, 2H), 1.57-1.73 (m, 2H), 4 H are shadowed by H2O peak; MS: 508 [M + 1] | C |
| 263 | 5,8-dichloro-2-[(4,6-dimethyl-2-oxo-1,2-dihydropyridin-3-yl)methyl]-7-{[1-(2-hydroxypropanoyl)piperidin-4-yl]oxy}-3,4-dihydroisoquinolin-1(2H)-one | $^1$H NMR (600 MHz, DMSO-17 mm) d ppm 7.54 (s, 1H), 7.16 (br. s., 1H), 5.90 (s, 1H), 4.82 (br. s., 1H), 4.56 (s, 2H), 4.45 (quin, J = 6.62 Hz, 1H), 3.59-3.79 (m, 2H), 2.82 (t, J = 6.29 Hz, 2H), 2.16 (s, 3H), 2.13 (s, 3H), 1.81-1.98 (m, 2H), 1.53-1.73 (m, 2H), 1.19 (d, J = 6.44 Hz, 3H). 3 Hs are shadowed by H2Opeak; MS: 522 [M + 1] | C |
| 264 | | $^1$H NMR (600 M Hz, DMSO-17 mm) d ppm 7.54 (s, 1H), 5.91 (s, 1H), 4.78-4.84 (m, 1H), 4.56 (s, 2H), 4.23 (q, J = 6.59 Hz, 1H), 3.65-3.77 (m, 2H), 3.46-3.50 (m, 4H), 3.21 (s, 3H), 2.82 (t, J = 6.22 Hz, 2H), 2.16 (s, 3H), 2.13 (s, 3H), 1.82-1.98 (m, 2H), 1.54-1.71 (m, 2H), 1.22 (d, J = 6.59 Hz, 3H); MS: 536 [M + 1] | C |

| Ex. | Structure/Name | 1H NMR/LCMS (M + H) | Method |
|---|---|---|---|
|  | 5,8-dichloro-2-[(4,6-dimethyl-2-oxo-1,2-dihydropyridin-3-yl)methyl]-7-{[1-(2-methoxypropanoyl)piperidin-4-yl]oxy}-3,4-dihydroisoquinolin-1(2H)-one | | |
| 265 | 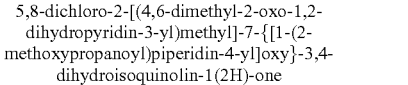 5,8-dichloro-2-[(4-cyclopropyl-6-methyl-2-oxo-1,2-dihydropyridin-3-yl)methyl]-7-[(3R)-tetrahydrofuran-3-yloxy]-3,4-dihydroisoquinolin-1(2H)-one | $^1$H NMR (600 M Hz, DMSO-17 mm) d ppm 7.42 (s, 1H), 5.51 (s, 1H), 5.18 (t, J = 5.56 Hz, 1H), 4.78 (s, 2H), 3.85-3.92 (m, 2H), 3.75-3.85 (m, 2H), 2.82 (t, J = 6.15 Hz, 2H), 2.19-2.27 (m, 1H), 2.08-2.14 (m, 4H), 1.98 (dd, J = 12.66, 6.07 Hz, 1H), 0.84-0.91 (m, 3H), 0.69-0.74 (m, 2H); MS: 463 [M + 1] | C |
| 266 | 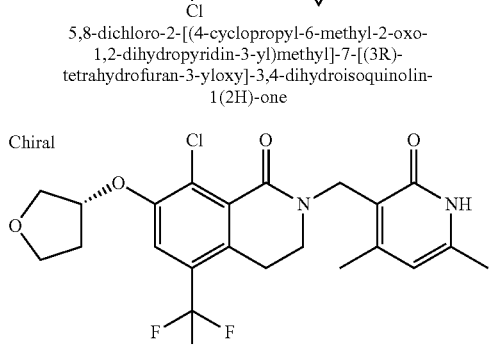 8-chloro-2-[(4,6-dimethyl-2-oxo-1,2-dihydropyridin-3-yl)methyl]-7-[(3R)-tetrahydrofuran-3-yloxy]-5-(trifluoromethyl)-3,4-dihydroisoquinolin-1(2H)-one | $^1$H NMR (400 M Hz, DMSO-d6): δ 11.57 (br. s., 1H), 7.48 (s, 1H), 5.90 (s, 1H), 5.23-5.39 (m, J = 4.30 Hz, 1H), 4.58 (s, 2H), 3.83-3.96 (m, 3H), 3.72-3.83 (m, 1H), 3.45 (t, J = 5.75 Hz, 2H), 2.81-2.93 (m, 2H), 2.19-2.30 (m, 1H), 2.18 (s, 3H), 2.13 (s, 3H), 1.93-2.03 (m, 1H); MS: 471 [M + 1] | F |
| 267 | 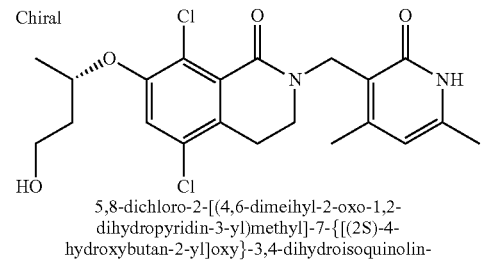 5,8-dichloro-2-[(4,6-dimeihyl-2-oxo-1,2-dihydropyridin-3-yl)methyl]-7-{[(2S)-4-hydroxybutan-2-yl]oxy}-3,4-dihydroisoquinolin-1(2H)-one | $^1$H NMR (400 MHz, methanol-d4) d ppm: 7.31 (s, 1H), 6.10 (s, 1H), 4.75 (s, 2H), 4.66 (dq, J = 12.23, 6.11 Hz, 1H), 3.66-3.78 (m, 2H), 3.48 (t, J = 6.24 Hz, 2H), 2.90 (t, J = 6.24 Hz, 2H), 2.28 (s, 3H), 2.24 (s, 3H), 1.94-2.05 (m, 1H), 1.84 (m, 1H), 1.33 (d, J = 6.11 Hz, 3H); MS: 439 [M + 1] | C |
| 268 | 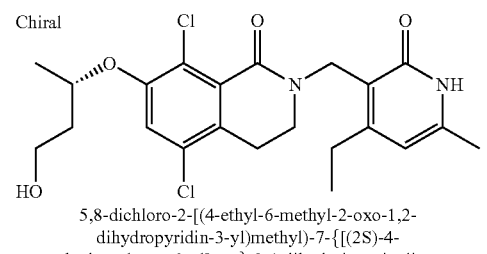 5,8-dichloro-2-[(4-ethyl-6-methyl-2-oxo-1,2-dihydropyridin-3-yl)methyl)-7-{[(2S)-4-hydroxybutan-2-yl]oxy}-3,4-dihydroisoquinolin-1(2H)-one | $^1$H NMR (400 MHz, methanol-d4) d ppm 7.31 (s, 1H), 6.14 (s, 1H), 4.78 (s, 2H), 4.66 (dq, J = 12.20, 6.00 Hz, 1H), 3.67-3.76 (m, 2H), 3.47 (t, J = 6.24 Hz, 2H), 2.90 (t, J = 6.24 Hz, 2H), 2.66 (q, J = 7.50 Hz, 2H), 2.26 (s, 3H), 1.94-2.06 (m, 1H), 1.79-1.91 (m, 1H), 1.34 (d, J = 6.11 Hz, 3H), 1.13 (t, J = 7.58 Hz, 3H); MS: 453 [M + 1] | C |
| 269 | 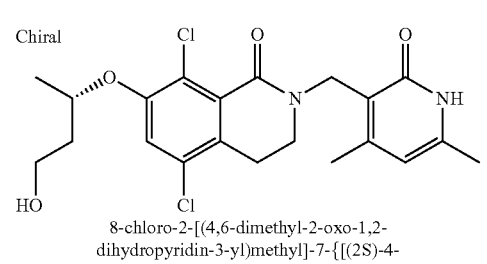 8-chloro-2-[(4,6-dimethyl-2-oxo-1,2-dihydropyridin-3-yl)methyl]-7-{[(2S)-4-hydroxybutan-2-yl]oxy}-3,4-dihydroisoquinolin-1(2H)-one | $^1$H NMR (400 MHz, methanol-d4) d ppm 7.15-7.20 (m, 1H), 7.07-7.14 (m, 1H), 6.10 (s, 1H), 4.76 (s, 2H), 4.63 (dq, J = 12.32, 6.12 Hz, 1H), 3.69-3.78 (m, 2H), 3.39-3.48 (m, 2H), 2.79 (t, J = 6.17 Hz, 2H), 2.28 (s, 3H), 2.24 (s, 3H), 1.95-2.06 (m, 1H), 1.79-1.90 (m, 1H), 1.32 (d, J = 6.11 Hz, 3H); MS: 405 [M + 1] | C |

TABLE 2-continued

| Ex. | Structure/Name | 1H NMR/LCMS (M + H) | Method |
|---|---|---|---|
| 270 | 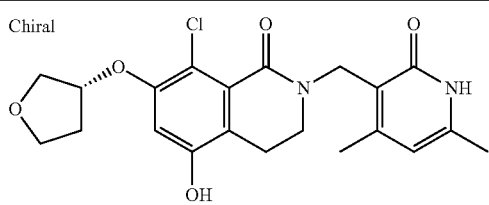<br>8-chloro-2-[(4,6-dimethyl-2-oxo-1,2-dihydropyridin-3-yl)methyl]-5-hydroxy-7-[(3R)-tetrahydrofuran-3-yloxy]-3,4-dihydroisoquinolin-1(2H)-one | $^1$H NMR (400 MHz, DMSO-d6): δ 11.55 (br. s., 1H), 6.69 (s, 1H), 5.89 (s, 1H), 4.94 (br. s., 1H), 4.56 (s, 2H), 3.70-3.93 (m, 5H), 2.61 (t, J = 6.05 Hz, 2H), 2.15-2.24 (m, 1H), 2.14 (s, 3H), 2.13 (s, 3H), 1.88-2.03 (m, 1H); MS: 419 [M + 1] | F |
| 271 | 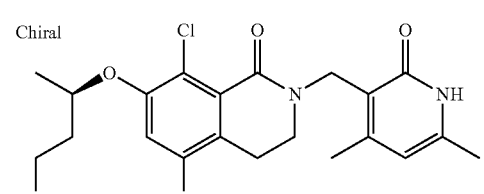<br>5,8-dichloro-2-[(4,6-dimethyl-2-oxo-1,2-dihydropyridin-3-yl)methyl]-7-{[(2R)-4-hydroxybutan-2-yl]oxy}-3,4-dihydroisoquinolin-1(2H)-one | $^1$H NMR (400 MHz, methanol-d4) d ppm 7.31 (s, 1H), 6.09 (s, 1 H), 4.75 (s, 2H), 4.66 (dq, J = 12.32, 6.16 Hz, 1H), 3.67-3.79 (m, 2H), 3.48 (t, J = 6.24 Hz, 2H), 2.90 (t, J = 6.24 Hz, 2H), 2.28 (s, 3H), 2.24 (s, 3H), 1.94-2.05 (m, 1H), 1.79-1.90 (m, 1 H), 1.33 (d, J = 5.99 Hz, 3H); MS: 439 [M + 1] | C |
| 272 | 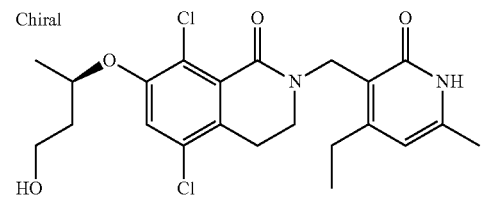 [SMILES: CCc1cc(C)[nH]c(=O)c1CN1CCc2c(Cl)cc(O[C@H](C)CCO)c(Cl)c2C1=O]<br>5,8-dichloro-2-[(4-ethyl-6-methyl-2-oxo-1,2-dihydropyridin-3-yl)methyl]-7-{[(2R)-4-hydroxybutan-2-yl]oxy}-3,4-dihydroisoquinolin-1(2H)-one | $^1$H NMR (400 MHz, methanol-d4) d ppm 7.31 (s, 1H), 6.14 (s, 1 H), 4.78 (s, 2H), 4.66 (dq, J = 12.35, 6.11 Hz, 1H), 3.67-3.76 (m, 2H), 3.47 (t, J = 6.24 Hz, 2H), 2.90 (t, J = 6.24 Hz, 2H), 2.66 (q, J = 7.58 Hz, 2H), 2.26 (s, 3H), 1.95-2.05 (m, 1H), 1.80-1.90 (m, 1H), 1.34 (d, J = 6.11 Hz, 3H), 1.13 (t, J = 7.52 Hz, 3H); MS: 453 [M + 1] | C |
| 273 | 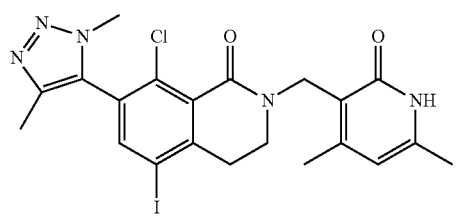 [SMILES: Cc1cc(C)c(CN2CCc3c(I)cc(-c4c(C)nnn4C)c(Cl)c3C2=O)c(=O)[nH]1]<br>8-chloro-2-[(4,6-dimethyl-2-oxo-1,2-dihydropyridin-3-yl)methyl]-7-(1,4-dimethyl-1H-1,2,3-triazol-5-yl)-5-iodo-3,4-dihydroisoquinolin-1(2H)-one | $^1$H NMR (400 MHz, DMSO-d6): δ ppm 11.59 (s, 1H), 8.04 (s, 1H), 5.90 (s, 1H), 4.56 (s, 2H), 3.77 (s, 3H), 3.52 (t, J = 6.2 Hz, 2H), 2.92 (t, J = 6 Hz, 2H), 2.19 (s, 3H), 2.13 (s, 3H), 2.08 (s, 3H); MS: 538 [M + 1] | X |
| 274 | 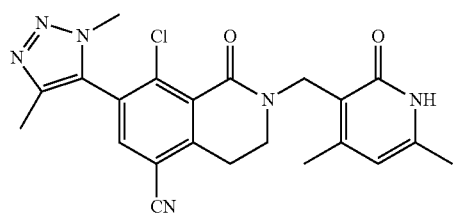 [SMILES: Cc1cc(C)c(CN2CCc3c(C#N)cc(-c4c(C)nnn4C)c(Cl)c3C2=O)c(=O)[nH]1]<br>8-chloro-2-[(4,6-dimethyl-2-oxo-1,2-dihydropyridin-3-yl)methyl]-7-(1,4-dimethyl-1H-1,2,3-triazol-5-yl)-1-oxo-1,2,3,4-tetrahydroisoquinoline-5-carbonitrile | $^1$H NMR (400 MHz, DMSO): δ 11.60 (br s, 1H), 8.13 (s, 1H), 5.90 (s, 1H), 4.57 (s, 2H), 3.78 (s, 3H), 3.60-3.57 (m, 2H), 3.13-3.10 (m, 2H), 2.19 (s, 3H), 2.13 (s, 3H), 2.09 (s, 3H); MS: 437 [M + 1] | X |

TABLE 2-continued

| Ex. | Structure/Name | 1H NMR/LCMS (M + H) | Method |
|---|---|---|---|
| 275 | 8-chloro-2-[(4,6-dimethyl-2-oxo-1,2-dihydropyridin-3-yl)methyl]-7-{[(2R)-4-hydroxybutan-2-yl]oxy}-3,4-dihydroisoquinolin-1(2H)-one | ¹H NMR (400 MHz, methanol-d4) d ppm: 7.14-7.20 (m, 1H), 7.08-7.14 (m, 1H), 6.09 (s, 1H), 4.76 (s, 2H), 4.63 (dq, J = 12.32, 6.12 Hz, 1H), 3.67-3.79 (m, 2 H), 3.40-3.48 (m, 2H), 2.80 (t, J = 6.17 Hz, 2H), 2.27 (s, 3H), 2.24 (s, 3H), 1.94-2.06 (m, 1H), 1.78-1.90 (m, 1H), 1.32 (d, J = 6.11 Hz, 3H); MS: 405 [M + 1] | C |
| 276 | 8-chloro-2-[(4,6-dimethyl-2-oxo-1,2-dihydropyridin-3-yl)methyl]-4-(hydroxymethyl)-7-(propan-2-yloxy)-3,4-dihydroisoquinolin-1(2H)-one | ¹H NMR (400 MHz, DMSO-d6): δ 11.60 (br. s., 1H), 7.22-7.30 (m, 1H), 7.11-7.22 (m, 1H), 5.91 (s, 1H), 4.89 (t, J = 5.56 Hz, 1H), 4.62 (td, J = 6.05, 12.10 Hz, 1H), 4.34-4.59 (m, 2H), 3.63 (dd, J = 2.75, 13.02 Hz, 1H), 3.36-3.48 (m, 3H), 2.81 (br. s., 1H), 2.20 (s, 3H), 2.13 (s, 3H), 1.28 (dd, J = 4.10, 5.81 Hz, 6H); MS: 405 [M + 1] | V |
| 277 | 8-chloro-2-[(4,6-dimethyl-2-oxo-1,2-dihydropyridin-3-yl)methyl]-4-(hydroxymethyl)-7-(propan-2-yloxy)-3,4-dihydroisoquinolin-1(2H)-one | ¹H NMR (400 MHz, DMSO-d6): δ 11.60 (br. s., 1H), 7.22-7.28 (m, 1H), 7.07-7.22 (m, 1H), 5.91 (s, 1H), 4.89 (t, J = 5.38 Hz, 1H), 4.62 (td, J = 6.01, 12.07 Hz, 1H), 4.41-4.58 (m, 2H), 3.59-3.69 (m, 1H), 3.36-3.48 (m, 3H), 2.81 (br. s., 1H), 2.20 (s, 3H), 2.13 (s, 3H), 1.28 (dd, J = 4.03, 5.75 Hz, 6H); MS: 405 [M + 1] | V |
| 278 | 5,8-dichloro-2-[(4,6-dimethyl-2-oxo-1,2-dihydropyridin-3-yl)methyl]-7-(oxetan-3-yloxy)-3,4-dihydroisoquinolin-1(2H)-one | ¹H NMR (400 MHz, DMSO): δ 11.58 (s, 1H), 7.04 (s, 1H), 5.89 (s, 1H), 5.41-5.39 (m, 1H), 4.95 (t, J = 6.8, 2H), 4.56 (m, J = 4, 4H), 3.44-3.40 (m, 2H), 2.81 (t, J = 6.8, 2H), 2.16 (s, 3H), 2.12 (s, 3H); MS: 423 [M + 1] | C |
| 279 | 8-chloro-5-cyclopropyl-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one | ¹H NMR (400 MHz, MeOD): δ 7.18 (s, 1H), 6.15 (s, 1H), 4.60 (s, 2H), 3.84 (s, 3H), 3.62-3.59 (m, 2H), 3.18-3.16 (m, 2H), 2.33 (s, 3H), 2.28 (s, 3H), 2.16 (s, 3H), 1.98-1.96 (m, 1H), 1.04-1.01 (m, 2H), 0.71-0.68 (m, 2H); MS: 452 [M + 1] | X |

TABLE 2-continued

| Ex. | Structure/Name | 1H NMR/LCMS (M + H) | Method |
|---|---|---|---|
| 280 | 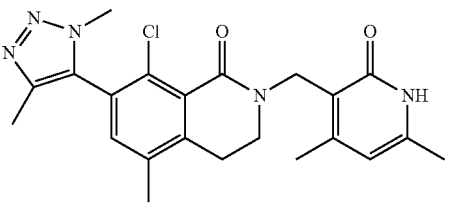 [SMILES: Cc1cc(C)c(CN2CCc3c(C)cc(-c4c(C)nnn4C)c(Cl)c3C2=O)c(=O)[nH]1]<br>8-chloro-2-[(4,6-dimethyl-2-oxo-1,2-dihydropyridin-3-yl)methyl]-7-(1,4-dimethyl-1H-1,2,3-triazol-5-yl)-5-methyl-3,4-dihydroisoquinolin-1(2H)-one | $^1$H NMR (Methanol-d4 400 MHz): δ ppm 7.35 (s, 1H), 6.14 (s, 1H), 4.80 (s, 2H), 3.86 (s, 3H), 3.58 (t, J = 6.2 Hz, 2H), 2.94 (t, J = 6.2 Hz, 2H), 2.36 (s, 3H), 2.33 (s, 3H), 2.27 (s, 3H), 2.17 (s, 3H); MS: 425 [M + 1] | X |
| 281 | Chiral<br>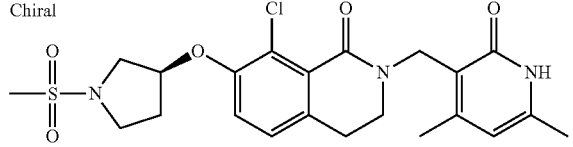<br>8-chloro-2-[(4,6-dimethyl-2-oxo-1,2-dihydropyridin-3-yl)methyl]-7-{[(3S)-1-(methylsulfonyl)pyrrolidin-3-yl]oxy}-3,4-dihydroisoquinolin-1(2H)-one | $^1$H NMR (400 MHz, CDCl3): δ 11.80 (s, 1H), 7.02 (d, J = 8.4 Hz, 1H), 6.92 (d, J = 8.4 Hz, 1H), 5.93 (s, 1H), 4.95 (s, 1H), 4.822-4.743 (m, 2H), 3.67-3.63 (m, 2H), 3.60-3.51 (m, 4H), 2.91 (s, 3H), 2.80-2.77 (t, 2H), 2.34-2.27 (m, 7H), 2.20-2.10 (m, 1H); MS: 480 [M + 1] | A |
| 282 | Chiral<br>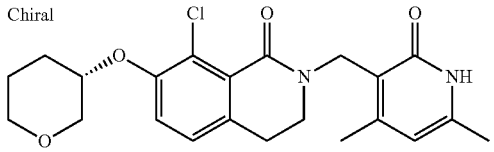 [SMILES: Cc1cc(C)c(CN2CCc3ccc(O[C@H]4CCCOC4)c(Cl)c3C2=O)c(=O)[nH]1]<br>8-chloro-2-[(4,6-dimethyl-2-oxo-1,2-dihydropyridin-3-yl)methyl]-7-[(3S)-tetrahydro-2H-pyran-3-yloxy]-3,4-dihydroisoquinolin-1(2H)-one | $^1$H NMR (400 MHz, CDCl3): δ 11.11 (brs, 1H), 7.02 (d, J = 8.4 Hz, 1H), 6.97 (d, J = 8.4 Hz, 1H), 5.92 (s,1H),4.80 (s, 2H), 4.24-4.20 (m, 1H), 3.96 (d, J = 11.2 Hz 1H), 3.78-3.75 (m, 1H), 3.62-3.56 (m, 4H), 2.79-2.76 (m, 2H), 2.34 (s, 3H), 2.26 (s, 3H), 2.09-2.05 (m, 1H), 1.92-1.84 (m, 2H), 1.58-1.53 (m, 1H); MS:417 [M + 1] | A |
| 283 | Chiral<br>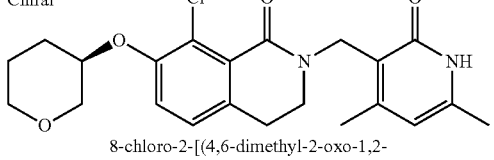<br>8-chloro-2-[(4,6-dimethyl-2-oxo-1,2-dihydropyridin-3-yl)methyl]-7-[(3R)-tetrahydro-2H-pyran-3-yloxy]-3,4-dihydroisoquinolin-1(2H)-one | $^1$H NMR (400 MHz, CDCl3): δ 12.03 (brs, 1H), 7.02-7.00 (d, J = 8.4 Hz, 1H), 6.98-6.96 (d, J = 8.4 Hz, 1H), 5.94 (s, 1H), 4.80 (s, 2H), 4.24-4.20 (m, 1H), 3.98-3.95 (d, J = 11.2 Hz, 1H), 3.78-3.75 (m, 1H), 3.62-3.56 (m, 4H), 2.79-2.76 (m, 2H), 2.34 (s, 3H), 2.26 (s, 3H), 2.09-2.05 (m, 1H), 1.92-1.84 (m, 2H), 1.58-1.53 (m, 1H); MS: 417 [M + 1] | A |
| 284 | 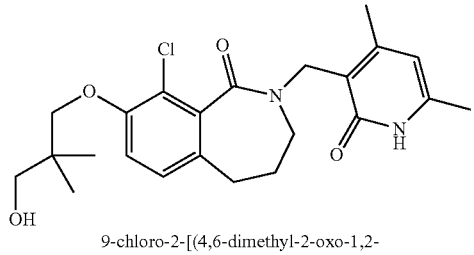<br>9-chloro-2-[(4,6-dimethyl-2-oxo-1,2-dihydropyridin-3-yl)methyl]-8-(3-hydroxy-2,2-dimethylpropoxy)-2,3,4,5-tetrahydro-1H-2-benzazepin-1-one | $^1$H NMR (400 MHz, DMSO-d6) δ 11.54 (br. s., 1H), 7.04-7.12 (m, 2H), 5.91 (s, 1H), 4.55-4.68 (m, 3H), 3.71-3.80 (m, 2H), 2.83 (d, J = 3.67 Hz, 1H), 2.57-2.71 (m, 1H), 2.39-2.47 (m, 1H), 2.22 (s, 3H), 2.13 (s, 3H), 1.86 (d, J = 6.60 Hz, 1H), 1.41-1.52 (m, 1H), 1.24 (br. s., 1H), 0.95 (s, 6H); MS: 433 [M + 1] | S |
| 285 | Chiral<br>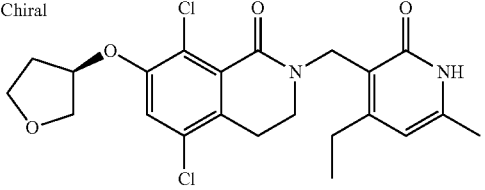 [SMILES: CCc1cc(C)[nH]c(=O)c1CN1CCc2c(Cl)cc(O[C@@H]3CCOC3)c(Cl)c2C1=O]<br>5,8-dichloro-2-[(4-ethyl-6-methyl-2-oxo-1,2-dihydropyridin-3-yl)methyl]-7-[(3R)- | $^1$H NMR (400 MHz, methanol-d4) d ppm: 7.43 (s, 1H), 6.02 (s, 1H), 4.67 (s, 2H), 3.48 (t, J = 6.24 Hz, 2H), 2.95 (t, J = 6.24 Hz, 2H), 2.21 (s, 3H), 2.18 (s, 3H), 2.15 (s, 3H), 2.02 (s, 3H); MS: 451 [M + 1] | C |

TABLE 2-continued

| Ex. | Structure/Name | 1H NMR/LCMS (M + H) | Method |
|---|---|---|---|
|  | tetrahydrofuran-3-yloxy]-3,4-dihydroisoquinolin-1(2H)-one |  |  |
| 286 | 8-chloro-2-[(4,6-dimethyl-2-oxo-1,2-dihydropyridin-3-yl)methyl]-3-methyl-7-[(3R)-tetrahydrofuran-3-yloxy]-3,4-dihydroisoquinolin-1(2H)-one | ¹H NMR (400 MHz, MeOD): δ 7.19-7.13 (m, 2H), 6.13 (s, 1H), 5.09-5.08 (m, 1H), 4.96-4.92 (m, 1H), 4.65-4.61 (m, 1H), 4.03-4.00 (m, 3H), 3.99-3.92 (m, 2H), 3.33-3.32 (m, 1H), 2.63-2.62 (d, J = 1.6, 3H), 2.59 (s, 3H), 2.59-2.31 (m, 5H), 1.01-0.99 (d, J = 6.8, 2H); MS: 417 [M + 1] | W |
| 287 | 2,5-anhydro-1,3-dideoxy-4-O-{5,8-dichloro-2-[(4,6-dimethyl-2-oxo-1,2-dihydropyridin-3-yl)methyl]-1-oxo-1,2,3,4-tetrahydroisoquinolin-7-yl}-L-threo-pentitol | ¹H NMR (400 MHz, DMSO-d6): δ 11.54 (brs, 1H), 7.33 (s, 1H), 5.87 (s, 1H), 5.12 (brs, 1H), 4.54 (s, 2H), 3.98-3.90 (m, 2H), 3.79-3.75 (dd, J = 4.5 Hz, 1H), 3.41-3.40 (m, 2H), 3.29 (m, 1H), 2.81-2.78 (t, J = 6 Hz, 2H), 2.13 (s, 3H), 2.10 (s, 3H), 1.54-1.49 (m, 1H), 1.23-1.22 (t, J = 6.3 Hz, 3H); MS: 451 [M + 1] | C |
| 288 | 1,4-anhydro-3,5-dideoxy-2-O-{5,8-dichloro-2-[(4,6-dimethyl-2-oxo-1,2-dihydropyridin-3-yl)methyl]-1-oxo-[(2,3,4-tetrahydroisoquinolin-7-yl}-D-erythro-pentitol | ¹H NMR (400 MHz, DMSO-d6): δ 11.55 (brs, 1H), 7.37 (s, 1H), 5.87 (s, 1H), 5.17 (brs, 1H), 4.54 (s, 2H), 4.17-4.01 (m, 2H), 3.70-3.67 (d, J = 10 Hz, 1H), 3.41-3.38 (m, 3H), 3.29 (m, 1H), 2.81-2.78 (t, J = 6 Hz, 2H), 2.13 (s, 3H), 2.10 (s, 3H), 1.73-1.65 (m, 1H), 1.18-1.17 (t, J = 6.3 Hz, 3H); MS: 451 [M + 1] | C |
| 289 | 5,8-dichloro-2-[(4,6-dimethyl-2-oxo-1,2-dihydropyridin-3-yl)methyl]-7-[(4-methyltetrahydrofuran-3-yl)oxy]-3,4-dihydroisoquinolin-1(2H)-one | ¹H NMR (400 MHz, CDCl3): δ 11.34 (brs, 1H), 6.88 (s, 1H), 5.93 (s, 1H), 4.79 (s, 2H), 4.72-4.73 (m, 1H), 4.12-4.13 (m, 1H), 4.03-4.05 (t, J = 7.6 Hz, 1H), 3.89-3.92 (dd, 1H), 3.60-3.61 (m, 1H), 3.59-3.60 (m, 2H), 2.85-2.88 (m, 2H), 2.50-2.51 (m, 1H), 2.47 (s, 3H), 2.32 (s, 3H), 1.19-1.21 (d, 3H); MS: 451 [M + 1] | C |
| 290 | 5,8-dichloro-2-[(4,6-dimethyl-2-oxo-1,2-dihydropyridin-3-yl)methyl]-7-[(4-methyltetrahydrofuran-3-yl)oxy]-3,4-dihydroisoquinolin-1(2H)-one | ¹H NMR (400 MHz, CDCl3): δ 11.04 (brs, 1H), 6.87 (s, 1H), 5.93 (s, 1H), 4.78 (s, 2H), 4.72-4.73 (m, 1H), 4.12-4.13 (m, 1H), 4.03-4.05 (t, J = 7.6 Hz, 1H), 3.89-3.92 (dd, 1H), 3.60-3.61 (m, 1H), 3.59-3.60 (m, 2H), 2.85-2.88 (m, 2H), 2.50-2.51 (m, 1H), 2.47 (s, 3H), 2.27 (s, 3H), 1.19-1.21 (d, 3H); MS: 451 [M + 1] | C |

TABLE 2-continued

| Ex. | Structure/Name | 1H NMR/LCMS (M + H) | Method |
|---|---|---|---|
| 291 | 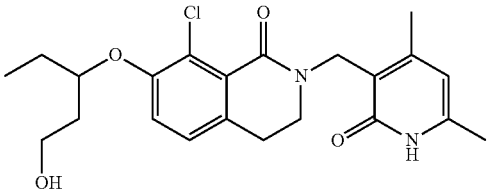 [SMILES: CCC(CCO)Oc1ccc2c(c1Cl)C(=O)N(Cc1c(C)cc(C)[nH]c1=O)CC2]<br>8-chloro-2-[(4,6-dimethyl-2-oxo-1,2-dihydropyridin-3-yl)methyl)-7-[(1-hydroxypentan-3-yl)oxy]-3,4-dihydroisoquinolin-1(2H)-one | $^1$H NMR (400 MHz, DMSO-d6) δ 11.51 (br. s., 1H), 7.18-7.30 (m, 1H), 7.08-7.18 (m, 1H), 5.88 (s, 1H), 4.57 (s, 2H), 4.50 (t, J = 5.01 Hz, 1H), 4.42-4.47 (m, 1H), 3.44-3.58 (m, 2H), 3.37 (t, J = 6.11 Hz, 2H), 2.73 (t, J = 5.99 Hz, 2H), 2.15 (s, 3H), 2.12 (s, 3H), 1.70-1.88 (m, 2H), 1.54-1.68 (m, 2H), 0.91 (t, J = 7.34 Hz, 3H); MS: 419 [M + 1] | C |
| 292 | 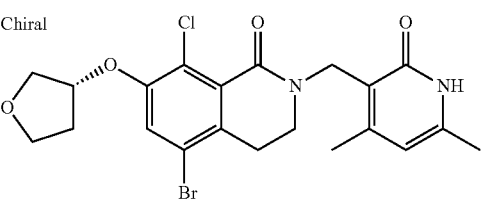<br>5-bromo-8-chloro-2-[(4,6-dimethyl-2-oxo-1,2-dihydropyridin-3-yl)methyl]-7-[(3R)-tetrahydrofuran-3-yloxy]-3,4-dihydroisoquinolin-1(2H)-one | $^1$H NMR (400 MHz, CDCl3): δ 12.38 (s, 1H), 7.13 (s, 1H), 5.94 (s, 1H), 4.93 (s, 1H), 4.78 (s, 2H), 3.93-4.05 (m, 4H), 3.62-3.58 (m, 2H), 2.88-2.85 (m, 2H), 2.33 (s, 3H), 2.28 (s, 3H), 2.18-2.17 (m. 2H); MS:483 [M + 1] | C |
| 294 | 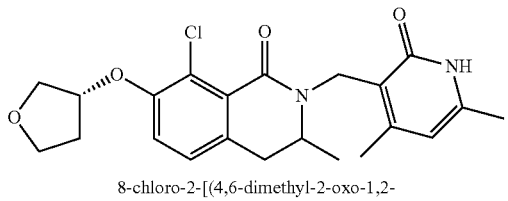<br>8-chloro-2-[(4,6-dimethyl-2-oxo-1,2-dihydropyridin-3-yl)methyl]-3-methyl-7-[(3R)-tetrahydrofuran-3-yloxy]-3,4-dihydroisoquinolin-1(2H)-one | $^1$H NMR (400 MHz, CDCl3) d 10.60 (br. s., 1H), 6.97 (s, 1H), 6.90-6.94 (m, 1H), 5.92 (s, 1H), 5.07 (d, J = 14.06 Hz, 1H), 4.94 (d, J = 2.08 Hz, 1H), 4.51 (d, J = 14.06 Hz, 1H), 4.03 (d, J = 4.52 Hz, 2H), 3.99-4.11 (m, 2H), 3.94 (td, J = 8.13, 4.03 Hz, 1H), 3.16 (s, 1H) 2.48 (dd, J = 15.41, 1.71 Hz, 1H), 2.36 (s, 3H), 2.26 (s, 3H), 2.12-2.23 (m, 2H), 1.08 (d, J = 6.60 Hz, 3H); MS: 417 [M + 1] | unique |
| 295 | 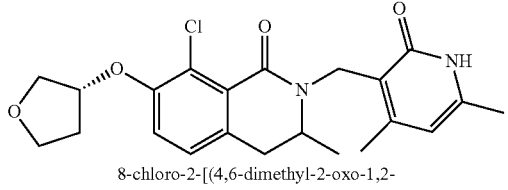<br>8-chloro-2-[(4,6-dimethyl-2-oxo-1,2-dihydropyridin-3-yl)methyl]-3-methyl-7-[(3R)-tetrahydrofuran-3-yloxy]-3,4-dihydroisoquinolin-1(2H)-one | $^1$H NMR (400 MHz, CDCl3) d 10.60 (br. s., 1H), 6.97 (s, 1H), 6.90-6.94 (m, 1H), 5.92 (s, 1H), 5.07 (d, J = 14.06 Hz, 1H), 4.94 (d, J = 2.08 Hz, 1H), 4.51 (d, J = 14.06 Hz, 1H), 4.03 (d, J = 4.52 Hz, 2H), 3.99-4.11 (m, 2H), 3.94 (td, J = 8.13, 4.03 Hz, 1H), 3.16 (s, 1H) 2.48 (dd, J = 15.41, 1.71 Hz, 1H), 2.36 (s, 3H), 2.26 (s, 3H), 2.12-2.23 (m, 2H), 1.08 (d, J = 6.60 Hz, 3H); MS: 417 [M + 1] | unique |
| 297 | 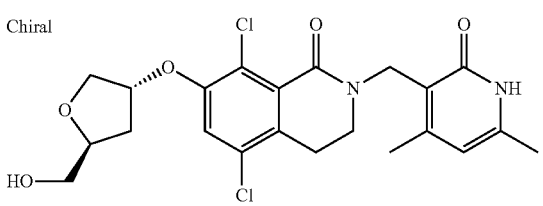 [SMILES: Cc1cc(C)c(CN2CCc3c(Cl)cc(O[C@H]4CO[C@H](CO)C4)c(Cl)c3C2=O)c(=O)[nH]1]<br>1,4-anhydro-3-deoxy-2-O-{5,8-dichloro-2-[(4,6-dimethyl-2-oxo-1,2-dihydropyridin-3-yl)methyl]-1-oxo-1,2,3,4-tetrahydroisoquinolin-7-yl}-D-erythro-pentitol | $^1$H NMR (400 MHz, methanol-d4) d ppm: 7.28 (s, 1H), 6.12 (s, 1 H), 5.13 (t, J = 4.65 Hz, 1H), 4.75 (s, 2H), 4.24-4.32 (m, 1H), 4.17 (dd, J = 10.15, 4.28 Hz, 1H), 3.96 (d, J = 10.15 Hz, 1H), 3.65-3.73 (m, 1H), 3.56 (dd, J = 11.80, 5.07 Hz, 1H), 3.48 (t, J = 6.24 Hz, 2H), 2.90 (t, J = 6.24 Hz, 2H), 2.29 (s, 3H), 2.25 (s, 3H), 2.12-2.19 (m, 1H), 2.01-2.10 (m, 1H); MS: 467 [M + 1] | C |

TABLE 2-continued

| Ex. | Structure/Name | 1H NMR/LCMS (M + H) | Method |
|---|---|---|---|
| 298 | 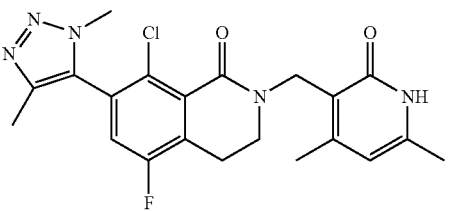 [SMILES: Cc1cc(C)c(CN2CCc3c(F)cc(-c4c(C)nnn4C)c(Cl)c3C2=O)c(=O)[nH]1]<br>8-chloro-2-[(4,6-dimethyl-2-oxo-1,2-dihydropyridin-3-yl)methyl]-7-(1,4-dimethyl-1H-1,2,3-triazol-5-yl)-5-fluoro-3,4-dihydroisoquinolin-1(2H)-one | $^1$H NMR (400 MHz, MeOD): δ 7.42 (d, J = 8.8 Hz, 1H), 6.13 (s, 1H), 4.79 (s, 2H), 3.87 (s, 3H), 3.64-3.61 (m, 2H), 3.03-2.99 (m, 2H), 2.33 (s, 3H), 2.27 (s, 3H), 2.19 (s, 3H); MS: 430 [M + 1] | X |
| 299 | 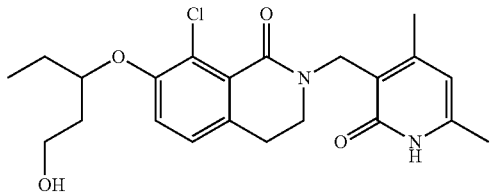 [SMILES: CCC(CCO)Oc1ccc2c(c1Cl)C(=O)N(Cc1c(C)cc(C)[nH]c1=O)CC2]<br>8-chloro-2-[(4,6-dimethyl-2-oxo-1,2-dihydropyridin-3-yl)methyl]-7-[(1-hydroxypentan-3-yl)oxy]-3,4-dihydroisoquinolin-1(2H)-one | MS: 419 [M + 1] | C |
| 300 | 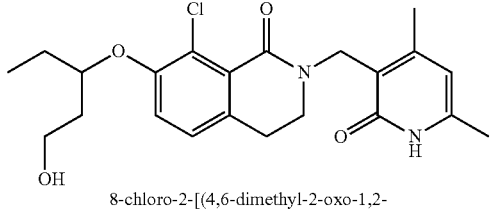<br>8-chloro-2-[(4,6-dimethyl-2-oxo-1,2-dihydropyridin-3-yl)methyl]-7-[(1-hydroxypentan-3-yl)oxy]-3,4-dihydroisoquinolin-1(2H)-one | MS: 419 [M + 1] | C |
| 301 | 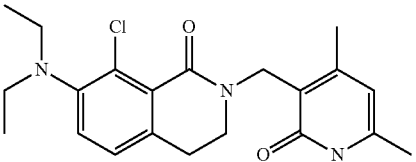<br>8-chloro-7-(diethylamino)-2-[(4,6-dimethyl-2-oxo-1,2-dihydropyridin-3-yl)methyl]-3,4-dihydroisoquinolin-1(2H)-one | $^1$H NMR (400 MHz, DMSO-d6) δ 7.23 (d, J = 8.07 Hz, 1H), 7.09-7.17 (m, 1H), 5.88 (s, 1H), 4.57 (s, 2H), 3.34-3.42 (m, 5H), 3.03 (q, J = 7.01 Hz, 4H), 2.75 (t, J = 5.87 Hz, 2H), 2.15 (s, 3H), 2.12 (s, 3H), 1.62 (s, 2H), 0.92 (t, J = 6.97 Hz, 6H); MS: 389 [M + 1] | A |
| 302 | 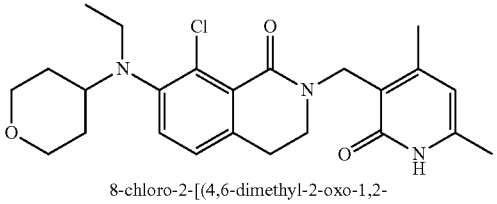<br>8-chloro-2-[(4,6-dimethyl-2-oxo-1,2-dihydropyridin-3-yl)methyl]-7-[ethyl(tetrahydro-2H-pyran-4-yl)amino]-3,4-dihydroisoquinolin-1(2H)-one | $^1$H NMR (400 MHz, DMSO-d6) δ 7.32 (d, J = 8.07 Hz, 1H), 7.14 (d, J = 8.07 Hz, 1H), 5.88 (s, 1H), 4.57 (s, 2H), 3.83 (d, J = 11.00 Hz, 3H), 3.35-3.44 (m, 5H), 3.24 (t, J = 11.07 Hz, 3H), 3.07 (q, J = 6.85 Hz, 4H), 2.76 (t, J = 5.81 Hz, 2H), 2.16 (s, 3H), 2.12 (s, 3H), 1.64 (d, J = 11.25 Hz, 2H), 1.53 (br. s., 2H), 0.80 (t, J = 6.97 Hz, 3H); MS: 445 [M + 1] | A |

Biological Assays and Data
Purification of WT and Mutant EZH2 Y641N

WT and mutant EZH2 were purified using the same procedure. The genes for EZH2, EED, SUZ12, and RBBP4 proteins were cloned into pBacPAK9 vectors (Clontech). RBBP4 was FLAG tagged on the N-terminal end. The baculovirus expressions of these proteins were used to co-infect SF9 insect cells. Insect cell pellets were lysed in a buffer containing 25 mM Tris pH8.0, 300 mM NaCl, 0.5 mM TCEP, cOmplete EDTA-free protease inhibitor (Roche), 0.1% NP-40. The supernatant from the lysate was incubated with FLAG® M2 antibody resin (Sigma). The resin was washed on the chromatography column and eluted with 0.2 mg/ml FLAG peptide. The elute was incubated with omnicleave nucleases (Epicentre Technologies) at 4° C. overnight, then concentrated and loaded onto a Superdex 200 (GE Healthcare) column. The Superdex 200 column was eluted with 25 mM Tris pH8.0, 150 mM NaCl, 0.5 mM TCEP. Fractions containing the PRC2 complex were pooled.

Nucleosome Assay Protocol:

The same protocol was used for the WT and mutant EZH2 Y6412N assays.

A. Compound preparation
1. Prepare 10 mM stock solutions in 100% DMSO from solid material
2. Serial dilute 10 mM compound stocks either 2 or 3-fold in 100% DMSO to generate compounds for 11 point dose response B. Reagent preparation
1. Prepare 1× assay buffer containing 100 mM Tris pH 8.5, 4 mM DTT and 0.01% Tween-20
2. Dilute purified HeLA oligonucleosomes and recombinant histone H1 (New England Biolabs) in assay buffer to 1.67×.
3. Dilute PRC2 4 protein complex (EZH2, EED, SUZ12, RbAp48) to 3.5× in assay buffer
4. Prepare 10×$^3$H SAM solution in assay buffer using 0.94 µCi/well of radioactive SAM (Perkin Elmer) and sufficient non-labeled SAM (Sigma) for 1.5 µM final concentration.
5. Dilute TCA to 20% in DI water C. Enzyme reaction
1. Final reaction conditions are PRC2 4-protein complex at 4 nM when using WT EZH2 or 6 nM when using Y641N mutant EZH2, 1.5 µM SAM, 25 µg/mL oligonucleosomes, 50 nM rH1 in a 50 µl reaction volume.
2. Add 1 µl of diluted compound to the assay plate (96-well V-bottom polypropylene plates) or 1 µl of DMSO for control wells.
3. Add 30 µl of nucleosomes to the assay plate
4. Add 14 µl of either WT or Y641N mutant PRC2 4 protein complex to the assay plate
5. Add 5 µl of $^3$H SAM to start the reaction.
6. Stop the reaction after 60 minutes with the addition of 100 µl of 20% TCA
7. Transfer 150 µl of quenched reaction into a prepared filterplate (Millipore #MSIPN4B10)
8. Apply vacuum to the filterplate to filter the reaction mix through the membrane.
9. Wash the filterplate with 5×200 µl of PBS, blot dry and dry in an oven for 30 minutes
10. Add 50 µl of microscint-20 scintillation fluid (Perkin Elmer) to each well, wait 30 minutes and count on a liquid scintillation counter.

D. Data analysis
1. IC$_{50}$ values were determined by fitting the data to a 4-parameter IC$_{50}$ equation using proprietary curve fitting software.

Preparation of HeLA Oligonucleosomes:

Reagents

Cell Pellet: 15 L HeLa S3 (Accelgen)+6 L HeLa S3 (in house)

Mnase (Worthington Biochemicals)

Equipment

SW-28 Rotor

Dounce Homogenizer/B Pestle

Buffers

Lysis: 20 mM Hepes pH 7.5, 0.25M Sucrose, 3 mM MgCl$_2$, 0.5% Nonidet P-40, 0.5 mM TCEP, 1 Roche Protease Tablet B: 20 mM Hepes pH7.5, 3 mM MgCl$_2$, 0.5 mM EDTA, 0.5 mM TCEP, 1 Roche Protease Tablet MSB: 20 mM Hepes pH7.5, 0.4 M NaCl, 1 mM EDTA, 5% v/v Glycerol, 0.5 mM TCEP, 0.2 mM PMSF LSB: 20 mM Hepes pH7.5, 0.1M NaCl, 1 mM EDTA, 0.5 mM TCEP, 0.2 mM PMSF NG: 20 mM Hepes pH7.5, 1 mM EDTA, 0.4m NaCl, 0.2 mM PMSF, 0.5 mM TCEP Storage: 20 mM Hepes pH7.5, 1 mM EDTA, 10% Glycerol, 0.2 mM PMSF, 0.5 mM TCEP Protocol A. Nuclei
1. Resuspend ~10 L pellet in 2×40 mL lysis using dounce homogenizer
2. Spin 3000×g 15'
3. Repeat 2 more times
4. Resuspend pellet in 2×40 mL B
5. Spin 3000×g 15'

B. Nuclei Resuspension
1. Resuspend pellet in 2×40 mL MSB. Spin 5000×g 20'
2. Resuspend pellet in 2×15 mL HSB
3. Pool and Homogenize 40 Strokes to shear DNA
4. Pellet 10000×g 20'
5. Dialyze O/N 4° C. in LSB except for Batch A which was Dialyzed LSB at 50 nM NaCl for 3 hr C. Mnase Digestion Test Mnase digestion (200 ul)
1. Warm to 37° C. for 5'
2. Add CaCl$_2$ to 3 mM and add 10U of Mnase
3. 37° C. 30' taking 25 µL sample every 5'
4. Process reaction with 1 µL 0.5M EDTA, 40 µL H$_2$O, 15 µL 10% SDS, 10 µL 5M NaCl, and 100 µL phenol-chloroform vortexing after each addition
5. Spin 5' 13 k
6. Run 5 µL of Aqueous phase on 1% agarose gel
7. Take time that yields ~2 kb fragments
8. Selected 15' for A & B and 20' for C & D for scale up Added NaCl to 0.6M D. Sucrose Gradient 1
1. Poured 6× 34 mL gradient from 5 to 35% sucrose in NG using AKTA purifier in 38.5 mL pollyallomer tubes
2. Lead ~4.0 mL on top of MN1 digest
3. Spin 26 k 16 hr 4° C.
4. Take 2 mL fractions from top
5. Run on Page Gel
6. Dialyze Fractions 7-14 O/N 4° C. in 4 L LSB except Batch D which had 2× 2 hr
7. Repeat 3×

E. Final
1. Pool all and concentrate in Amicon (somewhat cloudy)
2. Added 10% Glycerol
3. Spun 5K 15'
4. 1.8 mg/mL at 80 mL for 144 mg Total Biological Activity Biological activity of selected examples in the EZH2 nucleosome assay are provided in Table 3. Data is presented as WT EZH2 and Mutant Y641N EZH2 IC$_{50}$ values (µM).

TABLE 3

| Ex. No. | WT EZH2 IC$_{50}$ (µM) | EZH2 Mutant Y641N IC$_{50}$ (µM) |
|---|---|---|
| 1 | 0.538 | — |
| 2 | 0.128 | 0.924 |
| 3 | 0.346 | — |
| 4 | 8.09 | 66.5 |
| 5 | 21.3 | — |
| 6 | 0.0411 | 0.161 |
| 7 | 7.41 | 36.8 |

TABLE 3-continued

| Ex. No. | WT EZH2 IC$_{50}$ (μM) | EZH2 Mutant Y641N IC$_{50}$ (μM) |
|---|---|---|
| 8 | 2.42 | 8.25 |
| 9 | — | — |
| 10 | — | — |
| 11 | — | — |
| 12 | 0.466 | 2.58 |
| 13 | 0.211 | 1.01 |
| 14 | — | — |
| 15 | — | — |
| 16 | 0.449 | 2.26 |
| 17 | 0.248 | 1.73 |
| 18 | 1.12 | 5.53 |
| 19 | — | — |
| 20 | 3.13 | 11.1 |
| 21 | 0.111 | 0.685 |
| 22 | 0.0788 | 0.342 |
| 23 | 0.0327 | 0.217 |
| 24 | 0.654 | 3.35 |
| 25 | 0.306 | 1.86 |
| 26 | 0.795 | 5.64 |
| 27 | 0.0615 | 0.415 |
| 28 | 0.0869 | 0.724 |
| 29 | 0.312 | 1.65 |
| 30 | 0.0502 | 0.262 |
| 31 | 0.199 | 1.04 |
| 32 | 0.670 | 2.82 |
| 33 | 0.0357 | 0.207 |
| 34 | 0.356 | 2.13 |
| 35 | 0.148 | 0.729 |
| 36 | 0.919 | 3.83 |
| 37 | 0.177 | 0.977 |
| 38 | 1.62 | 5.02 |
| 39 | 1.60 | 6.55 |
| 40 | 0.491 | 2.07 |
| 41 | 0.147 | 0.766 |
| 42 | 0.207 | 1.25 |
| 43 | 0.0398 | 0.258 |
| 44 | 0.184 | 0.822 |
| 45 | 0.0203 | 0.0844 |
| 46 | 0.0129 | 0.0522 |
| 47 | 25.0 | >200 |
| 48 | 61.0 | >200 |
| 49 | 0.0116 | 0.0536 |
| 50 | 0.246 | 1.24 |
| 51 | 0.0185 | — |
| 52 | 5.66 | 29.1 |
| 53 | >200 | >200 |
| 54 | >200 | — |
| 55 | 50.2 | >200 |
| 56 | >176 | — |
| 57 | 5.21 | 6.31 |
| 58 | 0.0317 | 0.196 |
| 59 | 0.0912 | — |
| 60 | 0.233 | 0.994 |
| 61 | 0.682 | 6.10 |
| 62 | 0.0389 | 0.177 |
| 63 | 0.931 | 5.29 |
| 64 | 1.91 | 12.3 |
| 65 | 10.2 | 33.1 |
| 66 | 0.288 | 1.93 |
| 67 | 0.0243 | 0.312 |
| 68 | 24.7 | — |
| 69 | 17.4 | — |
| 70 | 0.219 | 0.830 |
| 71 | 2.04 | — |
| 72 | 5.43 | — |
| 73 | 0.269 | — |
| 74 | 0.569 | — |
| 75 | 0.0171 | 0.0756 |
| 76 | 5.20 | 40.1 |
| 77 | 0.0123 | 0.0429 |
| 78 | 0.0205 | 0.0584 |
| 79 | 0.0759 | 0.339 |
| 80 | 0.333 | — |
| 81 | 0.006 | 0.019 |
| 82 | 0.306 | 1.08 |
| 83 | 0.0250 | 0.141 |
| 84 | 0.0326 | 0.117 |
| 85 | 0.0209 | 0.0663 |
| 86 | 0.0547 | 0.212 |
| 87 | 0.04 | 0.126 |
| 88 | 0.00661 | 0.0177 |
| 89 | 0.115 | 0.450 |
| 90 | 0.595 | — |
| 91 | 0.121 | — |
| 92 | 0.0437 | 0.227 |
| 93 | 0.490 | — |
| 94 | 0.176 | 0.656 |
| 95 | 0.404 | 1.57 |
| 96 | 0.295 | 1.26 |
| 97 | 0.305 | 1.21 |
| 98 | 0.377 | 1.29 |
| 99 | 0.193 | 0.746 |
| 100 | 1.29 | 5.53 |
| 101 | 0.0611 | 0.229 |
| 102 | 1.06 | 5.71 |
| 103 | 0.124 | — |
| 104 | 0.0705 | 0.272 |
| 105 | 0.205 | 0.867 |
| 106 | 2.20 | — |
| 107 | 0.283 | 1.85 |
| 108 | 0.0844 | 0.474 |
| 109 | 17.0 | 150 |
| 110 | 15.0 | 56.1 |
| 111 | >154 | — |
| 112 | 0.121 | 0.626 |
| 113 | 112 | — |
| 114 | 0.911 | 5.26 |
| 115 | 0.321 | — |
| 116 | 0.112 | 0.681 |
| 117 | 7.93 | — |
| 118 | 11.4 | — |
| 119 | 0.215 | — |
| 120 | 0.476 | — |
| 121 | 0.0536 | 0.244 |
| 122 | 0.129 | — |
| 123 | 93.9 | — |
| 124 | 0.566 | — |
| 125 | 0.454 | — |
| 126 | 0.158 | 1.46 |
| 127 | 0.233 | — |
| 128 | 0.0471 | 0.234 |
| 129 | 0.0911 | 0.517 |
| 130 | 84.5 | — |
| 131 | 0.558 | 6.35 |
| 132-A | 0.143 | 1.41 |
| 132-B | 63 | >200 |
| 133 | 99.6 | — |
| 134 | >200 | — |
| 135 | >200 | — |
| 136 | 0.0437 | 0.227 |
| 137 | 0.0171 | 0.0756 |
| 138 | 0.0398 | 0.258 |
| 139 | 0.0502 | 0.262 |
| 140 | 0.211 | 1.01 |
| 141 | 0.0123 | 0.0429 |
| 142 | 7.41 | 36.8 |
| 143 | 0.404 | 1.57 |
| 144 | 0.176 | 0.656 |
| 145 | 1.91 | 12.3 |
| 146 | 0.246 | 1.24 |
| 146 | 0.0389 | 0.177 |
| 148 | 0.0116 | 0.0536 |
| 149 | 61.0 | >200 |
| 150 | 25.0 | >200 |
| 151 | 0.115 | 0.450 |
| 152 | 0.00661 | 0.0177 |
| 153 | 0.04 | 0.126 |
| 154 | 0.0547 | 0.212 |
| 155 | 0.931 | 5.29 |
| 156 | 0.205 | 0.867 |
| 157 | 0.0209 | 0.0663 |
| 158 | 0.0326 | 0.117 |

TABLE 3-continued

| Ex. No. | WT EZH2 IC$_{50}$ (µM) | EZH2 Mutant Y641N IC$_{50}$ (µM) |
|---|---|---|
| 159 | 5.66 | 29.1 |
| 160 | 0.0250 | 0.141 |
| 161 | 0.0705 | 0.272 |
| 162 | 0.0129 | 0.0522 |
| 163 | 0.0203 | 0.0844 |
| 164 | 0.306 | 1.08 |
| 165 | 0.0062 | 0.019 |
| 166 | 0.260 | 1.49 |
| 167 | 0.059 | 0.176 |
| 168 | >200 | >200 |
| 169 | 0.0224 | 0.0682 |
| 170 | 0.168 | 0.701 |
| 171 | 0.190 | 0.704 |
| 172 | 0.536 | 2.17 |
| 173 | 0.0285 | 0.110 |
| 174 | 0.665 | 3.39 |
| 175 | 0.0342 | 0.153 |
| 176 | 0.0657 | 0.393 |
| 177 | 2.74 | 9.39 |
| 178 | 0.0101 | 0.0651 |
| 179 | 4.21 | 22.9 |
| 180 | 0.0365 | 0.127 |
| 181 | 7.96 | 31.3 |
| 182 | 0.00947 | 0.0361 |
| 183 | 0.555 | 2.00 |
| 184 | 0.385 | 1.23 |
| 185 | 0.426 | 1.56 |
| 186 | 0.434 | 1.78 |
| 187 | 0.0253 | 0.184 |
| 188 | 0.792 | 4.96 |
| 189 | 0.0195 | 0.0680 |
| 190 | 0.0526 | 0.229 |
| 191 | 0.132 | 0.450 |
| 192 | 17.3 | >200 |
| 193 | 0.0184 | 0.0774 |
| 194 | 0.0166 | 0.0672 |
| 195 | 0.688 | 4.59 |
| 196 | 0.0302 | 0.0952 |
| 197 | 0.0280 | 0.127 |
| 198 | 0.214 | 0.474 |
| 199 | 0.0747 | 0.350 |
| 200 | 0.163 | 0.846 |
| 201 | 0.286 | 1.33 |
| 202 | 0.0298 | 0.119 |
| 203 | 16.5 | 36.8 |
| 204 | 0.0834 | 0.398 |
| 205 | 6.57 | 26.6 |
| 206 | 0.0944 | 0.400 |
| 207 | 0.0878 | 0.475 |
| 208 | 0.214 | 1.63 |
| 209 | 0.142 | 0.725 |
| 210 | 0.186 | 0.788 |
| 211 | 0.09 | 0.353 |
| 212 | 0.540 | 1.90 |
| 213 | 0.0846 | 0.400 |
| 214 | 0.0194 | 0.0710 |
| 215 | 0.017 | 0.066 |
| 216 | 0.0214 | 0.0603 |
| 217 | 0.172 | 1.14 |
| 218 | 0.0381 | 0.136 |
| 219 | 1.29 | 10.8 |
| 220 | 0.0262 | 0.116 |
| 221 | 15.3 | 65.5 |
| 222 | 0.00644 | 0.0224 |
| 223 | >200 | >200 |
| 224 | 0.0567 | 0.216 |
| 225 | 0.008 | 0.024 |
| 226 | 0.380 | 1.70 |
| 227 | 0.0309 | 0.133 |
| 228 | 0.0277 | 0.140 |
| 229 | 0.00952 | 0.0273 |
| 230 | 0.275 | 1.67 |
| 231 | 0.0351 | 0.129 |
| 232 | 0.263 | 8.27 |
| 233 | 0.00993 | 0.104 |
| 234 | 0.114 | 0.556 |
| 235 | 0.0130 | 0.0432 |
| 236 | 0.00526 | 0.0188 |
| 237 | 0.0897 | 0.444 |
| 238 | 0.0536 | 0.292 |
| 239 | 0.0334 | 0.144 |
| 240 | 0.0459 | 0.195 |
| 241 | 0.276 | 1.63 |
| 242 | 0.0941 | 0.553 |
| 243 | 0.00858 | 0.0248 |
| 244 | 0.170 | 0.772 |
| 245 | 0.373 | 1.21 |
| 246 | 0.0335 | 0.137 |
| 247 | 0.0154 | 0.0627 |
| 248 | 0.0128 | 0.0487 |
| 249 | 1.97 | 8.40 |
| 250 | 0.170 | 0.677 |
| 251 | 0.883 | 3.85 |
| 252 | 0.267 | 1.22 |
| 253 | <0.00383 | 0.00507 |
| 254 | 0.502 | 3.41 |
| 255 | 1.29 | 5.01 |
| 256 | 1.81 | 11.3 |
| 257 | 0.0714 | 0.467 |
| 258 | 0.0186 | 0.0629 |
| 259 | 0.0390 | 0.276 |
| 260 | 0.0453 | 0.284 |
| 261 | 0.0180 | 0.101 |
| 262 | 0.0129 | 0.0539 |
| 263 | 0.0109 | 0.0410 |
| 264 | 0.0954 | 0.406 |
| 265 | 0.0291 | 0.290 |
| 266 | 0.0294 | 0.151 |
| 267 | <0.00502 | 0.0200 |
| 268 | <0.00440 | 0.0150 |
| 269 | 0.0501 | 0.241 |
| 270 | 0.222 | 1.07 |
| 271 | 0.0715 | 0.418 |
| 272 | 0.0479 | 0.339 |
| 273 | 0.00357 | 0.00656 |
| 274 | 0.0402 | 0.230 |
| 275 | 0.380 | 2.16 |
| 276 | 0.563 | 3.56 |
| 277 | 0.0869 | 0.516 |
| 278 | 0.0530 | 0.311 |
| 279 | 0.0640 | 0.220 |
| 280 | 0.00696 | 0.0271 |
| 281 | 0.253 | 1.59 |
| 282 | 0.102 | 0.633 |
| 283 | 0.150 | 0.844 |
| 284 | 0.135 | 0.845 |
| 285 | 0.00717 | 0.0259 |
| 286 | 0.152 | 0.806 |
| 287 | 0.0271 | 0.105 |
| 288 | — | — |
| 289 | 0.0373 | 0.140 |
| 290 | 0.0513 | 0.189 |
| 291 | 0.0652 | 0.517 |
| 292 | 0.0121 | 0.0357 |
| 293 | 0.00794 | 0.0314 |
| 294 | 13.4 | 137 |
| 295 | 0.0361 | 0.271 |
| 296 | 0.0172 | 0.0888 |
| 297 | 0.0692 | 0.396 |
| 298 | 0.0356 | 0.202 |
| 299 | 0.125 | 0.905 |
| 300 | 0.0336 | 0.256 |
| 301 | 0.0148 | 0.053 |
| 302 | 0.0037 | 0.0063 |

All publications and patent applications cited in the specification are herein incorporated by reference in their entirety. Although the foregoing invention has been described in some detail by way of illustration and example, it will be readily apparent to those of ordinary skill in the art in light of the teachings of this invention that certain changes

We claim:
1. A compound of formula (II-A):

(II-A)

or a pharmaceutically acceptable salt thereof,
wherein:
$R^1$ is $C_1$-$C_4$ alkyl or halo;
$R^2$ is 5-12 membered heteroaryl, where said 5-12 membered heteroaryl is optionally substituted by 1 to 3 $R^{32}$ groups;
$R^3$ is H;
$R^4$ is H or halo;
m is 0;
$R^5$ is absent;
each $R^{32}$ is independently selected from the group consisting of —Cl, —F, —OH, —CH$_3$, —CH$_2$CH$_3$, —CF$_3$, —CH$_2$OH, —CH$_2$OCH$_3$, —OCH$_3$, —OC$_2$H$_5$, —OCF$_3$, —CN, —C(O)NH$_2$, —C(O)NHCH$_3$, —C(O)N(CH$_3$)$_2$, —NHC(O)CH$_3$, —NH$_2$, —NHCH$_3$, —N(CH$_3$)$_2$, cyclopropyl, 4-6 membered heterocyclyl, phenyl and 5-6 membered heteroaryl, where said 4-6 membered heterocyclyl, phenyl or 5-6 membered heteroaryl are optionally substituted by 1 to 3 halo, $C_1$-$C_4$ alkyl or $C_1$-$C_4$ alkoxy, which are independently selected;
X and Z are independently $C_1$-$C_4$ alkyl; and
Y is H.

2. The compound or salt of claim 1, wherein $R^1$ is chloro.

3. The compound or salt of claim 1, wherein $R^2$ is 5-12 membered heteroaryl selected from the group consisting of pyrazolyl, isoxazoyl and triazolyl, where said 5-12 membered heteroaryl is optionally substituted by 1 to 3 $R^{32}$ groups.

4. The compound or salt of claim 3, wherein each $R^{32}$ is independently selected from the group consisting of —CH$_3$ and —CH$_2$CH$_3$.

5. The compound or salt of claim 1, wherein $R^4$ is halo.

6. A pharmaceutical composition comprising a compound of claim 1, or a pharmaceutically acceptable salt thereof, and a pharmaceutically acceptable carrier or excipient.

7. A method for the treatment of abnormal cell growth in a subject, comprising administering to the subject a therapeutically effective amount of a compound of claim 1, or a pharmaceutically acceptable salt thereof.

8. The method of claim 7, wherein the abnormal cell growth is cancer.

9. The method of claim 7, wherein the subject is human.

10. A compound that is 5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one, or a pharmaceutically acceptable salt thereof.

11. A pharmaceutical composition comprising the compound of claim 10, or a pharmaceutically acceptable salt thereof, and a pharmaceutically acceptable carrier or excipient.

12. The compound of claim 10 that is 5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one.

13. A pharmaceutically acceptable salt of the compound of claim 10 that is 5-bromo-8-chloro-2-[(4,6-dimethyl-2-oxo-1,2-dihydropyridin-3-yl)methyl]-7-(1,4-dimethyl-1H-1,2,3-triazol-5-yl)-3,4-dihydroisoquinolin-1(2H)-one.

14. A pharmaceutical composition comprising the compound of claim 12, and a pharmaceutically acceptable carrier or excipient.

15. A pharmaceutical composition comprising the pharmaceutically acceptable salt of claim 13, and a pharmaceutically acceptable carrier or excipient.

16. A compound of formula (II-A):

(II-A)

or a pharmaceutically acceptable salt thereof, wherein:
$R^1$ is $C_1$-$C_4$ alkyl or halo;
$R^2$ is a 5-6 membered heteroaryl, optionally substituted by 1 to 3 $R^{32}$ groups;
$R^3$ is H;
$R^4$ is H or halo;
each $R^{32}$ is independently selected from the group consisting of halo, $C_1$-$C_8$ alkyl, —OR$^c$, —SR$^c$, —SO$_2$R$^c$ and —NR$^c$R$^d$, and each R$^c$ and R$^d$ is independently H or $C_1$-$C_8$ alkyl; or
each $R^{32}$ is independently selected from the group consisting of halo and $C_1$-$C_8$ alkyl, where each said $C_1$-$C_8$ alkyl is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl) and —N($C_1$-$C_4$ alkyl)$_2$;
m is 0 and $R^5$ is absent;
X and Z are independently $C_1$-$C_4$ alkyl; and
Y is H.

* * * * *